US012790303B2

(12) United States Patent
Nakajima et al.

(10) Patent No.: US 12,790,303 B2
(45) Date of Patent: Nov. 10, 2026

(54) SALT-INDUCIBLE KINASE INHIBITOR COMPOUND AND PHARMACEUTICAL COMPOSITION INCLUDING THE SAME

(71) Applicant: MITSUBISHI TANABE PHARMA CORPORATION, Osaka (JP)

(72) Inventors: Motoyuki Nakajima, Osaka (JP); Hiroaki Shitama, Osaka (JP); Yuuki Arai, Osaka (JP); Daiki Nakatake, Osaka (JP); Hiroshi Miyazaki, Osaka (JP); Yuzo Koda, Osaka (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 0 days.

(21) Appl. No.: 19/383,969

(22) Filed: Nov. 10, 2025

(65) Prior Publication Data

US 2026/0062387 A1 Mar. 5, 2026

Related U.S. Application Data

(63) Continuation of application No. PCT/JP2024/018995, filed on May 23, 2024.

(30) Foreign Application Priority Data

May 24, 2023 (JP) ................................ 2023-085585

(51) Int. Cl.

| | |
|---|---|
| ***C07D 231/56*** | (2006.01) |
| ***A61K 31/416*** | (2006.01) |
| ***A61K 31/4192*** | (2006.01) |
| ***A61K 31/422*** | (2006.01) |
| ***A61K 31/4245*** | (2006.01) |
| ***A61K 31/427*** | (2006.01) |
| ***A61K 31/4439*** | (2006.01) |
| ***A61K 31/4725*** | (2006.01) |
| ***A61K 31/497*** | (2006.01) |
| ***A61K 31/501*** | (2006.01) |
| ***A61K 31/5377*** | (2006.01) |
| ***C07D 401/14*** | (2006.01) |
| ***C07D 403/14*** | (2006.01) |
| ***C07D 405/14*** | (2006.01) |
| ***C07D 409/14*** | (2006.01) |
| ***C07D 413/14*** | (2006.01) |
| ***C07D 417/04*** | (2006.01) |
| ***C07D 417/14*** | (2006.01) |

(52) U.S. Cl.

CPC .......... *C07D 231/56* (2013.01); *A61K 31/416* (2013.01); *A61K 31/4192* (2013.01); *A61K 31/422* (2013.01); *A61K 31/4245* (2013.01); *A61K 31/427* (2013.01); *A61K 31/4439* (2013.01); *A61K 31/4725* (2013.01); *A61K 31/497* (2013.01); *A61K 31/501* (2013.01); *A61K 31/5377* (2013.01); *C07D 401/14* (2013.01); *C07D 403/14* (2013.01); *C07D 405/14* (2013.01); *C07D 409/14* (2013.01); *C07D 413/14* (2013.01); *C07D 417/04* (2013.01); *C07D 417/14* (2013.01)

(58) Field of Classification Search

CPC .. C07D 231/56; C07D 401/14; C07D 403/14; C07D 413/14; A61K 31/416; A61K 31/4192; A61K 31/422; A61K 31/4245; A61K 31/427; A61K 31/4439; A61K 31/4725; A61K 31/5377

See application file for complete search history.

(56) References Cited

U.S. PATENT DOCUMENTS

| | | | | |
|---|---|---|---|---|
| 9,670,165 | B2 * | 6/2017 | Cohen | A61K 31/5377 |
| 9,890,153 | B2 * | 2/2018 | Vankayalapati | C07D 471/04 |
| 10,233,157 | B2 * | 3/2019 | Cohen | A61P 29/00 |

(Continued)

FOREIGN PATENT DOCUMENTS

| | | | |
|---|---|---|---|
| CN | 115448881 | A | 12/2022 |
| JP | 2021-505553 | A | 2/2021 |

(Continued)

OTHER PUBLICATIONS

Greicius (Journal of Neurol Neurosurg Psychiatry vol. 72 pp. 691-700 Published 2002) (Year: 2002).*

(Continued)

*Primary Examiner* — George W Kosturko
(74) *Attorney, Agent, or Firm* — Birch, Stewart, Kolasch & Birch, LLP

(57) ABSTRACT

An object is to provide a novel compound capable of effectively inhibiting all of SIK1, SIK2, and SIK3, and a pharmaceutical composition including the compound. A compound represented by formula (I) below or a pharmacologically acceptable salt thereof is provided:

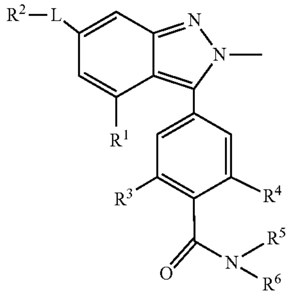

(I)

wherein the symbols are as defined in the description.

23 Claims, No Drawings

(56) References Cited

U.S. PATENT DOCUMENTS

| | | | | |
|---|---|---|---|---|
| 10,265,321 | B2 * | 4/2019 | Shamji | A61K 31/5377 |
| 10,954,242 | B2 * | 3/2021 | Gray | C07D 487/04 |
| 11,339,166 | B2 * | 5/2022 | Alvey | A61K 31/4184 |
| 11,690,897 | B2 * | 7/2023 | Stocco | A61K 31/138<br>514/9.9 |
| 2021/0101903 | A1 | 4/2021 | Alvey et al. | |
| 2022/0235048 | A1 | 7/2022 | Temal-Laib | |
| 2022/0340548 | A1 * | 10/2022 | Alvey | C07D 405/10 |
| 2022/0402911 | A1 | 12/2022 | Amantini et al. | |

FOREIGN PATENT DOCUMENTS

| | | | |
|---|---|---|---|
| JP | 2021-527106 | A | 10/2021 |
| JP | 2022-534576 | A | 8/2022 |
| JP | 2022-534578 | A | 8/2022 |
| WO | WO 2019/105886 | A1 | 6/2019 |
| WO | WO 2019/238424 | A1 | 12/2019 |
| WO | WO 2020/239658 | A1 | 12/2020 |
| WO | WO 2020/239660 | A1 | 12/2020 |

OTHER PUBLICATIONS

Darling et al., “Inhibition of SIK2 and SIK3 during differentiation enhances the anti-inflammatory phenotype of macrophages”, Biochemical Journal, 2017, vol. 474, pp. 521-537.

International Search Report (PCT/ISA/210) issued in PCT/JP2024/018995, dated Jul. 30, 2024.

Sato et al., “Structure-based design of selective, orally available salt-inducible kinase inhibitors that stimulate bone formation in mice”, PNAS, 2022, vol. 119, No. 50, pp. 1-9.

* cited by examiner

SALT-INDUCIBLE KINASE INHIBITOR COMPOUND AND PHARMACEUTICAL COMPOSITION INCLUDING THE SAME

CROSS REFERENCE TO RELATED APPLICATIONS

This application is a Continuation of PCT International Application No. PCT/JP2024/018995, filed on May 23, 2024, which claims priority under 35 U.S.C. 119(a) to Patent Application No. 2023-085585, filed in Japan on May 24, 2023, all of which are hereby expressly incorporated by reference into the present application.

TECHNICAL FIELD

The present invention relates to a salt-inducible kinase inhibitor compound and a pharmaceutical composition including the compound.

BACKGROUND ART

Salt-inducible kinases (SIK) belong to the AMP-activated protein kinase (AMPK) family and have functions mainly involved in regulating energy response-related physiological processes, such as gluconeogenesis and lipid metabolism. The SIK family consists of three isoforms, SIK1, SIK2, and SIK3. All these isoforms are known to act as metabolic transmitters. Salt-inducible kinases undergo autophosphorylation and play an important role in regulating the adrenocortical functions upon high salt intake or under stimulus of adrenocorticotropic hormones (ACTH).

All the three SIK family members, namely, SIK1, SIK2, and SIK3, are expressed widely. The expression of SIK1 mRNA is regulated by a plurality of stimuli, such as high salt intake, ACTH signals, glucagon signals, excitable cell depolarization, and circadian rhythms. On the other hand, the expression of SIK2 and SIK3 is constitutive in tissues in which these kinases are expressed. In humans, SIK2 and SIK3 are expressed ubiquitously. The expression level is highest in adipose tissues for SIK2 and at brains for SIK3. Furthermore, these SIK family members show abnormal regulations in various types of cancers, such as ovarian cancer, breast cancer, prostate cancer, and lung cancer. This fact suggests that SIK play important roles in the occurrence and progress of cancers.

SIK regulate a new molecular switch that regulates the polarity of macrophages. Pharmacological inhibition of SIK induces a macrophage phenotype characterized by high-level secretion of anti-inflammatory cytokines, such as interleukin (IL)-10, and extremely low secretion of inflammatory cytokines, such as tumor necrosis factor α. However, it has been unknown which one of the three isoforms, SIK1, SIK2, and SIK3, is the appropriate target. Non Patent Literature 1 addresses this problem and discloses a study using mouse macrophages. As compared to SIK2-inactivated macrophages, SIK1- and SIK2-inactivated macrophages that had been stimulated by lipopolysaccharide (LPS) suppressed the production of inflammatory cytokines (TNF-α, IL-12p40) and promoted the anti-inflammatory cytokine (IL-10) production. This has shown that the inhibition of both SIK1 and SIK2 is medicinally more important than the inhibition of SIK2 alone. Furthermore, an SIK1/2/3 inhibitor (HG-9-91-01, a compound having the following structure:

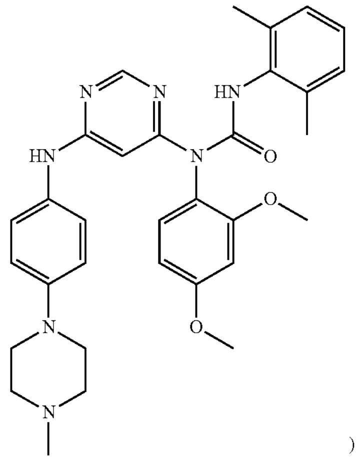 [SMILES: COc1ccc(N(C(=O)Nc2c(C)cccc2C)c2cc(Nc3ccc(N4CCN(C)CC4)cc3)ncn2)c(OC)c1]

)

was added to SIK1- and SIK2-inactivated macrophages. As compared to SIK1- and SIK2-inactivated macrophages, the macrophages in which SIK1, SIK2, and SIK3 had been all inactivated suppressed the production of TNF-α and IL-12p40 and promoted the anti-inflammatory cytokine (IL-10) production. This has shown that the inhibition of all SIK1, SIK2, and SIK3 is most important to benefit from the medicinal effects of macrophages.

Patent Literatures 1 to 5 disclose compounds that exhibit certain levels of SIK inhibitory effects.

CITATION LIST

Patent Literature

Patent Literature 1: WO 2019/105886
Patent Literature 2: WO 2019/238424
Patent Literature 3: WO 2020/239658
Patent Literature 4: WO 2020/239660
Patent Literature 5: CN 115448881 A

Non Patent Literature

Non Patent Literature 1: Darling N J, Toth R, Arthur J S, and Clark K., Inhibition of SIK2 and SIK3 during differentiation enhances the anti-inflammatory phenotype of macrophages., Biochem J. 2017; 474(4): 521-537

SUMMARY OF INVENTION

It has been suggested that the inhibition of all of SIK1, SIK2, and SIK3 is important for pharmaceutical usefulness of an SIK inhibitor compound. The development of such a compound capable of effectively inhibiting all of SIK1, SIK2, and SIK3 is desired.

It is therefore an object of the present invention to provide a novel compound capable of effectively inhibiting all of SIK1, SIK2, and SIK3, and a pharmaceutical composition including the compound.

Studies of the present invention have found that the object is achieved by the following specific configurations.

An aspect of the present invention resides in a compound represented by formula (I) below or a pharmacologically acceptable salt thereof:

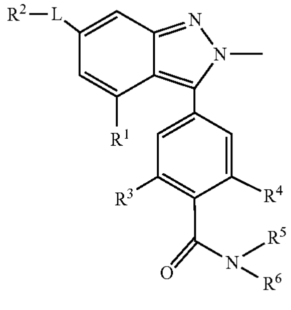

(I)

wherein $R^1$ is a cyano group, a $C_{1-4}$ alkyl group optionally substituted with one to three halogen atoms, or a $C_{1-4}$ alkoxy group optionally substituted with one to three substituents independently selected from $R^{1a}$, wherein $R^{1a}$ is a halogen atom; a 5- or 6-membered monocyclic aromatic heterocyclic group optionally substituted with one to three substituents independently selected from the group consisting of cyano groups, halogen atoms, and $C_{1-4}$ alkyl groups; a 4-membered monocyclic aliphatic heterocyclic group; a hydroxyl group; a $C_{3-4}$ cycloalkyl group; and a phenyl group, L is a single bond, a $C_{1-4}$ alkylene group, or a $C_{2-4}$ alkenylene group, $R^2$ is a 5-membered monocyclic aromatic heterocyclic group optionally substituted with $R^{2a}$, wherein $R^{2a}$ is a $C_{1-5}$ alkyl group optionally substituted with one to four substituents independently selected from $R^{2b}$, or a 5-membered monocyclic aliphatic heterocyclic group, wherein $R^{2b}$ is a hydroxyl group; a $C_{3-4}$ cycloalkyl group optionally substituted with a hydroxyl group; a halogen atom; a $C_{1-4}$ alkoxy group; a 4- to 6-membered monocyclic aliphatic heterocyclic group optionally substituted with one to three substituents independently selected from the group consisting of halogen atoms and oxo groups; an oxo group; an amino groups optionally substituted with one or two $C_{1-4}$ alkyl groups; a phenyl group; a 5-membered monocyclic aromatic heterocyclic group; and a $C_{1-4}$ alkylsulfonyl group, $R^3$ is a hydrogen atom or a $C_{1-4}$ alkoxy group optionally substituted with one to three halogen atoms, $R^4$ is a $C_{1-4}$ alkoxy group optionally substituted with one to three halogen atoms, $R^5$ is a hydrogen atom, $R^6$ is a hydrogen atom; a $C_{1-4}$ alkyl group substituted with a halocyclopropyl group; or a cyclopropyl group substituted with one or two halogen atoms, or $R^5$ and $R^6$, taken together with the nitrogen atom to which they are bonded, form an azetidine ring wherein the azetidine ring is substituted with one or two substituents independently selected from the group consisting of $C_{1-4}$ alkyl groups optionally substituted with one to three halogen atoms; hydroxyl groups; $C_{1-4}$ alkoxy groups optionally substituted with one or two halogen atoms; cyano groups; and amino groups, or $R^4$ and $R^6$, taken together with the benzene ring to which $R^4$ is bonded, form a tetrahydroisoquinolin-1-one ring wherein the ring is substituted with one or two $C_{1-4}$ alkyl groups.

Another aspect of the present invention resides in a pharmaceutical composition including the compound of formula (I) or the pharmacologically acceptable salt thereof as an active ingredient. The pharmaceutical composition is for use in the prevention or treatment of a disease and/or an accompanying symptom that can be improved by inhibiting salt-inducible kinases (SIK) or in the improvement of a prognosis of such a disease and/or an accompanying symptom.

Furthermore, another aspect of the present invention resides in a medicine including the compound of formula (I) or the pharmacologically acceptable salt thereof as an active ingredient. The medicine is for use in the prevention or treatment of a disease and/or an accompanying symptom that can be improved by inhibiting salt-inducible kinases (SIK) or in the improvement of a prognosis of such a disease and/or an accompanying symptom.

Furthermore, another aspect of the present invention resides in use of the compound of formula (I) or the pharmacologically acceptable salt thereof for the manufacture of a preventive agent or a therapeutic agent for a disease and/or an accompanying symptom that can be improved by inhibiting salt-inducible kinases (SIK).

Furthermore, another aspect of the present invention resides in a method for preventing or treating a disease and/or an accompanying symptom that can be improved by inhibiting salt-inducible kinases (SIK), the method including administering a therapeutically effective amount of the compound of formula (I) or the pharmacologically acceptable salt thereof to a patient.

Furthermore, another aspect of the present invention resides in the compound of formula (I) or the pharmacologically acceptable salt thereof for use in the prevention or treatment of a disease and/or an accompanying symptom that can be improved by inhibiting salt-inducible kinases (SIK) or in the improvement of a prognosis of such a disease and/or an accompanying symptom.

According to an aspect of the present invention, the novel compound that can effectively inhibit all of SIK1, SIK2, and SIK3, and the pharmaceutical composition including the compound are provided.

DESCRIPTION OF EMBODIMENTS

Definitions of Groups Used in the Description

Hereinbelow, the definitions of groups used in the present description will be described. The groups are as defined below unless otherwise specified. In the present description, the number of carbon atoms constituting a group is written as, for example, "1 to 6 carbon atoms" or "$C_{1-6}$", and the number of atoms constituting a ring is written as, for example, "3 to 6 ring-constituent atoms" or "3- to 6-membered".

When the compound has an acidic functional group and/or a basic functional group in the compound, the compound may form a salt. Examples of such salts include metal salts, ammonium salts, salts with organic bases, salts with inorganic acids, salts with organic acids, and salts with basic or acidic amino acids.

In the present description, examples of the "halogen atoms" include fluorine atom, chlorine atom, bromine atom, and iodine atom. In an embodiment, the halogen atom may be a fluorine atom.

In the present description, the "alkyl groups" (and the "alkyl" moieties in the definitions) are linear or branched alkyl groups having 1 to 6 carbon atoms, with examples including methyl, ethyl, propyl, isopropyl, butyl, isobutyl, sec-butyl, tert-butyl, pentyl, isopentyl, neopentyl, 1-ethyl-propyl, hexyl, isohexyl, 1,1-dimethylbutyl, 2,2-dimethylbutyl, and 3,3-dimethylbutyl. In the present description, "$C_{1-5}$ alkyl groups" are alkyl groups having 1 to 5 carbon atoms. In the present description, "$C_{1-4}$ alkyl groups" are alkyl groups having 1 to 4 carbon atoms.

When the alkyl groups have a substituent, the substituent may be present at any position where substitution is possible. When the alkyl groups have two or more substituents, the substituents may be the same as or different from one another. For example, $-CH_2CON(CH_3)_2$ corresponds to an alkyl group substituted with an oxo group and an amino group substituted with two methyl groups.

In the present description, the "alkylene groups" (and the "alkylene" moieties in the definitions) are linear or branched alkylene groups having 1 to 4 carbon atoms, with examples including $-CH_2-$, $-(CH_2)_2-$, $-(CH_2)_3-$, $-(CH_2)_4-$, $-CH(CH_3)-$, $-C(CH_3)_2-$, $-CH(C_2H_5)-$, $-CH(C_3H_7)-$, $-CH(CH(CH_3)_2)-$, $-(CH(CH_3))_2-$, $-CH_2-CH(CH_3)-$, and $-CH(CH_3)-CH_2-$.

In the present description, the "alkenylene groups" (and the "alkenylene" moieties in the definitions) are linear or branched alkenylene groups having 2 to 4 carbon atoms, with examples including $-CH=CH-$, $-CH_2-CH=CH-$, $-CH=CH-CH_2-$, $-CH_2-CH=CH-CH_2-$, $-CH_2-CH_2-CH=CH-$, $-CH=CH-CH_2-CH_2-$, and $-CH=CH-CH=CH-$.

In the present description, the "alkoxy groups" (and the "alkoxy" moieties in the definitions) are linear or branched alkoxy groups having 1 to 4 carbon atoms, with examples including methoxy, ethoxy, propoxy, isopropoxy, butoxy, isobutoxy, sec-butoxy, and tert-butoxy.

When the alkoxy groups have a substituent, the substituent may be present at any position where substitution is possible. When the alkoxy groups have two or more substituents, the substituents may be the same as or different from one another.

In the present description, the "cycloalkyl groups" (and the "cycloalkyl" moieties in the definitions) are monocyclic cycloalkyl groups having 3 or 4 carbon atoms, with examples including cyclopropyl and cyclobutyl. The cycloalkyl groups may have a valence bond at any position where substitution is possible.

When the cycloalkyl groups have a substituent, the substituent may be present at any position where substitution is possible. When the cycloalkyl groups have two or more substituents, the substituents may be the same as or different from one another.

In the present description, the "halocyclopropyl groups" are cyclopropyl groups substituted with 1 to 3 halogen atoms.

In the present description, the "monocyclic aliphatic heterocyclic groups" (and the "monocyclic aliphatic heterocyclic" moieties in the definitions) are saturated or partly unsaturated, 4- to 6-membered monocyclic aliphatic heterocyclic groups that contains one to three heteroatoms as ring-constituent atoms other than carbon independently selected from the group consisting of oxygen, nitrogen, and sulfur. Here, the phrase "partly unsaturated" means that the groups contain a double bond as part of the ring. Examples of the monocyclic aliphatic heterocyclic groups include azetidinyl (azetidine ring), oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisoxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, and thiomorpholinyl.

The monocyclic aliphatic heterocyclic groups may have a valence bond at any position where substitution is possible, and the valence bond may be present on a carbon atom or a nitrogen atom.

When the monocyclic aliphatic heterocyclic groups have a substituent, the substituent may be present at any position where substitution is possible and may be present on a carbon atom, a nitrogen atom, or a sulfur atom as the ring member. When the monocyclic aliphatic heterocyclic groups have two or more substituents, the substituents may be the same as or different from one another. For example, the structure illustrated below corresponds to a monocyclic aliphatic heterocyclic group substituted with two oxo groups:

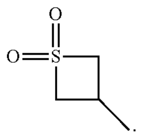

In the present description, the "monocyclic aromatic heterocyclic groups" (and the "monocyclic aromatic heterocyclic" moieties in the definitions) may be, for example, 5- or 6-membered monocyclic aromatic heterocyclic groups that contain one to four identical or different heteroatoms as ring-constituent atoms other than carbon selected from nitrogen atoms, oxygen atoms, and sulfur atoms.

Examples of the "monocyclic aromatic heterocyclic groups" include thienyl, furyl, pyrrolyl, imidazolyl, pyrazolyl, thiazolyl; isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, and triazinyl.

The monocyclic aromatic heterocyclic groups may have a valence bond at any position where substitution is possible, and the valence bond may be present on a carbon atom or a nitrogen atom.

When the monocyclic aromatic heterocyclic groups have a substituent, the substituent may be present at any position where substitution is possible and may be present on a carbon atom or a nitrogen atom as the ring member. When the monocyclic aromatic heterocyclic groups have two or more substituents, the substituents may be the same as or different from one another.

[Compounds Represented by Formula (I) or Pharmacologically Acceptable Salts Thereof]

A compound represented by formula (I) or a pharmacologically acceptable salt thereof according to an aspect of the present invention have embodiments described below.

Embodiment (1) resides in a compound represented by formula (I) below or a pharmacologically acceptable salt thereof:

(I)

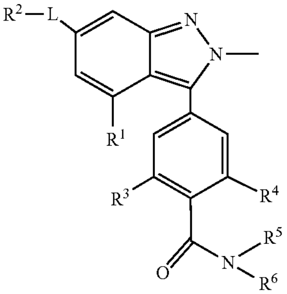

wherein $R^1$ is a cyano group, a $C_{1-4}$ alkyl group optionally substituted with one to three halogen atoms, or a $C_{1-4}$ alkoxy group optionally substituted with one to three substituents independently selected from $R^{1a}$, wherein $R^{1a}$ is a halogen atom; a 5- or 6-membered monocyclic aromatic heterocyclic group optionally substituted with one to three substituents independently selected from the group consisting of cyano groups, halogen atoms, and $C_{1-4}$ alkyl groups; a 4-membered monocyclic aliphatic heterocyclic group; a hydroxyl group; a $C_3$-4 cycloalkyl groups; and phenyl group, L is a single bond, a $C_{1-4}$ alkylene group, or a $C_{2-4}$ alkenylene group, $R^2$ is a 5-membered monocyclic aromatic heterocyclic group optionally substituted with $R^{2a}$, wherein $R^{2a}$ is a $C_{1-5}$ alkyl group optionally substituted with one to four substituents independently selected from $R^{2b}$, or a 5-membered monocyclic aliphatic heterocyclic group, wherein $R^{2b}$ is a hydroxyl group; a $C_{3-4}$ cycloalkyl group optionally substituted with a hydroxyl group; a halogen atom; a $C_{1-4}$ alkoxy group; a 4- to 6-membered monocyclic aliphatic heterocyclic group optionally substituted with one to three substituents independently selected from the group consisting of halogen atoms and oxo groups; an oxo group; an amino group optionally substituted with one or two $C_{1-4}$ alkyl groups; a phenyl group; a 5-membered monocyclic aromatic heterocyclic group; and a $C_{1-4}$ alkylsulfonyl group, $R^3$ is a hydrogen atom or a $C_{1-4}$ alkoxy group optionally substituted with one to three halogen atoms, $R^4$ is a $C_{1-4}$ alkoxy group optionally substituted with one to three halogen atoms, $R^5$ is a hydrogen atom, $R^6$ is a hydrogen atom; a $C_{1-4}$ alkyl group substituted with a halocyclopropyl group; or a cyclopropyl group substituted with one or two halogen atoms, or $R^5$ and $R^6$, taken together with the nitrogen atom to which they are bonded, form an azetidine ring wherein the azetidine ring is substituted with one or two substituents independently selected from the group consisting of $C_{1-4}$ alkyl groups optionally substituted with one to three halogen atoms; hydroxyl groups; $C_{1-4}$ alkoxy groups optionally substituted with one or two halogen atoms; cyano groups; and amino groups, or $R^4$ and $R^6$, taken together with the benzene ring to which $R^4$ is bonded, form a tetrahydroisoquinolin-1-one ring wherein the ring is substituted with one or two $C_{1-4}$ alkyl groups.

In Embodiment (1), the $C_{1-4}$ alkyl group optionally substituted with one to three halogen atoms, represented by $R^1$, is preferably $—CHF_2$, $—CH_2CH_2CH_2CH_3$, or, $—CH_2CH_2CH(CH_3)_2$.

In Embodiment (1), the $C_{1-4}$ alkoxy group optionally substituted with one to three substituents independently selected from $R^{1a}$, represented by $R^1$, is preferably $—OCH_3$, $—OCH_2CH_3$, $—OCHF_2$, $—OCH_2CHF_2$, $—OCH_2CF_3$, $—OCH(CH_3)_2$, $—OCH_2CH_2OH$, $—OCH_2CH_2CH_2OH$, $—OCH_2CH_2CH_2CH_2OH$, $—OCH_2CH_2CH(CH_3)OH$,

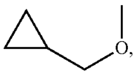, 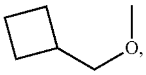, 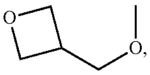, 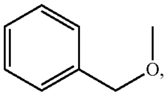, 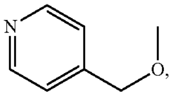, 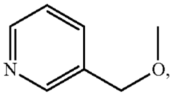, 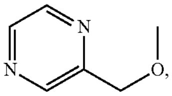, 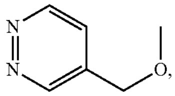, 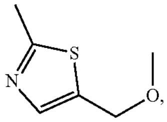, 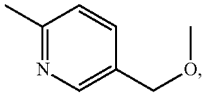, 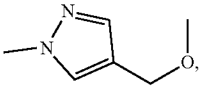, 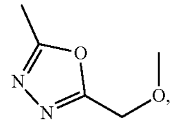, 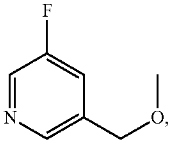, or 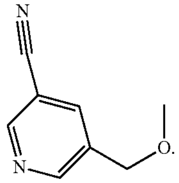.

In Embodiment (1), L is preferably a single bond or —CH═CH—.

In Embodiment (1), the 5-membered monocyclic aromatic heterocyclic group $R^2$ is preferably a pyrazolyl group, a triazolyl group, or an isothiazolyl group.

In Embodiment (1), when the 5-membered monocyclic aromatic heterocyclic group represented by $R^2$ is substituted with $R^{2a}$, $R^{2a}$ is preferably $—CH_3$, $—CHF_2$, $—CH_2CH_3$, $—CH_2CH_2CH_3$, $—CH_2CF_3$, $—CH_2CHF_2$, $—CH(CH_3)_2$, $—C(CH_3)_3$, $—CH_2CH(CH_3)_2$, $—CH_2CH(CH_3)OH$, $—CH_2C(CH_3)_2OH$, $—CH_2CH(OH)CF_3$, $—CH_2CH_2CH(CH_3)OH$, $—CH_2CH_2C(CH_3)_2OH$, $—CH_2CH(OH)CH_2CH_3$, $—CH_2CH_2OCH_3$, $—CH_2CH_2CH_2OCH_3$, $—CH_2CH_2OCH_2CH_3$, $—CH_2CON(CH_3)_2$, $—CH_2CH_2CON(CH_3)_2$, $—CH_2CH_2N(CH_3)_2$, $—CH_2CH_2SO_2CH_3$,

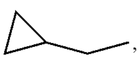, 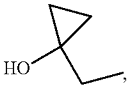, 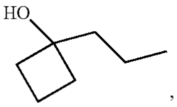, 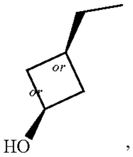, 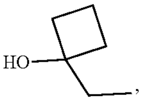, 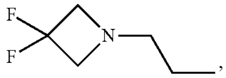, 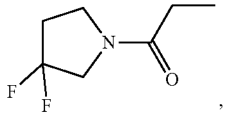, 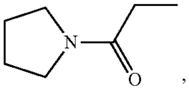, 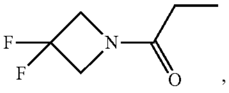, 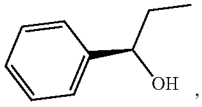, -continued

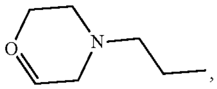, 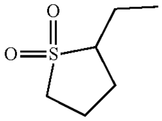, 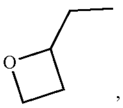,

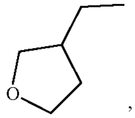, 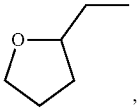, 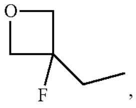, 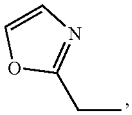,

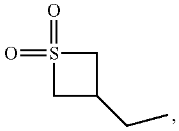, 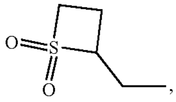, 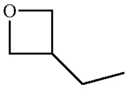,

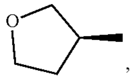, 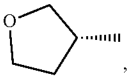, or 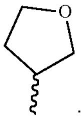.

In Embodiment (1), when the 5-membered monocyclic aromatic heterocyclic group represented by $R^2$ is substituted with $R^{2a}$, the substituent may be present at any position where substitution is possible, but is preferably present on the second ring-constituent atom as viewed from the ring-constituent carbon atom to which L is bonded, and is more preferably present at any of the following positions:

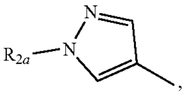, 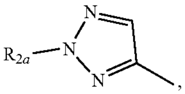,

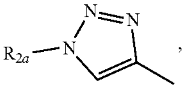, or 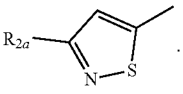.

In Embodiment (1), the $C_{1-4}$ alkoxy group optionally substituted with one to three halogen atoms, represented by $R^3$, is preferably —$OCH_3$ or —$OCHF_2$.

In Embodiment (1), the $C_{1-4}$ alkoxy group optionally substituted with one to three halogen atoms, represented by $R^4$, is preferably —$OCH_3$ or —$OCHF_2$.

In Embodiment (1), the $C_{1-4}$ alkyl group substituted with a halocyclopropyl group, represented by $R^6$, is preferably:

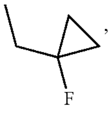, or 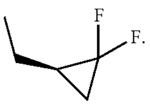.

In Embodiment (1), the cyclopropyl group substituted with one or two halogen atoms, represented by $R^6$, is preferably:

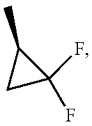, or 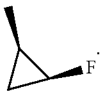.

In Embodiment (1), the substituted azetidine ring formed by $R^5$ and $R^6$ taken together with the nitrogen atom to which they are bonded is preferably substituted with one or two substituents independently selected from the group consisting of methyl group, —$CHF_2$, —$CF_3$, hydroxyl group, —$OCHF_2$, cyano group, and amino group, at the 3-position of the ring, and is more preferably:

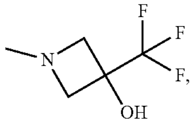 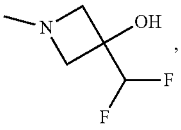,

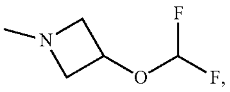 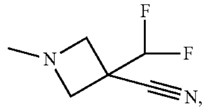

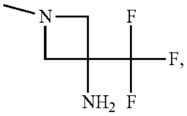 or 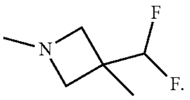

In Embodiment (1), the tetrahydroisoquinolin-1-one ring formed by $R^4$ and $R^6$ taken together with the benzene ring to which $R^4$ is bonded is preferably substituted with one or two methyl groups at the 4-position of the ring.

Embodiment (2) resides in the compound or the pharmacologically acceptable salt thereof as described in Embodiment (1), in which:

$R^1$ is a cyano group, a $C_{1-4}$ alkyl group optionally substituted with one to three halogen atoms, or a $C_{1-4}$ alkoxy group optionally substituted with one to three halogen atoms, L is a single bond, $R^2$ is a pyrazolyl group optionally substituted with a $C_{1-4}$ alkyl group optionally substituted with a substituent $R^{2b'}$, wherein the substituent $R^{2b'}$ is independently selected from the group consisting of a hydroxyl group, one to three halogen atoms, a $C_{1-4}$ alkoxy group, and a hydroxyl-substituted cyclobutyl group, $R^3$ is a $C_{1-4}$ alkoxy group optionally substituted with one to three halogen atoms, $R^4$ is a $C_{1-4}$ alkoxy group optionally substituted with one to three halogen atoms, $R^5$ is a hydrogen atom, $R^6$ is a hydrogen atom; a $C_{1-4}$ alkyl group substituted with a halocyclopropyl group; or a cyclopropyl group substituted with one or two halogen atoms, or $R^4$ and $R^6$, taken together with the benzene ring to which $R^4$ is bonded, form a tetrahydroisoquinolin-1-one ring wherein the ring is substituted with one or two $C_{1-4}$ alkyl groups at the 4-position of the ring.

Embodiment (3) resides in the compound or the pharmacologically acceptable salt thereof as described in Embodiment (2), in which:

$R^1$ is a cyano group, a $C_{1-2}$ alkyl group optionally substituted with one to three fluorine atoms, or a $C_{1-2}$ alkoxy group optionally substituted with one to three fluorine atoms, L is a single bond, $R^2$ is a pyrazolyl group optionally substituted with a $C_{1-3}$ alkyl group optionally substituted with a substituent $R^{2b''}$, wherein the substituent $R^{2b''}$ is independently selected from the group consisting of a hydroxyl group, one to three fluorine atoms, a methoxy group, and a hydroxyl-substituted cyclobutyl group, $R^3$ is a methoxy group optionally substituted with one to three fluorine atoms, $R^4$ is a methoxy group optionally substituted with one to three fluorine atoms, $R^5$ is a hydrogen atom, $R^6$ is a hydrogen atom; a fluorocyclopropyl-substituted methyl group; or a cyclopropyl group substituted with one or two fluorine atoms, or $R^4$ and $R^6$, taken together with the benzene ring to which $R^4$ is bonded, form a tetrahydroisoquinolin-1-one ring wherein the ring is substituted with one or two methyl groups at the 4-position of the ring.

Embodiment (4) resides in the compound or the pharmacologically acceptable salt thereof as described in any one of Embodiments (1) to (3), in which:

$R^1$ is a cyano group, $—CHF_2$, $—OCHF_2$, or $—OC_2H_5$.

Embodiment (5) resides in the compound or the pharmacologically acceptable salt thereof as described in any one of Embodiments (1) to (4), in which:

$R^2$-L- is:

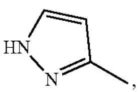,
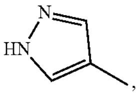, or
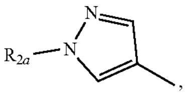, wherein $R^{2a}$ is $—CH_3$, $—CHF_2$, $—CH_2CH_3$, $—CH_2CF_3$, $—CH_2CH_2CH_3$, $—CH_2CH_2OCH_3$, $—CH_2CH(CH_3)OH$, or a 3-hydroxycyclobutylmethyl group.

Embodiment (6) resides in the compound or the pharmacologically acceptable salt thereof as described in any one of Embodiments (1) to (5), in which:

$R^3$ is $—OCH_3$ or $—OCHF_2$.

Embodiment (7) resides in the compound or the pharmacologically acceptable salt thereof described in any one of Embodiments (1) to (6) in which:

$R^4$ is $—OCH_3$ or $—OCHF_2$, $R^5$ is a hydrogen atom, $R^6$ is a hydrogen atom,

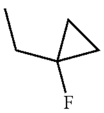, or
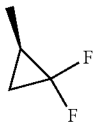, or $R^4$ and $R^6$, taken together with the benzene ring to which $R^4$ is bonded, form a tetrahydroisoquinolin-1-one ring wherein the ring is substituted with one $—CH_3$ at the 4-position of the ring.

Embodiment (8) resides in the compound or the pharmacologically acceptable salt thereof as described in Embodiment (3), in which:

$R^1$ is a cyano group, $—CHF_2$, $—OCHF_2$, or $—OC_2H_5$, $R^2$-L- is:

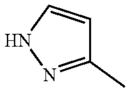,
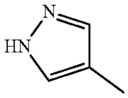, or
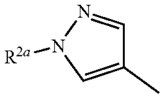, wherein $R^{2a}$ is $—CH_3$, $—CHF_2$, $—CH_2CH_3$, $—CH_2CF_3$, $—CH_2CH_2CH_3$, $—CH_2CH_2OCH_3$, $—CH_2CH(CH_3)OH$, or a 3-hydroxycyclobutylmethyl group, $R^3$ is $—OCH_3$ or $—OCHF_2$, $R^4$ is $—OCH_3$ or $—OCHF_2$, $R^5$ is a hydrogen atom, $R^6$ is a hydrogen atom,

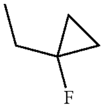, or
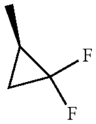, or $R^4$ and $R^6$, taken together with the benzene ring to which $R^4$ is bonded, form a tetrahydroisoquinolin-1-one ring wherein the ring is substituted with one $—CH_3$ at the 4-position of the ring.

Embodiment (9) resides in a compound selected from the group consisting of compounds illustrated below, or a pharmacologically acceptable salt thereof:

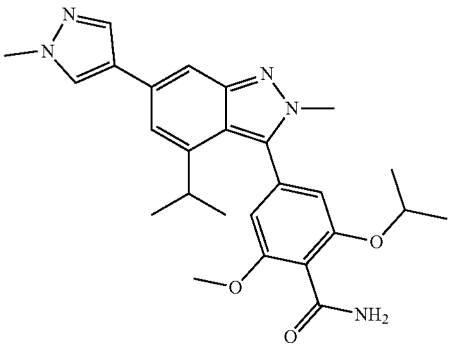,

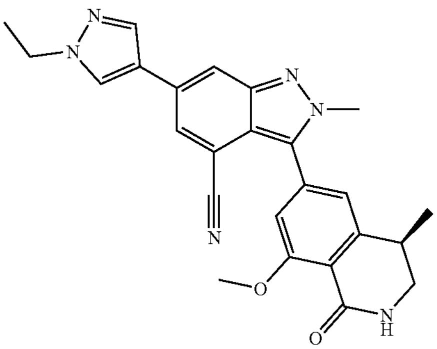

or an enantiomer thereof,
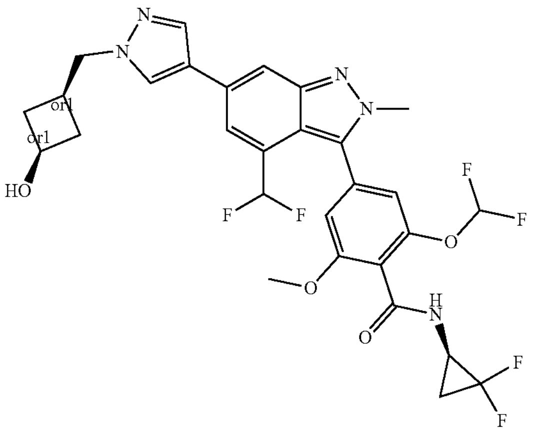 [SMILES: COc1cc(-c2c3c(C(F)F)cc(-c4cnn(C[C@H]5C[C@@H](O)C5)c4)cc3nn2C)cc(OC(F)F)c1C(=O)N[C@@H]1CC1(F)F]
and a mixture of stereoisomers thereof,
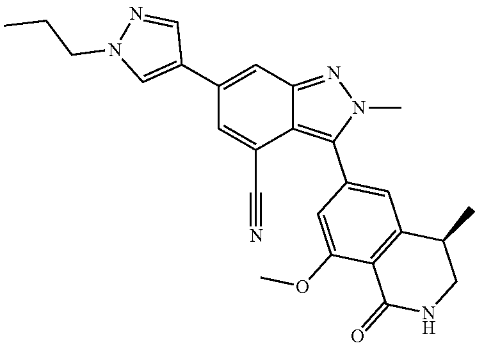 [SMILES: CCCn1cc(-c2cc(C#N)c3c(-c4cc(OC)c5c(c4)[C@@H](C)CNC5=O)n(C)nc3c2)cn1]
or an enantiomer thereof,
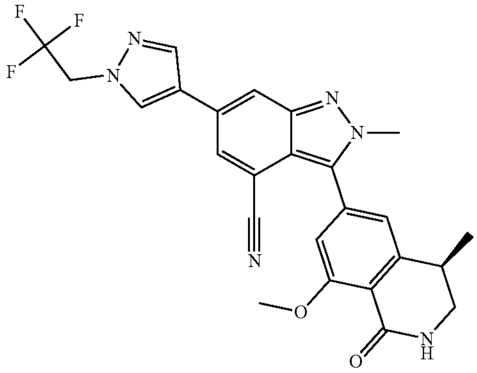 [SMILES: COc1cc(-c2c3c(C#N)cc(-c4cnn(CC(F)(F)F)c4)cc3nn2C)cc2c1C(=O)NC[C@@H]2C]
or an enantiomer thereof,
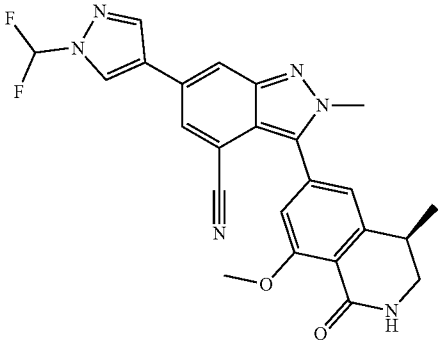 [SMILES: COc1cc(-c2c3c(C#N)cc(-c4cnn(C(F)F)c4)cc3nn2C)cc2c1C(=O)NC[C@@H]2C]
or an enantiomer thereof,
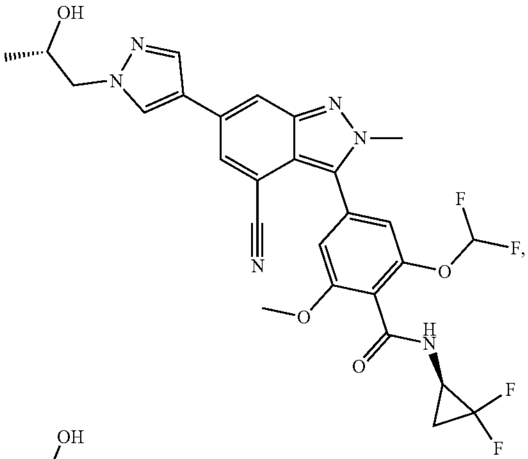
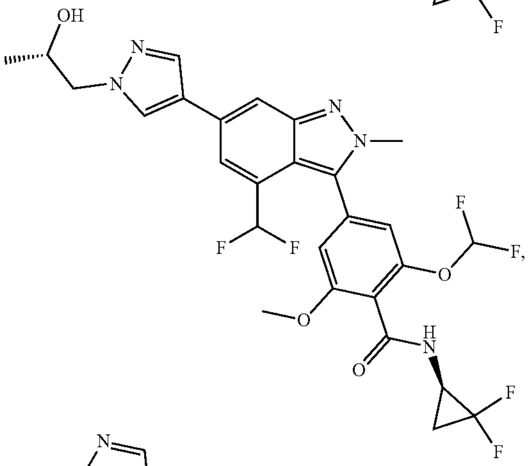
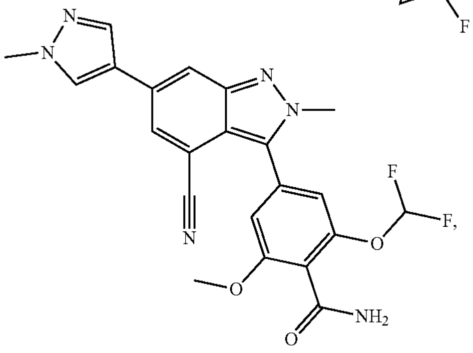

-continued
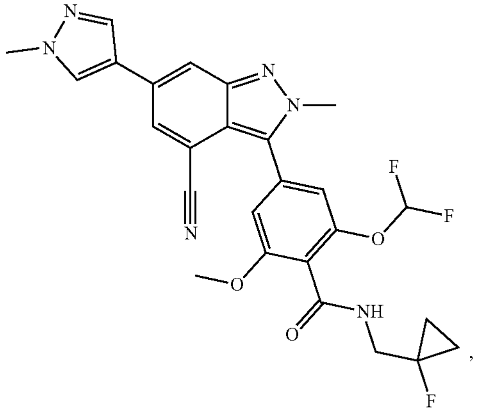
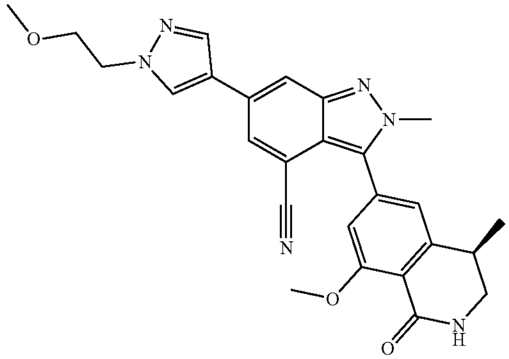
or an enantiomer thereof,
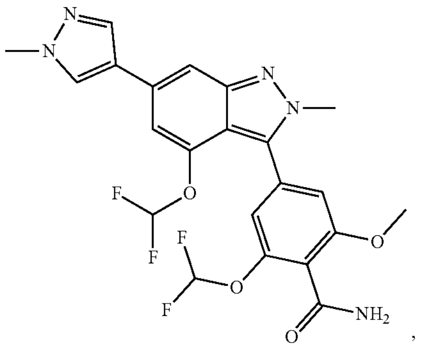
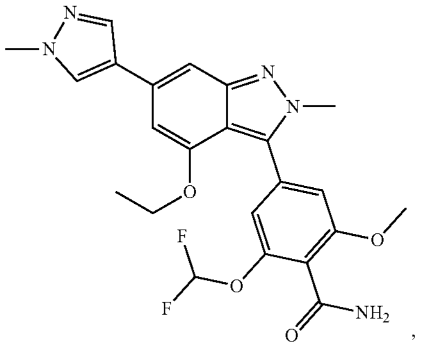
-continued
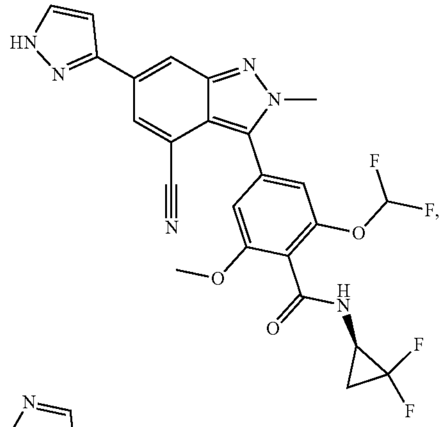
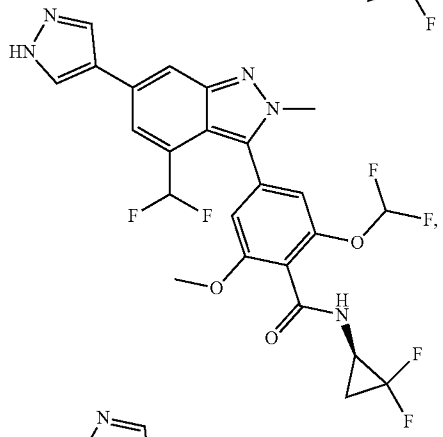
and
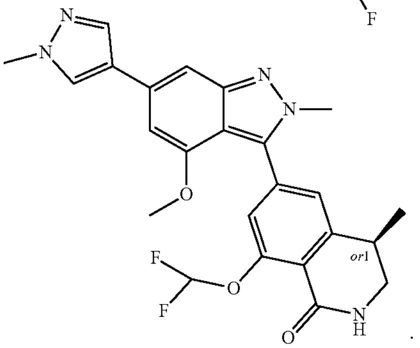
These compounds specified above are included in the compounds of formula (I) above.
Embodiment (9-2) resides in a compound selected from the group consisting of compounds illustrated below, or a pharmacologically acceptable salt thereof:
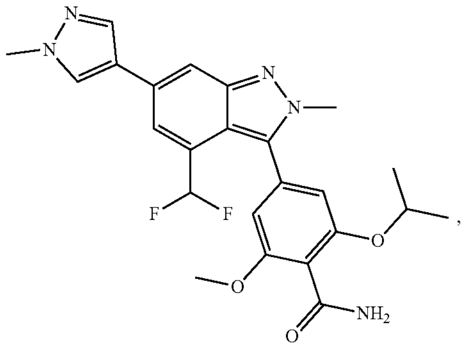

-continued

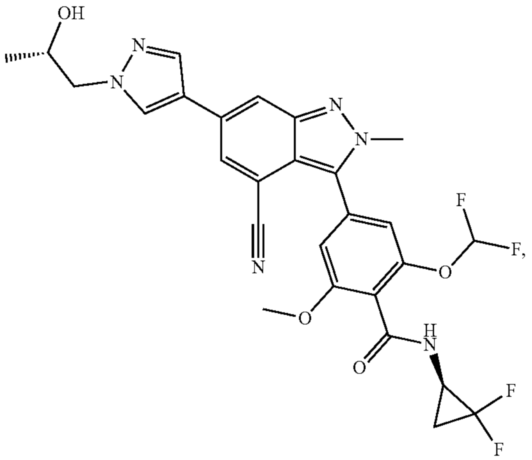

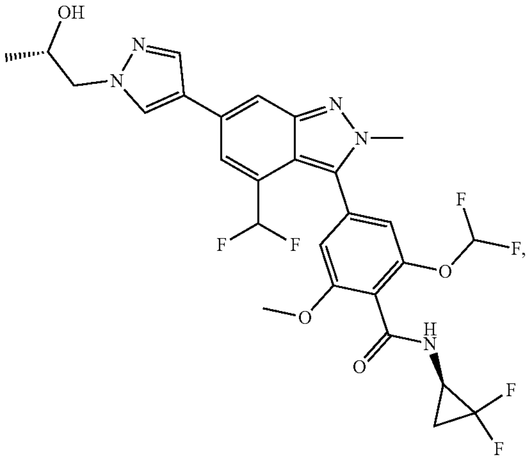

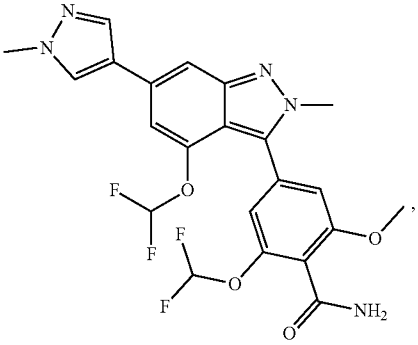

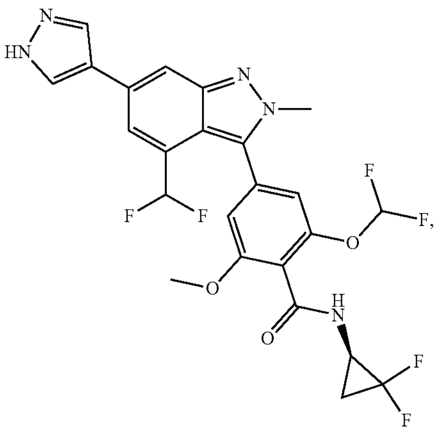

and

-continued

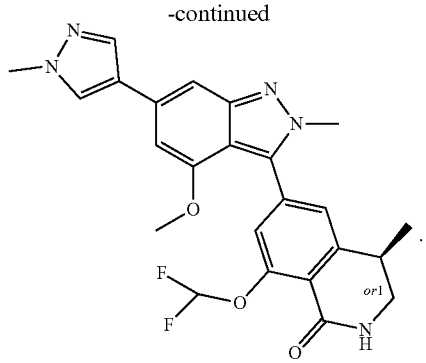

These compounds specified above are included in the compounds of formula (I) above.

When the compounds of formula (I) have optical isomeric forms (enantiomers and diastereomers), stereoisomeric forms, regioisomeric forms, and rotameric forms, these isomers are also included in the compounds of formula (I). The isomers may be obtained as an individual isomer by a known synthesis technique or a known separation technique (such as, for example, concentration, solvent extraction, column chromatography, or recrystallization).

The compounds of formula (I) may be appropriately converted to prodrugs. Such prodrugs form an aspect of the present invention. The prodrugs may be those described in “Iyakuhin No Kaihatsu (Development of Pharmaceuticals)”, Vol. 7, Bunshi Sekkei (Molecular Design), Hirokawa-Shoten Ltd., 1990, pp. 163-198, that transform into the compounds of formula (I) under physiological conditions.

The compounds of formula (I) may be any of hydrates, nonhydrates, solvates, and nonsolvates. Furthermore, the compounds of formula (I) may be compounds labeled or substituted with, for example, an isotope (such as, for example, $^{2}H$, $^{3}H$, $^{11}C$, $^{14}C$, $^{18}F$, $^{35}S$, $^{125}I$). For example, the isotopically labeled or substituted compounds may be used as tracers (PET tracers) in positron emission tomography (PET) and may be useful in such fields as medical diagnoses. Deuterated (1H to 2H (D)) compounds are also included in the compounds of formula (I).

Tautomers are also included in the compounds of formula (I).

Compound Production Methods

General Synthesis Approaches

For example, the compounds of formula (I) or intermediate compounds thereof may be produced by the following methods A to K. These methods and the steps may be combined with one another. For example, the methods and the steps may be combined with one another in such a manner that the first step and the second step in Synthesis Method D are followed by the first to the fourth steps in Synthesis Method A.

The compound production methods are not limited to those described herein.

In Synthesis Methods A to K, PG1 denotes a carboxylic acid protective group, and PG2 denotes an amide protective group. Ra and Rb each independently denote a hydrogen atom or an alkyl or are bonded to each other to form an alkylene group. X denotes a halogen atom. LG denotes a leaving group. $R^{1'}$ denotes an optionally substituted $C_{1-4}$ alkyl group. $R^2$ may encompass $R^2$-L. The rest of the symbols are the same as defined hereinabove.

The respective compounds as raw materials used in Synthesis Methods A to K may be produced by the methods described later in Reference Examples or methods similar thereto. Alternatively, the raw material compounds may be those commercially available.

Synthesis Method A

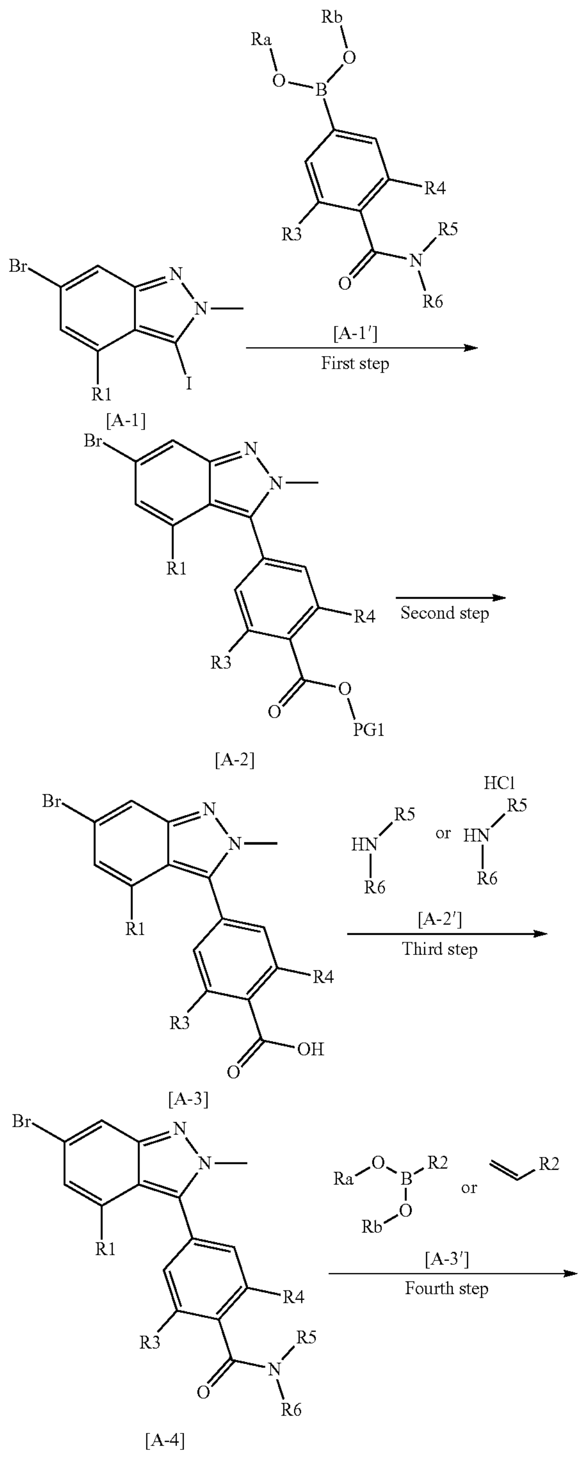

-continued

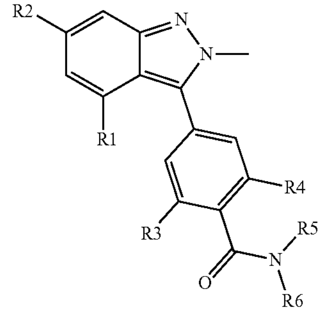

[A-5]

[In the formulas, the symbols are the same as defined hereinabove. With the proviso that, in general formulas [A-2'], [A-3'], [A-4], and [A-5], a group corresponding to $R^2$ and/or a group corresponding to $R^5$ may contain a protective group for a functional group, such as a carboxylic acid, an amine, or a hydroxyl.]

The compound of general formula [A-2] is obtained by the coupling reaction of the compound of general formula [A-1] and the compound of general formula [A-1']. The reaction may be performed in an appropriate solvent in the presence of a palladium catalyst and a base. A ligand may or may not be used. The reaction time varies depending on the raw materials and the solvent used, and the reaction temperature, but is usually 30 minutes to 24 hours. Examples of the palladium catalysts include tetrakis(triphenylphosphine) palladium (0), palladium (II) acetate, palladium (II) chloride, tris(benzylideneacetone)dipalladium (0), 1,1-bis(diphenylphosphino)ferrocene-palladium (II) dichloride, and 1,1-bis(di-tert-butylphosphino)ferrocene-palladium (II) dichloride. Examples of the bases include tripotassium phosphate, potassium carbonate, potassium fluoride, cesium fluoride, triethylamine, and N,N-diisopropylethylamine. Examples of the ligands include triphenylphosphine, tri(O-tolyl)phosphine, 2-(dicyclohexylphosphino)-2',4',6'-triisopropyl-1,1'-biphenyl (XPhos), 2-(dicyclohexylphosphino)-3,6-dimethoxy-2',4',6'-triisopropyl-1,1'-biphenyl (BrettPhos), 2-(dicyclohexylphosphino)-2,6-diisopropoxy-1,1'-biphenyl (RuPhos), 2-di-tert-butylphosphino-2',4',6'-triisopropyl-1,1'-biphenyl (tBuXPhos), 2-(dicyclohexylphosphino)-2',6'-dimethoxybiphenyl (SPhos), 2-(dicyclohexylphosphino)-2'-(N,N-dimethylamino)biphenyl (DavePhos), tri-ortho-tolylphosphine, 2-(dicyclohexylphosphino)biphenyl, 2-(di-tert-butylphosphino)biphenyl, 2-(di-tert-butylphosphino)-1,1-binaphthyl, tri-tert-butylphosphine, and tri-tert-butylphosphonium tetrafluoroborate. The palladium catalyst and the ligand may form a complex as a reagent. Any solvent that does not affect the reaction may be used, with examples including ethers, such as tetrahydrofuran, 1,4-dioxane, and 1,2-dimethoxyethane; aromatic hydrocarbons, such as toluene and xylene; amides, such as N,N-dimethylformamide and N-methyl-2-pyrrolidone; and mixed solvents of the above organic solvents and water. The reaction favorably proceeds at room temperature to 150 °C, especially at 40 °C to 120 °C.

For example, the compound of general formula [A-3] is obtained by either of the following two methods.

Method 1: The compound of general formula [A-3] is obtained by deprotecting the compound of general formula [A-2] with an acid. The reaction may be performed in an appropriate solvent using an appropriate acid. The reaction time varies depending on the raw materials and the solvent used, and the reaction temperature, but is usually 30 minutes to 24 hours. Examples of the acids include hydrochloric acid and trifluoroacetic acid. Any solvent that does not affect the reaction may be used, with examples including alcohols, such as methanol and ethanol; ethers, such as tetrahydrofuran and 1,4-dioxane; esters, such as ethyl acetate; and chlorinated hydrocarbons, such as dichloromethane and chloroform. The reaction favorably proceeds at 0 °C to 60 °C, especially at room temperature.

Method 2: The compound of general formula [A-3] is obtained by hydrolyzing the compound of general formula [A-2]. The reaction may be performed in an appropriate solvent in the presence of an appropriate base. The reaction time varies depending on the raw materials and the solvent used, and the reaction temperature, but is usually 30 minutes to 24 hours. Examples of the bases include alkali metal hydroxides, such as lithium hydroxide, sodium hydroxide, and potassium hydroxide. Any solvent that does not affect the reaction may be used, with examples including alcohols, such as methanol and ethanol; ethers, such as tetrahydrofuran and 1,4-dioxane; water; and mixtures of the above solvents. The reaction favorably proceeds at 0 °C to 100 °C, especially at room temperature to 60 °C.

For example, the compound of general formula [A-4] is obtained by any of the following three methods.

Method 1: The compound of general formula [A-4] is obtained by the condensation reaction of the compound of general formula [A-3] with the compound of general formula [A-2']. The reaction may be performed in an appropriate solvent in the presence of an appropriate base using a condensing agent. The reaction time varies depending on the raw materials and the solvent used, and the reaction temperature, but is usually 30 minutes to 24 hours. Examples of the condensing agents include 1-ethyl-3-(3-dimethylaminopropyl)carbodiimide hydrochloride (WSC·HCl), 1-[bis(dimethylamino)methylene]-1H-1,2,3-triazolo[4,5-b]pyridinium 3-oxidohexafluorophosphate (HATU), 4-(4,6-dimethoxy[1,3,5]triazin-2-yl)-4-methylmorpholinium chloride hydrate (DMT-MM), and 2-chloro-1-methylpyridinium iodide. The reaction is sometimes promoted by the addition of 1-hydroxybenzotriazole (HOBt). Examples of the bases include triethylamine, N,N-diisopropylethylamine, and pyridine. Any solvent that does not affect the reaction may be used, with examples including ethers, such as tetrahydrofuran and 1,4-dioxane; amides, such as N,N-dimethylformamide and N-methyl-2-pyrrolidone; and chlorinated hydrocarbons, such as chloroform and dichloromethane. The reaction favorably proceeds at 0 °C to 100 °C, especially at room temperature to 60 °C.

Method 2: The compound of general formula [A-4] is obtained by converting the compound of general formula [A-3] into an acid halide with a halogenating agent and reacting the acid halide with the compound of general formula [A-2']. The reaction may be performed in an appropriate solvent in the presence of an appropriate base using a halogenating agent. The reaction time varies depending on the raw materials and the solvent used, and the reaction temperature, but is usually 30 minutes to 24 hours. Examples of the halogenating agents include thionyl chloride, oxalyl chloride, and phenylphosphonyl dichloride. Any solvent that does not affect the reaction may be used, with examples including ethers, such as tetrahydrofuran and 1,4-dioxane; chlorinated hydrocarbons, such as dichloromethane, 1,2-dichloroethane, and chloroform; and amines, such as pyridine. The reaction favorably proceeds at 0 °C to 100 °C, especially at room temperature to 60 °C.

Method 3: The compound of general formula [A-4] is obtained by converting the compound of general formula [A-3] into a mixed acid anhydride and reacting the mixed acid anhydride with the compound of general formula [A-2']. The reaction may be performed in an appropriate solvent in the presence of a base using a mixed acid anhydride-forming reagent. The reaction time varies depending on the raw materials and the solvent used, and the reaction temperature, but is usually 30 minutes to 24 hours. Examples of the mixed acid anhydride-forming reagents include methyl chlorocarbonate, ethyl chlorocarbonate, isopropylthiocarbonyl chloride, and pivaloyl chloride. Examples of the bases include triethylamine, N,N-diisopropylethylamine, pyridine, and N-methylmorpholine. Any solvent that does not affect the reaction may be used, with examples including tetrahydrofuran, chloroform, N,N-dimethylformamide, and N-methyl-2-pyrrolidone. The reaction favorably proceeds at −20 °C to 100 °C, especially at 0 °C to room temperature.

The compound of general formula [A-5] is obtained by the coupling reaction of the compound of general formula [A-4] with the compound of general formula [A-3']. The reaction temperature and time, and the reagents and the solvent that are used are the same as those described in the first step.

In Synthesis Method A, the compound of general formula [A-2'] and/or the compound of general formula [A-3'] may be a compound in which the group corresponding to $R^2$ and/or the group corresponding to $R^5$ contains a protective group for a functional group, such as a carboxylic acid, an amine, or a hydroxyl. In this case, the compound of general formula [A-5] (in which the group corresponding to $R^2$ and/or the group corresponding to $R^5$ contains a protective group for a functional group, such as a carboxylic acid, an amine, or a hydroxyl) may be deprotected by removing the protective group. The deprotection may be performed by a common method, such as reduction, hydrolysis, or acid treatment, in accordance with the type of the protective group that will be removed.

When $R^2$ in the target compound of general formula [A-5] is a group containing an amide bond (—CONR'R"), such a target compound may be obtained by deprotecting a compound of general formula [A-5] in which the group corresponding to $R^2$ is a group containing an ester bond (—COOPG1), and amidating the group.

Synthesis Method A'

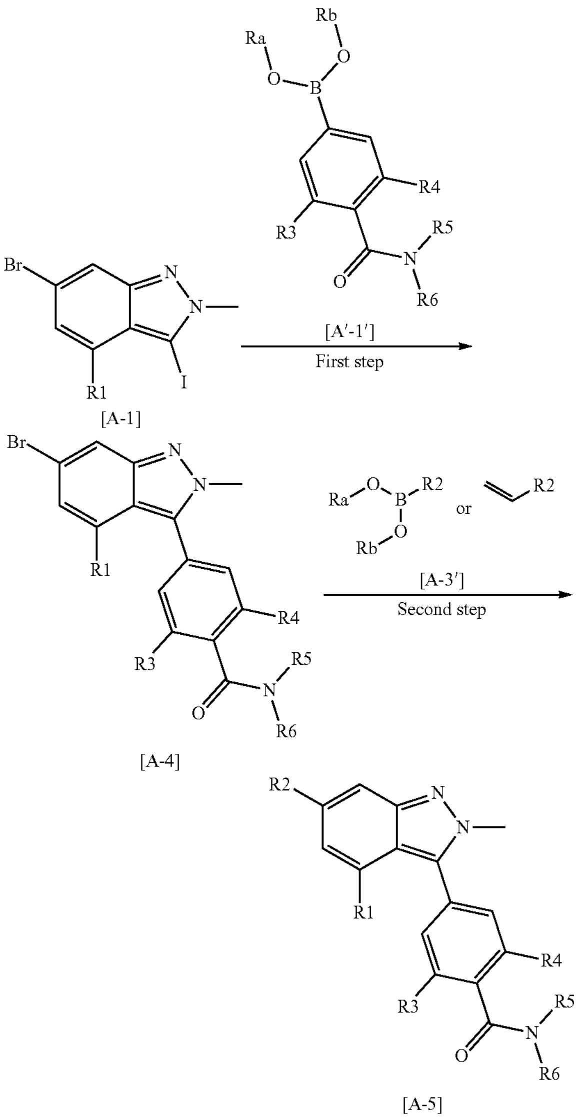

[A-1] [A-4] [A-5]

[In the formulas, the symbols are the same as defined hereinabove. With the proviso that, in general formulas [A'-1'], [A-3'], [A-4], and [A-5], a group corresponding to $R^2$ and/or a group corresponding to $R^5$ may contain a protective group for a functional group, such as a carboxylic acid, an amine, or a hydroxyl.]

The compound of general formula [A-4] is obtained by the coupling reaction of the compound of general formula [A-1] with the compound of general formula [A'-1']. The reaction temperature and time, and the reagents and the solvent that are used are the same as those described in the first step of Synthesis Method A.

The compound of general formula [A-5] is obtained by the coupling reaction of the compound of general formula [A-4] with the compound of general formula [A-3']. The reaction temperature and time, and the reagents and the solvent that are used are the same as those described in the first step of Synthesis Method A.

In Synthesis Method A', the compound of general formula [A'-1'] and/or the compound of general formula [A-3'] may be a compound in which the group corresponding to $R^2$ and/or the group corresponding to $R^5$ contains a protective group for a functional group, such as a carboxylic acid, an amine, or a hydroxyl. In this case, the compound of general formula [A-5] (in which the group corresponding to $R^2$ and/or the group corresponding to $R^5$ contains a protective group for a functional group, such as a carboxylic acid, an amine, or a hydroxyl) may be deprotected by removing the protective group. The deprotection may be performed by a common method, such as reduction, hydrolysis, or acid treatment, in accordance with the type of the protective group that will be removed.

Synthesis Method B

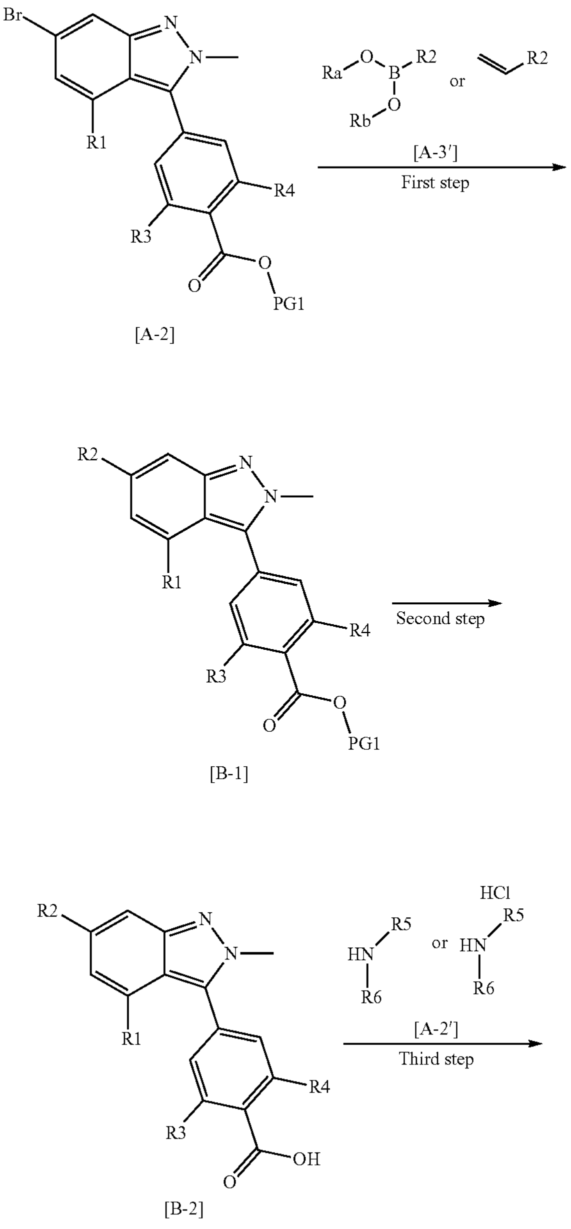

[A-2] [B-1] [B-2]

-continued

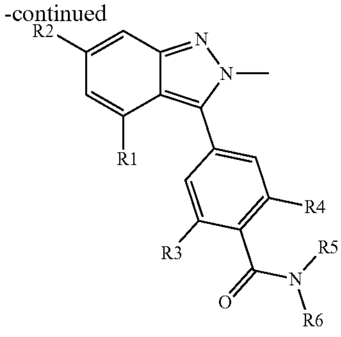

[A-5]

[In the formulas, the symbols are the same as defined hereinabove. With the proviso that, in general formula [A-2'], [A-3'], [B-1], [B-2], and [A-5], a group corresponding to $R^2$ and/or a group corresponding to $R^5$ may contain a protective group for a functional group, such as a carboxylic acid, an amine, or a hydroxyl.]

The compound of general formula [B-1] is obtained by the coupling reaction of the compound of general formula [A-2] obtained by Synthesis Method A with the compound of general formula [A-3']. The reaction temperature and time, and the reagents and the solvent that are used are the same as those described in the first step of Synthesis Method A.

The compound of general formula [B-2] is obtained by deprotecting the carboxylic acid in the compound of general formula [B-1]. The reaction temperature and time, and the reagents and the solvent that are used are the same as those described in the second step of Synthesis Method A.

The compound of general formula [A-5] is obtained by the amidation reaction of the compound of general formula [B-2] with the compound of general formula [A-2']. The reaction temperature and time, and the reagents and the solvent that are used are the same as those described in the third step of Synthesis Method A.

In Synthesis Method B, the compound of general formula [A-2'] and/or the compound of general formula [A-3'] may be a compound in which the group corresponding to $R^2$ and/or the group corresponding to $R^5$ contains a protective group for a functional group, such as a carboxylic acid, an amine, or a hydroxyl. In this case, the compound of general formula [A-5] (in which the group corresponding to $R^2$ and/or the group corresponding to $R^5$ contains a protective group for a functional group, such as a carboxylic acid, an amine, or a hydroxyl) may be deprotected by removing the protective group. The deprotection may be performed by a common method, such as reduction, hydrolysis, or acid treatment, in accordance with the type of the protective group that will be removed.

Synthesis Method C

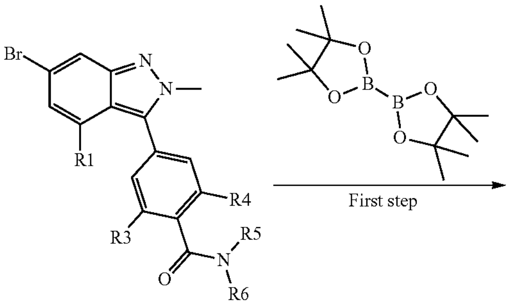

[A-4]

-continued

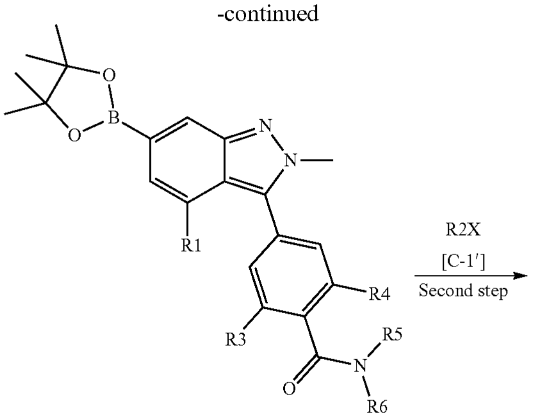

[C-1]

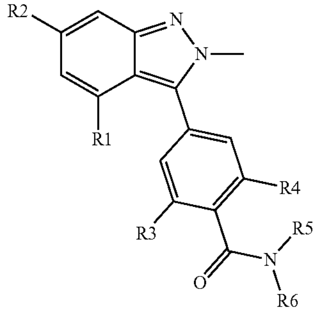

[A-5]

[In the formulas, the symbols are the same as defined hereinabove. With the proviso that, in general formulas [C-1'], [C-1], [A-4], and [A-5], a group corresponding to $R^2$ and/or a group corresponding to $R^5$ may contain a protective group for a functional group, such as a carboxylic acid, an amine, or a hydroxyl.]

The compound of general formula [C-1] is obtained by the coupling reaction of the compound of general formula [A-4] with bis(pinacolato)diboron. The reaction may be performed in an appropriate solvent in the presence of a base using a palladium catalyst. The reaction time varies depending on the raw materials and the solvent used, and the reaction temperature, but is usually 30 minutes to 24 hours. Examples of the palladium catalysts include tetrakis(triphenylphosphine)palladium (0), palladium (II) acetate, palladium (II) chloride, tris(benzylideneacetone)dipalladium (0), 1,1-bis(diphenylphosphino)ferrocene-palladium (II) dichloride, and 1,1-bis(di-tert-butylphosphino)ferrocene-palladium (II) dichloride. Examples of the bases include tripotassium phosphate, potassium carbonate, potassium fluoride, cesium fluoride, and potassium acetate. Any solvent that does not affect the reaction may be used, with examples including ethers, such as 1,4-dioxane and 1,2-dimethoxyethane; aromatic hydrocarbons, such as toluene and xylene; and amides, such as N,N-dimethylformamide and N-methyl-2-pyrrolidone. The reaction favorably proceeds at room temperature to 150 °C, especially at 60 °C to 100 °C.

The compound of general formula [A-5] is obtained by the coupling reaction of the compound of general formula [C-1] with the compound of general formula [C-1']. The reaction temperature and time, and the reagents and the solvent that are used are the same as those described in the first step of Synthesis Method A.

In Synthesis Method C, the compound of general formula [C-1'] and/or the compound of general formula [A-4] may be a compound in which the group corresponding to $R^2$ and/or the group corresponding to $R^5$ contains a protective group for a functional group, such as a carboxylic acid, an amine, or a hydroxyl. In this case, the compound of general formula [A-5] (in which the group corresponding to $R^2$ and/or the group corresponding to $R^5$ contains a protective group for a functional group, such as a carboxylic acid, an amine, or a hydroxyl) may be deprotected by removing the protective group. The deprotection may be performed by a common method, such as reduction, hydrolysis, or acid treatment, in accordance with the type of the protective group that will be removed.

Synthesis Method D

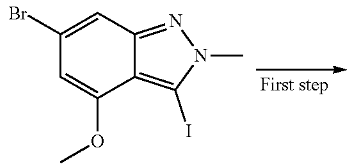

[D-1]

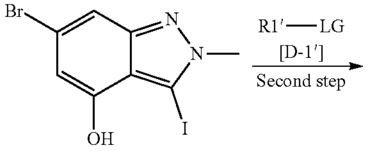

[D-2]

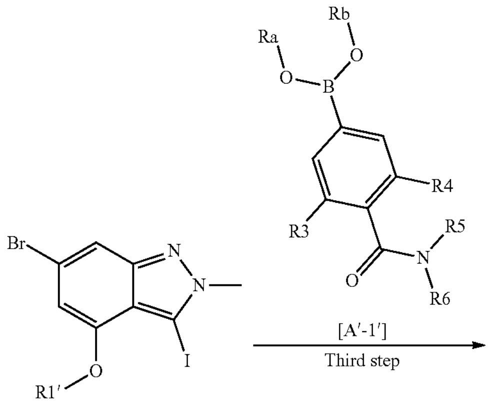

[D-3]

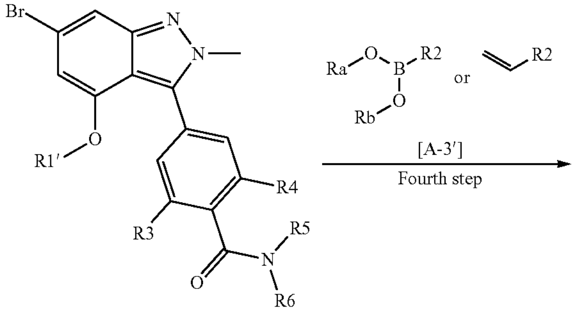

[D-4]

-continued

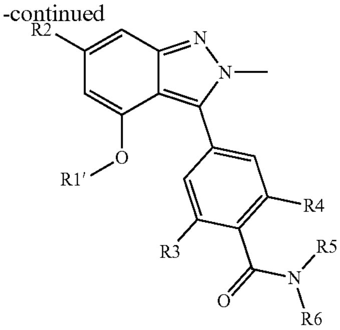

[D-5]

[In the formulas, the symbols are the same as defined hereinabove. With the proviso that, in general formulas [A'-1'], [A-3'], [D-1'], [D-3], [D-4], and [D-5], a group corresponding to $R^{1'}$, and/or a group corresponding to $R^2$, and/or a group corresponding to $R^5$ may contain a protective group for a functional group, such as a carboxylic acid, an amine, or a hydroxyl.]

The compound of general formula [D-2] is obtained by the O-demethylation reaction of the compound of general formula [D-1]. The reaction may be performed in an appropriate solvent using, for example, boron tribromide or aluminum chloride.

The reaction time varies depending on the raw materials and the solvent used, and the reaction temperature, but is usually 30 minutes to 24 hours. Any solvent that does not affect the reaction may be used, with examples including ethers, such as tetrahydrofuran, 1,4-dioxane, and 1,2-dimethoxyethane; aromatic hydrocarbons, such as toluene and xylene; acetonitrile; and chlorinated hydrocarbons, such as dichloromethane, chloroform, and 1,2-dichloroethane. The reaction favorably proceeds at −80 °C to 50 °C, especially at −20 °C to room temperature. The compound of general formula [D-3] is obtained by the O-alkylation reaction of the compound of general formula [D-2] using the compound of general formula [D-1'] (when $R^{1'}$=$CHF_2$, $CF_2BrPO(OEt)_2$ is used). The reaction may be performed in an appropriate solvent in the presence of a base. The reaction time varies depending on the raw materials and the solvent used, and the reaction temperature, but is usually 30 minutes to 24 hours. Examples of the bases include inorganic bases, such as potassium carbonate, cesium carbonate, sodium hydroxide, and potassium hydroxide, and alkoxides, such as potassium tert-butoxide and sodium tert-butoxide. Any solvent that does not affect the reaction may be used, with examples including ethers, such as 1,4-dioxane and 1,2-dimethoxyethane; aromatic hydrocarbons, such as toluene and xylene; acetonitrile; amides, such as N,N-dimethylformamide and N-methyl-2-pyrrolidone; and mixed solvents of the above organic solvents and water. The reaction favorably proceeds at −20 °C to 150 °C, especially at 60 °C to 100 °C.

The compound of general formula [D-4] is obtained by the coupling reaction of the compound of general formula [D-3] with the compound of general formula [A'-1']. The reaction temperature and time, and the reagents and the solvent that are used are the same as those described in the first step of Synthesis Method A.

The compound of general formula [D-5] is obtained by the coupling reaction of the compound of general formula [D-4] with the compound of general formula [A-3']. The reaction temperature and time, and the reagents and the solvent that are used are the same as those described in the first step of Synthesis Method A.

In Synthesis Method D, the compound of general formula [A'-1'], and/or the compound of general formula [A-3'], and/or the compound of general formula [D-1'] may be a compound in which the group corresponding to $R^{1'}$, and/or the group corresponding to $R^2$, and/or the group corresponding to $R^5$ contains a protective group for a functional group, such as a carboxylic acid, an amine, or a hydroxyl. In this case, the compound of general formula [D-5] (in which the group corresponding to $R^{1'}$, and/or the group corresponding to $R^2$, and/or the group corresponding to $R^5$ contains a protective group for a functional group, such as a carboxylic acid, an amine, or a hydroxyl) may be deprotected by removing the protective group. The deprotection may be performed by a common method, such as reduction, hydrolysis, or acid treatment, in accordance with the type of the protective group that will be removed.

Synthesis Method E

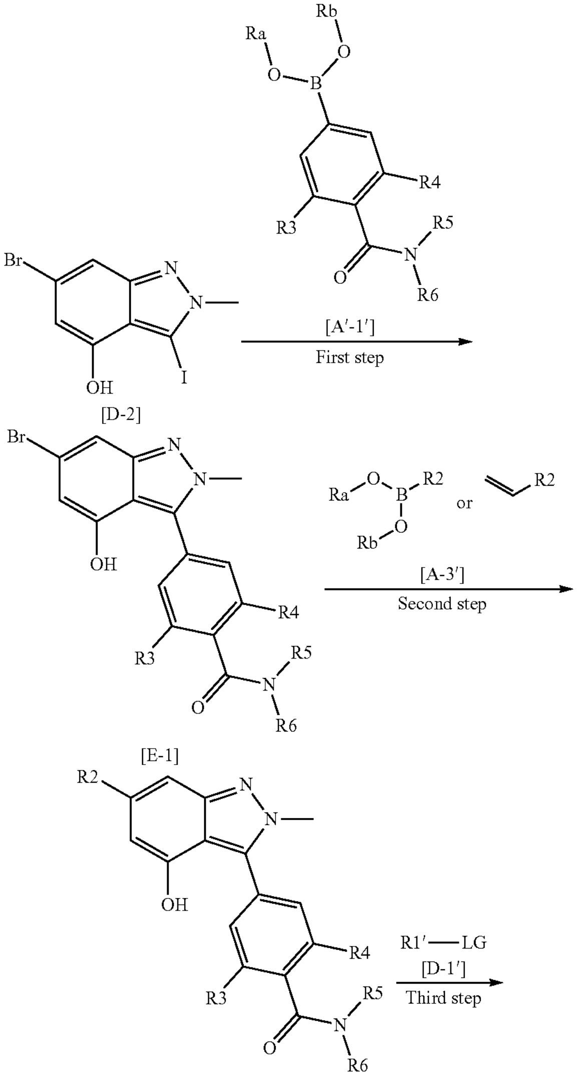

[D-2] [E-1] [E-2]

-continued

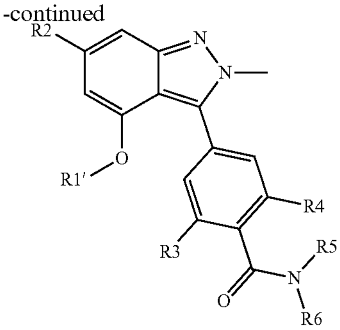

[D-5]

[In the formulas, the symbols are the same as defined hereinabove. With the proviso that, in general formulas [A'-1'], [A-3'], [D-1'], [D-5], [E-1], and [E-2], a group corresponding to $R^{1'}$, and/or a group corresponding to $R^2$, and/or a group corresponding to $R^5$ may contain a protective group for a functional group, such as a carboxylic acid, an amine, or a hydroxyl.]

The compound of general formula [E-1] is obtained by the coupling reaction of the compound of general formula [D-2] with the compound of general formula [A'-1']. The reaction temperature and time, and the reagents and the solvent that are used are the same as those described in the first step of Synthesis Method A.

The compound of general formula [E-2] is obtained by the coupling reaction of the compound of general formula [E-1] with the compound of general formula [A-3']. The reaction temperature and time, and the reagents and the solvent that are used are the same as those described in the first step of Synthesis Method A.

The compound of general formula [D-5] is obtained by the O-alkylation reaction of the compound of general formula [E-2] using the compound of general formula [D-1']. The reaction temperature and time, and the reagents and the solvent that are used are the same as those described in the second step of Synthesis Method D.

In Synthesis Method E, the compound of general formula [A'-1'], and/or the compound of general formula [A-3'], and/or the compound of general formula [D-1'] may be a compound in which the group corresponding to $R^{1'}$, and/or the group corresponding to $R^2$, and/or the group corresponding to $R^5$ contains a protective group for a functional group, such as a carboxylic acid, an amine, or a hydroxyl. In this case, the compound of general formula [D-5] (in which the group corresponding to $R^{1'}$, and/or the group corresponding to $R^2$, and/or the group corresponding to $R^5$ contains a protective group for a functional group, such as a carboxylic acid, an amine, or a hydroxyl) may be deprotected by removing the protective group. The deprotection may be performed by a common method, such as reduction, hydrolysis, or acid treatment, in accordance with the type of the protective group that will be removed.

Synthesis Method F

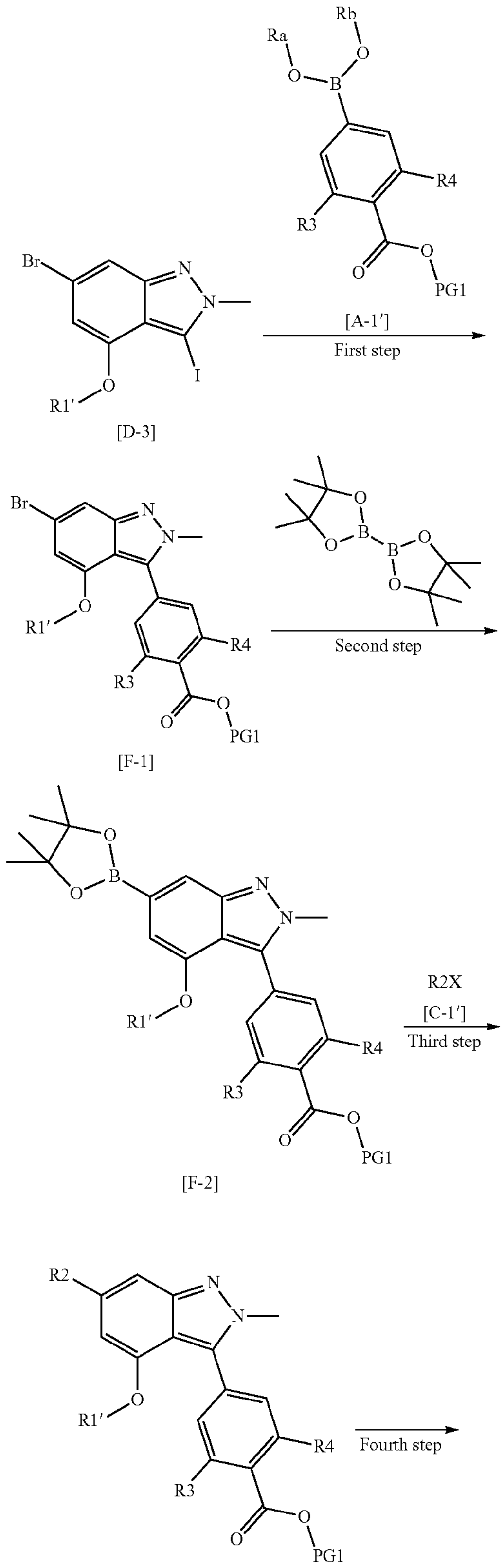

[D-3] [F-1] [F-2] [F-3]

-continued

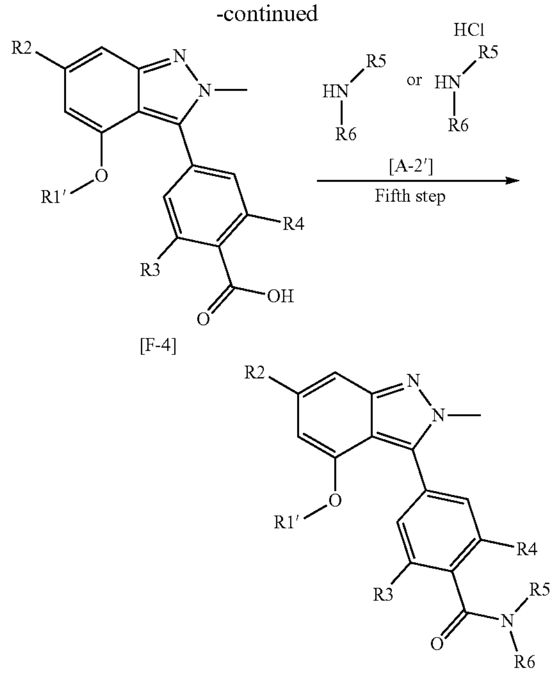

[F-4] [D-5]

[In the formulas, the symbols are the same as defined hereinabove. With the proviso that, in general formulas [A-2'], [C-1'], [D-3], [D-5], [F-1], [F-2], [F-3], and [F-4], a group corresponding to $R^{1'}$, and/or a group corresponding to $R^2$, and/or a group corresponding to $R^5$ may contain a protective group for a functional group, such as a carboxylic acid, an amine, or a hydroxyl.]

The compound of general formula [F-1] is obtained by the coupling reaction of the compound of general formula [D-3] with the compound of general formula [A-1']. The reaction temperature and time, and the reagents and the solvent that are used are the same as those described in the first step of Synthesis Method A.

The compound of general formula [F-2] is obtained by the coupling reaction of the compound of general formula [F-1] with bis(pinacolato)diboron. The reaction temperature and time, and the reagents and the solvent that are used are the same as those described in the first step of Synthesis Method C.

The compound of general formula [F-3] is obtained by the coupling reaction of the compound of general formula [F-2] with the compound of general formula [C-1']. The reaction temperature and time, and the reagents and the solvent that are used are the same as those described in the first step of Synthesis Method A.

The compound of general formula [F-4] is obtained by deprotecting the carboxylic acid in the compound of general formula [F-3]. The reaction temperature and time, and the reagents and the solvent that are used are the same as those described in the second step of Synthesis Method A.

The compound of general formula [D-5] is obtained by the amidation reaction of the compound of general formula [F-4] with the compound of general formula [A-2']. The reaction temperature and time, and the reagents and the solvent that are used are the same as those described in the third step of Synthesis Method A.

In Synthesis Method F, the compound of general formula [A-2'], and/or the compound of general formula [C-1'], and/or the compound of general formula [D-3] may be a compound in which the group corresponding to $R^{1'}$, and/or the group corresponding to $R^2$, and/or the group corresponding to $R^5$ contains a protective group for a functional group, such as a carboxylic acid, an amine, or a hydroxyl. In this case, the compound of general formula [D-5] (in which the group corresponding to $R^{1'}$, and/or the group corresponding to $R^2$, and/or the group corresponding to $R^5$ contains a protective group for a functional group, such as a carboxylic acid, an amine, or a hydroxyl) may be deprotected by removing the protective group. The deprotection may be performed by a common method, such as reduction, hydrolysis, or acid treatment, in accordance with the type of the protective group that will be removed.

Synthesis Method G

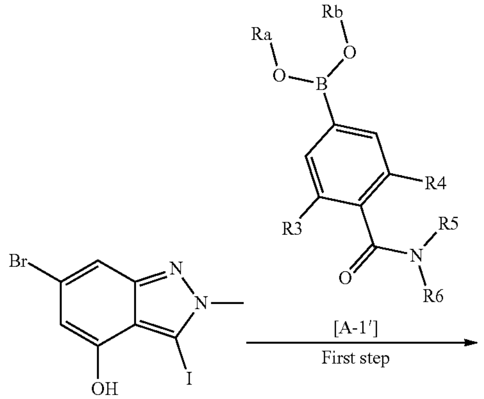

[D-2]

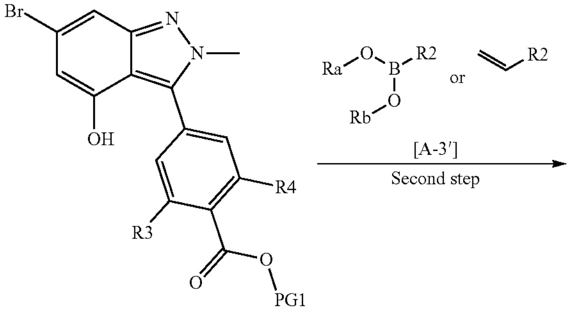

[G-1]

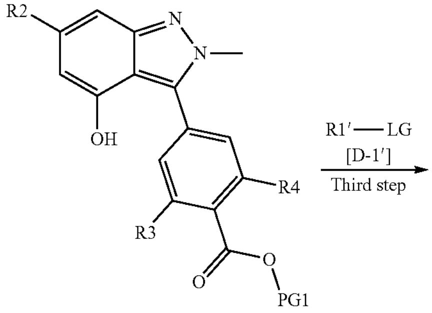

[G-2]

-continued

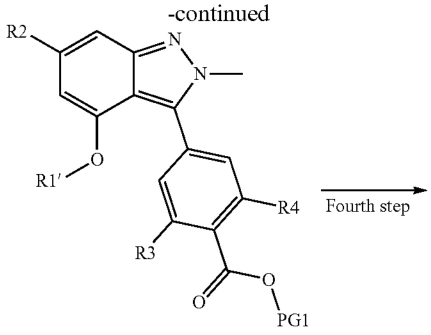

[F-3]

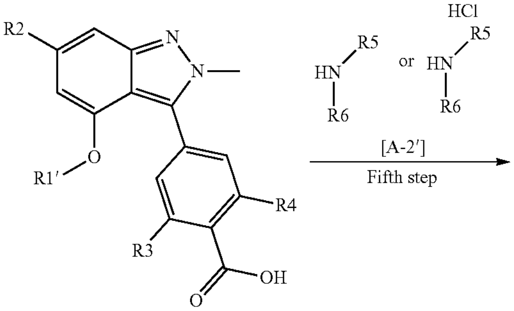

[F-4]

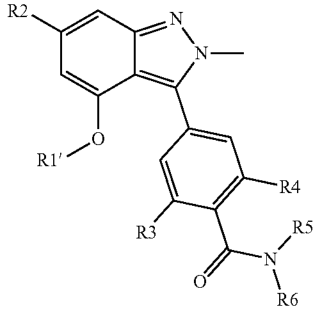

[D-5]

[In the formulas, the symbols are the same as defined hereinabove. With the proviso that, in general formulas [A-2'], [A-3'], [D-1'], [D-5], [F-3], [F-4], and [G-2], a group corresponding to $R^{1'}$, and/or a group corresponding to $R^2$, and/or a group corresponding to $R^5$ may contain a protective group for a functional group, such as a carboxylic acid, an amine, or a hydroxyl.]

The compound of general formula [G-1] is obtained by the coupling reaction of the compound of general formula [D-2] with the compound of general formula [A-1']. The reaction temperature and time, and the reagents and the solvent that are used are the same as those described in the first step of Synthesis Method A.

The compound of general formula [G-2] is obtained by the coupling reaction of the compound of general formula [G-1] with the compound of general formula [A-3']. The reaction temperature and time, and the reagents and the solvent that are used are the same as those described in the first step of Synthesis Method A.

The compound of general formula [F-3] is obtained by the O-alkylation reaction of the compound of general formula [G-2] using the compound of general formula [D-1'] (when $R^{1'}$=$CHF_2$, $CF_2BrPO(OEt)_2$ is used). The reaction temperature and time, and the reagents and the solvent that are used are the same as those described in the second step of Synthesis Method D.

The compound of general formula [F-4] is obtained by deprotecting the carboxylic acid in the compound of general formula [F-3]. The reaction temperature and time, and the reagents and the solvent that are used are the same as those described in the second step of Synthesis Method A.

The compound of general formula [D-5] is obtained by the amidation reaction of the compound of general formula [F-4] with the compound of general formula [A-2']. The reaction temperature and time, and the reagents and the solvent that are used are the same as those described in the third step of Synthesis Method A.

In Synthesis Method G, the compound of general formula [A-2'], and/or the compound of general formula [A-3'], and/or the compound of general formula [D-1'] may be a compound in which the group corresponding to $R^{1'}$, and/or the group corresponding to $R^2$, and/or the group corresponding to $R^5$ contains a protective group for a functional group, such as a carboxylic acid, an amine, or a hydroxyl. In this case, the compound of general formula [D-5] (in which the group corresponding to $R^{1'}$, and/or the group corresponding to $R^2$, and/or the group corresponding to $R^5$ contains a protective group for a functional group, such as a carboxylic acid, an amine, or a hydroxyl) may be deprotected by removing the protective group. The deprotection may be performed by a common method, such as reduction, hydrolysis, or acid treatment, in accordance with the type of the protective group that will be removed.

Synthesis Method H

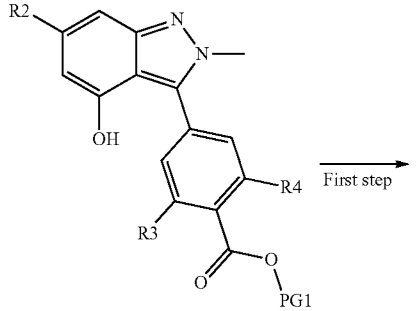

[G-2]

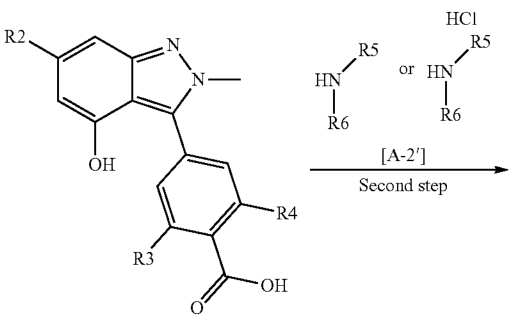

[H-1]

-continued

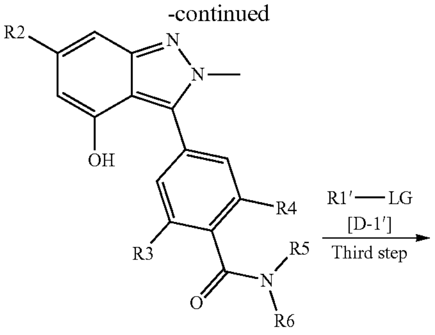

[E-2]

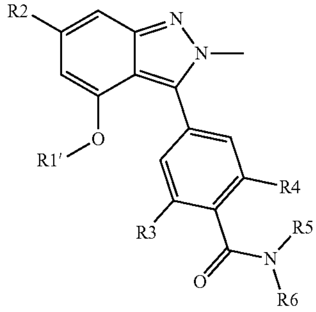

[D-5]

[In the formulas, the symbols are the same as defined hereinabove. With the proviso that, in general formulas [A-2'], [D-1'], [D-5], [E-2], [G-2], and [H-1], a group corresponding to $R^{1'}$, and/or a group corresponding to $R^2$, and/or a group corresponding to $R^5$ may contain a protective group for a functional group, such as a carboxylic acid, an amine, or a hydroxyl.]

The compound of general formula [H-1] is obtained by deprotecting the carboxylic acid in the compound of general formula [G-2]. The reaction temperature and time, and the reagents and the solvent that are used are the same as those described in the second step of Synthesis Method A.

The compound of general formula [E-2] is obtained by the amidation reaction of the compound of general formula [H-1] with the compound of general formula [A-2']. The reaction temperature and time, and the reagents and the solvent that are used are the same as those described in the third step of Synthesis Method A.

The compound of general formula [D-5] is obtained by the O-alkylation reaction of the compound of general formula [E-2] using the compound of general formula [D-1'] (when $R^{1'}$=$CHF_2$, $CF_2BrPO(OEt)_2$ is used). The reaction temperature and time, and the reagents and the solvent that are used are the same as those described in the second step of Synthesis Method D.

In Synthesis Method H, the compound of general formula [A-2'], and/or the compound of general formula [D-1'], and/or the compound of general formula [G-2] may be a compound in which the group corresponding to $R^{1'}$, and/or the group corresponding to $R^2$, and/or the group corresponding to $R^5$ contains a protective group for a functional group, such as a carboxylic acid, an amine, or a hydroxyl. In this case, the compound of general formula [D-5] (in which the group corresponding to $R^{1'}$, and/or the group corresponding to $R^2$, and/or the group corresponding to $R^5$ contains a protective group for a functional group, such as a carboxylic acid, an amine, or a hydroxyl) may be deprotected by removing the protective group. The deprotection may be performed by a common method, such as reduction, hydrolysis, or acid treatment, in accordance with the type of the protective group that will be removed.

Synthesis Method I

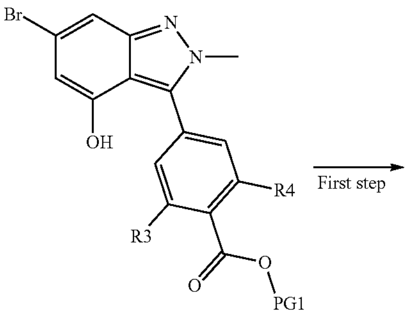

[G-1]

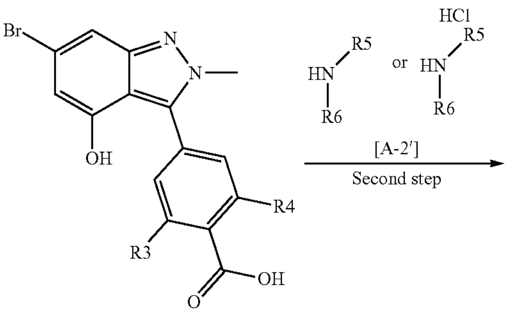

[I-1]

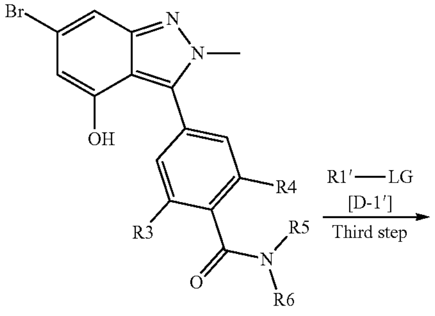

[E-1]

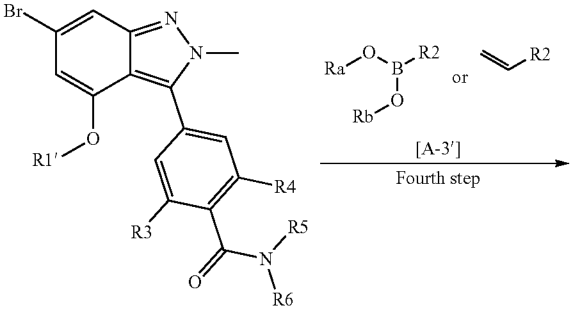

[D-4]

-continued

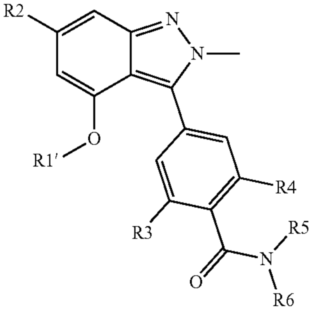

[D-5]

[In the formulas, the symbols are the same as defined hereinabove. With the proviso that, in general formula [A-2'], [A-3'], [D-1'], [D-4], [D-5], and [E-1], a group corresponding to $R^{1'}$, and/or a group corresponding to $R^2$, and/or a group corresponding to $R^5$ may contain a protective group for a functional group, such as a carboxylic acid, an amine, or a hydroxyl.]

The compound of general formula [I-1] is obtained by deprotecting the carboxylic acid in the compound of general formula [G-1]. The reaction temperature and time, and the reagents and the solvent that are used are the same as those described in the second step of Synthesis Method A.

The compound of general formula [E-1] is obtained by the amidation reaction of the compound of general formula [I-1] with the compound of general formula [A-2']. The reaction temperature and time, and the reagents and the solvent that are used are the same as those described in the third step of Synthesis Method A.

The compound of general formula [D-4] is obtained by the O-alkylation reaction of the compound of general formula [E-1] using the compound of general formula [D-1'] (when $R^1$=$CHF_2$, $CF_2BrPO(OEt)_2$ is used). The reaction temperature and time, and the reagents and the solvent that are used are the same as those described in the second step of Synthesis Method D.

The compound of general formula [D-5] is obtained by the coupling reaction of the compound of general formula [D-4] with the compound of general formula [A-3']. The reaction temperature and time, and the reagents and the solvent that are used are the same as those described in the first step of Synthesis Method A.

In Synthesis Method I, the compound of general formula [A-2'], and/or the compound of general formula [A-3'], and/or the compound of general formula [D-1'] may be a compound in which the group corresponding to $R^{1'}$, and/or the group corresponding to $R^2$, and/or the group corresponding to $R^5$ contains a protective group for a functional group, such as a carboxylic acid, an amine, or a hydroxyl. In this case, the compound of general formula [D-5] (in which the group corresponding to $R^{1'}$, and/or the group corresponding to $R^2$, and/or the group corresponding to $R^5$ contains a protective group for a functional group, such as a carboxylic acid, an amine, or a hydroxyl) may be deprotected by removing the protective group. The deprotection may be performed by a common method, such as reduction, hydrolysis, or acid treatment, in accordance with the type of the protective group that will be removed.

Synthesis Method J

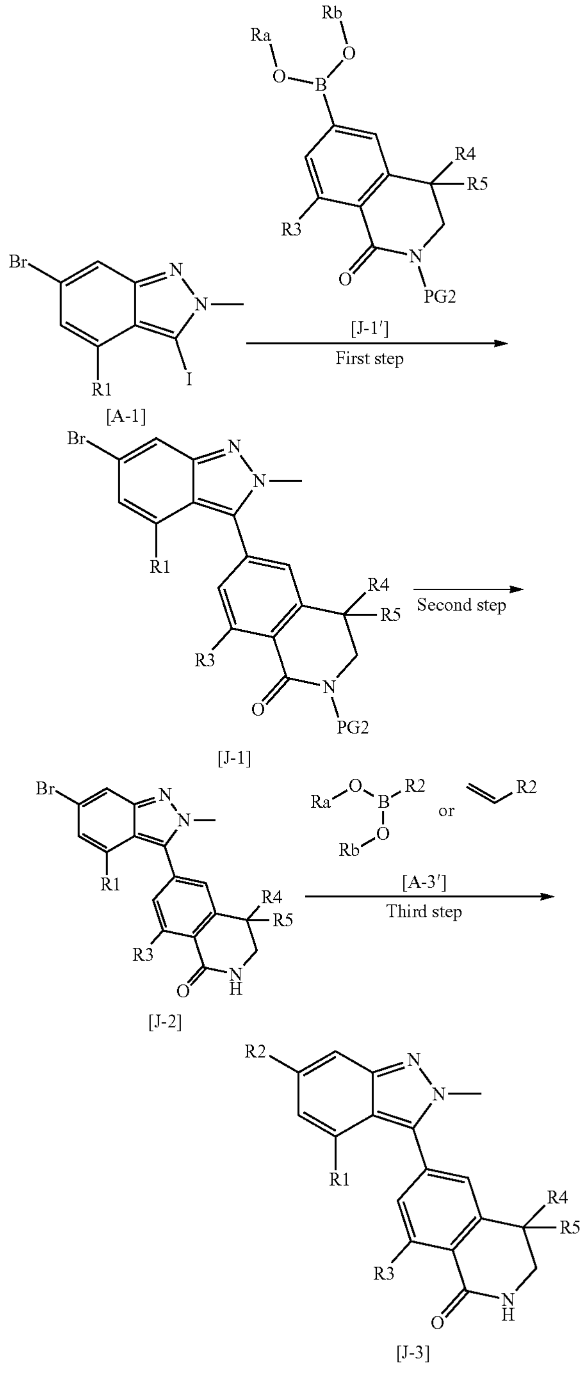

[A-1] [J-1'] [J-1] [A-3'] [J-2] [J-3]

[In the formulas, PG2 denotes an amide protective group, and the rest of the symbols are the same as defined hereinabove. With the proviso that, in general formulas [A-3'] and [J-3], a group corresponding to $R^2$ may contain a protective group for a functional group, such as a carboxylic acid, an amine, or a hydroxyl.]

The compound of general formula [J-1] is obtained by the coupling reaction of the compound of general formula [A-1] with the compound of general formula [J-1']. The reaction temperature and time, and the reagents and the solvent that are used are the same as those described in the first step of Synthesis Method A.

The compound of general formula [J-2] is obtained by deprotecting the compound of general formula [J-1]. The reaction temperature and time, and the reagents and the solvent that are used are the same as those described in the second step of Synthesis Method A.

The compound of general formula [J-3] is obtained by the coupling reaction of the compound of general formula [J-2] with the compound of general formula [A-3']. The reaction temperature and time, and the reagents and the solvent that are used are the same as those described in the first step of Synthesis Method A.

In Synthesis Method J, the compound of general formula [A-3'] may be a compound in which the group corresponding to $R^2$ contains a protective group for a functional group, such as a carboxylic acid, an amine, or a hydroxyl. In this case, the compound of general formula [J-3] (in which the group corresponding to $R^2$ contains a protective group for a functional group, such as a carboxylic acid, an amine, or a hydroxyl) may be deprotected by removing the protective group. The deprotection may be performed by a common method, such as reduction, hydrolysis, or acid treatment, in accordance with the type of the protective group that will be removed.

Synthesis Method K

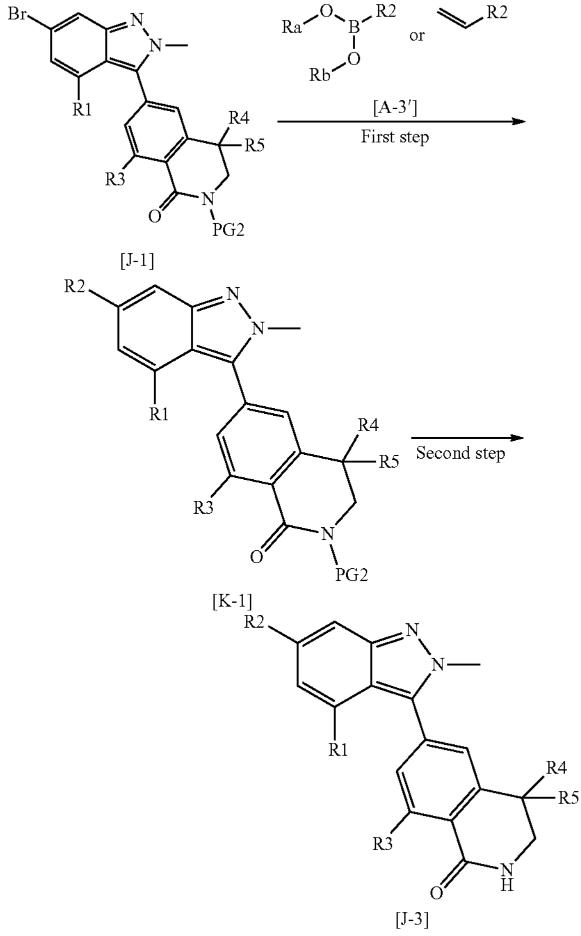

[J-1] [A-3'] [K-1] [J-3]

[In the formulas, PG2 denotes an amide protective group, and the rest of the symbols are the same as defined hereinabove. With the proviso that, in general formulas [A-3'], [K-1], and [J-3], a group corresponding to $R^2$ may contain a protective group for a functional group, such as a carboxylic acid, an amine, or a hydroxyl.]

The compound of general formula [K-1] is obtained by the coupling reaction of the compound of general formula [J-1] with the compound of general formula [A-3']. The reaction temperature and time, and the reagents and the solvent that are used are the same as those described in the first step of Synthesis Method A.

The compound of general formula [J-3] is obtained by deprotecting the compound of general formula [K-1]. The reaction temperature and time, and the reagents and the solvent that are used are the same as those described in the second step of Synthesis Method A.

In Synthesis Method K, the compound of general formula [A-3'] may be a compound in which the group corresponding to $R^2$ contains a protective group for a functional group, such as a carboxylic acid, an amine, or a hydroxyl. In this case, the compound of general formula [J-3] (in which the group corresponding to $R^2$ contains a protective group for a functional group, such as a carboxylic acid, an amine, or a hydroxyl) may be deprotected by removing the protective group. The deprotection may be performed by a common method, such as reduction, hydrolysis, or acid treatment, in accordance with the type of the protective group that will be removed.

The compounds as raw materials in the above methods may be produced by known methods and/or the methods described later in Examples.

The functional groups may be protected and deprotected with reference to known methods (such as PROTECTIVE GROUPS in ORGANIC SYNTHESIS (Theodora W. Greene, Peter G. M. Wuts)).

The compounds of the present aspect produced by the methods described hereinabove, and the intermediate compounds thereof may be further converted to other target compounds or intermediates by the methods described later in Examples, and/or known methods, or combinations thereof.

When the compounds of the present aspect produced by the methods described hereinabove, and the intermediate compounds thereof are racemic isomers, the enantiomers may be separated by a standard separation technique, such as chiral column chromatography.

The compound of formula (I) produced by the method described hereinabove may be purified to a desired purity by a common purification technique, such as, for example, concentration, extraction, chromatography, reprecipitation, or recrystallization. Where necessary, the compound may be obtained as a pharmacologically acceptable salt by treatment with, for example, an acid or a base in an appropriate solvent (such as water, alcohol, or ether). Furthermore, the compound of the present invention or the pharmacologically acceptable salt thereof thus obtained may be treated with water, an aqueous solvent, or other solvent to give a hydrate or a solvate.

The compounds of the above aspect of the present invention or the pharmacologically acceptable salts thereof include racemic isomers, stereoisomers, and mixtures of these compounds, and include isotopically labeled compounds and radioactively labeled compounds. These isomers may be separated by a standard separation technique, such as fractional crystallization or chiral column chromatography. Furthermore, the compounds of the above aspect of the present invention include enantiomers or diastereomers. A diastereomer mixture may be separated into individual diastereomers based on the physical/chemical differences between the diastereomers by a method known in the art, for example, chromatography and/or fractional crystallization. Enantiomers may be separated by chiral column chromatography or may be separated in such a manner that the enantiomer compounds are converted into a diastereomer mixture by reaction with an appropriate optically active compound, the diastereomers being then separated from one another, and the individual diastereomers are converted into the corresponding enantiomers. The compounds of the above aspect of the present invention may be any isomers including diastereomers, enantiomers, and mixtures thereof.

SIK regulate a new molecular switch that regulates the polarity of macrophages. Pharmacological inhibition of SIK induces a macrophage phenotype characterized by high-level secretion of anti-inflammatory cytokines, such as interleukin (IL)-10, and extremely low secretion of inflammatory cytokines, such as tumor necrosis factor $\alpha$ (TNF-$\alpha$). Non Patent Literature 1 has shown that the inhibition of all SIK1, SIK2, and SIK3 is most important to benefit from the medicinal effects of macrophages. The compound of formula (I) of the above aspect or the pharmacologically acceptable salt thereof can effectively inhibit all of SIK1, SIK2, and SIK3. For example, the compounds of formula (I) of the above aspect or the pharmacologically acceptable salts thereof have a 50% inhibition concentration ($IC_{50}$) of less than 20 nM against each of SIK1, SIK2, and SIK3 as shown by the SIK inhibition activity evaluation (Experimental Example 1) described later in Examples. Some systems are available for evaluating the SIK inhibition activity. For example, the evaluation method described later in Examples, and the method described in WO 2019/105886 may be used. The person skilled in the art can select an appropriate evaluation system. The person skilled in the art will understand that the value of 50% inhibition concentration ($IC_{50}$) can vary depending on the evaluation system that is adopted.

The compound of formula (I) of the above aspect or the pharmacologically acceptable salt thereof can inhibit the production of inflammatory cytokines, such as tumor necrosis factors $\alpha$ (TNF-$\alpha$).

In a preferred embodiment, the compound of formula (I) of the above aspect or the pharmacologically acceptable salt thereof has no or a very low risk of producing reactive metabolites. When foreign matters, such as pharmaceuticals, enter the body, their chemical structures can be changed by metabolism to form highly reactive intermediates, such as electrophilic compounds and free radicals, that develop toxicity or exhibit increased toxicity. The metabolites thus formed, called reactive metabolites, and this series of processes, called metabolic activation, have been topics of many studies. Reactive metabolites are considered to be often covalently bonded irreversibly to biological polymers (such as proteins and nucleic acids) to cause allergies, hepatotoxicity, tissue necrosis, mutagenicity, and carcinogenicity. Avoiding reactive metabolites is very important from the point of view of the safety of medicines. For example, the occurrence of reactive metabolites may be assayed by glutathione (GSH) trapping test described later in Examples.

For a patient, preferably a mammal (such as, for example, a mouse, a rat, a hamster, a rabbit, a cat, a dog, a cow, a sheep, a monkey, or a human), the compound of formula (I) of the above aspect or the pharmacologically acceptable salt thereof may be used as a medicine to prevent or treat a disease and/or an accompanying symptom that can be improved by inhibiting salt-inducible kinases (SIK) or to improve a prognosis of such a disease and/or an accompanying symptom.

Pharmaceutical Compositions

In another aspect of the present invention, a pharmaceutical composition includes the compound of formula (I) or the pharmacologically acceptable salt thereof as an active ingredient. The pharmaceutical composition may further include a pharmaceutically acceptable carrier. The pharmaceutical composition may be used to prevent or treat a disease and/or an accompanying symptom that can be improved by inhibiting salt-inducible kinases (SIK) or to improve a prognosis of such a disease and/or an accompanying symptom.

Specifically, embodiments of the pharmaceutical composition according to the present aspect include the following embodiments.

Embodiment (10) resides in a pharmaceutical composition that includes the compound or the pharmacologically acceptable salt thereof as described in any one of Embodiments (1) to (9) as an active ingredient.

Embodiment (11) resides in the pharmaceutical composition as described in Embodiment (10) for use in the prevention or treatment of a disease and/or an accompanying symptom that can be improved by inhibiting salt-inducible kinases (SIK) or in the improvement of a prognosis of such a disease and/or an accompanying symptom.

Embodiment (12) resides in the pharmaceutical composition as described in Embodiment (10), that is a preventive or therapeutic agent for a disease selected from inflammatory diseases, autoinflammatory diseases, autoimmune diseases, proliferative diseases, fibrotic diseases, transplant rejections, diseases involving cartilage turnover disorders, congenital cartilage malformations, diseases involving bone turnover disorders, diseases associated with hypersecretion of TNF-α, interferon, IL-6, IL-12, and/or IL-23, respiratory diseases, endocrine and/or metabolic diseases, cardiovascular diseases, skin diseases, and abnormal angiogenesis-related diseases.

Embodiment (13) resides in the pharmaceutical composition as described in Embodiment (10), that is a preventive or therapeutic agent for a disease selected from rheumatoid arthritis, arthritis deformans, psoriatic arthritis, chronic inflammatory demyelinating polyneuropathy, ulcerative colitis, Crohn's disease, autoimmune hepatitis, primary biliary cholangitis, primary sclerosing cholangitis, non-alcoholic fatty liver disease, non-alcoholic steatohepatitis, type 1 diabetes mellitus, type 2 diabetes mellitus, pancreatitis, systemic lupus erythematosus, cutaneous lupus erythematosus, central nervous system lupus, lupus nephritis, antiphospholipid antibody syndrome, chronic kidney disease, acute kidney disease, sarcoidosis, systemic scleroderma, localized scleroderma, Sjogren's syndrome, ANCA-associated vasculitis, immune complex small vessel vasculitis, polyarteritis nodosa, Kawasaki disease, Takayasu arteritis, giant cell arthritis, idiopathic inflammatory muscle disease (polymyositis, dermatomyositis, inclusion body myositis), IgG4-related diseases, juvenile Still's disease, pelvic inflammatory disease, psoriasis, pustular psoriasis, atopic dermatitis, asthma, allergic rhinitis, relapsing polychondritis, mixed connective tissue disease, graft-versus-host disease, idiopathic pulmonary fibrosis, idiopathic interstitial pneumonia, chronic obstructive pulmonary disease, myelofibrosis, multiple sclerosis, cerebral infarction, ischemic stroke, Alzheimer's disease, Parkinson's disease, depression, developmental epilepsy, Meniere's disease, narcolepsy, macrophage activation syndrome, sepsis, pulmonary hypertension, hyperlipidemia, Behcet's disease, uveitis, osteoporosis, bone fracture, osteosarcoma, cardiac insufficiency, hypertrophic myocardiopathy, atherosclerosis, female gestosis, ovarian cancer, breast cancer, prostate cancer, malignant lymphoma, leukemia, multiple myeloma, lung cancer, granuloma annulare, esophageal cancer, colorectal cancer, pancreatic cancer, gastric cancer, hepatocellular cancer, melanoma, and secondary hemophagocytic lymphohistiocytosis.

Embodiment (14) resides in the pharmaceutical composition as described in Embodiment (10), that is a preventive or therapeutic agent for a disease selected from rheumatoid arthritis, arthritis deformans, psoriatic arthritis, ulcerative colitis, primary biliary cholangitis, primary sclerosing cholangitis, pancreatitis, systemic lupus erythematosus, lupus nephritis, systemic scleroderma, Sjogren's syndrome, psoriasis, pustular psoriasis, Behcet's disease, ovarian cancer, and acute myeloid leukemia.

Embodiment (15) resides in the pharmaceutical composition as described in Embodiment (10), that is a preventive or therapeutic agent for a disease selected from rheumatoid arthritis, arthritis deformans, psoriatic arthritis, ulcerative colitis, pancreatitis, systemic lupus erythematosus, lupus nephritis, systemic scleroderma, Sjogren's syndrome, pustular psoriasis, and Behcet's disease.

In the present description, the term "preventive (or prevention)" includes the prevention of the onset of a disease (the whole of clinical conditions, or one or more clinical conditions), and the retardation of the onset of the disease. The phrase "prophylactically effective amount" means that the dosage of the compound of formula (I) is sufficient for achieving the prevention.

In the present description, the term "therapeutic (or treatment)" includes healing of a disease (the whole of clinical conditions, or one or more clinical conditions), improvement of the disease, and the suppression of the progress of the severity of the disease. The term "therapeutically effective amount" means that the dosage of the compound of formula (I) is sufficient for achieving the treatment.

Examples of the forms of the pharmaceutical compositions include tablets (including, for example, sugar-coated tablets, film-coated tablets, sublingual tablets, orally disintegrating tablets, and buccal tablets), pills, powders, granules, capsules (including soft capsules and microcapsules), syrups, liquids, emulsions, suspensions, release control preparations (for example, immediate-release preparations, sustained-release preparations, sustained-release microcapsules), aerosols, films (for example, orally disintegrating films, oral mucosa-adhesive films), injections (for example, subcutaneous injections, intravenous injections (for example, bolus), intramuscular injections, intraperitoneal injections), drip infusions, transdermal absorption type preparations, ointments, lotions, adhesive preparations, suppositories (for example rectal suppositories, vaginal suppositories), pellets, nasal preparations, pulmonary preparations (inhalants), and eye drops.

In the present description, the "pharmaceutically acceptable carriers" may be any carriers commonly used in the pharmaceutical field.

In the case of, for example, solid preparations, specific examples of the "pharmaceutically acceptable carriers" include excipients (such as, for example, lactose, saccharose, D-mannitol, starch, cone starch, crystalline cellulose, and light silicic anhydride), lubricants (such as, for example, magnesium stearate, talc, and colloidal silica), binders (such as, for example, crystalline cellulose, saccharose, D-mannitol, dextrin, hydroxypropylcellulose, hydroxypropylmethylcellulose, polyvinylpyrrolidone, starch, sucrose, gelatin, methylcellulose, and carboxymethylcellulose sodium), and disintegrants (such as, for example, starch, carboxymethylcellulose, carboxymethylcellulose calcium, carboxymethyl starch sodium, and L-hydroxypropylcellulose).

In the case of liquid preparations, specific examples of the "pharmaceutically acceptable carriers" include solvents (such as, for example, water for injection, isotonic saline, alcohols, propylene glycol, macrogol, and sesame oil), dissolution aids (such as, for example, polyethylene glycol, propylene glycol, D-mannitol, benzyl benzoate, ethanol, triethanolamine, sodium carbonate, and sodium citrate), suspending agents (such as, for example, surfactants, such as stearyltriethanolamine, sodium lauryl sulfate, laurylaminopropionic acid, lecithin, benzalkonium chloride, and glycerin monostearate; and hydrophilic polymers, such as, for example, polyvinyl alcohol, polyvinylpyrrolidone, carboxymethylcellulose sodium, methylcellulose, hydroxymethylcellulose, and hydroxypropylcellulose), tonicity agents (such as, for example, glucose, D-sorbitol, sodium chloride, glycerin, and D-mannitol), buffers (such as, for example, buffer solutions or phosphates and citrates), and soothing agents (such as, for example, benzyl alcohol).

Where necessary, pharmaceutical additives may be further added, with examples including preservatives (such as, for example, para-hydroxybenzoic acid esters, chlorobutanol, benzyl alcohols, and sorbic acid), antioxidants (such as, for example, sulfites, ascorbic acid, and α-tocopherol), colorants, and sweeteners.

The pharmaceutical composition of the present aspect may be produced by adding the compound of the above-described aspect usually in a proportion of 0.01 to 99% (w/w), preferably 0.1 to 85% (w/w), relative to the total weight of the preparation. The proportion may vary depending on factors, such as the type of the preparation, the manner of administration, and the type of the carrier. The pharmaceutical composition may be produced by a method that is common in the pharmaceutical field depending on the form of the pharmaceutical composition. The pharmaceutical composition of the present aspect may be formed as a sustained-release preparation including the active ingredient.

For example, relationships between SIK and diseases are described in the following literatures.

Darling N J, Cohen P. Nuts and bolts of the salt-inducible kinases (SIKs). Biochem J. 2021 Apr. 16; 478(7): 1377-1397.

Fu Y, Ma G, Zhang Y, Wang W, Shi T, Zhu J, Zhang J, Huang Z, Chen J. HG-9-91-01 Attenuates Murine Experimental Colitis by Promoting Interleukin-10 Production in Colonic Macrophages Through the SIK/CRTC3 Pathway. Inflamm Bowel Dis. 2021 Oct. 20; 27(11): 1821-1831.

Lombardi M S, Gilliéron C, Berkelaar M, Gabay C. Salt-inducible kinases (SIK) inhibition reduces RANKL-induced osteoclastogenesis. PLOS One. 2017 Oct. 3; 12(10): e0185426.

Taub M. Salt Inducible Kinase Signaling Networks: Implications for Acute Kidney Injury and Therapeutic Potential. Int J Mol Sci. 2019 Jun. 30; 20(13): 3219.

Chen F, Chen L, Qin Q, Sun X. Salt-Inducible Kinase 2: An Oncogenic Signal Transmitter and Potential Target for Cancer Therapy. Front Oncol. 2019 Jan. 22; 9:18.

Wein M N, Foretz M, Fisher D E, Xavier R J, Kronenberg H M. Salt-Inducible Kinases: Physiology, Regulation by cAMP, and Therapeutic Potential. Trends Endocrinol Metab. 2018 October; 29(10): 723-735.

Sasaki T, Takemori H, Yagita Y, Terasaki Y, Uebi T, Horike N, Takagi H, Susumu T, Teraoka H, Kusano K, Hatano O, Oyama N, Sugiyama Y, Sakoda S, Kitagawa K. SIK2 is a key regulator for neuronal survival after ischemia via TORC1-CREB. Neuron. 2011 Jan. 13; 69(1): 106-19.

Furthermore, another aspect of the present invention resides in the compound of formula (I) or the pharmacologically acceptable salt thereof for use in the prevention or treatment of a disease and/or an accompanying symptom that can be improved by inhibiting salt-inducible kinases (SIK) or in the improvement of a prognosis of such a disease and/or an accompanying symptom. Embodiments thereof include the following.

Embodiment (16) resides in the compound or the pharmacologically acceptable salt thereof as described in any one of Embodiments (1) to (9) for use in the prevention or treatment of a disease and/or an accompanying symptom that can be improved by inhibiting salt-inducible kinases (SIK) or in the improvement of a prognosis of such a disease and/or an accompanying symptom.

Embodiment (17) resides in the compound or the pharmacologically acceptable salt thereof as described in any one of Embodiments (1) to (9) for use in the prevention or treatment of a disease selected from inflammatory diseases, autoinflammatory diseases, autoimmune diseases, proliferative diseases, fibrotic diseases, transplant rejections, diseases involving cartilage turnover disorders, congenital cartilage malformations, diseases involving bone turnover disorders, diseases associated with hypersecretion of TNF-α, interferon, IL-6, IL-12, and/or IL-23, respiratory diseases, endocrine and/or metabolic diseases, cardiovascular diseases, skin diseases, and abnormal angiogenesis-related diseases.

Embodiment (18) resides in the compound or the pharmacologically acceptable salt thereof as described in any one of Embodiments (1) to (9) for use in the prevention or treatment of a disease selected from rheumatoid arthritis, arthritis deformans, psoriatic arthritis, chronic inflammatory demyelinating polyneuropathy, ulcerative colitis, Crohn's disease, autoimmune hepatitis, primary biliary cholangitis, primary sclerosing cholangitis, non-alcoholic fatty liver disease, non-alcoholic steatohepatitis, type 1 diabetes mellitus, type 2 diabetes mellitus, pancreatitis, systemic lupus erythematosus, cutaneous lupus erythematosus, central nervous system lupus, lupus nephritis, antiphospholipid antibody syndrome, chronic kidney disease, acute kidney disease, sarcoidosis, systemic scleroderma, localized scleroderma, Sjogren's syndrome, ANCA-associated vasculitis, immune complex small vessel vasculitis, polyarteritis nodosa, Kawasaki disease, Takayasu arteritis, giant cell arthritis, idiopathic inflammatory muscle disease (polymyositis, dermatomyositis, inclusion body myositis), IgG4-related diseases, juvenile Still's disease, pelvic inflammatory disease, psoriasis, pustular psoriasis, atopic dermatitis, asthma, allergic rhinitis, relapsing polychondritis, mixed connective tissue disease, graft-versus-host disease, idiopathic pulmonary fibrosis, idiopathic interstitial pneumonia, chronic obstructive pulmonary disease, myelofibrosis, multiple sclerosis, cerebral infarction, ischemic stroke, Alzheimer's disease, Parkinson's disease, depression, developmental epilepsy, Meniere's disease, narcolepsy, macrophage activation syndrome, sepsis, pulmonary hypertension, hyperlipidemia, Behcet's disease, uveitis, osteoporosis, bone fracture, osteosarcoma, cardiac insufficiency, hypertrophic myocardiopathy, atherosclerosis, female gestosis, ovarian cancer, breast cancer, prostate cancer, malignant lymphoma, leukemia, multiple myeloma, lung cancer, granuloma annulare, esophageal cancer, colorectal cancer, pancreatic cancer, gastric cancer, hepatocellular cancer, melanoma, and secondary hemophagocytic lymphohistiocytosis.

Embodiment (19) resides in the compound or the pharmacologically acceptable salt thereof as described in any one of Embodiments (1) to (9) for use in the prevention or treatment of a disease selected from rheumatoid arthritis, arthritis deformans, psoriatic arthritis, ulcerative colitis, primary biliary cholangitis, primary sclerosing cholangitis, pancreatitis, systemic lupus erythematosus, lupus nephritis, systemic scleroderma, Sjogren's syndrome, psoriasis, pustular psoriasis, Behcet's disease, ovarian cancer, and acute myeloid leukemia.

Embodiment (20) resides in the compound or the pharmacologically acceptable salt thereof as described in any one of Embodiments (1) to (9) for use in the prevention or treatment of a disease selected from rheumatoid arthritis, arthritis deformans, psoriatic arthritis, ulcerative colitis, pancreatitis, systemic lupus erythematosus, lupus nephritis, systemic scleroderma, Sjogren's syndrome, pustular psoriasis, and Behcet's disease.

Furthermore, another aspect of the present invention resides in a method for preventing or treating a disease and/or an accompanying symptom that can be improved by inhibiting salt-inducible kinases (SIK), the method including administering a therapeutically effective amount of the compound of formula (I) or the pharmacologically acceptable salt thereof to a patient. Embodiments thereof include the following.

Embodiment (21) resides in a method for preventing or treating a disease and/or an accompanying symptom that can be improved by inhibiting salt-inducible kinases (SIK), the method including administering a therapeutically effective amount of the compound or the pharmacologically acceptable salt thereof as described in any one of Embodiments (1) to (9) to a patient.

Embodiment (22) resides in a method for preventing or treating a disease selected from inflammatory diseases, autoinflammatory diseases, autoimmune diseases, proliferative diseases, fibrotic diseases, transplant rejections, diseases involving cartilage turnover disorders, congenital cartilage malformations, diseases involving bone turnover disorders, diseases associated with hypersecretion of TNF-$\alpha$, interferon, IL-6, IL-12, and/or IL-23, respiratory diseases, endocrine and/or metabolic diseases, cardiovascular diseases, skin diseases, and abnormal angiogenesis-related diseases, which includes administering a therapeutically effective amount of the compound or the pharmacologically acceptable salt thereof as described in any one of Embodiments (1) to (9) to a patient.

Embodiment (23) resides in a method for preventing or treating a disease selected from rheumatoid arthritis, arthritis deformans, psoriatic arthritis, chronic inflammatory demyelinating polyneuropathy, ulcerative colitis, Crohn's disease, autoimmune hepatitis, primary biliary cholangitis, primary sclerosing cholangitis, non-alcoholic fatty liver disease, non-alcoholic steatohepatitis, type 1 diabetes mellitus, type 2 diabetes mellitus, pancreatitis, systemic lupus erythematosus, cutaneous lupus erythematosus, central nervous system lupus, lupus nephritis, antiphospholipid antibody syndrome, chronic kidney disease, acute kidney disease, sarcoidosis, systemic scleroderma, localized scleroderma, Sjogren's syndrome, ANCA-associated vasculitis, immune complex small vessel vasculitis, polyarteritis nodosa, Kawasaki disease, Takayasu arteritis, giant cell arthritis, idiopathic inflammatory muscle disease (polymyositis, dermatomyositis, inclusion body myositis), IgG4-related diseases, juvenile Still's disease, pelvic inflammatory disease, psoriasis, pustular psoriasis, atopic dermatitis, asthma, allergic rhinitis, relapsing polychondritis, mixed connective tissue disease, graft-versus-host disease, idiopathic pulmonary fibrosis, idiopathic interstitial pneumonia, chronic obstructive pulmonary disease, myelofibrosis, multiple sclerosis, cerebral infarction, ischemic stroke, Alzheimer's disease, Parkinson's disease, depression, developmental epilepsy, Meniere's disease, narcolepsy, macrophage activation syndrome, sepsis, pulmonary hypertension, hyperlipidemia, Behcet's disease, uveitis, osteoporosis, bone fracture, osteosarcoma, cardiac insufficiency, hypertrophic myocardiopathy, atherosclerosis, female gestosis, ovarian cancer, breast cancer, prostate cancer, malignant lymphoma, leukemia, multiple myeloma, lung cancer, granuloma annulare, esophageal cancer, colorectal cancer, pancreatic cancer, gastric cancer, hepatocellular cancer, melanoma, and secondary hemophagocytic lymphohistiocytosis, which includes administering a therapeutically effective amount of the compound or the pharmacologically acceptable salt thereof as described in any one of Embodiments (1) to (9) to a patient.

Embodiment (24) resides in a method for preventing or treating a disease selected from rheumatoid arthritis, arthritis deformans, psoriatic arthritis, ulcerative colitis, primary biliary cholangitis, primary sclerosing cholangitis, pancreatitis, systemic lupus erythematosus, lupus nephritis, systemic scleroderma, Sjogren's syndrome, psoriasis, pustular psoriasis, Behcet's disease, ovarian cancer, and acute myeloid leukemia, which includes administering a therapeutically effective amount of the compound or the pharmacologically acceptable salt thereof as described in any one of Embodiments (1) to (9) to a patient.

Embodiment (25) resides in a method for preventing or treating a disease selected from rheumatoid arthritis, arthritis deformans, psoriatic arthritis, ulcerative colitis, pancreatitis, systemic lupus erythematosus, lupus nephritis, systemic scleroderma, Sjogren's syndrome, pustular psoriasis, and Behcet's disease, which includes administering a therapeutically effective amount of the compound or the pharmacologically acceptable salt thereof as described in any one of Embodiments (1) to (9) to a patient.

Furthermore, another aspect of the present invention resides in use of the compound of formula (I) or the pharmacologically acceptable salt thereof for the manufacture of a preventive or therapeutic agent for a disease and/or an accompanying symptom that can be improved by inhibiting salt-inducible kinases (SIK), or an agent for improving a prognosis of such a disease and/or an accompanying symptom. Embodiments thereof include the following.

Embodiment (26) resides in use of the compound or the pharmacologically acceptable salt thereof as described in any one of Embodiments (1) to (9) for the manufacture of a preventive or therapeutic agent for a disease and/or an accompanying symptom that can be improved by inhibiting salt-inducible kinases (SIK), or an agent for improving a prognosis of such a disease and/or an accompanying symptom.

Embodiment (27) resides in use of the compound or the pharmacologically acceptable salt thereof as described in any one of Embodiments (1) to (9) for the manufacture of a preventive or therapeutic agent for a disease selected from inflammatory diseases, autoinflammatory diseases, autoimmune diseases, proliferative diseases, fibrotic diseases, transplant rejections, diseases involving cartilage turnover disorders, congenital cartilage malformations, diseases involving bone turnover disorders, diseases associated with hypersecretion of TNF-$\alpha$, interferon, IL-6, IL-12, and/or IL-23, respiratory diseases, endocrine and/or metabolic diseases, cardiovascular diseases, skin diseases, and abnormal angiogenesis-related diseases.

Embodiment (28) resides in use of the compound or the pharmacologically acceptable salt thereof as described in any one of Embodiments (1) to (9) for the manufacture of a preventive or therapeutic agent for a disease selected from rheumatoid arthritis, arthritis deformans, psoriatic arthritis, chronic inflammatory demyelinating polyneuropathy, ulcerative colitis, Crohn's disease, autoimmune hepatitis, primary biliary cholangitis, primary sclerosing cholangitis, non-alcoholic fatty liver disease, non-alcoholic steatohepatitis, type 1 diabetes mellitus, type 2 diabetes mellitus, pancreatitis, systemic lupus erythematosus, cutaneous lupus erythematosus, central nervous system lupus, lupus nephritis, antiphospholipid antibody syndrome, chronic kidney disease, acute kidney disease, sarcoidosis, systemic scleroderma, localized scleroderma, Sjogren's syndrome, ANCA-associated vasculitis, immune complex small vessel vasculitis, polyarteritis nodosa, Kawasaki disease, Takayasu arteritis, giant cell arthritis, idiopathic inflammatory muscle disease (polymyositis, dermatomyositis, inclusion body myositis), IgG4-related diseases, juvenile Still's disease, pelvic inflammatory disease, psoriasis, pustular psoriasis, atopic dermatitis, asthma, allergic rhinitis, relapsing polychondritis, mixed connective tissue disease, graft-versus-host disease, idiopathic pulmonary fibrosis, idiopathic interstitial pneumonia, chronic obstructive pulmonary disease, myelofibrosis, multiple sclerosis, cerebral infarction, ischemic stroke, Alzheimer's disease, Parkinson's disease, depression, developmental epilepsy, Meniere's disease, narcolepsy, macrophage activation syndrome, sepsis, pulmonary hypertension, hyperlipidemia, Behcet's disease, uveitis, osteoporosis, bone fracture, osteosarcoma, cardiac insufficiency, hypertrophic myocardiopathy, atherosclerosis, female gestosis, ovarian cancer, breast cancer, prostate cancer, malignant lymphoma, leukemia, multiple myeloma, lung cancer, granuloma annulare, esophageal cancer, colorectal cancer, pancreatic cancer, gastric cancer, hepatocellular cancer, melanoma, and secondary hemophagocytic lymphohistiocytosis.

Embodiment (29) resides in use of the compound or the pharmacologically acceptable salt thereof as described in any one of Embodiments (1) to (9) for the manufacture of a preventive or therapeutic agent for a disease selected from rheumatoid arthritis, arthritis deformans, psoriatic arthritis, ulcerative colitis, primary biliary cholangitis, primary sclerosing cholangitis, pancreatitis, systemic lupus erythematosus, lupus nephritis, systemic scleroderma, Sjogren's syndrome, psoriasis, pustular psoriasis, Behcet's disease, ovarian cancer, and acute myeloid leukemia.

Embodiment (30) resides in use of the compound or the pharmacologically acceptable salt thereof as described in any one of Embodiments (1) to (9) for the manufacture of a preventive or therapeutic agent for a disease selected from rheumatoid arthritis, arthritis deformans, psoriatic arthritis, ulcerative colitis, pancreatitis, systemic lupus erythematosus, lupus nephritis, systemic scleroderma, Sjogren's syndrome, pustular psoriasis, and Behcet's disease.

Subjects of Administration

The compound of formula (I) of the above-described aspect or the pharmaceutical composition including the compound may be administered safely to a patient. In the present description, the term "patient" is an animal, preferably a mammal (such as, for example, a mouse, a rat, a hamster, a rabbit, a cat, a dog, a cow, a sheep, a monkey, or a human), and, in particular, a human.

Administration Routes

The compound of formula (I) of the above-described aspect or the pharmaceutical composition including the compound may be administered orally or parenterally (for example, intravenous, intramuscular, subcutaneous, intra-organ, intranasal, intradermal, ocular, intracerebral, intrarectal, intravaginal, intraperitoneal, or intralesional administration).

(Doses)

The dose of the compound of formula (I) of the above-described aspect or the pharmaceutical composition including the compound is not particularly limited and is variable depending on the subject of administration, the administration route, and the age and the symptom of the subject of administration. For example, the dose is 1 to 1000 mg active ingredient per oral administration and is 0.1 to 1000 mg active ingredient per parenteral administration.

For example, the injection dosage level is in the range of about 0.1 mg/kg/hr to at least 10 mg/kg/hr for about 1 to about 120 hours, in particular, for 24 to 96 hours. In order to achieve an appropriate steady-state level, the compound or the pharmaceutical composition may be bolus administered in about 0.1 mg/kg to about 10 mg/kg or more. The maximum total dosage will not exceed about 1 g/day for a human patient weighing 40 to 80 kg.

A therapeutic regimen for the prevention and/or the treatment of a long-term clinical condition, such as a regressive state, is usually several months or several years long, and thus oral administration is preferred for the convenience and tolerability of the patient. In the typical regimen in the case of oral administration, the customary dose is 1 to 4 administrations per day, in particular, 1 to 3 administrations per day, typically 1 to 2 administrations per day, and most typically 1 administration per day. In the case of a long-acting drug, the typical regimen is 1 oral administration per 2 weeks, 1 oral administration per week, or 1 oral administration per day. Specifically, the drug may be administered every 1 to 14 days, more specifically every 1 to 10 days, still more specifically every 1 to 7 days, and most specifically every 1 to 3 days.

The transdermal dosage is usually selected so that the blood level will be similar to or lower than that achieved with an injection dosage.

(Use as Prodrugs)

The compound of formula (I) of the above-described aspect may be used in the form of a prodrug thereof. The prodrug of the compound of formula (I) is a compound that is converted to the compound of formula (I) by reaction with, for example, enzyme or gastric acid under in-vivo physiological conditions, specifically, a compound that is enzymatically oxidized, reduced, or hydrolyzed into the compound of formula (I), or is a compound that undergoes reaction, for example, hydrolysis with gastric acid or the like and is thereby converted into the compound of formula (I). Examples of the prodrugs of the compounds of formula (I) include compounds in which an amino group in the compounds of formula (I) is acylated, alkylated, or phosphorylated [such as, for example, compounds in which an amino group in the compounds of formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated]; compounds in which a hydroxyl group in the compounds of formula (I) is acylated, alkylated, phosphorylated, or borated (such as, for example, compounds in which a hydroxyl group in the compounds of formula (I) is acetylated, palmitoylated, propanoylated, pivaloylated, succinylated, fumarylated, alanylated, or dimethylaminomethylcarbonylated); and compounds in which a carboxyl group in the compounds of formula (I) is esterified or amidated [such as, for example, compounds in which a carboxyl group in the compounds of formula (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, or methylamidated]. These compounds may be produced from the compounds of formula (I) by a method known per se.

The prodrugs of the compounds of formula (I) may be those described in "Iyakuhin No Kaihatsu (Development of Pharmaceuticals)", Vol. 7, Bunshi Sekkei (Molecular Design), Hirokawa-Shoten Ltd., 1990, pp. 163-198, that transform into the compounds of formula (I) under physiological conditions.

(Combined Use with Other Agents)

To prevent or treat a target disease, the compound of formula (I) may be used in combination with other pharmaceutical drugs. The combined use of other pharmaceutical drugs is expected to offer excellent preventive and/or therapeutic effects. Furthermore, such combination therapy is expected to reduce the side effects of other pharmaceutical drugs by lessening the dosage of the pharmaceutical drugs.

The pharmaceutical drugs that may be used in combination with the compounds of formula (I) (hereinafter, written simply as the companion pharmaceutical drugs) may be selected appropriately in accordance with, for example, the type of the disease suffered by the patient and the severity of the symptom. Examples of the companion pharmaceutical drugs include, but are not limited to:

immunomodulators, such as azathioprine, corticosteroids (for example, prednisolone or dexamethasone), cyclophosphamide, cyclosporin, voclosporin, tacrolimus, mofetil mycophenolate, muromonab-CD3 (OKT3, for example, Orthoclone®), ATG, aspirin, acetaminophen, ibuprofen, naproxen, and piroxicam;

arthritis (for example, rheumatoid arthritis) therapeutic agents, such as azathioprine, corticosteroids (for example, prednisolone or dexamethasone), cyclophosphamide, cyclosporin, tacrolimus, mofetil mycophenolate, muromonab-CD3 (OKT3, for example, Orthoclone®), ATG, aspirin, acetaminophen, ibuprofen, naproxen, piroxicam, tofacitinib, baricitinib, upadacitinib, filgotinib, and tocilizumab;

proliferative disorder therapeutic agents, such as methotrexate, leucovorin, adriamycin, prednisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibodies (for example, Herceptin®), capecitabine, raloxifene hydrochloride, EGFR inhibitors (for example, Iressa®, Tarceva®, Erbitux®), VEGF inhibitors (for example, Avastin®), proteasome inhibitors (for example, Velcade®), Glivec®, and hsp90 inhibitors (for example, 17-AAG);

autoimmune disorder therapeutic agents, such as glucocorticoids, cell growth inhibitors (for example, purine analogues), alkylating agents (for example, nitrogen mustard (cyclophosphamide), nitrosourea, and others), antimetabolites (for example, methotrexate, azathioprine, and mercaptopurine), cytotoxic antibiotics (for example, dactinomycin, anthracycline, mitomycin C, bleomycin, and mithramycin), antibodies (for example, anti-CD20, anti-CD25, or anti-CD3 (OTK3) monoclonal antibodies, Atgam®, and Thymoglobulin®), cyclosporin, tacrolimus, rapamycin (sirolimus), interferons (for example IFN-β), TNF binding proteins (for example, infliximab, etanercept, and adalimumab), mycophenolate, fingolimod, and myriocin;

transplant rejection therapeutic agents, such as calcineurin inhibitors (for example, cyclosporin and tacrolimus (FK506)), mTOR inhibitors (for example, sirolimus and everolimus), antiproliferative agents (for example, azathioprine and mycophenolic acid), corticosteroids (for example, prednisolone and hydrocortisone), antibodies (for example, monoclonal anti-IL-2Rα-receptor antibody, basiliximab, and daclizumab), and polyclonal anti-T-cell antibodies (for example, anti-thymocyte globulin (ATG) and anti-lymphocyte globulin (ALG));

asthma and/or rhinitis and/or COPD therapeutic agents, such as β2-adrenoceptor agonists (for example, salbutamol, levalbuterol, terbutaline, and bitolterol), epinephrine (inhaled or tablet), anticholinergics (for example, ipratropium bromide), glucocorticoids (oral or inhaled), long-acting β2-agonists (for example, salmeterol, formoterol, bambuterol, and sustained-release oral albuterol), combinations of inhaled steroids and long-acting bronchodilators (for example, fluticasone/salmeterol, and budesonide/formoterol), leukotriene antagonists and leukotriene synthesis inhibitors (for example, montelukast, zafirlukast, and zileuton), mediator release inhibitors (for example, cromoglicate and ketotifen), bioregulators of IgE response (for example, omalizumab), antihistamines (for example, cetirizine, cinnarizine, and fexofenadine), and vasoconstrictors (for example, oxymetazoline, xylometazoline, naphazoline, and tramazoline);

inflammatory bowel disease therapeutic agents, such as glucocorticoids (for example, prednisone and budesonide), synthetic disease-modifying immunomodulators (for example, methotrexate, leflunomide, sulfasalazine, mesalazine, azathioprine, 6-mercaptopurine, and cyclosporin), and biological disease-modifying immunomodulators (infliximab, adalimumab, rituximab, ustekinumab, guselkumab, mirikizumab, and abatacept);

systemic lupus erythematosus (SLE) or lupus nephritis (LN) therapeutic agents, such as human monoclonal antibodies (belimumab (Benlysta) and anifrolumab (Saphnelo)), disease-modifying anti-rheumatic drugs (DMARD), such as antimalarials (for example, Plaquenil and hydroxychloroquine), immunosuppressive agents (for example, methotrexate and azathioprine), cyclophosphamide and mycophenolic acid, cyclosporin, voclosporin, immunosuppressants and analgesics, such as nonsteroidal anti-inflammatory drugs, opiates (for example, dextropropoxyphene and co-codamol), opioids (for example, hydrocodone, oxycodone, MS contine, and methadone), and fentanyl-Duragesic transdermal patches;

psoriasis therapeutic agents, for example, topical therapeutic agents, such as bath liquids, moisturizers, medicated creams, and ointments containing coal tar, dithranol (anthralin), corticosteroid-like desoximetasone (Topicort (trademark)), fluocinonide, vitamin D3 analogues (for example, calcipotriol), argan oil, and retinoids (etretinate, acitretin, and tazarotene), systemic therapeutic agents, such as methotrexate, cyclosporin, retinoids, thioguanine, hydroxyurea, sulfasalazine, mofetil mycophenolate, azathioprine, tacrolimus, and fumaric acid esters, and biological preparations, such as Amevive (trademark), Enbrel (trademark), Humira (trademark), Remicade (trademark), Raptiva (trademark), Ustekinumab (IL-12 and IL-23 signaling blocker), and Secukinumab (IL-17 signaling blocker); and allergic reaction therapeutic agents, such as antihistamines (for example, cetirizine, diphenhydramine, fexofenadine, and levocetirizine), glucocorticoids (for example, prednisone, betamethasone, beclomethasone, and dexamethasone), epinephrine, theophylline or anti-leukotrienes (for example, montelukast and zafirlukast), anticholinergics, and decongestants.

The companion pharmaceutical drug may be administered in any manner without limitation. The compound of formula (I) and the companion pharmaceutical drug may be combined at the time of administration. For example, (1) a preparation containing a combination of the compound of formula (I) and the companion pharmaceutical drug may be administered, (2) a preparation containing the compound of formula (I) and a preparation containing the companion pharmaceutical drug may be administered concurrently or separately through the same administration route, or (3) a preparation containing the compound of formula (I) and a preparation containing the companion pharmaceutical drug may be administered concurrently or separately through respective administration routes. A preferred manner of administration may be selected appropriately in accordance with the actual conditions of the medical worksite.

A preparation containing a combination of the compound of formula (I) and the companion pharmaceutical drug may be produced appropriately by the skilled person in accordance with the above description of the pharmaceutical composition containing the compound of formula (I).

The dose of the companion pharmaceutical drug may be selected appropriately based on the dosage clinically used. Furthermore, the ratio of the compound of formula (I) to the companion pharmaceutical drug may be selected appropriately in accordance with factors, such as the disease or the symptom suffered by the subject of administration, the administration route, and the type of the companion pharmaceutical drug that is used. The ratio may be usually determined appropriately in accordance with the actual conditions of the medical worksite based on the common clinical dosage of the companion pharmaceutical drug that is used.

EXAMPLES

Hereinbelow, the present invention will be described in greater detail based on Reference Examples and Examples regarding the synthesis of the compounds of formula (I), and Test Examples regarding the activity of the compounds of formula (I). However, it should be construed that these examples are only illustrative and do not limit the scope of the present invention thereto. In the structural formulas in the following Reference Examples and Examples, "or1" and "or2" indicate that the carbon atom bearing the symbol has a single steric configuration but the absolute steric configuration has not been identified. A wavy line indicates that the compound having two or more asymmetric carbon atoms is a mixture of an R-isomer and an S-isomer distinguished by the stereochemistry of the carbon atom bearing the wavy line. When solid lines are bonded to asymmetric carbon atoms, the compound is a racemic isomer.

Here, typical abbreviations used in the following Reference Examples and Examples are described below.

ABBREVIATIONS

DMSO: dimethyl sulfoxide
ESI: electrospray ionization
g: gram
HATU: O-(7-azabenzotriazol-1-yl)-N,N,N',N'-tetramethyluronium hexafluorophosphate
HOBt: 1-hydroxybenzotriazole
HPLC: high-performance liquid chromatography
M: molar concentration
mmol: millimole
MS: mass spectrometry
NMR: nuclear magnetic resonance
p-: para
tert-: tertiary
TFA: trifluoroacetic acid
WSC·HCl: 1-ethyl-3-(3-dimethylaminopropyl)carbodiimide hydrochloride

Reference Example 1: Synthesis of 1-acetyl-6-bromoindazole-4-carbaldehyde

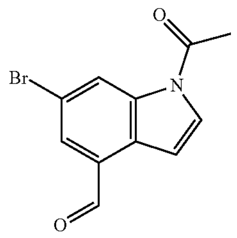

6-Bromo-1H-indazole-4-carbaldehyde (500 mg) was dissolved in tetrahydrofuran (11 mL), pyridine (0.20 mL), acetic anhydride (0.23 mL), and 4-dimethylaminopyridine (27 mg) were added, and stirring was performed at room temperature overnight. After the reaction was completed, the reaction mixture was diluted with ethyl acetate and washed twice with 1 N hydrochloric acid and once with saturated saline. Sodium sulfate was added to the organic layer, filtration was performed, and the filtrate was concentrated under reduced pressure. The residue was suspended and washed with diisopropyl ether to obtain the title compound (524 mg) as a white powder. MS(ESI)m/z:267.1/269.1 [M+H]+

Reference Example 2: Synthesis of [(3R)-3-hydroxybutyl] 4-methylbenzenesulfonate

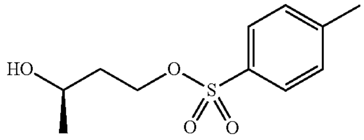 [SMILES: Cc1ccc(S(=O)(=O)OCC[C@@H](C)O)cc1]

Under ice cooling, p-toluenesulfonyl chloride (1.2 g) and triethylamine (1.2 mL) were added to a dichloromethane (10 mL) solution of (3R)-butane-1,3-diol (500 mg), and the mixture was stirred under a nitrogen atmosphere at room temperature for 19 hours. After the reaction was completed, water was added to the reaction mixture, and extraction was performed with chloroform. Sodium sulfate was added to the separated organic layer, and filtration was performed. The filtrate was concentrated under reduced pressure and purified by silica gel column chromatography (hexane:ethyl acetate=90:10 to 50:50) to obtain the title compound (701 mg) as a colorless oily product. MS(ESI)m/z:244.8 [M+H]+

Reference Example 3: Synthesis of 4-bromo-1-(oxetan-3-ylmethyl)pyrazole

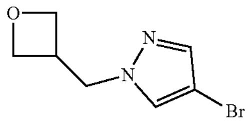 [SMILES: Brc1cnn(CC2COC2)c1]

Under ice cooling, sodium hydride (60%, dispersed in liquid paraffin) (90 mg) was added to an N,N-dimethylformamide (5.0 mL) solution of 4-bromo-1H-pyrazole (300 mg), the mixture was stirred under a nitrogen atmosphere at room temperature for minutes, 3-(bromomethyl) oxetane (370 mg) was added, and then the mixture was further stirred for 3 hours. After the reaction was completed, water was added to the reaction mixture, and extraction was performed with ethyl acetate. The separated organic layer was washed with saturated saline, sodium sulfate was added, and filtration was performed. The filtrate was concentrated under reduced pressure, and the resulting residue was purified by silica gel column chromatography (hexane:ethyl acetate=80:20 to 50:50) to obtain the title compound (355 mg) as a colorless oily product. MS(ESI)m/z:216.9/218.9 [M+H]+

Reference Example 4: Synthesis of 2-[(4-bromopyrazol-1-yl)methyl]-1,3-oxazole

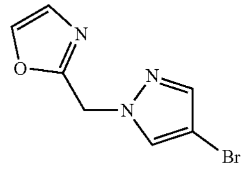 [SMILES: Brc1cnn(Cc2ncco2)c1]

Potassium carbonate (846 mg) was added to a mixture of 4-bromo-1H-pyrazole (300 mg), 2-(chloromethyl) oxazole (288 mg), and acetonitrile (3.0 mL), and the mixture was heated and stirred at 60 °C for 3 hours. After the reaction was completed, the reaction mixture was diluted with chloroform, and then insoluble matter was removed by filtration. The filtrate was concentrated under reduced pressure and then purified by silica gel column chromatography (hexane:ethyl acetate=80:20 to 50:50) to obtain the title compound (303 mg) as a colorless oily product. MS(ESI)m/z:227.7/229.7 [M+H]+

Reference Example 5: Synthesis of 4-bromo-1-[(3-fluorooxetan-3-yl)methyl]pyrazole

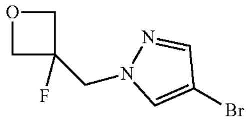 [SMILES: FC1(Cn2cc(Br)cn2)COC1]

Sodium hydride (60%, dispersed in liquid paraffin) (33 mg) was added to an N,N-dimethylformamide (2.0 mL) solution of 4-bromo-1H-pyrazole (100 mg) under ice cooling, and the mixture was stirred at room temperature for 15 minutes. (3-Fluorooxetan-3-yl)methyl p-toluenesulfonate (195 mg) was added, and the mixture was stirred at room temperature for 2 hours. After the reaction was completed, water was added to the reaction mixture, and extraction was performed with ethyl acetate. The organic layer was washed twice with saturated saline and separated with Phase-Separator®, and the organic layer was concentrated under reduced pressure. The residue was purified twice by silica gel column chromatography (hexane:ethyl acetate=90:10 to 70:30) to obtain the title compound (131 mg) as a colorless oily product. MS(ESI)m/z:234.9/236.9 [M+H]+

Reference Example 6: Synthesis of 4-iodo-1-(oxolan-3-ylmethyl)pyrazole

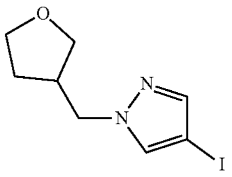 [SMILES: Ic1cnn(CC2CCOC2)c1]

A mixture of 4-iodo-1H-pyrazole (200 mg), potassium carbonate (428 mg), 3-(bromomethyl)tetrahydrofuran (0.15 mL), and N-methyl-2-pyrrolidone (5.2 mL) was heated and stirred at 80 °C for 4 hours. Water was added to the reaction mixture, and extraction was performed twice with ethyl acetate. Thereafter, the organic layer was washed with water and saturated saline, magnesium sulfate was added, and after stirring, insoluble matter was removed by filtration. The residue obtained by concentrating the filtrate under reduced pressure was purified by silica gel column chromatography (hexane:ethyl acetate=80:20 to 45:55) to obtain the title compound (175 mg) as a colorless oily product. MS(ESI) m/z:278.8 [M+H]+

Reference Example 7: Synthesis of 4-iodo-1-(oxolan-2-ylmethyl)pyrazole

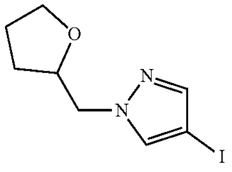 [SMILES: Ic1cnn(CC2CCCO2)c1]

A mixture of 4-iodo-1H-pyrazole (200 mg), potassium carbonate (428 mg), tetrahydrofurfuryl bromide (0.18 mL), and N-methyl-2-pyrrolidone (5.2 mL) was heated and stirred at 80 °C for 3 hours. Water was added to the reaction mixture, and extraction was performed twice with ethyl acetate. Magnesium sulfate was added to the resulting organic layer, the mixture was stirred, and then insoluble matter was removed by filtration. The residue obtained by concentrating the filtrate under reduced pressure was purified by silica gel column chromatography (hexane:ethyl acetate=80:20 to 50:50) to obtain the title compound (231 mg) as a colorless oily product. MS(ESI)m/z:278.9 [M+H]+

Reference Example 8: Synthesis of 4-iodo-1-[(3S)-oxolan-3-yl]pyrazole

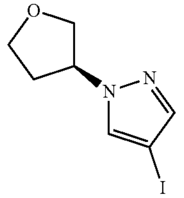 [SMILES: Ic1cnn([C@H]2CCOC2)c1]

A mixture of 4-iodo-1H-pyrazole (360 mg), cesium carbonate (807 mg), p-toluenesulfonic acid [(3R)-tetrahydrofuran-3-yl] (300 mg), and N,N-dimethylformamide (6.2 mL) was heated and stirred at 80 °C for 5 hours. Water was added to the reaction mixture, and extraction was performed with ethyl acetate. The organic layer was washed with water and saturated saline, sodium sulfate was added, the mixture was stirred, and then insoluble matter was removed by filtration. The residue obtained by concentrating the filtrate under reduced pressure was purified by column chromatography (hexane:ethyl acetate=85:15 to 60:40) using an NH silica gel column and a Si silica gel column in series to obtain the title compound (291 mg) as a white powder. MS(ESI)m/z:264.8 [M+H]+

Reference Example 9: Synthesis of 2-bromo-6-(difluoromethoxy)-N-(2-propenyl)benzamide

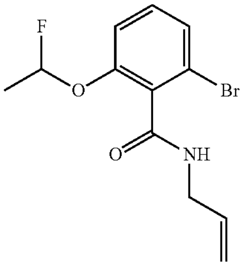 [SMILES: C=CCNC(=O)c1c(Br)cccc1OC(C)F]

2-Bromo-6-(difluoromethoxy)benzoic acid (1.5 g) was dissolved in dichloromethane (9.8 mL), oxalyl dichloride (1.3 mL) and 1 drop of DMF were added, and the mixture was stirred at room temperature for 2 hours. After the reaction was completed, the reaction solution was concentrated under reduced pressure, and then an azeotropic treatment was performed three times using toluene. The resulting residue was dissolved in dichloromethane (9.8 mL), allylamine hydrochloride (552 mg) was added, and the mixture was stirred under ice cooling. Triethylamine (3.4 mL) and dichloromethane (9.8 mL) were added, and the mixture was stirred at room temperature for 1 hour. After the reaction was completed, water was added to the reaction mixture, and extraction was performed twice with chloroform. The organic layers were combined and washed sequentially with a saturated aqueous ammonium chloride solution and saturated saline, and sodium sulfate was added. The filtrate obtained by filtration was concentrated under reduced pressure to obtain the title compound (1.5 g) as a white powder. MS(ESI)m/z:306.0/308.0 [M+H]+

Reference Example 10: Synthesis of tert-butyl N-[2-bromo-6-(difluoromethoxy)benzoyl]-N-(2-propenyl)carbamate

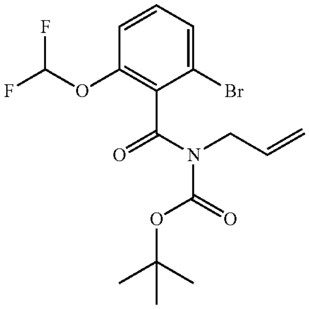 [SMILES: C=CCN(C(=O)OC(C)(C)C)C(=O)c1c(Br)cccc1OC(F)F]

2-Bromo-6-(difluoromethoxy)-N-(2-propenyl)benzamide (1.5 g) described in Reference Example 9 was dissolved in dichloromethane (9.8 mL), di-tert-butyl dicarbonate (2.1 g), triethylamine (0.82 mL), and 4-dimethylaminopyridine (60 mg) were added, and the mixture was stirred at room temperature overnight. After the reaction was completed, the reaction solution was diluted with ethyl acetate, washed twice with a saturated aqueous ammonium chloride solution and once with saturated saline, and sodium sulfate was added. The filtrate obtained by filtration was concentrated under reduced pressure to obtain the title compound (2.2 g) as an orange oily product. MS(ESI)m/z:350.1/352.0 [M−tBu+H]+

Reference Example 11: Synthesis of tert-butyl 8-(difluoromethoxy)-4-methyl-1-oxoisoquinoline-2-carboxylate

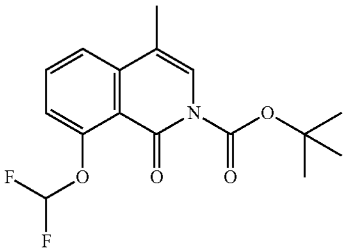 [SMILES: Cc1cn(C(=O)OC(C)(C)C)c(=O)c2c(OC(F)F)cccc12]

tert-Butyl N-[2-bromo-6-(difluoromethoxy)benzoyl]-N-(2-propenyl)carbamate (2.2 g) described in Reference Example 10, palladium(II) acetate (110 mg), and tetrabutylammonium chloride (1.5 g) were dissolved in N,N-dimethylformamide (20 mL), N,N-diisopropylethylamine (1.7 mL)

was added, and the mixture was stirred under a nitrogen atmosphere at 80 °C for 2 hours. Palladium (II) acetate (219 mg) was added, and the mixture was stirred under a nitrogen atmosphere at 80 °C for 3 hours. After the reaction was completed, water was added to the reaction mixture, and extraction was performed twice with a solvent obtained by mixing hexane and ethyl acetate at 1:1. The organic layers were combined and washed sequentially with a saturated aqueous ammonium chloride solution and saturated saline, and sodium sulfate and activated carbon were added and allowed to stand. The filtrate obtained by filtration was concentrated under reduced pressure to obtain the title compound (1.6 g) as a light yellow oily product. MS(ESI) m/z:270.1 [M−tBu+H]+

Reference Example 12: Synthesis of tert-butyl 4-bromo-2-fluoro-6-methoxybenzoate

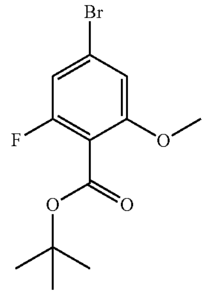 [SMILES: COc1cc(Br)cc(F)c1C(=O)OC(C)(C)C]

A 5 M sodium methoxide methanol solution (11 mL) was added to a tetrahydrofuran (110 mL) solution of tert-butyl 4-bromo-2,6-difluorobenzoate (15 g) under ice cooling, and the mixture was stirred at room temperature for 2 hours. The reaction solution was concentrated under reduced pressure, a saturated aqueous ammonium chloride solution was added to the resulting residue, and extraction was performed twice with ethyl acetate. The organic layer was separated with Phase-Separator®, and the organic layer was concentrated under reduced pressure. The concentrated residue was purified by silica gel column chromatography (hexane:ethyl acetate=100:0 to 90:10) to obtain the title compound (9.0 g) as a white powder. MS(ESI)m/z:248.7/250.7 [M+H−tBu]+

Reference Example 13: Synthesis of tert-butyl 4-bromo-2-hydroxy-6-methoxybenzoate

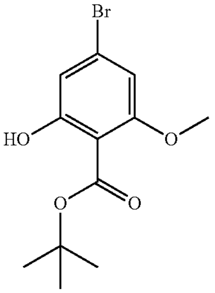 [SMILES: COc1cc(Br)cc(O)c1C(=O)OC(C)(C)C]

Sodium hydride (60%, dispersed in liquid paraffin) (2.7 g) was added to an N,N-dimethylformamide (49 mL) solution of 2-(methylsulfonyl) ethanol (3.6 mL) under ice cooling, the mixture was stirred for 30 minutes, and then an N,N-dimethylformamide (24 mL) solution of tert-butyl 4-bromo-2-fluoro-6-methoxybenzoate (9.0 g) described in Reference Example 12 was added. The reaction solution was stirred at room temperature for 2 days, 1 N hydrochloric acid (70 mL) was added under ice cooling, and then extraction was performed twice with ethyl acetate. The organic layer was washed twice with water and once with saturated saline, sodium sulfate was added, the mixture was filtered, and the filtrate was concentrated under reduced pressure. The resulting residue was purified twice by silica gel column chromatography (hexane:ethyl acetate=100:0 to 90:10) to obtain the title compound (6.1 g) as a colorless oily product. MS(ESI)m/z:246.7/248.7 [M+H−tBu]+

Reference Example 14: Synthesis of tert-butyl 4-bromo-2-(difluoromethoxy)-6-methoxybenzoate

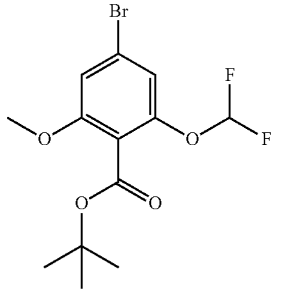 [SMILES: COc1cc(Br)cc(OC(F)F)c1C(=O)OC(C)(C)C]

To a solution of acetonitrile (29 mL) of tert-butyl 4-bromo-2-hydroxy-6-methoxybenzoate (6.1 g) described in Reference Example 13 and water (29 mL), potassium hydroxide (11 g) was added little by little under ice cooling, and the mixture was stirred for 10 minutes. Diethyl (bromodifluoromethyl)phosphonate (7.6 g) was added dropwise under ice cooling, and the mixture was stirred at room temperature for 2 hours. Water was added to the reaction solution, extraction was performed twice with ethyl acetate, sodium sulfate was added, the mixture was filtered, and the filtrate was concentrated under reduced pressure. The resulting residue was purified by silica gel column chromatography (hexane:ethyl acetate=100:0 to 80:20) to obtain the title compound (5.1 g) as a colorless oily product. MS(ESI)m/z:297.5/299.5 [M+H−tBu]+

Reference Example 15: Synthesis of 4-bromo-2-(difluoromethoxy)-6-methylbenzoic acid

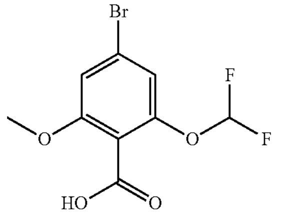 [SMILES: COc1cc(Br)cc(OC(F)F)c1C(=O)O]

To a dichloromethane (94 mL) solution of tert-butyl 4-bromo-2-(difluoromethoxy)-6-methoxybenzoate (10 g) described in Reference Example 14, TFA (33 mL) was added, and the mixture was stirred at room temperature for 6 hours. The reaction solution was concentrated under reduced pressure, toluene (50 mL) was added to the residue, and then the mixture was concentrated under reduced pressure again. The concentrated residue was suspended and washed with hexane to obtain the title compound (8.0 g) as a white powder. MS(ESI)m/z:296.7/298.7 [M+H]+

Reference Example 16: Synthesis of 4-bromo-2-(difluoromethoxy)-N-[(1R,2S)-2-fluorocyclopropyl]-6-methoxybenzamide

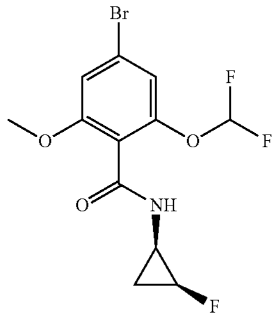 [SMILES: COc1cc(Br)cc(OC(F)F)c1C(=O)N[C@@H]1C[C@@H]1F]

To a dichloromethane (90 mL) suspension of 4-bromo-2-(difluoromethoxy)-6-methylbenzoic acid (8.0 g) described in Reference Example 15, oxalyl dichloride (11 mL) and N,N-dimethylformamide (0.21 mL) were added under ice cooling, and the mixture was stirred at room temperature for 1.5 hours. The reaction solution was concentrated under reduced pressure, triethylamine (19 mL) and (1R,2S)-2-fluorocyclopropan-1-amine hydrochloride (4.5 g) were added to a dichloromethane (90 mL) solution of the residue, and then the mixture was stirred at room temperature for 2 hours. Water was added to the reaction solution, extraction was performed with dichloromethane, the organic layer was separated with Phase-Separator®, and the organic layer was concentrated under reduced pressure. The resulting residue was purified by silica gel column chromatography (hexane: ethyl acetate=90:10 to 50:50) to obtain the title compound (6.9 g) as a white powder.

MS(ESI)m/z:353.8/355.8 [M+H]+

Reference Example 17: Synthesis of 2-(difluoromethoxy)-N-[(1R,2S)-2-fluorocyclopropyl]-6-methoxy-4-(4,4,5,5-tetramethyl-1,3,2-dioxaborolane-2-yl)benzamide

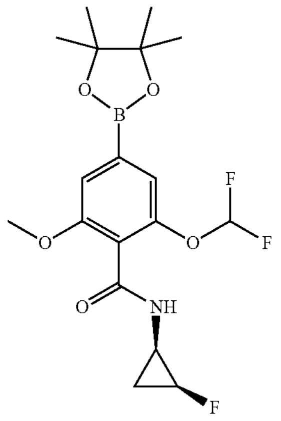 [SMILES: COc1cc(B2OC(C)(C)C(C)(C)O2)cc(OC(F)F)c1C(=O)N[C@@H]1C[C@@H]1F]

A 1,4-dioxane (21 mL) suspension of 4-bromo-2-(difluoromethoxy)-N-[(1R,2S)-2-fluorocyclopropyl]-6-methoxybenzamide (3.0 g) described in Reference Example 16, a [1,1'-bis(diphenylphosphino)ferrocene]palladium(II) dichloride dichloromethane adduct (692 mg), potassium acetate (2.5 g), and bis(pinacolato)diboron (2.6 g) was substituted with nitrogen and stirred at 100 °C for 2 hours. The insoluble matter was removed by filtration, and the filtrate was concentrated under reduced pressure. The resulting residue was purified by silica gel column chromatography (hexane:ethyl acetate=90:10 to 50:50) to obtain the title compound (1.9 g) as a brown viscous product. MS(ESI)m/z:401.9 [M+H]+

Reference Example 18: Synthesis of 6-bromo-3-iodo-1H-indazole-4-carbonitrile

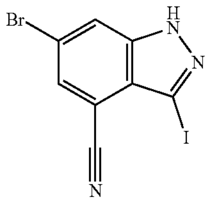 [SMILES: N#Cc1cc(Br)cc2[nH]nc(I)c12]

6-Bromo-1H-indazole-4-carbonitrile (2.0 g) was dissolved in N,N-dimethylformamide (20 mL), and stirring was performed under ice cooling. Potassium hydroxide (2.5 g) and iodine (6.9 g) were added, and the mixture was stirred under ice cooling for 30 minutes and then stirred at room temperature for 88 hours. After the reaction was completed, an aqueous sodium thiosulfate solution (50 mL) was added to the reaction solution under ice cooling, the mixture was stirred at room temperature for 1 hour, water (150 mL) was added, and then the mixture was stirred at room temperature for 1 hour. The solid was collected by filtration and washed with an excess amount of water to obtain the title compound (2.8 g) as a light brown powder. MS(ESI)m/z:345.9/347.9 [M−H]−

Reference Example 19: Synthesis of 6-bromo-3-iodo-2-methylindazole-4-carbonitrile

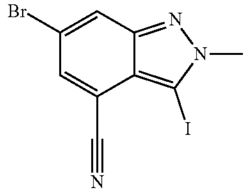

6-Bromo-3-iodo-1H-indazole-4-carbonitrile (2.8 g) described in Reference Example 18 was suspended in ethyl acetate (82 mL), and stirring was performed under ice cooling. Trimethyloxonium tetrafluoroborate (1.7 g) was added, and the mixture was stirred at room temperature for 90 hours. After the reaction was completed, a saturated aqueous sodium bicarbonate solution (30 mL) and water (50 mL) were added to the reaction mixture, and the mixture was stirred at room temperature for 1 hour. The solid was collected by filtration and washed with an excess amount of water to obtain the title compound (2.7 g) as a light brown powder.

MS(ESI)m/z:361.7/363.7 [M+H]+

Reference Example 20: Synthesis of 4-(6-bromo-4-cyano-2-methylindazol-3-yl)-2-(difluoromethoxy)-N-[(1R,2S)-2-fluorocyclopropyl]-6-methoxybenzamide

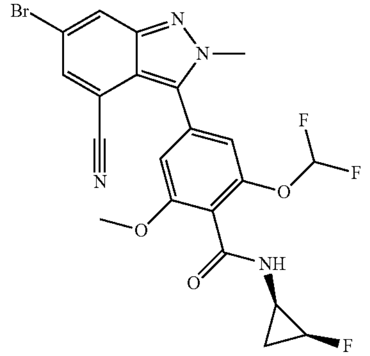 [SMILES: COc1cc(-c2c3c(C#N)cc(Br)cc3nn2C)cc(OC(F)F)c1C(=O)N[C@@H]1C[C@@H]1F]

A mixture of 6-bromo-3-iodo-2-methylindazole-4-carbonitrile (129 mg) described in Reference Example 19, 2-(difluoromethoxy)-N-[(1R,2S)-2-fluorocyclopropyl]-6-methoxy-4-(4,4,5,5-tetramethyl-1,3,2-dioxaborolane-2-yl) benzamide (172 mg) described in Reference Example 17, water (0.36 mL), potassium carbonate (99 mg), a [1,1'-bis (diphenylphosphino)ferrocene]palladium(II) dichloride dichloromethane adduct (29 mg), and 1,4-dioxane (3.6 mL) was heated and stirred under a nitrogen atmosphere at 100 °C for 4 hours. After the reaction was completed, water was added to the reaction mixture, extraction was performed twice with chloroform, the organic layer was separated with Phase-Separator®, and then the organic layer was concentrated under reduced pressure. The residue was purified by silica gel column chromatography (hexane:ethyl acetate=70:30 to 0:100) to obtain the title compound (73 mg) as a light yellow oily product.

MS(ESI)m/z:508.8/510.8 [M+H]+

Reference Example 21: Synthesis of 4-[4-cyano-2-methyl-6-(4,4,5,5-tetramethyl-1,3,2-dioxaborolan-2-yl)indazol-3-yl]-2-(difluoromethoxy)-N-[(1R,2S)-2-fluorocyclopropyl]-6-methoxybenzamide

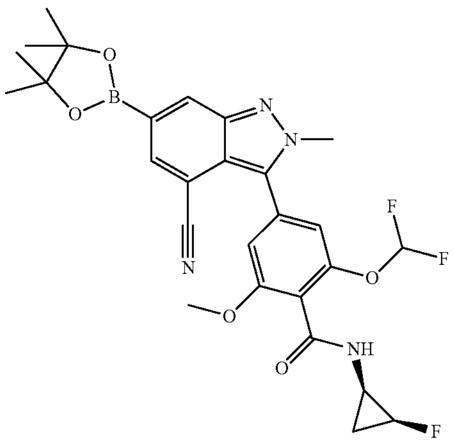 [SMILES: COc1cc(-c2c3c(C#N)cc(B4OC(C)(C)C(C)(C)O4)cc3nn2C)cc(OC(F)F)c1C(=O)N[C@@H]1C[C@@H]1F]

4-(6-Bromo-4-cyano-2-methylindazol-3-yl)-2-(difluoromethoxy)-N-[(1R,2S)-2-fluorocyclopropyl]-6-methoxybenzamide (3.5 g) described in Reference Example 20, bis(pinacolato)diboron (2.1 g), a [1,1'-bis(diphenylphosphino)ferrocene]palladium(II) dichloride dichloromethane adduct (560 mg), and potassium acetate (2.0 g) were suspended in 1,4-dioxane (17 mL), and stirring was performed under a nitrogen atmosphere at 95 °C for 3 hours. After the reaction was completed, the reaction solution was filtered, and the filtrate was concentrated under reduced pressure. The residue was purified by silica gel column chromatography (hexane:ethyl acetate=30:70 to 0:100) to obtain the title compound (2.1 g) as an orange oily product. MS(ESI) m/z:557.4 [M+H]+

Reference Example 22: Synthesis of 6-bromo-3-iodo-4-methoxy-1H-indazole

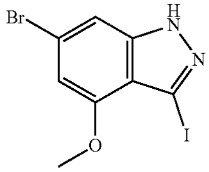

6-Bromo-4-methoxy-1H-indazole (16 g) was dissolved in N,N-dimethylformamide (150 mL), and stirring was performed under ice cooling. Potassium hydroxide (14 g) and iodine (35 g) were added, and the mixture was stirred at room temperature for overnight. After the reaction was completed, an aqueous sodium thiosulfate solution (100 mL) was added to the reaction solution under ice cooling, water (700 mL) was added, and the mixture was stirred at room temperature for 1 hour. The solid was collected by filtration and washed with an excess amount of water to obtain the title compound (24 g) as a light brown powder.

MS(ESI)m/z:352.9/354.8 [M+H]+

Reference Example 23: Synthesis of 6-bromo-3-iodo-4-methoxy-2-methylindazole

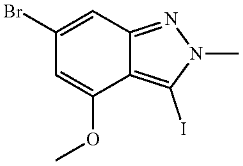

6-Bromo-3-iodo-4-methoxy-1H-indazole (12 g) described in Reference Example 22 was suspended in ethyl acetate (161 mL), trimethyloxonium tetrafluoroborate (5.7 g) was added, and the mixture was stirred at room temperature for 14 hours. After the reaction was completed, a saturated aqueous sodium bicarbonate solution (100 mL) and water (50 mL) were added to the reaction mixture. After stirring at room temperature for 2 hours, the organic layer was separated, and extraction from the aqueous layer was performed twice with a solvent obtained by mixing chloroform and methanol at 10:1. The organic layers were combined, sodium sulfate was added, the mixture was filtered, the residue obtained by concentrating the filtrate was purified by NH silica gel column chromatography (hexane:ethyl acetate=90:10 to 75:25), and then the purified residue was suspended and washed with diisopropyl ether to obtain the title compound (9.1 g) as a light brown powder.

MS(ESI)m/z:366.7/368.7 [M+H]+

Reference Example 24: Synthesis of 4-(6-bromo-4-methoxy-2-methylindazol-3-yl)-2-(difluoromethoxy)-N-[(1R,2S)-2-fluorocyclopropyl]-6-methoxybenzamide

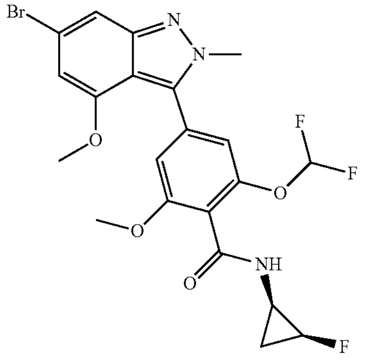 [SMILES: COc1cc(-c2c3c(OC)cc(Br)cc3nn2C)cc(OC(F)F)c1C(=O)N[C@@H]1C[C@@H]1F]

A mixture of 6-bromo-3-iodo-4-methoxy-2-methylindazole (100 mg) described in Reference Example 23, 2-(difluoromethoxy)-N-[(1R,2S)-2-fluorocyclopropyl]-6-methoxy-4-(4,4,5,5-tetramethyl-1,3,2-dioxaborolane-2-yl) benzamide (131 mg) described in Reference Example 17, water (0.27 mL), potassium carbonate (75 mg), a [1,1'-bis (diphenylphosphino)ferrocene]palladium(II) dichloride dichloromethane adduct (22 mg), and 1,4-dioxane (2.7 mL) was heated and stirred under a nitrogen atmosphere at 100 °C for 4 hours. After the reaction was completed, water was added to the reaction mixture, extraction was performed twice with chloroform, the organic layer was separated with Phase-Separator®, and then the organic layer was concentrated under reduced pressure. The residue was purified by silica gel column chromatography (hexane:ethyl acetate=70:30 to 0:100) to obtain the title compound (86 mg) as a light yellow oily product. MS(ESI)m/z:513.9/515.8 [M+H]+

Reference Example 25: Synthesis of N-[(1R,2S)-2-fluorocyclopropyl]-2-hydroxy-6-methoxybenzamide

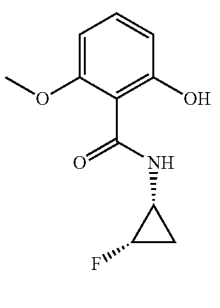 [SMILES: COc1cccc(O)c1C(=O)N[C@@H]1C[C@@H]1F]

1,1'-Carbonyldiimidazole (4.8 g) was added to a dichloromethane (30 mL) suspension of 2-hydroxy-6-methoxybenzoic acid (5.0 g), the mixture was stirred at room temperature for 45 minutes, (1R,2S)-2-fluorocyclopropan-1-amine hydrochloride (3.5 g) and triethylamine (5.0 mL) were added to the reaction solution, and then the mixture was stirred at room temperature for 15 hours. 1 N hydrochloric acid was added to the reaction solution, and the mixture was extracted twice with chloroform. The organic layer was washed with saturated aqueous sodium bicarbonate solution and separated with Phase-Separator®, and the organic layer was concentrated under reduced pressure. The resulting residue was purified by silica gel column chromatography (hexane:ethyl acetate=85:15 to 65:35) to obtain the title compound (4.6 g) as a colorless oily product. MS(ESI) m/z:225.9 [M+H]+

Reference Example 26: Synthesis of 2-(difluoromethoxy)-N-[(1R,2S)-2-fluorocyclopropyl]-6-methoxybenzamide

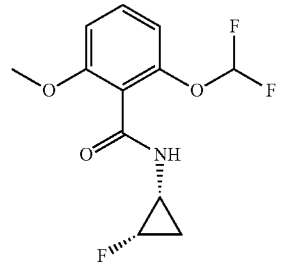 [SMILES: COc1cccc(OC(F)F)c1C(=O)N[C@@H]1C[C@@H]1F]

To a solution of acetonitrile (23 mL) of N-[(1R,2S)-2-fluorocyclopropyl]-2-hydroxy-6-methoxybenzamide (4.6 g) described in Reference Example 25 and water (23 mL), potassium hydroxide (11 g) was added little by little under ice cooling, and the mixture was stirred for 5 minutes. Under ice cooling, diethyl (bromodifluoromethyl)phosphonate (7.2 mL) was added dropwise, and the mixture was stirred at room temperature for 40 minutes. Ethyl acetate was added to the reaction solution for extraction, the organic layer was washed with saturated saline, magnesium sulfate was added for filtration, and then the filtrate was concentrated under reduced pressure. The resulting residue was purified by NH silica gel column chromatography (hexane:ethyl acetate=0:100) and then suspended and washed using diisopropyl ether to obtain the title compound (4.3 g) as a colorless powder. MS(ESI)m/z:276.0 [M+H]+

Reference Example 27: Synthesis of 2-(difluoromethoxy)-4-(1,3,6,2-dioxazaborocan-2-yl)-N-[(1R,2S)-2-fluorocyclopropyl]-6-methoxybenzamide

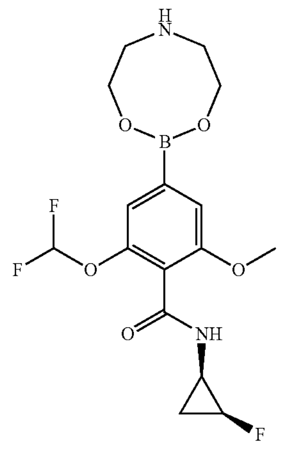 [SMILES: COc1cc(B2OCCNCCO2)cc(OC(F)F)c1C(=O)N[C@@H]1C[C@@H]1F]

To a tetrahydrofuran (5.0 mL) suspension of 2-(difluoromethoxy)-N-[(1R,2S)-2-fluorocyclopropyl]-6-methoxybenzamide (4.3 g) described in Reference Example 26, bis(pinacolato)diboron (4.2 g), 4,4'-di-tert-butyl-2,2'-bipyridyl (84 mg), and bis(1,5-cyclooctadiene)di-μ-methoxydiiridium(I) (104 mg) were added, and the mixture was stirred under a nitrogen atmosphere and heating and refluxing for 1.5 hours. Further, bis(1,5-cyclooctadiene)di-μ-methoxydiiridium(I) (208 mg) and 4,4'-di-tert-butyl-2,2'-bipyridyl (169 mg) were added to the reaction solution, and the mixture was stirred under heating and refluxing for 3 hours. Subsequently, THF (20 mL) and 2-(2-hydroxyethylamino) ethanol (3.3 g) were added to the reaction solution at room temperature, and the mixture was stirred for 14 hours. The reaction solution was filtered and washed with THF (about 40 mL) to obtain the title compound (5.5 g) as a gray powder. MS(ESI)m/z:319.9 [M+H–$C_4H_7N$]+

Reference Example 28: Synthesis of [3-(difluoromethoxy)-4-[(1R,2S)-2-fluorocyclopropyl]carbamoyl]-5-methoxyphenyl]boronic acid

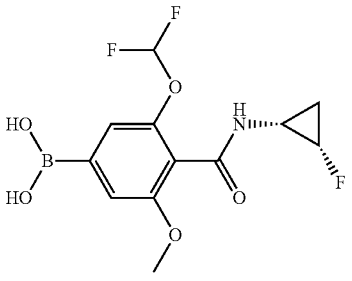 [SMILES: COc1cc(B(O)O)cc(OC(F)F)c1C(=O)N[C@@H]1C[C@@H]1F]

1 N hydrochloric acid (30 mL) was added to 2-(difluoromethoxy)-4-(1,3,6,2-dioxazaborocan-2-yl)-N-[(1R,2S)-2-fluorocyclopropyl]-6-methoxybenzamide (5.5 g) described in Reference Example 27, and the mixture was stirred at room temperature for 2 hours. The reaction solution was filtered and washed twice with a total of about 50 mL of water to obtain the title compound (3.7 g) as a gray powder.

MS(ESI)m/z:319.9 [M+H]+

Reference Example 29: Synthesis of 6-bromo-4-(difluoromethyl)-1H-indazole

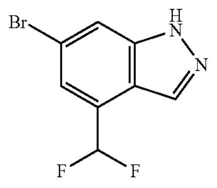 [SMILES: FC(F)c1cc(Br)cc2[nH]ncc12]

1-Acetyl-6-bromoindazole-4-carbaldehyde (2.3 g) described in Reference Example 1 was suspended in dichloromethane (43 mL), diethylaminosulfur trifluoride (2.3 mL) was added under ice cooling, and the mixture was stirred under ice cooling for 1 hour and at room temperature overnight. After the reaction was completed, the reaction solution was added dropwise to a saturated aqueous sodium bicarbonate solution (150 ml), water (100 ml) was added, and then extraction was performed twice with chloroform. The organic layers were combined and concentrated, the residue was dissolved in a mixed solvent of methanol (43 mL) and tetrahydrofuran (43 mL), a 1 N aqueous sodium hydroxide solution (17 mL) was added, and then the mixture was stirred at room temperature for 1 hour. After the reaction was completed, 1 N hydrochloric acid (17 mL) was added to the reaction solution, the mixture was extracted with chloroform, and the organic layer was separated with Phase-Separator® and then concentrated under reduced pressure to obtain the title compound (2.6 g) as a yellow powder. MS(ESI)m/z:246.7/248.7 [M+H]+

Reference Example 30: Synthesis of 6-bromo-4-(difluoromethyl)-3-iodo-1H-indazole

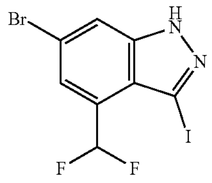 [SMILES: FC(F)c1cc(Br)cc2[nH]nc(I)c12]

6-Bromo-4-(difluoromethyl)-1H-indazole (229 mg) described in Reference Example 29 was dissolved in N,N-dimethylformamide (2.1 mL), potassium hydroxide (182 mg) and iodine (471 mg) were added, and the mixture was stirred at room temperature for 5 hours. After the reaction was completed, an aqueous sodium thiosulfate solution and an excess amount of water were added to the reaction solution under ice cooling, and the mixture was stirred at room temperature for 10 minutes. The solid was collected by filtration and washed with an excess amount of water to obtain the title compound (328 mg) as a light brown powder.

MS(ESI)m/z:373.0/375.0 [M+H]+

Reference Example 31: Synthesis of 6-bromo-4-(difluoromethyl)-3-iodo-2-methylindazole

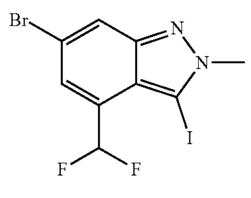

6-Bromo-4-(difluoromethyl)-3-iodo-1H-indazole (202 mg) described in Reference Example 30 was dissolved in ethyl acetate (2.6 mL), trimethyloxonium tetrafluoroborate (99 mg) was added, and the mixture was stirred at room temperature for 2 hours. After the reaction was completed, a saturated aqueous sodium bicarbonate solution and chloroform were added to the reaction mixture, the organic layer was separated with Phase-Separator®, and the organic layer was concentrated under reduced pressure. The residue was purified by silica gel column chromatography (hexane:ethyl acetate=95:5 to 75:25) to obtain the title compound (148 mg) as a white powder. MS(ESI)m/z:386.8/388.8 [M+H]+

Reference Example 32: Synthesis of 4-[6-bromo-4-(difluoromethyl)-2-methylindazol-3-yl]-2-(difluoromethoxy)-N-[(1R,2S)-2-fluorocyclopropyl]-6-methoxybenzamide

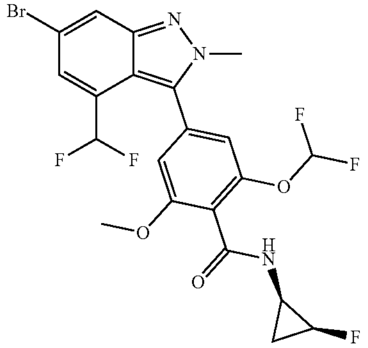 [SMILES: COc1cc(-c2c3c(C(F)F)cc(Br)cc3nn2C)cc(OC(F)F)c1C(=O)N[C@@H]1C[C@@H]1F]

A mixture of 6-bromo-4-(difluoromethyl)-3-iodo-2-methylindazole (40 mg) described in Reference Example 31, [3-(difluoromethoxy)-4-[(1R,2S)-2-fluorocyclopropyl]carbamoyl]-5-methoxyphenyl]boronic acid (33 mg) described in Reference Example 28, water (0.17 mL), a [1,1'-bis(diphenylphosphino)ferrocene]palladium(II) dichloride dichloromethane adduct (8.4 mg), potassium carbonate (43 mg), and 1,4-dioxane (0.69 mL) was heated and stirred under a nitrogen atmosphere at 100 °C for 1 hour. After the reaction was completed, water was added to the reaction mixture, extraction was performed with chloroform, the organic layer was separated with Phase-Separator®, and then the organic layer was concentrated under reduced pressure. The residue was purified by silica gel column chromatography (hexane:ethyl acetate=60:40 to 20:80) to obtain the title compound (24 mg) as a white powder. MS(ESI)m/z:534.3/536.3 [M+H]+

Reference Example 33: Synthesis of 6-bromo-3-iodo-2-methylindazol-4-ol

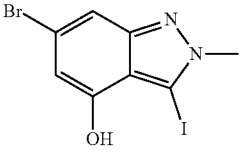

6-Bromo-3-iodo-4-methoxy-2-methylindazole (1.0 g) described in Reference Example 23 was dissolved in dichloromethane (25 mL), a 1 M boron tribromide dichloromethane solution (14 mL) was added dropwise under ice cooling for 20 minutes, and then the mixture was stirred at room temperature for 46 hours. After the reaction was completed, water was added to the reaction mixture under ice cooling, and the precipitate was collected by filtration and washed with water to obtain the title compound (1.2 g) as a light gray powder. MS(ESI)m/z:353.0/355.0 [M+H]+

Reference Example 34: Synthesis of 6-bromo-3-iodo-2-methyl-4-[3-(oxan-2-yloxy)propoxy]indazole

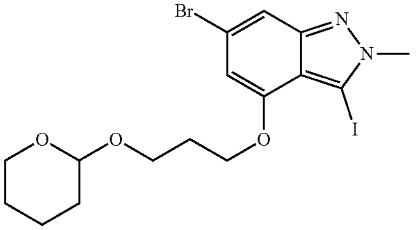 [SMILES: Cn1nc2cc(Br)cc(OCCCOC3CCCCO3)c2c1I]

6-Bromo-3-iodo-2-methylindazol-4-ol (100 mg) described in Reference Example 33 and potassium carbonate (117 mg) were suspended in N,N-dimethylformamide (3.0 mL), 2-(3-bromopropoxy)tetrahydropyran (95 mg) was added, and the mixture was stirred under a nitrogen atmosphere at 80 °C for 45 hours. After the reaction was completed, water was added to the reaction mixture, extraction was performed with ethyl acetate, and the organic layer was washed twice with saturated saline. The organic layer was filtrated with Phase-Separator®, and the organic layer was concentrated under reduced pressure. The residue was purified by NH silica gel column chromatography (hexane: ethyl acetate=95:5 to 80:20) to obtain the title compound (129 mg) as a colorless viscous product. MS(ESI)m/z:495.1/497.2 [M+H]+

Reference Example 35: Synthesis of 4-[6-bromo-2-methyl-4-[3-(oxan-2-yloxy)propoxy]indazol-3-yl]-2-(difluoromethoxy)-N-[(1R,2S)-2-fluorocyclopropyl]-6-methoxybenzamide

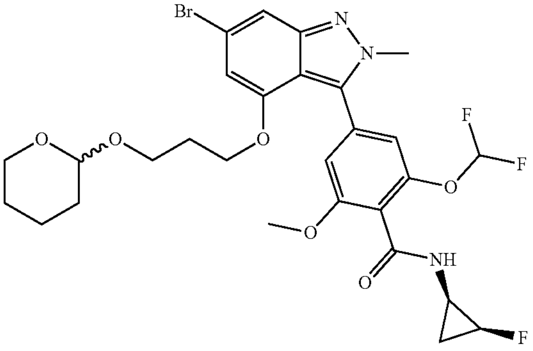 [SMILES: COc1cc(-c2c3c(OCCCOC4CCCCO4)cc(Br)cc3nn2C)cc(OC(F)F)c1C(=O)N[C@@H]1C[C@@H]1F]

A mixture of 6-bromo-3-iodo-2-methyl-4-[3-(oxan-2-yloxy)propoxy]indazole (125 mg) described in Reference Example 34, [3-(difluoromethoxy)-4-[[(1R,2S)-2-fluorocyclopropyl]carbamoyl]-5-methoxyphenyl]boronic acid (97 mg) described in Reference Example 28, potassium carbonate (70 mg), a [1,1'-bis(diphenylphosphino)ferrocene]palladium(II) dichloride dichloromethane adduct (21 mg), 1,4-dioxane (5.0 mL), and water (0.50 mL) was heated and stirred under a nitrogen atmosphere at 100 °C for 2 hours. After the reaction was completed, ethyl acetate was added to the reaction solution, and the mixture was filtered. Water was added to the filtrate, extraction was performed with ethyl acetate, and then the organic layer was washed with saturated saline. Sodium sulfate was added to the organic layer, insoluble matter was removed by filtration, and the organic layer was concentrated under reduced pressure. The residue was purified by NH silica gel column chromatography (hexane:ethyl acetate=70:30 to 30:70) to obtain the title compound (108 mg) as a colorless powder. MS(ESI) m/z:642.0/643.9 [M+H]+

Reference Example 36: Synthesis of 2-(difluoromethoxy)-N-[(1R,2S)-2-fluorocyclopropyl]-6-methoxy-4-[2-methyl-6-(1-methylpyrazol-4-yl)-4-[3-(oxan-2-yloxy)propoxy]indazol-3-yl]benzamide

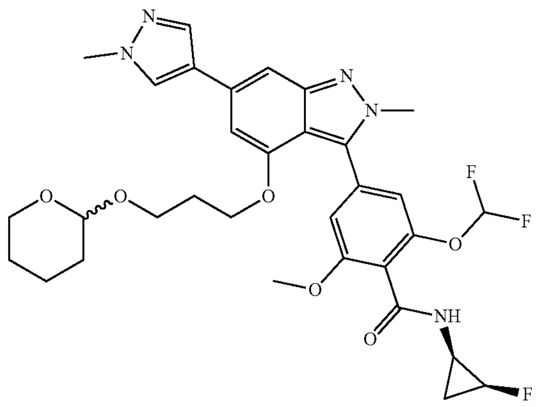 [SMILES: COc1cc(-c2c3c(OCCCOC4CCCCO4)cc(-c4cnn(C)c4)cc3nn2C)cc(OC(F)F)c1C(=O)N[C@@H]1C[C@@H]1F]

A mixture of 4-[6-bromo-2-methyl-4-[3-(oxan-2-yloxy)propoxy]indazol-3-yl]-2-(difluoromethoxy)-N-[(1R,2S)-2-fluorocyclopropyl]-6-methoxybenzamide (104 mg) described in Reference Example 35, 1-methyl-4-(4,4,5,5-tetramethyl-1,3,2-dioxaborolan-2-yl)pyrazole (51 mg), potassium carbonate (45 mg), a [1,1'-bis(diphenylphosphino)ferrocene]palladium(II) dichloride dichloromethane adduct (13 mg), 1,4-dioxane (3.0 mL), and water (0.30 mL) was heated and stirred under a nitrogen atmosphere at 100 °C for 2 hours. After the reaction was completed, water was added to the reaction mixture, and extraction was performed with chloroform. The organic layer was separated with Phase-Separator® and concentrated under reduced pressure, and then the organic layer was purified by NH silica gel column chromatography (hexane:ethyl acetate=50:50 to 0:100) to obtain the title compound (80 mg) as a light yellow powder. MS(ESI)m/z:644.5 [M+H]

Reference Example 37: Synthesis of 6-bromo-3-iodo-2-methyl-4-phenylmethoxyindazole

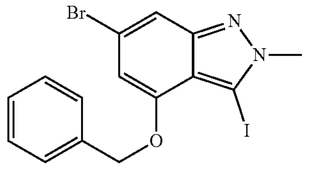 [SMILES: Cn1nc2cc(Br)cc(OCc3ccccc3)c2c1I]

6-Bromo-3-iodo-2-methylindazol-4-ol (100 mg) described in Reference Example 33 and potassium carbonate (117 mg) were suspended in N,N-dimethylformamide (3.0 mL), bromomethylbenzene (73 mg) was added, and the mixture was stirred under a nitrogen atmosphere at 80 °C for 6 hours. After the reaction was completed, water was added to the reaction mixture, extraction was performed with ethyl acetate, and the organic layer was washed twice with saturated saline. The organic layer was filtrated with Phase-Separator®, and the organic layer was concentrated under reduced pressure. The residue was purified by silica gel column chromatography (hexane:ethyl acetate=99:1 to 90:10) to obtain the title compound (75 mg) as a colorless powder. MS(ESI)m/z:443.1/445.1 [M+H]+

Reference Example 38: Synthesis of 4-(6-bromo-2-methyl-4-phenylmethoxyindazol-3-yl)-2-(difluoromethoxy)-N-[(1R,2S)-2-fluorocyclopropyl]-6-methoxybenzamide

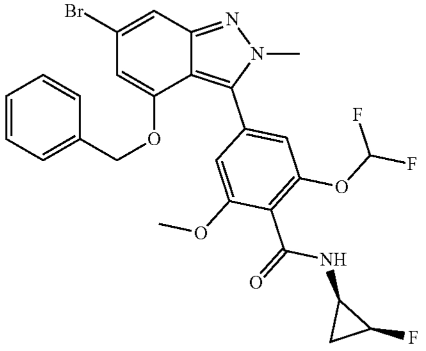 [SMILES: COc1cc(-c2c3c(OCc4ccccc4)cc(Br)cc3nn2C)cc(OC(F)F)c1C(=O)N[C@@H]1C[C@@H]1F]

A mixture of 6-bromo-3-iodo-2-methyl-4-phenylmethoxyindazole (72 mg) described in Reference Example 37, [3-(difluoromethoxy)-4-[(1R,2S)-2-fluorocyclopropyl]carbamoyl]-5-methoxyphenyl]boronic acid (62 mg) described in Reference Example 28, potassium carbonate (45 mg), a [1,1'-bis(diphenylphosphino)ferrocene]palladium(II) dichloride dichloromethane adduct (13 mg), 1,4-dioxane (3.0 mL), and water (0.30 mL) was heated and stirred under a nitrogen atmosphere at 100 °C for 4 hours. After the reaction was completed, water was added to the reaction solution, extraction was performed with chloroform, the organic layer was separated with Phase-Separator®, and then the organic layer was concentrated under reduced pressure. The residue was purified by NH silica gel column chromatography (hexane:ethyl acetate=80:20 to 50:50) to obtain the title compound (55 mg) as a colorless powder. MS(ESI)m/z:590.3/592.3 [M+H]+

Reference Example 39: Synthesis of 6-bromo-4-(difluoromethoxy)-3-iodo-2-methylindazole

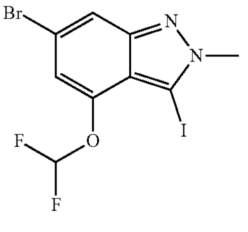 [SMILES: Cn1nc2cc(Br)cc(OC(F)F)c2c1I]

6-Bromo-3-iodo-2-methylindazol-4-ol (1.0 g) described in Reference Example 33 was dissolved in a mixed solvent of acetonitrile (10 mL) and water (5.0 mL), potassium hydroxide (1.6 g) was added under ice cooling, and the mixture was stirred under ice cooling for 10 minutes. Acetonitrile (5.0 mL) and diethyl (bromodifluoromethyl) phosphonate (0.70 mL) were added under ice cooling, and the mixture was stirred under ice cooling for 1 hour and 40 minutes. After the reaction was completed, water was added to the reaction solution, and extraction was performed with ethyl acetate. The organic layer was sequentially washed with water and saturated saline, drying was performed with magnesium sulfate, and the filtrate obtained by filtration was concentrated under reduced pressure. The residue was purified by silica gel column chromatography (hexane:ethyl acetate=85:15 to 60:40) to obtain the title compound (737 mg) as a colorless powder. MS(ESI)m/z:402.9/404.9 [M+H]+

Reference Example 40: Synthesis of 4-[6-bromo-4-(difluoromethoxy)-2-methylindazol-3-yl]-2-(difluoromethoxy)-N-[(1R,2S)-2-fluorocyclopropyl]-6-methoxybenzamide

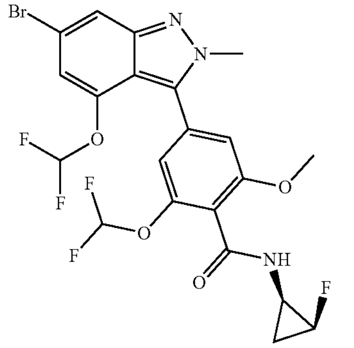 [SMILES: COc1cc(-c2c3c(OC(F)F)cc(Br)cc3nn2C)cc(OC(F)F)c1C(=O)N[C@@H]1C[C@@H]1F]

A mixture of 6-bromo-4-(difluoromethoxy)-3-iodo-2-methylindazole (65 mg) described in Reference Example 39, [3-(difluoromethoxy)-4-[[(1R,2S)-2-fluorocyclopropyl]carbamoyl]-5-methoxyphenyl]boronic acid (51 mg) described in Reference Example 28, water (0.27 mL), a [1,1'-bis(diphenylphosphino)ferrocene]palladium(II) dichloride dichloromethane adduct (13 mg), potassium carbonate (45 mg), and 1,4-dioxane (1.1 mL) was heated and stirred under a nitrogen atmosphere at 100 °C for 2 hours. After the reaction was completed, the reaction solution was purified by silica gel column chromatography (hexane:ethyl acetate=50:50 to 20:80) to obtain the title compound (41 mg) as a light yellow powder. MS(ESI)m/z:550.2/552.3 [M+H]+.

Reference Example 41: Synthesis of tert-butyl 4-[4-cyano-2-methyl-6-(1-methylpyrazol-4-yl)indazol-3-yl]-2-(difluoromethoxy)-6-methoxybenzoate

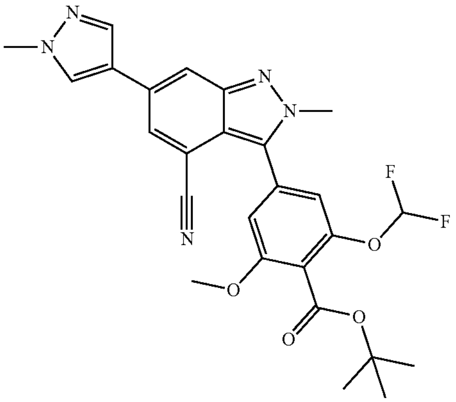 [SMILES: COc1cc(-c2c3c(C#N)cc(-c4cnn(C)c4)cc3nn2C)cc(OC(F)F)c1C(=O)OC(C)(C)C]

A mixture of tert-butyl 4-(6-bromo-4-cyano-2-methylindazol-3-yl)-2-(difluoromethoxy)-6-methoxybenzoate (4.5 g) described in Reference Example 44, 1-methyl-4-(4,4,5,5-tetramethyl-1,3,2-dioxaborolan-2-yl)pyrazole (2.2 g), potassium carbonate (2.5 g), a [1,1'-bis(diphenylphosphino)ferrocene]palladium(II) dichloride dichloromethane adduct (725 mg), 1,4-dioxane (59 mL), and water (15 mL) was heated and stirred under a nitrogen atmosphere at 100 °C for 2.5 hours. After the reaction was completed, water was added to the reaction mixture, and extraction was performed twice with ethyl acetate. The combined organic layer was passed through Phase-Separator® and then concentrated under reduced pressure, the organic layer was purified by NH silica gel column chromatography (hexane:ethyl acetate=90:10 to 30:70) to obtain the title compound (4.3 g) as a light yellow powder.

MS(ESI)m/z:510.0 [M+H]+

Reference Example 42: Synthesis of 4-[4-cyano-2-methyl-6-(1-methylpyrazol-4-yl)indazol-3-yl]-2-(difluoromethoxy)-6-methoxybenzoic acid

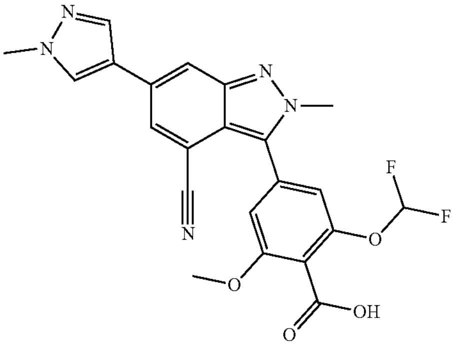 [SMILES: COc1cc(-c2c3c(C#N)cc(-c4cnn(C)c4)cc3nn2C)cc(OC(F)F)c1C(=O)O]

TFA (21 mL) was added dropwise to a dichloromethane (21 mL) solution of tert-butyl 4-[4-cyano-2-methyl-6-(1-methylpyrazol-4-yl)indazol-3-yl]-2-(difluoromethoxy)-6-methoxybenzoate (4.3 g) described in Reference Example 41 under ice cooling, and then the mixture was stirred at room temperature for 3 hours. After the reaction was completed, the reaction mixture was concentrated under reduced pressure, and then an azeotropic treatment was performed using toluene. The resulting residue was suspended and washed with diethyl ether to obtain the title compound (3.4 g) as a white powder. MS(ESI)m/z:454.0 [M+H]+

Reference Example 43: Synthesis of tert-butyl 2-(difluoromethoxy)-6-methoxy-4-(4,4,5,5-tetramethyl-1,3,2-dioxaborolan-2-yl)benzoate

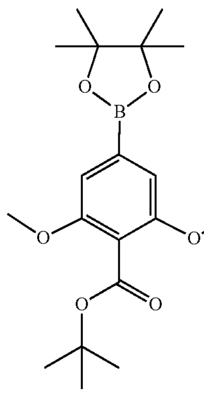

A 1,4-dioxane (42 mL) suspension of tert-butyl 4-bromo-2-(difluoromethoxy)-6-methoxybenzoate (6.0 g) described in Reference Example 14, bis(pinacolato)diboron (5.2 g), potassium acetate (5.0 g), and a [1,1'-bis(diphenylphosphino)ferrocene]palladium(II) dichloride dichloromethane adduct (1.4 g) was stirred under a nitrogen atmosphere at 100 °C for 6 hours. Ethyl acetate was added to the reaction solution, insoluble matter was removed by filtration, and the filtrate was concentrated under reduced pressure. The resulting residue was purified by silica gel column chromatography (hexane:ethyl acetate=80:20 to 50:50) to obtain the title compound (7.3 g) as a light yellow oily product. MS(ESI) m/z:345.3 [M+H-tBu]+

Reference Example 44: Synthesis of tert-butyl 4-(6-bromo-4-cyano-2-methylindazol-3-yl)-2-(difluoromethoxy)-6-methoxybenzoate

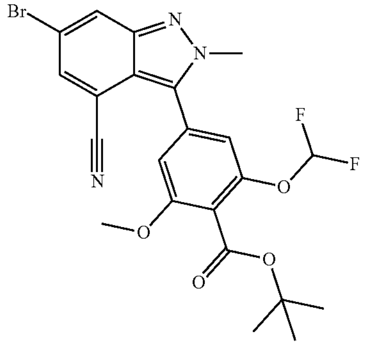 [SMILES: COc1cc(-c2c3c(C#N)cc(Br)cc3nn2C)cc(OC(F)F)c1C(=O)OC(C)(C)C]

A mixture of 6-bromo-3-iodo-2-methylindazole-4-carbonitrile (5.0 g) described in Reference Example 19, tert-butyl 2-(difluoromethoxy)-6-methoxy-4-(4,4,5,5-tetramethyl-1,3,2-dioxaborolan-2-yl)benzoate (6.3 g) described in Reference Example 43, a [1,1'-bis(diphenylphosphino)ferrocene] palladium(II) dichloride dichloromethane adduct (1.1 g), potassium carbonate (3.8 g), water (12 mL), and 1,4-dioxane (46 mL) was heated and stirred under a nitrogen atmosphere at 100 °C for 2 hours and 30 minutes. After the reaction was completed, water was added to the reaction mixture, extraction was performed twice with ethyl acetate, the organic layer was separated with Phase-Separator®, and then the organic layer was concentrated under reduced pressure. The residue was purified by silica gel column chromatography (hexane:ethyl acetate=90:10 to 50:50) to obtain the title compound (4.5 g) as a light yellow powder. MS(ESI)m/z: 507.9/509.8 [M+H]+

Reference Example 45: Synthesis of tert-butyl 4-[6-bromo-4-(difluoromethyl)-2-methylindazol-3-yl]-2-(difluoromethoxy)-6-methoxybenzoate

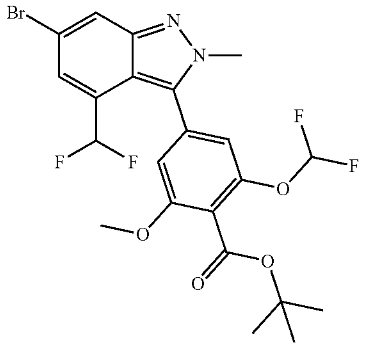 [SMILES: COc1cc(-c2c3c(C(F)F)cc(Br)cc3nn2C)cc(OC(F)F)c1C(=O)OC(C)(C)C]

A mixture of 6-bromo-4-(difluoromethyl)-3-iodo-2-methylindazole (1.7 g) described in Reference Example 31, tert-butyl 2-(difluoromethoxy)-6-methoxy-4-(4,4,5,5-tetramethyl-1,3,2-dioxaborolan-2-yl)benzoate (1.9 g) described in Reference Example 43, potassium carbonate (1.8 g), a [1,1'-bis(diphenylphosphino)ferrocene]palladium (II) dichloride dichloromethane adduct (361 mg), water (7.4 mL), and 1,4-dioxane (29 mL) was heated and stirred under a nitrogen atmosphere at 100 °C for 1 hour. After the reaction was completed, water was added to the reaction mixture, extraction was performed twice with chloroform, the organic layer was separated with Phase-Separator®, and then the organic layer was concentrated under reduced pressure. The residue was purified by silica gel column chromatography (hexane:ethyl acetate=90:10 to 50:50) to obtain the title compound (1.6 g) as a light yellow powder. MS(ESI)m/z:532.8/534.8 [M+H]+

Reference Example 46: Synthesis of 2-(difluoromethoxy)-4-[4-(difluoromethyl)-2-methyl-6-(1-methylpyrazol-4-yl)indazol-3-yl]-6-methoxybenzoic acid

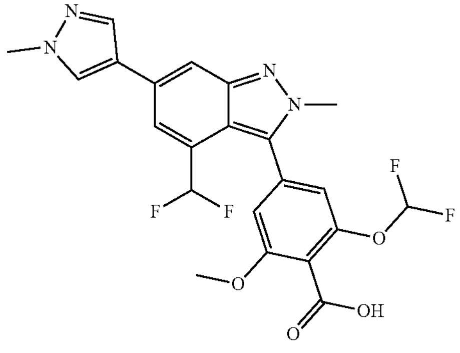 [SMILES: COc1cc(-c2c3c(C(F)F)cc(-c4cnn(C)c4)cc3nn2C)cc(OC(F)F)c1C(=O)O]

A mixture of tert-butyl 4-[6-bromo-4-(difluoromethyl)-2-methylindazol-3-yl]-2-(difluoromethoxy)-6-methoxybenzoate (1.6 g) described in Reference Example 45, 1-methyl-4-(4,4,5,5-tetramethyl-1,3,2-dioxaborolan-2-yl)pyrazole (695 mg), potassium carbonate (1.3 g), a [1,1'-bis(diphenylphosphino)ferrocene]palladium(II) dichloride dichloromethane adduct (248 mg), 1,4-dioxane (20 mL), and water (5.1 mL) was heated and stirred under a nitrogen atmosphere at 100 °C for 2 hours. After the reaction was completed, water was added to the reaction mixture, and extraction was performed with chloroform. The organic layer was separated with Phase-Separator® and concentrated under reduced pressure, and then the organic layer was purified by silica gel column chromatography (chloroform:methanol=100:0 to 95:5). The resulting intermediate product was dissolved in dichloromethane (19 mL), TFA (4.6 mL) was added, and the mixture was stirred at room temperature overnight. After the reaction was completed, the reaction mixture was concentrated under reduced pressure, and then an azeotropic treatment was performed twice using toluene. The resulting crude product was suspended and washed with diethyl ether to obtain the title compound (1.1 g) as a light red powder. MS(ESI)m/z:479.2 [M+H]+

Reference Example 47: Synthesis of [4-bromo-2-(difluoromethoxy)-6-methoxyphenyl]-[3-hydroxy-3-(trifluoromethyl)azetidin-1-yl]methanone

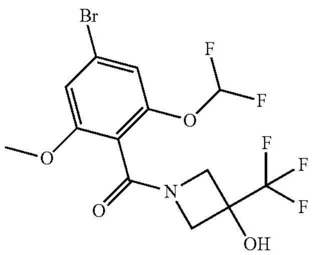 [SMILES: COc1cc(Br)cc(OC(F)F)c1C(=O)N1CC(O)(C(F)(F)F)C1]

3-(Trifluoromethyl)azetidin-3-ol hydrochloride (2.2 g) was added to a mixture of 4-bromo-2-(difluoromethoxy)-6-methylbenzoic acid (2.4 g) described in Reference Example 15, HATU (4.6 g), N,N-diisopropylethylamine (4.2 mL), and N,N-dimethylformamide (12 mL), and the mixture was stirred at room temperature for 30 minutes. Water was added to the reaction solution, and then extraction was performed with ethyl acetate. The organic layer was washed with water and saturated saline, sodium sulfate was added, the mixture was filtered, and the filtrate was concentrated under reduced pressure. The resulting residue was purified by silica gel column chromatography (hexane:ethyl acetate=65:35 to 30:70) to obtain the title compound (3.5 g) as a light yellow powder. MS(ESI)m/z:419.8/421.7 [M+H]

Reference Example 48: Synthesis of [2-(difluoromethoxy)-6-methoxy-4-(4,4,5,5-tetramethyl-1,3,2-dioxaborolan-2-yl)phenyl]-[3-hydroxy-3-(trifluoromethyl)azetidin-1-yl]methanone

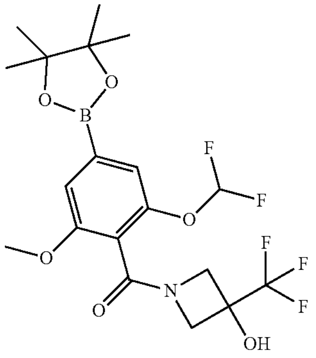 [SMILES: COc1cc(B2OC(C)(C)C(C)(C)O2)cc(OC(F)F)c1C(=O)N1CC(O)(C(F)(F)F)C1]

A 1,4-dioxane (10 mL) suspension of [4-bromo-2-(difluoromethoxy)-6-methoxyphenyl]-[3-hydroxy-3-(trifluoromethyl)azetidin-1-yl]methanone (1.7 g) described in Reference Example 47, bis(pinacolato)diboron (1.3 g), a [1,1'-bis(diphenylphosphino)ferrocene]palladium(II) dichloride dichloromethane adduct (339 mg), and potassium acetate (1.2 g) was stirred under a nitrogen atmosphere at 100 °C for 155 minutes. Ethyl acetate was added to the reaction solution, insoluble matter was removed by filtration, and the filtrate was concentrated under reduced pressure. The resulting residue was purified by silica gel column chromatography (hexane:ethyl acetate=90:10 to 34:66) to obtain the title compound (1.9 g) as a brown viscous product. MS(ESI)m/z:467.8 [M+H]+

Reference Example 49: Synthesis of tert-butyl 4-(6-bromo-4-methoxy-2-methylindazol-3-yl)-2-(difluoromethoxy)-6-methoxybenzoate

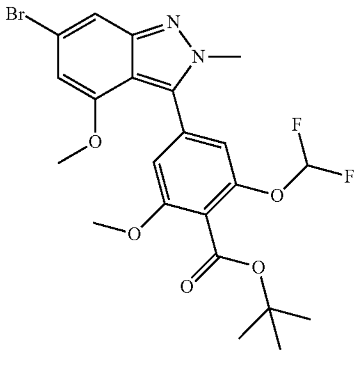 [SMILES: COc1cc(-c2c3c(OC)cc(Br)cc3nn2C)cc(OC(F)F)c1C(=O)OC(C)(C)C]

A mixture of 6-bromo-3-iodo-4-methoxy-2-methylindazole (1.8 g) described in Reference Example 23, tert-butyl 2-(difluoromethoxy)-6-methoxy-4-(4,4,5,5-tetramethyl-1,3,2-dioxaborolan-2-yl)benzoate (2.2 g) described in Reference Example 43, a [1,1'-bis(diphenylphosphino)ferrocene] palladium(II) dichloride dichloromethane adduct (400 mg), potassium carbonate (1.4 g), water (6.1 mL), and 1,4-dioxane (25 mL) was heated and stirred under a nitrogen atmosphere at 100 °C for 1 hour. After the reaction was completed, the reaction mixture was filtered, saturated saline was added to the filtrate, and extraction was performed with chloroform. Sodium sulfate was added to the organic layer, stirring was performed, insoluble matter was removed by filtration, and the filtrate was concentrated under reduced pressure. The residue was purified by silica gel column chromatography (hexane:ethyl acetate=75:25 to 50:50) using a Si silica gel column and an NH silica gel column in series to obtain the title compound (1.8 g) as a white powder. MS(ESI)m/z:512.9/514.8 [M+H]+

Reference Example 50: Synthesis of tert-butyl 2-(difluoromethoxy)-6-methoxy-4-[4-methoxy-2-methyl-6-(1-methylpyrazol-4-yl)indazol-3-yl]benzoate

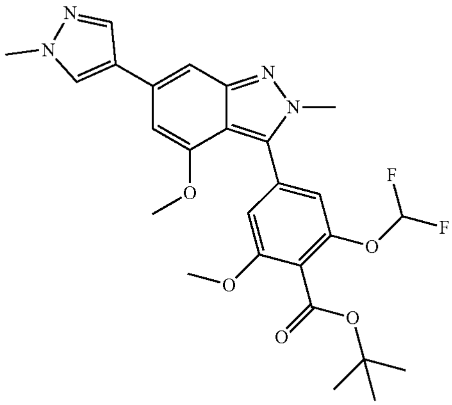 [SMILES: COc1cc(-c2c3c(OC)cc(-c4cnn(C)c4)cc3nn2C)cc(OC(F)F)c1C(=O)OC(C)(C)C]

A mixture of tert-butyl 4-(6-bromo-4-methoxy-2-methyl-indazol-3-yl)-2-(difluoromethoxy)-6-methoxybenzoate (1.8 g) described in Reference Example 49, 1-methyl-4-(4,4,5,5-tetramethyl-1,3,2-dioxaborolan-2-yl)pyrazole (732 mg), potassium carbonate (884 mg), a [1,1'-bis(diphenylphosphino)ferrocene]palladium(II) dichloride dichloromethane adduct (261 mg), 1,4-dioxane (16 mL), and water (4.0 mL) was heated and stirred under a nitrogen atmosphere at 100 °C for 2 hours. After the reaction was completed, the reaction mixture was diluted with chloroform, and then drying was performed by adding sodium sulfate. A filtrate obtained by removing insoluble matter by filtration was concentrated under reduced pressure and purified by NH silica gel column chromatography (hexane:ethyl acetate=90:10 to 30:70) to obtain the title compound (2.1 g) as a light yellow oily product. MS(ESI)m/z:515.3 [M+H]+

Reference Example 51: Synthesis of 2-(difluoromethoxy)-6-methoxy-4-[4-methoxy-2-methyl-6-(1-methylpyrazol-4-yl)indazol-3-yl]benzoic acid

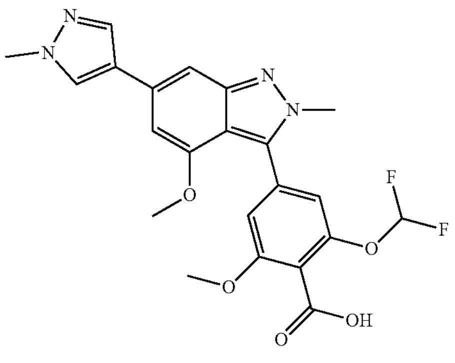 [SMILES: COc1cc(-c2c3c(OC)cc(-c4cnn(C)c4)cc3nn2C)cc(OC(F)F)c1C(=O)O]

TFA (7.1 mL) was added to a dichloromethane (7.1 mL) solution of tert-butyl 2-(difluoromethoxy)-6-methoxy-4-[4-methoxy-2-methyl-6-(1-methylpyrazol-4-yl)indazol-3-yl] benzoate (2.1 g) described in Reference Example 50 under ice cooling, and then the mixture was stirred at room temperature overnight. After the reaction was completed, the reaction mixture was concentrated under reduced pressure, and then an azeotropic treatment was performed using toluene. The resulting crude product was suspended and washed with diethyl ether to obtain the title compound (1.1 g) as a light yellow powder. MS(ESI)m/z:459.2 [M+H]+

Reference Example 52: Synthesis of [3-(difluoromethoxy)-5-methoxy-4-[(2-methylpropan-2-yl) oxycarbonyl] phenyl]boronic acid

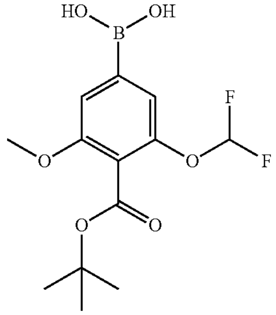 [SMILES: COc1cc(B(O)O)cc(OC(F)F)c1C(=O)OC(C)(C)C]

A 1 M aqueous ammonium acetate solution (1.5 mL) was added to an acetone (3.0 mL) suspension of tert-butyl 2-(difluoromethoxy)-6-methoxy-4-(4,4,5,5-tetramethyl-1,3,2-dioxaborolan-2-yl)benzoate (200 mg) described in Reference Example 43 and sodium periodate (802 mg), and the mixture was stirred at room temperature for 5 hours. 1 N hydrochloric acid (4 mL) was added to the reaction solution and stirred for 10 minutes, water and ethyl acetate were added, and then extraction was performed. The organic layer was washed twice with water and once with saturated saline and separated with Phase-Separator®, and then the organic layer was concentrated under reduced pressure. The concentrated residue was suspended and washed with diisopropyl ether to obtain the title compound (72 mg) as a white powder. MS(ESI)m/z:263.0 [M+H−tBu]+

Reference Example 53: Synthesis of [4-(6-bromo-4-hydroxy-2-methylindazol-3-yl)-2-(difluoromethoxy)-6-methoxyphenyl]-[3-hydroxy-3-(trifluoromethyl)azetidine-1-yl]methanone

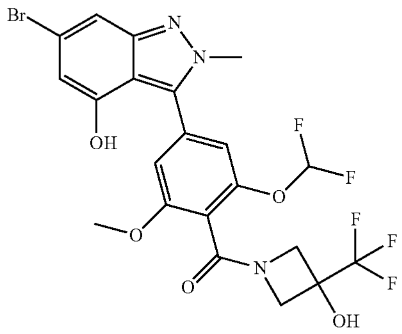 [SMILES: COc1cc(-c2c3c(O)cc(Br)cc3nn2C)cc(OC(F)F)c1C(=O)N1CC(O)(C(F)(F)F)C1]

A mixture of 6-bromo-3-iodo-2-methylindazol-4-ol (2.0 g) described in Reference Example 33, [2-(difluoromethoxy)-6-methoxy-4-(4,4,5,5-tetramethyl-1,3,2-dioxaborolan-2-yl)phenyl]-[3-hydroxy-3-(trifluoromethyl)azetidin-1-yl]methanone (2.9 g) described in Reference Example 48, potassium carbonate (1.6 g), a [1,1'-bis(diphenylphosphino)ferrocene]palladium(II) dichloride dichloromethane adduct (463 mg), 1,4-dioxane (50 mL), and water (5.0 mL) was heated and stirred under a nitrogen atmosphere at 100 °C for 2 hours and 30 minutes. After the reaction was completed, 1 N hydrochloric acid was added to the reaction mixture, and extraction was performed three times with a mixed solvent of chloroform and methanol. The organic layer was separated with Phase-Separator®, and the organic layer was concentrated under reduced pressure. The residue was purified by silica gel column chromatography (chloroform:methanol=100:0 to 95:5) to obtain the title compound (1.8 g) as a brown powder. MS(ESI)m/z:565.8/567.8 [M+H]+

Reference Example 54: Synthesis of [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone

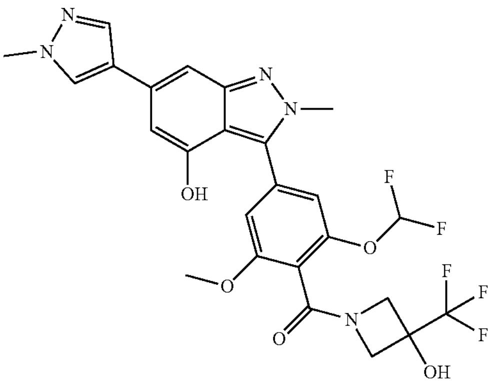 [SMILES: COc1cc(-c2c3c(O)cc(-c4cnn(C)c4)cc3nn2C)cc(OC(F)F)c1C(=O)N1CC(O)(C(F)(F)F)C1]

A mixture of [4-(6-bromo-4-hydroxy-2-methylindazol-3-yl)-2-(difluoromethoxy)-6-methoxyphenyl]-[3-hydroxy-3-(trifluoromethyl)azetidine-1-yl]methanone (1.8 g) described in Reference Example 53, 1-methyl-4-(4,4,5,5-tetramethyl-1,3,2-dioxaborolan-2-yl)pyrazole (976 mg), potassium carbonate (864 mg), a [1,1'-bis(diphenylphosphino)ferrocene] palladium(II) dichloride dichloromethane adduct (255 mg), 1,4-dioxane (50 mL), and water (5.0 mL) was heated and stirred under a nitrogen atmosphere at 100 °C for 2.5 hours. After the reaction was completed, the reaction mixture was neutralized by adding 1 N hydrochloric acid, methanol was added, and then extraction was performed three times with chloroform. The combined organic layer was passed through Phase-Separator® and then concentrated under reduced pressure, the organic layer was purified by silica gel column chromatography (chloroform:methanol=100:0 to 90:10) to obtain the title compound (1.3 g) as a brown powder. MS(ESI)m/z:568.1 [M+H]+

Reference Example 55: Synthesis of [4-[6-bromo-4-(difluoromethoxy)-2-methylindazol-3-yl]-2-(difluoromethoxy)-6-methoxyphenyl]-[3-hydroxy-3-(trifluoromethyl)azetidin-1-yl]methanone

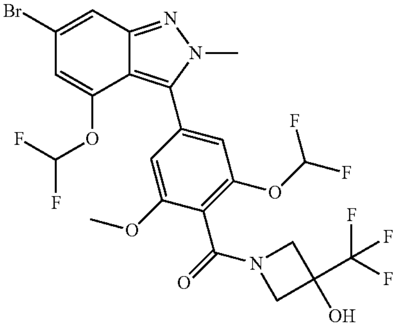 [SMILES: COc1cc(-c2c3c(OC(F)F)cc(Br)cc3nn2C)cc(OC(F)F)c1C(=O)N1CC(O)(C(F)(F)F)C1]

A mixture of 6-bromo-4-(difluoromethoxy)-3-iodo-2-methylindazole (110 mg) described in Reference Example 39, [2-(difluoromethoxy)-6-methoxy-4-(4,4,5,5-tetramethyl-1,3,2-dioxaborolan-2-yl)phenyl]-[3-hydroxy-3-(trifluoromethyl)azetidin-1-yl]methanone (153 mg) described in Reference Example 48, water (0.34 mL), potassium carbonate (75 mg), a [1,1'-bis(diphenylphosphino)ferrocene]palladium(II) dichloride dichloromethane adduct (22 mg), and 1,4-dioxane (1.4 mL) was heated and stirred under a nitrogen atmosphere at 100 °C for 2 hours. After the reaction was completed, the reaction solution was purified by silica gel column chromatography (hexane:ethyl acetate=20:80 to 0:100) to obtain the title compound (111 mg) as a light orange viscous product. MS(ESI)m/z:615.9/617.8 [M+H]+

Reference Example 56: Synthesis of 6-bromo-3-[3-(difluoromethoxy)-4-[3-hydroxy-3-(trifluoromethyl) azetidine-1-carbonyl]-5-methoxyphenyl]-2-methyl-indazole-4-carbonitrile

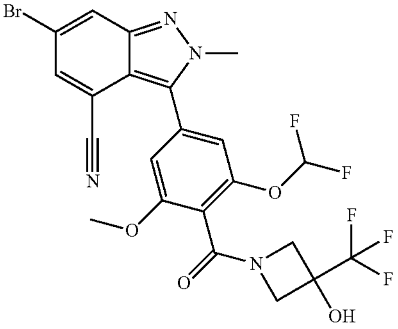 [SMILES: COc1cc(-c2c3c(C#N)cc(Br)cc3nn2C)cc(OC(F)F)c1C(=O)N1CC(O)(C(F)(F)F)C1]

A mixture of 6-bromo-3-iodo-2-methylindazole-4-carbonitrile (400 mg) described in Reference Example 19, [2-(difluoromethoxy)-6-methoxy-4-(4,4,5,5-tetramethyl-1,3,2-dioxaborolan-2-yl)phenyl]-[3-hydroxy-3-(trifluoromethyl) azetidin-1-yl]methanone (671 mg) described in Reference Example 48, water (1.4 mL), potassium carbonate (305 mg), a [1,1'-bis(diphenylphosphino)ferrocene]palladium(II) dichloride dichloromethane adduct (90 mg), and 1,4-dioxane (5.5 mL) was heated and stirred under a nitrogen atmosphere at 100 °C for 2 hours. After the reaction was completed, the reaction solution was purified by silica gel column chromatography (hexane:ethyl acetate=20:80 to 0:100) to obtain the title compound (502 mg) as an orange viscous product. MS(ESI)m/z:575.6/577.7 [M+H]

Reference Example 57: Synthesis of [2-(difluoromethoxy)-6-methoxy-4-[2-methyl-6-(1-methylpyrazol-4-yl)-4-[3-(oxan-2-yloxy)propoxy]indazol-3-yl]phenyl]-[3-hydroxy-3-(trifluoromethyl)azetidin-1-yl]methanone

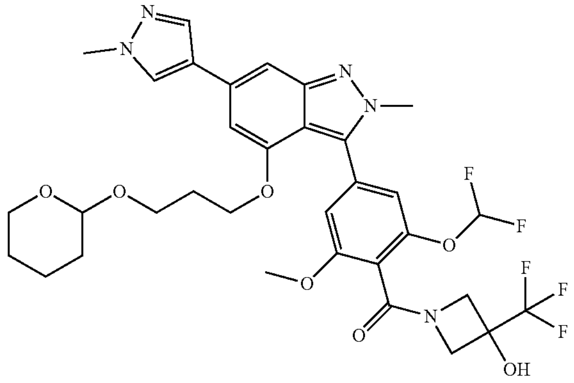 [SMILES: COc1cc(-c2c3c(OCCCOC4CCCCO4)cc(-c4cnn(C)c4)cc3nn2C)cc(OC(F)F)c1C(=O)N1CC(O)(C(F)(F)F)C1]

2-(3-Bromopropoxy)tetrahydropyran (45 mg) was added to a mixture of [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone (77 mg) described in Reference Example 54, potassium carbonate (56 mg), and N,N-dimethylformamide (3.0 mL), and the mixture was heated and stirred under a nitrogen atmosphere at 80 °C for 3 hours. After the reaction was completed, water was added to the reaction mixture, and extraction was performed with ethyl acetate. The separated organic layer was washed with water saturated saline, sodium sulfate was added, the mixture was dried, and then insoluble matter was removed by filtration. The filtrate was concentrated under reduced pressure and then purified by NH silica gel column chromatography (chloroform:methanol=100:0 to 97:3) to obtain the title compound (64 mg) as an orange viscous product. MS(ESI)m/z:710.4 [M+H]+

Reference Example 58: Synthesis of tert-butyl 4-(6-bromo-4-hydroxy-2-methylindazol-3-yl)-2-(difluoromethoxy)-6-methoxybenzoate

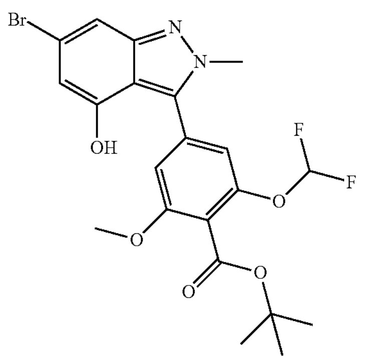 [SMILES: COc1cc(-c2c3c(O)cc(Br)cc3nn2C)cc(OC(F)F)c1C(=O)OC(C)(C)C]

A mixture of 6-bromo-3-iodo-2-methylindazol-4-ol (3.0 g) described in Reference Example 33, [3-(difluoromethoxy)-5-methoxy-4-[(2-methylpropan-2-yl)oxycarbonyl] phenyl]boronic acid (3.2 g) described in Reference Example 52, a [1,1'-bis(diphenylphosphino)ferrocene]palladium(II) dichloride dichloromethane adduct (694 mg), potassium carbonate (2.4 g), 1,4-dioxane (30 mL), and water (3.0 mL) was heated and stirred under a nitrogen atmosphere at 100 °C for 1 hour and 30 minutes. After the reaction was completed, a saturated aqueous ammonium chloride solution was added to the reaction mixture, and extraction was performed with a mixed solvent of chloroform and methanol. Sodium sulfate was added to the organic layer, stirring was performed, insoluble matter was removed by filtration, and the filtrate was concentrated under reduced pressure. The residue was purified by silica gel column chromatography (chloroform:methanol=100:0 to 95:5) to obtain the title compound (4.2 g) as a brown powder. MS(ESI)m/z: 499.1/501.1 [M+H]+

Reference Example 59: Synthesis of tert-butyl 2-(difluoromethoxy)-4-[4-hydroxy-2-methyl-6-(1-methylpyrazol-4-yl)indazol-3-yl]-6-methoxybenzoate

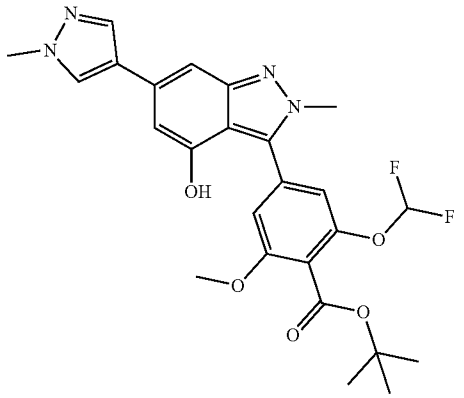 [SMILES: COc1cc(-c2c3c(O)cc(-c4cnn(C)c4)cc3nn2C)cc(OC(F)F)c1C(=O)OC(C)(C)C]

A mixture of tert-butyl 4-(6-bromo-4-hydroxy-2-methylindazol-3-yl)-2-(difluoromethoxy)-6-methoxybenzoate (4.2 g) described in Reference Example 58, 1-methyl-4-(4,4,5,5-tetramethyl-1,3,2-dioxaborolan-2-yl)pyrazole (2.7 g), potassium carbonate (2.4 g), a [1,1'-bis(diphenylphosphino) ferrocene]palladium(II) dichloride dichloromethane adduct (693 mg), 1,4-dioxane (30 mL), and water (3.0 mL) was heated and stirred under a nitrogen atmosphere at 100 °C for 3 hours. After the reaction was completed, the reaction mixture was diluted with a saturated aqueous ammonium chloride solution, and extraction was performed with chloroform to which methanol was added. Sodium sulfate was added to the organic layer, filtration was performed, and the filtrate was concentrated under reduced pressure. The residue was purified by silica gel column chromatography (chloroform:methanol=100:0 to 95:5) to obtain the title compound (1.7 g) as a brown powder. MS(ESI)m/z:501.3 [M+H]+

Reference Example 60: Synthesis of tert-butyl 2-(difluoromethoxy)-4-[4-ethoxy-2-methyl-6-(1-methylpyrazol-4-yl)indazol-3-yl]-6-methoxybenzoate

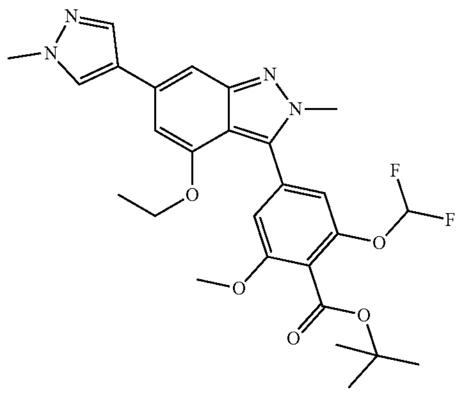 [SMILES: CCOc1cc(-c2cnn(C)c2)cc2nn(C)c(-c3cc(OC)c(C(=O)OC(C)(C)C)c(OC(F)F)c3)c12]

A mixture of tert-butyl 2-(difluoromethoxy)-4-[4-hydroxy-2-methyl-6-(1-methylpyrazol-4-yl)indazol-3-yl]-6-methoxybenzoate (165 mg) described in Reference Example 59, potassium carbonate (137 mg), N,N-dimethylformamide (3.3 mL), and iodoethane (77 mg) was heated and stirred at 80 °C for 2 hours. After the reaction was completed, water, saturated saline, and chloroform were added to the reaction mixture and stirred for several minutes, the organic layer was separated with Phase-Separator®, and then the organic layer was concentrated under reduced pressure. The resulting residue was purified by preparative HPLC (10 mM aqueous ammonium carbonate solution-acetonitrile) to obtain the title compound (82 mg) as a brown powder. MS(ESI)m/z:529.4 [M+H]+

Reference Example 61: Synthesis of [2-(difluoromethoxy)-6-methoxy-4-[2-methyl-6-(1-methylpyrazol-4-yl)-4-[4-(oxan-2-yloxy)butoxy]indazol-3-yl]phenyl]-[3-hydroxy-3-(trifluoromethyl)azetidin-1-yl]methanone

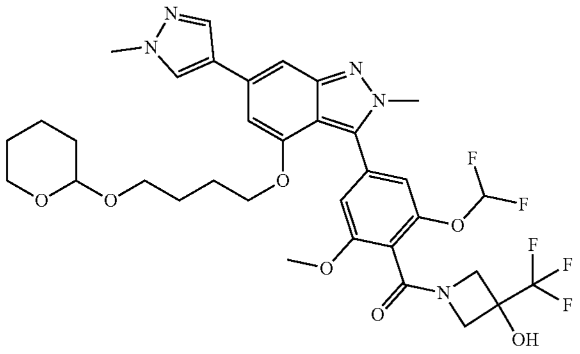 [SMILES: COc1cc(-c2c3c(OCCCCOC4CCCCO4)cc(-c4cnn(C)c4)cc3nn2C)cc(OC(F)F)c1C(=O)N1CC(O)(C(F)(F)F)C1]

2-(4-Bromobutoxy)tetrahydropyran (43 mg) was added to a mixture of [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone (68 mg) described in Reference Example 54, potassium carbonate (50 mg), and N,N-dimethylformamide (3.0 mL), and the mixture was heated and stirred under a nitrogen atmosphere at 80 °C for 2 hours. After the reaction was completed, water was added to the reaction mixture, and extraction was performed with ethyl acetate. The organic layer was washed with saturated saline and passed through Phase-Separator®, and then the organic layer was concentrated under reduced pressure. The resulting residue was purified by NH silica gel column chromatography (chloroform:methanol=100:0 to 97:3 to obtain the title compound (26 mg) as an orange powder.

MS(ESI)m/z:724.2 [M+H]+

Reference Example 62: Synthesis of 4-(6-bromo-4-cyano-2-methylindazol-3-yl)-2-(difluoromethoxy)-6-methoxybenzoic acid

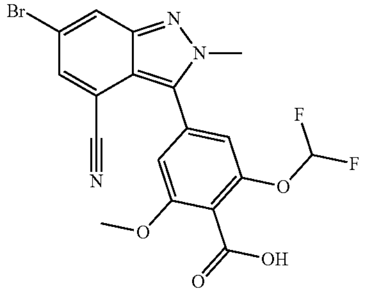

To a mixture of tert-butyl 4-(6-bromo-4-cyano-2-methylindazol-3-yl)-2-(difluoromethoxy)-6-methoxybenzoate (4.5 g) described in Reference Example 44 and dichloromethane (22 mL), TFA (22 mL) was added at room temperature, and the mixture was stirred for 2 hours. The reaction solution was concentrated under reduced pressure, and then subjected to an azeotropic treatment using toluene twice to obtain the title compound (4.9 g) as a white powder. MS(ESI)m/z:451.7/453.7 [M+H]+

Reference Example 63: Synthesis of 4-(6-bromo-4-cyano-2-methylindazol-3-yl)-2-(difluoromethoxy)-N-[(1-fluorocyclopropyl)methyl]-6-methoxybenzamide

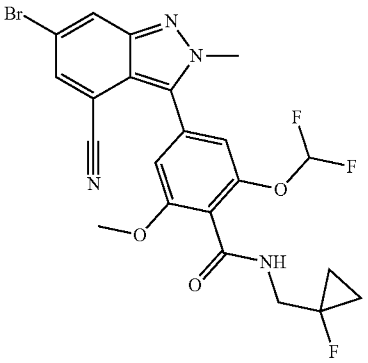 [SMILES: COc1cc(-c2c3c(C#N)cc(Br)cc3nn2C)cc(OC(F)F)c1C(=O)NCC1(F)CC1]

To a mixture of 4-(6-bromo-4-cyano-2-methylindazol-3-yl)-2-(difluoromethoxy)-6-methoxybenzoic acid (2.0 g) described in Reference Example 62, (1-fluorocyclopropyl) methanamine hydrochloride (561 mg), and N,N-dimethylformamide (20 mL), N,N-diisopropylethylamine (2.8 mL) and HATU (1.7 g) were added at room temperature, and the mixture was stirred at the same temperature overnight. After the reaction was completed, water was added to the reaction solution, extraction was performed twice with ethyl acetate, the organic layer was separated with Phase-Separator®, and then the organic layer was concentrated under reduced pressure. The residue was purified by silica gel column chromatography (hexane:ethyl acetate=70:30 to 0:100) to obtain the title compound (1.7 g) as a white powder. MS(ESI)m/z:522.8/524.8 [M+H]+

Reference Example 64: Synthesis of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxybenzamide

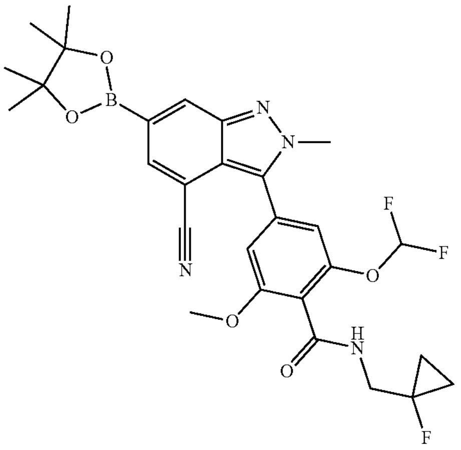 [SMILES: COc1cc(-c2c3c(C#N)cc(B4OC(C)(C)C(C)(C)O4)cc3nn2C)cc(OC(F)F)c1C(=O)NCC1(F)CC1]

A mixture of 4-(6-bromo-4-cyano-2-methylindazol-3-yl)-2-(difluoromethoxy)-N-[(1-fluorocyclopropyl)methyl]-6-methoxybenzamide (1.7 g) described in Reference Example 63, bis(pinacolato)diboron (843 mg), potassium acetate (889 mg), a [1,1'-bis(diphenylphosphino)ferrocene]palladium(II) dichloride dichloromethane adduct (247 mg), and 1,4-dioxane (12 mL) was heated and stirred under a nitrogen atmosphere at 100 °C for 1 hour. After the reaction was completed, ethyl acetate was added to the reaction mixture, and filtration was performed. The filtrate was concentrated under reduced pressure, and the residue was purified by silica gel column chromatography (chloroform: ethyl acetate=100:0 to 50:50) to obtain the title compound (1.7 g) as a brown powder. MS(ESI)m/z:571.0 [M+H]+

Reference Example 65: Synthesis of tert-butyl 4-[6-bromo-4-(difluoromethoxy)-2-methylindazol-3-yl]-2-(difluoromethoxy)-6-methoxybenzoate

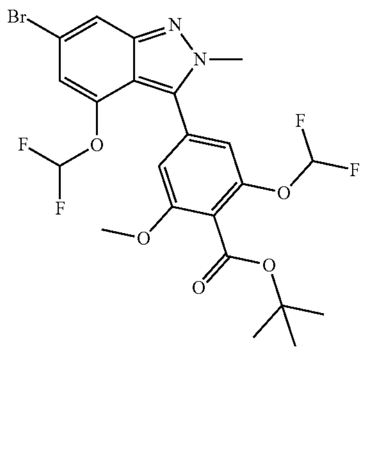 [SMILES: COc1cc(-c2c3c(OC(F)F)cc(Br)cc3nn2C)cc(OC(F)F)c1C(=O)OC(C)(C)C]

A mixture of 6-bromo-4-(difluoromethoxy)-3-iodo-2-methylindazole (1.6 g) described in Reference Example 39, [3-(difluoromethoxy)-5-methoxy-4-[(2-methylpropan-2-yl)oxycarbonyl] phenyl]boronic acid (1.5 g) described in Reference Example 52, potassium carbonate (1.1 g), a [1,1'-bis(diphenylphosphino)ferrocene]palladium(II) dichloride dichloromethane adduct (324 mg), 1,4-dioxane (20 mL), and water (2.0 mL) was heated and stirred under a nitrogen atmosphere at 100 °C for 4 hours. After the reaction was completed, water was added to the reaction mixture, and extraction was performed with chloroform. Sodium sulfate was added to the organic layer, stirring was performed, and insoluble matter was removed by filtration. The filtrate was concentrated under reduced pressure, and the residue was purified by NH silica gel column chromatography (hexane: ethyl acetate=95:5 to 70:30) and silica gel column chromatography (hexane:ethyl acetate=95:5 to 70:30) to obtain the title compound (1.3 g) as a colorless powder.

MS(ESI)m/z:549.1/551.0 [M+H]+

Reference Example 66: Synthesis of tert-butyl 2-(difluoromethoxy)-4-[4-(difluoromethoxy)-2-methyl-6-(4,4,5,5-tetramethyl-1,3,2-dioxaborolan-2-yl)indazol-3-yl]-6-methoxybenzoate

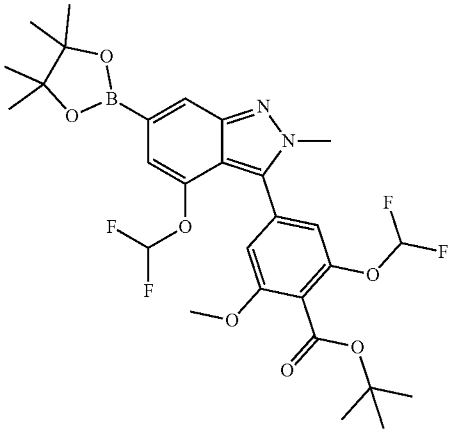 [SMILES: COc1cc(-c2c3c(OC(F)F)cc(B4OC(C)(C)C(C)(C)O4)cc3nn2C)cc(OC(F)F)c1C(=O)OC(C)(C)C]

A mixture of tert-butyl 4-[6-bromo-4-(difluoromethoxy)-2-methylindazol-3-yl]-2-(difluoromethoxy)-6-methoxybenzoate (1.3 g) described in Reference Example 65, potassium acetate (708 mg), a [1,1'-bis(diphenylphosphino)ferrocene] palladium(II) dichloride dichloromethane adduct (196 mg), bis(pinacolato)diboron (671 mg), and 1,4-dioxane (20 mL) was heated and stirred under a nitrogen atmosphere at 100 °C for 1 hour. After the reaction was completed, ethyl acetate was added to the reaction mixture, and filtration was performed. The filtrate was concentrated under reduced pressure, and the residue was purified by silica gel column chromatography (hexane:ethyl acetate=80:20 to 50:50) to obtain the title compound (1.6 g) as a brown viscous product. MS(ESI)m/z:597.3 [M+H]+

Reference Example 67: Synthesis of tert-butyl 2-(difluoromethoxy)-4-[4-(difluoromethoxy)-2-methyl-6-(1-methyltriazol-4-yl)indazol-3-yl]-6-methoxybenzoate

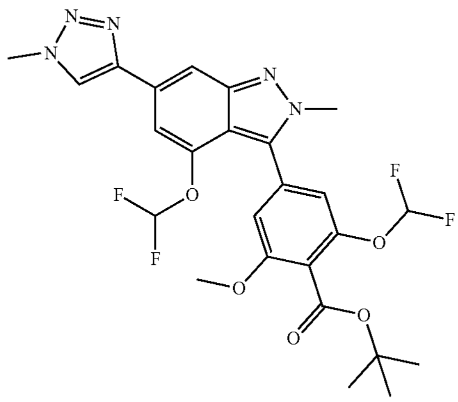 [SMILES: COc1cc(-c2c3c(OC(F)F)cc(-c4cn(C)nn4)cc3nn2C)cc(OC(F)F)c1C(=O)OC(C)(C)C]

A mixture of tert-butyl 2-(difluoromethoxy)-4-[4-(difluoromethoxy)-2-methyl-6-(4,4,5,5-tetramethyl-1,3,2-dioxaborolan-2-yl)indazol-3-yl]-6-methoxybenzoate (250 mg) described in Reference Example 66, 4-bromo-1-methyltriazole (136 mg), potassium carbonate (174 mg), tetrakis (triphenylphosphine)palladium (0) (48 mg), 1,4-dioxane (2.0 mL), and water (0.50 mL) was stirred under microwave irradiation at 110 °C for 30 minutes. After the reaction was completed, water was added to the reaction mixture, and extraction was performed with chloroform. The organic layer was separated with Phase-Separator® and concentrated under reduced pressure, and then the organic layer was purified by NH silica gel column chromatography (hexane:ethyl acetate=50:50 to 0:100) to obtain the title compound (153 mg) as a colorless viscous product. MS(ESI)m/z:552.3 [M+H]+

Reference Example 68: Synthesis of 2-(difluoromethoxy)-4-[4-(difluoromethoxy)-2-methyl-6-(1-methyltriazol-4-yl)indazol-3-yl]-6-methoxybenzoic acid

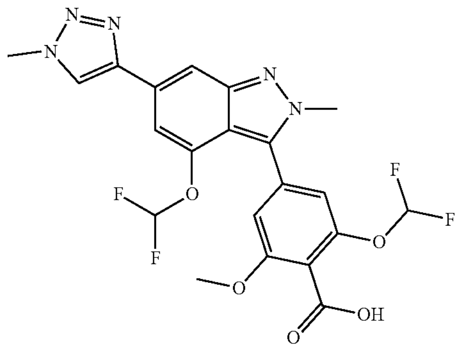 [SMILES: COc1cc(-c2c3c(OC(F)F)cc(-c4cn(C)nn4)cc3nn2C)cc(OC(F)F)c1C(=O)O]

TFA (1.0 mL) was added to a dichloromethane (2.0 mL) solution of tert-butyl 2-(difluoromethoxy)-4-[4-(difluoromethoxy)-2-methyl-6-(1-methyltriazol-4-yl)indazol-3-yl]-6-methoxybenzoate (150 mg) described in Reference Example 67, and the mixture was stirred at room temperature for 2 hours. After the reaction was completed, the reaction mixture was concentrated under reduced pressure, and then an azeotropic treatment was performed twice using toluene. The resulting crude product was suspended and washed with diethyl ether to obtain the title compound (118 mg) as a colorless powder. MS(ESI)m/z:496.1 [M+H]+

Reference Example 69: Synthesis of tert-butyl 2-(difluoromethoxy)-4-[4-(difluoromethoxy)-2-methyl-6-(2-methyltriazol-4-yl)indazol-3-yl]-6-methoxybenzoate

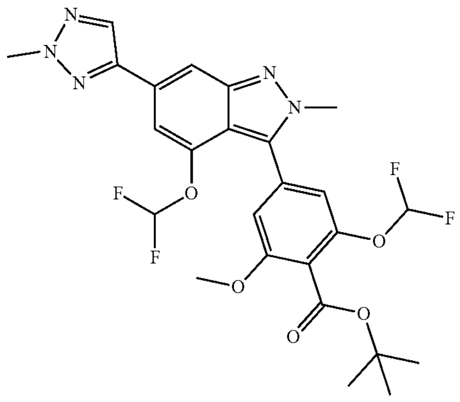 [SMILES: COc1cc(-c2c3c(OC(F)F)cc(-c4cnn(C)n4)cc3nn2C)cc(OC(F)F)c1C(=O)OC(C)(C)C]

A mixture of tert-butyl 2-(difluoromethoxy)-4-[4-(difluoromethoxy)-2-methyl-6-(4,4,5,5-tetramethyl-1,3,2-dioxaborolan-2-yl)indazol-3-yl]-6-methoxybenzoate (250 mg) described in Reference Example 66, 4-bromo-2-methyl-2H-1,2,3-triazole (136 mg), potassium carbonate (174 mg), tetrakis(triphenylphosphine)palladium (0) (48 mg), 1,4-dioxane (2.0 mL), and water (0.50 mL) was stirred under microwave irradiation at 110 °C for 30 minutes. After the reaction was completed, water was added to the reaction mixture, and extraction was performed with chloroform. The organic layer was separated with Phase-Separator® and concentrated under reduced pressure, and then the organic layer was purified by NH silica gel column chromatography (hexane:ethyl acetate=80:20 to 50:50) to obtain the title compound (197 mg) as a colorless viscous product. MS(ESI)m/z:552.3 [M+H]+

Reference Example 70: Synthesis of 2-(difluoromethoxy)-4-[4-(difluoromethoxy)-2-methyl-6-(2-methyltriazol-4-yl)indazol-3-yl]-6-methoxybenzoic acid

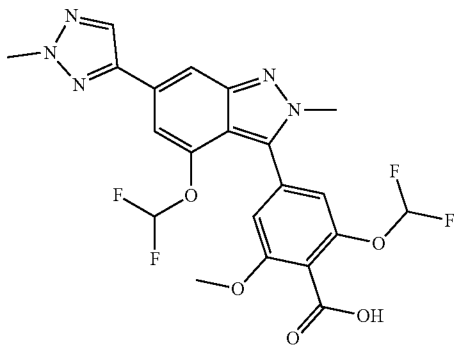 [SMILES: COc1cc(-c2c3c(OC(F)F)cc(-c4cnn(C)n4)cc3nn2C)cc(OC(F)F)c1C(=O)O]

TFA (1.0 mL) was added to a dichloromethane (2.0 mL) solution of tert-butyl 2-(difluoromethoxy)-4-[4-(difluoromethoxy)-2-methyl-6-(2-methyltriazol-4-yl)indazol-3-yl]-6-methoxybenzoate (193 mg) described in Reference Example 69, and the mixture was stirred at room temperature for 2 hours. After the reaction was completed, the reaction mixture was concentrated under reduced pressure, and then an azeotropic treatment was performed twice using toluene. The resulting crude product was suspended and washed with diethyl ether to obtain the title compound (134 mg) as a colorless powder. MS(ESI)m/z:496.1 [M+H]+

Reference Example 71: Synthesis of 4-[6-bromo-4-(difluoromethyl)-2-methylindazol-3-yl]-2-(difluoromethoxy)-6-methoxybenzoic acid

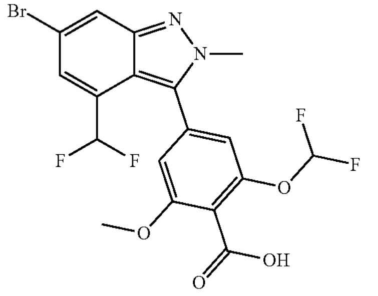 [SMILES: COc1cc(-c2c3c(C(F)F)cc(Br)cc3nn2C)cc(OC(F)F)c1C(=O)O]

To a mixture of tert-butyl 4-[6-bromo-4-(difluoromethyl)-2-methylindazol-3-yl]-2-(difluoromethoxy)-6-methoxybenzoate (1.5 g) described in Reference Example 45 and dichloromethane (10 mL), TFA (3.0 mL) was added at room temperature, and the mixture was stirred for 13 hours. The reaction solution was concentrated under reduced pressure, and then the residue was suspended and washed with diethyl ether to obtain the title compound (1.1 g) as a colorless powder.

MS(ESI)m/z:476.7/478.7 [M+H]+

Reference Example 72: Synthesis of [4-[6-bromo-4-(difluoromethyl)-2-methylindazol-3-yl]-2-(difluoromethoxy)-6-methoxyphenyl]-[3-hydroxy-3-(trifluoromethyl)azetidin-1-yl]methanone

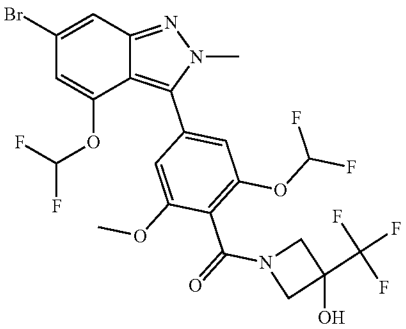 [SMILES: COc1cc(-c2c3c(OC(F)F)cc(Br)cc3nn2C)cc(OC(F)F)c1C(=O)N1CC(O)(C(F)(F)F)C1]

To a mixture of 4-[6-bromo-4-(difluoromethyl)-2-methylindazol-3-yl]-2-(difluoromethoxy)-6-methoxybenzoic acid (351 mg) described in Reference Example 71, 3-(trifluoromethyl)azetidin-3-ol hydrochloride (196 mg), HATU (419 mg), and N,N-dimethylformamide (5.0 mL), N,N-diisopropylethylamine (285 mg) was added at room temperature, and the mixture was stirred at 50 °C for 2 hours and 30 minutes. After the reaction was completed, water was added to the reaction solution, extraction was performed with ethyl acetate, and washing was performed twice with water. The organic layer was separated with Phase-Separator®, and the organic layer was concentrated under reduced pressure. The residue was purified by silica gel column chromatography (hexane:ethyl acetate=50:50 to 0:100) to obtain the title compound (385 mg) as an orange powder. MS(ESI)m/z:599.8/601.8 [M+H]+

Reference Example 73: Synthesis of [4-[6-bromo-4-(difluoromethyl)-2-methylindazol-3-yl]-2-(difluoromethoxy)-6-methoxyphenyl]-[3-(difluoromethyl)-3-hydroxyazetidin-1-yl]methanone

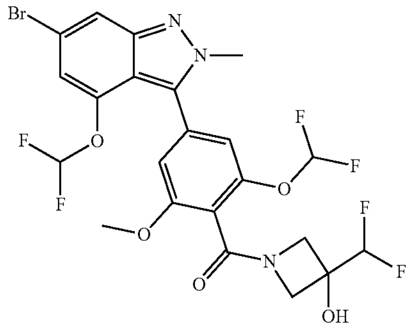 [SMILES: COc1cc(-c2c3c(OC(F)F)cc(Br)cc3nn2C)cc(OC(F)F)c1C(=O)N1CC(O)(C(F)F)C1]

To a mixture of 4-[6-bromo-4-(difluoromethyl)-2-methylindazol-3-yl]-2-(difluoromethoxy)-6-methoxybenzoic acid (300 mg) described in Reference Example 71, HATU (359 mg), 3-(difluoromethyl)azetidin-3-ol hydrochloride (167 mg), and N,N-dimethylformamide (3.0 mL), N,N-diisopropylethylamine (0.33 mL) was added at room temperature, and the mixture was stirred at 50 °C for 12 hours. After the reaction was completed, water was added to the reaction solution, extraction was performed with ethyl acetate, and washing was performed twice with water and once with saturated saline. The organic layer was separated with Phase-Separator®, and the organic layer was concentrated under reduced pressure. The residue was purified by NH silica gel column chromatography (chloroform:methanol=100:0 to 95:5 to 90:10) to obtain the title compound (375 mg) as a colorless powder. MS(ESI)m/z:581.8/583.7 [M+H]+

Reference Example 74: Synthesis of 5-(hydroxymethyl)pyridine-3-carbonitrile trifluoroacetate

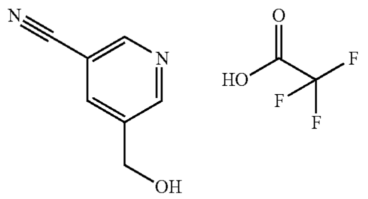 [SMILES: N#Cc1cncc(CO)c1 ; O=C(O)C(F)(F)F]

5-Cyanopyridine-3-carboxylic acid (300 mg) and N,N-dimethylformamide (16 μL) were dissolved in tetrahydrofuran (16 mL), oxalyl dichloride (0.21 mL) was added under ice cooling, and then the mixture was stirred for 2 hours. Under ice cooling, oxalyl dichloride (0.21 mL) was further added, and the mixture was stirred for 1 hour. The reaction solution was concentrated under reduced pressure, a residue obtained by performing toluene azeotropy twice was dissolved in a mixed solvent of tetrahydrofuran (7.8 mL) and 1,2-dimethoxyethane (7.8 mL), sodium borohydride (268 mg) was added under ice cooling, and the mixture was stirred for 2 hours. After the reaction was completed, methanol (2.3 mL) was added under ice cooling, and the mixture was stirred for 30 minutes and then stirred at room temperature for 15 minutes. Water was added to the reaction mixture, and extraction was performed with ethyl acetate. The organic layer was sequentially washed with water and saturated saline, drying was performed with magnesium sulfate, filtration was performed, and the filtrate was concentrated under reduced pressure. The resulting residue was purified by preparative HPLC (0.05% aqueous TFA solution-0.05% TFA acetonitrile solution) to obtain the title compound (60 mg) as a yellow viscous product. MS(ESI)m/z: 133.0 [M−H]−

Reference Example 75: Synthesis of N-[(2,2-difluorocyclopropyl)methyl]-1-(4-methoxyphenyl)methanamine

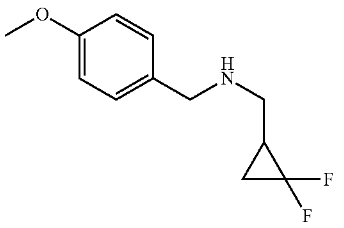 [SMILES: COc1ccc(CNCC2CC2(F)F)cc1]

(2,2-Difluorocyclopropyl)methanamine hydrochloride (1.1 g), 4-methoxybenzaldehyde (800 mg), N,N-diisopropylethylamine (1.3 mL), and acetic acid (0.34 mL) were dissolved in methanol (29 mL), sodium triacetoxyborohydride (1.9 g) was added, and the mixture was stirred at room temperature overnight. After the reaction was completed, a saturated aqueous sodium bicarbonate solution was added, and extraction was performed with chloroform. The organic layer was separated with Phase-Separator®, and the organic layer was concentrated under reduced pressure. The resulting residue was purified by silica gel column chromatography (chloroform:methanol=97:3 to 88:12) to obtain the title compound (1.1 g) as a light yellow oily product. MS(ESI) m/z:227.9 [M+H]+

Reference Example 76: Synthesis of hydrochloride of isomer that elutes earlier under chiral HPLC Conditions as described in experimental section in 1-(4-methoxyphenyl)-N-[[rel-(1R)-2,2-difluorocyclopropyl]methyl]methanamine

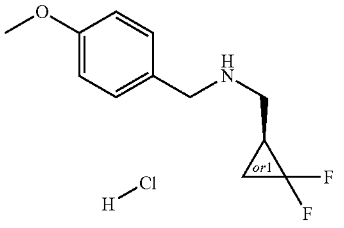 [SMILES: COc1ccc(CNC[C@@H]2CC2(F)F)cc1 ; Cl]

N-[(2,2-Difluorocyclopropyl)methyl]-1-(4-methoxyphenyl)methanamine (700 mg) described in Reference Example 75 was fractionated using a chiral column [CHIRALPAK® IG-3 (30*250), hexane:ethanol:methanol:diethylamine=80:7.5:7.5:0.1]. The residue obtained by recovering and concentrating the previous fractions was dissolved in diethyl ether (5.0 mL), and 4 M hydrochloric acid-dioxane (0.77 mL) was added dropwise at room temperature. The precipitated white solid was collected by filtration to obtain the title compound (370 mg) as a white powder. MS(ESI)m/z:228.0 [M+H]+

Reference Example 77: Synthesis of methyl 2-(difluoromethoxy)-4-(4,4,5,5-tetramethyl-1,3,2-dioxaborolan-2-yl)benzoate

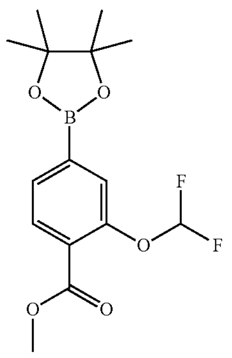 [SMILES: COC(=O)c1ccc(B2OC(C)(C)C(C)(C)O2)cc1OC(F)F]

An N,N-dimethylformamide (14 mL) suspension of methyl 2-(difluoromethoxy)-4-iodobenzoate (1.4 g), bis(pinacolato)diboron (1.1 g), a [1,1'-bis(diphenylphosphino)ferrocene]palladium(II) dichloride dichloromethane adduct (333 mg), and potassium acetate (1.2 g) was stirred under a nitrogen atmosphere at 100 °C for 4 hours. Ethyl acetate was added to the reaction solution, insoluble matter was removed by filtration, water was added to the filtrate, and extraction was performed with ethyl acetate. Sodium sulfate was added to the organic layer, filtration was performed, the filtrate was concentrated under reduced pressure, and the resulting residue was purified by silica gel column chromatography (hexane:ethyl acetate=70:30 to 0:100) to obtain the title compound (1.3 g) as a brown viscous product.

MS(ESI)m/z:329.1 [M+H]+

Reference Example 78: Synthesis of methyl 4-(6-bromo-4-cyano-2-methylindazol-3-yl)-2-(difluoromethoxy)benzoate

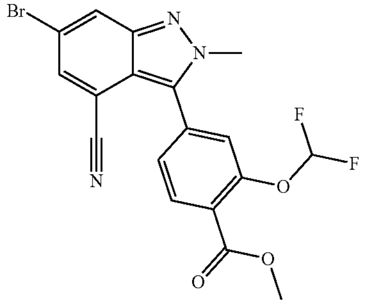 [SMILES: COC(=O)c1ccc(-c2c3c(C#N)cc(Br)cc3nn2C)cc1OC(F)F]

A mixture of methyl 2-(difluoromethoxy)-4-(4,4,5,5-tetramethyl-1,3,2-dioxaborolan-2-yl)benzoate (377 mg) described in Reference Example 77, 6-bromo-3-iodo-2-methylindazole-4-carbonitrile (438 mg) described in Reference Example 19, tripotassium phosphate (494 mg), a [1,1'-bis(diphenylphosphino)ferrocene]palladium(II) dichloride dichloromethane adduct (76 mg), water (0.62 mL), and 1,4-dioxane (6.2 mL) was heated and stirred under a nitrogen atmosphere at 100 °C for 2 hours. After the reaction was completed, water was added to the reaction mixture, and extraction was performed with chloroform. Sodium sulfate was added to the organic layer, filtration was performed, and then the filtrate was concentrated under reduced pressure. The resulting residue was purified by silica gel column chromatography (hexane:ethyl acetate=70:30 to 40:60) using an NH silica gel column and a Si silica gel column in series to obtain the title compound (254 mg) as a light yellow viscous product. MS(ESI)m/z:435.8/437.7 [M+H]+

Reference Example 79: Synthesis of methyl 4-[4-cyano-2-methyl-6-(1-methylpyrazol-4-yl)indazol-3-yl]-2-(difluoromethoxy)benzoate

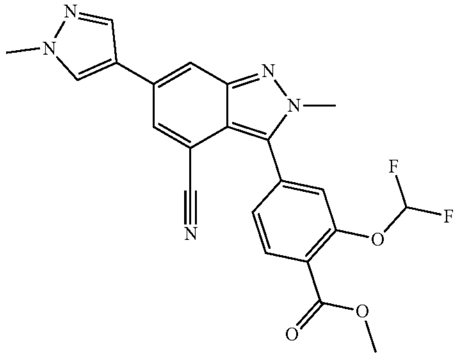 [SMILES: COC(=O)c1ccc(-c2c3c(C#N)cc(-c4cnn(C)c4)cc3nn2C)cc1OC(F)F]

A mixture of methyl 4-(6-bromo-4-cyano-2-methylindazol-3-yl)-2-(difluoromethoxy)benzoate (250 mg) described in Reference Example 78, 1-methyl-4-(4,4,5,5-tetramethyl-1,3,2-dioxaborolan-2-yl)pyrazole (122 mg), tripotassium phosphate (226 mg), a [1,1'-bis(diphenylphosphino)ferrocene]palladium(II) dichloride dichloromethane adduct (44 mg), 1,4-dioxane (3.6 mL), and water (0.36 mL) was heated and stirred under a nitrogen atmosphere at 100 °C for 2.5 hours. After the reaction was completed, water was added to the reaction mixture, and extraction was performed with chloroform. Sodium sulfate was added to the separated organic layer, and filtration was performed. The filtrate was concentrated under reduced pressure and then purified by NH silica gel column chromatography (hexane:ethyl acetate=50:50 to 30:70) to obtain the title compound (159 mg) as a light yellow powder. MS(ESI)m/z:438.2 [M+H]+

Reference Example 80: Synthesis of 4-[4-cyano-2-methyl-6-(1-methylpyrazol-4-yl)indazol-3-yl]-2-(difluoromethoxy)benzoic acid

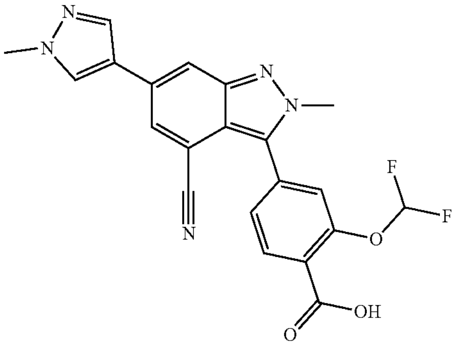 [SMILES: Cn1cc(-c2cc(C#N)c3c(-c4ccc(C(=O)O)c(OC(F)F)c4)n(C)nc3c2)cn1]

A 4 N aqueous sodium hydroxide solution (0.30 mL) was added to a mixed solution of methyl 4-[4-cyano-2-methyl-6-(1-methylpyrazol-4-yl)indazol-3-yl]-2-(difluoromethoxy)benzoate (155 mg) described in Reference Example 79, methanol (2.0 mL), and tetrahydrofuran (1.0 mL), and the mixture was stirred at room temperature for 10 minutes. After the reaction was completed, the reaction solution was concentrated under reduced pressure, and 1 N hydrochloric acid was added until a precipitate was formed. The precipitate was collected by filtration, washed with water, and then dried to obtain the title compound (111 mg) as a white powder. MS(ESI)m/z:423.9 [M+H]+

Reference Example 81: Synthesis of N,N-dimethyl-3-[4-(4,4,5,5-tetramethyl-1,3,2-dioxaborolan-2-yl)pyrazol-1-yl]propanamide

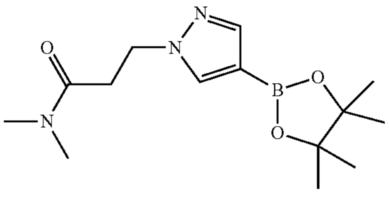

3-(4-Bromopyrazol-1-yl)-N,N-dimethylpropanamide (800 mg), bis(pinacolato)diboron (1.2 g), a [1,1'-bis(diphenylphosphino)ferrocene]palladium(II) dichloride dichloromethane adduct (266 mg), and potassium acetate (1.3 g) were suspended in 1,4-dioxane (10 mL), and stirring was performed under a nitrogen atmosphere at 100 °C for 2 hours. After the reaction was completed, water was added, and extraction was performed with chloroform. The organic layer was separated with Phase-Separator®, and the organic layer was concentrated under reduced pressure. The resulting residue was purified by silica gel column chromatography (ethyl acetate:methanol=100:0 to 90:10) to obtain the title compound (342 mg) as a brown oily product. MS(ESI) m/z:293.8 [M+H]+

Reference Example 82: Synthesis of 4-(6-bromo-4-cyano-2-methylindazol-3-yl)-N-[(1R)-2,2-difluoro-cyclopropyl]-2-(difluoromethoxy)-6-methoxybenzamide

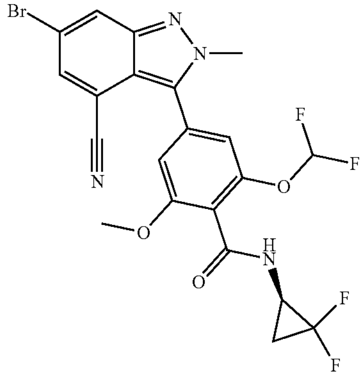 [SMILES: COc1cc(-c2c3c(C#N)cc(Br)cc3nn2C)cc(OC(F)F)c1C(=O)N[C@@H]1CC1(F)F]

N,N-Dimethylformamide (1 drop) and oxalyl dichloride (84 μL) were added to a tetrahydrofuran (1.7 mL) solution of 4-(6-bromo-4-cyano-2-methylindazol-3-yl)-2-(difluoromethoxy)-6-methoxybenzoic acid (150 mg) described in Reference Example 62, and the mixture was stirred at room temperature for 2 hours. After the reaction was completed, the reaction solution was concentrated under reduced pressure, and then an azeotropic treatment was performed using toluene. Dichloromethane (3.3 mL), (R)-2,2-difluorocyclopropan-1-amine hydrochloride (56 mg), and N,N-diisopropylethylamine (0.29 mL) were sequentially added to the residue at room temperature, and the mixture was stirred for 1 hour. After the reaction was completed, the reaction mixture was concentrated under reduced pressure, and the residue was purified by NH silica gel column chromatography (hexane:ethyl acetate=80:20 to 30:70) to obtain the title compound (123 mg) as a light yellow powder.

MS(ESI)m/z:527.2/529.2 [M+H]+

Reference Example 83: Synthesis of 4-[6-bromo-4-(difluoromethyl)-2-methylindazol-3-yl]-N-[(1R)-2,2-difluorocyclopropyl]-2-(difluoromethoxy)-6-methoxybenzamide

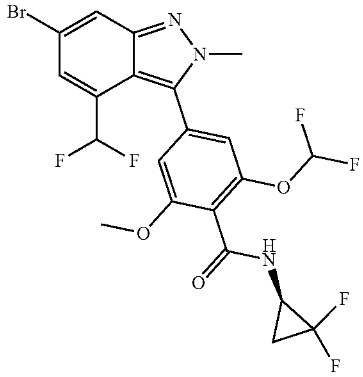 [SMILES: COc1cc(-c2c3c(C(F)F)cc(Br)cc3nn2C)cc(OC(F)F)c1C(=O)N[C@@H]1CC1(F)F]

Oxalyl dichloride (0.24 mL) and N,N-dimethylformamide (1 drop) were added to a tetrahydrofuran (4.7 mL) solution of 4-[6-bromo-4-(difluoromethyl)-2-methylindazol-3-yl]-2-(difluoromethoxy)-6-methoxybenzoic acid (450 mg) described in Reference Example 71, and the mixture was stirred at room temperature for 2 hours. After the reaction was completed, the reaction solution was concentrated under reduced pressure, and then an azeotropic treatment was performed three times using toluene. Dichloromethane (9.4 mL), (R)-2,2-difluorocyclopropan-1-amine hydrochloride (159 mg), and N,N-diisopropylethylamine (0.82 mL) were sequentially added to the residue at room temperature, and the mixture was stirred overnight. After the reaction was completed, a saturated aqueous sodium bicarbonate solution was added to the reaction mixture, extraction was performed with chloroform, the organic layer was separated with Phase-Separator®, and the organic layer was concentrated under reduced pressure. The residue was purified by NH silica gel column chromatography (hexane:ethyl acetate=75:25 to 40:60) to obtain the title compound (508 mg) as a colorless powder. MS(ESI)m/z:551.9/553.9 [M+H]+

Reference Example 84: Synthesis of 3-[(4-bromopyrazol-1-yl)methyl] thietane 1,1-dioxide

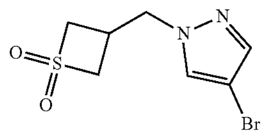 [SMILES: O=S1(=O)CC(Cn2cc(Br)cn2)C1]

(1,1-Dioxothietan-3-yl) methanol (145 mg), 4-bromo-1H-pyrazole (172 mg), and triphenylphosphine (419 mg) were dissolved in tetrahydrofuran (5.3 mL), diisopropyl azodicarboxylate (40% toluene solution) (0.84 mL) was added dropwise under ice cooling, and then the mixture was stirred as it was for 5 minutes and then further stirred at room temperature for 4 hours. After the reaction was completed, concentration was performed under reduced pressure, and the resulting residue was purified by silica gel column chromatography (chloroform:methanol=100:0 to 90:10 to 80:20) to obtain the title compound (485 mg) as a white powder.

MS(ESI)m/z:264.7/266.6 [M+H]+

Reference Example 85: Synthesis of 4-(6-bromo-4-cyano-2-methylindazol-3-yl)-2-(difluoromethoxy)-6-methoxy-N-[[rel-(1R)-2,2-difluorocyclopropyl]methyl]benzamide

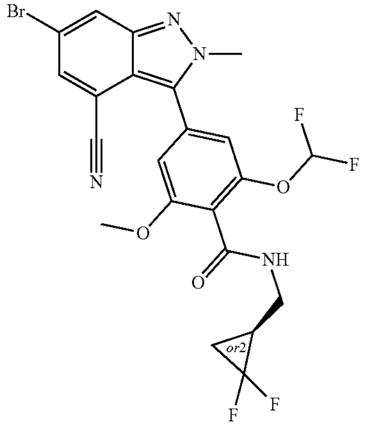 [SMILES: COc1cc(-c2c3c(C#N)cc(Br)cc3nn2C)cc(OC(F)F)c1C(=O)NC[C@@H]1CC1(F)F]

Hydrochloride (289 mg) of an isomer that elutes earlier under chiral HPLC conditions as described in the experimental section in 4-(6-bromo-4-cyano-2-1 methylindazol-3-yl)-2-(difluoromethoxy)-6-methoxybenzoic acid (450 mg) described in Reference Example 62 and 1-(4-methoxyphenyl)-N-[rel-(1R)-2,2-difluorocyclopropyl]methyl]methanamine described in Reference Example 76 was dissolved in N,N-dimethylformamide (5.0 mL), N,N-diisopropylethylamine (0.52 mL) and HATU (568 mg) were added, and the mixture was stirred at room temperature for 2 hours. After the reaction was completed, water was added to the reaction solution, and stirring was performed at room temperature for 1 hour. The precipitate was collected by filtration and washed with water to obtain a residue, and the residue was dissolved in TFA (10 mL) and stirred at 60 °C for 2 days. After the reaction was completed, the reaction solution was concentrated under reduced pressure, and toluene azeotropy was performed. The residue was purified by NH silica gel column chromatography (hexane:ethyl acetate=80:20 to 20:80) to obtain the title compound (463 mg) as a light yellow powder. MS(ESI)m/z:541.1/543.1 [M+H]+

Reference Example 86: Synthesis of 4-(6-bromo-4-cyano-2-methylindazol-3-yl)-2-(difluoromethoxy)-6-methoxybenzamide

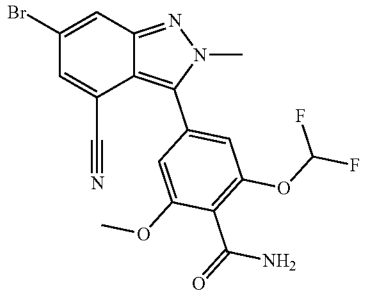 [SMILES: COc1cc(-c2c3c(C#N)cc(Br)cc3nn2C)cc(OC(F)F)c1C(N)=O]

4-(6-Bromo-4-cyano-2-methylindazol-3-yl)-2-(difluoromethoxy)-6-methoxybenzoic acid (500 mg) described in Reference Example 62, WSC·HCl (318 mg), HOBt (224 mg), ammonium chloride (237 mg), tetrahydrofuran (11 mL) were mixed, triethylamine (0.93 mL) was added, and the mixture was stirred at room temperature overnight. After the reaction was completed, a saturated aqueous sodium bicarbonate solution and water were added to the reaction mixture, and extraction was performed with ethyl acetate. The organic layer was washed with a saturated saline solution and dried with magnesium sulfate. Insoluble matter was filtered, the filtrate was concentrated under reduced pressure, and the resulting residue was suspended and washed with a mixed solvent of ethyl acetate: diethyl ether=1:1 to obtain the title compound (178 mg) as a colorless powder. MS(ESI)m/z:451.1/453.1 [M+H]+

Reference Example 87: Synthesis of 4-[4-cyano-2-methyl-6-(4,4,5,5-tetramethyl-1,3,2-dioxaborolan-2-yl)indazol-3-yl]-2-(difluoromethoxy)-6-methoxy-N-[[rel-(1R)-2,2-difluorocyclopropyl]methyl]benzamide

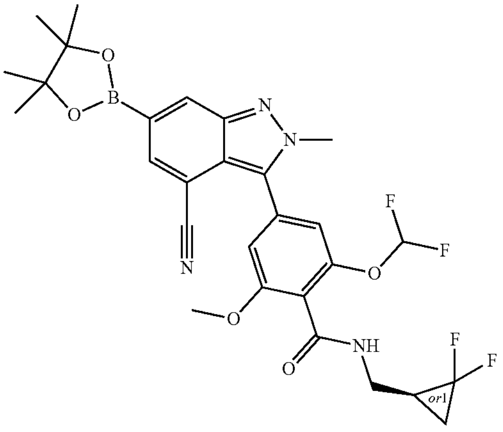 [SMILES: COc1cc(-c2c3c(C#N)cc(B4OC(C)(C)C(C)(C)O4)cc3nn2C)cc(OC(F)F)c1C(=O)NC[C@@H]1CC1(F)F]

4-(6-Bromo-4-cyano-2-methylindazol-3-yl)-2-(difluoromethoxy)-6-methoxy-N-[[rel-(1R)-2,2-difluorocyclopropyl]methyl]benzamide (230 mg) described in Reference Example 85, bis(pinacolato)diboron (119 mg), a [1,1'-bis(diphenylphosphino)ferrocene]palladium(II) dichloride dichloromethane adduct (35 mg), and potassium acetate (125 mg) were suspended in 1,4-dioxane (1.7 mL), and stirring was performed under a nitrogen atmosphere at 100 °C for 1.5 hours. After the reaction was completed, the reaction mixture was diluted with ethyl acetate and filtered, and the filtrate was concentrated under reduced pressure. The residue was purified by silica gel column chromatography (chloroform: ethyl acetate=90:10 to 50:50) to obtain the title compound (229 mg) as a brown powder. MS(ESI) m/z:589.3 [M+H]+

Reference Example 88: Synthesis of 4-bromo-1-[2-(3,3-difluoroazetidin-1-yl)ethyl]pyrazole

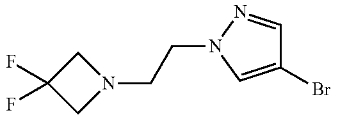 [SMILES: FC1(F)CN(CCn2cc(Br)cn2)C1]

To a mixture of 4-bromo-1-(2-bromoethyl)pyrazole (150 mg) synthesized by the method described in Anti-Cancer Agents in Medicinal Chemistry, 2018, 18, 1639-1648, 3,3-difluoroazetidine hydrochloride (191 mg), and acetonitrile (3.0 mL), N,N-diisopropylethylamine (0.31 mL) was added at room temperature, and the mixture was stirred at 60 °C. overnight. After the reaction was completed, saturated saline was added, and extraction was performed twice with ethyl acetate. The organic layer was separated with Phase-Separator®, and the organic layer was concentrated under reduced pressure. The resulting residue was purified by silica gel column chromatography (hexane:ethyl acetate=90: 10 to 40:60) to obtain the title compound (49 mg) as a colorless powder. MS(ESI)m/z:266.0/268.0 [M+H]+

Reference Example 89: Synthesis of 2-bromo-6-methoxy-N-[(4-methoxyphenyl)methyl]benzamide

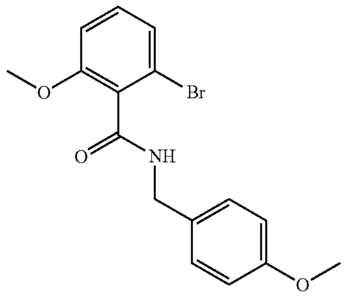

To a mixture of 2-bromo-6-methoxy-benzoic acid (1.5 g) and N,N-dimethylformamide (13 mL), HATU (2.7 g), 4-methoxybenzylamine (0.92 mL), and N,N-diisopropylethylamine (2.2 mL) were added, and the mixture was stirred at room temperature for 30 minutes. Water was added to the reaction solution, extraction was performed with ethyl acetate, and the organic layer was washed with 1 N hydrochloric acid, a saturated aqueous sodium bicarbonate solution, and saturated saline. Sodium sulfate was added, the mixture was filtered, and the filtrate was concentrated under reduced pressure. The concentrated residue was purified by silica gel column chromatography (hexane:ethyl acetate=70:30 to 30:70) to obtain the title compound (1.7 g) as a white powder. MS(ESI)m/z:349.8/351.8 [M+H]+

Reference Example 90: Synthesis of 2-bromo-6-methoxy-N-[(4-methoxyphenyl)methyl]-N-(2-propenyl)benzamide

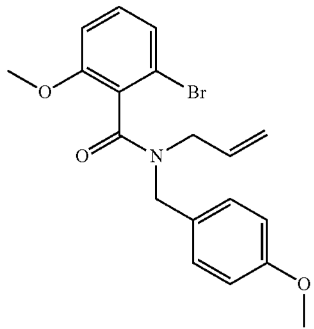

To a tetrahydrofuran (5.7 mL) solution of 2-bromo-6-methoxy-N-[(4-methoxyphenyl)methyl]benzamide (1.0 g) described in Reference Example 89, sodium hydride (60%, dispersed in liquid paraffin) (130 mg) was added little by little under ice cooling, the mixture was stirred for 1.5 hours, allyl bromide (380 mg) was added, and the mixture was stirred at 60 °C for 1 hour. Under ice cooling, a saturated aqueous ammonium chloride solution was added to the reaction solution, extraction was performed twice with ethyl acetate, and the organic layer was washed with saturated saline. Sodium sulfate was added, the mixture was filtered, the filtrate was concentrated under reduced pressure, and the resulting residue was purified by silica gel column chromatography (hexane:ethyl acetate=75:25 to 55:45) to obtain the title compound (1.0 g) as a colorless oily product. MS(ESI) m/z:390.1/392.0 [M+H]+

Reference Example 91: Synthesis of 8-methoxy-2-[(4-methoxyphenyl)methyl]-4-methylisoquinolin-1-one

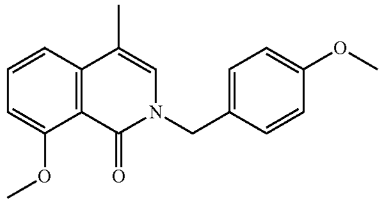 [SMILES: COc1ccc(Cn2cc(C)c3cccc(OC)c3c2=O)cc1]

An N,N-dimethylformamide (6.4 mL) suspension of 2-bromo-6-methoxy-N-[(4-methoxyphenyl)methyl]-N-(2-propenyl)benzamide (700 mg) described in Reference Example 90, palladium(II) acetate (18 mg), tetrabutylammonium chloride (490 mg), sodium formate (120 mg), and triethylamine (406 mg) was stirred under a nitrogen atmosphere at 80 °C for 3 hours. Water was added to the reaction solution, and extraction was performed three times with ethyl acetate. Sodium sulfate was added to the organic layer, filtration was performed, the filtrate was concentrated under reduced pressure, and the resulting residue was purified by NH silica gel column chromatography (hexane:ethyl acetate=50:50 to 20:80) to obtain the title compound (513 mg) as a colorless oily product. MS(ESI)m/z:310.0 [M+H]+

Reference Example 92: Synthesis of 8-methoxy-2-[(4-methoxyphenyl)methyl]-4-methyl-3,4-dihydroisoquinolin-1-one

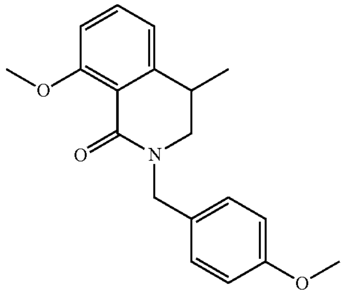

To an acetic acid (25 mL) solution of 8-methoxy-2-[(4-methoxyphenyl)methyl]-4-methylisoquinolin-1-one (2.7 g) described in Reference Example 91, 7.5% Pd/C (500 mg) was added, and the mixture was stirred under a hydrogen atmosphere at 50 °C for 4.5 hours and at 60 °C for 3 hours. The reaction solution was diluted with chloroform, and insoluble matter was removed by filtration.

The filtrate was concentrated under reduced pressure, the concentrated residue was dissolved again in acetic acid (25 mL), 10% Pd/C (500 mg) was added, and the mixture was stirred under a hydrogen atmosphere at 50 °C. overnight. The reaction solution was diluted with chloroform, insoluble matter was removed by filtration, and the filtrate was concentrated under reduced pressure. The concentrated residue was purified by silica gel column chromatography (chloroform:methanol=100:0 to 95:5) and NH silica gel column chromatography (hexane:ethyl acetate=50:50 to 20:80) to obtain the title compound (297 mg) as a white viscous product. MS(ESI)m/z:312.2 [M+H]+

Reference Example 93: Synthesis of 8-methoxy-2-[(4-methoxyphenyl)methyl]-4-methyl-6-(4,4,5,5-tetramethyl-1,3,2-dioxaborolan-2-yl)-3,4-dihydroisoquinolin-1-one

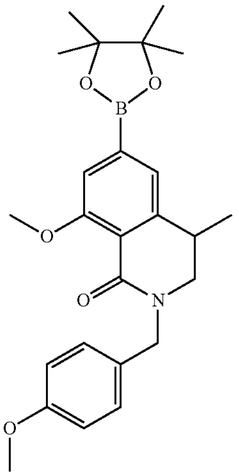

A tetrahydrofuran (4.9 mL) suspension of 8-methoxy-2-[(4-methoxyphenyl)methyl]-4-methyl-3,4-dihydroisoquinolin-1-one (812 mg) described in Reference Example 92, bis(pinacolato)diboron (650 mg), bis(1,5-cyclooctadiene)di-μ-methoxydiiridium(I) (81 mg), and 4,4'-di-tert-butyl-2,2'-bipyridyl (65 mg) was stirred under a nitrogen atmosphere at 70 °C. overnight. 1 N hydrochloric acid was added to the reaction solution, extraction was performed with chloroform, the organic layer was separated with Phase-Separator®, and the organic layer was concentrated under reduced pressure. The concentrated residue was purified by silica gel column chromatography (chloroform:methanol=100:0 to 93:7) to obtain the title compound (986 mg) as an orange viscous product. MS(ESI)m/z:438.4 [M+H]+

Reference Example 94: Synthesis of 3-[8-methoxy-2-[(4-methoxyphenyl)methyl]-4-methyl-1-oxo-3,4-dihydroisoquinolin-6-yl]-2-methyl-6-(1-methylpyrazol-4-yl)indazole-4-carbonitrile

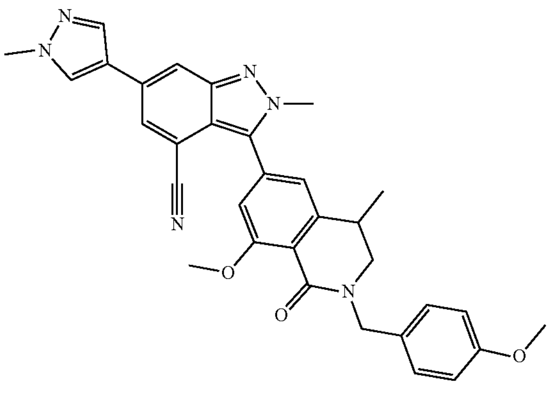

A mixture of 8-methoxy-2-[(4-methoxyphenyl)methyl]-4-methyl-6-(4,4,5,5-tetramethyl-1,3,2-dioxaborolan-2-yl)-3,4-dihydroisoquinolin-1-one (215 mg) described in Reference Example 93, 6-bromo-3-iodo-2-methylindazole-4-carbonitrile (167 mg) described in Reference Example 19, potassium carbonate (98 mg), a [1,1'-bis(diphenylphosphino)ferrocene]palladium(II) dichloride dichloromethane adduct (29 mg), 1,4-dioxane (2.4 mL), and water (0.59 mL) was heated and stirred under a nitrogen atmosphere at 100 °C for 3 hours. After the reaction was completed, the reaction mixture was diluted with chloroform, sodium sulfate was added and dried, and then insoluble matter was removed by filtration. The residue obtained by concentrating the filtrate under reduced pressure and then purifying the filtrate by NH silica gel column chromatography (hexane: ethyl acetate=50:50 to 20:80) was mixed with 1-methyl-4-(4,4,5,5-tetramethyl-1,3,2-dioxaborolan-2-yl)pyrazole (47 mg), potassium carbonate (57 mg), a [1,1'-bis(diphenylphosphino)ferrocene]palladium(II) dichloride dichloromethane adduct (17 mg), 1,4-dioxane (1.4 mL), and water (0.34 mL), and the mixture was heated and stirred under a nitrogen atmosphere at 100 °C for 1.5 hours. After the reaction was completed, the reaction mixture was diluted with chloroform, and then drying was performed by adding sodium sulfate. A filtrate obtained by removing insoluble matter by filtration was concentrated under reduced pressure and purified by NH silica gel column chromatography (ethyl acetate: methanol=100:0 to 90:10) to obtain the title compound (112 mg) as a gray powder. MS(ESI)m/z:547.1 [M+H]+

Reference Example 95: Synthesis of 6-bromo-3-[8-methoxy-2-[(4-methoxyphenyl)methyl]-4-methyl-1-oxo-3,4-dihydroisoquinolin-6-yl]-2-methylindazole-4-carbonitrile

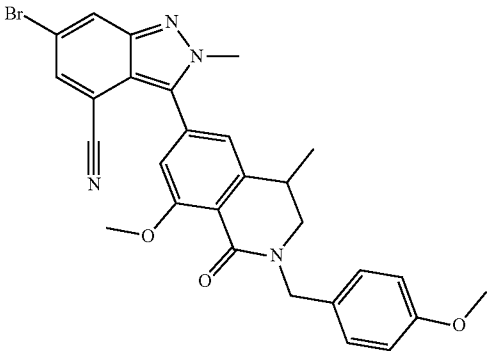 [SMILES: COc1ccc(CN2CC(C)c3cc(-c4c5c(C#N)cc(Br)cc5nn4C)cc(OC)c3C2=O)cc1]

A mixture of 8-methoxy-2-[(4-methoxyphenyl)methyl]-4-methyl-6-(4,4,5,5-tetramethyl-1,3,2-dioxaborolan-2-yl)-3,4-dihydroisoquinolin-1-one (980 mg) described in Reference Example 93, 6-bromo-3-iodo-2-methylindazole-4-carbonitrile (808 mg) described in Reference Example 19, potassium carbonate (588 mg), a [1,1'-bis(diphenylphosphino)ferrocene]palladium(II) dichloride dichloromethane adduct (174 mg), 1,4-dioxane (14 mL), and water (3.5 mL) was stirred under a nitrogen atmosphere at 100 °C for 2 hours. After the reaction was completed, chloroform was added to the reaction mixture, the organic layer was separated with Phase-Separator®, and the organic layer was concentrated under reduced pressure. The residue was purified by NH silica gel column chromatography (hexane:ethyl acetate=50:50 to 20:80) to obtain the title compound (494 mg) as an orange powder. MS(ESI)m/z:545.3/547.3 [M+H]+

Reference Example 96: Synthesis of 6-bromo-3-(8-methoxy-4-methyl-1-oxo-3,4-dihydro-2H-isoquinolin-6-yl)-2-methylindazole-4-carbonitrile

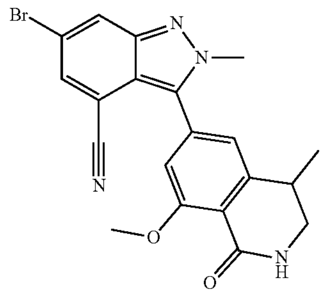 [SMILES: COc1cc(-c2c3c(C#N)cc(Br)cc3nn2C)cc2c1C(=O)NCC2C]

6-Bromo-3-[8-methoxy-2-[(4-methoxyphenyl)methyl]-4-methyl-1-oxo-3,4-dihydroisoquinolin-6-yl]-2-methylindazole-4-carbonitrile (490 mg) described in Reference Example 95 was dissolved in a mixed solvent of TFA (1.9 mL) and anisole (0.44 mL), and stirring was performed under microwave irradiation at 100 °C for 8 hours. After the reaction was completed, the reaction solution was concentrated under reduced pressure, a saturated aqueous sodium bicarbonate solution was added, and extraction was performed with chloroform. The organic layer was concentrated, the residue was purified by NH silica gel column chromatography (ethyl acetate:methanol=100:0 to 90:10) to obtain the title compound (213 mg) as a light yellow powder. MS(ESI)m/z:424.9/426.9 [M+H]+

Reference Example 97: Synthesis of isomer that elutes earlier under chiral HPLC conditions as described in experimental section in 6-bromo-2-methyl-3-[rel-(4R)-8-methoxy-4-methyl-1-oxo-3,4-dihydro-2H-isoquinolin-6-yl] indazole-4-carbonitrile

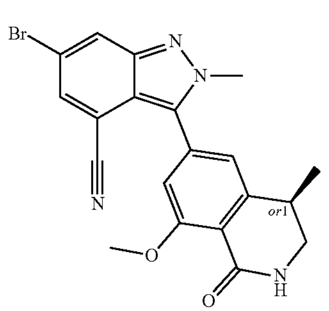 [SMILES: COc1cc(-c2c3c(C#N)cc(Br)cc3nn2C)cc2c1C(=O)NC[C@@H]2C]

6-Bromo-3-(8-methoxy-4-methyl-1-oxo-3,4-dihydro-2H-isoquinolin-6-yl)-2-methylindazole-4-carbonitrile (210 mg) described in Reference Example 96 was fractionated using a chiral column [CHIRALPAK® IC (30*250), ethanol: acetonitrile=80:20]. The previous fractions were collected and concentrated to obtain the title compound (91 mg) as a white powder. MS(ESI)m/z:425.2/427.1 [M+H]+

Reference Example 98: Synthesis of [2-(difluoromethoxy)-4-[4-(difluoromethyl)-2-methyl-6-(4,4,5,5-tetramethyl-1,3,2-dioxaborolan-2-yl)indazol-3-yl]-6-methoxyphenyl]-[3-hydroxy-3-(trifluoromethyl)azetidin-1-yl]methanone

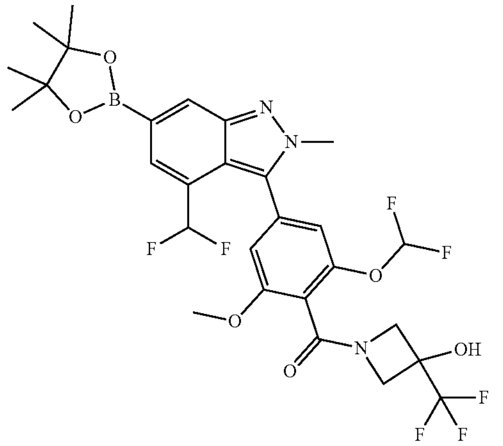 [SMILES: COc1cc(-c2c3c(C(F)F)cc(B4OC(C)(C)C(C)(C)O4)cc3nn2C)cc(OC(F)F)c1C(=O)N1CC(O)(C(F)(F)F)C1]

A mixture of [4-[6-bromo-4-(difluoromethyl)-2-methylindazol-3-yl]-2-(difluoromethoxy)-6-methoxyphenyl]-[3-hydroxy-3-(trifluoromethyl)azetidin-1-yl]methanone (129 mg) described in Reference Example 72, a [1,1'-bis(diphenylphosphino)ferrocene]palladium(II) dichloride dichloromethane adduct (18 mg), bis(pinacolato)diboron (60 mg), potassium acetate (63 mg), and 1,4-dioxane (3.0 mL) was heated and stirred under a nitrogen atmosphere at 100 °C for 3 hours. After the reaction was completed, ethyl acetate was added to the reaction mixture, and filtration was performed. The filtrate was concentrated under reduced pressure, and the residue was purified by silica gel column chromatography (hexane:ethyl acetate=50:50 to 0:100) to obtain the title compound (105 mg) as a light brown powder. MS(ESI)m/z:648.2 [M+H]+

Reference Example 99: Synthesis of 4-[4-cyano-2-methyl-6-(4,4,5,5-tetramethyl-1,3,2-dioxaborolan-2-yl)indazol-3-yl]-N-[(1R)-2,2-difluorocyclopropyl]-2-(difluoromethoxy)-6-methoxybenzamide

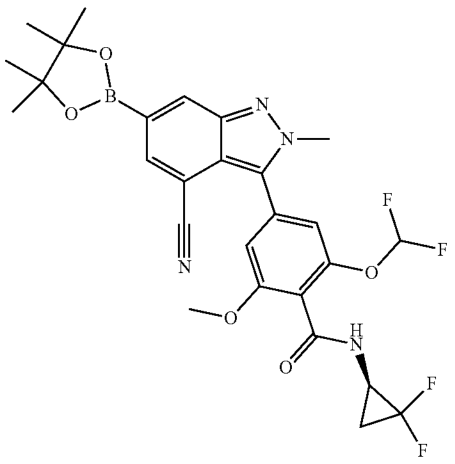 [SMILES: COc1cc(-c2c3c(C#N)cc(B4OC(C)(C)C(C)(C)O4)cc3nn2C)cc(OC(F)F)c1C(=O)N[C@@H]1CC1(F)F]

4-(6-Bromo-4-cyano-2-methylindazol-3-yl)-N-[(1R)-2,2-difluorocyclopropyl]-2-(difluoromethoxy)-6-methoxybenzamide (75 mg) described in Reference Example 82, bis(pinacolato)diboron (54 mg), [1,1'-bis(di-tert-butylphosphino)ferrocene]palladium(II) dichloride (9.3 mg), and potassium acetate (42 mg) were suspended in 1,4-dioxane (2.0 mL), and stirring was performed under a nitrogen atmosphere at 50 °C for 16 hours. After the reaction was completed, the reaction mixture was diluted with ethyl acetate and filtered, and the filtrate was concentrated under reduced pressure. The residue was purified by silica gel column chromatography (chloroform: ethyl acetate=100:0 to 40:60) to obtain the title compound (78 mg) as a brown oily product. MS(ESI)m/z:575.1 [M+H]+

Reference Example 100: Synthesis of 1-[(4-iodopyrazol-1-yl)methyl]cyclobutan-1-ol

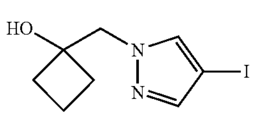 [SMILES: OC1(Cn2cc(I)cn2)CCC1]

1-(Hydroxymethyl)cyclobutan-1-ol (150 mg) was dissolved in ethyl acetate (4.9 mL), and under ice cooling, methanesulfonic anhydride (307 mg) and triethylamine (0.41 mL) were added, and the mixture was stirred for 30 minutes. After the reaction was completed, and under ice cooling, a saturated aqueous sodium bicarbonate solution was added, and extraction was performed with chloroform. The organic layer was separated with Phase-Separator®, and the organic layer was concentrated under reduced pressure. The resulting residue was dissolved in N,N-dimethylformamide (6.2 mL), 4-iodopyrazole (240 mg) and cesium carbonate (806 mg) were added at room temperature, and the mixture was stirred at 90 °C for 6 hours. Under ice cooling, water was added to the reaction solution, and extraction was performed with ethyl acetate. The organic layer was sequentially washed with water and saturated saline, drying was performed with magnesium sulfate, filtration was performed, and the filtrate was concentrated under reduced pressure. The resulting mixture was purified by silica gel column chromatography (hexane:ethyl acetate=72:25 to 50:50) to obtain the title compound (163 mg) as a colorless powder. MS(ESI)m/z:279.1 [M+H]+

Reference Example 101: Synthesis of 4-(4-iodopyrazol-1-yl)-2-methylbutan-2-ol

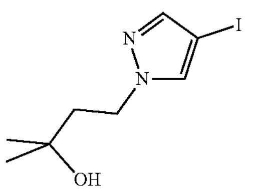

Methanesulfonic acid (3-hydroxy-3-methylbutyl) (416 mg), 4-iodopyrazole (295 mg), and cesium carbonate (991 mg) were suspended in N,N-dimethylformamide (7.6 mL), and stirring was performed at 90 °C for 3 hours. After the reaction was completed, water (30 mL) was added to the reaction solution, and extraction was performed with ethyl acetate (30 mL). The organic layer was sequentially washed with water and saturated saline, drying was performed with sodium sulfate, filtration was performed, and the filtrate was concentrated under reduced pressure. The resulting residue was purified by silica gel column chromatography (hexane: ethyl acetate=75:25 to 50:50) to obtain the title compound (343 mg) as a colorless oily product. MS(ESI)m/z:281.1 [M+H]+

Reference Example 102: Synthesis of N-[(1R)-2,2-difluorocyclopropyl]-2-(difluoromethoxy)-4-[4-(difluoromethyl)-2-methyl-6-(4,4,5,5-tetramethyl-1,3,2-dioxaborolan-2-yl)indazol-3-yl]-6-methoxybenzamide

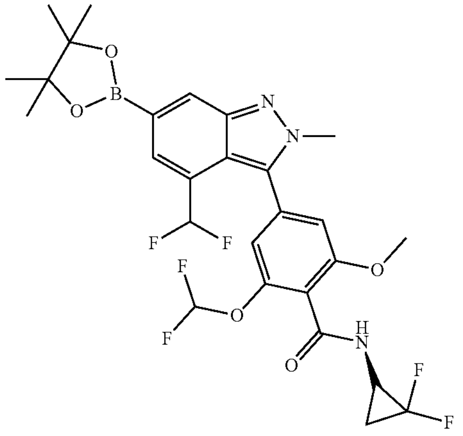

4-[6-Bromo-4-(difluoromethyl)-2-methylindazol-3-yl]-N-[(1R)-2,2-difluorocyclopropyl]-2-(difluoromethoxy)-6-methoxybenzamide (404 mg) described in Reference Example 83, bis(pinacolato)diboron (212 mg), a [1,1'-bis(diphenylphosphino)ferrocene]palladium(II) dichloride dichloromethane adduct (57 mg), potassium acetate (273 mg), and 1,4-dioxane (3.5 mL) were suspended, and stirring was performed under a nitrogen atmosphere at 45 °C. overnight. Bis(pinacolato)diboron (53 mg), a [1,1'-bis(diphenylphosphino)ferrocene]palladium(II) dichloride dichloromethane adduct (57 mg), and potassium acetate (136 mg) were added to the reaction mixture, and the mixture was stirred under a nitrogen atmosphere at 40 °C for 4 hours. A [1,1'-bis(diphenylphosphino)ferrocene]palladium(II) dichloride dichloromethane adduct (57 mg) was added to the reaction mixture, and the mixture was stirred under a nitrogen atmosphere at 100 °C for 1 hour. After the reaction was completed, magnesium sulfate was added to the reaction mixture, filtration was performed, and the filtrate was concentrated under reduced pressure. The residue was purified by silica gel column chromatography (ethyl acetate:chloroform=100:0 to 45:55) to obtain the title compound (561 mg) as a brown viscous product. MS(ESI)m/z:600.2 [M+H]+

Reference Example 103: Synthesis of cis-3-[(4-iodopyrazol-1-yl)methyl]cyclobutan-1-ol

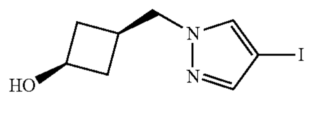 [SMILES: O[C@H]1C[C@@H](Cn2cc(I)cn2)C1]

Under ice cooling, a 1 M borane-tetrahydrofuran complex tetrahydrofuran solution (10 mL) was added dropwise to a tetrahydrofuran (10 mL) solution of cis-3-hydroxycyclobutanecarboxylic acid (517 mg) for 15 minutes, and then the mixture was stirred at room temperature. After 13 hours, insoluble matter in the reaction mixture was crushed with a spatula, and the mixture was further stirred for 1 hour. After the reaction was completed, methanol (5.0 mL) was added to the reaction mixture under ice cooling, the mixture was stirred for 10 minutes and concentrated under reduced pressure, and purification was performed by silica gel column chromatography (chloroform:methanol=100:0 to 90:10). The resulting intermediate product was dissolved in dichloromethane (10 mL), p-toluenesulfonyl chloride (810 mg) and triethylamine (0.81 mL) were added under ice cooling, and the mixture was stirred at room temperature for 18 hours. After the reaction was completed, water was added to the reaction mixture, and extraction was performed with chloroform. The organic layer was separated with Phase-Separator® and concentrated under reduced pressure, and then the organic layer was purified by silica gel column chromatography (hexane:ethyl acetate=80:20 to 25:75). 4-Iodo-1H-pyrazole (150 mg), cesium carbonate (504 mg), and N,N-dimethylformamide (3.9 mL) were added to 218 mg of 377 mg of the resulting intermediate product, and the mixture was stirred at 90 °C for 3 hours. After the reaction was completed, water was added to the reaction solution, and extraction was performed with ethyl acetate. The organic layer was sequentially washed with water and saturated saline, drying was performed with magnesium sulfate, filtration was performed, and the filtrate was concentrated under reduced pressure. The resulting residue was purified by silica gel column chromatography (hexane:ethyl acetate=70:30 to 25:75) to obtain the title compound (156 mg) as a colorless oily product. MS(ESI)m/z:279.0 [M+H]+

Reference Example 104: Synthesis of (2R)-4-(4-iodopyrazol-1-yl) butan-2-ol

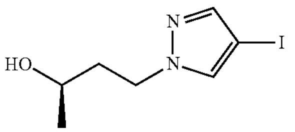

[(3R)-3-Hydroxybutyl] 4-methylbenzenesulfonate (302 mg) described in Reference Example 2, 4-iodo-1H-pyrazole (200 mg), and cesium carbonate (672 mg) were suspended in N,N-dimethylformamide (5.2 mL), and stirring was performed at 90 °C for 2 hours. After the reaction was completed, water was added to the reaction solution, and extraction was performed with chloroform. The organic layer was separated with Phase-Separator®, and the organic layer was concentrated under reduced pressure. The resulting residue was purified by preparative HPLC (10 mM aqueous ammonium carbonate solution-acetonitrile) to obtain the title compound (237 mg) as a colorless oily product. MS(ESI)m/z: 267.0 [M+H]+

Reference Example 105: Synthesis of 4-[4-cyano-2-methyl-6-(4,4,5,5-tetramethyl-1,3,2-dioxaborolan-2-yl)indazol-3-yl]-2-(difluoromethoxy)-6-methoxybenzamide

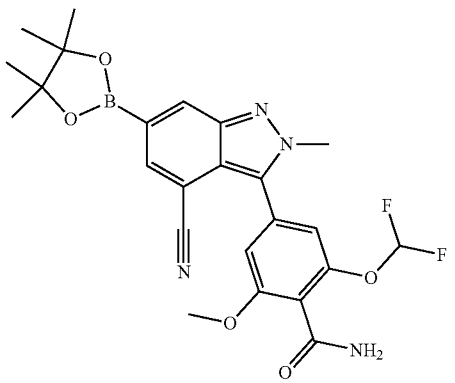 [SMILES: COc1cc(-c2c3c(C#N)cc(B4OC(C)(C)C(C)(C)O4)cc3nn2C)cc(OC(F)F)c1C(N)=O]

4-(6-Bromo-4-cyano-2-methylindazol-3-yl)-2-(difluoromethoxy)-6-methoxybenzamide (275 mg) described in Reference Example 86, bis(pinacolato)diboron (166 mg), a [1,1'-bis(diphenylphosphino)ferrocene]palladium(II) dichloride dichloromethane adduct (45 mg), and potassium acetate (160 mg) were suspended in 1,4-dioxane (2.7 mL), and stirring was performed at 100 °C for 1 hour. After the reaction was completed, ethyl acetate was added to the reaction mixture, filtration was performed, and the filtrate was concentrated under reduced pressure. The residue was purified by silica gel column chromatography (chloroform: methanol=100:0 to 90:10) to obtain the title compound (265 mg) as a brown powder. MS(ESI)m/z:499.3 [M+H]+

Reference Example 106: Synthesis of 2-methylidene thietane 1,1-dioxide

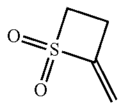

(1,1-Dioxothietan-2-yl) methanol (129 mg), 4-iodo-1H-pyrazole (202 mg), and triphenylphosphine (373 mg) were dissolved in tetrahydrofuran (4.7 mL), diisopropyl azodicarboxylate (40% toluene solution) (0.75 mL) was added at room temperature, and then the mixture was stirred for 4 hours. After the reaction was completed, concentration was performed under reduced pressure, and the resulting residue was purified by silica gel column chromatography (hexane: ethyl acetate=40:60 to 30:70) to obtain the title compound (69 mg) as a colorless oily product. 1H NMR (400 MHz, CHLOROFORM-d) δ ppm 5.93-5.89 (m, 1H), 5.57-5.53 (m, 1H), 4.01-3.95 (m, 2H), 2.88-2.81 (m, 2H)

Reference Example 107: Synthesis of 2-[(4-iodopyrazol-1-yl)methyl] thietane 1,1-dioxide

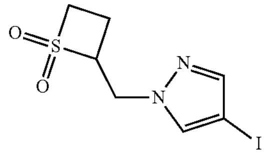 [SMILES: O=S1(=O)CCC1Cn1cc(I)cn1]

2-Methylidene thietane 1,1-dioxide (62 mg) described in Reference Example 106 and 4-iodo-1H-pyrazole (153 mg) were dissolved in N,N-dimethylformamide (5.2 mL), sodium hydride (60%, dispersed in liquid paraffin) (25 mg) was added under ice cooling, and the mixture was stirred at room temperature for 2 hours. After the reaction was completed, under ice cooling, water (30 mL) and a saturated aqueous ammonium chloride solution (5 mL) were added, and the mixture was extracted twice with ethyl acetate (10 mL). The organic layers were combined and washed with saturated saline, dried with sodium sulfate, filtered, and then concentrated under reduced pressure. The resulting residue was purified by silica gel column chromatography (hexane: ethyl acetate=60:40 to 35:65) to obtain the title compound (32 mg) as a white powder. MS(ESI)m/z:313.0 [M+H]+

Reference Example 108: Synthesis of 2-[(4-iodopyrazol-1-yl)methyl]thiolane=1,1-dioxide

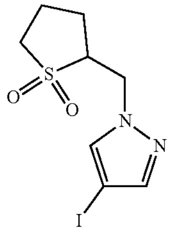 [SMILES: O=S1(=O)CCCC1Cn1cc(I)cn1]

Methanesulfonic acid (1,1-dioxothiolan-2-yl)methyl (353 mg) synthesized by the method described in US 2020/0079772 A and 4-iodo-1H-pyrazole (599 mg) were dissolved in acetonitrile (7.7 mL), potassium carbonate (1.1 g) was added at room temperature, and the mixture was stirred at 75 °C for 20 hours. After the reaction was completed, water (20 mL) was added, and extraction was performed twice with ethyl acetate (20 mL). The organic layers were combined and washed with saturated saline, dried with sodium sulfate, filtered, and then concentrated under reduced pressure. The resulting residue was purified by silica gel column chromatography (hexane:ethyl acetate=60:40 to 35:65) to obtain the title compound (360 mg) as a white powder. MS(ESI)m/z:327.0 [M+H]+

Reference Example 109: Synthesis of (2S)-1-[4-(4,4,5,5-tetramethyl-1,3,2-dioxaborolan-2-yl)pyrazol-1-yl]butan-2-ol

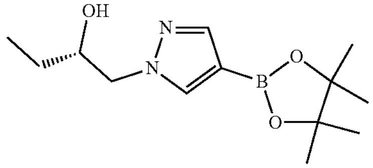 [SMILES: CC[C@H](O)Cn1cc(B2OC(C)(C)C(C)(C)O2)cn1]

4-(4,4,5,5-Tetramethyl-1,3,2-dioxaborolan-2-yl)-1H-pyrazole (250 mg), (2S)-2-ethyloxirane (0.27 mL), and cesium carbonate (630 mg) were suspended in acetonitrile (2.6 mL), and stirring was performed under microwave irradiation at 130 °C. for 1 hour. After the reaction was completed, the reaction solution was filtered, and the filtrate was concentrated under reduced pressure. Dichloromethane (10 mL) was added to the resulting residue, the mixture was stirred at room temperature for 30 minutes and then filtered again, and the filtrate was concentrated under reduced pressure to obtain the title compound (300 mg) as a colorless oily product.

MS(ESI)m/z:267.3 [M+H]+

Reference Example 110: Synthesis of tert-butyl 2-[4-[4-cyano-3-[3-(difluoromethoxy)-4-[(1-fluorocyclopropyl)methylcarbamoyl]-5-methoxyphenyl]-2-methylindazol-6-yl]pyrazol-1-yl]acetate

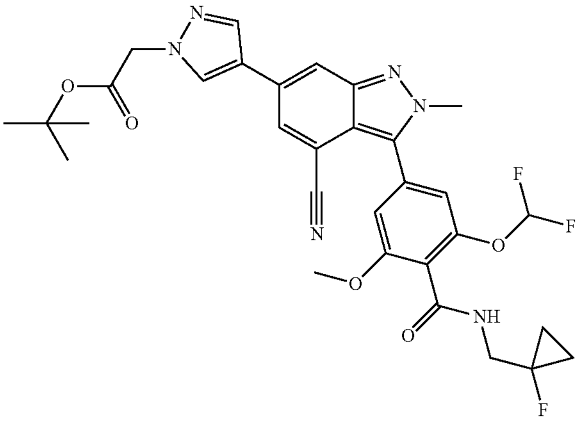 [SMILES: COc1cc(-c2c3c(C#N)cc(-c4cnn(CC(=O)OC(C)(C)C)c4)cc3nn2C)cc(OC(F)F)c1C(=O)NCC1(F)CC1]

A mixture of tert-butyl 2-[4-(4,4,5,5-tetramethyl-1,3,2-dioxaborolan-2-yl)pyrazol-1-yl]acetate (276 mg), 4-(6-bromo-4-cyano-2-methylindazol-3-yl)-2-(difluoromethoxy)-N-[(1-fluorocyclopropyl)methyl]-6-methoxybenzamide (312 mg) described in Reference Example 63, tripotassium phosphate (253 mg), a [1,1'-bis(diphenylphosphino)ferrocene]palladium(II) dichloride dichloromethane adduct (49 mg), 1,4-dioxane (6.0 mL), and water (0.60 mL) was heated and stirred under a nitrogen atmosphere at 100 °C for 2 hours. After the reaction was completed, water was added to the reaction mixture, and extraction was performed three times with chloroform.

The combined organic layers were concentrated under reduced pressure and then purified by NH silica gel column chromatography (hexane:ethyl acetate=90:10 to 0:100) to obtain the title compound (392 mg) as a light yellow viscous product. MS(ESI)m/z:625.5 [M+H]+

Reference Example 111: Synthesis of 2-[4-[4-cyano-3-[3-(difluoromethoxy)-4-[(1-fluorocyclopropyl)methylcarbamoyl]-5-methoxyphenyl]-2-methylindazol-6-yl]pyrazol-1-yl]acetate

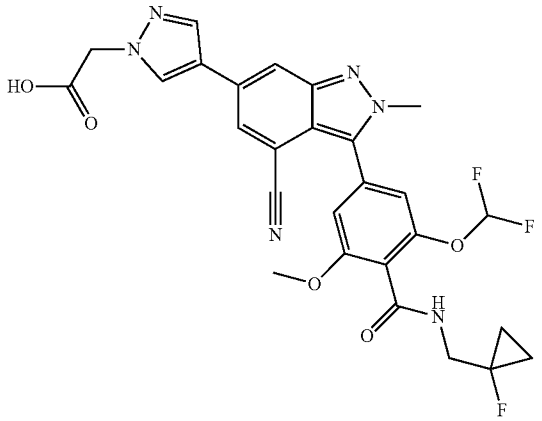 [SMILES: COc1cc(-c2c3c(C#N)cc(-c4cnn(CC(=O)O)c4)cc3nn2C)cc(OC(F)F)c1C(=O)NCC1(F)CC1]

To a 1,4-dioxane (2.0 mL) solution of tert-butyl 2-[4-[4-cyano-3-[3-(difluoromethoxy)-4-[(1-fluorocyclopropyl)methylcarbamoyl]-5-methoxyphenyl]-2-methylindazol-6-yl]pyrazol-1-yl]acetate (385 mg) described in Reference Example 110, 4 M hydrochloric acid-dioxane (4.0 mL) and tetrahydrofuran (1.0 mL) were added, and the mixture was stirred at room temperature for 17 hours. After the reaction was completed, the reaction mixture was concentrated, and ethyl acetate was added to the residue. The precipitated solid was collected by filtration and dried to obtain the title compound (354 mg) as a colorless powder. MS(ESI)m/z: 569.1 [M+H]+

Reference Example 112: Synthesis of tert-butyl 2-(difluoromethoxy)-4-[4-(difluoromethyl)-6-(1-ethylpyrazol-4-yl)-2-methylindazol-3-yl]-6-methoxybenzoate

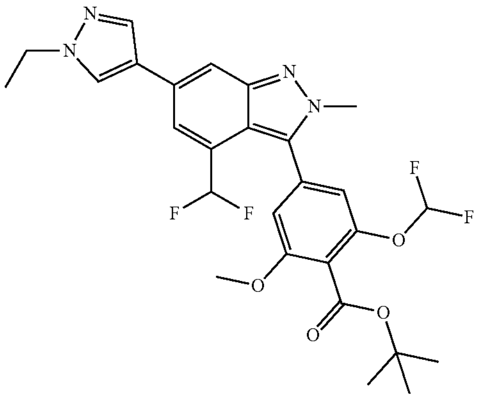 [SMILES: CCn1cc(-c2cc(C(F)F)c3c(-c4cc(OC)c(C(=O)OC(C)(C)C)c(OC(F)F)c4)n(C)nc3c2)cn1]

A mixture of tert-butyl 4-[6-bromo-4-(difluoromethyl)-2-methylindazol-3-yl]-2-(difluoromethoxy)-6-methoxybenzoate (303 mg) described in Reference Example 45, 1-ethyl-4-(4,4,5,5-tetramethyl-1,3,2-dioxaborolan-2-yl)-1H-pyrazole (189 mg), tripotassium phosphate (362 mg), a [1,1'-bis(diphenylphosphino)ferrocene]palladium(II) dichloride dichloromethane adduct (46 mg), 1,4-dioxane (6.0 mL), and water (0.60 mL) was heated and stirred under a nitrogen atmosphere at 100 °C for 3 hours. After the reaction was completed, water was added to the reaction mixture, and extraction was performed three times with chloroform. The combined organic layers were concentrated under reduced pressure and then purified by NH silica gel column chromatography (hexane:ethyl acetate=95:5 to 40:60) to obtain the title compound (398 mg) as a light yellow oily product. MS(ESI)m/z:549.1 [M+H]+

Reference Example 113: Synthesis of 2-(difluoromethoxy)-4-[4-(difluoromethyl)-6-(1-ethylpyrazol-4-yl)-2-methylindazol-3-yl]-6-methoxybenzoic acid

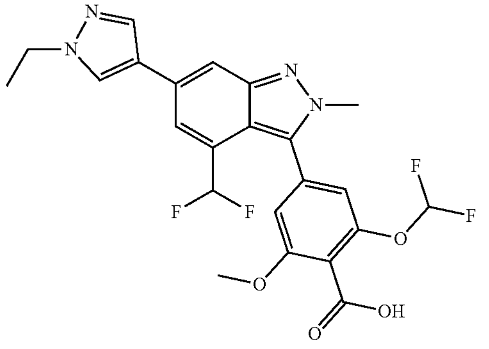

TFA (3.0 mL) was added to a dichloromethane (3.0 mL) solution of tert-butyl 2-(difluoromethoxy)-4-[4-(difluoromethyl)-6-(1-ethylpyrazol-4-yl)-2-methylindazol-3-yl]-6-methoxybenzoate (354 mg) described in Reference Example 112, and the mixture was stirred at room temperature for 1 hour. After the reaction was completed, the reaction mixture was concentrated under reduced pressure, ethyl acetate was added, and then the mixture was stirred at room temperature for 2 hours. The precipitated solid was collected by filtration and dried to obtain the title compound (190 mg) as a colorless powder. MS(ESI)m/z:493.0 [M+H]+

Reference Example 114: Synthesis of tert-butyl 2-(difluoromethoxy)-4-[4-(difluoromethyl)-2-methyl-6-(1-propylpyrazol-4-yl)indazol-3-yl]-6-methoxybenzoate

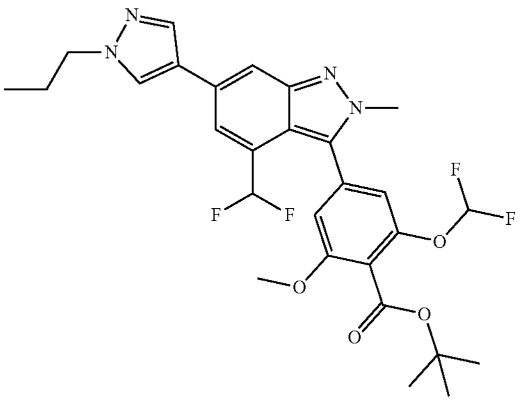 [SMILES: CCCn1cc(-c2cc(C(F)F)c3c(-c4cc(OC)c(C(=O)OC(C)(C)C)c(OC(F)F)c4)n(C)nc3c2)cn1]

A mixture of tert-butyl 4-[6-bromo-4-(difluoromethyl)-2-methylindazol-3-yl]-2-(difluoromethoxy)-6-methoxybenzoate (150 mg) described in Reference Example 45, 1-propyl-4-(4,4,5,5-tetramethyl-1,3,2-dioxaborolan-2-yl)-1H-pyrazole (100 mg), tripotassium phosphate (179 mg), a [1,1'-bis(diphenylphosphino)ferrocene]palladium(II) dichloride dichloromethane adduct (23 mg), 1,4-dioxane (3.0 mL), and water (0.30 mL) was heated and stirred under a nitrogen atmosphere at 100 °C for 3 hours. After the reaction was completed, water was added to the reaction mixture, and extraction was performed three times with chloroform. The combined organic layers were concentrated under reduced pressure and then purified by NH silica gel column chromatography (hexane:ethyl acetate=95:5 to 50:50) to obtain the title compound (145 mg) as a colorless oily product. MS(ESI)m/z:563.1 [M+H]+

Reference Example 115: Synthesis of 2-(difluoromethoxy)-4-[4-(difluoromethyl)-2-methyl-6-(1-propylpyrazol-4-yl)indazol-3-yl]-6-methoxybenzoic acid

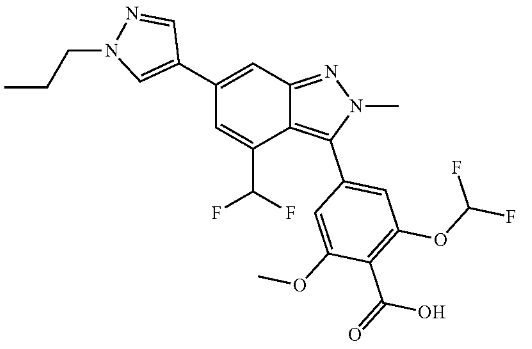 [SMILES: CCCn1cc(-c2cc(C(F)F)c3c(-c4cc(OC)c(C(=O)O)c(OC(F)F)c4)n(C)nc3c2)cn1]

TFA (1.0 mL) was added to a dichloromethane (2.0 mL) solution of tert-butyl 2-(difluoromethoxy)-4-[4-(difluoromethyl)-2-methyl-6-(1-propylpyrazol-4-yl)indazol-3-yl]-6-methoxybenzoate (135 mg) described in Reference Example 114, and the mixture was stirred at room temperature for 1 hour. After the reaction was completed, the reaction mixture was concentrated once under reduced pressure, ethyl acetate was added, and then the mixture was concentrated under reduced pressure again. Diethyl ether was added to the residue, and the precipitated solid was collected by filtration and dried to obtain the title compound (96 mg) as a colorless powder.

MS(ESI)m/z:507.0 [M+H]+

Reference Example 116: Synthesis of 1-[2-(4-iodopyrazol-1-yl)ethyl] cyclobutan-1-ol

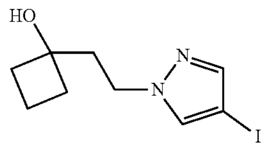 [SMILES: OC1(CCn2cc(I)cn2)CCC1]

2-(1-Hydroxycyclobutyl)ethyl 4-methylbenzenesulfonate (501 mg) synthesized by the method described in WO 2013/144191 A, 4-iodopyrazole (360 mg), and cesium carbonate (1.8 g) were suspended in N,N-dimethylformamide (9.0 mL), and stirring was performed at 60 °C for 2 hours. After the reaction was completed, water was added, and extraction was performed three times with ethyl acetate. The organic layers were combined and washed with saturated saline, drying was performed with sodium sulfate, filtration was performed, and the filtrate was concentrated under reduced pressure.

The resulting residue was purified by silica gel column chromatography (hexane:ethyl acetate=95:5 to 75:25 to 70:30) to obtain the title compound (545 mg) as a colorless oily product. MS(ESI)m/z:292.8 [M+H]+

Reference Example 117: Synthesis of 4-[4-cyano-2-methyl-6-[1-(oxan-2-yl)pyrazol-4-yl]indazol-3-yl]-N-[(1R)-2,2-difluorocyclopropyl]-2-(difluoromethoxy)-6-methoxybenzamide

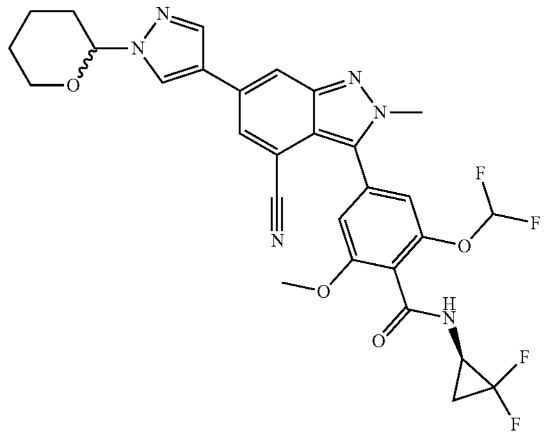 [SMILES: COc1cc(-c2c3c(C#N)cc(-c4cnn(C5CCCCO5)c4)cc3nn2C)cc(OC(F)F)c1C(=O)N[C@@H]1CC1(F)F]

A mixture of 4-(6-bromo-4-cyano-2-methylindazol-3-yl)-N-[(1R)-2,2-difluorocyclopropyl]-2-(difluoromethoxy)-6-methoxybenzamide (90 mg) described in Reference Example 82, 1-(tetrahydro-2H-pyran-2-yl)-4-(4,4,5,5-tetramethyl-1,3,2-dioxaborolan-2-yl)-1H-pyrazole (57 mg), tripotassium phosphate (72 mg), [1,1'-bis(di-tert-butylphosphino)ferrocene]palladium(II) dichloride (5.6 mg), 1,4-dioxane (1.5 mL), and water (0.15 mL) was heated and stirred under a nitrogen atmosphere at 50 °C for 1.5 hours. After the reaction was completed, water was added to the reaction mixture, and extraction was performed three times with chloroform. The combined organic layers were concentrated under reduced pressure and then purified by NH silica gel column chromatography (hexane:ethyl acetate=95:5 to 15:85) to obtain the title compound (96 mg) as a colorless powder. MS(ESI)m/z:599.0 [M+H]+

Reference Example 118: Synthesis of 4-[4-cyano-2-methyl-6-[1-(oxan-2-yl)pyrazol-3-yl]indazol-3-yl]-N-[(1R)-2,2-difluorocyclopropyl]-2-(difluoromethoxy)-6-methoxybenzamide

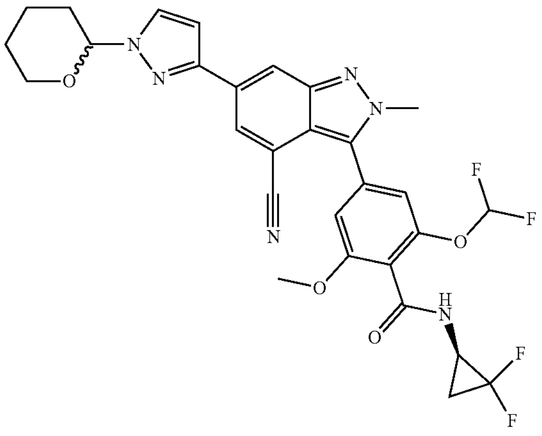 [SMILES: COc1cc(-c2c3c(C#N)cc(-c4ccn(C5CCCCO5)n4)cc3nn2C)cc(OC(F)F)c1C(=O)N[C@@H]1CC1(F)F]

A mixture of 4-(6-bromo-4-cyano-2-methylindazol-3-yl)-N-[(1R)-2,2-difluorocyclopropyl]-2-(difluoromethoxy)-6-methoxybenzamide (96 mg) described in Reference Example 82, 1-(tetrahydro-2H-pyran-2-yl)-3-(4,4,5,5-tetramethyl-1,3,2-dioxaborolan-2-yl)-1H-pyrazole (61 mg), tripotassium phosphate (77 mg), [1,1'-bis(di-tert-butylphosphino)ferrocene]palladium(II) dichloride (5.9 mg), 1,4-dioxane (2.0 mL), and water (0.20 mL) was heated and stirred under a nitrogen atmosphere at 50 °C for 1.5 hours. After the reaction was completed, water was added to the reaction mixture, and extraction was performed three times with chloroform. The combined organic layers were concentrated under reduced pressure and then purified by NH silica gel column chromatography (hexane:ethyl acetate=95:5 to 0:100 to ethyl acetate:methanol=97:3) to obtain the title compound (107 mg) as a light yellow powder.

MS(ESI)m/z:599.0 [M+H]+

Reference Example 119: Synthesis of N-[(1R)-2,2-difluorocyclopropyl]-2-(difluoromethoxy)-4-[4-(difluoromethyl)-2-methyl-6-[1-(oxan-2-yl)pyrazol-4-yl]indazol-3-yl]-6-methoxybenzamide

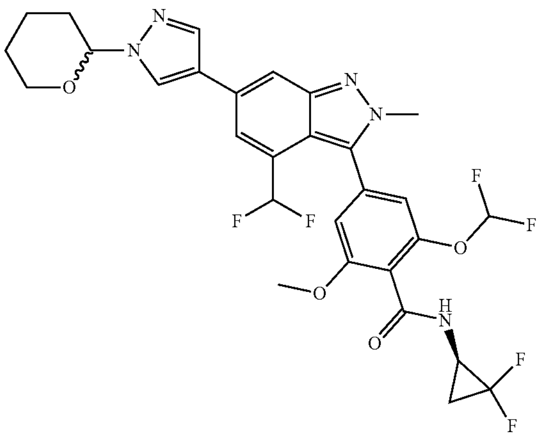 [SMILES: COc1cc(-c2c3c(C(F)F)cc(-c4cnn(C5CCCCO5)c4)cc3nn2C)cc(OC(F)F)c1C(=O)N[C@@H]1CC1(F)F]

A mixture of 4-[6-bromo-4-(difluoromethyl)-2-methylindazol-3-yl]-N-[(1R)-2,2-difluorocyclopropyl]-2-(difluoromethoxy)-6-methoxybenzamide (118 mg) described in Reference Example 83, 1-(tetrahydro-2H-pyran-2-yl)-4-(4,4,5,5-tetramethyl-1,3,2-dioxaborolan-2-yl)-1H-pyrazole (71 mg), tripotassium phosphate (91 mg), [1,1'-bis(di-tert-butylphosphino)ferrocene]palladium(II) dichloride (7.0 mg), 1,4-dioxane (2.0 mL), and water (0.20 mL) was heated and stirred under a nitrogen atmosphere at 50 °C for 2 hours. After the reaction was completed, water was added to the reaction mixture, and extraction was performed three times with chloroform. The combined organic layers were concentrated under reduced pressure and then purified by.

NH silica gel column chromatography (hexane:ethyl acetate=95:5 to 0:100) to obtain the title compound (127 mg) as a light yellow viscous product.

MS(ESI)m/z:624.3 [M+H]+

Reference Example 120: Synthesis of 2-bromo-6-methoxy-N-(2-propenyl)benzamide

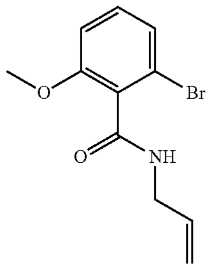

Oxalyl dichloride (7.4 mL) and N,N-dimethylformamide (10 μL) were sequentially added to a mixture of 2-bromo-6-methoxy-benzoic acid (10 g) and toluene (87 mL), and the mixture was stirred under a nitrogen atmosphere at 60 °C for 1 hour. The reaction solution was concentrated under reduced pressure, toluene was added to the concentrated residue, and then the mixture was concentrated under reduced pressure again. Tetrahydrofuran (87 mL) was added to the concentrated residue, allylamine hydrochloride (4.3 g) and triethylamine (24 mL) were sequentially added under ice cooling, and the mixture was stirred under a nitrogen atmosphere at room temperature for 1.5 hours. The reaction solution was concentrated under reduced pressure, water was added to the concentrated residue, filtration was performed, and washing was performed with water. After the filtered product was dissolved in ethyl acetate, sodium sulfate was added and filtered, and the filtrate was concentrated under reduced pressure. Suspension and water washing were performed with hexane (about 30 mL) to obtain the title compound (10 g) as a white powder.

MS(ESI)m/z:269.9/271.8 [M+H]+

Reference Example 121: Synthesis of 2-bromo-6-methoxy-N-(2-propenyl)-N-(2-trimethylsilylethoxymethyl)benzamide

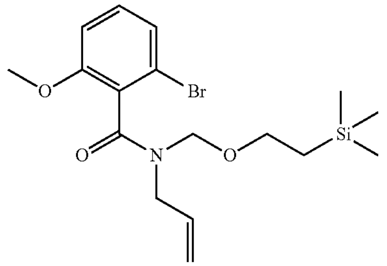

To an N,N-dimethylformamide (40 mL) solution of 2-bromo-6-methoxy-N-(2-propenyl)benzamide (5.1 g) described in Reference Example 120, sodium hydride (60%, dispersed in liquid paraffin) (824 mg) was added under ice cooling, and then the mixture was stirred for 5 minutes and then stirred at room temperature for 15 minutes. Under ice cooling, 2-(chloromethoxy)ethyltrimethylsilane (3.7 g) was added, and the mixture was stirred under a nitrogen atmosphere at room temperature for 3 hours. Under ice cooling, water was added to the reaction solution, and extraction was performed twice with ethyl acetate. The organic layer was washed with saturated saline, sodium sulfate was added, the mixture was filtered, and then the filtrate was concentrated under reduced pressure to obtain the title compound (8.6 g) as a light yellow oily product. MS(ESI)m/z:399.9/401.9 [M+H]+

Reference Example 122: Synthesis of 8-methoxy-4-methyl-2-(2-trimethylsilylethoxymethyl)isoquinolin-1-one

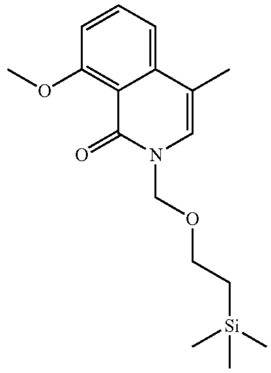

A mixture of 2-bromo-6-methoxy-N-(2-propenyl)-N-(2-trimethylsilylethoxymethyl)benzamide (7.5 g) described in Reference Example 121, palladium(II) acetate (210 mg), triethylamine (6.5 mL), tetrabutylammonium chloride (5.7 g), and N,N-dimethylformamide (40 mL) was stirred under a nitrogen atmosphere at 80 °C for 1 hour. Water (100 mL) and ethyl acetate (70 mL) were added to the reaction solution, the mixture was filtered, and the filtrate was extracted twice with ethyl acetate. The organic layer was washed with 1 N hydrochloric acid, a saturated aqueous sodium bicarbonate solution, and saturated saline, sodium sulfate was added, the mixture was filtered, and the filtrate was concentrated under reduced pressure. The concentrated residue was purified by column chromatography (hexane:ethyl acetate=90:10 to 20:80) using an NH silica gel column and a Si silica gel column in series to obtain the title compound (5.2 g) as a colorless powder. MS(ESI)m/z:320.0 [M+H]+

Reference Example 123: Synthesis of 8-methoxy-4-methyl-2-(2-trimethylsilylethoxymethyl)-3,4-dihydroisoquinolin-1-one

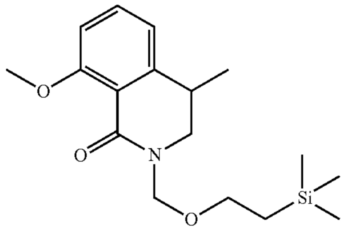

10% Pd/C (3.7 g) was added to an ethanol (140 mL) solution of 8-methoxy-4-methyl-2-(2-trimethylsilylethoxymethyl)isoquinolin-1-one (5.2 g) described in Reference Example 122, and the mixture was stirred under a hydrogen atmosphere at room temperature overnight. The reaction solution was filtered, and the filtrate was concentrated under reduced pressure. The concentrated residue was purified by silica gel column chromatography (hexane:ethyl acetate=90:10 to 50:50) to obtain the title compound (3.7 g) as a light yellow oily product. MS(ESI)m/z:322.0 [M+H]+

Reference Example 124: Synthesis of isomer that elutes earlier under chiral HPLC conditions as described in experimental section in rel-(4R)-8-methoxy-4-methyl-2-(2-trimethylsilylethoxymethyl)-3,4-dihydroisoquinolin-1-one

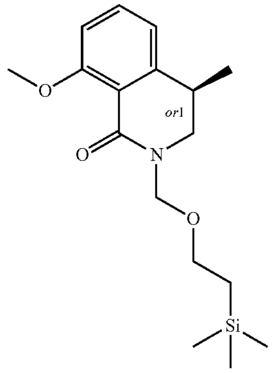

8-Methoxy-4-methyl-2-(2-trimethylsilylethoxymethyl)-3,4-dihydroisoquinolin-1-one (206 mg) described in Reference Example 123 was fractionated using a chiral column [CHIRALPAK® ID (30*250), hexane:ethanol: 2-propanol=80:20]. The previous fractions were collected and concentrated to obtain the title compound (72 mg) as a colorless oily product. MS(ESI)m/z:322.0 [M+H]+

Reference Example 125: Synthesis of rel-(4R)-8-methoxy-4-methyl-6-(4,4,5,5-tetramethyl-1,3,2-dioxaborolan-2-yl)-2-(2-trimethylsilylethoxymethyl)-3,4-dihydroisoquinolin-1-one

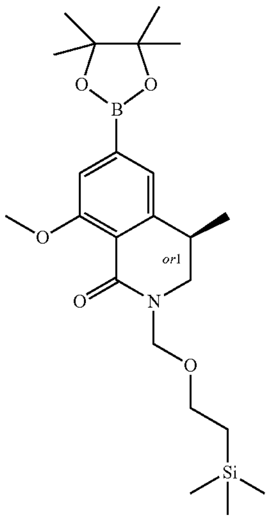

A mixture of an isomer (70 mg) that elutes earlier under chiral HPLC conditions as described in the experimental section of rel-(4R)-8-methoxy-4-methyl-2-(2-trimethylsilylethoxymethyl)-3,4-dihydroisoquinolin-1-one described in Reference Example 124, bis(pinacolato)diboron (66 mg), bis(1,5-cyclooctadiene)di-μ-methoxydiiridium(I) (4.3 mg), 4,4'-di-tert-butyl-2,2'-bipyridyl (3.5 mg), and heptane (0.22 mL) was stirred under a nitrogen atmosphere at 80 °C for 2 hours. The reaction solution was diluted with ethyl acetate and purified by silica gel column chromatography (hexane: ethyl acetate=70:30 to 30:70) to obtain the title compound (95 mg) as a light yellow oily product. MS(ESI)m/z:448.4 [M+H]+

Reference Example 126: Synthesis of tert-butyl 8-methoxy-4,4-dimethyl-1-oxo-3H-isoquinoline-2-carboxylate

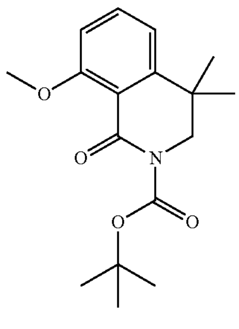

A mixture of tert-butyl N-(2-bromo-6-methoxybenzoyl)-N-(2-methyl-2-propenyl)carbamate (1.3 g) described in Reference Example 130, tetrabutylammonium chloride (909 mg), sodium formate (303 mg), triethylamine (1.0 mL), palladium(II) acetate (67 mg), and N,N-dimethylformamide (12 mL) was stirred under a nitrogen atmosphere at 80 °C for 4 hours. Water was added to the reaction solution, and extraction was performed three times with ethyl acetate. Sodium sulfate was added to the organic layer, filtration was performed, and the filtrate was concentrated under reduced pressure. The resulting residue was purified by silica gel column chromatography (chloroform:methanol=100:0 to 93:7 to obtain the title compound (597 mg) as a light yellow powder. MS(ESI)m/z:249.9 [M+H−tBu]+

Reference Example 127: Synthesis of tert-butyl 8-methoxy-4,4-dimethyl-1-oxo-6-(4,4,5,5-tetramethyl-1,3,2-dioxaborolan-2-yl)-3H-isoquinoline-2-carboxylate

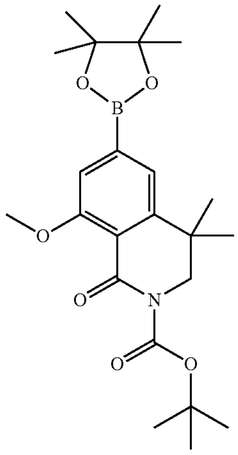

Tetrahydrofuran (1.2 mL) was added to tert-butyl 8-methoxy-4,4-dimethyl-1-oxo-3H-isoquinoline-2-carboxylate (380 mg) described in Reference Example 126, bis(pinacolato)diboron (379 mg), 4,4'-di-tert-butyl-2,2'-bipyridyl (20 mg), and bis(1,5-cyclooctadiene)di-μ-methoxydiiridium(I) (25 mg), and the mixture was stirred under a nitrogen atmosphere at 70 °C for 2 hours. The reaction solution was diluted with ethyl acetate and purified by silica gel column chromatography (hexane:ethyl acetate=50:50 to 25:75) as it was to obtain the title compound (534 mg) as a light yellow powder. MS(ESI)m/z:376.3 [M+H−tBu]+

Reference Example 128: Synthesis of 6-bromo-3-(8-methoxy-4,4-dimethyl-1-oxo-2,3-dihydroisoquinolin-6-yl)-2-methylindazole-4-carbonitrile

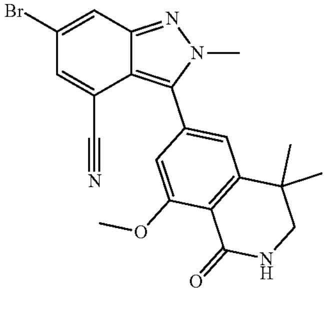 [SMILES: COc1cc(-c2c3c(C#N)cc(Br)cc3nn2C)cc2c1C(=O)NCC2(C)C]

tert-Butyl 8-methoxy-4,4-dimethyl-1-oxo-6-(4,4,5,5-tetramethyl-1,3,2-dioxaborolan-2-yl)-3H-isoquinoline-2-carboxylate (900 mg) described in Reference Example 127 and 6-bromo-3-iodo-2-methylindazole-4-carbonitrile (700 mg) described in Reference Example 19 were suspended in a mixed solvent of 1,4-dioxane (13 mL) and water (3.2 mL), and stirring was performed under a nitrogen atmosphere at 100 °C. for 10 minutes. After the suspension was allowed to cool to room temperature, potassium carbonate (535 mg) and a [1,1'-bis(diphenylphosphino)ferrocene]palladium(II) dichloride dichloromethane adduct (158 mg) were added, and the mixture was stirred under a nitrogen atmosphere at 100 °C for 3 hours. After the reaction was completed, chloroform was added to the reaction mixture, and the organic layer separated with Phase-Separator® was concentrated under reduced pressure. The residue was dissolved in dichloromethane (9.7 mL), TFA (1.5 mL) was added, and the mixture was stirred at room temperature for 30 minutes. After the reaction was completed, a saturated aqueous sodium bicarbonate solution and chloroform were added to the residue obtained by concentrating the reaction solution under reduced pressure, and then the organic layer separated with Phase-Separator® was concentrated under reduced pressure. The residue was purified by NH silica gel column chromatography (ethyl acetate:methanol=100:0 to 93:7) and suspended and washed with diethyl ether to obtain the title compound (536 mg) as a white powder. MS(ESI)m/z:439.2/441.2 [M+H]+

Reference Example 129: Synthesis of 2-bromo-6-methoxy-N-(2-methyl-2-propenyl)benzamide

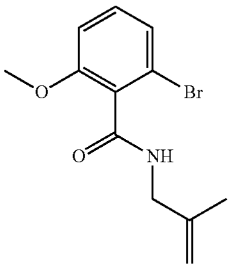 [SMILES: C=C(C)CNC(=O)c1c(Br)cccc1OC]

Oxalyl dichloride (7.4 mL) was added to a dichloromethane (144 mL) solution of 2-bromo-6-methoxybenzoic acid (10 g) under ice cooling, the mixture was stirred at 60 °C for 3 hours, and the reaction solution was concentrated under reduced pressure. Toluene was added to the concentrated residue, and the operation of concentrating under reduced pressure again was repeated three times. To a dichloromethane (144 mL) mixed solution of the concentrated residue and triethylamine (18 mL), a dichloromethane (20 mL) solution of 2-methylallylamine (4.7 mL) was added dropwise under ice cooling, and the mixture was stirred at room temperature for 2 days. The reaction solution was concentrated under reduced pressure and diluted with ethyl acetate, water was added, and extraction was performed. The organic layer was washed three times with 1 N hydrochloric acid and three times with a saturated aqueous sodium bicarbonate solution. After washing was performed with saturated saline, sodium sulfate was added and filtered, and the filtrate was concentrated under reduced pressure. The concentrated residue was suspended and washed with diisopropyl ether to obtain the title compound (8.1 g) as a white powder.

MS(ESI)m/z:284.1/286.1 [M+H]+

Reference Example 130: Synthesis of tert-butyl N-(2-bromo-6-methoxybenzoyl)-N-(2-methyl-2-propenyl)carbamate

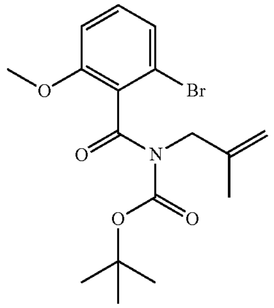 [SMILES: C=C(C)CN(C(=O)OC(C)(C)C)C(=O)c1c(Br)cccc1OC]

To a dichloromethane (6.0 mL) solution of 2-bromo-6-methoxy-N-(2-methyl-2-propenyl)benzamide (1.0 g) described in Reference Example 129 and triethylamine (0.50 mL), di-tert-butyl dicarbonate (1.3 g) and 4-dimethylaminopyridine (37 mg) were sequentially added under ice cooling, and the mixture was stirred at room temperature overnight. The reaction solution was concentrated under reduced pressure, and the concentrated residue was purified by silica gel column chromatography (hexane:ethyl acetate=80:20 to 50:50) to obtain the title compound (1.3 g) as a white powder. MS(ESI)m/z:328.1/330.1 [M+H−tBu]+

Reference Example 131: Synthesis of tert-butyl 2-(difluoromethoxy)-4-[4-(difluoromethoxy)-2-methyl-6-(1-methylpyrazol-4-yl)indazol-3-yl]-6-methoxybenzoate

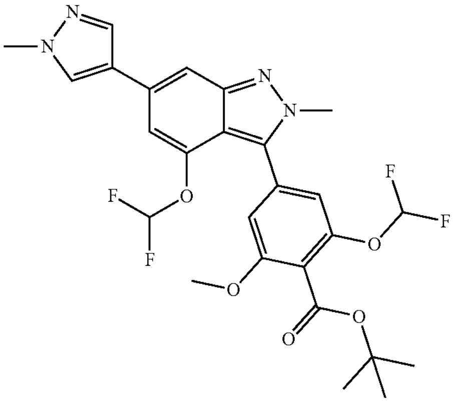 [SMILES: COc1cc(-c2c3c(OC(F)F)cc(-c4cnn(C)c4)cc3nn2C)cc(OC(F)F)c1C(=O)OC(C)(C)C]

A mixture of tert-butyl 2-(difluoromethoxy)-4-[4-(difluoromethoxy)-2-methyl-6-(4,4,5,5-tetramethyl-1,3,2-dioxaborolan-2-yl)indazol-3-yl]-6-methoxybenzoate (200 mg) described in Reference Example 66, 4-iodo-1-methyl-pyrazole (84 mg), potassium carbonate (139 mg), a [1,1'-bis(diphenylphosphino)ferrocene]palladium(II) dichloride dichloromethane adduct (27 mg), 1,4-dioxane (2.0 mL), and water (0.40 mL) was heated and stirred at 100 °C. under a nitrogen atmosphere. After 1 hour, a [1,1'-bis(diphenylphosphino)ferrocene]palladium(II) dichloride dichloromethane adduct (27 mg) was added to the reaction mixture that was allowed to cool to room temperature, and the mixture was further heated and stirred under a nitrogen atmosphere at 100 °C. overnight. After the reaction was completed, the reaction mixture was diluted with ethyl acetate, and then drying was performed by adding sodium sulfate. After filtering off insoluble matter, the filtrate was concentrated under reduced pressure and purified by preparative HPLC (10 mM aqueous ammonium carbonate solution-acetonitrile) to obtain the title compound (41 mg) as a gray powder. MS(ESI)m/z:551.3 [M+H]+

Reference Example 132: Synthesis of 4-[6-bromo-4-(difluoromethoxy)-2-methylindazol-3-yl]-2-(difluoromethoxy)-6-methoxybenzamide

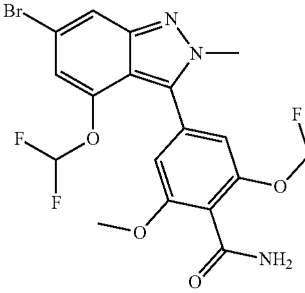

tert-Butyl 4-[6-bromo-4-(difluoromethoxy)-2-methylindazol-3-yl]-2-(difluoromethoxy)-6-methoxybenzoate (302 mg) described in Reference Example 65 was dissolved in dichloromethane (1.0 mL), TFA (1.0 mL) was added, and the mixture was stirred at room temperature for 1.5 hours. After the reaction was completed, the reaction solution was concentrated under reduced pressure and azeotroped twice with toluene. The residue, ammonium chloride (118 mg), WSC·HCl (158 mg), and HOBt (111 mg) were suspended in tetrahydrofuran (5.5 mL), triethylamine (0.46 mL) was added, and the mixture was stirred at room temperature for 2 days. After the reaction was completed, a saturated aqueous sodium bicarbonate solution and water were added to the reaction mixture, and extraction was performed with ethyl acetate. The organic layer was washed with water and saturated saline, and dried with magnesium sulfate. The residue obtained by concentrating the filtered filtrate under reduced pressure was purified by silica gel column chromatography (ethyl acetate:methanol=100:0 to 95:5) to obtain the title compound (209 mg) as a colorless powder.

MS(ESI)m/z:492.1/494.1 [M+H]+

Reference Example 133: Synthesis of 6-bromo-4-ethoxy-3-iodo-2-methylindazole

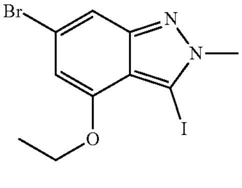

6-Bromo-3-iodo-2-methylindazol-4-ol (356 mg) described in Reference Example 33, iodoethane (0.40 mL), and potassium carbonate (279 mg) were suspended in N,N-dimethylformamide (4.0 mL), and the mixture was stirred under a nitrogen atmosphere at 80 °C for 2 hours. After the reaction was completed, water was added to the reaction mixture, and extraction was performed three times with ethyl acetate. The organic layers were combined and washed with saturated saline, sodium sulfate was added, filtration was performed, and the filtrate was concentrated under reduced pressure. The residue was purified by NH silica gel column chromatography (hexane:ethyl acetate=95:5 to 75:25) to obtain the title compound (363 mg) as a light yellow powder. MS(ESI)m/z:380.7/382.7 [M+H]+

Reference Example 134: Synthesis of 2-(difluoromethoxy)-4-[4-hydroxy-2-methyl-6-(1-methylpyrazol-4-yl)indazol-3-yl]-6-methoxybenzamide

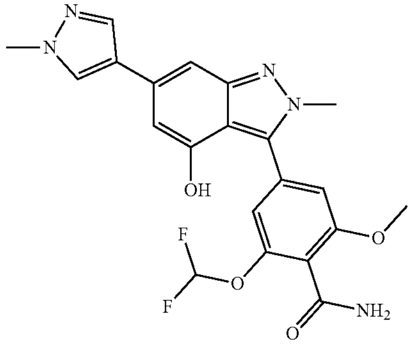

TFA (1.6 mL) was added to a dichloromethane (1.6 mL) solution of tert-butyl 2-(difluoromethoxy)-4-[4-hydroxy-2-methyl-6-(1-methylpyrazol-4-yl)indazol-3-yl]-6-methoxybenzoate (330 mg) described in Reference Example 59, and the mixture was stirred at room temperature for 21 hours. After the reaction was completed, the reaction mixture was concentrated under reduced pressure, and then an azeotropic treatment was performed three times using toluene. The resulting residue was dissolved in N,N-dimethylformamide (3.3 mL), HATU (301 mg) and N,N-diisopropylethylamine (0.50 mL) were added, the mixture was stirred at room temperature for 10 minutes, ammonium carbonate (76 mg) was added, and the mixture was stirred at room temperature for 1 hour. After the reaction was completed, water and 1 N hydrochloric acid were added to the reaction mixture, and extraction was performed with ethyl acetate. The organic layer was sequentially washed with water and saturated saline, magnesium sulfate was added, and filtration was performed. The filtrate was concentrated under reduced pressure, and the residue was purified by silica gel column chromatography (chloroform:methanol=100:0 to 80:20) to obtain the title compound (129 mg) as a brown powder. MS(ESI)m/z:444.3 [M+H]+

Reference Example 135: Synthesis of 4-[6-bromo-4-(difluoromethyl)-2-methylindazol-3-yl]-2-(difluoromethoxy)-6-methoxybenzamide

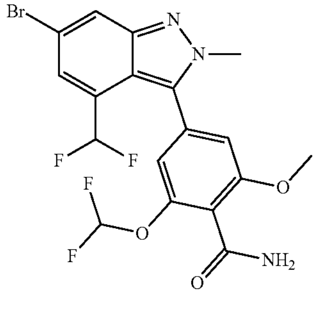 [SMILES: COc1cc(-c2c3c(C(F)F)cc(Br)cc3nn2C)cc(OC(F)F)c1C(N)=O]

4-[6-Bromo-4-(difluoromethyl)-2-methylindazol-3-yl]-2-(difluoromethoxy)-6-methoxybenzoic acid (400 mg) described in Reference Example 71, WSC·HCl (241 mg), HOBt (170 mg), and ammonium chloride (179 mg) were dissolved in tetrahydrofuran (8.4 mL), triethylamine (0.70 mL) was added, and the mixture was stirred at room temperature overnight. After the reaction was completed, a saturated aqueous sodium bicarbonate solution and water were added to the reaction mixture, and extraction was performed with ethyl acetate. The organic layer was washed with a saturated saline solution and dried with magnesium sulfate. The residue obtained by concentrating the filtered filtrate under reduced pressure was suspended and washed with diethyl ether to obtain the title compound (361 mg) as a colorless powder. MS(ESI)m/z:475.8/477.8 [M+H]+

Reference Example 136: Synthesis of 4-(6-bromo-4-hydroxy-2-methylindazol-3-yl)-2-(difluoromethoxy)-6-methoxybenzamide

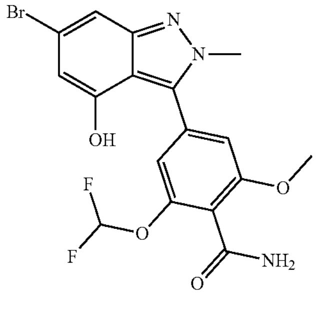 [SMILES: COc1cc(-c2c3c(O)cc(Br)cc3nn2C)cc(OC(F)F)c1C(N)=O]

tert-Butyl 4-(6-bromo-4-hydroxy-2-methylindazol-3-yl)-2-(difluoromethoxy)-6-methoxybenzoate (680 mg) described in Reference Example 58 was dissolved in dichloromethane (3.4 mL), TFA (3.4 mL) was added, and the mixture was stirred at room temperature for 1 hour. After the reaction was completed, the reaction solution was concentrated under reduced pressure and azeotroped three times with toluene. The residue, ammonium chloride (291 mg), WSC·HCl (392 mg), HOBt (276 mg), and tetrahydrofuran (14 mL) were mixed, triethylamine (1.1 mL) was added, and the mixture was stirred at room temperature overnight. After the reaction was completed, 1 N hydrochloric acid was added to the reaction solution, and extraction was performed with ethyl acetate. The organic layer was washed with a saturated saline solution and dried with magnesium sulfate. The residue obtained by concentrating the filtered filtrate under reduced pressure was purified by silica gel column chromatography (ethyl acetate:methanol=100:0 to 90:10) to obtain the title compound (368 mg) as a light yellow powder. MS(ESI)m/z:441.8/443.8 [M+H]+

Reference Example 137: Synthesis of 4-[6-bromo-4-(2,2-difluoroethoxy)-2-methylindazol-3-yl]-2-(difluoromethoxy)-6-methoxybenzamide

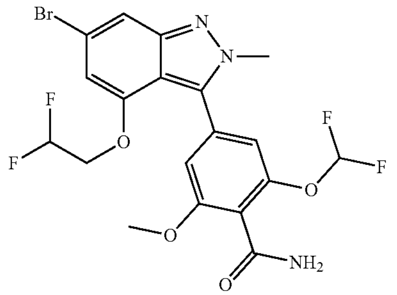 [SMILES: COc1cc(-c2c3c(OCC(F)F)cc(Br)cc3nn2C)cc(OC(F)F)c1C(N)=O]

4-(6-Bromo-4-hydroxy-2-methylindazol-3-yl)-2-(difluoromethoxy)-6-methoxybenzamide (50 mg) described in Reference Example 136 and potassium carbonate (47 mg) were suspended in N,N-dimethylformamide (0.57 mL), stirring was performed at room temperature for 5 minutes, 2,2-difluoroethyl trifluoromethanesulfonate (23 μL) was added, and the mixture was stirred at 80 °C for 1 hour. After the reaction was completed, chloroform and water were added to the reaction mixture, separation was performed with Phase-Separator®, and the organic layer was concentrated under reduced pressure. The residue was purified by preparative HPLC (10 mM aqueous ammonium carbonate solution-acetonitrile) and column chromatography (hexane: ethyl acetate=50:50 to 0:100 to ethyl acetate:methanol=95:5) using an NH silica gel column and a Si silica gel column in series to obtain the title compound (36 mg) as a colorless powder.

MS(ESI)m/z:506.1/508.1 [M+H]+

Reference Example 138: Synthesis of 4-[6-bromo-2-methyl-4-(2,2,2-trifluoroethoxy)indazol-3-yl]-2-(difluoromethoxy)-6-methoxybenzamide

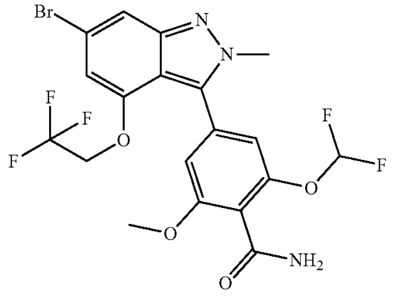 [SMILES: COc1cc(-c2c3c(OCC(F)(F)F)cc(Br)cc3nn2C)cc(OC(F)F)c1C(N)=O]

4-(6-Bromo-4-hydroxy-2-methylindazol-3-yl)-2-(difluoromethoxy)-6-methoxybenzamide (50 mg) described in Reference Example 136 and potassium carbonate (47 mg) were suspended in N,N-dimethylformamide (0.57 mL), stirring was performed at room temperature for 5 minutes, 2,2,2-trifluoroethyl trifluoromethanesulfonate (25 μL) was added, and the mixture was stirred at 80 °C for 1 hour. After the reaction was completed, chloroform and water were added to the reaction mixture, separation was performed with Phase-Separator®, and the organic layer was concentrated under reduced pressure. The residue was purified by preparative HPLC (10 mM aqueous ammonium carbonate solution-acetonitrile) and column chromatography (hexane: ethyl acetate=50:50 to 0:100 to ethyl acetate:methanol=95:5) using an NH silica gel column and a Si silica gel column in series to obtain the title compound (35 mg) as a brown powder.

MS(ESI)m/z:524.1/526.1 [M+H]+

Reference Example 139: Synthesis of tert-butyl 8-(difluoromethoxy)-4-methyl-1-oxo-3,4-dihydroisoquinoline-2-carboxylate

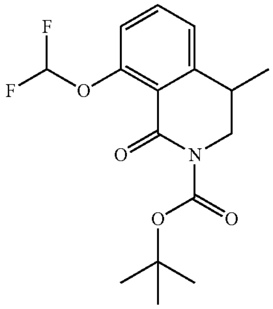 [SMILES: CC1CN(C(=O)OC(C)(C)C)C(=O)c2c(OC(F)F)cccc21]

tert-Butyl 8-(difluoromethoxy)-4-methyl-1-oxoisoquinoline-2-carboxylate (324 mg) described in Reference Example 11 was dissolved in tetrahydrofuran (5.0 mL), 10% Pd/C (100 mg) was added under a nitrogen atmosphere, and the mixture was stirred under a hydrogen atmosphere at room temperature for 7 hours. After the reaction was completed, the reaction mixture was diluted with chloroform, filtered, and then the filtrate was concentrated and dried to obtain the title compound (318 mg) as a colorless oily product. MS(ESI)m/z:272.1 [M−tBu+H]+

Reference Example 140: Synthesis of tert-butyl 8-(difluoromethoxy)-4-methyl-1-oxo-6-(4,4,5,5-tetramethyl-1,3,2-dioxaborolan-2-yl)-3,4-dihydroisoquinoline-2-carboxylate

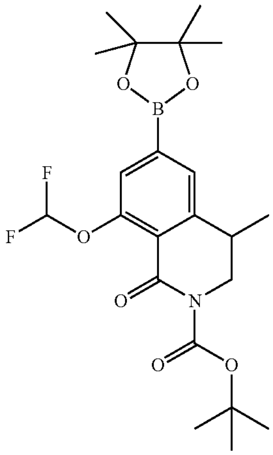 [SMILES: CC1CN(C(=O)OC(C)(C)C)C(=O)c2c(OC(F)F)cc(B3OC(C)(C)C(C)(C)O3)cc21]

A heptane (0.94 mL) suspension of tert-butyl 8-(difluoromethoxy)-4-methyl-1-oxo-3,4-dihydroisoquinoline-2-carboxylate (315 mg) described in Reference Example 139, bis(pinacolato)diboron (285 mg), 4,4'-di-tert-butyl-2,2'-bipyridyl (15 mg), and bis(1,5-cyclooctadiene)di-μ-methoxydiiridium(I) (19 mg) was stirred under a nitrogen atmosphere at 80 °C for 2 hours. The reaction solution was diluted with ethyl acetate and purified by silica gel column chromatography (hexane:ethyl acetate=70:30 to 30:70) as it was to obtain the title compound (389 mg) as an orange oily product. MS(ESI)m/z:398.2 [M+H−tBu]+

Reference Example 141: Synthesis of 6-bromo-3-[8-(difluoromethoxy)-4-methyl-1-oxo-3,4-dihydro-2H-isoquinolin-6-yl]-2-methylindazole-4-carbonitrile

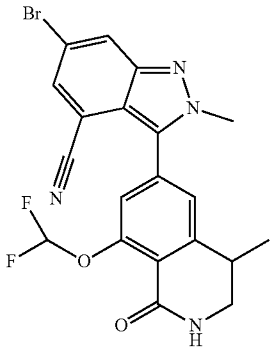 [SMILES: CC1CNC(=O)c2c(OC(F)F)cc(-c3c4c(C#N)cc(Br)cc4nn3C)cc21]

A mixture of tert-butyl 8-(difluoromethoxy)-4-methyl-1-oxo-6-(4,4,5,5-tetramethyl-1,3,2-dioxaborolan-2-yl)-3,4-dihydroisoquinoline-2-carboxylate (189 mg) described in Reference Example 140, 6-bromo-3-iodo-2-methylindazole-4-carbonitrile (125 mg) described in Reference Example 19, potassium carbonate (95 mg), a [1,1'-bis(diphenylphosphino)ferrocene]palladium(II) dichloride dichloromethane adduct (28 mg), 1,4-dioxane (2.3 mL), and water (0.58 mL) was stirred under a nitrogen atmosphere at 100 °C for 3 hours. After the reaction was completed, chloroform and water were added to the reaction mixture, the organic layer was separated with Phase-Separator®, and the organic layer was concentrated under reduced pressure. The residue was dissolved in dichloromethane (0.86 mL), TFA (0.86 mL) was added, and the mixture was stirred at room temperature for 3 hours. After the reaction was completed, the reaction solution was concentrated under reduced pressure, and then an azeotropic treatment was performed using toluene. A saturated aqueous sodium bicarbonate solution and chloroform were added to the residue, the organic layer was separated with Phase-Separator®, and the organic layer was concentrated under reduced pressure. The residue was purified by NH silica gel column chromatography (ethyl acetate: methanol=100:0 to 94:6) and then suspended and washed with diisopropyl ether to obtain the title compound (57 mg) as a yellow powder.

MS(ESI)m/z:460.9/462.8 [M+H]+

Reference Example 142: Synthesis of 6-(6-bromo-4-methoxy-2-methylindazol-3-yl)-8-(difluoromethoxy)-4-methyl-3,4-dihydro-2H-isoquinolin-1-one

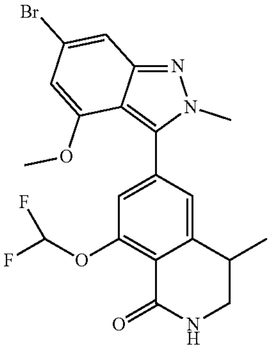 [SMILES: COc1cc(Br)cc2nn(C)c(-c3cc(OC(F)F)c4c(c3)C(C)CNC4=O)c12]

The same reaction and treatment as in Reference Example 141 were performed using 6-bromo-3-iodo-4-methoxy-2-methylindazole described in Reference Example 23 as a starting material to obtain the title compound. MS(ESI)m/z:465.9/467.8 [M+H]+

Reference Example 143: Synthesis of rel-(4R)-6-(6-bromo-4-ethoxy-2-methylindazol-3-yl)-8-methoxy-4-methyl-2-(2-trimethylsilylethoxymethyl)-3,4-dihydroisoquinolin-1-one

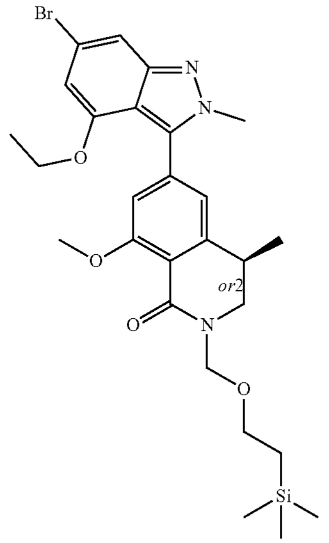 [SMILES: CCOc1cc(Br)cc2nn(C)c(-c3cc(OC)c4c(c3)[C@@H](C)CN(COCC[Si](C)(C)C)C4=O)c12]

A mixture of 6-bromo-4-ethoxy-3-iodo-2-methylindazole (100 mg) described in Reference Example 133, rel-(4R)-8-methoxy-4-methyl-6-(4,4,5,5-tetramethyl-1,3,2-dioxaborolan-2-yl)-2-(2-trimethylsilylethoxymethyl)-3,4-dihydroisoquinolin-1-one (149 mg) described in Reference Example 125, a [1,1'-bis(diphenylphosphino)ferrocene]palladium(II) dichloride dichloromethane adduct (21 mg), potassium carbonate (73 mg), 1,4-dioxane (1.6 mL), and water (0.40 mL) was stirred under a nitrogen atmosphere at 100 °C for 2 hours and 30 minutes. After the reaction was completed, chloroform and water were added to the reaction mixture, and the organic layer separated with Phase-Separator® was concentrated under reduced pressure. The residue was purified by NH silica gel column chromatography (hexane:ethyl acetate=70:30 to 30:70) to obtain the title compound (126 mg) as a light yellow viscous product. MS(ESI)m/z:574.0/576.0 [M+H]+

Reference Example 144: Synthesis of rel-(4R)-6-(6-bromo-4-ethoxy-2-methyl-indazol-3-yl)-8-methoxy-4-methyl-3,4-dihydro-2H-isoquinolin-1-one

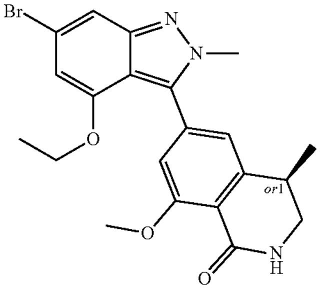 [SMILES: CCOc1cc(Br)cc2nn(C)c(-c3cc(OC)c4c(c3)[C@@H](C)CNC4=O)c12]

rel-(4R)-6-(6-Bromo-4-ethoxy-2-methylindazol-3-yl)-8-methoxy-4-methyl-2-(2-trimethylsilylethoxymethyl)-3,4-dihydroisoquinolin-1-one (125 mg) described in Reference Example 143 was dissolved in dichloromethane (0.98 mL), TFA (0.45 mL) was added, and the mixture was stirred at room temperature for 1 hour. After the reaction was completed, the reaction solution was added to a 4 N aqueous sodium hydroxide solution (2.0 mL), the mixture was stirred, and the organic layer separated with Phase-Separator® was concentrated under reduced pressure. The residue was dissolved in methanol (2.0 mL), potassium carbonate (81 mg) was added, and the mixture was stirred at 60 °C for 1 hour. After the reaction was completed, ethyl acetate was added to the reaction mixture, filtration was performed, and the filtrate was concentrated under reduced pressure. The residue was purified by NH silica gel column chromatography (ethyl acetate:methanol=100:0 to 94:6) to obtain the title compound (70 mg) as a white powder. MS(ESI)m/z:444.2/446.2 [M+H]+

Reference Example 145: Synthesis of 2-bromo-6-(difluoromethoxy)-N-(2-methylallyl)benzamide

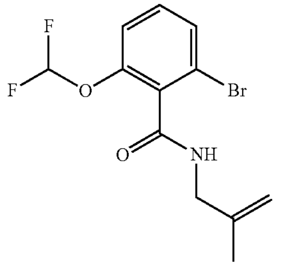 [SMILES: C=C(C)CNC(=O)c1c(Br)cccc1OC(F)F]

N,N-diisopropylethylamine (0.39 mL), 2-methyallylamine (0.16 mL), and HATU (690 mg) were sequentially added to an N,N-dimethylformamide (3.8 mL) solution of 2-bromo-6-(difluoromethoxy)benzoic acid (443 mg), and then the mixture was stirred at room temperature for 5 hours.

After the reaction was completed, ethyl acetate and 1 N hydrochloric acid were added to the reaction mixture, and then extraction was performed with ethyl acetate. The organic layer was sequentially washed with a saturated aqueous sodium bicarbonate solution and saturated saline, sodium sulfate was added, the mixture was filtered, and the filtrate was concentrated under reduced pressure. The resulting residue was purified by silica gel column chromatography (hexane:ethyl acetate=80:20 to 60:40) to obtain the title compound (404 mg) as a white powder. MS(ESI)m/z:320.1/322.1 [M+H]+

Reference Example 146: Synthesis of tert-butyl N-[2-bromo-6-(difluoromethoxy)benzoyl]-N-(2-methylallyl)carbamate

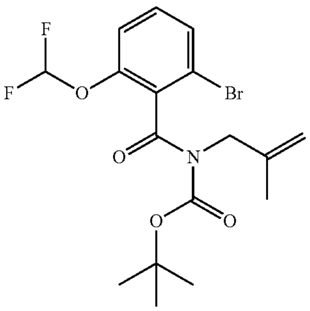 [SMILES: C=C(C)CN(C(=O)OC(C)(C)C)C(=O)c1c(Br)cccc1OC(F)F]

To a dichloromethane (2.5 mL) solution of 2-bromo-6-(difluoromethoxy)-N-(2-methylallyl)benzamide (400 mg) described in Reference Example 145, under ice cooling, di-tert-butyl dicarbonate (545 mg), triethylamine (0.21 mL), and 4-dimethylaminopyridine (15 mg) were sequentially added, and then the mixture was stirred at room temperature for 20 hours. After the reaction was completed, ethyl acetate was added to the reaction mixture, and the mixture was sequentially washed with a saturated aqueous ammonium chloride solution and saturated saline. Sodium sulfate was added, the mixture was filtered, and the filtrate was concentrated under reduced pressure to obtain the title compound (544 mg) as a yellow oily product. MS(ESI)m/z:320.1/322.1 [M−Boc+H]+

Reference Example 147: Synthesis of tert-butyl 8-(difluoromethoxy)-4,4-dimethyl-1-oxo-3H-isoquinoline-2-carboxylate

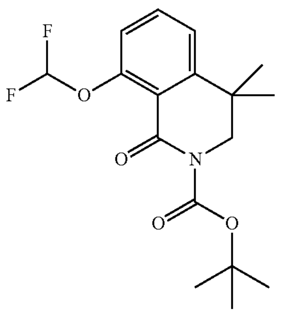 [SMILES: CC(C)(C)OC(=O)N1CC(C)(C)c2cccc(OC(F)F)c2C1=O]

A mixture of tert-butyl N-[2-bromo-6-(difluoromethoxy)benzoyl]-N-(2-methylallyl)carbamate (525 mg) described in Reference Example 146, sodium formate (128 mg), tetrabutylammonium chloride (382 mg), palladium(II) acetate (28 mg), N,N-dimethylformamide (5.0 mL), and triethylamine (0.44 mL) was heated and stirred at 80 °C for 2 hours. After the reaction was completed, ethyl acetate and water were added to the reaction mixture, the mixture was filtered, and then extraction was performed twice using ethyl acetate. The combined organic layers were sequentially washed with a saturated aqueous ammonium chloride solution, a saturated aqueous sodium bicarbonate solution, and saturated saline, sodium sulfate was added, the mixture was filtered, and the filtrate was concentrated under reduced pressure. The resulting residue was purified by silica gel column chromatography (hexane:ethyl acetate=85:15 to 70:30) to obtain the title compound (397 mg) as a colorless oily product. MS(ESI)m/z:286.1 [M−tBu+H]+

Reference Example 148: Synthesis of tert-butyl 8-(difluoromethoxy)-4,4-dimethyl-1-oxo-6-(4,4,5,5-tetramethyl-1,3,2-dioxaborolan-2-yl)-3H-isoquinoline-2-carboxylate

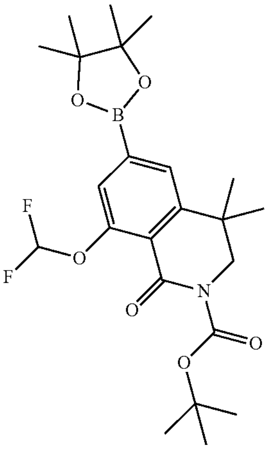 [SMILES: CC(C)(C)OC(=O)N1CC(C)(C)c2cc(B3OC(C)(C)C(C)(C)O3)cc(OC(F)F)c2C1=O]

A mixture of tert-butyl 8-(difluoromethoxy)-4,4-dimethyl-1-oxo-3H-isoquinoline-2-carboxylate (396 mg) described in Reference Example 147, bis(pinacolato)diboron (343 mg), 4,4'-di-tert-butyl-2,2'-bipyridyl (18 mg), bis(1,5-cyclooctadiene)di-μ-methoxydiiridium(I) (22 mg), and tetrahydrofuran (1.1 mL) was heated and stirred under at 70 °C for 2 hours. After the reaction was completed, the reaction mixture was ice-cooled, ethanol was added little by little until no foaming occurred, and the mixture was quenched. The resulting mixture was purified by silica gel column chromatography (hexane:ethyl acetate=50:50 to 25:75) and then suspended and washed using hexane to obtain the title compound (392 mg) as a white powder. MS(ESI)m/z:412.0 [M−tBu+H]+

Reference Example 149: Synthesis of rel-(4R)-6-[6-bromo-4-(difluoromethoxy)-2-methyl-indazol-3-yl]-8-methoxy-4-methyl-2-(2-trimethylsilylethoxymethyl)-3,4-dihydroisoquinolin-1-one

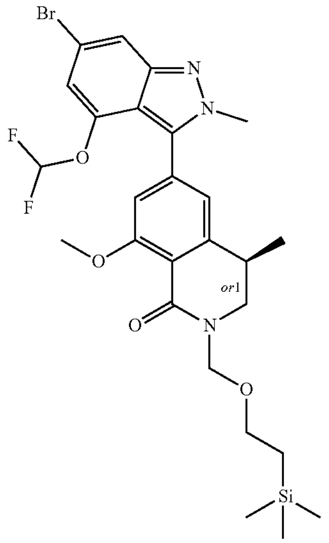 [SMILES: COc1cc(-c2c3c(OC(F)F)cc(Br)cc3nn2C)cc2c1C(=O)N(COCC[Si](C)(C)C)C[C@@H]2C]

A mixture of 6-bromo-4-(difluoromethoxy)-3-iodo-2-methylindazole (150 mg) described in Reference Example 39, rel-(4R)-8-methoxy-4-methyl-6-(4,4,5,5-tetramethyl-1,3,2-dioxaborolan-2-yl)-2-(2-trimethylsilylethoxymethyl)-3,4-dihydroisoquinolin-1-one (200 mg) described in Reference Example 125, potassium carbonate (103 mg), a [1,1'-bis(diphenylphosphino)ferrocene]palladium(II) dichloride dichloromethane adduct (30 mg), 1,4-dioxane (2.4 mL), and water (0.48 mL) was heated and stirred under a nitrogen atmosphere at 100 °C. After 1 hour, the reaction mixture was allowed to cool to room temperature, a [1,1'-bis(diphenylphosphino)ferrocene]palladium(II) dichloride dichloromethane adduct (30 mg) was added, and the mixture was further heated and stirred under a nitrogen atmosphere at 100 °C for 2.5 hours. After the reaction was completed, chloroform and water were added to the reaction mixture, the organic layer was separated with Phase-Separator®, and then the organic layer was concentrated under reduced pressure. The resulting residue was purified by NH silica gel column chromatography (hexane:ethyl acetate=70:30 to 25:75) to obtain the title compound (143 mg) as a colorless viscous product. MS(ESI)m/z:596.2/598.2 [M+H]+

Reference Example 150: Synthesis of 6-bromo-3-[8-(difluoromethoxy)-4,4-dimethyl-1-oxo-2,3-dihydroisoquinolin-6-yl]-2-methyl-indazole-4-carbonitrile

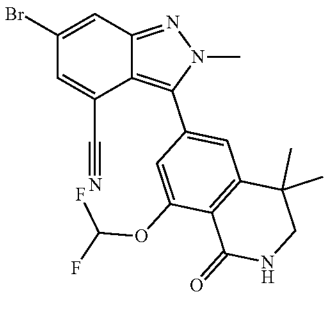 [SMILES: Cn1nc2cc(Br)cc(C#N)c2c1-c1cc(OC(F)F)c2c(c1)C(C)(C)CNC2=O]

'A mixture of 6-bromo-3-iodo-2-methylindazole-4-carbonitrile (100 mg) described in Reference Example 19, tert-butyl 8-(difluoromethoxy)-4,4-dimethyl-1-oxo-6-(4,4,5,5-tetramethyl-1,3,2-dioxaborolan-2-yl)-3H-isoquinoline-2-carboxylate (190 mg) described in Reference Example 148, potassium carbonate (76 mg), a [1,1'-bis(diphenylphosphino)ferrocene]palladium(II) dichloride dichloromethane adduct (23 mg), 1,4-dioxane (1.8 mL), and water (0.46 mL) was heated and stirred under a nitrogen atmosphere at 100 °C for 2.5 hours. After the reaction was completed, chloroform was added to the reaction mixture, the organic layer was separated with Phase-Separator®, and then the organic layer was concentrated under reduced pressure. The resulting residue was dissolved in dichloromethane (0.69 mL), TFA (0.69 mL) was added, and the mixture was stirred at room temperature for 30 minutes. After the reaction was completed, the reaction mixture was concentrated under reduced pressure, and then an azeotropic treatment was performed using toluene. The resulting residue was purified by NH silica gel column chromatography (hexane:ethyl acetate=30:70 to 0:100) and then suspended and washed using diisopropyl ether to obtain the title compound (30 mg) as a light yellow powder. MS(ESI)m/z:474.9/476.8 [M+H]+

Reference Example 151: Synthesis of rel-(4R)-6-[6-bromo-4-(difluoromethoxy)-2-methyl-indazol-3-yl]-8-methoxy-4-methyl-3,4-dihydro-2H-isoquinolin-1-one

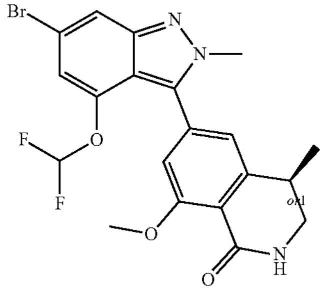 [SMILES: COc1cc(-c2c3c(OC(F)F)cc(Br)cc3nn2C)cc2c1C(=O)NC[C@@H]2C]

TFA (0.48 mL) was added to a dichloromethane (1.0 mL) solution of rel-(4R)-6-[6-bromo-4-(difluoromethoxy)-2-methyl-indazol-3-yl]-8-methoxy-4-methyl-2-(2-trimethylsilylethoxymethyl)-3,4-dihydroisoquinolin-1-one (141 mg) described in Reference Example 149, and the mixture was stirred at room temperature for 1 hour. After the reaction was completed, a 4 N aqueous sodium hydroxide solution (2.1 mL) was added to the reaction mixture, and the mixture was stirred for 5 minutes. The organic layer was separated with Phase-Separator® and concentrated under reduced pressure, methanol (2.1 mL) and potassium carbonate (86 mg) were added to the resulting residue, and the mixture was heated and stirred at 60 °C for 1 hour. After the reaction was completed, ethyl acetate was added to the reaction mixture, filtration was performed, and then the filtrate was concentrated under reduced pressure. The resulting residue was purified by NH silica gel column chromatography (ethyl acetate:methanol=100:0 to 90:10) to obtain the title compound (84 mg) as a colorless viscous product. MS(ESI)m/z:465.8/467.8 [M+H]+

Reference Example 152: Synthesis of tert-butyl 6-(6-bromo-4-cyano-2-methyl-indazol-3-yl)-8-(difluoromethoxy)-4-methyl-1-oxo-3,4-dihydroisoquinoline-2-carboxylate

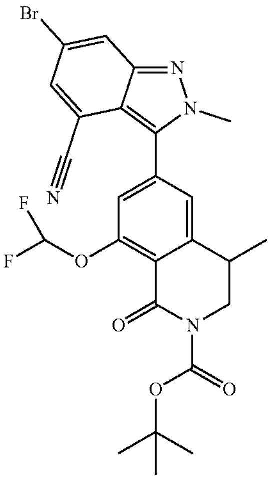 [SMILES: CC1CN(C(=O)OC(C)(C)C)C(=O)c2c(OC(F)F)cc(-c3c4c(C#N)cc(Br)cc4nn3C)cc21]

A mixture of 6-bromo-3-iodo-2-methylindazole-4-carbonitrile (2,400 mg) described in Reference Example 19, tert-butyl 8-(difluoromethoxy)-4-methyl-1-oxo-6-(4,4,5,5-tetramethyl-1,3,2-dioxaborolan-2-yl)-3,4-dihydroisoquinoline-2-carboxylate (3,156 mg) described in Reference Example 140, potassium phosphate (2,815 mg), [1,1'-bis(di-tert-butylphosphino)ferrocene]palladium(II) dichloride (432 mg), 1,4-dioxane (35 mL), and water (5.0 mL) was stirred under a nitrogen atmosphere at 100 °C. for 2.5 hours. After the reaction was completed, water was added to the reaction mixture, and extraction was performed three times with chloroform. The organic layers were combined, sodium sulfate was added, the mixture was filtered, and the filtrate was concentrated under reduced pressure. The residue was purified by silica gel column chromatography (hexane:ethyl acetate=90:10 to 40:60) to obtain the title compound (982 mg) as a yellow powder. MS(ESI)m/z:504.8/506.8 [M+H]+

Reference Example 153: Synthesis of tert-butyl 6-[4-cyano-6-[1-(2-methoxyethyl)pyrazol-4-yl]-2-methyl-indazol-3-yl]-8-(difluoromethoxy)-4-methyl-1-oxo-3,4-dihydroisoquinoline-2-carboxylate

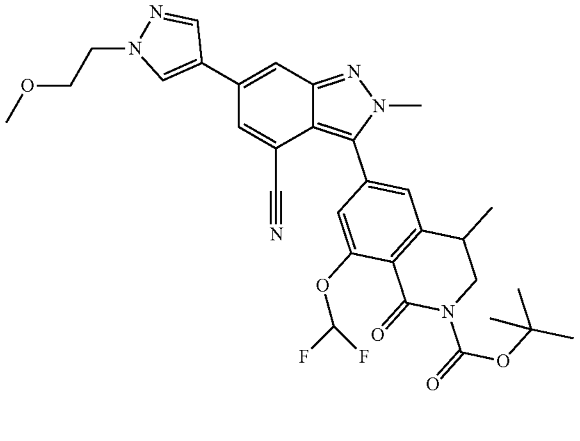 [SMILES: COCCn1cc(-c2cc(C#N)c3c(-c4cc(OC(F)F)c5c(c4)C(C)CN(C(=O)OC(C)(C)C)C5=O)n(C)nc3c2)cn1]

A mixture of tert-butyl 6-(6-bromo-4-cyano-2-methyl-indazol-3-yl)-8-(difluoromethoxy)-4-methyl-1-oxo-3,4-dihydroisoquinoline-2-carboxylate (325 mg) described in Reference Example 152, 1-(2-methoxyethyl)-4-(4,4,5,5-tetramethyl-1,3,2-dioxaborolan-2-yl)pyrazole (175 mg), [1,1'-bis(di-tert-butylphosphino)ferrocene]palladium(II) dichloride (38 mg), potassium phosphate (369 mg), 1,4-dioxane (3.0 mL), and water (0.40 mL) was heated and stirred under a nitrogen atmosphere at 100 °C for 2 hours. After the reaction was completed, water and chloroform were added to the reaction mixture, the organic layer was separated with Phase-Separator®, and then the organic layer was concentrated under reduced pressure.

The residue was sequentially purified by NH silica gel column chromatography (hexane:ethyl acetate=70:30 to 30:70) and preparative HPLC (10 mM aqueous ammonium carbonate solution-acetonitrile) to obtain the title compound (226 mg) as a colorless powder. MS(ESI)m/z:507.3 [M-Boc+H]+

Reference Example 154: Synthesis of tert-butyl 6-[4-cyano-6-(1-ethylpyrazol-4-yl)-2-methyl-indazol-3-yl]-8-(difluoromethoxy)-4-methyl-1-oxo-3,4-dihydroisoquinoline-2-carboxylate

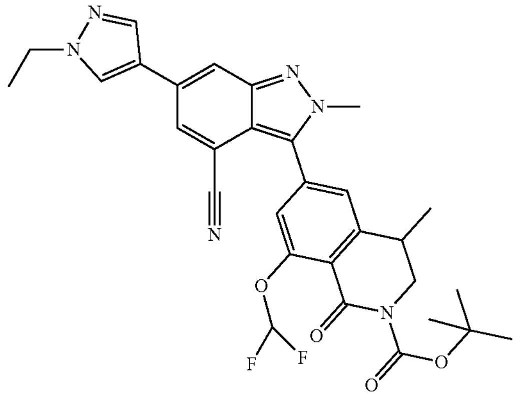 [SMILES: CCn1cc(-c2cc(C#N)c3c(-c4cc(OC(F)F)c5c(c4)C(C)CN(C(=O)OC(C)(C)C)C5=O)n(C)nc3c2)cn1]

A mixture of tert-butyl 6-(6-bromo-4-cyano-2-methyl-indazol-3-yl)-8-(difluoromethoxy)-4-methyl-1-oxo-3,4-dihydroisoquinoline-2-carboxylate (325 mg) described in Reference Example 152, 1-ethyl-4-(4,4,5,5-tetramethyl-1,3,2-dioxaborolan-2-yl)pyrazole (257 mg), [1,1'-bis(di-tert-butylphosphino)ferrocene]palladium(II) dichloride (38 mg), potassium phosphate (369 mg), 1,4-dioxane (3.0 mL), and water (0.40 mL) was heated and stirred under a nitrogen atmosphere at 100 °C for 2 hours. After the reaction was completed, water and chloroform were added to the reaction mixture, the organic layer was separated with Phase-Separator®, and then the organic layer was concentrated under reduced pressure. The residue was sequentially purified by NH silica gel column chromatography (hexane:ethyl acetate=75:25 to 40:60) and preparative HPLC (10 mM aqueous ammonium carbonate solution-acetonitrile) to obtain the title compound (64 mg) as a colorless oily product. MS(ESI)m/z:577.3 [M+H]+

Reference Example 155: Synthesis of 3-[8-(difluoromethoxy)-4-methyl-1-oxo-3,4-dihydro-2H-isoquinolin-6-yl]-6-[1-(2-methoxyethyl)pyrazol-4-yl]-2-methyl-indazole-4-carbonitrile

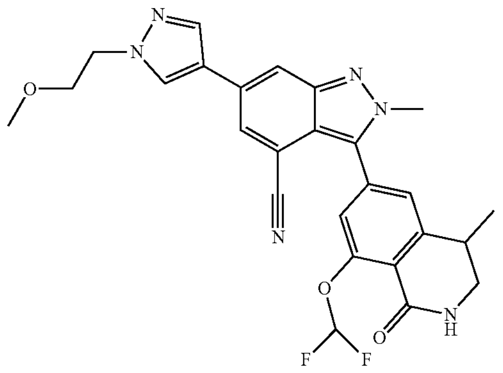

tert-Butyl 6-[4-cyano-6-[1-(2-methoxyethyl)pyrazol-4-yl]-2-methyl-indazol-3-yl]-8-(difluoromethoxy)-4-methyl-1-oxo-3,4-dihydroisoquinoline-2-carboxylate (223 mg) described in Reference Example 153 was dissolved in dichloromethane (2.0 mL), TFA (2.0 mL) was added, and the mixture was stirred at room temperature for 50 minutes. After the reaction was completed, a saturated aqueous sodium bicarbonate solution was added to the reaction solution, and extraction was performed three times with chloroform. The organic layers were combined, concentrated under reduced pressure, and then purified by NH silica gel column chromatography (ethyl acetate:methanol=100:0 to 98:2 to 95:5) to obtain the title compound (173 mg) as a colorless powder. MS(ESI)m/z:507.0 [M+H]+

Reference Example 156: Synthesis of 3-[8-(difluoromethoxy)-4-methyl-1-oxo-3,4-dihydro-2H-isoquinolin-6-yl]-6-(1-ethylpyrazol-4-yl)-2-methyl-indazole-4-carbonitrile

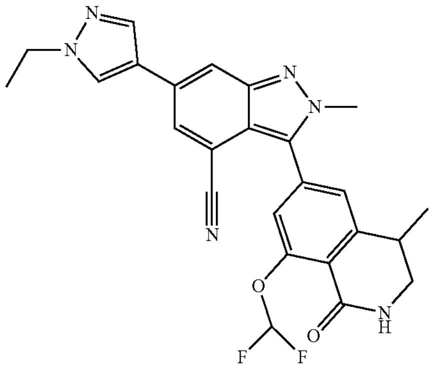 [SMILES: CCn1cc(-c2cc(C#N)c3c(-c4cc(OC(F)F)c5c(c4)C(C)CNC5=O)n(C)nc3c2)cn1]

tert-Butyl 6-[4-cyano-6-(1-ethylpyrazol-4-yl)-2-methyl-indazol-3-yl]-8-(difluoromethoxy)-4-methyl-1-oxo-3,4-dihydroisoquinoline-2-carboxylate (61 mg) described in Reference Example 154 was dissolved in dichloromethane (1.0 mL), TFA (1.0 mL) was added, and the mixture was stirred at room temperature for 45 minutes. After the reaction was completed, a saturated aqueous sodium bicarbonate solution was added to the reaction solution, and extraction was performed three times with chloroform. The organic layers were combined, concentrated under reduced pressure, and then purified by NH silica gel column chromatography (ethyl acetate:methanol=100:0 to 98:2 to 95:5) to obtain the title compound (46 mg) as a light yellow powder. MS(ESI) m/z:477.0 [M+H]+

Reference Example 157: Synthesis of 8-(difluoromethoxy)-6-[6-[1-[(2S)-2-hydroxypropyl]pyrazol-4-yl]-4-methoxy-2-methyl-indazol-3-yl]-4-methyl-3,4-dihydro-2H-isoquinolin-1-one

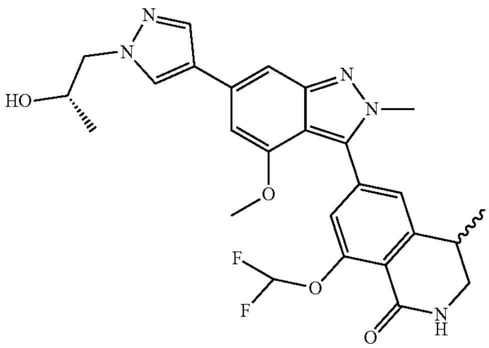 [SMILES: COc1cc(-c2cnn(C[C@H](C)O)c2)cc2nn(C)c(-c3cc(OC(F)F)c4c(c3)C(C)CNC4=O)c12]

A mixture of 6-(6-bromo-4-methoxy-2-methylindazol-3-yl)-8-(difluoromethoxy)-4-methyl-3,4-dihydro-2H-isoquinolin-1-one (200 mg) described in Reference Example 142, (2S)-1-[4-(4,4,5,5-tetramethyl-1,3,2-dioxaborolan-2-yl)pyrazol-1-yl]propan-2-ol (130 mg) synthesized by the method described in WO 2022/081627 A, [1,1'-bis(di-tert-butylphosphino)ferrocene]palladium(II) dichloride (28 mg), potassium phosphate (273 mg), 1,4-dioxane (2.1 mL), and water (0.20 mL) was heated and stirred under a nitrogen atmosphere at 100 °C for 2 hours. After the reaction was completed, water and chloroform were added to the reaction mixture, the organic layer was separated with Phase-Separator®, and then the organic layer was concentrated under reduced pressure. The residue was purified by NH silica gel column chromatography (ethyl acetate:methanol=100:0 to 90:10) to obtain the title compound (198 mg) as a beige powder. MS(ESI)m/z:512.0 [M+H]+

Reference Example 158: Synthesis of 8-(difluoromethoxy)-6-[4-methoxy-6-[1-(2-methoxyethyl)pyrazol-4-yl]-2-methyl-indazol-3-yl]-4-methyl-3,4-dihydro-2H-isoquinolin-1-one

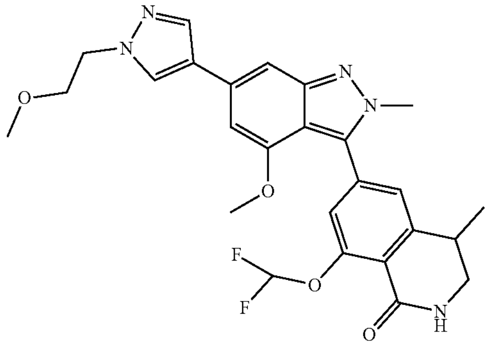

A mixture of 6-(6-bromo-4-methoxy-2-methylindazol-3-yl)-8-(difluoromethoxy)-4-methyl-3,4-dihydro-2H-isoquinolin-1-one (200 mg) described in Reference Example 142, 1-(2-methoxyethyl)-4-(4,4,5,5-tetramethyl-1,3,2-dioxaborolan-2-yl)pyrazole (130 mg), [1,1'-bis(di-tert-butylphosphino)ferrocene]palladium(II) dichloride (28 mg), potassium phosphate (273 mg), 1,4-dioxane (2.1 mL), and water (0.20 mL) was heated and stirred under a nitrogen atmosphere at 100 °C for 2 hours. After the reaction was completed, water and chloroform were added to the reaction mixture, the organic layer was separated with Phase-Separator® and concentrated under reduced pressure, and then the organic layer was purified by NH silica gel column chromatography (ethyl acetate:methanol=100:0 to 93:7). The resulting crude product was suspended and washed with a solvent obtained by mixing ethyl acetate and diethyl ether at 1:1 to obtain the title compound (190 mg) as a beige powder.

MS(ESI)m/z:512.3 [M+H]+

Reference Example 159: Synthesis of 8-(difluoromethoxy)-6-[6-(1-ethylpyrazol-4-yl)-4-methoxy-2-methyl-indazol-3-yl]-4-methyl-3,4-dihydro-2H-isoquinolin-1-one

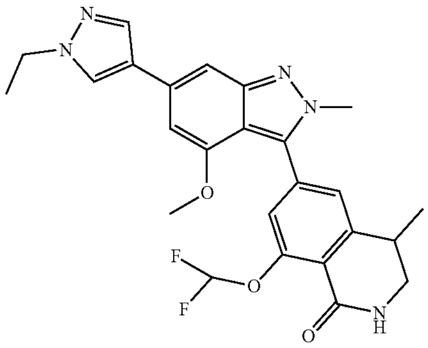 [SMILES: CCn1cc(-c2cc(OC)c3c(-c4cc(OC(F)F)c5c(c4)C(C)CNC5=O)n(C)nc3c2)cn1]

A mixture of 6-(6-bromo-4-methoxy-2-methylindazol-3-yl)-8-(difluoromethoxy)-4-methyl-3,4-dihydro-2H-isoquinolin-1-one (300 mg) described in Reference Example 142, 1-ethyl-4-(4,4,5,5-tetramethyl-1,3,2-dioxaborolan-2-yl) pyrazole (172 mg), [1,1'-bis(di-tert-butylphosphino)ferrocene]palladium(II) dichloride (42 mg), potassium phosphate (410 mg), 1,4-dioxane (2.0 mL), and water (0.40 mL) was heated and stirred under a nitrogen atmosphere at 100 °C for 1.5 hours. After the reaction was completed, water and chloroform were added to the reaction mixture, the organic layer was separated with Phase-Separator® and concentrated under reduced pressure, and then the organic layer was purified by column chromatography (ethyl acetate: methanol=100:0 to 90:10) using an NH silica gel column and a Si silica gel column in series. The resulting crude product was suspended and washed with a solvent obtained by mixing ethyl acetate and diethyl ether at 1:1 to obtain the title compound (292 mg) as a light yellow powder. MS(ESI) m/z:482.0 [M+H]+

Reference Example 160: Synthesis of tert-butyl N-[(1R)-2,2-difluorocyclopropyl]carbamate

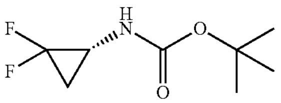

Diphenylphosphoryl azide (58 mL) was added dropwise to a solution of (1S)-2,2-difluorocyclopropanecarboxylic acid (30 g) and triethylamine (34 mL) in tert-butyl alcohol (360 mL) at 75 to 80 °C. over 2 hours, and the mixture was stirred for 2.5 hours. After the reaction was completed, the reaction mixture was cooled to room temperature, saturated aqueous sodium bicarbonate solution (300 mL) and water (1200 mL) were added thereto, and the mixture was stirred for 2.5 hours. The resulting suspension was allowed to stand overnight at room temperature, and the precipitated solid was filtered out and washed three times with water (150 mL) to obtain the title compound (32 g) as a pale yellow powder. 1H NMR (400 MHz, $CDCl_3$) δ ppm 4.83 (brs, 1H), 3.16 (brs, 1H), 1.79-1.65 (m, 1H), 1.46 (s, 9H), 1.41-1.29 (m, 1H)

Reference Example 161: Synthesis of (1R)-2,2-difluorocyclopropan-1-amine hydrochloride

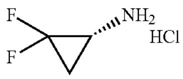

A solution of (1S)-2,2-difluorocyclopropanecarboxylic acid (20 g) in tert-butyl alcohol (360 mL) was concentrated under reduced pressure to about 120 mL, tert-butyl alcohol (200 mL) was added thereto and the solution was again concentrated under reduced pressure to about 120 mL. Diphenylphosphoryl azid (47 g) was added to the resulting solution at 75 °C, followed by the addition of triethylamine (17 g) dropwise over 2 hours at the same temperature, and the mixture was stirred for 4 hours. After the reaction was completed, the reaction mixture was cooled to room temperature, a solution of sodium bicarbonate (14 g) dissolved in water (280 mL) and tert-butyl N-[(1R)-2,2-difluorocyclopropyl]carbamate described in Reference Example 160 as a seed crystal (10 mg) were added thereto, and the mixture was stirred at room temperature for 30 minutes. Water (200 mL) was further added dropwise thereto over 30 minutes at room temperature, and the mixture was stirred for 2 hours at 5 °C. or lower. The precipitated solid was filtered out and washed with cold water (140 mL), and the resulting powder was dissolved in ethyl acetate (36 mL) and washed with 10% brine (40 mL). 4M Hydrochloric acid solution-ethyl acetate (98 mL) was added dropwise to the organic layer over 40 minutes at 20 to 30 °C, and the mixture was stirred at the same temperature for 2 hours. The precipitated solid was filtered out and washed three times with ethyl acetate (60 mL) to obtain the title compound (16 g) as a colorless powder. 1H NMR (400 MHz, $CD_3OD$) δ ppm 3.44-3.38 (m, 1H), 2.10-2.00 (m, 1H), 1.87-1.78 (m, 1H), enantiomeric excess >99.8% ee Reference Example 162: Determination of enantiomeric excess of (1R)-2,2-difluorocyclopropan-1-amine hydrochloride (1R)-2,2-Difluorocyclopropan-1-amine hydrochloride (100 mg) described in Reference Example 161 was suspended in chloroform (2.0 mL), benzoyl chloride (0.13 mL) and triethylamine (0.28 mL) were added thereto at room temperature, and the mixture was stirred at the same temperature all night. After the reaction was completed, 1N hydrochloric acid solution was added to the reaction mixture, and the mixture was extracted with chloroform three times. The organic layers were combined and concentrated under reduced pressure, and purified by column chromatography (hexane:ethyl acetate=95:5 to 60:40 to 50:50) using NH silica gel column and Si silica gel column in series to obtain N-[(1R)-2,2-difluorocyclopropyl]benzamide (86 mg) as a colorless powder. MS(ESI)m/z:197.9 [M+H]+

N-[(1R)-2,2-difluorocyclopropyl]benzamide was analized by chiral column chromatography [CHIRALPAK® IA-3 (4.6*150), hexane: 2-propanol=88:12, column temperature: 25 °C, injection solution: 2 mg/mL ethanol solution, injection volume: 0.7 μL, flow rate: 0.5 ml/min, detection wavelength: 227 nm, retention time: 9.8 min (1R form), 11.1 min (1S form)] to calculate the enantiomeric excess of (1R)-2,2-difluorocyclopropan-1-amine hydrochloride.

Example 1: Synthesis of 4-[4-cyano-2-methyl-6-(1-methylpyrazol-4-yl)indazol-3-yl]-2-(difluoromethoxy)-N-[(1R,2S)-2-fluorocyclopropyl]-6-methoxybenzamide

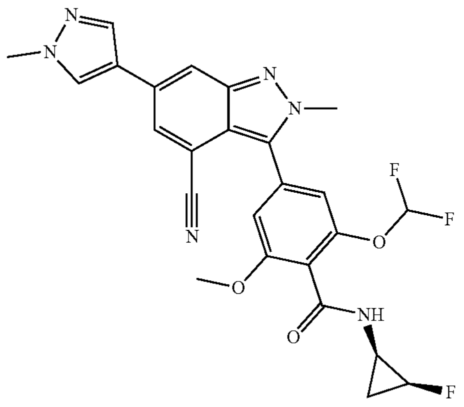 [SMILES: COc1cc(-c2c3c(C#N)cc(-c4cnn(C)c4)cc3nn2C)cc(OC(F)F)c1C(=O)N[C@@H]1C[C@@H]1F]

A mixture of 4-(6-bromo-4-cyano-2-methylindazol-3-yl)-2-(difluoromethoxy)-N-[(1R,2S)-2-fluorocyclopropyl]-6-methoxybenzamide (70 mg) described in Reference Example 20, 1-methyl-4-(4,4,5,5-tetramethyl-1,3,2-dioxaborolan-2-yl)pyrazole (43 mg), a [1,1'-bis(diphenylphosphino)ferrocene]palladium(II) dichloride dichloromethane adduct (11 mg), potassium carbonate (38 mg), 1,4-dioxane (1.4 mL), and water (0.14 mL) was heated and stirred under a nitrogen atmosphere at 100 °C for 3 hours. After the reaction was completed, water was added to the reaction mixture, and extraction was performed three times with chloroform. The organic layer was separated with Phase-Separator®, and the organic layer was concentrated under reduced pressure. The resulting residue was purified by preparative HPLC (10 mM aqueous ammonium carbonate solution-acetonitrile) to obtain the title compound (48 mg) as a gray powder. MS(ESI)m/z:511.0 [M+H]+

Example 2: Synthesis of 2-(difluoromethoxy)-N-[(1R,2S)-2-fluorocyclopropyl]-6-methoxy-4-[4-methoxy-2-methyl-6-(1-methylpyrazol-4-yl)indazol-3-yl]benzamide

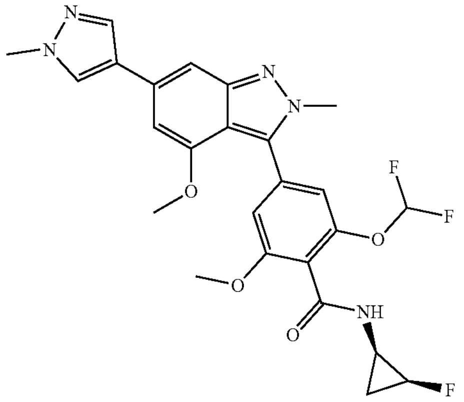 [SMILES: COc1cc(-c2c3c(OC)cc(-c4cnn(C)c4)cc3nn2C)cc(OC(F)F)c1C(=O)N[C@@H]1C[C@@H]1F]

The same reaction and treatment as in Example 1 were performed using 4-(6-bromo-4-methoxy-2-methylindazol-3-yl)-2-(difluoromethoxy)-N-[(1R,2S)-2-fluorocyclopropyl]-6-methoxybenzamide described in Reference Example 24 to obtain the title compound. MS(ESI)m/z:516.0 [M+H]+

Example 3: Synthesis of 2-(difluoromethoxy)-4-[4-(difluoromethyl)-2-methyl-6-(1-methylpyrazol-4-yl)indazol-3-yl]-N-[(1R,2S)-2-fluorocyclopropyl]-6-methoxybenzamide

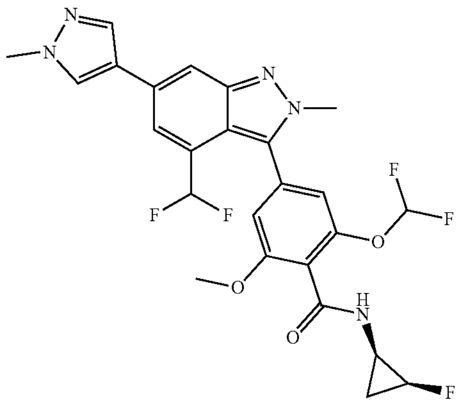 [SMILES: COc1cc(-c2c3c(C(F)F)cc(-c4cnn(C)c4)cc3nn2C)cc(OC(F)F)c1C(=O)N[C@@H]1C[C@@H]1F]

4-[6-Bromo-4-(difluoromethyl)-2-methylindazol-3-yl]-2-(difluoromethoxy)-N-[(1R,2S)-2-fluorocyclopropyl]-6-methoxybenzamide (24 mg) described in Reference Example 32, 1-methyl-4-(4,4,5,5-tetramethyl-1,3,2-dioxaborolan-2-yl)pyrazole (9.5 mg), potassium carbonate (17 mg), and a [1,1'-bis(diphenylphosphino)ferrocene]palladium(II) dichloride dichloromethane adduct (3.4 mg) were suspended in a mixed solvent of 1,4-dioxane (0.28 mL) and water (69 μL), and heating and stirring were performed under a nitrogen atmosphere at 100 °C for 2 hours. After the reaction was completed, the reaction mixture was diluted with ethyl acetate, sodium sulfate was added, filtration was performed, and then the filtrate was concentrated under reduced pressure. The resulting residue was purified by column chromatography (ethyl acetate:methanol=100:0 to 90:10) using an NH silica gel column and a Si silica gel column in series to obtain the title compound (18 mg) as a light yellow powder. MS(ESI)m/z:536.1 [M+H]+

Example 4: Synthesis of 2-(difluoromethoxy)-N-[(1R,2S)-2-fluorocyclopropyl]-4-[4-(3-hydroxy-propoxy)-2-methyl-6-(1-methylpyrazol-4-yl)indazol-3-yl]-6-methoxybenzamide

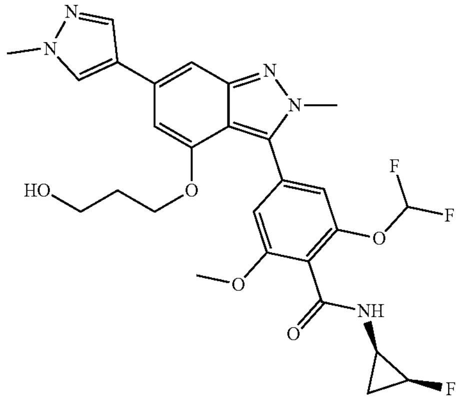 [SMILES: COc1cc(-c2c3c(OCCCO)cc(-c4cnn(C)c4)cc3nn2C)cc(OC(F)F)c1C(=O)N[C@@H]1C[C@@H]1F]

Under a nitrogen atmosphere, 1 N hydrochloric acid (0.35 mL) was added to a methanol (2.0 mL) solution of 2-(difluoromethoxy)-N-[(1R,2S)-2-fluorocyclopropyl]-6-methoxy-4-[2-methyl-6-(1-methylpyrazol-4-yl)-4-[3-(oxan-2-yloxy)propoxy]indazol-3-yl]benzamide (75 mg) described in Reference Example 36, and the mixture was stirred at room temperature for 2 hours. A 1 N aqueous sodium hydroxide solution (0.35 mL) was added to the reaction solution, and the mixture was concentrated under reduced pressure. Water was added to the concentrated residue, extraction was performed with chloroform, the organic layer was separated with Phase-Separator®, and the organic layer was concentrated under reduced pressure again. The resulting residue was purified by silica gel column chromatography (chloroform:methanol=100:0 to 97:3 to 95:5) and then suspended and washed with diethyl ether to obtain the title compound (45 mg) as a light yellow powder. MS(ESI)m/z:560.4 [M+H]+

Example 5: Synthesis of 2-(difluoromethoxy)-4-[4-(difluoromethoxy)-2-methyl-6-(1-methylpyrazol-4-yl)indazol-3-yl]-N-[(1R,2S)-2-fluorocyclopropyl]-6-methoxybenzamide

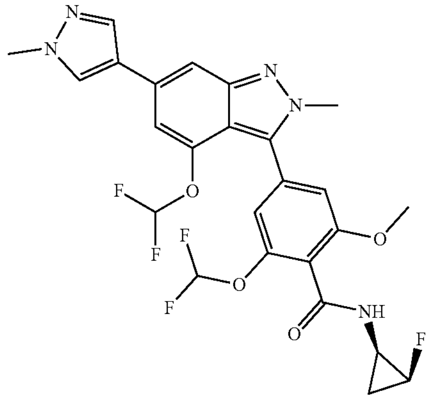 [SMILES: COc1cc(-c2c3c(OC(F)F)cc(-c4cnn(C)c4)cc3nn2C)cc(OC(F)F)c1C(=O)N[C@@H]1C[C@@H]1F]

4-[6-Bromo-4-(difluoromethoxy)-2-methylindazol-3-yl]-2-(difluoromethoxy)-N-[(1R,2S)-2-fluorocyclopropyl]-6-methoxybenzamide (40 mg) described in Reference Example 40, 1-methyl-4-(4,4,5,5-tetramethyl-1,3,2-dioxaborolan-2-yl)pyrazole (18 mg), a [1,1'-bis(diphenylphosphino)ferrocene]palladium(II) dichloride dichloromethane adduct (6.0 mg), and potassium carbonate (20 mg) were suspended in a mixed solvent of 1,4-dioxane (0.49 mL) and water (0.12 mL), and heating and stirring were performed under a nitrogen atmosphere at 100 °C for 80 minutes. The reaction solution was purified by silica gel column chromatography (ethyl acetate:methanol=100:0 to 85:15) as it was. The resulting crude product was purified by preparative HPLC (10 mM aqueous ammonium carbonate solution-acetonitrile) to obtain the title compound (31 mg) as a gray powder. MS(ESI)m/z:552.3 [M+H]+

Example 6: Synthesis of 2-(difluoromethoxy)-N-[(1R,2S)-2-fluorocyclopropyl]-6-methoxy-4-[2-methyl-6-(1-methylpyrazol-4-yl)-4-phenylmethoxy-indazol-3-yl]benzamide

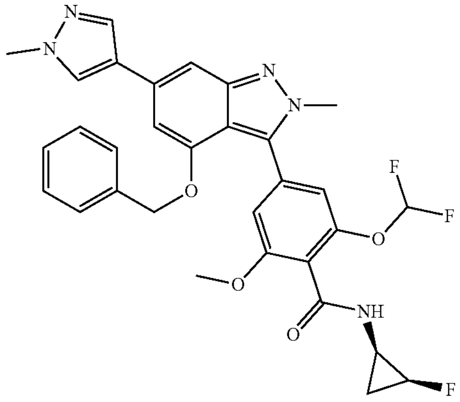 [SMILES: COc1cc(-c2c3c(OCc4ccccc4)cc(-c4cnn(C)c4)cc3nn2C)cc(OC(F)F)c1C(=O)N[C@@H]1C[C@@H]1F]

4-(6-Bromo-2-methyl-4-phenylmethoxyindazol-3-yl)-2-(difluoromethoxy)-N-[(1R,2S)-2-fluorocyclopropyl]-6-methoxybenzamide (52 mg) described in Reference Example 38, 1-methyl-4-(4,4,5,5-tetramethyl-1,3,2-dioxaborolan-2-yl)pyrazole (27 mg), a [1,1'-bis(diphenylphosphino)ferrocene]palladium(II) dichloride dichloromethane adduct (7.2 mg), and potassium carbonate (24 mg) were suspended in a mixed solvent of 1,4-dioxane (3.0 mL) and water (0.30 mL), and heating and stirring were performed under a nitrogen atmosphere at 100 °C for 3 hours. The reaction solution was extracted by adding water and chloroform, the organic layer was separated with Phase-Separator®, and the organic layer was concentrated under reduced pressure. Purification was performed by silica gel column chromatography (hexane:ethyl acetate=50:50 to 0:100 to chloroform:methanol=97:3) again after purification with NH silica gel column chromatography (hexane:ethyl acetate=50:50 to 0:100), and suspension and washing were performed with diethyl ether to obtain the title compound (29 mg) as a colorless powder. MS(ESI)m/z:592.4 [M+H]+

Example 7: Synthesis of 3-[3-(difluoromethoxy)-4-[3-hydroxy-3-(trifluoromethyl)azetidin-1-carbonyl]-5-methoxyphenyl]-2-methyl-6-(1-methylpyrazol-4-yl)indazole-4-carbonitrile

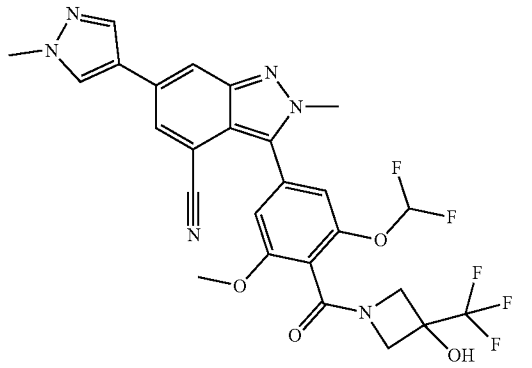 [SMILES: COc1cc(-c2c3c(C#N)cc(-c4cnn(C)c4)cc3nn2C)cc(OC(F)F)c1C(=O)N1CC(O)(C(F)(F)F)C1]

4-[4-Cyano-2-methyl-6-(1-methylpyrazol-4-yl)indazol-3-yl]-2-(difluoromethoxy)-6-methoxybenzoic acid (40 mg) described in Reference Example 42, HATU (49 mg), and N,N-diisopropylethylamine (44 μL) were suspended in N,N-dimethylformamide (1.0 mL), 3-(trifluoromethyl)azetidin-3-ol hydrochloride (23 mg) was added at room temperature, and the mixture was stirred for 18 minutes. After the reaction was completed, the reaction solution was purified by preparative HPLC (10 mM aqueous ammonium carbonate solution-acetonitrile) to obtain the title compound (49 mg) as a white powder. MS(ESI)m/z:577.1 [M+H]+

Example 8: Synthesis of 3-[3-(difluoromethoxy)-4-[3-(difluoromethyl)-3-methylazetidin-1-carbonyl]-5-methoxyphenyl]-2-methyl-6-(1-methylpyrazol-4-yl)indazole-4-carbonitrile

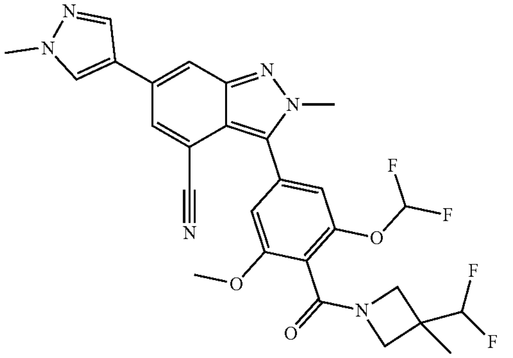 [SMILES: COc1cc(-c2c3c(C#N)cc(-c4cnn(C)c4)cc3nn2C)cc(OC(F)F)c1C(=O)N1CC(C)(C(F)F)C1]

The same reaction and treatment as in Example 7 were performed using 4-[4-cyano-2-methyl-6-(1-methylpyrazol-4-yl)indazol-3-yl]-2-(difluoromethoxy)-6-methoxybenzoic acid described in Reference Example 42 and 3-(difluoromethyl)-3-methylazetidine hydrochloride to obtain the title compound.

MS(ESI)m/z:557.2 [M+H]+

Example 9: Synthesis of 3-[3-(difluoromethoxy)-4-[3-(difluoromethoxy)azetidine-1-carbonyl]-5-methoxyphenyl]-2-methyl-6-(1-methylpyrazol-4-yl)indazole-4-carbonitrile

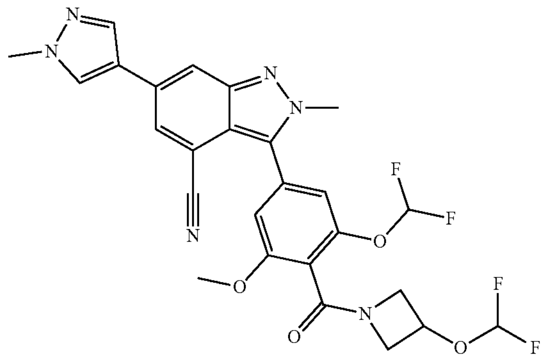 [SMILES: COc1cc(-c2c3c(C#N)cc(-c4cnn(C)c4)cc3nn2C)cc(OC(F)F)c1C(=O)N1CC(OC(F)F)C1]

The same reaction and treatment as in Example 7 were performed using 4-[4-cyano-2-methyl-6-(1-methylpyrazol-4-yl)indazol-3-yl]-2-(difluoromethoxy)-6-methoxybenzoic acid described in Reference Example 42 and 3-(difluoromethoxy)azetidine hydrochloride to obtain the title compound. MS(ESI)m/z:559.3 [M+H]+

Example 10: Synthesis of 4-[4-cyano-2-methyl-6-(1-methylpyrazol-4-yl)indazol-3-yl]-N-[(2,2-difluorocyclopropyl)methyl]-2-(difluoromethoxy))-6-methoxybenzamide

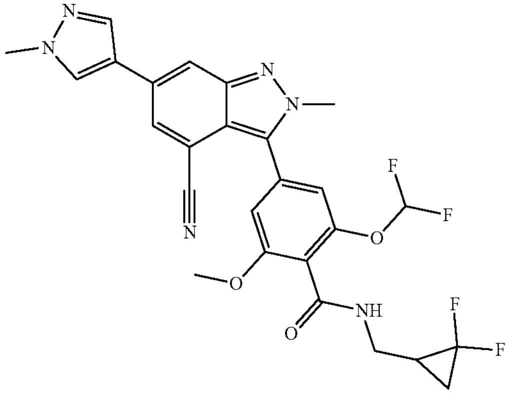 [SMILES: COc1cc(-c2c3c(C#N)cc(-c4cnn(C)c4)cc3nn2C)cc(OC(F)F)c1C(=O)NCC1CC1(F)F]

The same reaction and treatment as in Example 7 were performed using 4-[4-cyano-2-methyl-6-(1-methylpyrazol-4-yl)indazol-3-yl]-2-(difluoromethoxy)-6-methoxybenzoic acid described in Reference Example 42 and (2,2-difluorocyclopropyl)methanamine hydrochloride to obtain the title compound. MS(ESI)m/z:543.3 [M+H]+

Example 11: Synthesis of N-[(1R)-2,2-difluorocyclopropyl]-2-(difluoromethoxy)-4-[4-(difluoromethyl)-2-methyl-6-(1-methylpyrazol-4-yl)indazol-3-yl]-6-methoxybenzamide

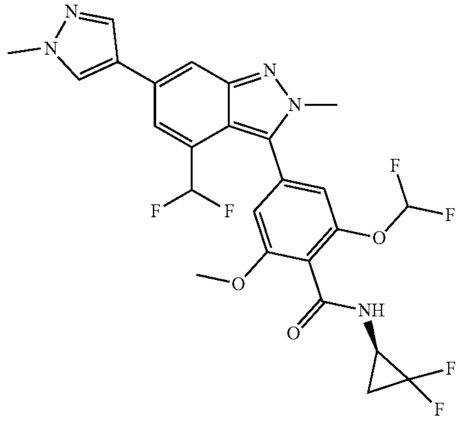 [SMILES: COc1cc(-c2c3c(C(F)F)cc(-c4cnn(C)c4)cc3nn2C)cc(OC(F)F)c1C(=O)N[C@@H]1CC1(F)F]

To a tetrahydrofuran (0.31 mL) suspension of 2-(difluoromethoxy)-4-[4-(difluoromethyl)-2-methyl-6-(1-methylpyrazol-4-yl)indazol-3-yl]-6-methoxybenzoic acid (30 mg) described in Reference Example 46, oxalyl dichloride (24 mg) and N,N-dimethylformamide (1 drop) were sequentially added at room temperature, and the mixture was stirred at room temperature for 2 hours. The reaction solution was concentrated under reduced pressure, toluene was added to the resulting residue, and the mixture was concentrated under reduced pressure again. Dichloromethane (1.0 mL) and (R)-2,2-difluorocyclopropan-1-amine hydrochloride (11 mg) were sequentially added to the residue, the mixture was suspended, N,N-diisopropylethylamine (54 μL) was added, and the mixture was stirred at room temperature for 10 minutes. The reaction solution was concentrated again, and the residue was dissolved in DMSO and purified by preparative HPLC (10 mM aqueous ammonium carbonate solution-acetonitrile) to obtain the title compound (27 mg) as a white powder.

MS(ESI)m/z:554.4 [M+H]+

Example 12: Synthesis of 4-[4-cyano-2-methyl-6-(1-methylpyrazol-4-yl)indazol-3-yl]-2-(difluoromethoxy)-N-[(1-fluorocyclopropyl)methyl]-6-methoxybenzamide

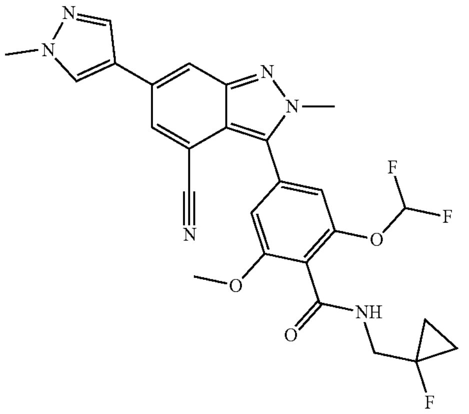 [SMILES: COc1cc(-c2c3c(C#N)cc(-c4cnn(C)c4)cc3nn2C)cc(OC(F)F)c1C(=O)NCC1(F)CC1]

To an N,N-dimethylformamide (2.2 mL) solution of 4-[4-cyano-2-methyl-6-(1-methylpyrazol-4-yl)indazol-3-yl]-2-(difluoromethoxy)-6-methoxybenzoic acid (100 mg) described in Reference Example 42 and (1-fluorocyclopropyl)methanamine hydrochloride (30 mg), N,N-diisopropylethylamine (0.11 mL) and HATU (92 mg) were sequentially added at room temperature, and the mixture was stirred for 1.5 hours. A saturated aqueous sodium bicarbonate solution was added to the reaction solution, extraction was performed twice with ethyl acetate, the organic layer was separated with Phase-Separator®, and then the organic layer was concentrated under reduced pressure. The concentrated residue was purified by preparative HPLC (10 mM aqueous ammonium carbonate solution-acetonitrile) to obtain the title compound (80 mg) as a white powder. MS(ESI)m/z: 525.1 [M+H]+

Example 13: Synthesis of [2-(difluoromethoxy)-6-methoxy-4-[4-methoxy-2-methyl-6-(1-methylpyrazol-4-yl)indazol-3-yl]phenyl]-[3-hydroxy-3-(trifluoromethyl)azetidin-1-yl]methanone

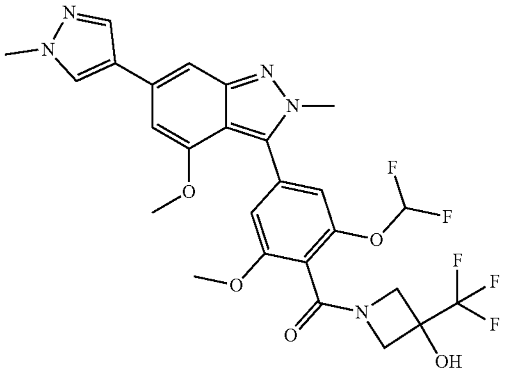 [SMILES: COc1cc(-c2c3c(OC)cc(-c4cnn(C)c4)cc3nn2C)cc(OC(F)F)c1C(=O)N1CC(O)(C(F)(F)F)C1]

To an N,N-dimethylformamide (1.1 mL) solution of 2-(difluoromethoxy)-6-methoxy-4-[4-methoxy-2-methyl-6-(1-methylpyrazol-4-yl)indazol-3-yl]benzoic acid (100 mg) described in Reference Example 51, HATU (100 mg), and 3-(trifluoromethyl)azetidin-3-ol hydrochloride (46 mg), N,N-diisopropylethylamine (0.11 mL) was added, and the mixture was stirred at room temperature for 1 hour. After the reaction was completed, the reaction solution was purified by preparative HPLC (10 mM aqueous ammonium carbonate solution-acetonitrile) to obtain the title compound (86 mg) as a colorless powder. MS(ESI)m/z:582.3 [M+H]+

Example 14: Synthesis of [2-(difluoromethoxy)-4-[4-(difluoromethoxy)-2-methyl-6-(1-methylpyrazol-4-yl)indazol-3-yl]-6-methoxyphenyl]-[3-hydroxy-3-(trifluoromethyl)azetidin-1-yl]methanone

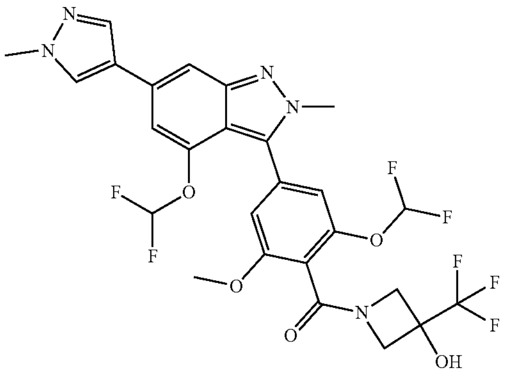

[4-[6-Bromo-4-(difluoromethoxy)-2-methylindazol-3-yl]-2-(difluoromethoxy)-6-methoxyphenyl]-[3-hydroxy-3-(trifluoromethyl)azetidin-1-yl]methanone (106 mg) described in Reference Example 55, 1-methyl-4-(4,4,5,5-tetramethyl-1,3,2-dioxaborolan-2-yl)pyrazole (43 mg), a [1,1'-bis(diphenylphosphino)ferrocene]palladium(II) dichloride dichloromethane adduct (14 mg), and potassium carbonate (48 mg) were suspended in a mixed solvent of 1,4-dioxane (0.86 mL) and water (0.22 mL), and heating and stirring were performed under a nitrogen atmosphere at 100 °C for 95 minutes. The reaction solution was purified by silica gel column chromatography (chloroform:methanol=100:0 to 85:15) as it was.

The resulting crude product was purified by preparative HPLC (10 mM aqueous ammonium carbonate solution-acetonitrile) to obtain the title compound (53 mg) as a light brown powder. MS(ESI)m/z:618.1 [M+H]+

Example 15: Synthesis of 3-[3-(difluoromethoxy)-4-[3-hydroxy-3-(trifluoromethyl)azetidin-1-carbonyl]-5-methoxyphenyl]-6-(1-ethylpyrazol-4-yl)-2-methylindazole-4-carbonitrile

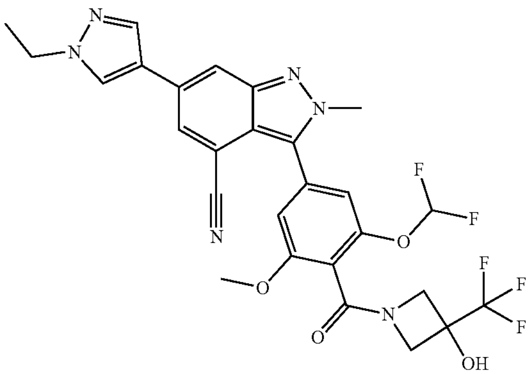 [SMILES: CCn1cc(-c2cc(C#N)c3c(-c4cc(OC)c(C(=O)N5CC(O)(C(F)(F)F)C5)c(OC(F)F)c4)n(C)nc3c2)cn1]

6-Bromo-3-[3-(difluoromethoxy)-4-[3-hydroxy-3-(trifluoromethyl)azetidine-1-carbonyl]-5-methoxyphenyl]-2-methylindazole-4-carbonitrile (90 mg) described in Reference Example 56, 1-ethyl-4-(4,4,5,5-tetramethyl-1,3,2-dioxaborolan-2-yl)pyrazole (42 mg), a [1,1'-bis(diphenylphosphino)ferrocene]palladium(II) dichloride dichloromethane adduct (13 mg), and potassium carbonate (43 mg) were suspended in a mixed solvent of 1,4-dioxane (0.78 mL) and water (0.20 mL), and heating and stirring were performed under a nitrogen atmosphere at 100 °C for 175 minutes. The reaction solution was purified by silica gel column chromatography (chloroform:methanol=100:0 to 91:9) as it was. The resulting crude product was purified by preparative HPLC (10 mM aqueous ammonium carbonate solution-acetonitrile) to obtain the title compound (44 mg) as a light brown powder. MS(ESI)m/z:591.3 [M+H]+

Example 16: Synthesis of 3-[3-(difluoromethoxy)-4-[3-hydroxy-3-(trifluoromethyl)azetidine-1-carbonyl]-5-methoxyphenyl]-6-[1-(2-hydroxy-2-methylpropyl)pyrazol-4-yl]-2-methylindazole-4-carbonitrile

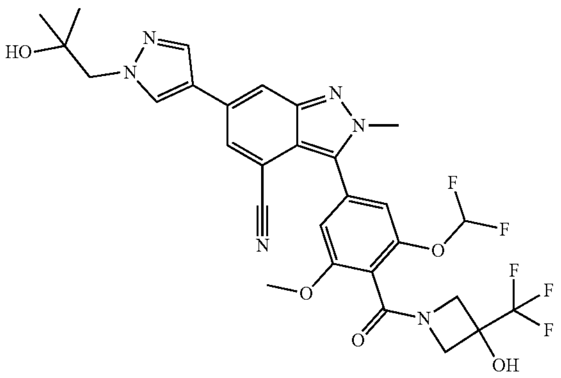 [SMILES: COc1cc(-c2c3c(C#N)cc(-c4cnn(CC(C)(C)O)c4)cc3nn2C)cc(OC(F)F)c1C(=O)N1CC(O)(C(F)(F)F)C1]

6-Bromo-3-[3-(difluoromethoxy)-4-[3-hydroxy-3-(trifluoromethyl)azetidine-1-carbonyl]-5-methoxyphenyl]-2-methylindazole-4-carbonitrile (85 mg) described in Reference Example 56, 2-methyl-1-[4-(4,4,5,5-tetramethyl-1,3,2-dioxaborolan-2-yl)pyrazol-1-yl]propan-2-ol (47 mg), a [1,1'-bis(diphenylphosphino)ferrocene]palladium(II) dichloride dichloromethane adduct (12 mg), and potassium carbonate (41 mg) were suspended in a mixed solvent of 1,4-dioxane (0.74 mL) and water (0.18 mL), and heating and stirring were performed under a nitrogen atmosphere at 100 °C for 70 minutes. The reaction solution was purified by silica gel column chromatography (chloroform:methanol=100:0 to 85:15) as it was.

The resulting crude product was purified by preparative HPLC (10 mM aqueous ammonium carbonate solution-acetonitrile) to obtain the title compound (49 mg) as a light brown powder. MS(ESI)m/z:635.4 [M+H]+

Example 17: Synthesis of 2-[4-[4-cyano-3-[3-(difluoromethoxy)-4-[3-hydroxy-3-(trifluoromethyl)azetidin-1-carbonyl]-5-methoxyphenyl]-2-methylindazol-6-yl]pyrazol-1-yl]-N,N-dimethylacetamide

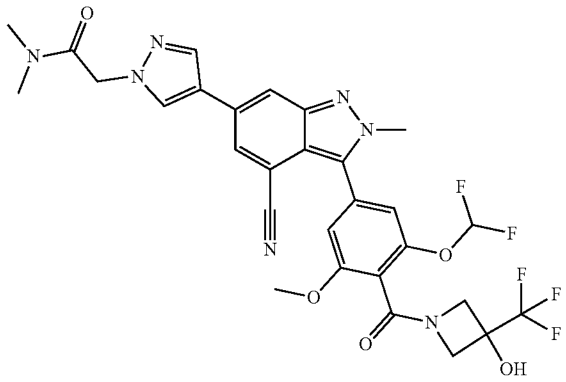 [SMILES: COc1cc(-c2c3c(C#N)cc(-c4cnn(CC(=O)N(C)C)c4)cc3nn2C)cc(OC(F)F)c1C(=O)N1CC(O)(C(F)(F)F)C1]

6-Bromo-3-[3-(difluoromethoxy)-4-[3-hydroxy-3-(trifluoromethyl)azetidine-1-carbonyl]-5-methoxyphenyl]-2-methylindazole-4-carbonitrile (90 mg) described in Reference Example 56, N,N-dimethyl-2-[4-(4,4,5,5-tetramethyl- 1,3,2-dioxaborolan-2-yl)pyrazol-1-yl]acetamide (52 mg), a [1,1'-bis(diphenylphosphino)ferrocene]palladium(II) dichloride dichloromethane adduct (13 mg), and potassium carbonate (43 mg) were suspended in a mixed solvent of 1,4-dioxane (0.78 mL) and water (0.20 mL), and heating and stirring were performed under a nitrogen atmosphere at 100 °C for 70 minutes. The reaction solution was purified by silica gel column chromatography (chloroform:methanol=100:0 to 85:15) as it was.

The resulting crude product was purified by preparative HPLC (10 mM aqueous ammonium carbonate solution-acetonitrile) to obtain the title compound (54 mg) as a light brown powder. MS(ESI)m/z:648.4 [M+H]+

Example 18: Synthesis of 4-[4-cyano-6-(1-ethylpyrazol-4-yl)-2-methylindazol-3-yl]-2-(difluoromethoxy)-N-[(1R,2S)-2-fluorocyclopropyl]-6-methoxybenzamide

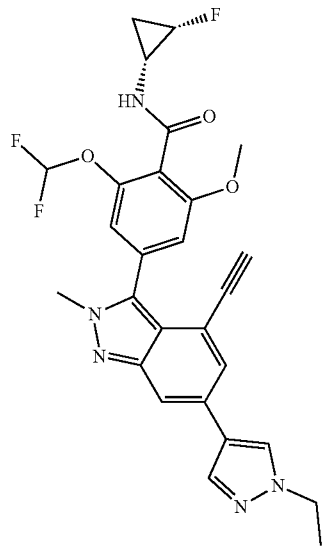 [SMILES: C#Cc1cc(-c2cnn(CC)c2)cc2nn(C)c(-c3cc(OC)c(C(=O)N[C@@H]4C[C@@H]4F)c(OC(F)F)c3)c12]

To an N,N-dimethylformamide (1.0 mL) suspension of 4-[4-cyano-2-methyl-6-(4,4,5,5-tetramethyl-1,3,2-dioxaborolan-2-yl)indazol-3-yl]-2-(difluoromethoxy)-N-[(1R,2S)-2-fluorocyclopropyl]-6-methoxybenzamide (50 mg) described in Reference Example 21 and 1-ethyl-4-iodopyrazole (24 mg), a solution of water (0.20 mL) of sodium carbonate (19 mg) and tetrakis(triphenylphosphine)palladium (0) (10 mg) were added, and the mixture was stirred at 80 °C. overnight. SiliaMetS DMT® was added, the mixture was shaken for 1 hour, and then insoluble matter was removed by filtration, and washed with N,N-dimethylformamide. The filtrate was purified by preparative HPLC (0.1% aqueous TFA solution-acetonitrile) and then NH silica gel column chromatography (dichloromethane:methanol=4:1) to obtain the title compound (14 mg) as a yellow powder. MS(ESI)m/z:525.1 [M+H]+

Example 19: Synthesis of 4-[4-cyano-6-[1-[2-(dimethylamino)ethyl]pyrazol-4-yl]-2-methylindazol-3-yl]-2-(difluoromethoxy)-N-[(1R,2S)-2-fluorocyclopropyl]-6-methoxybenzamide

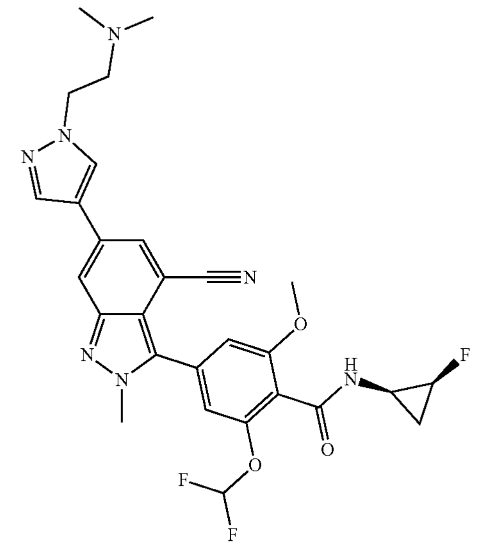 [SMILES: COc1cc(-c2c3c(C#N)cc(-c4cnn(CCN(C)C)c4)cc3nn2C)cc(OC(F)F)c1C(=O)N[C@@H]1C[C@@H]1F]

The same reaction and treatment as in Example 18 were performed using 4-[4-cyano-2-methyl-6-(4,4,5,5-tetramethyl-1,3,2-dioxaborolan-2-yl)indazol-3-yl]-2-(difluoromethoxy)-N-[(1R,2S)-2-fluorocyclopropyl]-6-methoxybenzamide described in Reference Example 21 and 2-(4-iodopyrazol-1-yl)-N,N-dimethylethanamine to obtain the title compound. MS(ESI)m/z:568.1 [M+H]+

Example 20: Synthesis of 4-[6-(1-tert-butylpyrazol-4-yl)-4-cyano-2-methylindazol-3-yl]-2-(difluoromethoxy)-N-[(1R,2S)-2-fluorocyclopropyl]-6-J methoxybenzamide

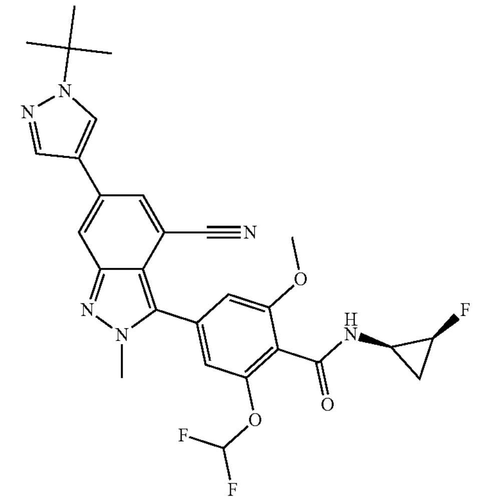 [SMILES: COc1cc(-c2c3c(C#N)cc(-c4cnn(C(C)(C)C)c4)cc3nn2C)cc(OC(F)F)c1C(=O)N[C@@H]1C[C@@H]1F]

The same reaction and treatment as in Example 18 were performed using 4-[4-cyano-2-methyl-6-(4,4,5,5-tetramethyl-1,3,2-dioxaborolan-2-yl)indazol-3-yl]-2-(difluoromethoxy)-N-[(1R,2S)-2-fluorocyclopropyl]-6-methoxybenzamide described in Reference Example 21 and 1-tert-butyl-4-iodopyrazole to obtain the title compound. MS(ESI) m/z:553.1 [M+H]+

Example 21: Synthesis of 4-[4-cyano-2-methyl-6-(3-methyl-1,2-thiazol-5-yl)indazol-3-yl]-2-(difluoromethoxy)-N-[(1R,2S)-2-fluorocyclopropyl]-6-methoxybenzamide

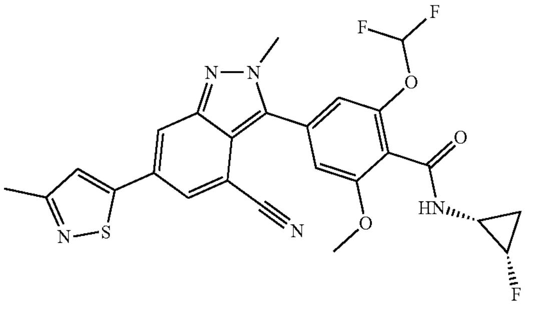 [SMILES: COc1cc(-c2c3c(C#N)cc(-c4cc(C)ns4)cc3nn2C)cc(OC(F)F)c1C(=O)N[C@@H]1C[C@@H]1F]

The same reaction and treatment as in Example 18 were performed using 4-[4-cyano-2-methyl-6-(4,4,5,5-tetramethyl-1,3,2-dioxaborolan-2-yl)indazol-3-yl]-2-(difluoromethoxy)-N-[(1R,2S)-2-fluorocyclopropyl]-6-methoxybenzamide described in Reference Example 21 and 5-iodo-3-methyl-1,2-thiazole to obtain the title compound. MS(ESI)m/z:528.0 [M+H]+

Example 22: Synthesis of 4-[4-cyano-2-methyl-6-[1-(oxolan-3-yl)pyrazol-4-yl]indazol-3-yl]-2-(difluoromethoxy)-N-[(1R,2S)-2-fluorocyclopropyl]-6-methoxybenzamide

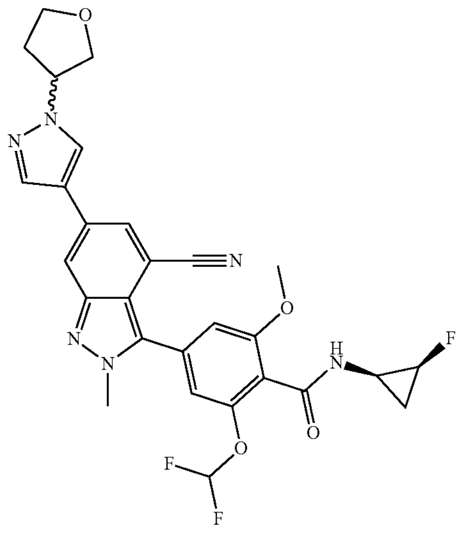 [SMILES: COc1cc(-c2c3c(C#N)cc(-c4cnn(C5CCOC5)c4)cc3nn2C)cc(OC(F)F)c1C(=O)N[C@@H]1C[C@@H]1F]

To an N,N-dimethylformamide (1.0 mL) suspension of 4-[4-cyano-2-methyl-6-(4,4,5,5-tetramethyl-1,3,2-dioxaborolan-2-yl)indazol-3-yl]-2-(difluoromethoxy)-N-[(1R,2S)-2-fluorocyclopropyl]-6-methoxybenzamide (50 mg) described in Reference Example 21 and 4-iodo-1-(oxolan-3-yl)pyrazole (29 mg), a solution of water (0.20 mL) of sodium carbonate (19 mg) and tetrakis(triphenylphosphine) palladium (0) (10 mg) were added, and the mixture was stirred at 80 °C. overnight. SiliaMetS DMT® was added, the mixture was shaken for 1 hour, and then insoluble matter was removed by filtration and washed with N,N-dimethylformamide. The filtrate was purified by preparative HPLC (0.1% aqueous TFA solution-acetonitrile). A saturated aqueous sodium bicarbonate solution and dichloromethane were added to the fractions containing the target product, and the mixture was extracted and concentrated under reduced pressure to obtain the title compound (15 mg) as a yellow powder. MS(ESI)m/z:567.1 [M+H]+

Example 23: Synthesis of 4-[4-cyano-2-methyl-6-(1-methylpyrazol-4-yl)indazol-3-yl]-N-[(1R)-2,2-difluorocyclopropyl]-2-(difluoromethoxy)-6-methoxybenzamide

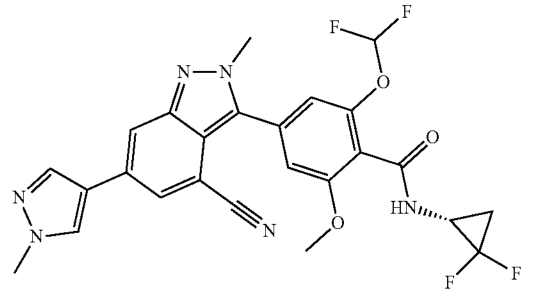 [SMILES: COc1cc(-c2c3c(C#N)cc(-c4cnn(C)c4)cc3nn2C)cc(OC(F)F)c1C(=O)N[C@@H]1CC1(F)F]

To a tetrahydrofuran (0.44 mL) solution of 4-[4-cyano-2-methyl-6-(1-methylpyrazol-4-yl)indazol-3-yl]-2-(difluoromethoxy)-6-methoxybenzoic acid (40 mg) described in Reference Example 42, oxalyl dichloride (34 mg) and N,N-dimethylformamide (1 drop) were sequentially added at room temperature, and the mixture was stirred at room temperature for 7 hours. The reaction solution was concentrated under reduced pressure, toluene was added to the resulting residue, and the mixture was concentrated under reduced pressure again. (1S)-2,2-Difluorocyclopropanamine hydrochloride (15 mg) and dichloromethane (2.0 mL) were added to the residue, the mixture was suspended, N,N-diisopropylethylamine (76 μL) was added, and the mixture was stirred at room temperature for overnight. 1 N hydrochloric acid was added to the reaction mixture, and extraction was performed with chloroform. The organic layer was separated with Phase-Separator®, sodium sulfate was added, the mixture was filtered, and then the filtrate was concentrated under reduced pressure. The resulting residue was sequentially purified by NH silica gel column chromatography (ethyl acetate:methanol=100:0 to 95:5) and silica gel column chromatography (chloroform:methanol=100:0 to 90:10 to 80:20 to 70:30) to obtain the title compound (29 mg) as a white powder. MS(ESI)m/z:529.3 [M+H]+

Example 24: Synthesis of 4-[4-cyano-2-methyl-6-(1H-pyrazol-3-yl)indazol-3-yl]-2-(difluoromethoxy)-N-[(1R,2S)-2-fluorocyclopropyl]-6-methoxybenzamide

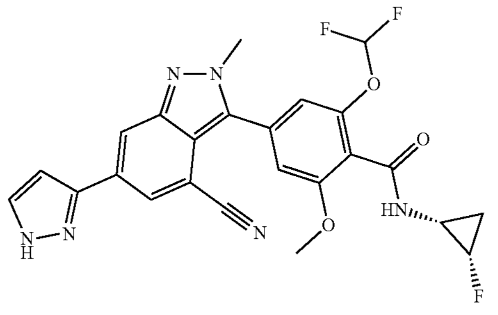 [SMILES: COc1cc(-c2c3c(C#N)cc(-c4cc[nH]n4)cc3nn2C)cc(OC(F)F)c1C(=O)N[C@@H]1C[C@@H]1F]

To an N,N-dimethylformamide (1.0 mL) suspension of 4-[4-cyano-2-methyl-6-(4,4,5,5-tetramethyl-1,3,2-dioxaborolan-2-yl)indazol-3-yl]-2-(difluoromethoxy)-N-[(1R,2S)-2-fluorocyclopropyl]-6-methoxybenzamide (50 mg) described in Reference Example 21 and 3-iodo-1H-pyrazole (21 mg), a solution of water (0.20 mL) of sodium carbonate (19 mg) and tetrakis(triphenylphosphine)palladium (0) (10 mg) were added, and the mixture was stirred at 100 °C. overnight. SiliaMetS DMT® was added, the mixture was shaken for 1 hour, and then insoluble matter was removed by filtration and washed with N,N'-dimethylformamide. The filtrate was purified by preparative HPLC (0.1% aqueous TFA solution-acetonitrile), and the fractions containing the target product were concentrated and purified by NH silica gel column chromatography (dichloromethane:methanol=4:1) to obtain the title compound (5.6 mg) as a white powder. MS(ESI)m/z:497.0 [M+H]+

Example 25: Synthesis of 3-[3-(difluoromethoxy)-4-[3-(difluoromethyl)-3-hydroxyazetidine-1-carbonyl]-5-methoxyphenyl]-2-methyl-6-(1-methylpyrazol-4-yl)indazole-4-carbonitrile

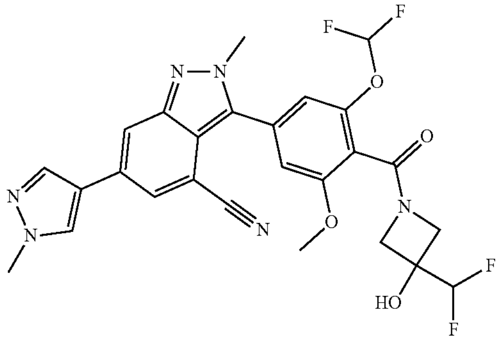 [SMILES: COc1cc(-c2c3c(C#N)cc(-c4cnn(C)c4)cc3nn2C)cc(OC(F)F)c1C(=O)N1CC(O)(C(F)F)C1]

An N,N-dimethylformamide (1.0 mL) solution of 4-[4-cyano-2-methyl-6-(1-methylpyrazol-4-yl)indazol-3-yl]-2-(difluoromethoxy)-6-methoxybenzoic acid (50 mg) described in Reference Example 42, N,N-diisopropylethylamine (77 μL), and HATU (63 mg) was added to 3-(difluoromethyl)azetidin-3-ol hydrochloride (26 mg), and the mixture was stirred at room temperature for 1 hour. The reaction solution was filtered by a filter, and the filtrate was purified by preparative HPLC (0.1% aqueous TFA solution-acetonitrile). A saturated aqueous sodium bicarbonate solution was added to the fraction containing the target product, extraction was performed with dichloromethane, the organic layer was washed with saturated saline, and then the organic layer was concentrated under reduced pressure to obtain the title compound (21 mg) as a white powder. MS(ESI)m/z:559.1 [M+H]+

Example 26: Synthesis of [2-(difluoromethoxy)-6-methoxy-4-[2-methyl-6-(1-methylpyrazol-4-yl)-4-(oxetan-3-ylmethoxy)indazol-3-yl]phenyl]-[3-hydroxy-3-(trifluoromethyl)azetidin-1-yl]methanone

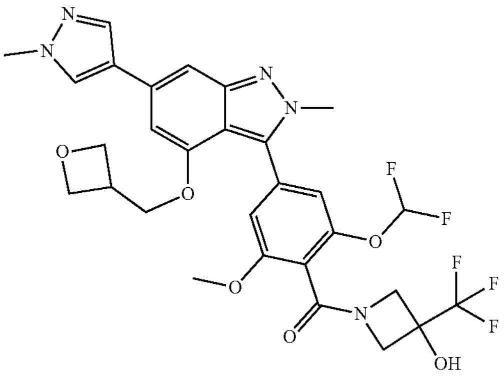 [SMILES: COc1cc(-c2c3c(OCC4COC4)cc(-c4cnn(C)c4)cc3nn2C)cc(OC(F)F)c1C(=O)N1CC(O)(C(F)(F)F)C1]

To an N,N-dimethylformamide (3.0 mL) suspension of [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone (40 mg) described in Reference Example 54 and potassium carbonate (29 mg), 3-(bromomethyl) oxetane (16 mg) was added under a nitrogen atmosphere at room temperature, and the mixture was stirred at 80 °C for 3 hours. The reaction solution was allowed to cool, water was added, and extraction was performed with ethyl acetate. The organic layer was washed twice with saturated saline, and then the organic layer was separated with Phase-Separator® and concentrated under reduced pressure. The resulting residue was purified by preparative HPLC (10 mM aqueous ammonium carbonate solution-acetonitrile) and then NH silica gel column chromatography (chloroform:methanol=100:0 to 97:3) and then suspended and washed with diethyl ether to obtain the title compound (13 mg) as a light yellow powder. MS(ESI)m/z:638.3 [M+H]+

Example 27: Synthesis of [4-[4-(cyclobutylmethoxy)-2-methyl-6-(1-methylpyrazol-4-yl)indazol-3-yl]-2-(difluoromethoxy)-6-methoxyphenyl]-[3-hydroxy-3-(trifluoromethyl)azetidin-1-yl]methanone

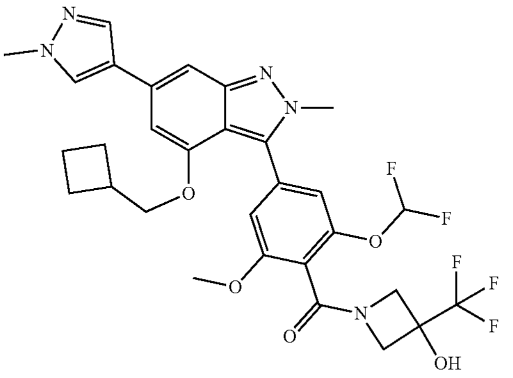 [SMILES: COc1cc(-c2c3c(OCC4CCC4)cc(-c4cnn(C)c4)cc3nn2C)cc(OC(F)F)c1C(=O)N1CC(O)(C(F)(F)F)C1]

The same reaction and treatment as in Example 26 were performed using [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl] methanone described in Reference Example 54 and bromomethylcyclobutane to obtain the title compound. MS(ESI)m/z:636.4 [M+H]+

Example 28: Synthesis of [2-(difluoromethoxy)-4-[4-(3-hydroxypropoxy)-2-methyl-6-(1-methylpyrazol-4-yl)indazol-3-yl]-6-methoxyphenyl]-[3-Hydroxy-3-(trifluoromethyl)azetidin-1-yl]methanone

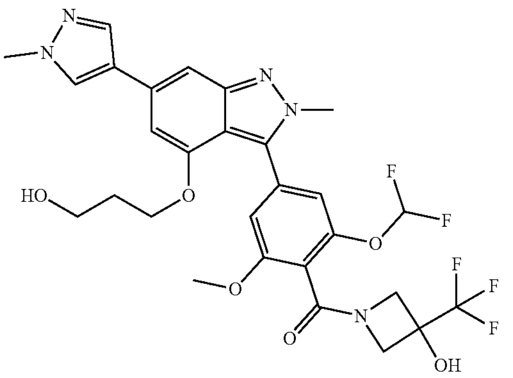 [SMILES: COc1cc(-c2c3c(OCCCO)cc(-c4cnn(C)c4)cc3nn2C)cc(OC(F)F)c1C(=O)N1CC(O)(C(F)(F)F)C1]

Under a nitrogen atmosphere, 1 N hydrochloric acid (0.14 mL) was added to a methanol (2.0 mL) solution of [2-(difluoromethoxy)-6-methoxy-4-[2-methyl-6-(1-methylpyrazol-4-yl)-4-[3-(oxan-2-yloxy)propoxy]indazol-3-yl] phenyl]-[3-hydroxy-3-(trifluoromethyl)azetidin-1-yl] methanone (34 mg) described in Reference Example 57, and the mixture was stirred at room temperature for 20 hours. A 1 N aqueous sodium hydroxide solution (0.14 mL) was added to the reaction solution, and the mixture was concentrated under reduced pressure. Water was added to the concentrated residue, extraction was performed with chloroform, the organic layer was separated with Phase-Separator®, and the organic layer was concentrated under reduced pressure again. The resulting residue was purified by NH silica gel column chromatography (chloroform: methanol=100:0 to 95:5) and then suspended and washed with diethyl ether to obtain the title compound (21 mg) as an orange powder.

MS(ESI)m/z:626.3 [M+H]+

Example 29: Synthesis of [4-[4-(cyclopropylmethoxy)-2-methyl-6-(1-methylpyrazol-4-yl)indazol-3-yl]-2-(difluoromethoxy)-6-methoxyphenyl]-[3-hydroxy-3-(trifluoromethyl)azetidin-1-yl]methanone

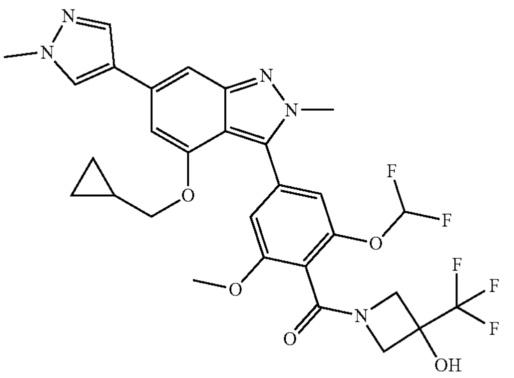 [SMILES: COc1cc(-c2c3c(OCC4CC4)cc(-c4cnn(C)c4)cc3nn2C)cc(OC(F)F)c1C(=O)N1CC(O)(C(F)(F)F)C1]

To an N,N-dimethylformamide (3.0 mL) solution of [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone (40 mg) described in Reference Example 54 and potassium carbonate (29 mg), bromomethylcyclopropane (14 mg) was added under a nitrogen atmosphere at room temperature, and the mixture was stirred at 80 °C for 2 hours. Water was added to the reaction solution, extraction was performed with ethyl acetate, and the organic layer was washed twice with saturated saline. The organic layer was separated with Phase-Separator®, and the organic layer was concentrated under reduced pressure. The resulting residue was purified by NH silica gel column chromatography (chloroform:methanol=100:0 to 97:3) and then suspended and washed with diethyl ether to obtain the title compound (21 mg) as a light yellow powder. MS(ESI)m/z:622.3 [M+H]+

Example 30: Synthesis of [2-(difluoromethoxy)-6-methoxy-4-[2-methyl-6-(1-methylpyrazol-4-yl)-4-(2,2,2-trifluoroethoxy)indazol-3-yl]phenyl]-[3-hydroxy-3-(trifluoromethyl)azetidin-1-yl]methanone

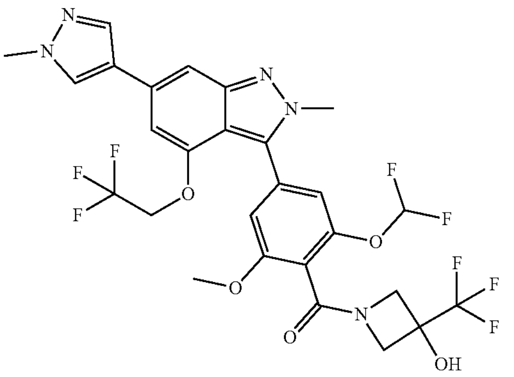 [SMILES: COc1cc(-c2c3c(OCC(F)(F)F)cc(-c4cnn(C)c4)cc3nn2C)cc(OC(F)F)c1C(=O)N1CC(O)(C(F)(F)F)C1]

The same reaction and treatment as in Example 29 were performed using [2-(difluoromethoxy)-4-[4-hydroxy-2-methyl-6-(1-methylpyrazol-4-yl)indazol-3-yl]-6-methoxy-phenyl]-[3-hydroxy-3-(trifluoromethyl)azetidin-1-yl] methanone described in Reference Example 54 and 2,2,2-trifluoroethyl trifluoromethanesulfonate to obtain the title compound. MS(ESI)m/z:650.3 [M+H]+

Example 31: Synthesis of 4-[4-cyano-6-[1-(2,2-difluoroethyl)pyrazol-4-yl]-2-methylindazol-3-yl]-2-(difluoromethoxy)-N-[(1R, 2S)-2-fluorocyclopropyl]-6-methoxybenzamide

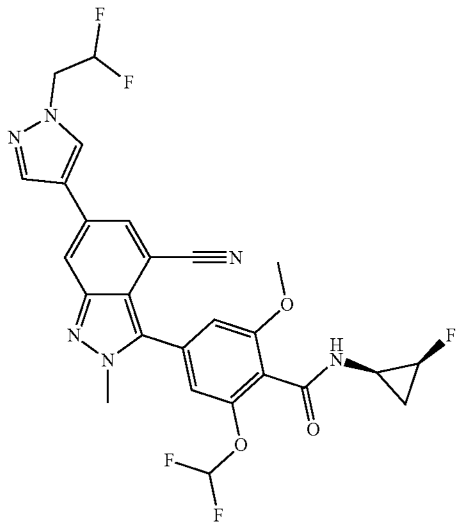 [SMILES: COc1cc(-c2c3c(C#N)cc(-c4cnn(CC(F)F)c4)cc3nn2C)cc(OC(F)F)c1C(=O)N[C@@H]1C[C@@H]1F]

To an N,N-dimethylformamide (1.0 mL) suspension of 4-[4-cyano-2-methyl-6-(4,4,5,5-tetramethyl-1,3,2-dioxaborolan-2-yl)indazol-3-yl]-2-(difluoromethoxy)-N-[(1R, 2S)-2-fluorocyclopropyl]-6-methoxybenzamide (50 mg) described in Reference Example 21 and 1-(2,2-difluoroethyl)-4-iodopyrazole (28 mg), a solution of water (0.20 mL) of sodium carbonate (19 mg) and tetrakis(triphenylphosphine)palladium (0) (10 mg) were added, and the mixture was stirred at 80 °C. overnight. SiliaMetS DMT® was added, the mixture was shaken for 1 hour, and then insoluble matter was removed by filtration and washed with N,N-dimethylformamide. The filtrate was purified by preparative HPLC (0.1% aqueous TFA solution-acetonitrile), and the fractions containing the target product were concentrated and purified by NH silica gel column chromatography (dichloromethane:methanol=4:1). The crude product was purified by preparative HPLC (10 mM aqueous ammonium carbonate solution-acetonitrile) again to obtain the title compound (9.2 mg) as a white powder.

MS(ESI)m/z:561.0 [M+H]+

Example 32: Synthesis of 4-[4-cyano-6-[1-(cyclopropylmethyl)pyrazol-4-yl]-2-methylindazol-3-yl]-2-(difluoromethoxy)-N-[(1R, 2S)-2-fluorocyclopropyl]-6-methoxybenzamide

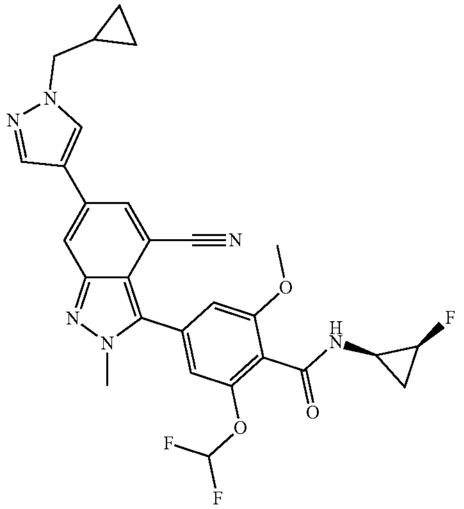 [SMILES: COc1cc(-c2c3c(C#N)cc(-c4cnn(CC5CC5)c4)cc3nn2C)cc(OC(F)F)c1C(=O)N[C@@H]1C[C@@H]1F]

The same reaction and treatment as in Example 31 were performed using 4-[4-cyano-2-methyl-6-(4,4,5,5-tetramethyl-1,3,2-dioxaborolan-2-yl)indazol-3-yl]-2-(difluoromethoxy)-N-[(1R,2S)-2-fluorocyclopropyl]-6-methoxybenzamide described in Reference Example 21 and 1-(cyclopropylmethyl)-4-iodopyrazole to obtain the title compound. MS(ESI)m/z:551.1 [M+H]+

Example 33: Synthesis of 4-[4-cyano-2-methyl-6-(1-propan-2-ylpyrazol-4-yl)indazol-3-yl]-2-(difluoromethoxy)-N-[(1R,2S)-2-fluorocyclopropyl]-6-methoxybenzamide

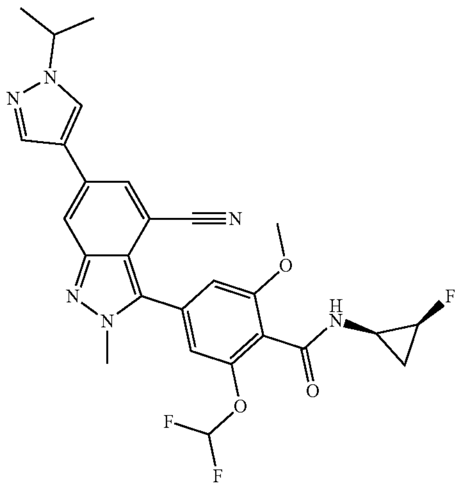 [SMILES: COc1cc(-c2c3c(C#N)cc(-c4cnn(C(C)C)c4)cc3nn2C)cc(OC(F)F)c1C(=O)N[C@@H]1C[C@@H]1F]

The same reaction and treatment as in Example 31 were performed using 4-[4-cyano-2-methyl-6-(4,4,5,5-tetramethyl-1,3,2-dioxaborolan-2-yl)indazol-3-yl]-2-(difluoromethoxy)-N-[(1R,2S)-2-fluorocyclopropyl]-6-methoxybenzamide described in Reference Example 21 and 4-iodo-1-propan-2-yl-pyrazole to obtain the title compound. MS(ESI)m/z:539.1 [M+H]+

Example 34: Synthesis of [2-(difluoromethoxy)-6-methoxy-4-[2-methyl-6-(1-methylpyrazol-4-yl)-4-(pyridin-3-ylmethoxy)indazol-3-yl]phenyl]-[3-hydroxy-3-(trifluoromethyl)azetidin-1-yl]methanone

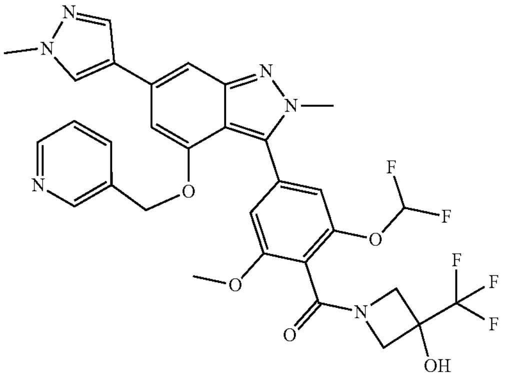 [SMILES: COc1cc(-c2c3c(OCc4cccnc4)cc(-c4cnn(C)c4)cc3nn2C)cc(OC(F)F)c1C(=O)N1CC(O)(C(F)(F)F)C1]

To an N,N-dimethylformamide (3.0 mL) suspension of [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone (60 mg) described in Reference Example 54 and potassium carbonate (73 mg), 3-(bromomethyl)pyridine hydrobromide (32 mg) was added under a nitrogen atmosphere at room temperature, and the mixture was heated and stirred at 80 °C for 1 hour. After the reaction was completed, water was added to the reaction mixture, extraction was performed with ethyl acetate, and the organic layer was washed twice with saturated saline. The organic layer was separated with Phase-Separator®, and the organic layer was concentrated under reduced pressure. The resulting residue was purified by preparative HPLC (0.05% aqueous TFA solution-0.05% TFA acetonitrile solution), a saturated aqueous sodium bicarbonate solution was added to the fractions containing the target product, and the mixture was extracted with ethyl acetate. The organic layer was separated with Phase-Separator®, and the organic layer was concentrated under reduced pressure. The crude product obtained by purifying the residue by NH silica gel column chromatography (chloroform:methanol=100:0 to 97:3) was suspended and washed with diethyl ether to obtain the title compound (10 mg) as a colorless powder. MS(ESI)m/z:659.4 [M+H]+

Example 35: Synthesis of [2-(difluoromethoxy)-6-methoxy-4-[2-methyl-6-(1-methylpyrazol-4-yl)-4-(pyridin-4-ylmethoxy)indazol-3-yl]phenyl]-[3-hydroxy-3-(trifluoromethyl)azetidin-1-yl]methanone

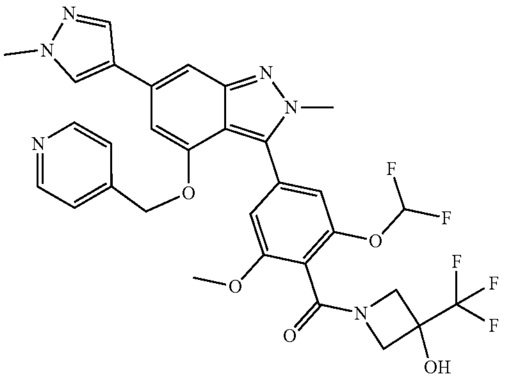 [SMILES: COc1cc(-c2c3c(OCc4ccncc4)cc(-c4cnn(C)c4)cc3nn2C)cc(OC(F)F)c1C(=O)N1CC(O)(C(F)(F)F)C1]

To an N,N-dimethylformamide (3.0 mL) suspension of [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone (40 mg) described in Reference Example 54 and potassium carbonate (49 mg), 4-(bromomethyl)pyridine hydrobromide (27 mg) was added under a nitrogen atmosphere at room temperature, and the mixture was heated and stirred at 80 °C for 2 hours. After the reaction was completed, water was added to the reaction mixture, extraction was performed with ethyl acetate, and the organic layer was washed twice with saturated saline. The organic layer was separated with Phase-Separator®, and the organic layer was concentrated under reduced pressure. The residue was purified by NH silica gel column chromatography (chloroform:methanol=100:0 to 97:3) and preparative HPLC (0.05% aqueous TFA solution-0.05% TFA acetonitrile solution), a saturated aqueous sodium bicarbonate solution was added to the fractions containing the target product, and then the mixture was extracted with ethyl acetate. The organic layer was separated with Phase-Separator®, and the organic layer was concentrated under reduced pressure. The residue was suspended and washed with diethyl ether to obtain the title compound (8.7 mg) as a colorless powder. MS(ESI)m/z:659.4 [M+H]+

Example 36: Synthesis of 3-[4-[3-amino-3-(trifluoromethyl)azetidin-1-carbonyl]-3-(difluoromethoxy)-5-methoxyphenyl]-2-methyl-6-(1-methylpyrazol-4-yl)indazole-4-carbonitrile

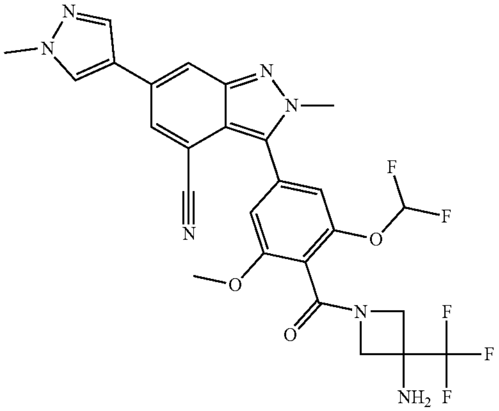 [SMILES: COc1cc(-c2c3c(C#N)cc(-c4cnn(C)c4)cc3nn2C)cc(OC(F)F)c1C(=O)N1CC(N)(C(F)(F)F)C1]

4-[4-Cyano-2-methyl-6-(1-methylpyrazol-4-yl)indazol-3-yl]-2-(difluoromethoxy)-6-methoxybenzoic acid (40 mg) described in Reference Example 42, 3-(trifluoromethyl)azetidin-3-amine dihydrochloride (23 mg), and HATU (40 mg) were suspended in N,N-dimethylformamide (1.0 mL), N,N-diisopropylethylamine (46 μL) was added, and the mixture was stirred at room temperature for 30 minutes. After the reaction was completed, the reaction solution was purified by preparative HPLC (10 mM aqueous ammonium carbonate solution-acetonitrile) to obtain the title compound (47 mg) as a white powder. MS(ESI)m/z:576.3 [M+H]+

Example 37: Synthesis of [2-(difluoromethoxy)-6-methoxy-4-[4-methoxy-2-methyl-6-(1-methylpyrazol-4-yl)indazol-3-yl]phenyl]-[3-(difluoromethyl)-3-hydroxyazetidin-1-yl]methanone

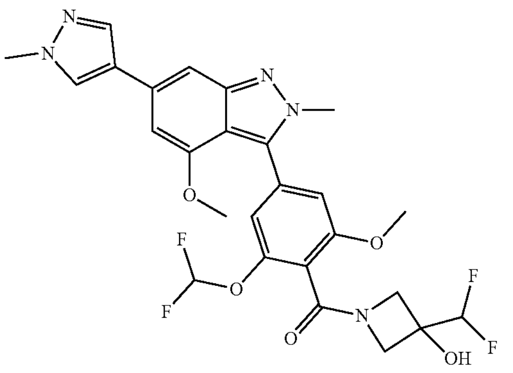 [SMILES: COc1cc(-c2c3c(OC)cc(-c4cnn(C)c4)cc3nn2C)cc(OC(F)F)c1C(=O)N1CC(O)(C(F)F)C1]

The same reaction and treatment as in Example 36 were performed using 2-(difluoromethoxy)-6-methoxy-4-[4-methoxy-2-methyl-6-(1-methylpyrazol-4-yl)indazol-3-yl] benzoic acid described in Reference Example 51 and 3-(difluoromethyl)azetidin-3-ol hydrochloride to obtain the title compound. MS(ESI)m/z:564.2 [M+H]+

Example 38: Synthesis of [2-(difluoromethoxy)-4-[4-(difluoromethyl)-2-methyl-6-(1-methylpyrazol-4-yl)indazol-3-yl]-6-methoxyphenyl]-[3-(difluoromethyl)-3-hydroxyazetidin-1-yl]methanone

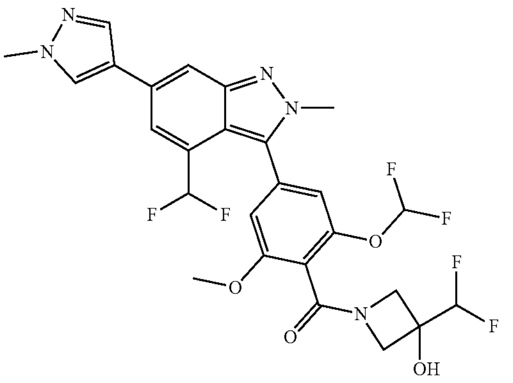 [SMILES: COc1cc(-c2c3c(C(F)F)cc(-c4cnn(C)c4)cc3nn2C)cc(OC(F)F)c1C(=O)N1CC(O)(C(F)F)C1]

The same reaction and treatment as in Example 36 were performed using 2-(difluoromethoxy)-4-[4-(difluoromethyl)-2-methyl-6-(1-methylpyrazol-4-yl)indazol-3-yl]-6-methoxybenzoic acid described in Reference Example 46 and 3-(difluoromethyl)azetidin-3-ol hydrochloride to obtain the title compound. MS(ESI)m/z:584.3 [M+H]+

Example 39: Synthesis of 3-[4-[3-cyano-3-(difluoromethyl)azetidin-1-carbonyl]-3-(difluoromethoxy)-5-methoxyphenyl]-2-methyl-6-(1-methylpyrazol-4-yl)indazole-4-carbonitrile

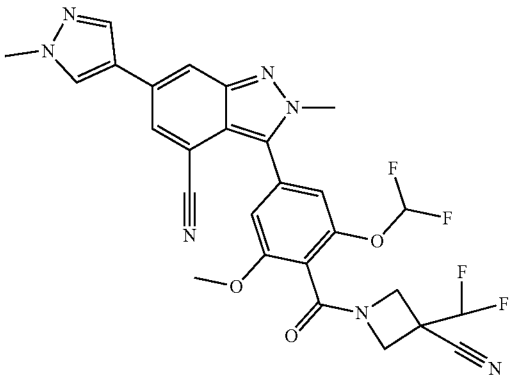 [SMILES: COc1cc(-c2c3c(C#N)cc(-c4cnn(C)c4)cc3nn2C)cc(OC(F)F)c1C(=O)N1CC(C#N)(C(F)F)C1]

4-[4-Cyano-2-methyl-6-(1-methylpyrazol-4-yl)indazol-3-yl]-2-(difluoromethoxy)-6-methoxybenzoic acid (30 mg) described in Reference Example 42 and 3-(difluoromethyl) azetidine-3-carbonitrile hydrochloride (13 mg) were suspended in N,N-dimethylformamide (0.50 mL), HATU (29 mg) and N,N-diisopropylethylamine (33 μL) were sequentially added, and the mixture was stirred at room temperature for 2 days. After the reaction was completed, a saturated aqueous sodium bicarbonate solution was added to the reaction solution, and extraction was performed with chloroform. The organic layer was separated with Phase-Separator®, and the organic layer was concentrated under reduced pressure. The residue was purified by silica gel column chromatography (ethyl acetate:methanol=100:0 to 93:7) and preparative HPLC (10 mM aqueous ammonium carbonate solution-acetonitrile) to obtain the title compound (26 mg) as a colorless powder. MS(ESI)m/z:568.1 [M+H]+

Example 40: Synthesis of 4-[4-cyano-2-methyl-6-[(E)-2-(1-methylpyrazol-4-yl)ethenyl]indazol-3-yl]-2-(difluoromethoxy)-N-[(1R,2S)-2-fluorocyclopropyl]-6-methoxybenzamide

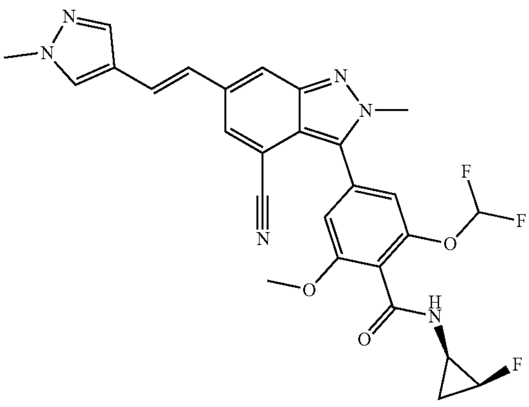 [SMILES: COc1cc(-c2c3c(C#N)cc(/C=C/c4cnn(C)c4)cc3nn2C)cc(OC(F)F)c1C(=O)N[C@@H]1C[C@@H]1F]

4-(6-Bromo-4-cyano-2-methylindazol-3-yl)-2-(difluoromethoxy)-N-[(1R,2S)-2-fluorocyclopropyl]-6-methoxybenzamide (100 mg) described in Reference Example 20, palladium(II) acetate (4.4 mg), tri (o-tolyl)phosphine (12 mg), triethylamine (0.11 mL), and 1-methyl-4-vinyl-pyrazole (42 mg) were dissolved in N,N-dimethylformamide (0.98 mL), and heating and stirring were performed under a nitrogen atmosphere at 120 °C for 15 hours. After the reaction was completed, water was added to the reaction mixture, and extraction was performed with ethyl acetate. The organic layer was washed with 1 N hydrochloric acid and saturated saline, sodium sulfate was added, and then insoluble matter was removed by filtration. The organic layer was concentrated under reduced pressure, and the residue was purified by NH silica gel column chromatography (ethyl acetate:methanol=100:0 to 95:5) and preparative HPLC (10 mM aqueous ammonium carbonate solution-acetonitrile) to obtain the title compound (40 mg) as a light yellow powder. MS(ESI)m/z:537.3 [M+H]+

Example 41: Synthesis of [4-[4-(2,2-difluoroethoxy)-2-methyl-6-(1-methylpyrazol-4-yl)indazol-3-yl]-2-(difluoromethoxy)-6-methoxyphenyl]-[3-hydroxy-3-(trifluoromethyl)azetidin-1-yl]methanone

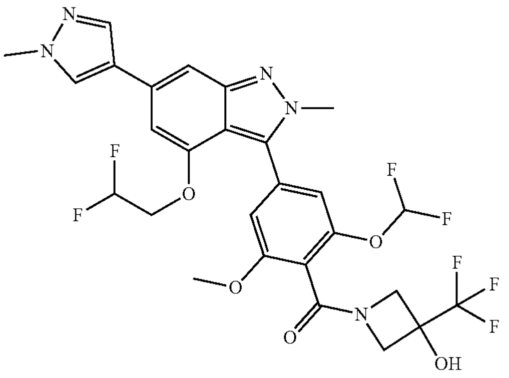 [SMILES: COc1cc(-c2c3c(OCC(F)F)cc(-c4cnn(C)c4)cc3nn2C)cc(OC(F)F)c1C(=O)N1CC(O)(C(F)(F)F)C1]

To an N,N-dimethylformamide (3.0 mL) suspension of [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone (40 mg) described in Reference Example 54 and potassium carbonate (29 mg), 2,2-difluoroethyl trifluoromethanesulfonate (23 mg) was added under a nitrogen atmosphere at room temperature, and the mixture was stirred at room temperature for 30 minutes. After the reaction was completed, water was added to the reaction solution, extraction was performed with ethyl acetate, and the organic layer was washed twice with saturated saline. The organic layer was separated with Phase-Separator®, and the organic layer was concentrated under reduced pressure. The resulting residue was purified by preparative HPLC (10 mM aqueous ammonium carbonate solution-acetonitrile) and then suspended and washed using diethyl ether to obtain the title compound (30 mg) as a colorless powder. MS(ESI)m/z:632.3 [M+H]+

Example 42: Synthesis of [2-(difluoromethoxy)-4-[4-ethoxy-2-methyl-6-(1-methylpyrazol-4-yl)indazol-3-yl]-6-methoxyphenyl]-[3-hydroxy-3-(trifluoromethyl)azetidin-1-yl]methanone

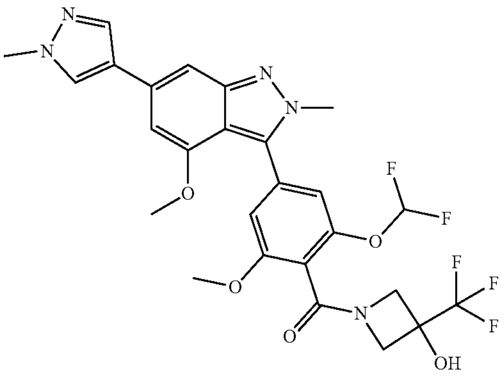 [SMILES: COc1cc(-c2c3c(OC)cc(-c4cnn(C)c4)cc3nn2C)cc(OC(F)F)c1C(=O)N1CC(O)(C(F)(F)F)C1]

To an N,N-dimethylformamide (3.0 mL) suspension of [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone (40 mg) described in Reference Example 54 and potassium carbonate (29 mg), iodoethane (16 mg) was added under a nitrogen atmosphere at room temperature, and the mixture was stirred at 80 °C for 1 hour. After the reaction was completed, water was added to the reaction solution, extraction was performed with ethyl acetate, and the organic layer was washed twice with saturated saline. The organic layer was separated with Phase-Separator®, and the organic layer was concentrated under reduced pressure. The resulting residue was purified by preparative HPLC (10 mM aqueous ammonium carbonate solution-acetonitrile) and then suspended and washed using diethyl ether to obtain the title compound (19 mg) as a light brown powder. MS(ESI)m/z:596.3 [M+H]+

Example 43: Synthesis of [2-(difluoromethoxy)-6-methoxy-4-[2-methyl-6-(1-methylpyrazol-4-yl)-4-propan-2-yloxyindazol-3-yl]phenyl]-[3-hydroxy-3-(trifluoromethyl)azetidin-1-yl]methanone

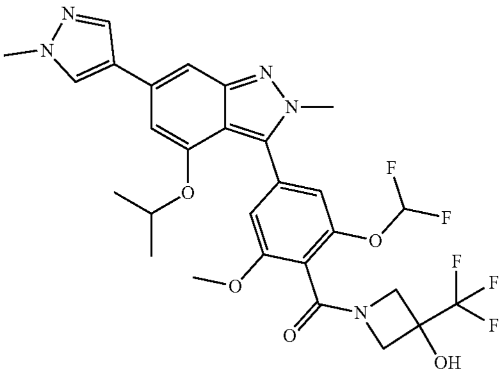 [SMILES: COc1cc(-c2c3c(OC(C)C)cc(-c4cnn(C)c4)cc3nn2C)cc(OC(F)F)c1C(=O)N1CC(O)(C(F)(F)F)C1]

The same reaction and treatment as in Example 42 were performed using [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]

methanone described in Reference Example 54 and 2-iodopropane to obtain the title compound. MS(ESI)m/z:610.3 [M+H]+

Example 44: Synthesis of [2-(difluoromethoxy)-4-[4-(4-hydroxybutoxy)-2-methyl-6-(1-methylpyrazol-4-yl)indazol-3-yl]-6-methoxyphenyl]-[3-hydroxy-3-(trifluoromethyl)azetidin-1-yl]methanone

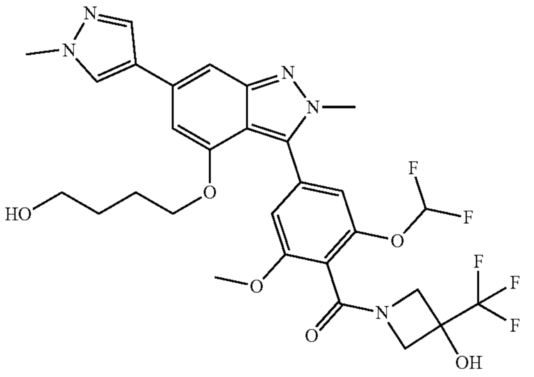 [SMILES: COc1cc(-c2c3c(OCCCCO)cc(-c4cnn(C)c4)cc3nn2C)cc(OC(F)F)c1C(=O)N1CC(O)(C(F)(F)F)C1]

To a methanol (2.0 mL) solution of [2-(difluoromethoxy)-6-methoxy-4-[2-methyl-6-(1-methylpyrazol-4-yl)-4-[4-(oxan-2-yloxy)butoxy]indazol-3-yl]phenyl]-[3-hydroxy-3-(trifluoromethyl)azetidin-1-yl]methanone (25 mg) described in Reference Example 61, 1 N hydrochloric acid (0.10 mL) was added under a nitrogen atmosphere at room temperature, and the mixture was stirred at room temperature for 24 hours. After the reaction was completed, a 1 N aqueous sodium hydroxide solution (0.10 mL) was added to the reaction solution, and the mixture was concentrated under reduced pressure. Water was added to the residue, and extraction was performed with chloroform. The organic layer was separated with Phase-Separator®, and the organic layer was concentrated under reduced pressure. The resulting residue was purified by NH silica gel column chromatography (chloroform:methanol=100:0 to 97:3) and then suspended and washed using diethyl ether to obtain the title compound (12 mg) as a light orange powder. MS(ESI)m/z: 640.3 [M+H]+

Example 45: Synthesis of N-[(1R)-2,2-difluorocyclopropyl]-2-(difluoromethoxy)-6-methoxy-4-[4-methoxy-2-methyl-6-(1-methylpyrazol-4-yl)indazol-3-yl]benzamide

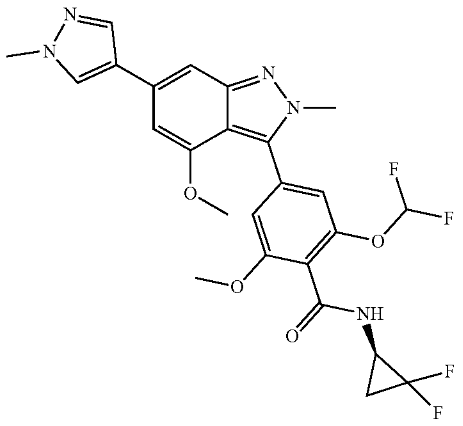 [SMILES: COc1cc(-c2c3c(OC)cc(-c4cnn(C)c4)cc3nn2C)cc(OC(F)F)c1C(=O)N[C@@H]1CC1(F)F]

To a mixture of 2-(difluoromethoxy)-6-methoxy-4-[4-methoxy-2-methyl-6-(1-methylpyrazol-4-yl)indazol-3-yl] benzoic acid (100 mg) described in Reference Example 51 and tetrahydrofuran (1.1 mL), oxalyl dichloride (55 μL) and N,N-dimethylformamide (20 μL) were added at room temperature, and the mixture was stirred for 1 hour. Thereafter, oxalyl dichloride (55 μL) and N,N-dimethylformamide (20 μL) were added at room temperature, and the mixture was stirred at the same temperature for 1 hour. After the reaction was completed, the reaction solution was concentrated under reduced pressure, and then an azeotropic treatment was performed twice using toluene. (R)-2,2-Difluorocyclopropan-1-amine hydrochloride (37 mg), dichloromethane (1.1 mL), and N,N-diisopropylethylamine (0.19 mL) were sequentially added to the resulting residue, and the mixture was stirred at room temperature for 30 minutes. A saturated aqueous sodium bicarbonate solution was added to the reaction solution, extraction was performed with chloroform, the organic layer was separated with Phase-Separator®, and then the organic layer was concentrated under reduced pressure. The resulting residue was purified by preparative HPLC (10 mM aqueous ammonium carbonate solution-acetonitrile) to obtain the title compound (70 mg) as a colorless powder. MS(ESI)m/z:534.3 [M+H]+

Example 46: Synthesis of isomer that elutes later under chiral HPLC conditions as described in experimental section in 4-[4-cyano-2-methyl-6-(1-methylpyrazol-4-yl)indazol-3-yl]-2-(difluoromethoxy)-6-methoxy-N-[[rel-(1R)-2,2-difluorocyclopropyl]methyl]benzamide

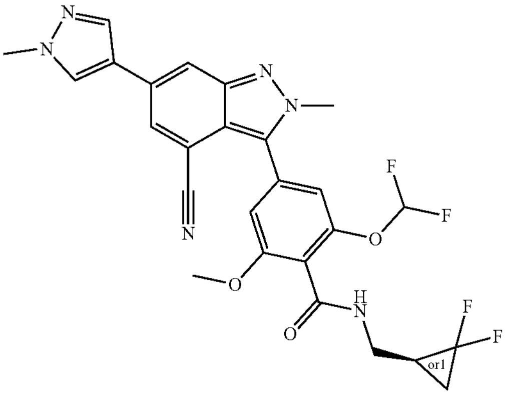 [SMILES: COc1cc(-c2c3c(C#N)cc(-c4cnn(C)c4)cc3nn2C)cc(OC(F)F)c1C(=O)NC[C@@H]1CC1(F)F]

4-[4-Cyano-2-methyl-6-(1-methylpyrazol-4-yl)indazol-3-yl]-N-[(2,2-difluorocyclopropyl)methyl]-2-(difluoromethoxy))-6-methoxybenzamide (27 mg) described in Example 10 was fractionated using a chiral column [CHIRALPAK® IB N-3 (30*250), 2-methoxy-2-methylpropane: methanol:diethylamine=96:4:0.1]. The subsequent fractions were collected and concentrated to obtain the title compound (13 mg) as a white powder. MS(ESI)m/z:543.1 [M+H]+

Example 47: Synthesis of [2-(difluoromethoxy)-4-[4-[(3S)-3-hydroxybutoxy]-2-methyl-6-(1-methylpyrazol-4-yl)indazol-3-yl]-6-methoxyphenyl]-[3-hydroxy-3-(trifluoromethyl)azetidin-1-yl]methanone

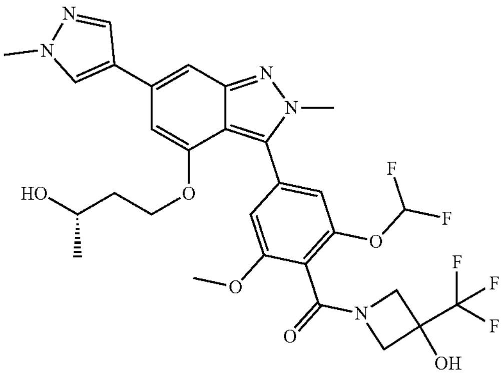 [SMILES: COc1cc(-c2c3c(OCC[C@H](C)O)cc(-c4cnn(C)c4)cc3nn2C)cc(OC(F)F)c1C(=O)N1CC(O)(C(F)(F)F)C1]

To an N,N-dimethylformamide (3.0 mL) suspension of [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone (60 mg) described in Reference Example 54 and potassium carbonate (44 mg), [(3S)-3-hydroxybutyl] 4-methylbenzenesulfonate (39 mg) was added under a nitrogen atmosphere at room temperature, and the mixture was stirred at 80 °C for 1 hour and 30 minutes. After the reaction was completed, water was added to the reaction solution, and extraction was performed with ethyl acetate. The organic layer was washed twice with saturated saline and separated with Phase-Separator®, and the organic layer was concentrated under reduced pressure. The resulting residue was purified by NH silica gel column chromatography (chloroform:methanol=100:0 to 97:3) and then suspended and washed using diethyl ether to obtain the title compound (35 mg) as a light orange powder. MS(ESI) m/z:640.1 [M+H]+

Example 48: Synthesis of [2-(difluoromethoxy)-6-methoxy-4-[2-methyl-6-(1-methylpyrazol-4-yl)-4-(pyrazin-2-ylmethoxy)indazol-3-yl]phenyl]-[3-hydroxy-3-(trifluoromethyl)azetidin-1-yl]methanone

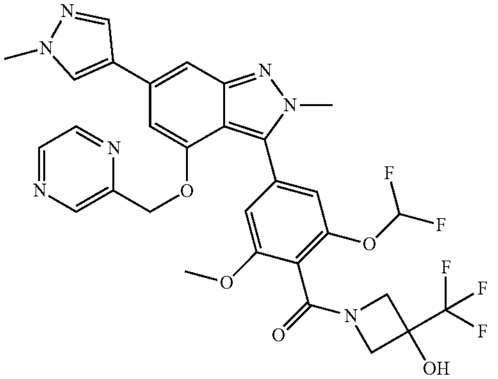 [SMILES: COc1cc(-c2c3c(OCc4cnccn4)cc(-c4cnn(C)c4)cc3nn2C)cc(OC(F)F)c1C(=O)N1CC(O)(C(F)(F)F)C1]

To an N,N-dimethylformamide (3.0 mL) suspension of [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone (60 mg) described in Reference Example 54 and potassium carbonate (73 mg), 2-(bromomethyl) pyrazine hydrobromide (32 mg) was added under a nitrogen atmosphere at room temperature, and the mixture was stirred at 80 °C for 2 hours. After the reaction was completed, water was added to the reaction solution, extraction was performed with ethyl acetate, and the organic layer was washed twice with saturated saline. The organic layer was separated with Phase-Separator®, and the organic layer was concentrated under reduced pressure. The resulting residue was purified by silica gel column chromatography (chloroform:methanol=100:0 to 95:5) and NH silica gel column chromatography (chloroform:methanol=100:0 to 97:3) and then suspended and washed using diethyl ether to obtain the title compound (29 mg) as a light yellow powder.

MS(ESI)m/z:660.3 [M+H]+

Example 49: Synthesis of [2-(difluoromethoxy)-6-methoxy-4-[2-methyl-6-(1-methylpyrazol-4-yl)-4-[(2-methyl-1,3-thiazol-5-yl)methoxy]indazol-3-yl]phenyl]-[3-hydroxy-3-(trifluoromethyl)azetidin-1-yl]methanone

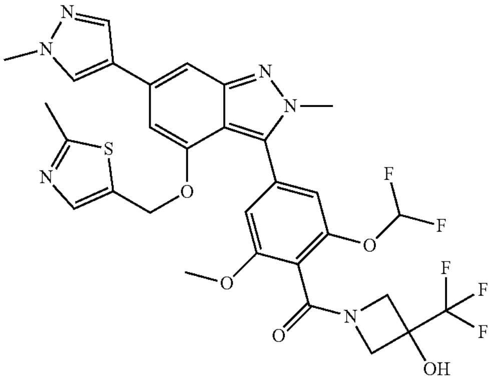 [SMILES: COc1cc(-c2c3c(OCc4cnc(C)s4)cc(-c4cnn(C)c4)cc3nn2C)cc(OC(F)F)c1C(=O)N1CC(O)(C(F)(F)F)C1]

To a mixture of [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone (50 mg) described in Reference Example 54, 5-(chloromethyl)-2-methyl-thiazole hydrochloride (19 mg), and N,N-dimethylformamide (0.88 mL), potassium carbonate (37 mg) was added under a nitrogen atmosphere at room temperature, and the mixture was stirred at 80 °C for 2 hours. After the reaction was completed, water was added to the reaction solution, extraction was performed with ethyl acetate, the organic layer was separated with Phase-Separator®, and then the organic layer was concentrated under reduced pressure. The resulting residue was purified by preparative HPLC (10 mM aqueous ammonium carbonate solution-acetonitrile) and silica gel column chromatography (ethyl acetate:methanol=100:0 to 90:10) to obtain the title compound (9.0 mg) as a white powder. MS(ESI)m/z:679.1 [M+H]+

Example 50: Synthesis of [2-(difluoromethoxy)-6-methoxy-4-[2-methyl-6-(1-methylpyrazol-4-yl)-4-[(6-methylpyridin-3-yl)methoxy]indazol-3-yl]phenyl]-[3-hydroxy-3-(trifluoromethyl)azetidin-1-yl]methanone

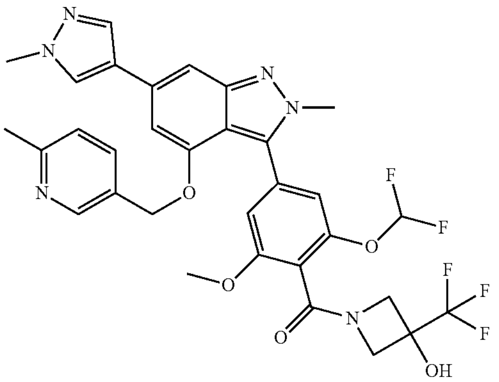 [SMILES: COc1cc(-c2c3c(OCc4ccc(C)nc4)cc(-c4cnn(C)c4)cc3nn2C)cc(OC(F)F)c1C(=O)N1CC(O)(C(F)(F)F)C1]

To an N,N-dimethylformamide (3.0 mL) suspension of [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone (60 mg) described in Reference Example 54 and potassium carbonate (73 mg), 5-(chloromethyl)-2-methyl-pyridine hydrochloride (23 mg) was added under a nitrogen atmosphere at room temperature, and the mixture was stirred at 80 °C for 18 hours. After the reaction was completed, water was added to the reaction solution, extraction was performed with ethyl acetate, and the resulting organic layer was washed twice with saturated saline. The organic layer was separated with Phase-Separator®, and the organic layer was concentrated under reduced pressure. The resulting residue was purified by NH silica gel column chromatography (chloroform:methanol=100:0 to 97:3) and silica gel column chromatography (chloroform:methanol=100:0 to 95:5) and then suspended and washed using diethyl ether to obtain the title compound (12 mg) as a colorless powder. MS(ESI)m/z: 673.3 [M+H]+

Example 51: Synthesis of [2-(difluoromethoxy)-6-methoxy-4-[2-methyl-6-(1-methylpyrazol-4-yl)-4-(pyridazin-4-ylmethoxy)indazol-3-yl]phenyl]-[3-hydroxy-3-(trifluoromethyl)azetidin-1-yl]methanone

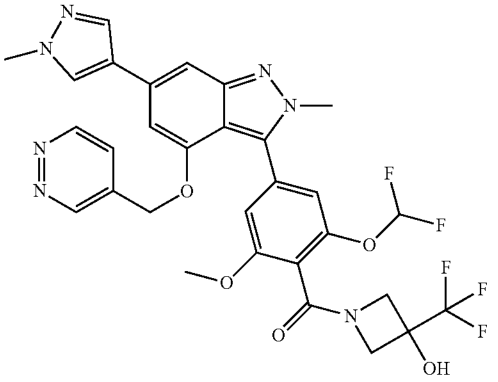 [SMILES: COc1cc(-c2c3c(OCc4ccnnc4)cc(-c4cnn(C)c4)cc3nn2C)cc(OC(F)F)c1C(=O)N1CC(O)(C(F)(F)F)C1]

A mixture of [2-(difluoromethoxy)-4-[4-hydroxy-2-methyl-6-(1-methylpyrazol-4-yl)indazol-3-yl]-6-methoxyphenyl]-[3-hydroxy-3-: (trifluoromethyl)azetidin-1-yl]methanone (50 mg) described in Reference Example 54, 4-(chloromethyl)pyridazine hydrochloride (20 mg), potassium carbonate (37 mg), and N,N-dimethylformamide (0.44 mL) was stirred at 80 °C for 1 hour and 30 minutes. Water was added to the reaction solution, extraction was performed with chloroform, the organic layer was separated with Phase-Separator®, and the organic layer was concentrated under reduced pressure. The resulting residue was purified by preparative HPLC (10 mM aqueous ammonium carbonate solution-acetonitrile) and NH silica gel column chromatography (ethyl acetate:methanol=100:0 to 85:15) to obtain the title compound (13 mg) as a light yellow powder. MS(ESI)m/z:660.1 [M+H]+.

Example 52: Synthesis of [2-(difluoromethoxy)-6-methoxy-4-[2-methyl-6-(1-methylpyrazol-4-yl)-4-[(1-methylpyrazol-4-yl)methoxy]indazol-3-yl]phenyl]-[3-hydroxy-3-(trifluoromethyl)azetidin-1-yl]methanone

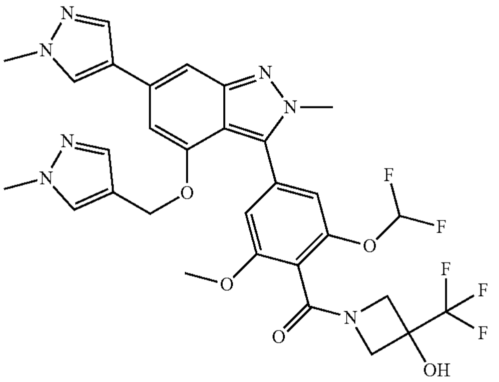 [SMILES: COc1cc(-c2c3c(OCc4cnn(C)c4)cc(-c4cnn(C)c4)cc3nn2C)cc(OC(F)F)c1C(=O)N1CC(O)(C(F)(F)F)C1]

To an N,N-dimethylformamide (3.0 mL) suspension of [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone (60 mg) described in Reference Example 54 and potassium carbonate (73 mg), 4-(chloromethyl)-1-methyl-pyrazole hydrochloride (21 mg) was added under a nitrogen atmosphere at room temperature, and the mixture was stirred at 80 °C for 3 hours. After the reaction was completed, water was added to the reaction solution, extraction was performed with ethyl acetate, and the resulting organic layer was washed twice with saturated saline. The organic layer was separated with Phase-Separator®, and the organic layer was concentrated under reduced pressure. The resulting residue was purified by NH silica gel column chromatography (chloroform:methanol=100:0 to 97:3) and then suspended and washed using diethyl ether to obtain the title compound (3.8 mg) as a colorless powder. MS(ESI)m/z:662.3 [M+H]+

Example 53: Synthesis of [2-(difluoromethoxy)-6-methoxy-4-[2-methyl-4-[(5-methyl-1,3,4-oxadiazol-2-yl)methoxy]-6-(1-methylpyrazol-4-yl)indazol-3-yl]phenyl]-[3-hydroxy-3-(trifluoromethyl)azetidin-1-yl]methanone

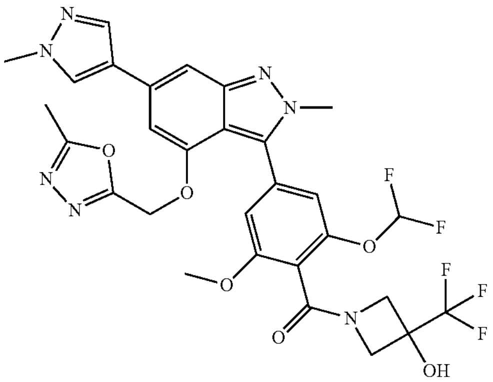 [SMILES: COc1cc(-c2c3c(OCc4nnc(C)o4)cc(-c4cnn(C)c4)cc3nn2C)cc(OC(F)F)c1C(=O)N1CC(O)(C(F)(F)F)C1]

To an N,N-dimethylformamide (3.0 mL) suspension of [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone (60 mg) described in Reference Example 54 and potassium carbonate (44 mg), 2-(chloromethyl)-5-methyl-1,3,4-oxadiazole (17 mg) was added under a nitrogen atmosphere at room temperature, and the mixture was stirred at 80 °C for 1 hour. After the reaction was completed, water was added to the reaction solution, extraction was performed with ethyl acetate, and the resulting organic layer was washed twice with saturated saline. The organic layer was separated with Phase-Separator®, and the organic layer was concentrated under reduced pressure. The resulting residue was purified by NH silica gel column chromatography (chloroform: methanol=100:0 to 97:3) and silica gel column chromatography (chloroform:methanol=100:0 to 95:5) and then suspended and washed using diethyl ether to obtain the title compound (22 mg) as a light yellow powder.

MS(ESI)m/z:664.3 [M+H]+

Example 54: Synthesis of 4-[4-cyano-2-methyl-6-[1-(2-methylsulfonylethyl)pyrazol-4-yl]indazol-3-yl]-2-(difluoromethoxy)-N-[(1-fluorocyclopropyl)methyl]-6-methoxybenzamide

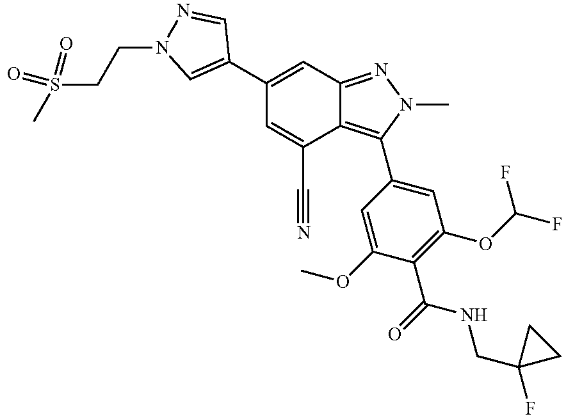 [SMILES: COc1cc(-c2c3c(C#N)cc(-c4cnn(CCS(C)(=O)=O)c4)cc3nn2C)cc(OC(F)F)c1C(=O)NCC1(F)CC1]

A mixture of 4-(6-bromo-4-cyano-2-methylindazol-3-yl)-2-(difluoromethoxy)-N—[(1-fluorocyclopropyl)methyl]-6-methoxybenzamide (50 mg) described in Reference Example 63, 1-(2-methylsulfonylethyl)-4-(4,4,5,5-tetramethyl-1,3,2-dioxaborolan-2-yl)pyrazole (43 mg), a [1,1'-bis(diphenylphosphino)ferrocene]palladium(II) dichloride dichloromethane adduct (7.8 mg), potassium carbonate (26 mg), 1,4-dioxane (2.0 mL), and water (0.20 mL) was heated and stirred under a nitrogen atmosphere at 100 °C for 2 hours. After the reaction was completed, water was added to the reaction mixture, extraction was performed with chloroform, the organic layer was separated with Phase-Separator®, and then the organic layer was concentrated under reduced pressure. The resulting residue was purified by silica gel column chromatography (chloroform:methanol=100:0 to 95:5) using an NH silica gel column and a Si silica gel column in series and then suspended and washed using diethyl ether to obtain the title compound (29 mg) as a colorless powder. MS(ESI)m/z:617.3 [M+H]+

Example 55: Synthesis of 4-[4-cyano-2-methyl-6-(1-methylpyrazol-4-yl)indazol-3-yl]-N-[(1R)-2,2-difluorocyclopropyl]-2-(difluoromethoxy)benzamide

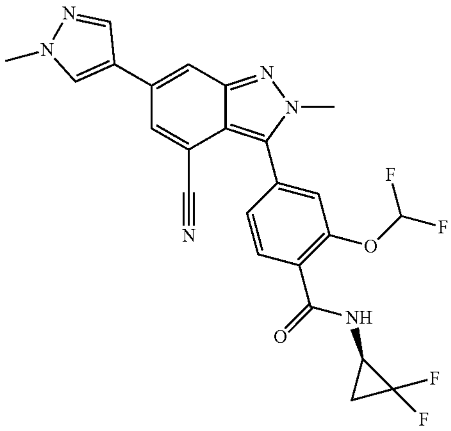 [SMILES: Cn1cc(-c2cc(C#N)c3c(-c4ccc(C(=O)N[C@@H]5CC5(F)F)c(OC(F)F)c4)n(C)nc3c2)cn1]

To a mixture of 4-[4-cyano-2-methyl-6-(1-methylpyrazol-4-yl)indazol-3-yl]-2-(difluoromethoxy)benzoic acid (40 mg) described in Reference Example 80 and tetrahydrofuran (0.95 mL), oxalyl dichloride (24 μL) was added at room temperature, and the mixture was stirred at room temperature. Thereafter, N,N-dimethylformamide (1 drop) was added, and the mixture was stirred at the same temperature for 3 hours. After the reaction was completed, the reaction solution was concentrated under reduced pressure, (1R)-2,2-difluorocyclopropanamine hydrochloride (15 mg), dichloromethane (0.95 mL), and N,N-diisopropylethylamine (49 μL) were sequentially added to the resulting residue, and the mixture was stirred at room temperature for 1 hour. After the reaction was completed, water was added to the reaction solution, and extraction was performed with chloroform. The organic layer was separated with Phase-Separator®, and the organic layer was concentrated under reduced pressure. The resulting residue was purified by preparative HPLC (10 mM aqueous ammonium carbonate solution-acetonitrile), and then the fractions containing the target product were extracted with chloroform. Sodium sulfate was added to the organic layer, and then insoluble matter was removed by filtration. The filtrate was concentrated under reduced pressure to obtain the title compound (19 mg) as a white powder. MS(ESI)m/z:499.0 [M+H]+

Example 56: Synthesis of 4-[4-cyano-6-[1-(2-hydroxy-2-methylpropyl)pyrazol-4-yl]-2-methylindazol-3-yl]-2-(difluoromethoxy)-N-[(1-fluorocyclopropyl)methyl]-6-methoxybenzamide

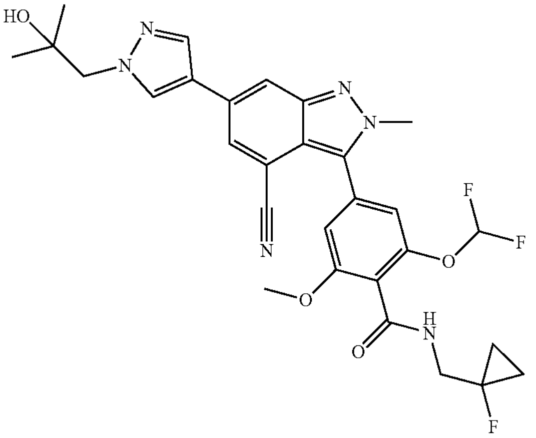 [SMILES: COc1cc(-c2c3c(C#N)cc(-c4cnn(CC(C)(C)O)c4)cc3nn2C)cc(OC(F)F)c1C(=O)NCC1(F)CC1]

A mixture of 4-(6-bromo-4-cyano-2-methylindazol-3-yl)-2-(difluoromethoxy)-N-[(1-fluorocyclopropyl)methyl]-6-methoxybenzamide (50 mg) described in Reference Example 63, 2-methyl-1-[4-(4,4,5,5-tetramethyl-1,3,2-dioxaborolan-2-yl)pyrazol-1-yl]propan-2-ol (28 mg), a [1,1'-bis(diphenylphosphino)ferrocene]palladium(II) dichloride dichloromethane adduct (7.1 mg), potassium carbonate (24 mg), water (58 μL), and 1,4-dioxane (0.58 mL) was heated and stirred under a nitrogen atmosphere at 100 °C for 1 hour and 30 minutes. After the reaction was completed, water was added to the reaction mixture, extraction was performed with chloroform, the organic layer was separated with Phase-Separator®, and then the organic layer was concentrated under reduced pressure. The resulting residue was purified by preparative HPLC (10 mM aqueous ammonium carbonate solution-acetonitrile), and the fractions containing the target product were extracted with chloroform. Sodium sulfate was added to the organic layer, and then insoluble matter was removed by filtration. The filtrate was concentrated under reduced pressure to obtain the title compound (41 mg) as a white powder. MS(ESI)m/z:583.1 [M+H]+

Example 57: Synthesis of 4-[4-cyano-6-[1-[(2R)-2-hydroxypropyl]pyrazol-4-yl]-2-methylindazol-3-yl]-2-(difluoromethoxy)-N-[(1-fluorocyclopropyl)methyl]-6-methoxybenzamide

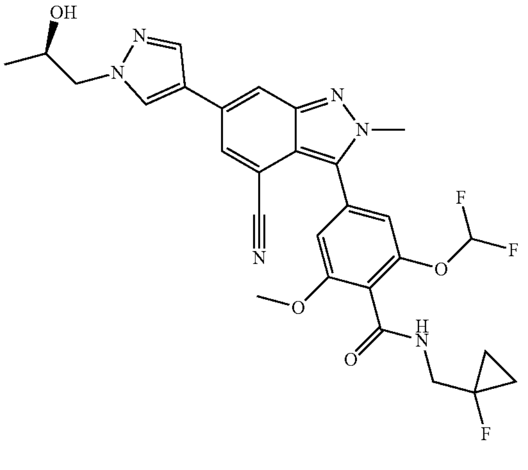 [SMILES: COc1cc(-c2c3c(C#N)cc(-c4cnn(C[C@@H](C)O)c4)cc3nn2C)cc(OC(F)F)c1C(=O)NCC1(F)CC1]

(2R)-1-[4-(4,4,5,5-Tetramethyl-1,3,2-dioxaborolan-2-yl)pyrazol-1-yl]propan-2-ol (72 mg) synthesized by the method described in WO 2022/081627 A, 4-(6-bromo-4-cyano-2-methylindazol-3-yl)-2-(difluoromethoxy)-N-[(1-fluorocyclopropyl)methyl]-6-methoxybenzamide (100 mg) described in Reference Example 63, a [1,1'-bis(diphenylphosphino)ferrocene]palladium(II) dichloride dichloromethane adduct (16 mg), and tripotassium phosphate (81 mg) were suspended in a mixed solvent of 1,4-dioxane (1.3 mL) and water (0.32 mL), and heating and stirring were performed under a nitrogen atmosphere at 100 °C for 2 hours. After the reaction was completed, water: was added to the reaction mixture, and extraction was performed with chloroform. The organic layer was separated with Phase-Separator®, and the organic layer was concentrated under reduced pressure. The residue was purified by NH silica gel column chromatography (ethyl acetate:methanol=100:0 to 95:5) and silica gel column chromatography (chloroform: methanol=99:1 to 90:10) and suspended and washed with diethyl ether to obtain the title compound (59 mg) as a white powder. MS(ESI)m/z:569.1 [M+H]+

Example 58: Synthesis of 4-[4-cyano-6-[1-[(2S)-2-hydroxypropyl]pyrazol-4-yl]-2-methylindazol-3-yl]-2-(difluoromethoxy)-N-[(1-fluorocyclopropyl)methyl]-6-methoxybenzamide

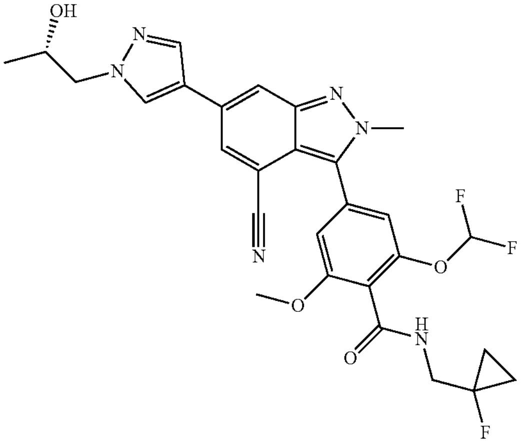 [SMILES: COc1cc(-c2c3c(C#N)cc(-c4cnn(C[C@H](C)O)c4)cc3nn2C)cc(OC(F)F)c1C(=O)NCC1(F)CC1]

A mixture of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxybenzamide (150 mg) described in Reference Example 64, (2S)-1-(4-iodopyrazol-1-yl)propan-2-ol (68 mg), a [1,1'-bis(diphenylphosphino)ferrocene]palladium(II) dichloride dichloromethane adduct (18 mg), tripotassium phosphate (96 mg), water (0.38 mL), and 1,4-dioxane (1.5 mL) was heated and stirred under a nitrogen atmosphere at 100 °C for 2 hours. After the reaction was completed, water was added to the reaction mixture, extraction was performed with chloroform, the organic layer was separated with Phase-Separator®, and then the organic layer was concentrated under reduced pressure. The resulting residue was purified by NH silica gel column chromatography (ethyl acetate: methanol=100:0 to 92:8) and silica gel column chromatography (chloroform:methanol=98:2 to 88:12) to obtain the title compound (68 mg) as a white powder. MS(ESI)m/z: 569.3 [M+H]+

Example 59: Synthesis of 4-[4-cyano-2-methyl-6-[1-(oxetan-3-ylmethyl)pyrazol-4-yl]indazol-3-yl]-2-(difluoromethoxy)-N-[(1-fluorocyclopropyl)methyl]-6-methoxybenzamide

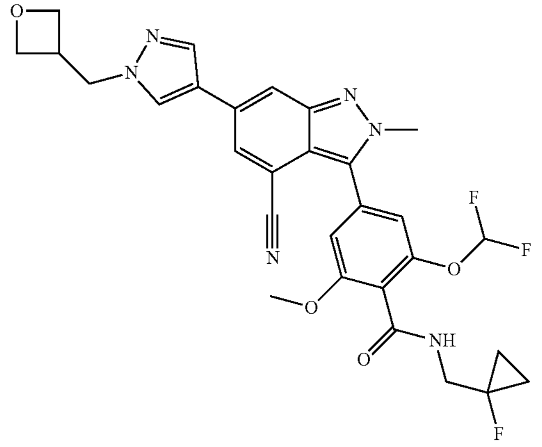 [SMILES: COc1cc(-c2c3c(C#N)cc(-c4cnn(CC5COC5)c4)cc3nn2C)cc(OC(F)F)c1C(=O)NCC1(F)CC1]

A mixture of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxybenzamide (126 mg) described in Reference Example 64, 4-bromo-1-(oxetan-3-ylmethyl)pyrazole (62 mg) described in Reference Example 3, a [1,1'-bis(diphenylphosphino)ferrocene]palladium(II) dichloride dichloromethane adduct (15 mg), tripotassium phosphate (80 mg), water (0.32 mL), and 1,4-dioxane (1.3 mL) was heated and stirred under a nitrogen atmosphere at 100 °C for 2 hours. After the reaction was completed, water was added to the reaction mixture, extraction was performed three times with chloroform, the organic layer was separated with Phase-Separator®, and then the organic layer was concentrated under reduced pressure. The resulting residue was purified by NH silica gel column chromatography (ethyl acetate:methanol=100:0 to 95:5) and silica gel column chromatography (ethyl acetate: methanol=100:0 to 90:10) to obtain the title compound (43 mg) as a white powder. MS(ESI)m/z:581.3 [M+H]+

Example 60: Synthesis of 2-[4-[3-[3-(difluoromethoxy)-4-[3-hydroxy-3-(trifluoromethyl)azetidin-1-carbonyl]-5-methoxyphenyl]-4-(difluoromethyl)-2-methylindazol-6-yl]pyrazol-1-yl]-N,N-dimethylacetamide

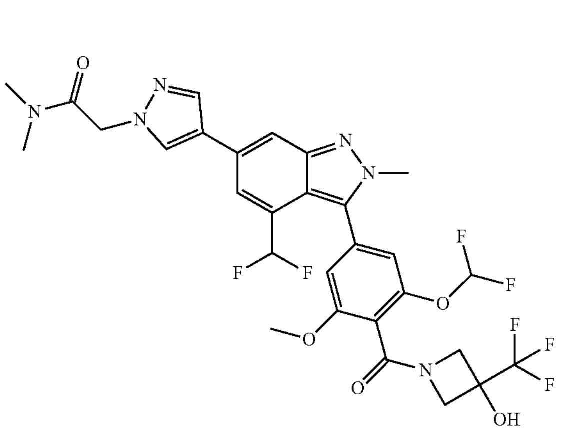 [SMILES: COc1cc(-c2c3c(C(F)F)cc(-c4cnn(CC(=O)N(C)C)c4)cc3nn2C)cc(OC(F)F)c1C(=O)N1CC(O)(C(F)(F)F)C1]

A mixture of [4-[6-bromo-4-(difluoromethyl)-2-methylindazol-3-yl]-2-(difluoromethoxy)-6-methoxyphenyl]-[3-hydroxy-3-(trifluoromethyl)azetidin-1-yl]methanone (75 mg) described in Reference Example 72, N,N-dimethyl-2-[4-(4,4,5,5-tetramethyl-1,3,2-dioxaborolan-2-yl)pyrazol-1-yl]acetamide (42 mg), a [1,1'-bis(diphenylphosphino)ferrocene]palladium(II) dichloride dichloromethane adduct (10 mg), potassium carbonate (35 mg), water (1.0 mL), and 1,4-dioxane (4.0 mL) was heated and stirred under a nitrogen atmosphere at 100 °C for 2 hours. After the reaction was completed, water was added to the reaction mixture, extraction was performed with chloroform, the organic layer was separated with Phase-Separator®, and then the organic layer was concentrated under reduced pressure. The resulting residue was purified by NH silica gel column chromatography (chloroform:methanol=100:0 to 95:5) and then suspended and washed using ethyl acetate to obtain the title compound (38 mg) as a gray powder. MS(ESI)m/z:673.0 [M+H]+

Example 61: Synthesis of 2-[4-[3-[3-(difluoromethoxy)-4-[3-(difluoromethyl)-3-hydroxyazetidin-1-carbonyl]-5-methoxyphenyl]-4-(difluoromethyl)-2-methylindazol-6-yl]pyrazol-1-yl]-N,N-dimethylacetamide

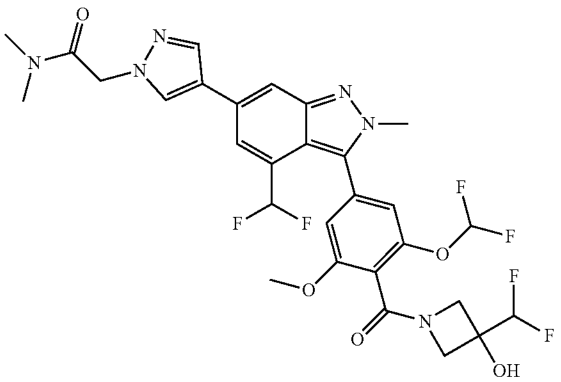 [SMILES: COc1cc(-c2c3c(C(F)F)cc(-c4cnn(CC(=O)N(C)C)c4)cc3nn2C)cc(OC(F)F)c1C(=O)N1CC(O)(C(F)F)C1]

A mixture of [4-[6-bromo-4-(difluoromethyl)-2-methylindazol-3-yl]-2-(difluoromethoxy)-6-methoxyphenyl]-[3-(difluoromethyl)-3-hydroxyazetidin-1-yl]methanone (75 mg) described in Reference Example 73, N,N-dimethyl-2-[4-(4,4,5,5-tetramethyl-1,3,2-dioxaborolan-2-yl)pyrazol-1-yl]acetamide (43 mg), a [1,1'-bis(diphenylphosphino)ferrocene]palladium(II) dichloride dichloromethane adduct (11 mg), potassium carbonate (36 mg), water (1.0 mL), and 1,4-dioxane (4.0 mL) was heated and stirred under a nitrogen atmosphere at 100 °C for 2 hours and 30 minutes. After the reaction was completed, water was added to the reaction mixture, extraction was performed with chloroform, the organic layer was separated with Phase-Separator®, and then the organic layer was concentrated under reduced pressure. The resulting residue was purified by NH silica gel column chromatography (ethyl acetate:methanol=100:0 to 90:10) and suspended and washed using diethyl ether to obtain the title compound (43 mg) as a colorless powder. MS(ESI)m/z:655.1 [M+H]+

Example 62: Synthesis of [2-(difluoromethoxy)-4-[4-(difluoromethoxy)-2-methyl-6-(1-methyltriazol-4-yl)indazol-3-yl]-6-methoxyphenyl]-[3-hydroxy-3-(trifluoromethyl)azetidin-1-yl]methanone

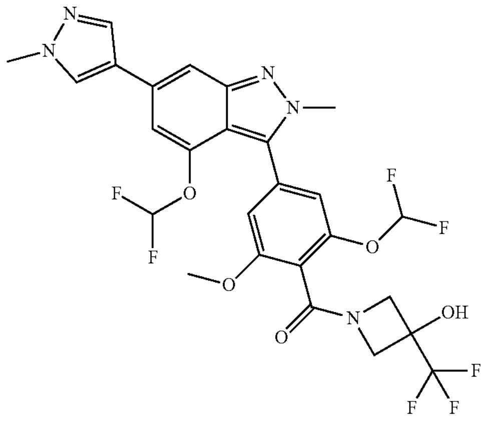 [SMILES: COc1cc(-c2c3c(OC(F)F)cc(-c4cnn(C)c4)cc3nn2C)cc(OC(F)F)c1C(=O)N1CC(O)(C(F)(F)F)C1]

2-(Difluoromethoxy)-4-[4-(difluoromethoxy)-2-methyl-6-(1-methyltriazol-4-yl)indazol-3-yl]-6-methoxybenzoic acid (55 mg) described in Reference Example 68 and 3-(trifluoromethyl)azetidin-3-ol hydrochloride (30 mg) were suspended in N,N-dimethylformamide (2.0 mL), N,N-diisopropylethylamine (77 μL) and HATU (63 mg) were added at room temperature, and the mixture was stirred for 2 hours. After the reaction was completed, water was added to the reaction solution, and extraction was performed with ethyl acetate. The organic layer was washed twice with saturated saline and separated with Phase-Separator®, and the organic layer was concentrated under reduced pressure. The residue was purified by NH silica gel column chromatography (chloroform:methanol=100:0 to 97:3 to 95:5) and then suspended and washed using diethyl ether to obtain the title compound (55 mg) as a colorless powder. MS(ESI)m/z: 619.2 [M+H]+

Example 63: Synthesis of [2-(difluoromethoxy)-4-[4-(difluoromethoxy)-2-methyl-6-(1-methyltriazol-4-yl)indazol-3-yl]-6-methoxyphenyl]-[3-(difluoromethyl)-3-hydroxyazetidin-1-yl]methanone

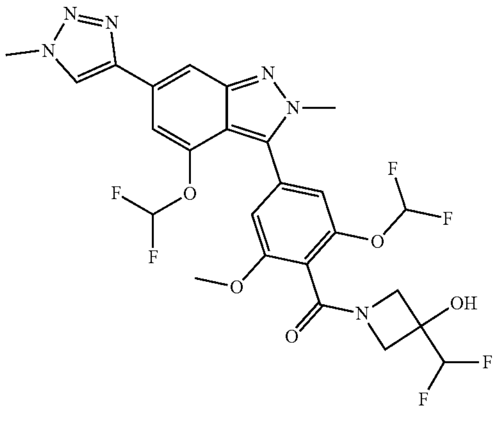 [SMILES: COc1cc(-c2c3c(OC(F)F)cc(-c4cn(C)nn4)cc3nn2C)cc(OC(F)F)c1C(=O)N1CC(O)(C(F)F)C1]

2-(Difluoromethoxy)-4-[4-(difluoromethoxy)-2-methyl-6-(1-methyltriazol-4-yl)indazol-3-yl]-6-methoxybenzoic acid (55 mg) described in Reference Example 68 and 3-(difluoromethyl)azetidin-3-ol hydrochloride (27 mg) were suspended in N,N-dimethylformamide (2.0 mL), N,N-diisopropylethylamine (77 μL) and HATU (63 mg) were added, and the mixture was stirred at room temperature for 2 hours. After the reaction was completed, water was added to the reaction solution, extraction was performed with ethyl acetate, and the resulting organic layer was washed twice with saturated saline. The organic layer was separated with Phase-Separator®, and the organic layer was concentrated under reduced pressure. The resulting residue was purified by NH silica gel column chromatography (chloroform: methanol=100:0 to 95:5) and suspended and washed using diethyl ether to obtain the title compound (51 mg) as a colorless powder. MS(ESI)m/z:601.2 [M+H]+

Example 64: Synthesis of [2-(difluoromethoxy)-4-[4-(difluoromethoxy)-2-methyl-6-(2-methyltriazol-4-yl)indazol-3-yl]-6-methoxyphenyl]-[3-(difluoromethyl)-3-hydroxyazetidin-1-yl]methanone

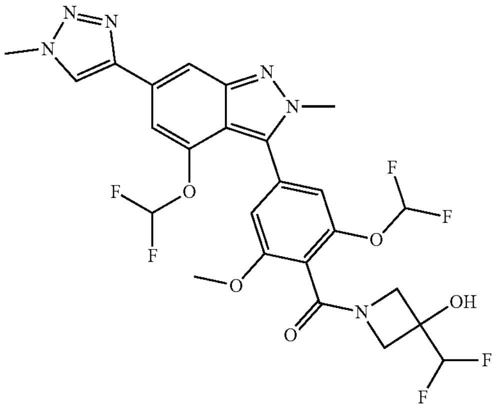 [SMILES: COc1cc(-c2c3c(OC(F)F)cc(-c4cn(C)nn4)cc3nn2C)cc(OC(F)F)c1C(=O)N1CC(O)(C(F)F)C1]

2-(Difluoromethoxy)-4-[4-(difluoromethoxy)-2-methyl-6-(2-methyltriazol-4-yl)indazol-3-yl]-6-methoxybenzoic acid (60 mg) described in Reference Example 70 and 3-(difluoromethyl)azetidin-3-ol hydrochloride (29 mg) were suspended in N,N-dimethylformamide (2.0 mL), N,N-diisopropylethylamine (84 μL) and HATU (69 mg) were added at room temperature, and the mixture was stirred for 2 hours. After the reaction was completed, water was added to the reaction solution, extraction was performed with ethyl acetate, and the resulting organic layer was washed twice with saturated saline. The organic layer was separated with Phase-Separator®, and the organic layer was concentrated under reduced pressure. The resulting residue was purified by NH silica gel column chromatography (chloroform: methanol=100:0 to 97:3) and silica gel column chromatography (chloroform:methanol=100:0 to 95:5) to obtain the title compound (56 mg) as a colorless powder. MS(ESI)m/z:601.2 [M+H]+

Example 65: Synthesis of 3-[4-[3-[3-(difluoromethoxy)-4-[3-hydroxy-3-(trifluoromethyl)azetidin-1-carbonyl]-5-methoxyphenyl]-4-(difluoromethyl)-2-methylindazol-6-yl]pyrazol-1-yl]-N,N-dimethylpropanamide

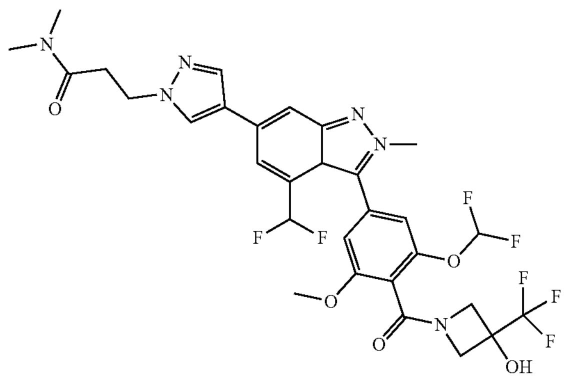

A mixture of N,N-dimethyl-3-[4-(4,4,5,5-tetramethyl-1,3,2-dioxaborolan-2-yl)pyrazol-1-yl]propanamide (35 mg) described in Reference Example 81, [4-[6-bromo-4-(difluoromethyl)-2-methylindazol-3-yl]-2-(difluoromethoxy)-6-methoxyphenyl]-[3-hydroxy-3-(trifluoromethyl)azetidin-1-yl]methanone (65 mg) described in Reference Example 72, a [1,1'-bis(diphenylphosphino)ferrocene]palladium(II) dichloride dichloromethane adduct (8.8 mg), potassium carbonate (30 mg), water (1.0 mL), and 1,4-dioxane (4.0 mL) was heated and stirred under a nitrogen atmosphere at 100 °C for 1 hour and 30 minutes. After the reaction was completed, water was added to the reaction mixture, extraction was performed with chloroform, the organic layer was separated with Phase-Separator®, and then the organic layer was concentrated under reduced pressure. The resulting residue was purified by NH silica gel column chromatography (ethyl acetate:methanol=100:0 to 90:10) and suspended and washed using diethyl ether to obtain the title compound (32 mg) as a light yellow powder.

MS(ESI)m/z:687.1 [M+H]+

Example 66: Synthesis of [2-(difluoromethoxy)-4-[4-(difluoromethyl)-2-methyl-6-[1-(2-methylsulfonylethyl)pyrazol-4-yl)indazol-3-yl]-6-methoxyphenyl]-[3-(difluoromethyl)-3-hydroxyazetidin-1-yl]methanone

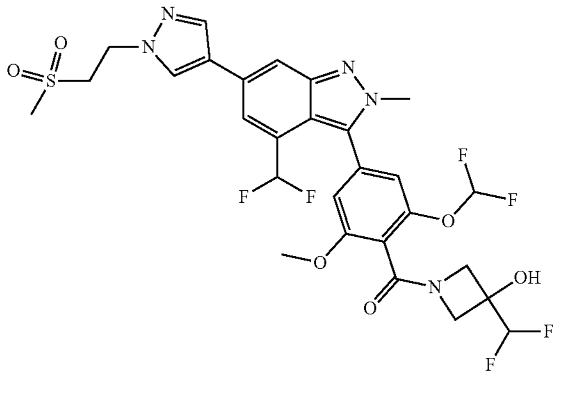 [SMILES: COc1cc(-c2c3c(C(F)F)cc(-c4cnn(CCS(C)(=O)=O)c4)cc3nn2C)cc(OC(F)F)c1C(=O)N1CC(O)(C(F)F)C1]

A mixture of [4-[6-bromo-4-(difluoromethyl)-2-methylindazol-3-yl]-2-(difluoromethoxy)-6-methoxyphenyl]-[3-(difluoromethyl)-3-hydroxyazetidin-1-yl]methanone (50 mg) described in Reference Example 73, 1-(2-methylsulfonylethyl)-4-(4,4,5,5-tetramethyl-1,3,2-dioxaborolan-2-yl)pyrazole (31 mg), potassium carbonate (36 mg), a [1,1'-bis(diphenylphosphino)ferrocene]palladium(II) dichloride dichloromethane adduct (7.0 mg), 1,4-dioxane (1.0 mL), and water (0.20 mL) was heated and stirred under a nitrogen atmosphere at 100 °C for 2 hours. After the reaction was completed, magnesium sulfate was added to the reaction mixture, the mixture was stirred for several minutes, and then insoluble matter was removed by filtration. The residue obtained by concentrating the filtrate under reduced pressure was sequentially purified by preparative HPLC (10 mM aqueous ammonium carbonate solution-acetonitrile) and silica gel column chromatography (chloroform:methanol=100:0 to 90:10) to obtain the title compound (48 mg) as a colorless powder. MS(ESI)m/z:676.3 [M+H]+

Example 67: Synthesis of [2-(difluoromethoxy)-4-[4-(difluoromethyl)-6-[1-[(2S)-2-hydroxypropyl]pyrazol-4-yl]-2-methylindazol-3-yl]-6-methoxyphenyl]-[3-(difluoromethyl)-3-hydroxyazetidin-1-yl]methanone

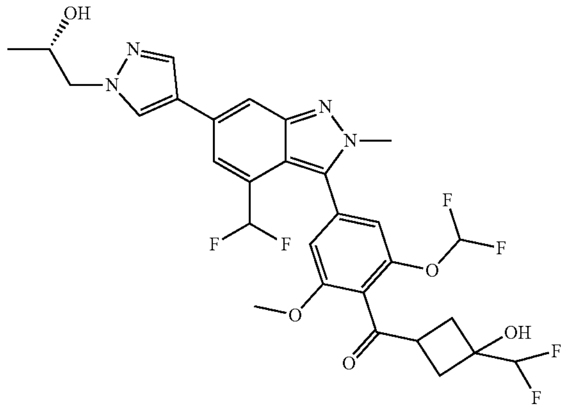 [SMILES: COc1cc(-c2c3c(C(F)F)cc(-c4cnn(C[C@H](C)O)c4)cc3nn2C)cc(OC(F)F)c1C(=O)C1CC(O)(C(F)F)C1]

A mixture of [4-[6-bromo-4-(difluoromethyl)-2-methylindazol-3-yl]-2-(difluoromethoxy)-6-methoxyphenyl]-[3-(difluoromethyl)-3-hydroxyazetidin-1-yl]methanone (100 mg) described in Reference Example 73, bis(pinacolato)diboron (48 mg), potassium acetate (51 mg), a [1,1'-bis(diphenylphosphino)ferrocene]palladium(II) dichloride dichloromethane adduct (14 mg), and 1,4-dioxane (1.0 mL) was heated and stirred under a nitrogen atmosphere at 100 °C for 2 hours. (2S)-1-(4-Iodopyrazol-1-yl)propan-2-ol (52 mg), potassium carbonate (71 mg), water (0.20 mL), and a [1,1'-bis(diphenylphosphino)ferrocene]palladium(II) dichloride dichloromethane adduct (14 mg) were added to the reaction mixture that was allowed to cool to room temperature, and the mixture was heated and stirred under a nitrogen atmosphere at 100 °C. again. After 2 hours, (2S)-1-(4-iodopyrazol-1-yl)propan-2-ol (52 mg) and a [1,1'-bis(diphenylphosphino)ferrocene]palladium(II) dichloride dichloromethane adduct (14 mg) were added to the reaction mixture that was once allowed to cool to room temperature, and the mixture was further heated and stirred under a nitrogen atmosphere at 100 °C. overnight. After the reaction was completed, ethyl acetate and magnesium sulfate were added to the reaction mixture, the mixture was stirred for several minutes, and then insoluble matter was removed by filtration. The residue obtained by concentrating the filtrate under reduced pressure was sequentially purified by preparative HPLC (10 mM aqueous ammonium carbonate solution-acetonitrile) and silica gel column chromatography (chloroform:methanol=100:0 to 90:10) to obtain the title compound (22 mg) as a colorless powder. MS(ESI)m/z: 628.1 [M+H]+

Example 68: Synthesis of [2-(difluoromethoxy)-4-[4-(difluoromethyl)-2-methyl-6-(1H-pyrazol-4-yl)indazol-3-yl]-6-methoxyphenyl]-[3-hydroxy-3-(trifluoromethyl)azetidin-1-yl]methanone

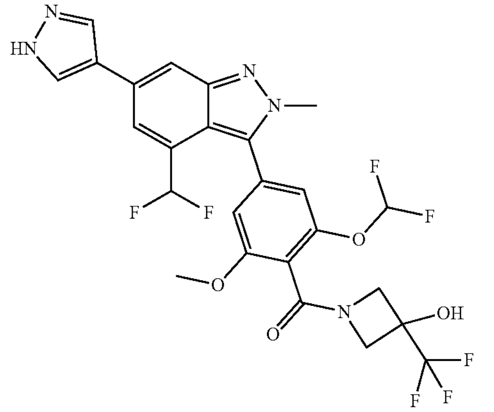 [SMILES: COc1cc(-c2c3c(C(F)F)cc(-c4cn[nH]c4)cc3nn2C)cc(OC(F)F)c1C(=O)N1CC(O)(C(F)(F)F)C1]

A mixture of [4-[6-bromo-4-(difluoromethyl)-2-methyl-indazol-3-yl]-2-(difluoromethoxy)-6-methoxyphenyl]-[3-hydroxy-3-(trifluoromethyl)azetidin-1-yl]methanone (100 mg) described in Reference Example 72, 1-tetrahydropyran-2-yl-4-(4,4,5,5-tetramethyl-1,3,2-dioxaborolan-2-yl)pyrazole (70 mg), potassium carbonate (46 mg), a [1,1'-bis(diphenylphosphino)ferrocene]palladium(II) dichloride dichloromethane adduct (14 mg), 1,4-dioxane (3.0 mL), and water (0.30 mL) was heated and stirred under a nitrogen atmosphere at 100 °C for 1 hour. After the reaction was completed, water was added to the reaction mixture, and extraction was performed with chloroform. The organic layer was separated with Phase-Separator® and concentrated under reduced pressure, and then the organic layer was purified by NH silica gel column chromatography (chloroform:methanol=100:0 to 97:3). Dichloromethane (1.0 mL) and TFA (1.0 mL) were added to the resulting residue, and the mixture was stirred under a nitrogen atmosphere at room temperature for 4 hours. After the reaction was completed, the reaction solution was concentrated under reduced pressure, and then an azeotropic treatment was performed twice using toluene. The resulting crude product was purified by preparative HPLC (10 mM aqueous ammonium carbonate solution-acetonitrile) and then suspended and washed using diethyl ether to obtain the title compound (60 mg) as a colorless powder. MS(ESI)m/z:588.1 [M+H]+

Example 69: Synthesis of [2-(difluoromethoxy)-4-[4-(difluoromethyl)-2-methyl-6-(1H-pyrazol-4-yl)indazol-3-yl]-6-methoxyphenyl]-[3-(difluoromethyl)-3-hydroxyazetidin-1-yl]methanone

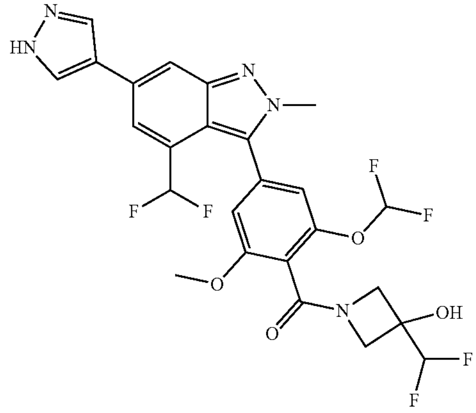 [SMILES: COc1cc(-c2c3c(C(F)F)cc(-c4cn[nH]c4)cc3nn2C)cc(OC(F)F)c1C(=O)N1CC(O)(C(F)F)C1]

A mixture of [4-[6-bromo-4-(difluoromethyl)-2-methyl-indazol-3-yl]-2-(difluoromethoxy)-6-methoxyphenyl]-[3-(difluoromethyl)-3-hydroxyazetidin-1-yl]methanone (100 mg) described in Reference Example 73, 1-tetrahydropyran-2-yl-4-(4,4,5,5-tetramethyl-1,3,2-dioxaborolan-2-yl)pyrazole (72 mg), potassium carbonate (47 mg), a [1,1'-bis(diphenylphosphino)ferrocene]palladium(II) dichloride dichloromethane adduct (14 mg), 1,4-dioxane (3.0 mL), and water (0.30 mL) was heated and stirred under a nitrogen atmosphere at 100 °C for 3 hours. After the reaction was completed, water was added to the reaction mixture, and extraction was performed with chloroform. The organic layer was separated with Phase-Separator® and concentrated under reduced pressure, and then the organic layer was purified by NH silica gel column chromatography (chloroform:methanol=100:0 to 97:3). Dichloromethane (2.0 mL) and TFA (1.0 mL) were added to the resulting residue, and the mixture was stirred under a nitrogen atmosphere at room temperature for 3 hours. After the reaction was completed, the reaction solution was concentrated under reduced pressure, and then an azeotropic treatment was performed twice using toluene. The resulting residue was purified by preparative HPLC (10 mM aqueous ammonium carbonate solution-acetonitrile) and then suspended and washed using diethyl ether. The thus obtained crude product was purified by NH silica gel column chromatography (chloroform:methanol=100:0 to 95:5) and then suspended and washed using diethyl ether again to obtain the title compound (43 mg) as a colorless powder. MS(ESI)m/z: 570.2 [M+H]+

Example 70: Synthesis of 3-[3-(difluoromethoxy)-4-[3-hydroxy-3-(trifluoromethyl)azetidin-1-carbonyl]-5-methoxyphenyl]-2-methyl-6-(1H-pyrazol-4-yl)indazole-4-carbonitrile

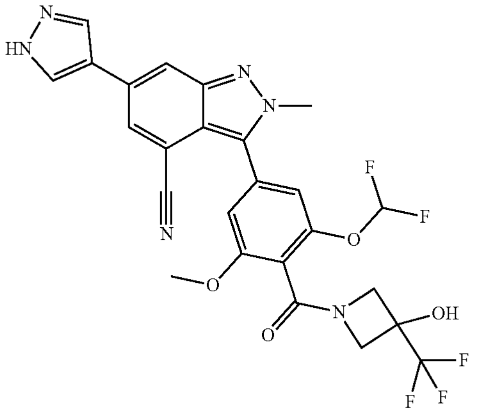 [SMILES: COc1cc(-c2c3c(C#N)cc(-c4cn[nH]c4)cc3nn2C)cc(OC(F)F)c1C(=O)N1CC(O)(C(F)(F)F)C1]

A mixture of 6-bromo-3-[3-(difluoromethoxy)-4-[3-hydroxy-3-(trifluoromethyl)azetidine-1-carbonyl]-5-methoxyphenyl]-2-methylindazole-4-carbonitrile (100 mg) described in Reference Example 56, 1-tetrahydropyran-2-yl-4-(4,4,5,5-tetramethyl-1,3,2-dioxaborolan-2-yl)pyrazole (73 mg), potassium carbonate (48 mg), a [1,1'-bis(diphenylphosphino)ferrocene]palladium(II) dichloride dichloromethane adduct (14 mg), 1,4-dioxane (3.0 mL), and water (0.30 mL) was heated and stirred under a nitrogen atmosphere at 100 °C for 3 hours. After the reaction was completed, water was added to the reaction mixture, and extraction was performed with chloroform. The organic layer was separated with Phase-Separator® and concentrated under reduced pressure, the organic layer was purified by NH silica gel column chromatography (chloroform:methanol=100:0 to 97:3), and the fractions containing the target product were concentrated under reduced pressure. Dichloromethane (2.0 mL) and TFA (1.0 mL) were added to the resulting residue, and the mixture was stirred under a nitrogen atmosphere at room temperature for 3 hours. After the reaction was completed, the reaction solution was concentrated under reduced pressure, and then an azeotropic treatment was performed twice using toluene. The resulting residue was purified by preparative HPLC (10 mM aqueous ammonium carbonate solution-acetonitrile) and then suspended and washed using diethyl ether. The thus obtained crude product was purified by NH silica gel column chromatography (chloroform:methanol=100:0 to 95:5) and then suspended and washed using diethyl ether again to obtain the title compound (35 mg) as a colorless powder. MS(ESI) m/z:563.2 [M+H]+

Example 71: Synthesis of [2-(difluoromethoxy)-4-[4-(difluoromethyl)-6-[1-[(2R)-2-hydroxypropyl]pyrazol-4-yl]-2-methylindazol-3-yl]-6-methoxyphenyl]-[3-hydroxy-3-(trifluoromethyl)azetidin-1-yl]methanone

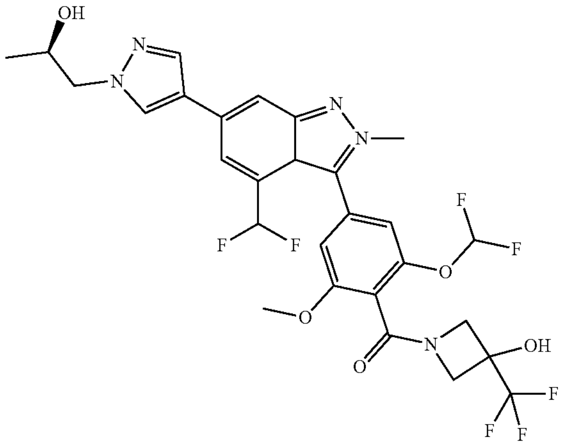

A mixture of [2-(difluoromethoxy)-4-[4-(difluoromethyl)-2-methyl-6-(4,4,5,5-tetramethyl-1,3,2-dioxaborolan-2-yl)indazol-3-yl]-6-methoxyphenyl]-[3-hydroxy-3-(trifluoromethyl)azetidin-1-yl]methanone (50 mg) described in Reference Example 98, (2R)-1-(4-iodopyrazol-1-yl)propan-2-ol (23 mg), potassium carbonate (21 mg), tetrakis(triphenylphosphine)palladium (0) (8.9 mg), 1,4-dioxane (3.0 mL), and water (0.30 mL) was stirred under a nitrogen atmosphere and microwave irradiation at 110 °C. for 1 hour. After the reaction was completed, water was added to the reaction mixture, and extraction was performed with chloroform. The organic layer separated using Phase-Separator® was concentrated under reduced pressure, and the resulting crude product was purified by NH silica gel column chromatography (chloroform:methanol=100:0 to 95:5) and then suspended and washed using diethyl ether to obtain the title compound (6.7 mg) as a colorless powder. MS(ESI)m/z: 646.3 [M+H]+

Example 72: Synthesis of [2-(difluoromethoxy)-4-[4-(difluoromethyl)-6-[1-[(2S)-2-hydroxypropyl]pyrazol-4-yl]-2-methylindazol-3-yl]-6-methoxyphenyl]-[3-hydroxy-3-(trifluoromethyl)azetidin-1-yl]methanone

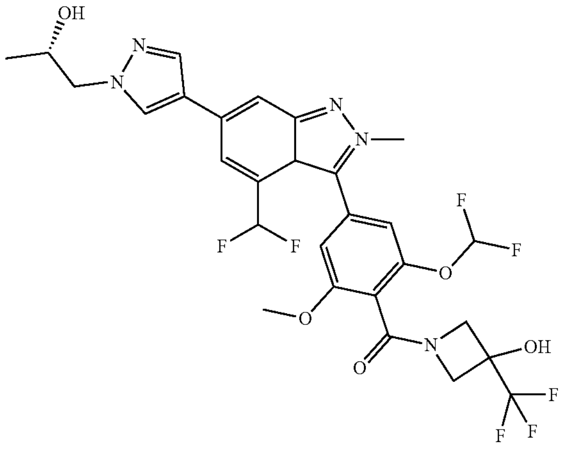

A mixture of [2-(difluoromethoxy)-4-[4-(difluoromethyl)-2-methyl-6-(4,4,5,5-tetramethyl-1,3,2-dioxaborolan-2-yl)indazol-3-yl]-6-methoxyphenyl]-[3-hydroxy-3-(trifluoromethyl)azetidin-1-yl]methanone (50 mg) described in Reference Example 98, (2S)-1-(4-iodopyrazol-1-yl)propan-2-ol (29 mg), potassium carbonate (21 mg), a [1,1'-bis(diphenylphosphino)ferrocene]palladium(II) dichloride dichloromethane adduct (6.3 mg), 1,4-dioxane (2.0 mL), and water (0.20 mL) was heated and stirred under a nitrogen atmosphere at 100 °C for 3 hours. After the reaction was completed, water was added to the reaction mixture, and extraction was performed with chloroform. The organic layer separated using Phase-Separator® was concentrated under reduced pressure, and the resulting crude product was purified by NH silica gel column chromatography (chloroform:methanol=100:0 to 95:5) and then suspended and washed using diethyl ether to obtain the title compound (8.4 mg) as a yellow powder.

MS(ESI)m/z:646.3 [M+H]+

Example 73: Synthesis of 4-[4-cyano-2-methyl-6-(1-methylpyrazol-4-yl)indazol-3-yl]-2-(difluoromethoxy)-6-methoxybenzamide

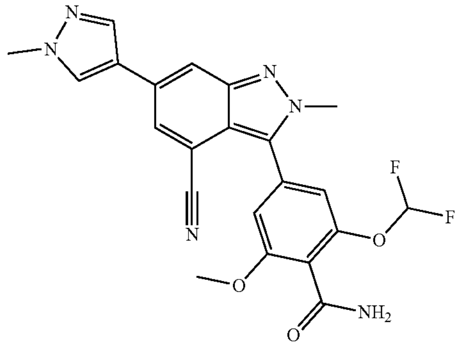

4-[4-Cyano-2-methyl-6-(1-methylpyrazol-4-yl)indazol-3-yl]-2-(difluoromethoxy)-6-methoxybenzoic acid (50 mg) described in Reference Example 42 was dissolved in N,N-dimethylformamide (1.1 mL), a 0.4 N ammonia-dioxane solution (0.40 mL), N,N-diisopropylethylamine (38 μL), and HATU (63 mg) were added, and then the mixture was stirred at room temperature. After 4 hours, a 0.4 N ammonia-dioxane solution (0.40 mL), N,N-diisopropylethylamine (38 μL), and HATU (63 mg) were added, and the mixture was further stirred for 4 hours. After the reaction was completed, the reaction mixture was diluted with DMSO and then purified by preparative HPLC (10 mM aqueous ammonium carbonate solution-acetonitrile) to obtain the title compound (39 mg) as a white powder. MS(ESI)m/z:453.2 [M+H]+

Example 74: Synthesis of 4-[4-cyano-6-[1-[(1,1-dioxothietan-3-yl)methyl]pyrazol-4-yl]-2-methylindazol-3-yl]-2-(difluoromethoxy)-N-[(1-fluorocyclopropyl)methyl]-6-methoxybenzamide

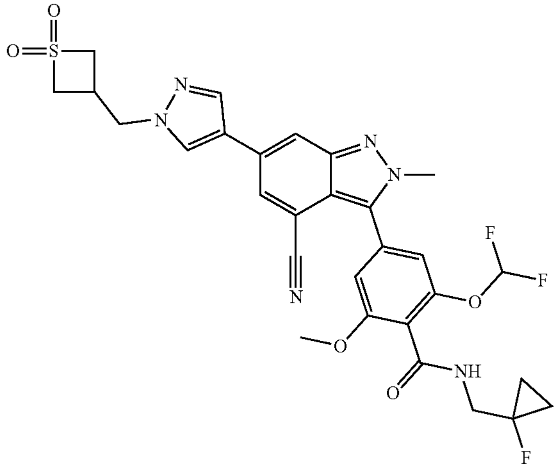 [SMILES: COc1cc(-c2c3c(C#N)cc(-c4cnn(CC5CS(=O)(=O)C5)c4)cc3nn2C)cc(OC(F)F)c1C(=O)NCC1(F)CC1]

A mixture of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxybenzamide (70 mg) described in Reference Example 64, 3-[(4-bromopyrazol-1-yl)methyl] thietane 1,1-dioxide (144 mg) described in Reference Example 84, potassium carbonate (58 mg), tetrakis(triphenylphosphine)palladium (0) (12 mg), 1,4-dioxane (1.0 mL), and water (0.26 mL) was stirred under a nitrogen atmosphere and microwave irradiation at 110 °C for 1.5 hours. After the reaction was completed, water was added to the reaction mixture, and extraction was performed twice with chloroform. The organic layer was separated with Phase-Separator®, concentrated under reduced pressure, and then sequentially purified by preparative HPLC (10 mM aqueous ammonium carbonate solution-acetonitrile) and silica gel column chromatography (ethyl acetate:methanol=100:0 to 90:10) to obtain the title compound (11 mg) as a white powder. MS(ESI)m/z:629.1 [M+H]+

Example 75: Synthesis of 4-[4-cyano-2-methyl-6-[1-(1,3-oxazol-2-ylmethyl)pyrazol-4-yl]indazol-3-yl]-2-(difluoromethoxy)-N-[(1-fluorocyclopropyl)methyl]-6-methoxybenzamide

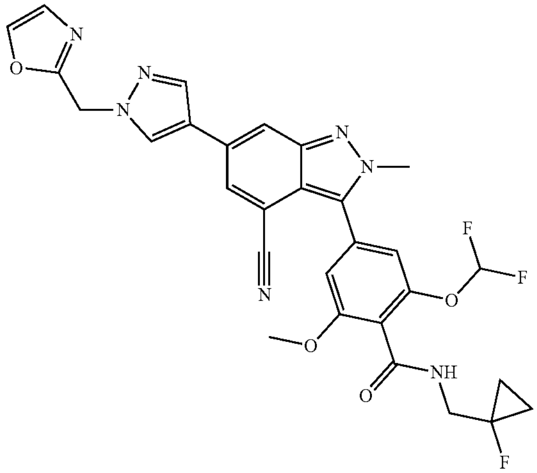 [SMILES: COc1cc(-c2c3c(C#N)cc(-c4cnn(Cc5ncco5)c4)cc3nn2C)cc(OC(F)F)c1C(=O)NCC1(F)CC1]

A mixture of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxybenzamide (170 mg) described in Reference Example 64, 2-[(4-bromopyrazol-1-yl)methyl]-1,3-oxazole (87 mg) described in Reference Example 4, 1,4-dioxane (2.5 mL) a 1 N aqueous tripotassium phosphate solution (0.51 mL), and a [1,1'-bis(diphenylphosphino)ferrocene]palladium(II) dichloride dichloromethane adduct (21 mg) was heated and stirred under a nitrogen atmosphere at 100 °C for 2 hours. After the reaction was completed, water was added to the reaction mixture, and extraction was performed with chloroform. The organic layer separated using Phase-Separator® was concentrated under reduced pressure, sequentially purified by NH silica gel column chromatography (hexane:ethyl acetate=80:20 to 20:80) and preparative HPLC (10 mM aqueous ammonium carbonate solution-acetonitrile), and then suspended and washed using diethyl ether to obtain the title compound (35 mg) as a white powder. MS(ESI)m/z: 592.4 [M+H]+

Example 76: Synthesis of 4-[4-cyano-6-[1-[(3-fluorooxetan-3-yl)methyl]pyrazol-4-yl]-2-methylindazol-3-yl]-2-(difluoromethoxy)-N-[(1-fluorocyclopropyl)methyl]-6-methoxybenzamide

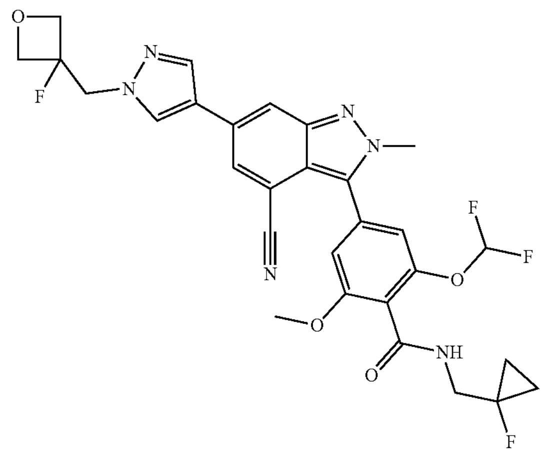 [SMILES: COc1cc(-c2c3c(C#N)cc(-c4cnn(CC5(F)COC5)c4)cc3nn2C)cc(OC(F)F)c1C(=O)NCC1(F)CC1]

A mixture of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxybenzamide (80 mg) described in Reference Example 64, 4-bromo-1-[(3-fluorooxetan-3-yl)methyl]pyrazole (42 mg) described in Reference Example 5, potassium carbonate (33 mg), a [1,1'-bis(diphenylphosphino)ferrocene]palladium(II) dichloride dichloromethane adduct (9.8 mg), 1,4-dioxane (3.0 mL), and water (0.30 mL) was heated and stirred under a nitrogen atmosphere at 100 °C for 2 hours. After the reaction was completed, water was added to the reaction mixture, and extraction was performed with chloroform. The organic layer separated with Phase-Separator® was concentrated under reduced pressure, sequentially purified by NH silica gel column chromatography (hexane:ethyl acetate=50:50 to 0:100) and silica gel column chromatography (chloroform:methanol=100:0 to 97:3), and then suspended and washed using diethyl ether. The resulting crude product was purified by preparative HPLC (10 mM aqueous ammonium carbonate solution-acetonitrile) and then suspended and washed using diethyl ether again to obtain the title compound (13 mg) as a colorless powder. MS(ESI)m/z:599.3 [M+H]+

Example 77: Synthesis of 3-(8-methoxy-4-methyl-1-oxo-3,4-dihydro-2H-isoquinolin-6-yl)-2-methyl-6-(1-methylpyrazol-4-yl)indazol-4-carbonitrile

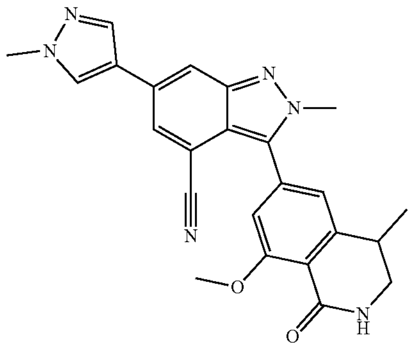

3-[8-Methoxy-2-[(4-methoxyphenyl)methyl]-4-methyl-1-oxo-3,4-dihydroisoquinolin-6-yl]-2-methyl-6-(1-methylpyrazol-4-yl)indazole-4-carbonitrile (47 mg) described in Reference Example 94 was dissolved in TFA (2.0 mL) and then stirred under microwave irradiation at 100 °C for 9 hours. After the reaction was completed, the reaction mixture was concentrated under reduced pressure, a saturated aqueous sodium bicarbonate solution was added, and then extraction was performed with chloroform. The residue obtained by concentrating the separated organic layer under reduced pressure was sequentially purified by NH silica gel column chromatography (ethyl acetate:methanol=100:0 to 95:5) and silica gel column chromatography (chloroform:methanol=95:5 to 85:15) to obtain the title compound (28 mg) as a light yellow powder. MS(ESI)m/z:427.3 [M+H]+

Example 78: Synthesis of 4-[4-cyano-2-methyl-6-[1-(oxolan-3-ylmethyl)pyrazol-4-yl]indazol-3-yl]-2-(difluoromethoxy)-N-[(1-fluorocyclopropyl)methyl]-6-methoxybenzamide

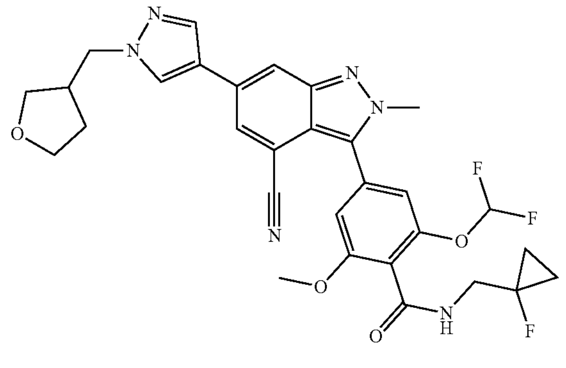 [SMILES: COc1cc(-c2c3c(C#N)cc(-c4cnn(CC5CCOC5)c4)cc3nn2C)cc(OC(F)F)c1C(=O)NCC1(F)CC1]

A mixture of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxy-benzamide (70 mg) described in Reference Example 64, 4-iodo-1-(oxolan-3-ylmethyl)pyrazole (41 mg) described in Reference Example 6, 1,4-dioxane (2.0 mL) a 1 N aqueous tripotassium phosphate solution (0.25 mL), and a [1,1'-bis(diphenylphosphino)ferrocene]palladium(II) dichloride dichloromethane adduct (10 mg) was heated and stirred under a nitrogen atmosphere at 100 °C for 3 hours. After the reaction was completed, ethyl acetate and magnesium sulfate were added to the reaction mixture, the mixture was stirred for several minutes, and then insoluble matter was removed by filtration. The residue obtained by concentrating the filtrate under reduced pressure was sequentially purified by preparative HPLC (10 mM aqueous ammonium carbonate solution-acetonitrile) and column chromatography (ethyl acetate:methanol=100:0 to 90:10) using an NH silica gel column and a silica gel column in series to obtain the title compound (25 mg) as a colorless powder. MS(ESI)m/z: 595.2 [M+H]+

Example 79: Synthesis of 4-[4-cyano-2-methyl-6-[1-(oxolan-2-ylmethyl)pyrazol-4-yl]indazol-3-yl]-2-(difluoromethoxy)-N-[(1-fluorocyclopropyl)methyl]-6-methoxybenzamide

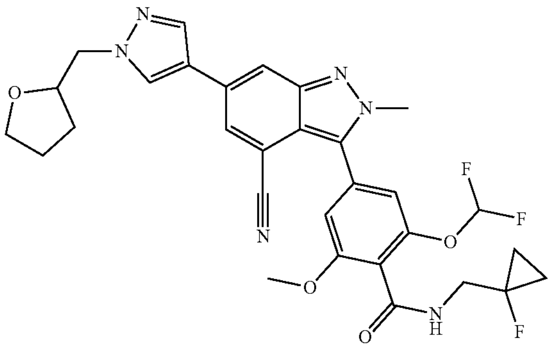 [SMILES: COc1cc(-c2c3c(C#N)cc(-c4cnn(CC5CCCO5)c4)cc3nn2C)cc(OC(F)F)c1C(=O)NCC1(F)CC1]

A mixture of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxy-benzamide (70 mg) described in Reference Example 64, 4-iodo-1-(oxolan-2-ylmethyl)pyrazole (41 mg) described in Reference Example 7, 1,4-dioxane (2.0 mL) a 1 N aqueous tripotassium phosphate solution (0.25 mL), and a [1,1'-bis(diphenylphosphino)ferrocene]palladium(II) dichloride dichloromethane adduct (10 mg) was heated and stirred under a nitrogen atmosphere at 100 °C for 3 hours. After the reaction was completed, ethyl acetate and magnesium sulfate were added to the reaction mixture, the mixture was stirred for several minutes, and then insoluble matter was removed by filtration. The residue obtained by concentrating the filtrate under reduced pressure was sequentially purified by preparative HPLC (10 mM aqueous ammonium carbonate solution-acetonitrile) and silica gel column chromatography (ethyl acetate:methanol=100:0 to 92:8) to obtain the title compound (23 mg) as a colorless powder. MS(ESI)m/z:595.2 [M+H]+

Example 80: Synthesis of 4-[4-cyano-2-methyl-6-[1-(oxetan-2-ylmethyl)pyrazol-4-yl]indazol-3-yl]-2-(difluoromethoxy)-N-[(1-fluorocyclopropyl)methyl]-6-methoxybenzamide

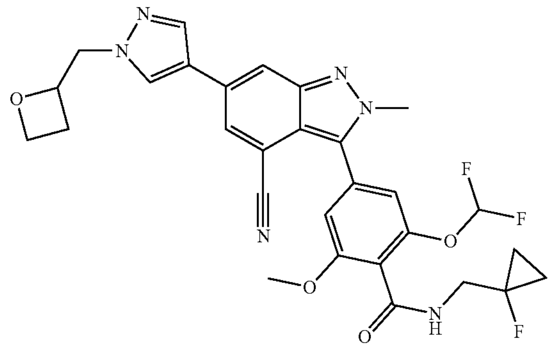 [SMILES: COc1cc(-c2c3c(C#N)cc(-c4cnn(CC5CCO5)c4)cc3nn2C)cc(OC(F)F)c1C(=O)NCC1(F)CC1]

A mixture of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxy-benzamide (70 mg) described in Reference Example 64, 4-iodo-1-(oxetan-2-ylmethyl)pyrazole (39 mg), 1,4-dioxane (2.0 mL) a 1 N aqueous tripotassium phosphate solution (0.25 mL), and a [1,1'-bis(diphenylphosphino)ferrocene]palladium(II) dichloride dichloromethane adduct (10 mg) was heated and stirred under a nitrogen atmosphere at 100 °C for 3 hours. After the reaction was completed, ethyl acetate and magnesium sulfate were added to the reaction mixture, the mixture was stirred for several minutes, and then insoluble matter was removed by filtration. The residue obtained by concentrating the filtrate under reduced pressure was sequentially purified by preparative HPLC (10 mM aqueous ammonium carbonate solution-acetonitrile) and column chromatography (ethyl acetate:methanol=100:0 to 90:10) using an NH silica gel column and a silica gel column in series to obtain the title compound (22 mg) as a colorless powder. MS(ESI)m/z:581.2. [M+H]+

Example 81: Synthesis of 4-[4-cyano-6-[1-[(1,1-dioxothietan-2-yl)methyl]pyrazol-4-yl]-2-methylindazol-3-yl]-2-(difluoromethoxy)-N-[(1-fluorocyclopropyl)methyl]-6-methoxybenzamide

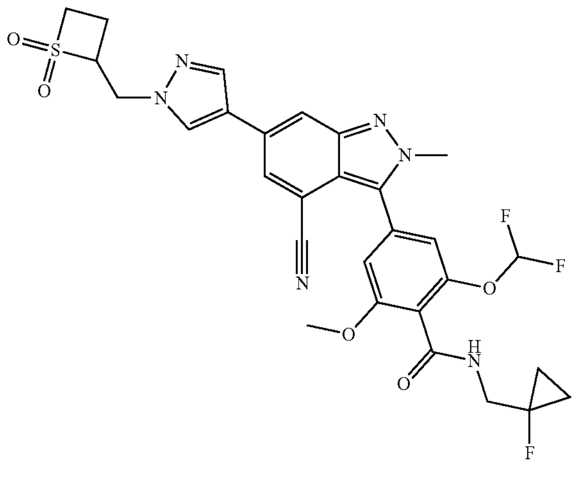 [SMILES: COc1cc(-c2c3c(C#N)cc(-c4cnn(CC5CCS5(=O)=O)c4)cc3nn2C)cc(OC(F)F)c1C(=O)NCC1(F)CC1]

A mixed solution of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxybenzamide (55 mg) described in Reference Example 64, 2-[(4-iodopyrazol-1-yl)methyl] thietane 1,1-dioxide (30 mg) described in Reference Example 107, 1,4-dioxane (0.87 mL), a 1 N aqueous tripotassium phosphate solution (0.17 mL), and a [1,1'-bis(diphenylphosphino)ferrocene]palladium(II) dichloride dichloromethane adduct (7.1 mg) was heated and stirred under a nitrogen atmosphere at 100 °C for 1.5 hours. After the reaction was completed, water was added to the reaction mixture, and extraction was performed with chloroform. The organic layer was separated with Phase-Separator®, concentrated under reduced pressure, and then sequentially purified by preparative HPLC (10 mM aqueous ammonium carbonate solution-acetonitrile) and NH silica gel column chromatography (ethyl acetate:methanol=100:0 to 90:10) to obtain the title compound (23 mg) as a white powder. MS(ESI)m/z:629.3 [M+H]+

Example 82: Synthesis of 4-[4-cyano-6-[1-[(1,1-dioxothiolan-2-yl)methyl]pyrazol-4-yl]-2-methylindazol-3-yl]-2-(difluoromethoxy)-N-[(1-fluorocyclopropyl)methyl]-6-methoxybenzamide

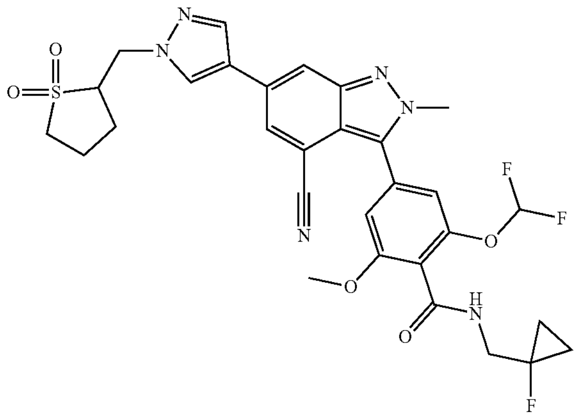 [SMILES: COc1cc(-c2c3c(C#N)cc(-c4cnn(CC5CCCS5(=O)=O)c4)cc3nn2C)cc(OC(F)F)c1C(=O)NCC1(F)CC1]

A mixed solution of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxybenzamide (60 mg) described in Reference Example 64, 2-[(4-iodopyrazol-1-yl)methyl]thiolane=1,1-dioxide (37 mg) described in Reference Example 108, 1,4-dioxane (0.95 mL) a 1 N aqueous tripotassium phosphate solution (0.19 mL), and a [1,1'-bis(diphenylphosphino)ferrocene]palladium(II) dichloride dichloromethane adduct (7.7 mg) was heated and stirred under a nitrogen atmosphere at 100 °C for 1.5 hours. After the reaction was completed, water was added to the reaction mixture, and extraction was performed with chloroform. The organic layer was separated with Phase-Separator®, concentrated under reduced pressure, and then sequentially purified by preparative HPLC (10 mM aqueous ammonium carbonate solution-acetonitrile) and NH silica gel column chromatography (ethyl acetate:methanol=100:0 to 95:5) to obtain the title compound (25 mg) as a white powder. MS(ESI)m/z:643.3 [M+H]+

Example 83: Synthesis of 4-[4-cyano-6-[1-[(1-hydroxycyclopropyl)methyl]pyrazol-4-yl]-2-methylindazol-3-yl]-2-(difluoromethoxy)-N-[(1-fluorocyclopropyl)methyl]-6-methoxybenzamide

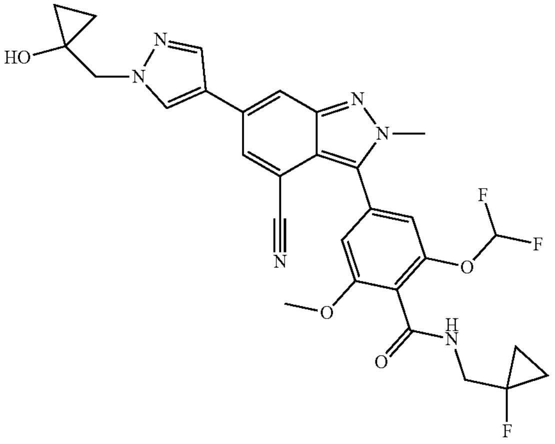 [SMILES: COc1cc(-c2c3c(C#N)cc(-c4cnn(CC5(O)CC5)c4)cc3nn2C)cc(OC(F)F)c1C(=O)NCC1(F)CC1]

A mixed solution of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxybenzamide (60 mg) described in Reference Example 64, 1-[(4-bromopyrazol-1-yl)methyl] cyclopropan-1-ol (25 mg) synthesized by the method described in WO 2022/081626 A, 1,4-dioxane (0.95 mL), a 1 N aqueous tripotassium phosphate solution (0.19 mL), and a [1,1'-bis(diphenylphosphino)ferrocene]palladium(II) dichloride dichloromethane adduct (7.7 mg) was heated and stirred under a nitrogen atmosphere at 100 °C for 1.5 hours. Thereafter, 1-[(4-bromopyrazol-1-yl)methyl] cyclopropan-1-ol (21 mg) was added to the reaction mixture, and the mixture was stirred under microwave irradiation at 120 °C for 40 minutes. After the reaction was completed, ethyl acetate and magnesium sulfate were added to the reaction mixture, the mixture was stirred for several minutes, and then insoluble matter was removed by filtration. The residue obtained by concentrating the filtrate under reduced pressure was purified by column chromatography (hexane:ethyl acetate=50:50 to 0:100 to ethyl acetate:methanol=90:10) using an NH silica gel column and a silica gel column in series. The resulting crude product was purified by NH silica gel column chromatography (chloroform:methanol=100:0 to 90:10) again to obtain the title compound (10 mg) as a white powder. MS(ESI)m/z:581.1 [M+H]+

Example 84: Synthesis of 4-[4-cyano-6-[1-[(1-hydroxycyclobutyl)methyl]pyrazol-4-yl]-2-methylindazol-3-yl]-2-(difluoromethoxy)-N-[(1-fluorocyclopropyl)methyl]-6-methoxybenzamide

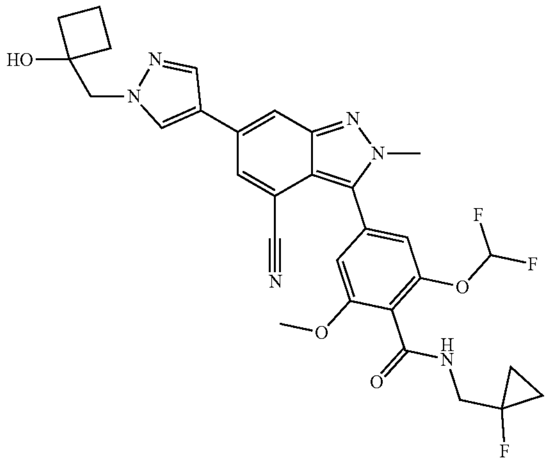 [SMILES: COc1cc(-c2c3c(C#N)cc(-c4cnn(CC5(O)CCC5)c4)cc3nn2C)cc(OC(F)F)c1C(=O)NCC1(F)CC1]

A mixed solution of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxybenzamide (70 mg) described in Reference Example 64, 1-[(4-iodopyrazol-1-yl)methyl]cyclobutan-1-ol (41 mg), 1,4-dioxane (0.61 mL), a 1 N aqueous tripotassium phosphate solution (0.37 mL), and a [1,1'-bis(diphenylphosphino)ferrocene]palladium(II) dichloride dichloromethane adduct (10 mg) was heated and stirred under a nitrogen atmosphere at 100 °C for 2 hours. After the reaction was completed, ethyl acetate and magnesium sulfate were added to the reaction mixture, the mixture was stirred for several minutes, and then insoluble matter was removed by filtration. The residue obtained by concentrating the filtrate under reduced pressure was purified by NH silica gel column chromatography (hexane:ethyl acetate=50:50 to 0:100 to ethyl acetate:methanol=100:0 to 90:10) to obtain the title compound (33 mg) as a light brown powder. MS(ESI)m/z: 595.2 [M+H]+

Example 85: Synthesis of 4-[4-cyano-2-methyl-6-[1-(2-morpholin-4-ylethyl)pyrazol-4-yl]indazol-3-yl]-2-(difluoromethoxy)-6-methoxy-N-[rel-(1R)-2,2-difluorocyclopropyl]methyl]benzamide

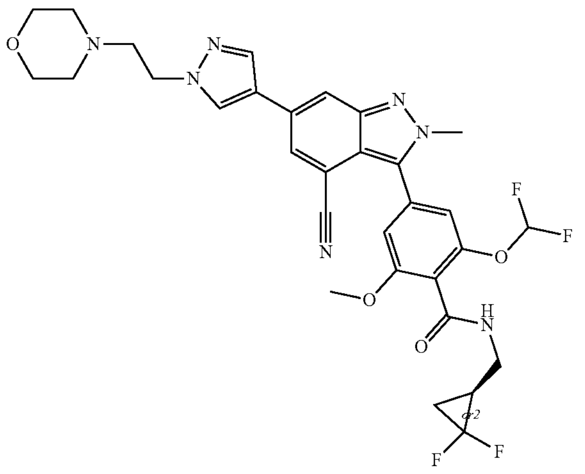 [SMILES: COc1cc(-c2c3c(C#N)cc(-c4cnn(CCN5CCOCC5)c4)cc3nn2C)cc(OC(F)F)c1C(=O)NC[C@@H]1CC1(F)F]

A mixed solution of 4-(6-bromo-4-cyano-2-methylindazol-3-yl)-2-(difluoromethoxy)-6-methoxy-N-[[rel-(1R)-2,2-difluorocyclopropyl]methyl]benzamide (60 mg) described in Reference Example 85, 4-(2-(4-(4,4,5,5-tetramethyl-1,3,2-dioxaborolan-2-yl)-1H-pyrazol-1-yl)ethyl) morpholine (41 mg), 1,4-dioxane (1.1 mL), a 1 N aqueous potassium carbonate solution (0.33 mL), and a [1,1'-bis(diphenylphosphino)ferrocene]palladium(II) dichloride dichloromethane adduct (9.1 mg) was heated and stirred under a nitrogen atmosphere at 100 °C for 2 hours. After the reaction was completed, ethyl acetate and magnesium sulfate were added to the reaction mixture, the mixture was stirred for several minutes, and then insoluble matter was removed by filtration. The residue obtained by concentrating the filtrate under reduced pressure was sequentially purified by preparative HPLC (10 mM aqueous ammonium carbonate solution-acetonitrile) and NH silica gel column chromatography (hexane:ethyl acetate=50:50 to 0:100) to obtain the title compound (53 mg) as a white powder. MS(ESI)m/z:642.3 [M+H]+

Example 86: Synthesis of 4-[4-cyano-6-[1-(2-hydroxy-2-methylpropyl)pyrazol-4-yl]-2-methylindazol-3-yl]-2-(difluoromethoxy)-6-methoxy-N-[[rel-(1R)-2,2-difluorocyclopropyl]methyl]benzamide

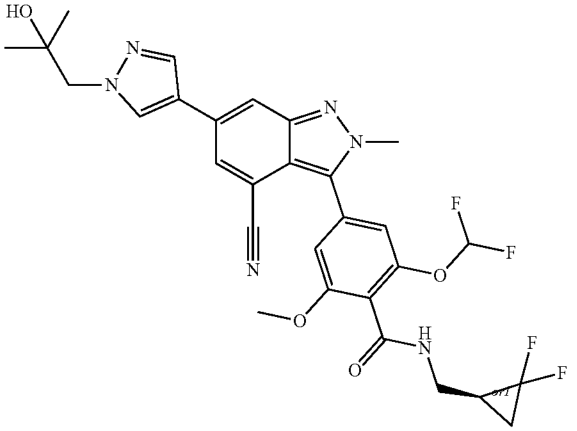 [SMILES: COc1cc(-c2c3c(C#N)cc(-c4cnn(CC(C)(C)O)c4)cc3nn2C)cc(OC(F)F)c1C(=O)NC[C@@H]1CC1(F)F]

A mixed solution of 4-(6-bromo-4-cyano-2-methylindazol-3-yl)-2-(difluoromethoxy)-6-methoxy-N-[rel-(1R)-2,2-difluorocyclopropyl]methyl]benzamide (50 mg) described in Reference Example 85, 2-methyl-1-[4-(4,4,5,5-tetramethyl-1,3,2-dioxaborolan-2-yl)pyrazol-1-yl]propan-2-ol (27 mg), potassium carbonate (26 mg), a [1,1'-bis(diphenylphosphino)ferrocene]palladium(II) dichloride dichloromethane adduct (7.5 mg), water (0.15 mL), and 1,4-dioxane (0.62 mL) was heated and stirred under a nitrogen atmosphere at 100 °C for 1 hour. After the reaction was completed, water was added to the reaction mixture, and extraction was performed with chloroform. The organic layer was separated with Phase-Separator®, concentrated under reduced pressure, and then sequentially purified by NH silica gel column chromatography (ethyl acetate:methanol=100:0 to 95:5) and preparative HPLC (10 mM aqueous ammonium carbonate solution-acetonitrile) to obtain the title compound (25 mg) as a white powder. MS(ESI)m/z:601.4 [M+H]+

Example 87: Synthesis of 2-(difluoromethoxy)-4-[4-(difluoromethyl)-2-methyl-6-(1-methylpyrazol-4-yl)indazol-3-yl]-6-methoxybenzamide

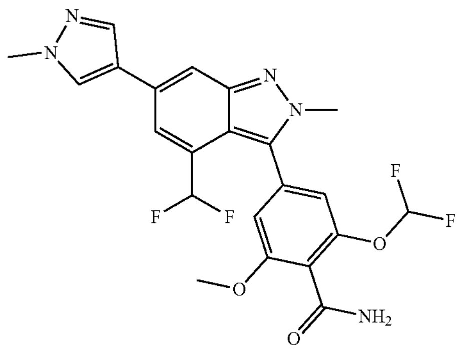 [SMILES: COc1cc(-c2c3c(C(F)F)cc(-c4cnn(C)c4)cc3nn2C)cc(OC(F)F)c1C(N)=O]

To an N,N-dimethylformamide (1.0 mL) solution of 2-(difluoromethoxy)-4-[4-(difluoromethyl)-2-methyl-6-(1-methylpyrazol-4-yl)indazol-3-yl]-6-methoxybenzoic acid (50 mg) described in Reference Example 46, a 0.4 N ammonia-dioxane solution (0.80 mL), HATU (60 mg), and N,N-diisopropylethylamine (72 µL) were added, and the mixture was stirred at room temperature. After 7 hours, a 0.4 N ammonia-dioxane solution (0.80 mL) and HATU (60 mg) were added to the reaction mixture, and the mixture was further stirred at room temperature overnight. After the reaction was completed, the reaction mixture was diluted with dimethyl sulfoxide and then purified by preparative HPLC (10 mM aqueous ammonium carbonate solution-acetonitrile), and the resulting crude product was suspended and washed with diethyl ether to obtain the title compound (22 mg) as a light brown powder. MS(ESI)m/z:478.0 [M+H]+

Example 88: Synthesis of 2-methyl-6-(1-methylpyrazol-4-yl)-3-[rel-(4R)-8-methoxy-4-methyl-1-oxo-3,4-dihydro-2H-isoquinolin-6-yl]indazole-4-carbonitrile

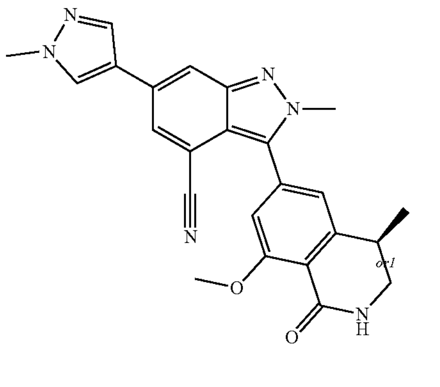

A mixture of an isomer (23 mg) that eluted earlier under chiral HPLC conditions as described in the experimental section of 6-bromo-2-methyl-3-[rel-(4R)-8-methoxy-4-methyl-1-oxo-3,4-dihydro-2H-isoquinolin-6-yl]indazole-4-carbonitrile described in Reference Example 97, 1-methyl-4-(4,4,5,5-tetramethyl-1,3,2-dioxaborolan-2-yl)pyrazole (11 mg), potassium carbonate (13 mg), a [1,1'-bis(diphenylphosphino)ferrocene]palladium(II) dichloride dichloromethane adduct (3.9 mg), water (80 µL), and 1,4-dioxane (0.32 mL) was heated and stirred under a nitrogen atmosphere at 100 °C for 2 hours. After the reaction was completed, water was added to the reaction mixture, and extraction was performed with chloroform. The organic layer was separated with Phase-Separator®, concentrated under reduced pressure, and then sequentially purified by NH silica gel column chromatography (ethyl acetate:methanol=100:0 to 90:10) and preparative HPLC (10 mM aqueous ammonium carbonate solution-acetonitrile) to obtain the title compound (17 mg) as a white powder. MS(ESI)m/z:427.3 [M+H]+

Example 89: Synthesis of N-[(1R)-2,2-difluorocyclopropyl]-2-(difluoromethoxy)-4-[4-(difluoromethyl)-6-[1-[(2S)-2-hydroxypropyl]pyrazol-4-yl]-2-methylindazol-3-yl]-6-methoxybenzamide

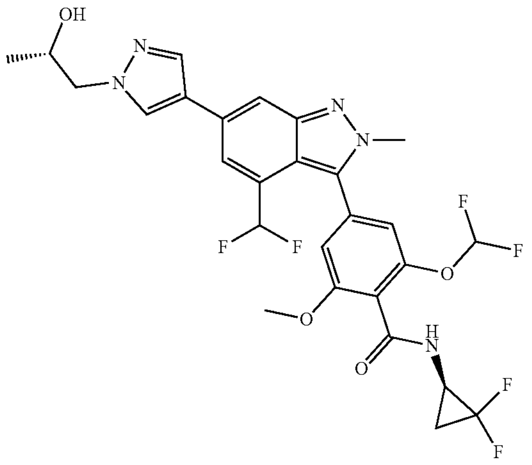 [SMILES: COc1cc(-c2c3c(C(F)F)cc(-c4cnn(C[C@H](C)O)c4)cc3nn2C)cc(OC(F)F)c1C(=O)N[C@@H]1CC1(F)F]

A mixed solution of 4-[6-bromo-4-(difluoromethyl)-2-methylindazol-3-yl]-N-[(1R)-2,2-difluorocyclopropyl]-2-(difluoromethoxy)-6-methoxybenzamide (51 mg) described in Reference Example 83, (2S)-1-[4-(4,4,5,5-tetramethyl-1,3,2-dioxaborolan-2-yl)pyrazol-1-yl]propan-2-ol (111 mg) synthesized by the method described in WO 2022/081627 A, 1,4-dioxane (1.1 mL), a 1 N aqueous tripotassium phosphate solution (0.44 mL), and a [1,1'-bis(diphenylphosphino)ferrocene]palladium(II) dichloride dichloromethane adduct (7.2 mg) was heated and stirred under a nitrogen atmosphere at 40 °C for 17 hours. After the reaction was completed, water and chloroform were added to the reaction mixture, and the mixture was stirred vigorously for several minutes. The organic layer was separated with Phase-Separator®, concentrated under reduced pressure, and then sequentially purified by NH silica gel column chromatography (hexane:ethyl acetate=50:50 to 0:100) and silica gel column chromatography (ethyl acetate:methanol=100:0 to 95:5) to obtain the title compound (34 mg) as a white powder. MS(ESI)m/z:598.1 [M+H]+

Example 90: Synthesis of 4-[4-cyano-6-[1-(3-hydroxy-3-methylbutyl)pyrazol-4-yl]-2-methylindazol-3-yl]-2-(difluoromethoxy)-N-[(1-fluorocyclopropyl)methyl]-6-methoxybenzamide

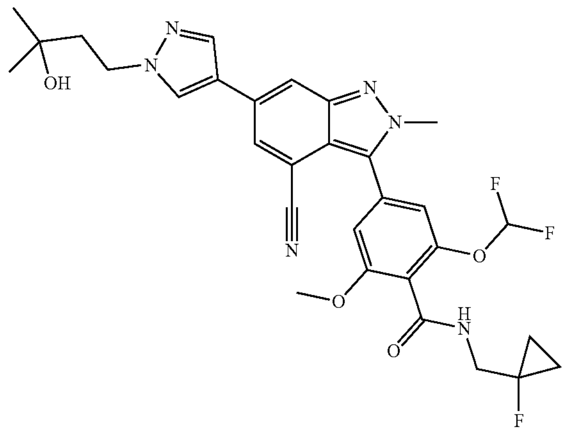 [SMILES: COc1cc(-c2c3c(C#N)cc(-c4cnn(CCC(C)(C)O)c4)cc3nn2C)cc(OC(F)F)c1C(=O)NCC1(F)CC1]

A mixed solution of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxybenzamide (90 mg) described in Reference Example 64, 4-(4-iodopyrazol-1-yl)-2-methylbutan-2-ol (48 mg) described in Reference Example 101, 1,4-dioxane (1.4 mL), a 1 N aqueous tripotassium phosphate solution (0.28 mL), and a [1,1'-bis(diphenylphosphino)ferrocene]palladium(II) dichloride dichloromethane adduct (12 mg) was heated and stirred under a nitrogen atmosphere at 100 °C for 2 hours. After the reaction was completed, water and chloroform were added to the reaction mixture, and the mixture was stirred vigorously for several minutes. The organic layer was separated with Phase-Separator®, concentrated under reduced pressure, and then sequentially purified by NH silica gel column chromatography (hexane:ethyl acetate=30:70 to 0:100) and column chromatography (chloroform:methanol=100:0 to 95:5) using an NH silica gel column and a silica gel column in series to obtain the title compound (34 mg) as a white powder. MS(ESI)m/z:597.5 [M+H]+

Example 91: Synthesis of 4-[4-cyano-6-[1-[(cis-3-hydroxycyclobutyl)methyl]pyrazol-4-yl]-2-methylindazol-3-yl]-2-(difluoromethoxy)-N-[(1-fluorocyclopropyl)methyl]-6-methoxybenzamide

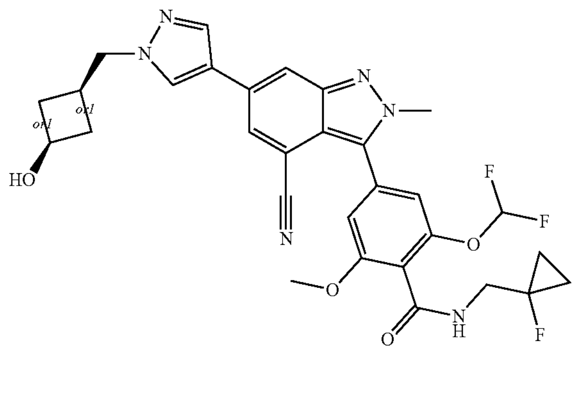 [SMILES: COc1cc(-c2c3c(C#N)cc(-c4cnn(C[C@H]5C[C@@H](O)C5)c4)cc3nn2C)cc(OC(F)F)c1C(=O)NCC1(F)CC1]

A mixed solution of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxybenzamide (90 mg) described in Reference Example 64, cis-3-[(4-iodopyrazol-1-yl)methyl]cyclobutan-1-ol (53 mg) described in Reference Example 103, 1,4-dioxane (0.79 mL), a 1 N aqueous tripotassium phosphate solution (0.47 mL), and a [1,1'-bis(diphenylphosphino)ferrocene]palladium(II) dichloride dichloromethane adduct (13 mg) was heated and stirred under a nitrogen atmosphere at 100 °C for 2 hours. After the reaction was completed, ethyl acetate and magnesium sulfate were added to the reaction mixture, the mixture was stirred for several minutes, and then insoluble matter was removed by filtration. The residue obtained by concentrating the filtrate under reduced pressure was sequentially purified by column chromatography (ethyl acetate:methanol=100:0 to 90:10) using an NH silica gel column and a silica gel column in series to obtain the title compound (39 mg) as a colorless powder.

MS(ESI)m/z:595.4 [M+H]+

Example 92: Synthesis of 4-[4-cyano-6-[1-[(3R)-3-hydroxybutyl]pyrazol-4-yl]-2-methylindazol-3-yl]-2-(difluoromethoxy)-N-[(1-fluorocyclopropyl)methyl]-6-methoxybenzamide

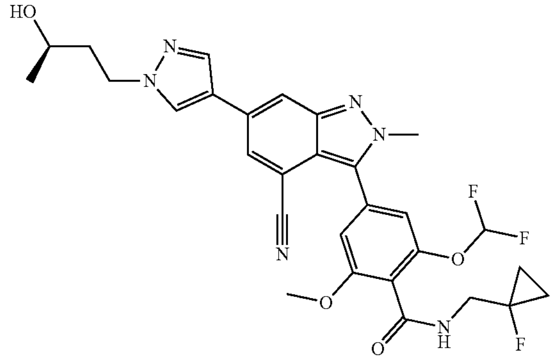 [SMILES: COc1cc(-c2c3c(C#N)cc(-c4cnn(CC[C@@H](C)O)c4)cc3nn2C)cc(OC(F)F)c1C(=O)NCC1(F)CC1]

A mixture of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxybenzamide (90 mg) described in Reference Example 64, (2R)-4-(4-iodopyrazol-1-yl) butan-2-ol (50 mg) described in Reference Example 104, 1,4-dioxane (0.79 mL), a 1 N aqueous tripotassium phosphate solution (0.47 mL), and a [1,1'-bis(diphenylphosphino)ferrocene]palladium(II) dichloride dichloromethane adduct (13 mg) was heated and stirred under a nitrogen atmosphere at 100 °C for 2 hours. After the reaction was completed, ethyl acetate and magnesium sulfate were added to the reaction mixture, the mixture was stirred for several minutes, and then insoluble matter was removed by filtration. The residue obtained by concentrating the filtrate under reduced pressure was sequentially purified by column chromatography (ethyl acetate:methanol=100:0 to 90:10) using an NH silica gel column and a silica gel column in series to obtain the title compound (36 mg) as a light yellow powder. MS(ESI)m/z:583.4 [M+H]+

Example 93: Synthesis of 4-[4-cyano-6-[1-[(2S)-2-hydroxybutyl]pyrazol-4-yl]-2-methylindazol-3-yl]-2-(difluoromethoxy)-N-[(1-fluorocyclopropyl)methyl]-6-methoxybenzamide

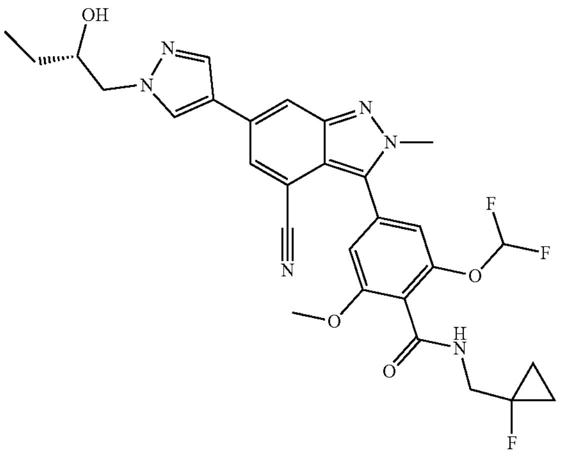 [SMILES: CC[C@H](O)Cn1cc(-c2cc(C#N)c3c(-c4cc(OC)c(C(=O)NCC5(F)CC5)c(OC(F)F)c4)n(C)nc3c2)cn1]

A mixed solution of 4-(6-bromo-4-cyano-2-methylindazol-3-yl)-2-(difluoromethoxy)-N-[(1-fluorocyclopropyl)methyl]-6-methoxybenzamide (50 mg) described in Reference Example 63, (2S)-1-[4-(4,4,5,5-tetramethyl-1,3,2-dioxaborolan-2-yl)pyrazol-1-yl]butan-2-ol (64 mg) described in Reference Example 109, 1,4-dioxane (0.96 mL), a 1 N aqueous potassium carbonate solution (0.29 mL), and a [1,1'-bis(diphenylphosphino)ferrocene]palladium(II) dichloride dichloromethane adduct (7.8 mg) was heated and stirred under a nitrogen atmosphere at 100 °C for 2 hours. After the reaction was completed, water and chloroform were added to the reaction mixture, and the mixture was stirred vigorously for several minutes. The organic layer was separated with Phase-Separator®, concentrated under reduced pressure, and then sequentially purified by preparative HPLC (10 mM aqueous ammonium carbonate solution-acetonitrile) and column chromatography (hexane:ethyl acetate=30:70 to 0:100 to ethyl acetate:methanol=95:5) using a silica gel column and an NH silica gel column in series to obtain the title compound (43 mg) as a white powder. MS(ESI)m/z:583.2 [M+H]+

Example 94: Synthesis of 4-[4-cyano-6-[1-[(2S)-2-hydroxypropyl]pyrazol-4-yl]-2-methylindazol-3-yl]-N-[(1R)-2,2-difluorocyclopropyl]-2-(difluoromethoxy)-6-methoxybenzamide

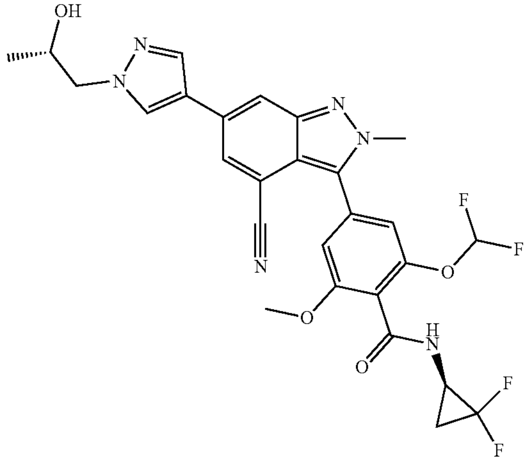 [SMILES: COc1cc(-c2c3c(C#N)cc(-c4cnn(C[C@H](C)O)c4)cc3nn2C)cc(OC(F)F)c1C(=O)N[C@@H]1CC1(F)F]

A mixture of 4-(6-bromo-4-cyano-2-methylindazol-3-yl)-N-[(1R)-2,2-difluorocyclopropyl]-2-(difluoromethoxy)-6-methoxybenzamide (120 mg) described in Reference Example 82, (2S)-1-[4-(4,4,5,5-tetramethyl-1,3,2-dioxaborolan-2-yl)pyrazol-1-yl]propan-2-ol (222 mg) synthesized by the method described in WO 2022/081627 A, 1,4-dioxane (2.2 mL), a 1 N aqueous tripotassium phosphate solution (1.1 mL), and a [1,1'-bis(diphenylphosphino)ferrocene]palladium(II) dichloride dichloromethane adduct (18 mg) was heated and stirred under a nitrogen atmosphere at 40 °C. overnight. After the reaction was completed, water was added to the reaction mixture, and extraction was performed three times with chloroform. The organic layer was separated with Phase-Separator®, concentrated under reduced pressure, and then sequentially purified by NH silica gel column chromatography (hexane:ethyl acetate=70:30 to 0:100) and silica gel column chromatography (ethyl acetate:methanol=100:0 to 90:10). The resulting crude product was suspended and washed with diethyl ether to obtain the title compound (40 mg) as a white powder. MS(ESI)m/z:573.1 [M+H]+

Example 95: Synthesis of 4-[4-cyano-6-[1-[(2S)-2-hydroxypropyl]pyrazol-4-yl]-2-methylindazol-3-yl]-N-[(1R*)-2,2-difluorocyclopropyl]methyl]-2-(difluoromethoxy)-6-methoxybenzamide

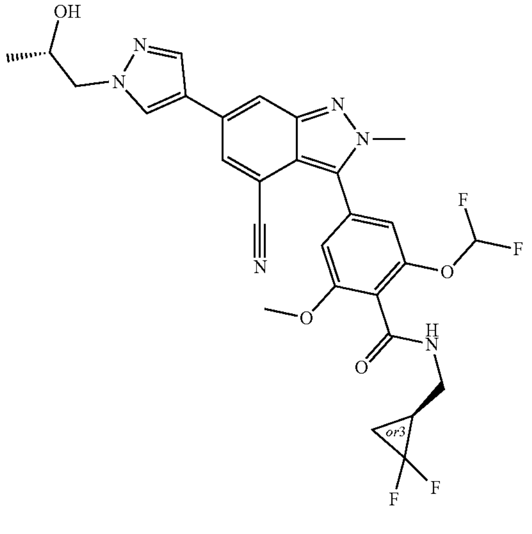 [SMILES: COc1cc(-c2c3c(C#N)cc(-c4cnn(C[C@H](C)O)c4)cc3nn2C)cc(OC(F)F)c1C(=O)NC[C@@H]1CC1(F)F]

A mixture of 4-(6-bromo-4-cyano-2-methylindazol-3-yl)-2-(difluoromethoxy)-6-methoxy-N-[[rel-(1R)-2,2-difluorocyclopropyl]methyl]benzamide (80 mg) described in Reference Example 85, (2S)-1-[4-(4,4,5,5-tetramethyl-1,3,2-dioxaborolan-2-yl)pyrazol-1-yl]propan-2-ol (56 mg) synthesized by the method described in WO 2022/081627 A, 1,4-dioxane (1.5 mL), a 1 N aqueous tripotassium phosphate solution (0.30 mL), and a [1,1'-bis(diphenylphosphino)ferrocene]palladium(II) dichloride dichloromethane adduct (12 mg) was heated and stirred under a nitrogen atmosphere at 100 °C. After 2 hours, (2S)-1-[4-(4,4,5,5-tetramethyl-1,3,2-dioxaborolan-2-yl)pyrazol-1-yl]propan-2-ol (56 mg) synthesized by the method described in WO 2022/081627 A and a [1,1'-bis(diphenylphosphino)ferrocene]palladium(II) dichloride dichloromethane adduct (12 mg) were added to the reaction mixture, and the mixture was further heated and stirred at 100 °C for 1 hour. After the reaction was completed, water was added to the reaction mixture, and extraction was performed twice with chloroform. The organic layer was separated with Phase-Separator®, concentrated under reduced pressure, and then sequentially purified by NH silica gel column chromatography (hexane:ethyl acetate=70:30 to 0:100) and preparative HPLC (10 mM aqueous ammonium carbonate solution-acetonitrile). The resulting crude product was suspended and washed with diethyl ether to obtain the title compound (15 mg) as a gray powder. MS(ESI)m/z:587.1 [M+H]+

Example 96: Synthesis of 4-[4-cyano-2-methyl-6-(1-propylpyrazol-4-yl)indazol-3-yl]-2-(difluoromethoxy)-6-methoxybenzamide

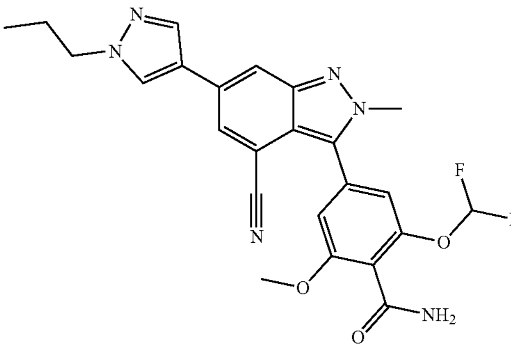

A mixture of 4-(6-bromo-4-cyano-2-methylindazol-3-yl)-2-(difluoromethoxy)-6-methoxybenzamide (80 mg) described in Reference Example 86, (1-propylpyrazol-4-yl) boronic acid (26 mg), potassium carbonate (42 mg), a [1,1'-bis(diphenylphosphino)ferrocene]palladium(II) dichloride dichloromethane adduct (12 mg), water (0.25 mL), and 1,4-dioxane (1.0 mL) was heated and stirred under a nitrogen atmosphere at 100 °C for 2 hours. After the reaction was completed, ethyl acetate and sodium sulfate were added to the reaction mixture, the mixture was stirred for several minutes, and then insoluble matter was removed by filtration. The residue obtained by concentrating the filtrate under reduced pressure was sequentially purified by NH silica gel column chromatography (hexane:ethyl acetate=70:30 to 0:100) and preparative HPLC (10 mM aqueous ammonium carbonate solution-acetonitrile). The resulting crude product was suspended and washed with diethyl ether to obtain the title compound (33 mg) as a white powder. MS(ESI)m/z:481.1 [M+H]+

Example 97: Synthesis of 4-[4-cyano-6-[1-[(2S)-2-hydroxy-2-phenylethyl]pyrazol-4-yl]-2-methylindazol-3-yl]-2-(difluoromethoxy)-N-[(1-fluorocyclopropyl)methyl]-6-methoxybenzamide

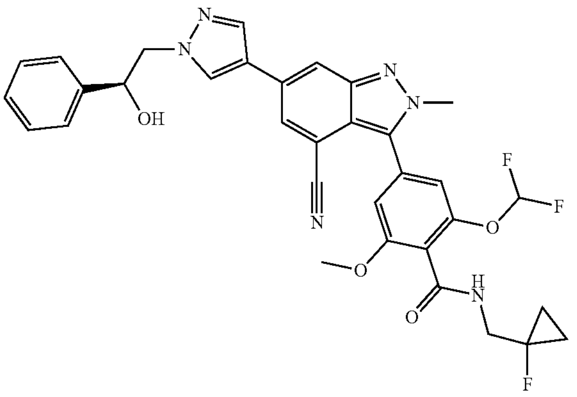 [SMILES: COc1cc(-c2c3c(C#N)cc(-c4cnn(C[C@@H](O)c5ccccc5)c4)cc3nn2C)cc(OC(F)F)c1C(=O)NCC1(F)CC1]

A mixture of 4-(4,4,5,5-tetramethyl-1,3,2-dioxaborolan-2-yl)-1H-pyrazole (60 mg), (2S)-2-phenyloxirane (93 mg), cesium carbonate (151 mg), and acetonitrile (0.62 mL) was stirred under microwave irradiation at 130 °C for 1 hour. After the reaction was completed, the reaction mixture was filtered, and the filtrate was concentrated under reduced pressure. The concentrated product was diluted with methylene chloride, stirred for 30 minutes, filtered again, and concentrated under reduced pressure. The resulting concentrated residue was mixed with 4-(6-bromo-4-cyano-2-methylindazol-3-yl)-2-(difluoromethoxy)-N-[(1-fluorocyclopropyl)methyl]-6-methoxybenzamide (40 mg) described in Reference Example 63, 1,4-dioxane (0.90 mL), a 1 N aqueous potassium carbonate solution (0.29 mL), and a [1,1'-bis(diphenylphosphino)ferrocene]palladium(II) dichloride dichloromethane adduct (5.9 mg), and the mixture was heated and stirred under a nitrogen atmosphere at 100 °C for 2 hours. After the reaction was completed, water and chloroform were added to the reaction mixture, and the mixture was stirred vigorously for several minutes. The organic layer was separated with Phase-Separator®, concentrated under reduced pressure, and then sequentially purified by NH silica gel column chromatography (hexane: ethyl acetate=50:50 to 0:100) and preparative HPLC (10 mM aqueous ammonium carbonate solution-acetonitrile). The resulting crude product was dissolved in ethyl acetate: methanol=10:1, treated with InertSep Slim-J NH2®, and then concentrated and dried to obtain the title compound (37 mg) as a white powder. MS(ESI)m/z:631.2 [M+H]+

Example 98: Synthesis of 4-[4-cyano-6-[1-[2-(dimethylamino)-2-oxoethyl]pyrazol-4-yl]-2-methylindazol-3-yl]-2-(difluoromethoxy)-N-[(1-fluorocyclopropyl)methyl]-6-methoxybenzamide

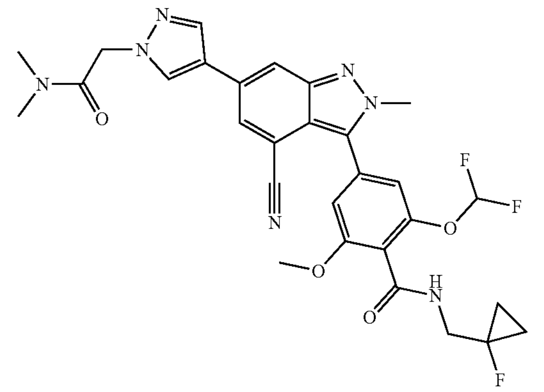 [SMILES: COc1cc(-c2c3c(C#N)cc(-c4cnn(CC(=O)N(C)C)c4)cc3nn2C)cc(OC(F)F)c1C(=O)NCC1(F)CC1]

2-[4-[4-Cyano-3-[3-(difluoromethoxy)-4-[(1-fluorocyclopropyl)methylcarbamoyl]-5-methoxyphenyl]-2-methyl-indazol-6-yl]pyrazol-1-yl]acetate (50 mg) described in Reference Example 111, dimethylamine hydrochloride (14 mg), and HATU (50 mg) were suspended in N,N-dimethylformamide (1.0 mL), N,N-diisopropylethylamine (61 μL) was added at room temperature, and the mixture was stirred for 1 hour. After the reaction was completed, the crude product obtained by preparative HPLC (10 mM aqueous ammonium carbonate solution-acetonitrile) was purified by silica gel column chromatography (chloroform:methanol=100:0 to 90:10) to obtain the title compound (37 mg) as a colorless powder. MS(ESI)m/z:596.1 [M+H]+

Example 99: Synthesis of 4-[4-cyano-6-[1-[2-(3,3-difluoroazetidin-1-yl)-2-oxoethyl]pyrazol-4-yl]-2-methylindazol-3-yl]-2-(difluoromethoxy)-N-[(1-fluorocyclopropyl)methyl]-6-methoxybenzamide

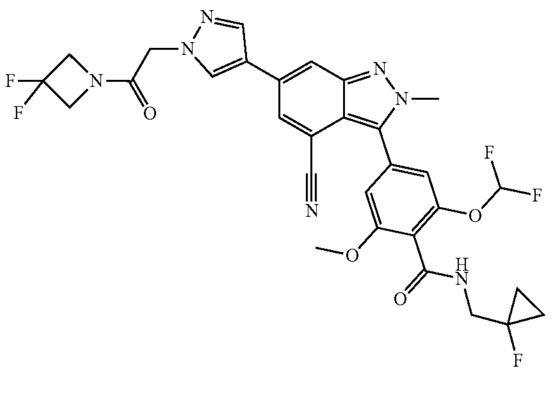 [SMILES: COc1cc(-c2c3c(C#N)cc(-c4cnn(CC(=O)N5CC(F)(F)C5)c4)cc3nn2C)cc(OC(F)F)c1C(=O)NCC1(F)CC1]

2-[4-[4-Cyano-3-[3-(difluoromethoxy)-4-[(1-fluorocyclopropyl)methylcarbamoyl]-5-methoxyphenyl]-2-methyl-indazol-6-yl]pyrazol-1-yl]acetate (50 mg) described in Reference Example 111, 3,3-difluoroazetidine hydrochloride (23 mg), and HATU (50 mg) were suspended in N,N-dimethylformamide (1.0 mL), N,N-diisopropylethylamine (61 μL) was added at room temperature, and the mixture was stirred for 1 hour. After the reaction was completed, the crude product obtained by preparative HPLC (10 mM aqueous ammonium carbonate solution-acetonitrile) was purified by NH silica gel column chromatography (ethyl acetate: methanol=100:0 to 97:3) to obtain the title compound (37 mg) as a colorless powder. MS(ESI)m/z:644.1 [M+H]+

Example 100: Synthesis of 4-[4-cyano-2-methyl-6-[1-(2-oxo-2-pyrrolidin-1-ylethyl)pyrazol-4-yl]indazol-3-yl]-2-(difluoromethoxy)-N-[(1-fluorocyclopropyl)methyl]-6-methoxybenzamide

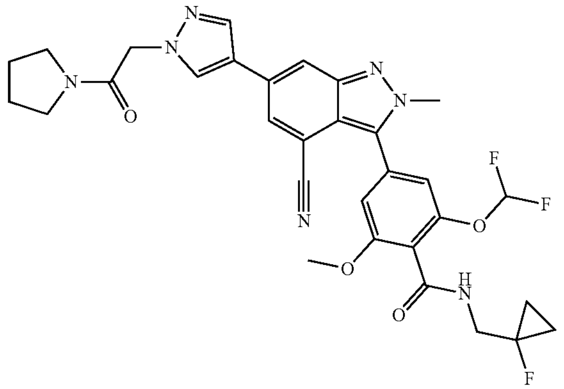 [SMILES: COc1cc(-c2c3c(C#N)cc(-c4cnn(CC(=O)N5CCCC5)c4)cc3nn2C)cc(OC(F)F)c1C(=O)NCC1(F)CC1]

2-[4-[4-Cyano-3-[3-(difluoromethoxy)-4-[(1-fluorocyclopropyl)methylcarbamoyl]-5-methoxyphenyl]-2-methyl-indazol-6-yl]pyrazol-1-yl]acetate (50 mg) described in Reference Example 111 and HATU (50 mg) were suspended in N,N-dimethylformamide (1.0 mL), N,N-diisopropylethylamine (30 μL) and pyrrolidine (15 μL) were added at room temperature, and the mixture was stirred for 1 hour. After the reaction was completed, the crude product obtained by preparative HPLC (10 mM aqueous ammonium carbonate solution-acetonitrile) was purified by NH silica gel column chromatography (ethyl acetate:methanol=100:0 to 96:4) to obtain the title compound (36 mg) as a colorless powder. MS(ESI)m/z:622.2 [M+H]+

Example 101: Synthesis of 4-[4-cyano-6-[1-[2-(3,3-difluoropyrrolidin-1-yl)-2-oxoethyl]pyrazol-4-yl]-2-methylindazol-3-yl]-2-(difluoromethoxy)-N-[(1-fluorocyclopropyl)methyl]-6-methoxybenzamide

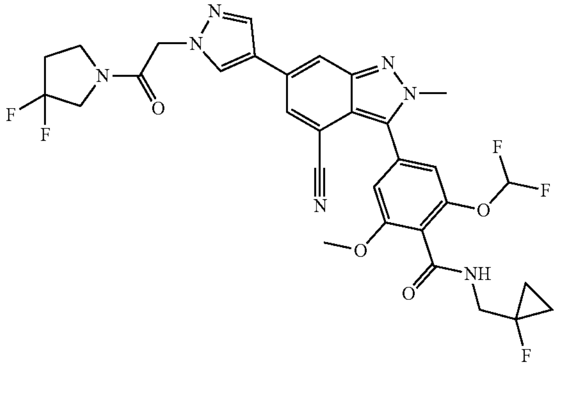 [SMILES: COc1cc(-c2c3c(C#N)cc(-c4cnn(CC(=O)N5CCC(F)(F)C5)c4)cc3nn2C)cc(OC(F)F)c1C(=O)NCC1(F)CC1]

2-[4-[4-Cyano-3-[3-(difluoromethoxy)-4-[(1-fluorocyclopropyl)methylcarbamoyl]-5-methoxyphenyl]-2-methyl-indazol-6-yl]pyrazol-1-yl]acetate (50 mg) described in Reference Example 111, 3,3-difluoropyrrolidine hydrochloride (25 mg), and HATU (50 mg) were suspended in N,N-dimethylformamide (1.0 mL), N,N-diisopropylethylamine (61 μL) was added at room temperature, and the mixture was stirred for 1 hour. After the reaction was completed, the crude product obtained by preparative HPLC (10 mM aqueous ammonium carbonate solution-acetonitrile) was purified by NH silica gel column chromatography (ethyl acetate: methanol=100:0 to 95:5 to 93:7) to obtain the title compound (42 mg) as a colorless powder. MS(ESI)m/z:658.1 [M+H]+

Example 102: Synthesis of 4-[4-cyano-6-[1-(2,2-difluoroethyl)pyrazol-4-yl]-2-methylindazol-3-yl]-2-(difluoromethoxy)-6-methoxybenzamide

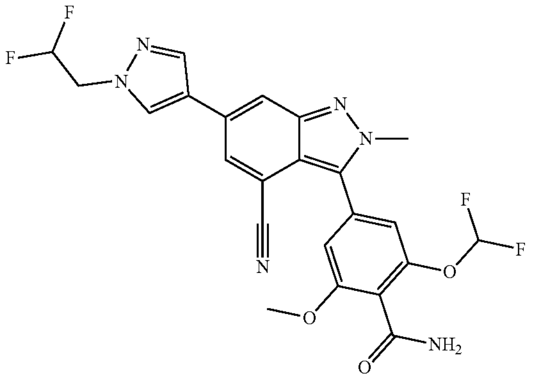 [SMILES: COc1cc(-c2c3c(C#N)cc(-c4cnn(CC(F)F)c4)cc3nn2C)cc(OC(F)F)c1C(N)=O]

A mixture of 4-(6-bromo-4-cyano-2-methylindazol-3-yl)-2-(difluoromethoxy)-6-methoxybenzamide (78 mg) described in Reference Example 86, 1-(2,2-difluoroethyl)-4-(tetramethyl-1,3,2-dioxaborolan-2-yl)-1H-pyrazole (42 mg), a [1,1'-bis(diphenylphosphino)ferrocene]palladium(II) dichloride dichloromethane adduct (12 mg), 1,4-dioxane (1.5 mL), and a 1 N aqueous tripotassium phosphate solution (0.45 mL) was heated and stirred under a nitrogen atmosphere at 100 °C for 2 hours and 30 minutes. After the reaction was completed, water was added to the reaction mixture, and extraction was performed twice with chloroform. The organic layer was separated with Phase-Separator®, and the organic layer was concentrated under reduced pressure. The residue was sequentially purified by NH silica gel column chromatography (hexane:ethyl acetate=70:30 to 0:100) and preparative HPLC (10 mM aqueous ammonium carbonate solution-acetonitrile) and then suspended and washed with diethyl ether to obtain the title compound (37 mg) as a white powder.

MS(ESI)m/z:503.0 [M+H]+

Example 103: Synthesis of [2-(difluoromethoxy)-4-[4-[(5-fluoropyridin-3-yl)methoxy]-2-methyl-6-(1-methylpyrazol-4-yl)indazol-3-yl]-6-methoxyphenyl]-[3-hydroxy-3-(trifluoromethyl)azetidin-1-yl] methanone

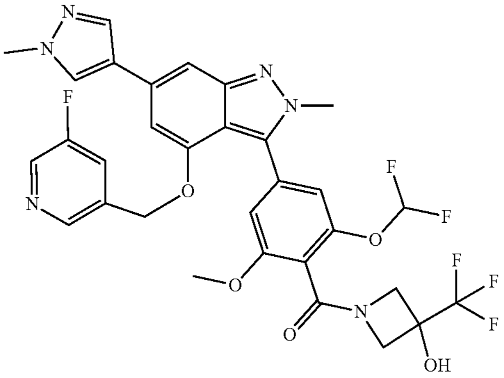 [SMILES: COc1cc(-c2c3c(OCc4cncc(F)c4)cc(-c4cnn(C)c4)cc3nn2C)cc(OC(F)F)c1C(=O)N1CC(O)(C(F)(F)F)C1]

To a dichloromethane (8.8 mL) solution of (5-fluoropyridin-3-yl) methanol (168 mg), thionyl chloride (0.96 mL) was added under ice cooling, and the mixture was stirred under ice cooling for 2 hours. The reaction solution was concentrated under reduced pressure and azeotroped with toluene. 25 mg of the 241 mg resulting residue, and [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone (60 mg) described in Reference Example 54 and potassium carbonate (58 mg) were suspended in N,N-dimethylformamide (1.0 mL), and heating and stirring were performed at 80 °C. for 1 hour. After the reaction was completed, water was added to the reaction mixture, and extraction was performed twice with chloroform. The organic layer was separated with Phase-Separator®, and the organic layer was concentrated under reduced pressure. Sequential purification was performed by NH silica gel column chromatography (ethyl acetate:methanol=100:0 to 90:10) and preparative HPLC (10 mM aqueous ammonium carbonate solution-acetonitrile), and then suspension and washing were performed with a mixed solvent of diethyl ether and hexane to obtain the title compound (12 mg) as a colorless powder. MS(ESI) m/z:677.3 [M+H]+

Example 104: Synthesis of 5-[[3-[3-(difluoromethoxy)-4-[3-hydroxy-3-(trifluoromethyl)azetidin-1-carbonyl]-5-methoxyphenyl]-2-methyl-6-(1-methylpyrazol-4-yl)indazol-4-yl]oxymethyl] pyridine-3-carbonitrile

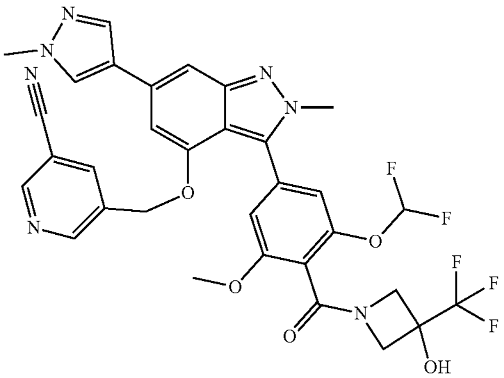 [SMILES: COc1cc(-c2c3c(OCc4cncc(C#N)c4)cc(-c4cnn(C)c4)cc3nn2C)cc(OC(F)F)c1C(=O)N1CC(O)(C(F)(F)F)C1]

To a dichloromethane (1.3 mL) solution of (5-(hydroxymethyl)pyridine-3-carbonitrile trifluoroacetate (64 mg) described in Reference Example 74, thionyl chloride (0.19 mL) was added under ice cooling, and the mixture was stirred at room temperature for 2 hours. The reaction solution was concentrated under reduced pressure and azeotroped with toluene. 20 mg of the 49 mg resulting residue, and [2-(difluoromethoxy)-4-[4-hydroxy-2-methyl-6-(1-methylpyrazol-4-yl)indazol-3-yl]-6-methoxyphenyl]-[3-hydroxy-3-(trifluoromethyl)azetidin-1-yl]methanone (60 mg) described in Reference Example 54 and potassium carbonate (58 mg) were suspended in N,N-dimethylformamide (1.0 mL), and heating and stirring were performed at 80 °C. for 1.5 hours. After the reaction was completed, water was added to the reaction mixture, and extraction was performed twice with chloroform. The organic layer was separated with Phase-Separator®, and the organic layer was concentrated under reduced pressure. The residue was sequentially purified by preparative HPLC (0.05% aqueous TFA solution-0.05% TFA acetonitrile solution), silica gel column chromatography (chloroform:methanol=100:0 to 90:10), and preparative HPLC (10 mM aqueous ammonium carbonate solution-acetonitrile) to obtain the title compound (6.3 mg) as a colorless powder. MS(ESI)m/z:684.1 [M+H]+

Example 105: Synthesis of 6-(1-ethylpyrazol-4-yl)-2-methyl-3-[rel-(4R)-8-methoxy-4-methyl-1-oxo-3,4-dihydro-2H-isoquinolin-6-yl]indazole-4-carbonitrile

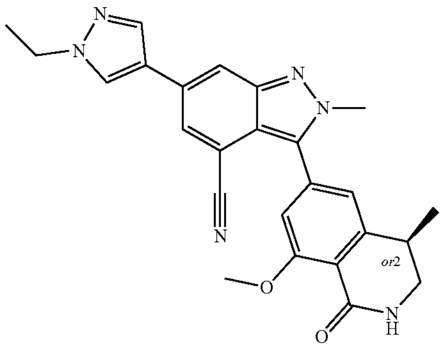 [SMILES: CCn1cc(-c2cc(C#N)c3c(-c4cc(OC)c5c(c4)[C@@H](C)CNC5=O)n(C)nc3c2)cn1]

A mixture of an isomer (20 mg) that eluted earlier under chiral HPLC conditions as described in the experimental section of 6-bromo-2-methyl-3-[rel-(4R)-8-methoxy-4-methyl-1-oxo-3,4-dihydro-2H-isoquinolin-6-yl]indazole-4-carbonitrile described in Reference Example 97, (1-ethylpyrazol-4-yl) boronic acid (7.2 mg), a [1,1'-bis(diphenylphosphino)ferrocene]palladium(II) dichloride dichloromethane adduct (3.8 mg), potassium carbonate (13 mg), 1,4-dioxane (0.31 mL), and water (78 μL) was heated and stirred under a nitrogen atmosphere at 100 °C for 2 hours. After the reaction was completed, water was added to the reaction mixture, and extraction was performed twice with chloroform. The organic layer was separated with Phase-Separator®, and the organic layer was concentrated under reduced pressure.

Purification was performed by NH silica gel column chromatography (ethyl acetate:methanol=100:0 to 90:10), and the resulting crude product was purified by preparative HPLC (10 mM aqueous ammonium carbonate solution-acetonitrile) to obtain the title compound (11 mg) as a white powder. MS(ESI)m/z:441.4 [M+H]+

Example 106: Synthesis of 2-methyl-6-(1-propylpyrazol-4-yl)-3-[rel-(4R)-8-methoxy-4-methyl-1-oxo-3,4-dihydro-2H-isoquinolin-6-yl]indazole-4-carbonitrile

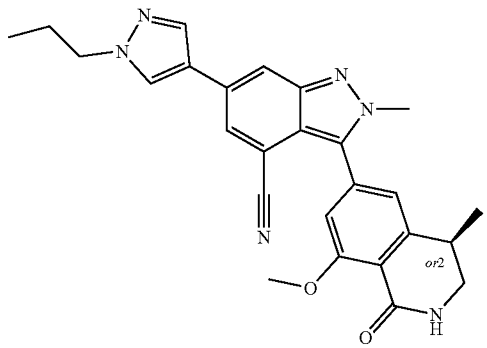 [SMILES: CCCn1cc(-c2cc(C#N)c3c(-c4cc(OC)c5c(c4)[C@@H](C)CNC5=O)n(C)nc3c2)cn1]

A mixture of an isomer (20 mg) that eluted earlier under chiral HPLC conditions as described in the experimental section of 6-bromo-2-methyl-3-[rel-(4R)-8-methoxy-4-methyl-1-oxo-3,4-dihydro-2H-isoquinolin-6-yl]indazole-4-carbonitrile described in Reference Example 97, (1-propylpyrazol-4-yl) boronic acid (8.0 mg), a [1,1'-bis(diphenylphosphino)ferrocene]palladium(II) dichloride dichloromethane adduct (3.8 mg), potassium carbonate (13 mg), 1,4-dioxane (0.31 mL), and water (78 μL) was heated and stirred under a nitrogen atmosphere at 100 °C for 2 hours. After the reaction was completed, water was added to the reaction mixture, and extraction was performed twice with chloroform. The organic layer was separated with Phase-Separator®, and the organic layer was concentrated under reduced pressure. Sequential purification was performed by preparative HPLC (10 mM aqueous ammonium carbonate solution-acetonitrile) and NH silica gel column chromatography (ethyl acetate:methanol=100:0 to 85:15) to obtain the title compound (13 mg) as a white powder. MS(ESI)m/z:455.4 [M+H]+

Example 107: Synthesis of 6-[1-(2,2-difluoroethyl)pyrazol-4-yl]-2-methyl-3-[rel-(4R)-8-methoxy-4-methyl-1-oxo-3,4-dihydro-2H-isoquinolin-6-yl]indazole-4-carbonitrile

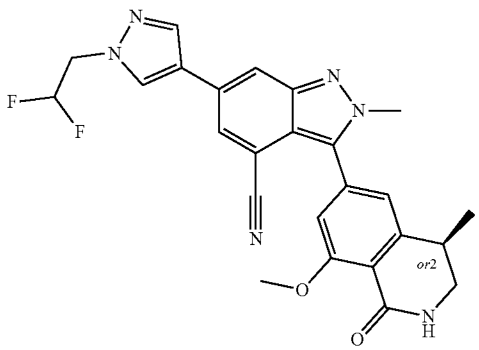 [SMILES: COc1cc(-c2c3c(C#N)cc(-c4cnn(CC(F)F)c4)cc3nn2C)cc2c1C(=O)NC[C@@H]2C]

A mixture of an isomer (20 mg) that eluted earlier under chiral HPLC conditions as described in the experimental section of 6-bromo-2-methyl-3-[rel-(4R)-8-methoxy-4-methyl-1-oxo-3,4-dihydro-2H-isoquinolin-6-yl]indazole-4-carbonitrile described in Reference Example 97, 1-(2,2-difluoroethyl)-4-(4,4,5,5-tetramethyl-1,3,2-dioxaborolan-2-yl)pyrazole (13 mg), a [1,1'-bis(diphenylphosphino)ferrocene]palladium(II) dichloride dichloromethane adduct (3.8 mg), potassium carbonate (13 mg), 1,4-dioxane (0.31 mL), and water (78 μL) was heated and stirred under a nitrogen atmosphere at 100 °C for 2 hours. After the reaction was completed, water was added to the reaction mixture, and extraction was performed twice with chloroform. The organic layer was separated with Phase-Separator®, and the organic layer was concentrated under reduced pressure. The residue was sequentially purified by preparative HPLC (10 mM aqueous ammonium carbonate solution-acetonitrile) and NH silica gel column chromatography (ethyl acetate: methanol=100:0 to 85:15) to obtain the title compound (10 mg) as a white powder. MS(ESI)m/z:477.4 [M+H]+

Example 108: Synthesis of 4-[4-cyano-6-[1-[2-(3,3-difluoroazetidin-1-yl)ethyl]pyrazol-4-yl]-2-methylindazol-3-yl]-2-(difluoromethoxy)-6-methoxy-N-[[rel-(1R)-2,2-difluorocyclopropyl]methyl]benzamide

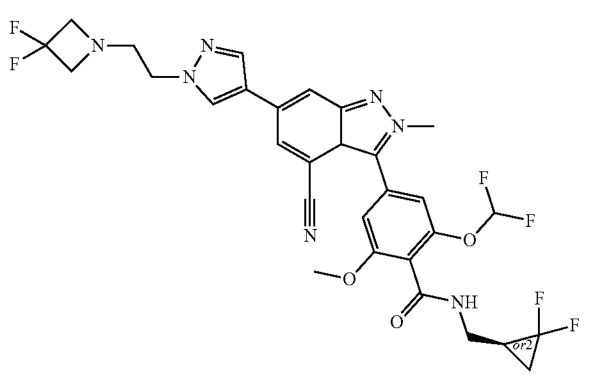

A mixture of 4-[4-cyano-2-methyl-6-(4,4,5,5-tetramethyl-1,3,2-dioxaborolan-2-yl)indazol-3-yl]-2-(difluoromethoxy)-6-methoxy-N-[rel-(1R)-2,2-difluorocyclopropyl methyl]benzamide (75 mg) described in Reference Example 87, 4-bromo-1-[2-(3,3-difluoroazetidin-1-yl)ethyl] pyrazole (40 mg) described in Reference Example 88, a [1,1'-bis(diphenylphosphino)ferrocene]palladium(II) dichloride dichloromethane adduct (8.3 mg), 1,4-dioxane (1.0 mL), and a 1 N aqueous tripotassium phosphate solution (0.20 mL) was heated and stirred under a nitrogen atmosphere at 100 °C for 1 hour and 30 minutes. After the reaction was completed, the reaction mixture was diluted with ethyl acetate and dried with sodium sulfate, insoluble matter was filtered, and the filtrate was concentrated under reduced pressure. The crude product obtained by purifying the residue by NH silica gel column chromatography (hexane:ethyl acetate=80:20 to 40:60) was purified by preparative HPLC (10 mM aqueous ammonium carbonate solution-acetonitrile) and then suspended and washed with diethyl ether to obtain the title compound (6.2 mg) as a white powder. MS(ESI)m/z:648.5 [M+H]+

Example 109: Synthesis of N-[(1R)-2,2-difluorocyclopropyl]-2-(difluoromethoxy)-4-[4-(difluoromethyl)-6-[1-(2-hydroxy-2-methylpropyl)pyrazol-4-yl]-2-methylindazol-3-yl]-6-methoxybenzamide

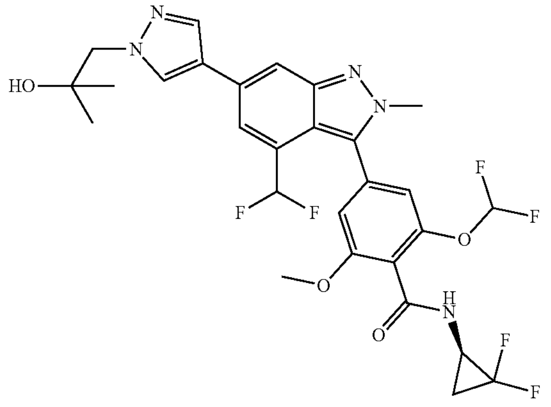 [SMILES: COc1cc(-c2c3c(C(F)F)cc(-c4cnn(CC(C)(C)O)c4)cc3nn2C)cc(OC(F)F)c1C(=O)N[C@@H]1CC1(F)F]

A mixture of 4-[6-bromo-4-(difluoromethyl)-2-methylindazol-3-yl]-N-[(1R)-2,2-difluorocyclopropyl]-2-(difluoromethoxy)-6-methoxybenzamide (83 mg) described in Reference Example 83, 2-methyl-1-(4-(4,4,5,5-tetramethyl-1,3,2-dioxaborolan-2-yl)-1H-pyrazol-1-yl)propan-2-ol (60 mg), a [1,1'-bis(diphenylphosphino)ferrocene]palladium(II) dichloride dichloromethane adduct (12 mg), tripotassium phosphate (64 mg), 1,4-dioxane (2.0 mL), and water (0.20 mL) was heated and stirred under a nitrogen atmosphere at 40 °C. overnight. After the reaction was completed, water was added to the reaction mixture, and extraction was performed three times with chloroform. The residue obtained by concentrating the organic layer under reduced pressure was purified by NH silica gel chromatography (hexane:ethyl acetate=60:40 to 0:100), and the resulting crude product was purified by silica gel column chromatography (ethyl acetate:methanol=100:0 to 97:3 to 95:5) to obtain the title compound (70 mg) as a colorless powder. MS(ESI)m/z:612.1 [M+H]+

Example 110: Synthesis of 4-[4-cyano-6-[1-[(1-hydroxycyclobutyl)methyl]pyrazol-4-yl]-2-methylindazol-3-yl]-N-[(1R)-2,2-difluorocyclopropyl]-2-(difluoromethoxy)-6-methoxybenzamide

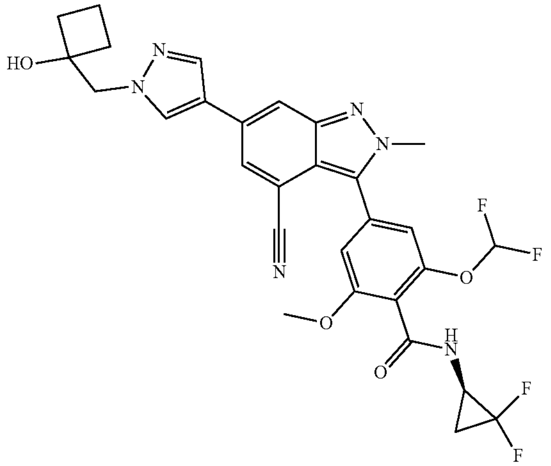 [SMILES: COc1cc(-c2c3c(C#N)cc(-c4cnn(CC5(O)CCC5)c4)cc3nn2C)cc(OC(F)F)c1C(=O)N[C@@H]1CC1(F)F]

A mixture of 4-[4-cyano-2-methyl-6-(4,4,5,5-tetramethyl-1,3,2-dioxaborolan-2-yl)indazol-3-yl]-N-[(1R)-2,2-difluorocyclopropyl]-2-(difluoromethoxy)-6-methoxybenzamide (120 mg) described in Reference Example 99, 1-[(4-iodopyrazol-1-yl)methyl]cyclobutan-1-ol (64 mg) described in Reference Example 100, a [1,1'-bis(diphenylphosphino) ferrocene]palladium(II) dichloride dichloromethane adduct (17 mg), 1,4-dioxane (2.0 mL), and a 1 N aqueous tripotassium phosphate solution (0.63 mL) was heated and stirred under a nitrogen atmosphere at 40 °C. overnight. After the reaction was completed, the reaction mixture was diluted with ethyl acetate and dried with magnesium sulfate, insoluble matter was filtered, and the filtrate was concentrated under reduced pressure. The crude product obtained by purifying the residue by NH silica gel column chromatography (hexane:ethyl acetate=50:50 to 0:100) was purified by preparative HPLC (10 mM aqueous ammonium carbonate solution-acetonitrile) to obtain the title compound (41 mg) as a colorless powder. MS(ESI)m/z:599.4 [M+H]+

Example 111: Synthesis of 4-[4-cyano-6-[1-(3-hydroxy-3-methylbutyl)pyrazol-4-yl]-2-methylindazol-3-yl]-N-[(1R)-2,2-difluoro[cyclopropyl]-2-(difluoromethoxy)-6-methoxybenzamide

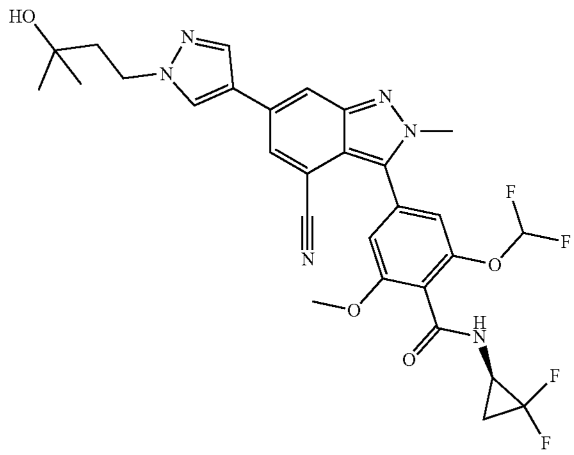 [SMILES: COc1cc(-c2c3c(C#N)cc(-c4cnn(CCC(C)(C)O)c4)cc3nn2C)cc(OC(F)F)c1C(=O)N[C@@H]1CC1(F)F]

A mixture of 4-(4-iodopyrazol-1-yl)-2-methylbutan-2-ol (76 mg) described in Reference Example 101, 4-[4-cyano-2-methyl-6-(4,4,5,5-tetramethyl-1,3,2-dioxaborolan-2-yl) indazol-3-yl]-N-[(1R)-2,2-difluorocyclopropyl]-2-(difluoromethoxy)-6-methoxybenzamide (123 mg) described in Reference Example 99, a [1,1'-bis(diphenylphosphino)ferrocene]palladium(II) dichloride dichloromethane adduct (17 mg), 1,4-dioxane (2.0 mL), and a 1 N aqueous tripotassium phosphate solution (0.64 mL) was heated and stirred under a nitrogen atmosphere at 40 °C. overnight. After the reaction was completed, the reaction mixture was diluted with ethyl acetate and dried with magnesium sulfate, insoluble matter was filtered, and the filtrate was concentrated under reduced pressure. The residue was sequentially purified by silica gel column chromatography (ethyl acetate:methanol=100:0 to 95:5) and NH silica gel column chromatography (ethyl acetate:methanol=100:0 to 90:10) to obtain the title compound (26 mg) as a colorless powder. MS(ESI)m/z:601.5 [M+H]+

Example 112: Synthesis of 2-(difluoromethoxy)-4-[4-(difluoromethyl)-6-(1-ethylpyrazol-4-yl)-2-methylindazol-3-yl]-6-methoxybenzamide

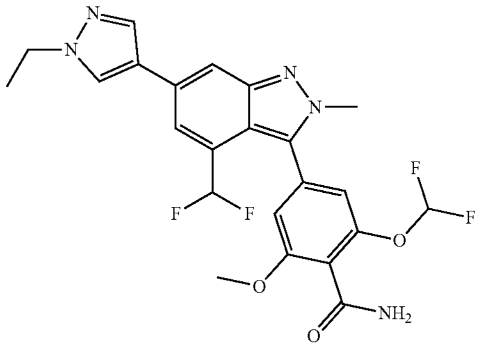 [SMILES: CCn1cc(-c2cc(C(F)F)c3c(-c4cc(OC)c(C(N)=O)c(OC(F)F)c4)n(C)nc3c2)cn1]

2-(Difluoromethoxy)-4-[4-(difluoromethyl)-6-(1-ethylpyrazol-4-yl)-2-methylindazol-3-yl]-6-methoxybenzoic acid (57 mg) described in Reference Example 113 and HATU (88 mg) were dissolved in N,N-dimethylformamide (1.5 mL), ammonium carbonate (22 mg) and N,N-diisopropylethylamine (50 μL) were added, and the mixture was stirred at room temperature for 1 hour. After the reaction was completed, the crude product obtained by preparative HPLC (10 mM aqueous ammonium carbonate solution-acetonitrile) was purified by silica gel column chromatography (chloroform:methanol=100:0 to 92:8) to obtain the title compound (42 mg) as a colorless powder. MS(ESI)m/z: 492.0 [M+H]+

Example 113: Synthesis of 2-(difluoromethoxy)-4-[4-(difluoromethyl)-2-methyl-6-(1-propylpyrazol-4-yl)indazol-3-yl]-6-methoxybenzamide

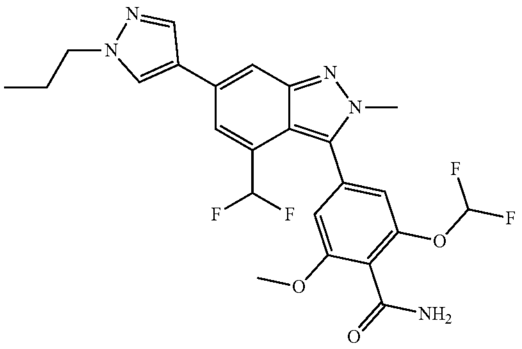 [SMILES: CCCn1cc(-c2cc(C(F)F)c3c(-c4cc(OC)c(C(N)=O)c(OC(F)F)c4)n(C)nc3c2)cn1]

2-(Difluoromethoxy)-4-[4-(difluoromethyl)-2-methyl-6-(1-propylpyrazol-4-yl)indazol-3-yl]-6-methoxybenzoic acid (60 mg) described in Reference Example 115 and HATU (90 mg) were dissolved in N,N-dimethylformamide (1.5 mL), ammonium carbonate (23 mg) and N,N-diisopropylethylamine (51 μL) were added, and the mixture was stirred at room temperature for 1 hour. After the reaction was completed, the crude product obtained by preparative HPLC (10 mM aqueous ammonium carbonate solution-acetonitrile) was purified by silica gel column chromatography (chloroform:methanol=100:0 to 92:8) to obtain the title compound (49 mg) as a colorless powder. MS(ESI)m/z:506.0 [M+H]+

Example 114: Synthesis of 4-[4-cyano-6-[1-(2-hydroxy-2-methylpropyl)pyrazol-4-yl]-2-methylindazol-3-yl]-N-[(1R)-2,2-difluorocyclopropyl]-2-(difluoromethoxy)-6-methoxybenzamide

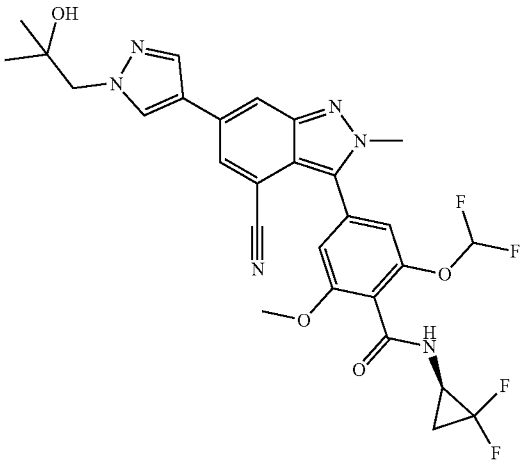 [SMILES: COc1cc(-c2c3c(C#N)cc(-c4cnn(CC(C)(C)O)c4)cc3nn2C)cc(OC(F)F)c1C(=O)N[C@@H]1CC1(F)F]

A mixture of 4-(6-bromo-4-cyano-2-methylindazol-3-yl)-N-[(1R)-2,2-difluorocyclopropyl]-2-(difluoromethoxy)-6-methoxybenzamide (70 mg) described in Reference Example 82, 2-methyl-1-[4-(4,4,5,5-tetramethyl-1,3,2-dioxaborolan-2-yl)pyrazol-1-yl]propan-2-ol (53 mg), tripotassium phosphate (85 mg), [1,1'-bis(di-tert-butylphosphino)ferrocene]palladium(II) dichloride (8.7 mg), 1,4-dioxane (1.3 mL), and water (0.28 mL) was heated and stirred under a nitrogen atmosphere at 40 °C for 1 hour. After the reaction was completed, the reaction mixture was diluted with ethyl acetate and dried with sodium sulfate, insoluble matter was filtered, and the filtrate was concentrated under reduced pressure. The residue was purified by column chromatography (ethyl acetate:methanol=100:0 to 90:10) using an NH silica gel column and a Si silica gel column in series and suspended and washed with diethyl ether to obtain the title compound (61 mg) as a white powder.

MS(ESI)m/z:587.1 [M+H]+

Example 115: Synthesis of 4-[4-cyano-6-[1-(2,2-difluoroethyl)pyrazol-4-yl]-2-methylindazol-3-yl]-N-[(1R)-2,2-difluorocyclopropyl]-2-(difluoromethoxy)-6-methoxybenzamide

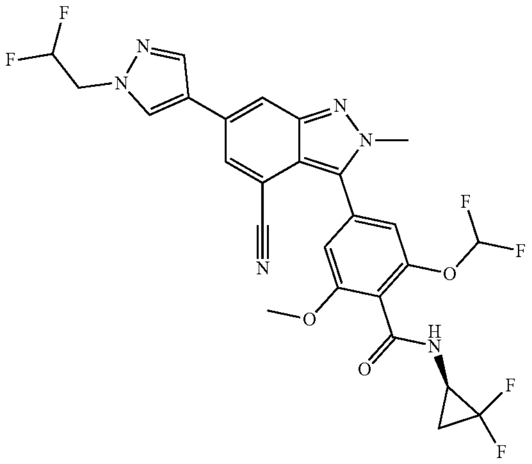 [SMILES: COc1cc(-c2c3c(C#N)cc(-c4cnn(CC(F)F)c4)cc3nn2C)cc(OC(F)F)c1C(=O)N[C@@H]1CC1(F)F]

A mixture of 4-(6-bromo-4-cyano-2-methylindazol-3-yl)-N-[(1R)-2,2-difluorocyclopropyl]-2-(difluoromethoxy)-6-methoxybenzamide (70 mg) described in Reference Example 82, 1-(2,2-difluoroethyl)-4-(4,4,5,5-tetramethyl-1,3,2-dioxaborolan-2-yl)pyrazole (48 mg), tripotassium phosphate (85 mg), [1,1'-bis(di-tert-butylphosphino)ferrocene]palladium(II) dichloride (4.3 mg), 1,4-dioxane (1.3 mL), and water (0.26 mL) was heated and stirred under a nitrogen atmosphere at 40 °C for 1 hour. After the reaction was completed, the reaction mixture was diluted with ethyl acetate and dried with sodium sulfate, insoluble matter was filtered, and the filtrate was concentrated under reduced pressure. The crude product obtained by purifying the residue by column chromatography (hexane:ethyl acetate=50:50 to 10:90 to 0:100) using an NH silica gel column and a Si silica gel column in series was suspended and washed with diethyl ether to obtain the title compound (43 mg) as a white powder. MS(ESI)m/z:579.0 [M+H]+

Example 116: Synthesis of N-[(1R)-2,2-difluorocyclopropyl]-2-(difluoromethoxy)-4-[4-(difluoromethyl)-6-(1-ethylpyrazol-4-yl)-2-methylindazol-3-yl]-6-methoxybenzamide

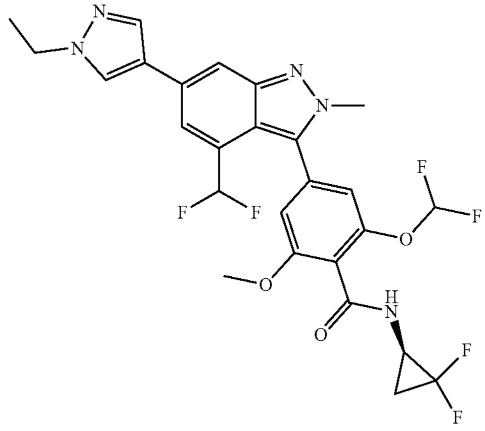 [SMILES: CCn1cc(-c2cc(C(F)F)c3c(-c4cc(OC)c(C(=O)N[C@@H]5CC5(F)F)c(OC(F)F)c4)n(C)nc3c2)cn1]

A mixture of 4-[6-bromo-4-(difluoromethyl)-2-methylindazol-3-yl]-N-[(1R)-2,2-difluorocyclopropyl]-2-(difluoromethoxy)-6-methoxybenzamide (70 mg) described in Reference Example 83, (1-ethylpyrazol-4-yl) boronic acid (21 mg), [1,1'-bis(di-tert-butylphosphino)ferrocene]palladium (II) dichloride (8.3 mg), tripotassium phosphate (81 mg), 1,4-dioxane (1.3 mL), and water (0.24 mL) was heated and stirred under a nitrogen atmosphere at 40 °C for 1 hour and 30 minutes. After the reaction was completed, the reaction mixture was diluted with ethyl acetate and dried with sodium sulfate, insoluble matter was filtered, and the filtrate was concentrated under reduced pressure. The residue was purified by column chromatography (hexane:ethyl acetate=50:50 to 0:100) using an NH silica gel column and a Si silica gel column in series to obtain the title compound (45 mg) as a colorless powder. MS(ESI)m/z:568.4 [M+H]+

Example 117: Synthesis of N-[(1R)-2,2-difluorocyclopropyl]-2-(difluoromethoxy)-4-[4-(difluoromethyl)-6-[1-[(1-hydroxycyclobutyl)methyl]pyrazol-4-yl]-2-methylindazol-3-yl]-6-methoxybenzamide

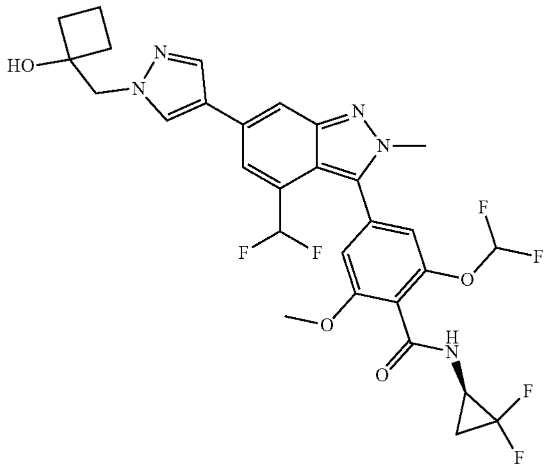 [SMILES: COc1cc(-c2c3c(C(F)F)cc(-c4cnn(CC5(O)CCC5)c4)cc3nn2C)cc(OC(F)F)c1C(=O)N[C@@H]1CC1(F)F]

A mixture of N-[(1R)-2,2-difluorocyclopropyl]-2-(difluoromethoxy)-4-[4-(difluoromethyl)-2-methyl-6-(4,4,5,5-tetramethyl-1,3,2-dioxaborolan-2-yl)indazol-3-yl]-6-methoxybenzamide (104 mg) described in Reference Example 102, 1-[(4-iodopyrazol-1-yl)methyl]cyclobutan-1-ol (58 mg) described in Reference Example 100, [1,1'-bis(di-tert-butylphosphino)ferrocene]palladium(II) dichloride (11 mg), tripotassium phosphate (111 mg), 1,4-dioxane (1.7 mL), and water (0.34 mL) was heated and stirred under a nitrogen atmosphere at 40 °C. overnight. After the reaction was completed, the reaction mixture was diluted with ethyl acetate and dried with sodium sulfate, insoluble matter was filtered, and the filtrate was concentrated under reduced pressure. The crude product obtained by purifying the residue by column chromatography (hexane:ethyl acetate=50:50 to 0:100) using an NH silica gel column and a Si silica gel column in series was suspended and washed with diethyl ether to obtain the title compound (35 mg) as a colorless powder. MS(ESI)m/z:624.4 [M+H]+

Example 118: Synthesis of 4-[4-cyano-6-(1-ethylpyrazol-4-yl)-2-methylindazol-3-yl]-N-[(1R)-2,2-difluorocyclopropyl]-2-(difluoromethoxy)-6-methoxybenzamide

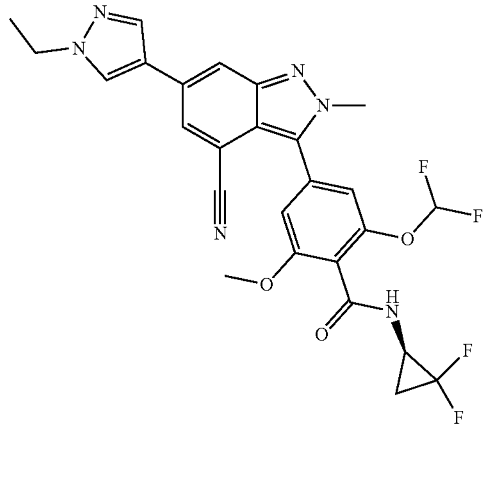 [SMILES: CCn1cc(-c2cc(C#N)c3c(-c4cc(OC)c(C(=O)N[C@@H]5CC5(F)F)c(OC(F)F)c4)n(C)nc3c2)cn1]

4-(6-Bromo-4-cyano-2-methylindazol-3-yl)-N-[(1R)-2,2-difluorocyclopropyl]-2-(difluoromethoxy)-6-methoxybenzamide (60 mg) described in Reference Example 82, [1,1'-bis(di-tert-butylphosphino)ferrocene]palladium(II) dichloride (3.7 mg), (1-ethylpyrazol-4-yl) boronic acid (22 mg), and tripotassium phosphate (72 mg) were suspended in a mixed solvent of 1,4-dioxane (1.2 mL) and water (0.24 mL), and heating and stirring were performed under a nitrogen atmosphere at 40 °C for 1 hour and 30 minutes. [1,1'-Bis(di-tert-butylphosphino)ferrocene]palladium(II) dichloride (3.7 mg) was added, and the mixture was heated and stirred at 40 °C for 2 hours and 30 minutes. The residue obtained by filtering and concentrating the reaction solution, [1,1'-bis(di-tert-butylphosphino)ferrocene]palladium(II) dichloride (3.7 mg), (1-ethylpyrazol-4-yl) boronic acid (22 mg), and tripotassium phosphate (72 mg) were suspended in a mixed solvent of 1,4-dioxane (1.2 mL) and water (0.24 mL), and heating and stirring were performed under a nitrogen atmosphere at 50 °C for 1 hour and 30 minutes. After the reaction was completed, the reaction mixture was diluted with ethyl acetate and dried with sodium sulfate, insoluble matter was filtered, and the filtrate was concentrated under reduced pressure. The residue was sequentially purified by column chromatography (ethyl acetate:methanol=100:0 to 90:10 using an NH silica gel column and a Si silica gel column in series and preparative HPLC (10 mM aqueous ammonium carbonate solution-acetonitrile) and then suspended and washed with diethyl ether to obtain the title compound (37 mg) as a white powder.

MS(ESI)m/z:543.4 [M+H]+

Example 119: Synthesis of N-[(1R)-2,2-difluorocyclopropyl]-2-(difluoromethoxy)-4-[4-(difluoromethyl)-6-[1-(3-hydroxy-3-methylbutyl)pyrazol-4-yl]-2-methylindazol-3-yl]-6-methoxybenzamide

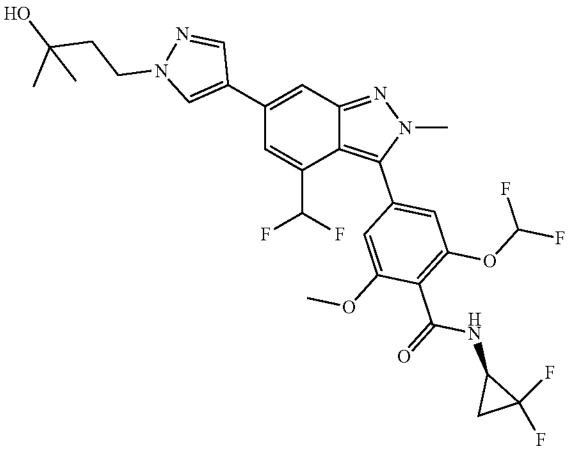 [SMILES: COc1cc(-c2c3c(C(F)F)cc(-c4cnn(CCC(C)(C)O)c4)cc3nn2C)cc(OC(F)F)c1C(=O)N[C@@H]1CC1(F)F]

A mixture of 4-(4-iodopyrazol-1-yl)-2-methylbutan-2-ol (60 mg) described in Reference Example 101, N-[(1R)-2,2-difluorocyclopropyl]-2-(difluoromethoxy)-4-[4-(difluoromethyl)-2-methyl-6-(4,4,5,5-tetramethyl-1,3,2-dioxaborolan-2-yl)indazol-3-yl]-6-methoxybenzamide (107 mg) described in Reference Example 102, [1,1'-bis(di-tert-butylphosphino)ferrocene]palladium(II) dichloride (12 mg), tripotassium phosphate (114 mg), 1,4-dioxane (1.8 mL), and water (0.34 mL) was heated and stirred under a nitrogen atmosphere at 40 °C for 1 hour. [1,1'-Bis(di-tert-butylphosphino)ferrocene]palladium(II) dichloride (12 mg) and tripotassium phosphate (38 mg) were added, and the mixture was heated and stirred at 40 °C for 2 hours. After the reaction was completed, the reaction mixture was diluted with ethyl acetate and dried with magnesium sulfate, insoluble matter was filtered, and the filtrate was concentrated under reduced pressure. The residue was sequentially purified by silica gel column chromatography (ethyl acetate:methanol=100:0 to 95:5) and NH silica gel column chromatography (hexane: ethyl acetate=50:50 to 0:100) to obtain the title compound (34 mg) as a colorless powder. MS(ESI)m/z:626.4 [M+H]+

Example 120: Synthesis of N-[(1R)-2,2-difluorocyclopropyl]-2-(difluoromethoxy)-4-[4-(difluoromethyl)-6-[1-[(3R)-3-hydroxybutyl]pyrazol-4-yl]-2-methylindazol-3-yl]-6-methoxybenzamide

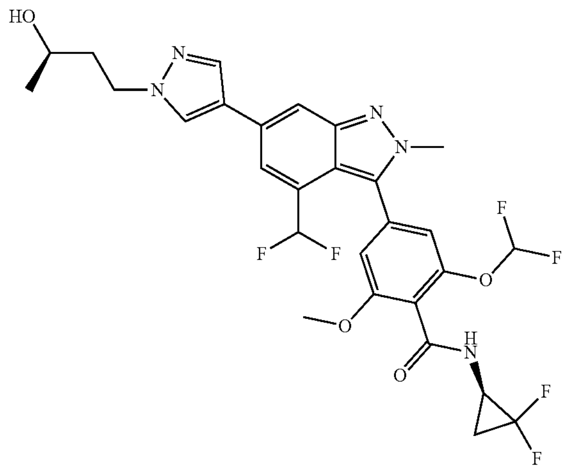 [SMILES: COc1cc(-c2c3c(C(F)F)cc(-c4cnn(CC[C@@H](C)O)c4)cc3nn2C)cc(OC(F)F)c1C(=O)N[C@@H]1CC1(F)F]

A mixture of N-[(1R)-2,2-difluorocyclopropyl]-2-(difluoromethoxy)-4-[4-(difluoromethyl)-2-methyl-6-(4,4,5,5-tetramethyl-1,3,2-dioxaborolan-2-yl)indazol-3-yl]-6-methoxybenzamide (100 mg) described in Reference Example 102, (2R)-4-(4-iodopyrazol-1-yl) butan-2-ol (53 mg) described in Reference Example 104, [1,1'-bis(di-tert-butylphosphino)ferrocene]palladium(II) dichloride (11 mg), tripotassium phosphate (106 mg), 1,4-dioxane (1.7 mL), and water (0.30 mL) was heated and stirred under a nitrogen atmosphere at 40 °C. overnight. After the reaction was completed, the reaction mixture was diluted with ethyl acetate and dried with magnesium sulfate, insoluble matter was filtered, and the filtrate was concentrated under reduced pressure. The residue was sequentially purified by preparative HPLC (10 mM aqueous ammonium carbonate solution-acetonitrile) and column chromatography (ethyl acetate: methanol=100:0 to 95:5) using an NH silica gel column and a Si silica gel column in series to obtain the title compound (36 mg) as a colorless powder. MS(ESI)m/z:612.4 [M+H]+

Example 121: Synthesis of N-[(1R)-2,2-difluorocyclopropyl]-2-(difluoromethoxy)-4-[4-(difluoromethyl)-6-[1-[(cis-3-hydroxycyclobutyl)methyl]pyrazol-4-yl]-2-methylindazol-3-yl]-6-methoxybenzamide

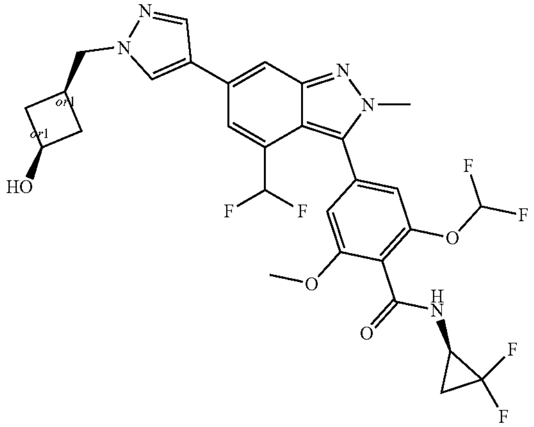 [SMILES: COc1cc(-c2c3c(C(F)F)cc(-c4cnn(C[C@H]5C[C@@H](O)C5)c4)cc3nn2C)cc(OC(F)F)c1C(=O)N[C@@H]1CC1(F)F]

A mixture of cis-3-[(4-iodopyrazol-1-yl)methyl]cyclobutan-1-ol (56 mg) described in Reference Example 103, N-[(1R)-2,2-difluorocyclopropyl]-2-(difluoromethoxy)-4-[4-(difluoromethyl)-2-methyl-6-(4,4,5,5-tetramethyl-1,3,2-dioxaborolan-2-yl)indazol-3-yl]-6-methoxybenzamide (100 mg) described in Reference Example 102, [1,1'-bis(di-tert-butylphosphino)ferrocene]palladium(II) dichloride (109 mg), tripotassium phosphate (106 mg), 1,4-dioxane (1.7 mL), and water (0.30 mL) was heated and stirred under a nitrogen atmosphere at 40 °C. overnight. After the reaction was completed, the reaction mixture was diluted with ethyl acetate and dried with magnesium sulfate, insoluble matter was filtered, and the filtrate was concentrated under reduced pressure. The residue was sequentially purified by preparative HPLC (10 mM aqueous ammonium carbonate solution-acetonitrile) and column chromatography (ethyl acetate: methanol=100:0 to 95:5) using an NH silica gel column and a Si silica gel column in series to obtain the title compound (31 mg) as a colorless powder. MS(ESI)m/z:624.4 [M+H]+

Example 122: Synthesis of 4-[4-cyano-6-[1-[2-(1-hydroxycyclobutyl)ethyl]pyrazol-4-yl]-2-methylindazol-3-yl]-2-(difluoromethoxy)-N-[(1-fluorocyclopropyl)methyl]-6-methoxybenzamide

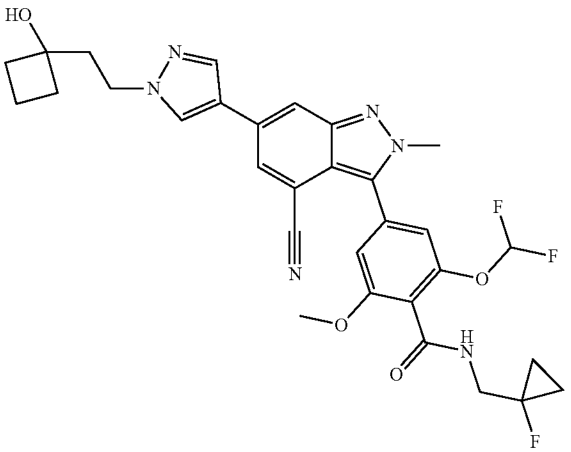 [SMILES: COc1cc(-c2c3c(C#N)cc(-c4cnn(CCC5(O)CCC5)c4)cc3nn2C)cc(OC(F)F)c1C(=O)NCC1(F)CC1]

A mixture of 4-[4-cyano-2-methyl-6-(4,4,5,5-tetramethyl-1,3,2-dioxaborolan-2-yl)indazol-3-yl]-2-(difluoromethoxy)-N-[(1-fluorocyclopropyl)methyl]-6-methoxybenzamide (89 mg) described in Reference Example 64, 1-[2-(4-iodopyrazol-1-yl)ethyl] cyclobutan-1-ol (53 mg) described in Reference Example 116, a [1,1'-bis(diphenylphosphino)ferrocene]palladium(II) dichloride dichloromethane adduct (9.9 mg), tripotassium phosphate (51 mg), 1,4-dioxane (2.0 mL), and water (0.20 mL) was heated and stirred under a nitrogen atmosphere at 100 °C for 2 hours and 30 minutes. After the reaction was completed, water was added to the reaction mixture, and extraction was performed three times with chloroform. The residue obtained by concentrating the organic layer under reduced pressure was sequentially purified by NH silica gel column chromatography (ethyl acetate:methanol=100:0 to 98:2) and silica gel column chromatography (chloroform:methanol=100:0 to 93:7) and then suspended and washed with a mixed solvent of diethyl ether and ethyl acetate to obtain the title compound (20 mg) as a colorless powder. MS(ESI)m/z:609.2 [M+H]+

Example 123: Synthesis of 4-[4-cyano-6-[1-[2-(1-hydroxycyclobutyl)ethyl]pyrazol-4-yl]-2-methylindazol-3-yl]-N-[(1R)-2,2-difluorocyclopropyl]-2-(difluoromethoxy)-6-methoxybenzamide

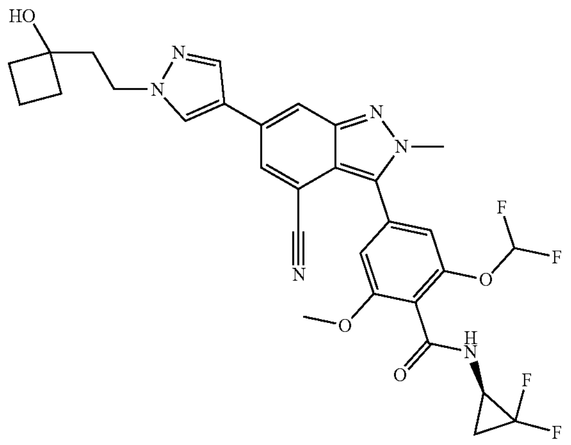 [SMILES: COc1cc(-c2c3c(C#N)cc(-c4cnn(CCC5(O)CCC5)c4)cc3nn2C)cc(OC(F)F)c1C(=O)N[C@@H]1CC1(F)F]

A mixture of 4-[4-cyano-2-methyl-6-(4,4,5,5-tetramethyl-1,3,2-dioxaborolan-2-yl)indazol-3-yl]-N-[(1R)-2,2-difluorocyclopropyl]-2-(difluoromethoxy)-6-methoxybenzamide (72 mg) described in Reference Example 99, 1-[2-(4-iodopyrazol-1-yl)ethyl] cyclobutan-1-ol (55 mg) described in Reference Example 116, [1,1'-bis(di-tert-butylphosphino)ferrocene]palladium(II) dichloride (8.2 mg), tripotassium phosphate (53 mg), 1,4-dioxane (1.5 mL), and water (0.15 mL) was heated and stirred under a nitrogen atmosphere at 50 °C for 2 hours and 30 minutes. After the reaction was completed, water was added to the reaction mixture, and extraction was performed three times with chloroform. The residue obtained by concentrating the organic layer under reduced pressure was sequentially purified by NH silica gel column chromatography (ethyl acetate: methanol=100:0 to 98:2), preparative HPLC (10 mM aqueous ammonium carbonate solution-acetonitrile), and silica gel column chromatography (chloroform:methanol=100:0 to 93:7) to obtain the title compound (28 mg) as a colorless powder. MS(ESI)m/z:613.1 [M+H]+

Example 124: Synthesis of 4-[4-cyano-2-methyl-6-[1-[(2S)-3,3,3-trifluoro-2-hydroxypropyl]pyrazol-4-yl]indazol-3-yl]-N-[(1R)-2,2-difluorocyclopropyl]-2-(difluoromethoxy)-6-methoxybenzamide

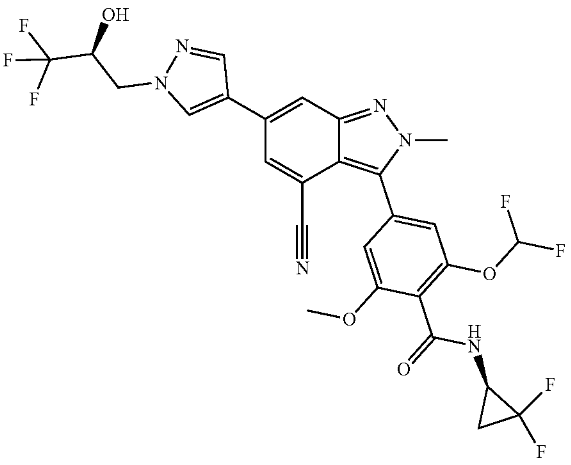 [SMILES: COc1cc(-c2c3c(C#N)cc(-c4cnn(C[C@H](O)C(F)(F)F)c4)cc3nn2C)cc(OC(F)F)c1C(=O)N[C@@H]1CC1(F)F]

'A mixture of (2S)-1,1,1-trifluoro-3-(4-iodopyrazol-1-yl) propan-2-ol (64 mg) synthesized by the method described in US 2016/0031892 A, 4-[4-cyano-2-methyl-6-(4,4,5,5-tetramethyl-1,3,2-dioxaborolan-2-yl)indazol-3-yl]-N-[(1R)-2,2-difluorocyclopropyl]-2-(difluoromethoxy)-6-methoxybenzamide (100 mg) described in Reference Example 99, [1,1'-bis(di-tert-butylphosphino)ferrocene]palladium(II) dichloride (11 mg), tripotassium phosphate (111 mg), 1,4-dioxane (1.2 mL), and water (0.20 mL) was heated and stirred under a nitrogen atmosphere at 40 °C. overnight. After the reaction was completed, the reaction mixture was diluted with ethyl acetate and dried with magnesium sulfate, insoluble matter was filtered, and the filtrate was concentrated under reduced pressure. The residue was sequentially purified by preparative HPLC (10 mM aqueous ammonium carbonate solution-acetonitrile) and NH silica gel column chromatography (hexane:ethyl acetate=100:0 to 20:80) to obtain the title compound (14 mg) as a colorless powder. MS(ESI)m/z:627.3 [M+H]+

Example 125: Synthesis of 4-[4-cyano-6-[1-[(2S)-2-hydroxypropyl]pyrazol-4-yl]-2-methylindazol-3-yl]-2-(difluoromethoxy)-6-methoxybenzamide

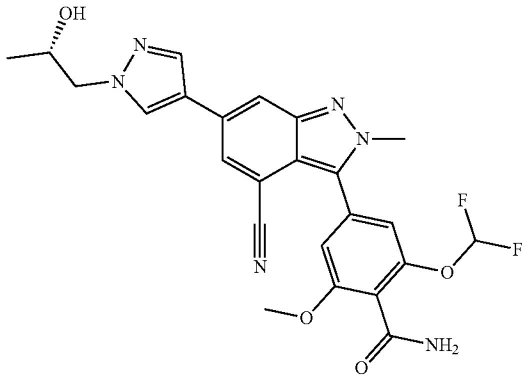 [SMILES: COc1cc(-c2c3c(C#N)cc(-c4cnn(C[C@H](C)O)c4)cc3nn2C)cc(OC(F)F)c1C(N)=O]

A mixture of 4-(6-bromo-4-cyano-2-methylindazol-3-yl)-2-(difluoromethoxy)-6-methoxybenzamide (80 mg) described in Reference Example 86, bis(pinacolato)diboron (50 mg), a [1,1'-bis(diphenylphosphino)ferrocene]palladium (II) dichloride dichloromethane adduct (7.2 mg), potassium acetate (52 mg), and 1-methylpyrrolidin-2-one (0.89 mL) was heated and stirred under a nitrogen atmosphere at 100 °C for 1.5 hours. After the reaction mixture was allowed to cool to room temperature, (2S)-1-(4-Iodopyrazol-1-yl)propan-2-ol (47 mg), tripotassium phosphate (75 mg), a [1,1'-bis(diphenylphosphino)ferrocene]palladium(II) dichloride dichloromethane adduct (7.2 mg), and water (0.18 mL) were added, and the mixture was heated and stirred under a nitrogen atmosphere at 80 °C. again for 1 hour. After the reaction was completed, the reaction mixture was diluted with ethyl acetate and dried with sodium sulfate, insoluble matter was filtered, and the filtrate was concentrated under reduced pressure. The crude product obtained by purifying the residue by column chromatography (ethyl acetate: methanol=98:2 to 90:10) using an NH silica gel column and a Si silica gel column in series was mixed with activated carbon (25 mg) and ethyl acetate (5.0 ml), and the mixture was allowed to stand at room temperature for 30 minutes. The mixture was filtered and concentrated under reduced pressure and suspended and washed with a solvent obtained by mixing diethyl ether and ethyl acetate at 9:1 to obtain the title compound (35 mg) as a light brown powder.

MS(ESI)m/z:497.0 [M+H]+

Example 126: Synthesis of 2-methyl-3-[rel-(4R)-8-methoxy-4-methyl-1-oxo-3,4-dihydro-2H-isoquinolin-6-yl]-6-[1-(2,2,2-trifluoroethyl)pyrazol-4-yl]indazole-4-carbonitrile

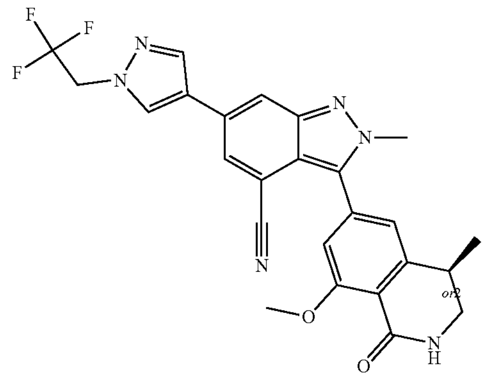 [SMILES: COc1cc(-c2c3c(C#N)cc(-c4cnn(CC(F)(F)F)c4)cc3nn2C)cc2c1C(=O)NC[C@@H]2C]

A mixture of an isomer (30 mg) that eluted earlier under chiral HPLC conditions as described in the experimental section of 6-bromo-2-methyl-3-[rel-(4R)-8-methoxy-4-methyl-1-oxo-3,4-dihydro-2H-isoquinolin-6-yl]indazole-4-carbonitrile described in Reference Example 97, 4-(4,4,5,5-tetramethyl-1,3,2-dioxaborolan-2-yl)-1-(2,2,2-trifluoroethyl)pyrazole (23 mg), a [1,1'-bis(diphenylphosphino)ferrocene]palladium(II) dichloride dichloromethane adduct (5.8 mg), potassium carbonate (20 mg), 1,4-dioxane (0.71 mL), and water (0.18 mL) was heated and stirred under a nitrogen atmosphere at 100 °C for 5 hours. After the reaction was completed, chloroform was added to the reaction mixture, and then the organic layer was separated with Phase-Separator® and concentrated under reduced pressure. The residue was purified by NH silica gel column chromatography (ethyl acetate:methanol=100:0 to 90:10) and preparative HPLC (10 mM aqueous ammonium carbonate solution-acetonitrile) to obtain the title compound (25 mg) as a white powder. MS(ESI)m/z:495.3 [M+H]+

Example 127: Synthesis of 6-[1-(2-methoxyethyl)pyrazol-4-yl]-2-methyl-3-[rel-(4R)-8-methoxy-4-methyl-1-oxo-3,4-dihydro-2H-isoquinolin-6-yl]indazole-4-carbonitrile

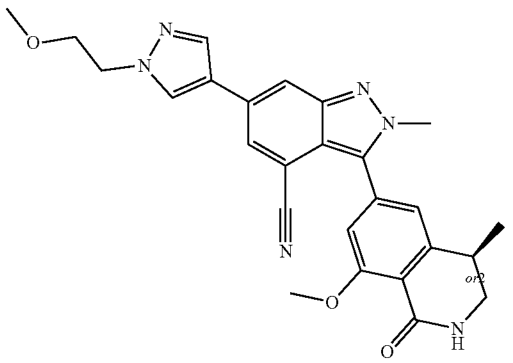

A mixture of an isomer (30 mg) that eluted earlier under chiral HPLC conditions as described in the experimental section of 6-bromo-2-methyl-3-[rel-(4R)-8-methoxy-4-methyl-1-oxo-3,4-dihydro-2H-isoquinolin-6-yl]indazole-4-carbonitrile described in Reference Example 97, 1-(2-methoxyethyl)-4-(4,4,5,5-tetramethyl-1,3,2-dioxaborolan-2-yl)pyrazole (17 mg), a [1,1'-bis(diphenylphosphino) ferrocene]palladium(II) dichloride dichloromethane adduct (4.6 mg), potassium carbonate (16 mg), 1,4-dioxane (0.56 mL), and water (0.14 mL) was heated and stirred under a nitrogen atmosphere at 100 °C for 2 hours. After the reaction was completed, chloroform, sodium sulfate, and activated carbon were added to the reaction mixture, and then the organic layer was separated with Phase-Separator® and concentrated under reduced pressure. The residue was purified by preparative HPLC (10 mM aqueous ammonium carbonate solution-acetonitrile) to obtain the title compound (14 mg) as a white powder. MS(ESI)m/z:471.0 [M+H]+

Example 128: Synthesis of 6-[1-(difluoromethyl)pyrazol-4-yl]-2-methyl-3-[rel-(4R)-8-methoxy-4-methyl-1-oxo-3,4-dihydro-2H-isoquinolin-6-yl]indazole-4-carbonitrile

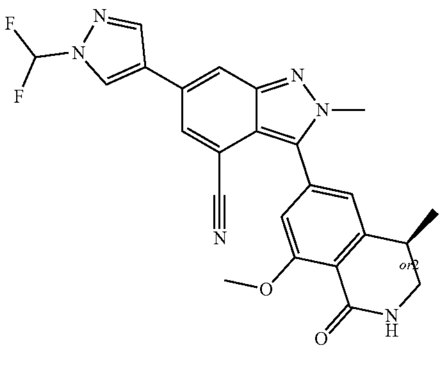 [SMILES: COc1cc(-c2c3c(C#N)cc(-c4cnn(C(F)F)c4)cc3nn2C)cc2c1C(=O)NC[C@@H]2C]

A mixture of an isomer (30 mg) that eluted earlier under chiral HPLC conditions as described in the experimental section of 6-bromo-2-methyl-3-[rel-(4R)-8-methoxy-4-methyl-1-oxo-3,4-dihydro-2H-isoquinolin-6-yl]indazole-4-carbonitrile described in Reference Example 97, 1-(difluoromethyl)-4-(4,4,5,5-tetramethyl-1,3,2-dioxaborolan-2-yl) pyrazole (21 mg), a [1,1'-bis(diphenylphosphino)ferrocene] palladium(II) dichloride dichloromethane adduct (5.8 mg), potassium carbonate (20 mg), 1,4-dioxane (0.71 mL), and water (0.18 mL) was heated and stirred under a nitrogen atmosphere at 100 °C for 3 hours. After the reaction was completed, chloroform was added to the reaction mixture, and then the organic layer was separated with Phase-Separator® and concentrated under reduced pressure. The residue was sequentially purified by NH silica gel column chromatography (ethyl acetate:methanol=100:0 to 90:10) and preparative HPLC (10 mM aqueous ammonium carbonate solution-acetonitrile) to obtain the title compound (26 mg) as a white powder. MS(ESI)m/z:463.3 [M+H]+

Example 129: Synthesis of 3-(8-methoxy-4,4-dimethyl-1-oxo-2,3-dihydroisoquinolin-6-yl)-2-methyl-6-(1-methylpyrazol-4-yl)indazol-4-carbonitrile

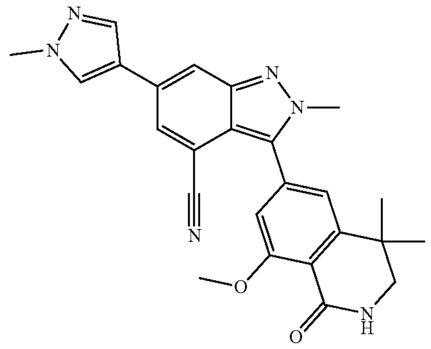

A mixture of 6-bromo-3-(8-methoxy-4,4-dimethyl-1-oxo-2,3-dihydroisoquinolin-6-yl)-2-methylindazole-4-carbonitrile (45 mg) described in Reference Example 128, 1-methyl-4-(4,4,5,5-tetramethyl-1,3,2-dioxaborolan-2-yl) pyrazole (26 mg), [1,1'-bis(di-tert-butylphosphino)ferrocene]palladium(II) dichloride (3.3 mg), potassium carbonate (28 mg), 1,4-dioxane (0.68 mL), and water (0.17 mL) was heated and stirred under a nitrogen atmosphere at 100 °C for 2 hours. After the reaction was completed, water was added to the reaction mixture, and extraction was performed three times with chloroform. The organic layer was separated with Phase-Separator®, and the organic layer was concentrated under reduced pressure. The residue was sequentially purified by NH silica gel column chromatography (ethyl acetate: methanol=100:0 to 90:10) and preparative HPLC (10 mM aqueous ammonium carbonate solution-acetonitrile) to obtain the title compound (38 mg) as a white powder. MS(ESI)m/z:441.3 [M+H]+

Example 130: Synthesis of 2-(difluoromethoxy)-6-methoxy-4-[4-methoxy-2-methyl-6-(1-methylpyrazol-4-yl)indazol-3-yl]benzamide

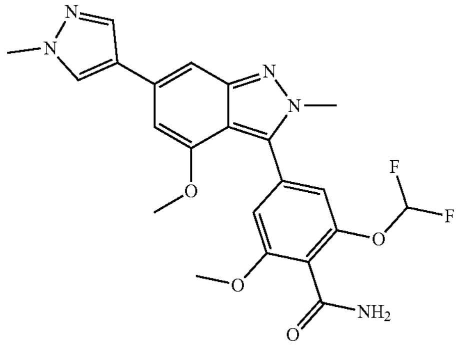 [SMILES: COc1cc(-c2c3c(OC)cc(-c4cnn(C)c4)cc3nn2C)cc(OC(F)F)c1C(N)=O]

2-(Difluoromethoxy)-6-methoxy-4-[4-methoxy-2-methyl-6-(1-methylpyrazol-4-yl)indazol-3-yl]benzoic acid (40 mg) described in Reference Example 51 was dissolved in N,N-dimethylformamide (0.87 mL), N,N-diisopropylethylamine (66 μL) and HATU (37 mg) were added, and the mixture was stirred at room temperature for 10 minutes. Next, ammonium carbonate (9.2 mg) was added, and the mixture was stirred under a nitrogen atmosphere at room temperature overnight. After the reaction was completed, water (10 mL) was added, the mixture was stirred for 30 minutes, and then a precipitate was collected by filtration. The resulting solid was washed with water and diethyl ether to obtain the title compound (25 mg) as a white powder. MS(ESI)m/z:458.3 [M+H]+

Example 131: Synthesis of 2-(difluoromethoxy)-4-[4-(difluoromethoxy)-2-methyl-6-(1-methylpyrazol-4-yl)indazol-3-yl]-6-methoxybenzamide

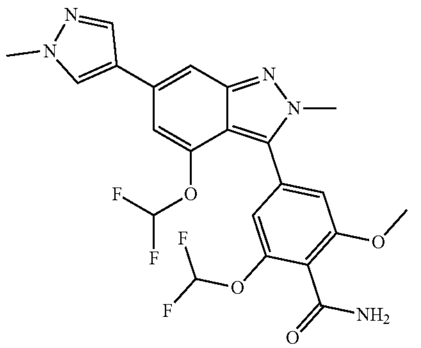

tert-Butyl 2-(difluoromethoxy)-4-[4-(difluoromethoxy)-2-methyl-6-(1-methylpyrazol-4-yl)indazol-3-yl]-6-methoxybenzoate (39 mg) described in Reference Example 131 was dissolved in dichloromethane (0.50 mL), TFA (0.50 mL) was added, and the mixture was stirred at room temperature for 1 hour. After the reaction was completed, the reaction mixture was concentrated under reduced pressure, and an azeotropic treatment was performed three times using toluene. The resulting residue was dissolved in N,N-dimethylformamide (0.71 mL), HATU (32 mg) and N,N-diisopropylethylamine (54 μL) were added, and the mixture was stirred at room temperature for 10 minutes. Next, ammonium carbonate (8.2 mg) was added, and the mixture was stirred at room temperature overnight. After the reaction was completed, purification was performed by preparative HPLC (10 mM aqueous ammonium carbonate solution-acetonitrile), and then suspension and washing were performed with diethyl ether to obtain the title compound (35 mg) as a colorless powder.

MS(ESI)m/z:494.3 [M+H]+

Example 132: Synthesis of 4-[4-cyano-2-methyl-6-(1-propan-2-ylpyrazol-4-yl)indazol-3-yl]-2-(difluoromethoxy)-6-methoxybenzamide

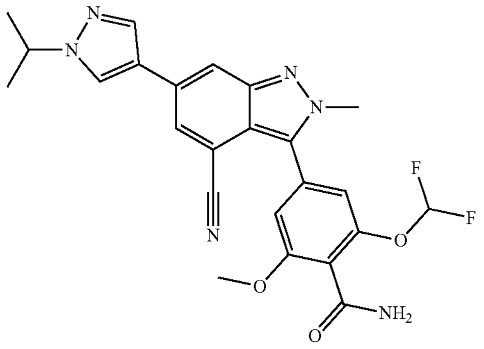 [SMILES: COc1cc(-c2c3c(C#N)cc(-c4cnn(C(C)C)c4)cc3nn2C)cc(OC(F)F)c1C(N)=O]

A mixture of 4-(6-bromo-4-cyano-2-methylindazol-3-yl)-2-(difluoromethoxy)-6-methoxybenzamide (55 mg) described in Reference Example 86, 1-isopropyl-4-(4,4,5,5-tetramethyl-1,3,2-dioxaborolan-2-yl)pyrazole (35 mg), tripotassium phosphate (78 mg), a [1,1'-bis(diphenylphosphino)ferrocene]palladium(II) dichloride dichloromethane adduct (10 mg), water (0.25 mL), and 1,4-dioxane (1.0 mL) was heated and stirred under a nitrogen atmosphere at 100 °C for 2 hours. After the reaction was completed, ethyl acetate and magnesium sulfate were added to the reaction mixture, and filtration was performed. The filtrate was concentrated under reduced pressure, and the resulting residue was purified by preparative HPLC (10 mM aqueous ammonium carbonate solution-acetonitrile) to obtain the title compound (53 mg) as a colorless powder. MS(ESI)m/z:481.4 [M+H]+

Example 133: Synthesis of 4-[4-cyano-6-[1-(2-methoxyethyl)pyrazol-4-yl]-2-methylindazol-3-yl]-2-(difluoromethoxy)-6-methoxybenzamide

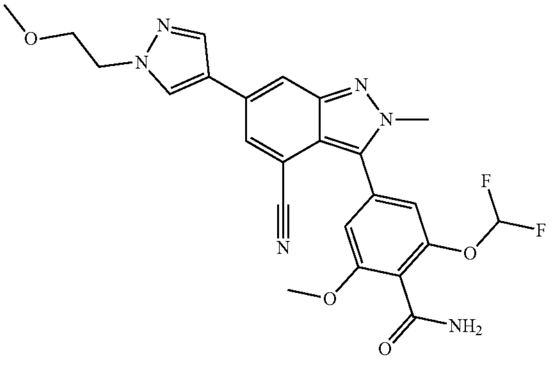 [SMILES: COCCn1cc(-c2cc(C#N)c3c(-c4cc(OC)c(C(N)=O)c(OC(F)F)c4)n(C)nc3c2)cn1]

A mixture of 4-(6-bromo-4-cyano-2-methylindazol-3-yl)-2-(difluoromethoxy)-6-methoxybenzamide (40 mg) described in Reference Example 86, 1-(2-methoxyethyl)-4-(4,4,5,5-tetramethyl-1,3,2-dioxaborolan-2-yl)-1H-pyrazole (27 mg), tripotassium phosphate (56 mg), a [1,1'-bis(diphenylphosphino)ferrocene]palladium(II) dichloride dichloromethane adduct (7.2 mg), water (0.20 mL), and 1,4-dioxane (1.0 mL) was heated and stirred under a nitrogen atmosphere at 100 °C for 2 hours. After the reaction was completed, ethyl acetate and magnesium sulfate were added to the reaction mixture, and filtration was performed. The filtrate was concentrated under reduced pressure, and the resulting residue was purified by preparative HPLC (10 mM aqueous ammonium carbonate solution-acetonitrile) to obtain the title compound (40 mg) as a colorless powder. MS(ESI)m/z:497.3 [M+H]+

Example 134: Synthesis of 2-(difluoromethoxy)-4-[4-(difluoromethyl)-6-[1-(2-methoxyethyl)pyrazol-4-yl]-2-methylindazol-3-yl]-6-methoxybenzamide

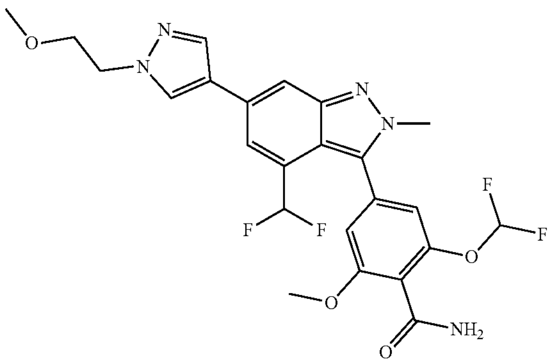 [SMILES: COCCn1cc(-c2cc(C(F)F)c3c(-c4cc(OC)c(C(N)=O)c(OC(F)F)c4)n(C)nc3c2)cn1]

The same reaction and treatment as in Example 133 were performed using 4-[6-bromo-4-(difluoromethyl)-2-methylindazol-3-yl]-2-(difluoromethoxy)-6-methoxybenzamide described in Reference Example 135 and 1-(2-methoxyethyl)-4-(4,4,5,5-tetramethyl-1,3,2-dioxaborolan-2-yl)-1H-pyrazole as raw materials to obtain the title compound. MS(ESI)m/z:522.3 [M+H]+

Example 135: Synthesis of 4-[4-cyano-2-methyl-6-[1-(2-methylpropyl)pyrazol-4-yl]indazol-3-yl]-2-(difluoromethoxy)-6-methoxybenzamide

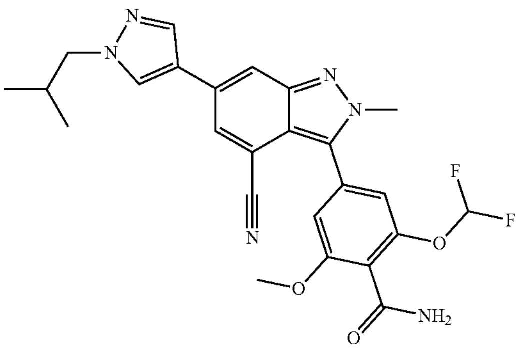 [SMILES: COc1cc(-c2c3c(C#N)cc(-c4cnn(CC(C)C)c4)cc3nn2C)cc(OC(F)F)c1C(N)=O]

A mixture of 4-(6-bromo-4-cyano-2-methylindazol-3-yl)-2-(difluoromethoxy)-6-methoxybenzamide (55 mg) described in Reference Example 86, 1-isobutyl-4-(4,4,5,5-tetramethyl-1,3,2-dioxaborolan-2-yl)pyrazole (37 mg), tripotassium phosphate (78 mg), a [1,1'-bis(diphenylphosphino)ferrocene]palladium(II) dichloride dichloromethane adduct (10 mg), water (0.25 mL), and 1,4-dioxane (1.0 mL) was heated and stirred under a nitrogen atmosphere at 100 °C for 2 hours. After the reaction was completed, ethyl acetate and magnesium sulfate were added to the reaction mixture, and filtration was performed. The filtrate was concentrated under reduced pressure, and the resulting residue was purified by preparative HPLC (10 mM aqueous ammonium carbonate solution-acetonitrile) and then suspended and washed with diethyl ether to obtain the title compound (48 mg) as a colorless powder.

MS(ESI)m/z:495.4 [M+H]+

Example 136: Synthesis of 2-(difluoromethoxy)-4-[4-ethoxy-2-methyl-6-(1-methylpyrazol-4-yl)indazol-3-yl]-6-methoxybenzamide

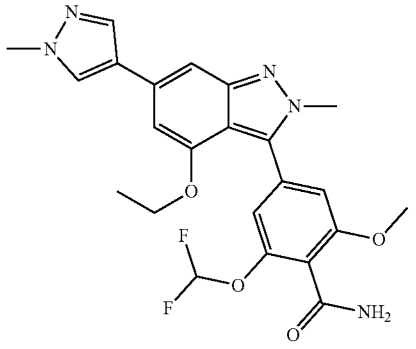

tert-Butyl 2-(difluoromethoxy)-4-[4-ethoxy-2-methyl-6-(1-methylpyrazol-4-yl)indazol-3-yl]-6-methoxybenzoate (79 mg) described in Reference Example 60 was dissolved in dichloromethane (1.0 mL), TFA (1.0 mL) was added thereto, and the mixture was stirred at room temperature for 1 hour. After the reaction was completed, the reaction mixture was concentrated under reduced pressure, and an azeotropic treatment was performed three times using toluene. The resulting residue was dissolved in N,N-dimethylformamide (0.83 mL), HATU (75 mg) and N,N-diisopropylethylamine (0.13 mL) were added, and the mixture was stirred at room temperature for 10 minutes. Next, ammonium carbonate (19 mg) was added, and the mixture was stirred at room temperature overnight. After the reaction was completed, purification was performed by preparative HPLC (10 mM aqueous ammonium carbonate solution-acetonitrile) to obtain the title compound (37 mg) as a colorless powder. MS(ESI)m/z:472.3 [M+H]+

Example 137: Synthesis of 4-[4-cyano-6-[1-[2-(1-hydroxycyclobutyl)ethyl]pyrazol-4-yl]-2-methylindazol-3-yl]-2-(difluoromethoxy)-6-methoxybenzamide

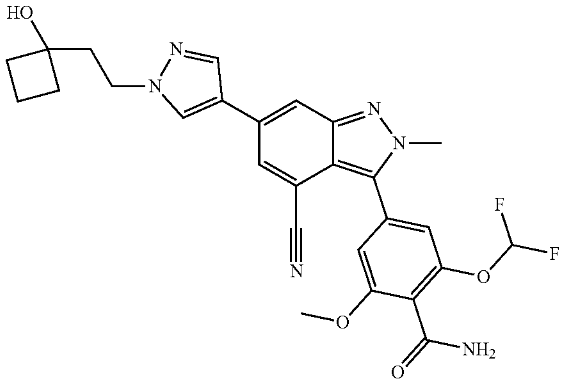 [SMILES: COc1cc(-c2c3c(C#N)cc(-c4cnn(CCC5(O)CCC5)c4)cc3nn2C)cc(OC(F)F)c1C(N)=O]

A mixture of 4-[4-cyano-2-methyl-6-(4,4,5,5-tetramethyl-1,3,2-dioxaborolan-2-yl)indazol-3-yl]-2-(difluoromethoxy)-6-methoxybenzamide (65 mg) described in Reference Example 105, 1-[2-(4-iodopyrazol-1-yl)ethyl]cyclobutan-1-ol (46 mg) described in Reference Example 116, tripotassium phosphate (83 mg), a [1,1'-bis(diphenylphosphino)ferrocene]palladium(II) dichloride dichloromethane adduct (11 mg), water (0.25 mL), and 1,4-dioxane (1.0 mL) was heated and stirred under a nitrogen atmosphere at 100 °C for 2 hours. After the reaction was completed, ethyl acetate and magnesium sulfate were added to the reaction mixture, and filtration was performed.

The filtrate was concentrated under reduced pressure, and the resulting residue was purified by preparative HPLC (10 mM aqueous ammonium carbonate solution-acetonitrile) to obtain the title compound (31 mg) as a colorless powder. MS(ESI)m/z:537.4 [M+H]+

Example 138: Synthesis of 4-[4-cyano-6-[1-(cyclopropylmethyl)pyrazol-4-yl]-2-methylindazol-3-yl]-2-(difluoromethoxy)-6-methoxybenzamide

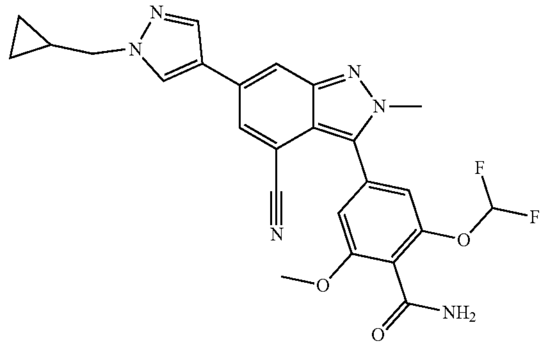 [SMILES: COc1cc(-c2c3c(C#N)cc(-c4cnn(CC5CC5)c4)cc3nn2C)cc(OC(F)F)c1C(N)=O]

A mixture of 4-(6-bromo-4-cyano-2-methylindazol-3-yl)-2-(difluoromethoxy)-6-methoxybenzamide (40 mg) described in Reference Example 86, 1-(cyclopropylmethyl)-4-(4,4,5,5-tetramethyl-1,3,2-dioxaborolan-2-yl)pyrazole (26 mg), tripotassium phosphate (56 mg), [1,1'-bis(di-tert-butylphosphino)ferrocene]palladium(II) dichloride (2.9 mg), 1,4-dioxane (0.75 mL), and water (0.13 mL) was stirred under a nitrogen atmosphere at 90 °C for 2 hours. After the reaction was completed, water was added, and extraction was performed twice with ethyl acetate. The organic layers were combined, washed with saturated saline, dried with sodium sulfate, and filtered. The filtrate was concentrated under reduced pressure, and the resulting residue was purified by NH silica gel column chromatography (ethyl acetate:methanol=100:0 to 90:10) to obtain the title compound (34 mg) as a light brown powder. MS(ESI)m/z: 493.4 [M+H]+

Example 139: Synthesis of 6-(1-ethylpyrazol-4-yl)-3-(8-methoxy-4,4-dimethyl-1-oxo-2,3-dihydroisoquinolin-6-yl)-2-methylindazole-4-carbonitrile

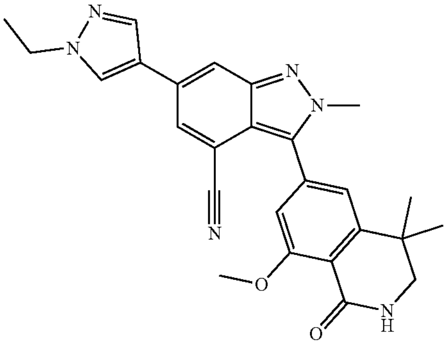 [SMILES: CCn1cc(-c2cc(C#N)c3c(-c4cc(OC)c5c(c4)C(C)(C)CNC5=O)n(C)nc3c2)cn1]

A mixture of 6-bromo-3-(8-methoxy-4,4-dimethyl-1-oxo-2,3-dihydroisoquinolin-6-yl)-2-methylindazole-4-carbonitrile (45 mg) described in Reference Example 128, (1-ethylpyrazol-4-yl) boronic acid (17 mg), potassium carbonate (28 mg), [1,1'-bis(di-tert-butylphosphino)ferrocene]palladium(II) dichloride (3.3 mg), 1,4-dioxane (0.68 mL), and water (0.17 mL) was stirred under a nitrogen atmosphere at 100 °C for 2 hours. After the reaction was completed, water was added, and extraction was performed with chloroform. The organic layer was separated with Phase-Separator®, and the organic layer was concentrated under reduced pressure. The resulting residue was purified by NH silica gel column chromatography (ethyl acetate:methanol=100:0 to 93:7) and suspended and washed with diethyl ether to obtain the title compound (11 mg) as a light brown powder.

MS(ESI)m/z:455.1 [M+H]+

Example 140: Synthesis of 3-(8-methoxy-4,4-dimethyl-1-oxo-2,3-dihydroisoquinolin-6-yl)-2-methyl-6-(1-propylpyrazol-4-yl)indazol-4-carbonitrile

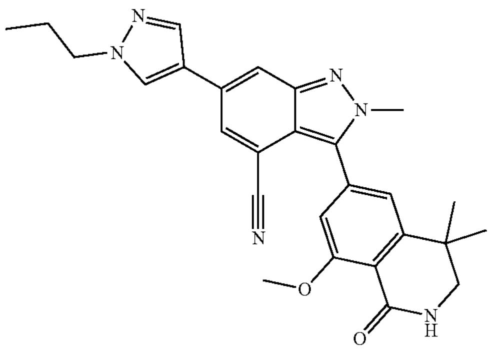 [SMILES: CCCn1cc(-c2cc(C#N)c3c(-c4cc(OC)c5c(c4)C(C)(C)CNC5=O)n(C)nc3c2)cn1]

The same reaction and treatment as in Example 139 were performed using (1-propylpyrazol-4-yl) boronic acid as a raw material to obtain the title compound. MS(ESI)m/z: 469.1 [M+H]+

Example 141: Synthesis of 4-[4-cyano-6-(1-ethylpyrazol-4-yl)-2-methylindazol-3-yl]-2-(difluoromethoxy)-6-methoxybenzamide

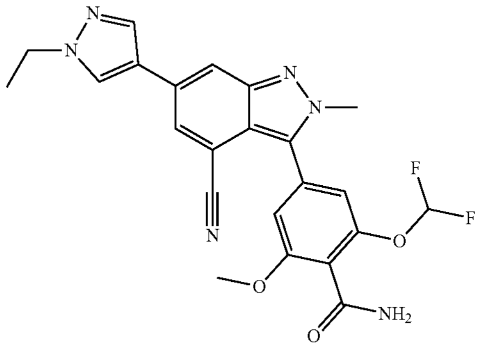 [SMILES: CCn1cc(-c2cc(C#N)c3c(-c4cc(OC)c(C(N)=O)c(OC(F)F)c4)n(C)nc3c2)cn1]

A mixture of 4-(6-bromo-4-cyano-2-methylindazol-3-yl)-2-(difluoromethoxy)-6-methoxybenzamide (50 mg) described in Reference Example 86, (1-ethyl-1H-pyrazol-4-yl) boronic acid (23 mg), a [1,1'-bis(diphenylphosphino) ferrocene]palladium(II) dichloride dichloromethane adduct (9.0 mg), tripotassium phosphate (71 mg), 1,4-dioxane (1.0 mL), and water (0.10 mL) was stirred under a nitrogen atmosphere at 100 °C for 3 hours. Water was added to reaction solution, and extraction was performed three times with chloroform. The organic layers were combined and concentrated under reduced pressure. The resulting residue and (1-ethyl-1H-pyrazol-4-yl) boronic acid (31 mg), [1,1'-bis(di-tert-butylphosphino)ferrocene]palladium(II) dichloride (7.2 mg), and tripotassium phosphate (71 mg) were suspended in 1,4-dioxane (1.0 mL) and water (0.10 mL), and stirring was performed under a nitrogen atmosphere at 100 °C for 1.5 hours. After the reaction was completed, water was added, and extraction was performed three times with chloroform. The organic layers were combined and concentrated under reduced pressure, and the resulting residue was sequentially purified by NH silica gel column chromatography (ethyl acetate:methanol=100:0 to 95:5), preparative HPLC (10 mM aqueous ammonium carbonate solution-acetonitrile), and NH silica gel column chromatography (ethyl acetate: methanol=100:0 to 95:5) to obtain the title compound (32 mg) as a colorless powder. MS(ESI)m/z:467.1 [M+H]+

Example 142: Synthesis of 4-[4-cyano-6-[1-(3-hydroxy-3-methylbutyl)pyrazol-4-yl]-2-methylindazol-3-yl]-2-(difluoromethoxy)-6-methoxybenzamide

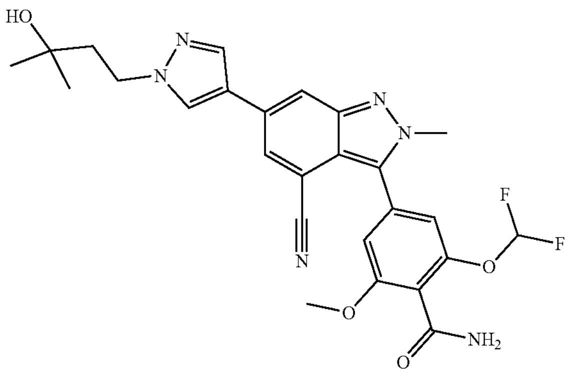 [SMILES: COc1cc(-c2c3c(C#N)cc(-c4cnn(CCC(C)(C)O)c4)cc3nn2C)cc(OC(F)F)c1C(N)=O]

A mixture of 4-[4-cyano-2-methyl-6-(4,4,5,5-tetramethyl-1,3,2-dioxaborolan-2-yl)indazol-3-yl]-2-(difluoromethoxy)-6-methoxybenzamide (70 mg) described in Reference Example 105, 4-(4-iodopyrazol-1-yl)-2-methylbutan-2-ol (47 mg) described in Reference Example 101, tripotassium phosphate (89 mg), a [1,1'-bis(diphenylphosphino)ferrocene]palladium(II) dichloride dichloromethane adduct (5.7 mg), water (0.23 mL), and 1,4-dioxane (0.94 mL) was heated and stirred under a nitrogen atmosphere at 100 °C for 3 hours. After the reaction was completed, ethyl acetate and magnesium sulfate were added to the reaction mixture, and filtration was performed. The filtrate was concentrated under reduced pressure, and the resulting residue was purified by preparative HPLC (10 mM aqueous ammonium carbonate solution-acetonitrile) and then purified by silica gel column chromatography (chloroform:methanol=100:0 to 90:10) to obtain the title compound (18 mg) as a colorless powder. MS(ESI)m/z:525.4 [M+H]+

Example 143: Synthesis of 3-(8-methoxy-4,4-dimethyl-1-oxo-2,3-dihydroisoquinolin-6-yl)-6-[1-(2-methoxyethyl)pyrazol-4-yl]-2-methylindazole-4-carbonitrile

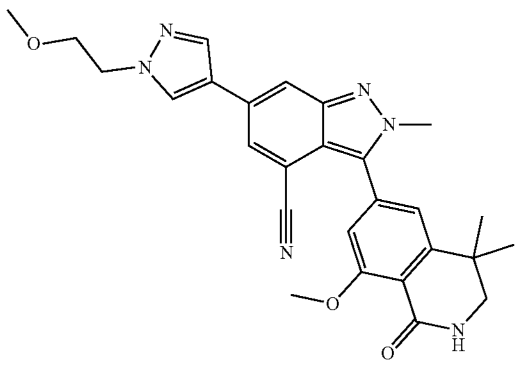

A mixture of 6-bromo-3-(8-methoxy-4,4-dimethyl-1-oxo-2,3-dihydroisoquinolin-6-yl)-2-methylindazole-4-carbonitrile (50 mg) described in Reference Example 128, 1-(2-methoxyethyl)-4-(4,4,5,5-tetramethyl-1,3,2-dioxaborolan-2-yl)pyrazole (34 mg), [1,1'-bis(di-tert-butylphosphino)ferrocene]palladium(II) dichloride (3.7 mg), potassium carbonate (31 mg), 1,4-dioxane (0.76 mL), and water (0.19 mL) was stirred under a nitrogen atmosphere at 100 °C for 2 hours. After the reaction was completed, water was added, and extraction was performed with chloroform. The organic layer was separated with Phase-Separator®, and the organic layer was concentrated under reduced pressure. The resulting residue was sequentially purified by NH silica gel column chromatography (ethyl acetate:methanol=100:0 to 90:10) and preparative HPLC (10 mM aqueous ammonium carbonate solution-acetonitrile) to obtain the title compound (43 mg) as a white powder.

MS(ESI)m/z:485.4 [M+H]+

Example 144: Synthesis of 6-[1-[(2S)-2-hydroxypropyl]pyrazol-4-yl]-3-(8-methoxy-4,4-dimethyl-1-oxo-2,3-dihydroisoquinolin-6-yl)-2-methylindazole-4-carbonitrile

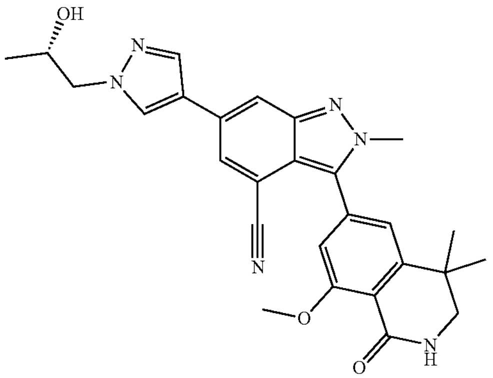 [SMILES: COc1cc(-c2c3c(C#N)cc(-c4cnn(C[C@H](C)O)c4)cc3nn2C)cc2c1C(=O)NCC2(C)C]

A mixture of 6-bromo-3-(8-methoxy-4,4-dimethyl-1-oxo-2,3-dihydroisoquinolin-6-yl)-2-methylindazole-4-carbonitrile (50 mg) described in Reference Example 128, (2S)-1-[4-(4,4,5,5-tetramethyl-1,3,2-dioxaborolan-2-yl)pyrazol-1-yl]propan-2-ol (37 mg) synthesized by the method described in WO 2022/081627 A, [1,1'-bis(di-tert-butylphosphino)ferrocene]palladium(II) dichloride (7.4 mg), potassium carbonate (31 mg), 1,4-dioxane (0.76 mL), and water (0.19 mL) was stirred under a nitrogen atmosphere at 100 °C for 1 hour. After the reaction was completed, water was added, and extraction was performed with chloroform. The organic layer was separated with Phase-Separator®, and the organic layer was concentrated under reduced pressure. The resulting residue was purified by NH silica gel column chromatography (ethyl acetate:methanol=100:0 to 90:10) and then suspended and washed with a mixed solvent of diethyl ether and ethyl acetate to obtain the title compound (38 mg) as a light brown powder. MS(ESI)m/z:485.1 [M+H]+

Example 145: Synthesis of 2-(difluoromethoxy)-4-[4-(2-hydroxyethoxy)-2-methyl-6-(1-methylpyrazol-4-yl)indazol-3-yl]-6-methoxybenzamide

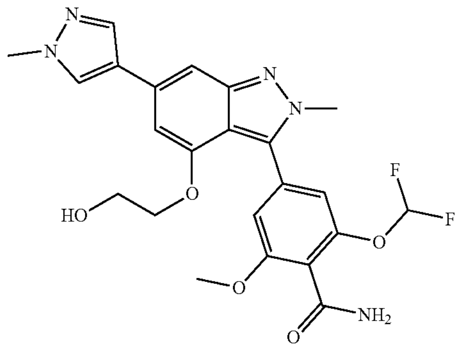 [SMILES: COc1cc(-c2c3c(OCCO)cc(-c4cnn(C)c4)cc3nn2C)cc(OC(F)F)c1C(N)=O]

2-(Difluoromethoxy)-4-[4-hydroxy-2-methyl-6-(1-methylpyrazol-4-yl)indazol-3-yl]-6-methoxybenzamide (60 mg) described in Reference Example 134 was dissolved in N,N-dimethylformamide (1.0 mL), 2-(2-bromoethoxy)tetrahydropyran (31 μL) and potassium carbonate (56 mg) were added, and the mixture was stirred at 80 °C for 1 hour. After the reaction was completed, water was added, and extraction was performed with chloroform. The organic layer was separated with Phase-Separator®, and the organic layer was concentrated under reduced pressure. The resulting residue was dissolved in methanol (2.0 mL), 1 N hydrochloric acid (0.41 mL) was added, and the mixture was stirred at room temperature for 2.5 hours. After the reaction was completed, a 1 N aqueous sodium hydroxide solution and a saturated aqueous sodium bicarbonate solution were added, and extraction was performed with chloroform. The organic layer was separated with Phase-Separator®, and the organic layer was concentrated under reduced pressure. The resulting residue was purified by preparative HPLC (10 mM aqueous ammonium carbonate solution-acetonitrile) and then suspended and washed with diethyl ether to obtain the title compound (46 mg) as a light yellow powder. MS(ESI) m/z:488.0 [M+H]+

Example 146: Synthesis of 3-(8-methoxy-4,4-dimethyl-1-oxo-2,3-dihydroisoquinolin-6-yl)-2-methyl-6-[1-(2,2,2-trifluoroethyl)pyrazol-4-yl]indazole-4-carbonitrile

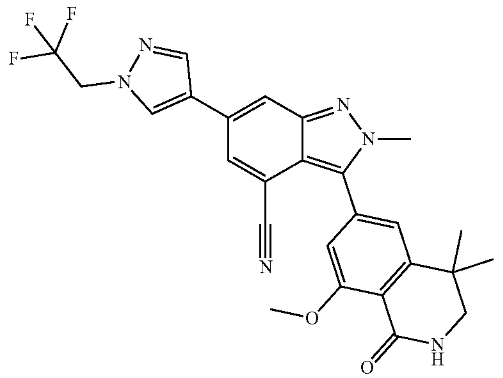 [SMILES: COc1cc(-c2c3c(C#N)cc(-c4cnn(CC(F)(F)F)c4)cc3nn2C)cc2c1C(=O)NCC2(C)C]

A mixture of 6-bromo-3-(8-methoxy-4,4-dimethyl-1-oxo-2,3-dihydroisoquinolin-6-yl)-2-methylindazole-4-carbonitrile (50 mg) described in Reference Example 128, 4-(4,4,5,5-tetramethyl-1,3,2-dioxaborolan-2-yl)-1-(2,2,2-trifluoroethyl)pyrazole (41 mg), [1,1'-bis(di-tert-butylphosphino)ferrocene]palladium(II) dichloride (3.7 mg), tripotassium phosphate (48 mg), 1,4-dioxane (1.5 mL), and water (0.30 mL) was stirred under a nitrogen atmosphere at 95 °C for 45 minutes. After the reaction was completed, water was added, and extraction was performed twice with ethyl acetate. The organic layers were combined, purified by NH silica gel column chromatography (ethyl acetate:methanol=100:0 to 90:10), and suspended and washed with ethyl acetate to obtain the title compound (36 mg) as a white powder. MS(ESI)m/z:509.0 [M+H]+

Example 147: Synthesis of 3-(8-methoxy-4,4-dimethyl-1-oxo-2,3-dihydroisoquinolin-6-yl)-2-methyl-6-(1H-pyrazol-4-yl)indazol-4-carbonitrile

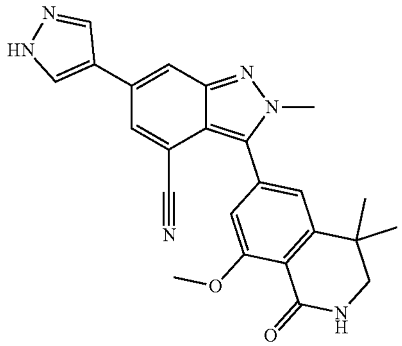 [SMILES: COc1cc(-c2c3c(C#N)cc(-c4cn[nH]c4)cc3nn2C)cc2c1C(=O)NCC2(C)C]

A mixture of 6-bromo-3-(8-methoxy-4,4-dimethyl-1-oxo-2,3-dihydroisoquinolin-6-yl)-2-methylindazole-4-carbonitrile (30 mg) described in Reference Example 128, 1-tetrahydropyran-2-yl-4-(4,4,5,5-tetramethyl-1,3,2-dioxaborolan-2-yl)pyrazole (23 mg), [1,1'-bis(di-tert-butylphosphino) ferrocene]palladium(II) dichloride (2.2 mg), potassium carbonate (19 mg), 1,4-dioxane (0.46 mL), and water (0.11 mL) was heated and stirred under a nitrogen atmosphere at 100 °C for 3 hours. After the reaction was completed, chloroform and sodium sulfate were added, filtration was performed, and the filtrate was concentrated. The resulting residue was dissolved in dichloromethane (0.34 mL), TFA (0.34 mL) was added, and the mixture was stirred at room temperature for 30 minutes. After the reaction was completed, a saturated aqueous sodium bicarbonate solution was added, and extraction was performed with chloroform. The organic layer was separated with Phase-Separator®, and the organic layer was concentrated under reduced pressure. The resulting residue was purified by NH silica gel column chromatography (ethyl acetate:methanol=100:0 to 93:7) and then suspended and washed with diethyl ether to obtain the title compound (10 mg) as a white powder. MS(ESI)m/z: 427.2 [M+H]+

Example 148: Synthesis of 4-[4-cyano-2-methyl-6-(1H-pyrazol-4-yl)indazol-3-yl]-N-[(1R)-2,2-difluorocyclopropyl]-2-(difluoromethoxy)-6-methoxybenzamide

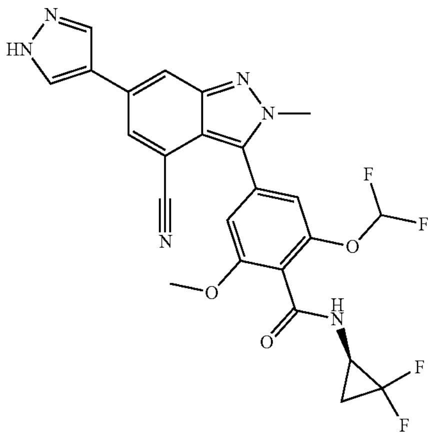 [SMILES: COc1cc(-c2c3c(C#N)cc(-c4cn[nH]c4)cc3nn2C)cc(OC(F)F)c1C(=O)N[C@@H]1CC1(F)F]

4-[4-Cyano-2-methyl-6-[1-(oxan-2-yl)pyrazol-4-yl]indazol-3-yl]-N-[(1R)-2,2-difluorocyclopropyl]-2-(difluoromethoxy)-6-methoxybenzamide (87 mg) described in Reference Example 117 was dissolved in methanol (2.0 mL), 6 N hydrochloric acid (73 μL) was added, and the mixture was stirred at room temperature for 2.5 hours. After the reaction was completed, a saturated aqueous sodium bicarbonate solution was added, and extraction was performed three times with chloroform. The organic layers were combined, concentrated under reduced pressure, purified by silica gel column chromatography (chloroform:methanol=100:0 to 92:8), and then suspended and washed with ethyl acetate to obtain the title compound (47 mg) as a colorless powder. MS(ESI)m/z:515.0 [M+H]+

Example 149: Synthesis of 4-[4-cyano-2-methyl-6-(1H-pyrazol-3-yl)indazol-3-yl]-N-[(1R)-2,2-difluorocyclopropyl]-2-(difluoromethoxy)-6-methoxybenzamide

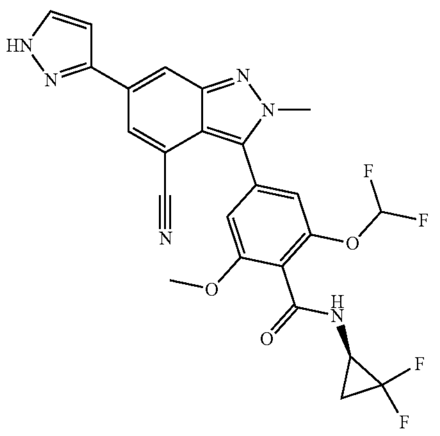 [SMILES: COc1cc(-c2c3c(C#N)cc(-c4cc[nH]n4)cc3nn2C)cc(OC(F)F)c1C(=O)N[C@@H]1CC1(F)F]

4-[4-Cyano-2-methyl-6-[1-(oxan-2-yl)pyrazol-3-yl]indazol-3-yl]-N-[(1R)-2,2-difluorocyclopropyl]-2-(difluoromethoxy)-6-methoxybenzamide (104 mg) described in Reference Example 118 was dissolved in a mixed solvent of methanol (2.0 mL) and tetrahydrofuran (3.0 mL), 6 N hydrochloric acid (87 μL) was added, and the mixture was stirred at room temperature for 2 hours. After the reaction was completed, a saturated aqueous sodium bicarbonate solution was added, and extraction was performed three times with chloroform. The organic layers were combined, concentrated under reduced pressure, and purified by silica gel column chromatography (chloroform:methanol=100:0 to 92:8) and preparative HPLC (10 mM aqueous ammonium carbonate solution-acetonitrile) to obtain the title compound (59 mg) as a colorless powder. MS(ESI)m/z:515.3 [M+H]+.

Example 150: Synthesis of N-[(1R)-2,2-difluorocyclopropyl]-2-(difluoromethoxy)-4-[4-(difluoromethyl)-2-methyl-6-(1H-pyrazol-4-yl)indazol-3-yl]-6-methoxybenzamide

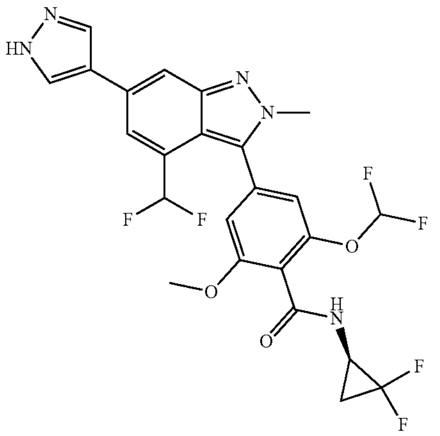 [SMILES: COc1cc(-c2c3c(C(F)F)cc(-c4cn[nH]c4)cc3nn2C)cc(OC(F)F)c1C(=O)N[C@@H]1CC1(F)F]

N-[(1R)-2,2-difluorocyclopropyl]-2-(difluoromethoxy)-4-[4-(difluoromethyl)-2-methyl-6-[1-(oxan-2-yl)pyrazol-4-yl]indazol-3-yl]-6-methoxybenzamide (123 mg) described in Reference Example 119 was dissolved in methanol (2.0 mL), 6 N hydrochloric acid (99 μL) was added, and the mixture was stirred at room temperature for 4.5 hours. After the reaction was completed, a saturated aqueous sodium bicarbonate solution was added, and extraction was performed three times with chloroform. The organic layers were combined, concentrated under reduced pressure, purified by silica gel column chromatography (chloroform: methanol=100:0 to 93:7), and suspended and washed with a mixed solvent of diethyl ether and ethyl acetate to obtain the title compound (64 mg) as a colorless powder. MS(ESI)m/z:540.0 [M+H]+

Example 151: Synthesis of 3-(8-methoxy-4,4-dimethyl-1-oxo-2,3-dihydroisoquinolin-6-yl)-6-[1-(3-methoxypropyl)pyrazol-4-yl]-2-methylindazole-4-carbonitrile

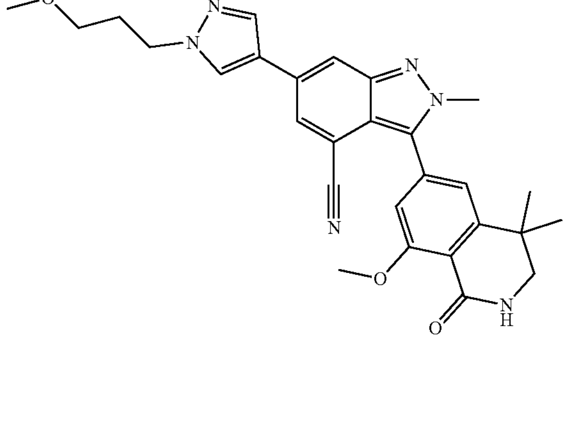

6-Bromo-3-(8-methoxy-4,4-dimethyl-1-oxo-2,3-dihydroisoquinolin-6-yl)-2-methylindazole-4-carbonitrile (40 mg) described in Reference Example 128, 1-(3-methoxypropyl)-4-(4,4,5,5-tetramethyl-1,3,2-dioxaborolan-2-yl)pyrazole (39 mg), [1,1'-bis(di-tert-butylphosphino)ferrocene]palladium(II) dichloride (3.0 mg), and potassium carbonate (25 mg) were suspended in a mixed solvent of 1,4-dioxane (0.61 mL) and water (0.15 mL), and stirring was performed under a nitrogen atmosphere at 100 °C for 1 hour. 1-(3-Methoxypropyl)-4-(4,4,5,5-tetramethyl-1,3,2-dioxaborolan-2-yl)pyrazole (39 mg) was added, and the mixture was stirred under a nitrogen atmosphere at 100 °C for 30 minutes. After the reaction was completed, chloroform and sodium sulfate were added to the reaction mixture, and filtration was performed. The filtrate was concentrated under reduced pressure, and the residue was purified by NH silica gel column chromatography (ethyl acetate:methanol=100:0 to 93:7) and preparative HPLC (10 mM aqueous ammonium carbonate solution-acetonitrile) and suspended and washed with diethyl ether to obtain the title compound (19 mg) as a white powder. MS(ESI)m/z:499.4 [M+H]+

Example 152: Synthesis of 6-[1-(2-ethoxyethyl)pyrazol-4-yl]-3-(8-methoxy-4,4-dimethyl-1-oxo-2,3-dihydroisoquinolin-6-yl)-2-methylindazole-4-carbonitrile

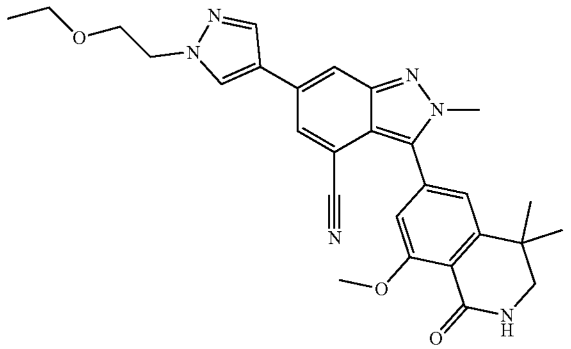 [SMILES: CCOCCn1cc(-c2cc(C#N)c3c(-c4cc(OC)c5c(c4)C(C)(C)CNC5=O)n(C)nc3c2)cn1]

6-Bromo-3-(8-methoxy-4,4-dimethyl-1-oxo-2,3-dihydroisoquinolin-6-yl)-2-methylindazole-4-carbonitrile (40 mg) described in Reference Example 128, 1-(2-ethoxyethyl)-4-(4,4,5,5-tetramethyl-1,3,2-dioxaborolan-2-yl)pyrazole (36 mg), [1,1'-bis(di-tert-butylphosphino)ferrocene]palladium(II) dichloride (3.0 mg), and potassium carbonate (25 mg) were suspended in a mixed solvent of 1,4-dioxane (0.61 mL) and water (0.15 mL), and stirring was performed under a nitrogen atmosphere at 100 °C for 1 hour. After the reaction was completed, chloroform and sodium sulfate were added, and filtration was performed. The filtrate was concentrated under reduced pressure, and the resulting residue was purified by NH silica gel column chromatography (ethyl acetate:methanol=100:0 to 93:7) and then suspended and washed with diethyl ether to obtain the title compound (23 mg) as a white powder. MS(ESI)m/z:499.4 [M+H]+

Example 153: Synthesis of 4-[4-cyano-6-[1-[(2R)-2-hydroxypropyl]pyrazol-4-yl]-2-methylindazol-3-yl]-N-[(1R)-2,2-difluorocyclopropyl]-2-(difluoromethoxy)-6-methoxybenzamide

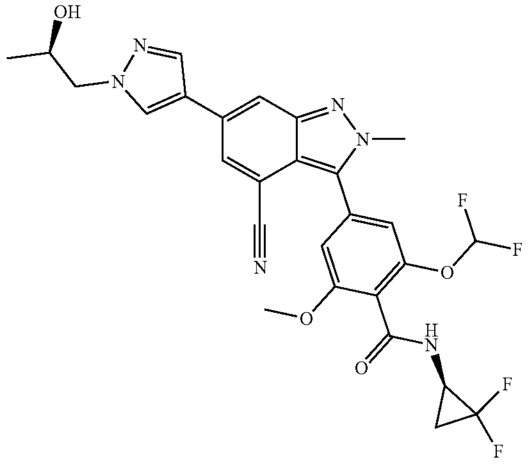 [SMILES: COc1cc(-c2c3c(C#N)cc(-c4cnn(C[C@@H](C)O)c4)cc3nn2C)cc(OC(F)F)c1C(=O)N[C@@H]1CC1(F)F]

4-(6-Bromo-4-cyano-2-methylindazol-3-yl)-N-[(1R)-2,2-difluorocyclopropyl]-2-(difluoromethoxy)-6-methoxybenzamide (113 mg) described in Reference Example 82, (2R)-1-[4-(4,4,5,5-tetramethyl-1,3,2-dioxaborolan-2-yl)pyrazol-1-yl]propan-2-ol (76 mg) synthesized by the method described in WO 2022/081627 A, tripotassium phosphate (137 mg), and [1,1'-bis(di-tert-butylphosphino)ferrocene]palladium(II) dichloride (7.0 mg) were suspended in a mixed solvent of 1,4-dioxane (2.0 mL) and water (0.40 mL), and stirring was performed under a nitrogen atmosphere at 45 °C for 30 minutes. [1,1'-Bis(di-tert-butylphosphino)ferrocene]palladium(II) dichloride (7.0 mg) was added, and the mixture was stirred under a nitrogen atmosphere at 45 °C for 30 minutes. After the reaction was completed, water was added, and extraction was performed twice with ethyl acetate. The organic layers were combined and washed with saturated saline, sodium sulfate was added, and filtration was performed. The filtrate was concentrated under reduced pressure, and the residue was purified by silica gel column chromatography (ethyl acetate:methanol=100:0 to 95:5) and then suspended and washed with a mixed solvent of ethyl acetate and diethyl ether to obtain the title compound (37 mg) as a white powder. MS(ESI)m/z:573.0 [M+H]+

Example 154: Synthesis of 2-(difluoromethoxy)-4-[4-(difluoromethoxy)-6-[1-(2-methoxyethyl)pyrazol-4-yl]-2-methylindazol-3-yl]-6-methoxybenzamide

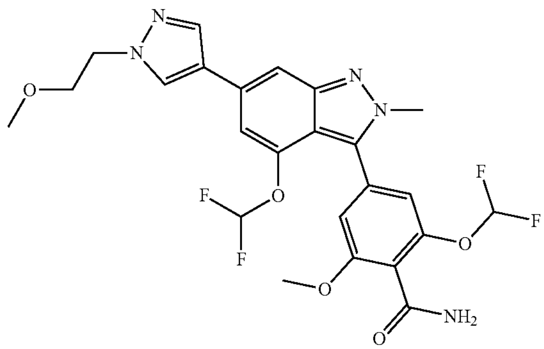 [SMILES: COCCn1cc(-c2cc(OC(F)F)c3c(-c4cc(OC)c(C(N)=O)c(OC(F)F)c4)n(C)nc3c2)cn1]

4-[6-Bromo-4-(difluoromethoxy)-2-methylindazol-3-yl]-2-(difluoromethoxy)-6-methoxybenzamide (70 mg) described in Reference Example 132, 1-(2-methoxyethyl)-4-(4,4,5,5-tetramethyl-1,3,2-dioxaborolan-2-yl)pyrazole (38 mg), [1,1'-bis(di-tert-butylphosphino)ferrocene]palladium (II) dichloride (8.2 mg), and potassium carbonate (35 mg) were suspended in a mixed solvent of water (0.20 mL) and 1,4-dioxane (2.0 mL), and heating and stirring were performed under a nitrogen atmosphere at 100 °C for 2 hours. After the reaction was completed, ethyl acetate and magnesium sulfate were added to the reaction mixture, and filtration was performed. The filtrate was concentrated under reduced pressure, and the resulting residue was purified by preparative HPLC (10 mM aqueous ammonium carbonate solution-acetonitrile) to obtain the title compound (47 mg) as a colorless powder. MS(ESI)m/z:538.3 [M+H]+

Example 155: Synthesis of 2-(difluoromethoxy)-4-[4-(difluoromethoxy)-6-(1-ethylpyrazol-4-yl)-2-methylindazol-3-yl]-6-methoxybenzamide

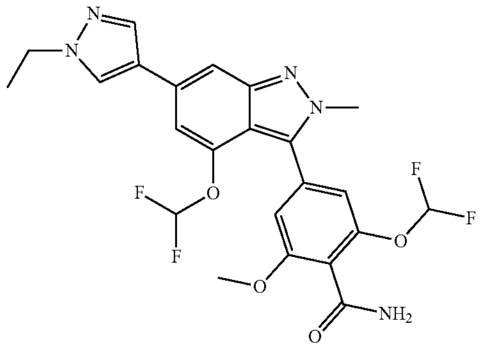 [SMILES: CCn1cc(-c2cc(OC(F)F)c3c(-c4cc(OC)c(C(N)=O)c(OC(F)F)c4)n(C)nc3c2)cn1]

4-[6-Bromo-4-(difluoromethoxy)-2-methylindazol-3-yl]-2-(difluoromethoxy)-6-methoxybenzamide (70 mg) described in Reference Example 132, 1-ethyl-4-(4,4,5,5-tetramethyl-1,3,2-dioxaborolan-2-yl)pyrazole (34 mg), [1,1'-bis(di-tert-butylphosphino)ferrocene]palladium(II) dichloride (8.2 mg), and potassium carbonate (35 mg) were suspended in a mixed solvent of water (0.20 mL) and 1,4-dioxane (0.63 mL), and heating and stirring were performed under a nitrogen atmosphere at 100 °C for 2 hours. After the reaction was completed, ethyl acetate and magnesium sulfate were added to the reaction mixture, and filtration was performed. The filtrate was concentrated under reduced pressure, and the resulting residue was purified by preparative HPLC (10 mM aqueous ammonium carbonate solution-acetonitrile) and preparative HPLC (0.05% aqueous TFA solution-0.05% TFA acetonitrile solution) to obtain the title compound (26 mg) as a colorless powder. MS(ESI) m/z:508.3 [M+H]+

Example 156: Synthesis of 4-[4-(2,2-difluoroethoxy)-2-methyl-6-(1-methylpyrazol-4-yl)indazol-3-yl]-2-(difluoromethoxy)-6-methoxybenzamide

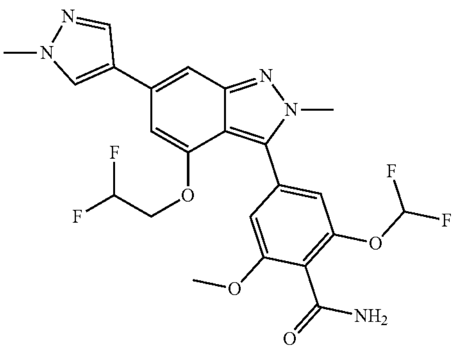 [SMILES: COc1cc(-c2c3c(OCC(F)F)cc(-c4cnn(C)c4)cc3nn2C)cc(OC(F)F)c1C(N)=O]

4-[6-Bromo-4-(2,2-difluoroethoxy)-2-methylindazol-3-yl]-2-(difluoromethoxy)-6-methoxybenzamide (33 mg) described in Reference Example 137, 1-methyl-4-(4,4,5,5-tetramethyl-1,3,2-dioxaborolan-2-yl)pyrazole (16 mg), [1,1'-bis(di-tert-butylphosphino)ferrocene]palladium(II) dichloride (4.2 mg), and potassium carbonate (27 mg) were suspended in a mixed solvent of water (0.20 mL) and 1,4-dioxane (1.0 mL), and heating and stirring were performed under a nitrogen atmosphere at 100 °C for 2 hours. After the reaction was completed, the reaction solution was purified by silica gel column chromatography (ethyl acetate: methanol=100:0 to 90:10 to 85:15) and suspended and washed with a mixed solvent of diethyl ether and ethyl acetate to obtain the title compound (20 mg) as a light yellow powder. MS(ESI)m/z:508.0 [M+H]+

Example 157: Synthesis of 2-(difluoromethoxy)-6-methoxy-4-[2-methyl-6-(1-methylpyrazol-4-yl)-4-(2,2,2-trifluoroethoxy)indazol-3-yl]benzamide

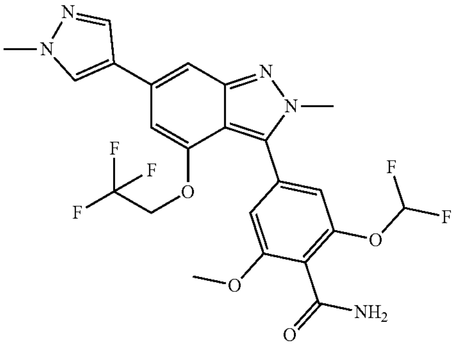 [SMILES: COc1cc(-c2c3c(OCC(F)(F)F)cc(-c4cnn(C)c4)cc3nn2C)cc(OC(F)F)c1C(N)=O]

4-[6-Bromo-2-methyl-4-(2,2,2-trifluoroethoxy)indazol-3-yl]-2-(difluoromethoxy)-6-methoxybenzamide (33 mg) described in Reference Example 138, 1-methyl-4-(4,4,5,5-tetramethyl-1,3,2-dioxaborolan-2-yl)pyrazole (16 mg), [1,1'-bis(di-tert-butylphosphino)ferrocene]palladium(II) dichloride (4.1 mg), and potassium carbonate (26 mg) were suspended in a mixed solvent of water (0.20 mL) and 1,4-dioxane (1.0 mL), and heating and stirring were performed under a nitrogen atmosphere at 100 °C for 2 hours. After the reaction was completed, ethyl acetate and magnesium sulfate were added to the reaction mixture, and filtration was performed. The filtrate was concentrated under reduced pressure, and the resulting residue was purified by NH silica gel column chromatography (ethyl acetate:methanol=100:0 to 90:10) and then suspended and washed with diethyl ether to obtain the title compound (20 mg) as a colorless powder. MS(ESI)m/z:526.0 [M+H]+

Example 158: Synthesis of 2-(difluoromethoxy)-4-[4-(difluoromethyl)-2-methyl-6-[1-[(3S)-oxolan-3-yl]pyrazol-4-yl]indazol-3-yl]-6-methoxybenzamide

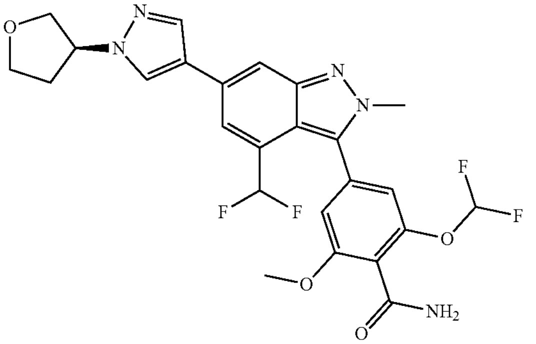 [SMILES: COc1cc(-c2c3c(C(F)F)cc(-c4cnn([C@H]5CCOC5)c4)cc3nn2C)cc(OC(F)F)c1C(N)=O]

4-[6-Bromo-4-(difluoromethyl)-2-methylindazol-3-yl]-2-(difluoromethoxy)-6-methoxybenzamide (150 mg) described in Reference Example 135, bis(pinacolato)diboron (88 mg), a [1,1'-bis(diphenylphosphino)ferrocene]palladium(II) dichloride dichloromethane adduct (26 mg), and potassium acetate (93 mg) were suspended in 1,4-dioxane (2.0 mL), and heating and stirring were performed under a nitrogen atmosphere at 100 °C for 4 hours. After the reaction was completed, chloroform was added to the reaction mixture, and filtration was performed. The 'filtrate was concentrated under reduced pressure, half of the resulting residue was dissolved in 1,4-dioxane (2.0 mL), 4-iodo-1-[(3S)-oxolan-3-yl]pyrazole (50 mg) described in Reference Example 8, tripotassium phosphate (101 mg), a [1,1'-bis(diphenylphosphino)ferrocene]palladium(II) dichloride dichloromethane adduct (13 mg), and water (0.20 mL) were added, and the mixture was stirred under a nitrogen atmosphere at 100 °C. again for 2 hours. After the reaction was completed, chloroform and magnesium sulfate were added, and filtration was performed. The filtrate was concentrated, and the resulting residue was purified by preparative HPLC (10 mM aqueous ammonium carbonate solution-acetonitrile) and preparative HPLC (0.05% aqueous TFA solution-0.05% TFA acetonitrile solution) to obtain the title compound (27 mg) as a light yellow powder. MS(ESI)m/z:534.0 [M+H]+

Example 159: Synthesis of 2-(difluoromethoxy)-4-[4-(difluoromethyl)-2-methyl-6-[1-[(3R)-oxolan-3-yl]pyrazol-4-yl]indazol-3-yl]-6-methoxybenzamide

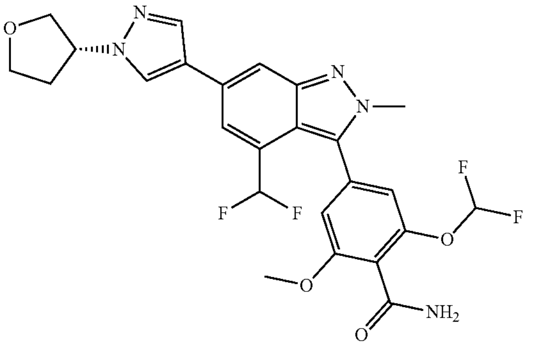 [SMILES: COc1cc(-c2c3c(C(F)F)cc(-c4cnn([C@@H]5CCOC5)c4)cc3nn2C)cc(OC(F)F)c1C(N)=O]

The same reaction and treatment as in Example 158 were performed using 4-iodo-1-[(3R)-oxolan-3-yl]pyrazole synthesized by the method described in US 2007/0219218 A as a raw material to obtain the title compound.

MS(ESI)m/z:534.0 [M+H]+

Example 160: Synthesis of 3-[8-(difluoromethoxy)-4-methyl-1-oxo-3,4-dihydro-2H-isoquinolin-6-yl]-2-methyl-6-(1-methylpyrazol-4-yl)indazol-4-carbonitrile

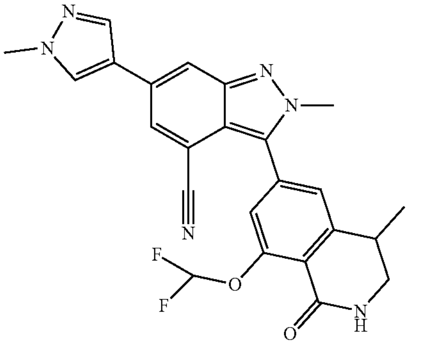

6-Bromo-3-[8-(difluoromethoxy)-4-methyl-1-oxo-3,4-dihydro-2H-isoquinolin-6-yl]-2-methylindazole-4-carbonitrile (57 mg) described in Reference Example 141, 1-methyl-4-(4,4,5,5-tetramethyl-1,3,2-dioxaborolan-2-yl)pyrazole (39 mg), [1,1'-bis(di-tert-butylphosphino)ferrocene]palladium(II) dichloride (3.1 mg), and tripotassium phosphate (40 mg) were suspended in a mixed solvent of water (0.16 mL) and 1,4-dioxane (0.63 mL), and heating and stirring were performed under a nitrogen atmosphere at 100 °C for 1 hour. After the reaction was completed, the reaction mixture was diluted with chloroform, activated carbon and sodium sulfate were added, and filtration was performed. The filtrate was concentrated under reduced pressure, and the resulting residue was purified by preparative HPLC (10 mM aqueous ammonium carbonate solution-acetonitrile) and then suspended and washed with diethyl ether to obtain the title compound (12 mg) as a white powder.

MS(ESI)m/z:463.3 [M+H]+

Example 161: Synthesis of 8-(difluoromethoxy)-6-[4-methoxy-2-methyl-6-(1-methylpyrazol-4-yl)indazol-3-yl]-4-methyl-3,4-dihydro-2H-isoquinolin-1-one

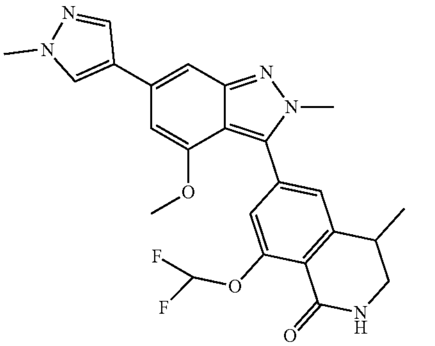

The same reaction and treatment as in Example 160 were performed using 6-(6-bromo-4-methoxy-2-methylindazol-3-yl)-8-(difluoromethoxy)-4-methyl-3,4-dihydro-2H-isoquinolin-1-one described in Reference Example 142 as a raw material to obtain the title compound. MS(ESI)m/z: 468.3 [M+H]+

Example 162: Synthesis of 3-[8-(difluoromethoxy)-4,4-dimethyl-1-oxo-2,3-dihydroisoquinolin-6-yl]-2-methyl-6-(1-methylpyrazol-4-yl)indazol-4-carbonitrile

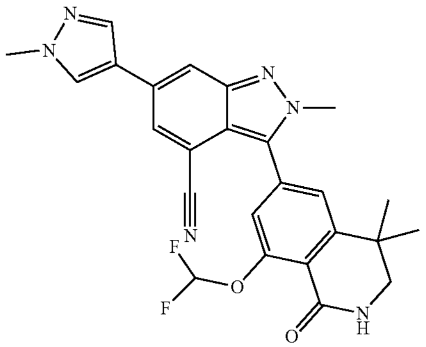

A mixture of 6-bromo-3-[8-(difluoromethoxy)-4,4-dimethyl-1-oxo-2,3-dihydroisoquinolin-6-yl]-2-methyl-indazole-4-carbonitrile (30 mg) described in Reference Example 150, 1-methyl-4-(4,4,5,5-tetramethyl-1,3,2-dioxaborolan-2-yl)pyrazole (16 mg), [1,1'-bis(di-tert-butylphosphino)ferrocene]palladium(II) dichloride (2.1 mg), potassium carbonate (17 mg), 1,4-dioxane (0.42 mL), and water (0.11 mL) was heated and stirred under a nitrogen atmosphere at 100 °C for 1 hour. After the reaction was completed, the reaction mixture was diluted with water, and extraction was performed with chloroform. The organic layer was separated with Phase-Separator® and concentrated under reduced pressure, and then the resulting residue was purified by NH silica gel column chromatography (ethyl acetate:methanol=100:0 to 93:7) and then purified by preparative HPLC (10 mM aqueous ammonium carbonate solution-acetonitrile) to obtain the title compound (17 mg) as a white powder.

MS(ESI)m/z:477.0 [M+H]+

Example 163: Synthesis of rel-(4R)-6-[4-ethoxy-2-methyl-6-(1-methylpyrazol-4-yl)indazol-3-yl]-8-methoxy-4-methyl-3,4-dihydro-2H-isoquinolin-1-one

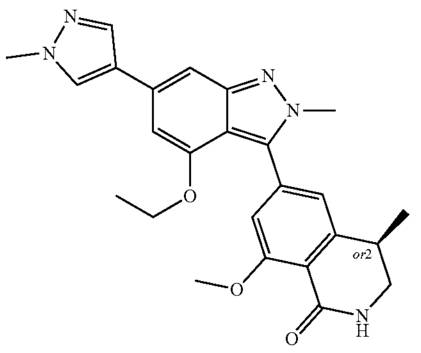

A mixture of rel-(4R)-6-(6-bromo-4-ethoxy-2-methyl-indazol-3-yl)-8-methoxy-4-methyl-3,4-dihydro-2H-isoquinolin-1-one (70 mg) described in Reference Example 144, 1-methyl-4-(4,4,5,5-tetramethyl-1,3,2-dioxaborolan-2-yl) pyrazole (39 mg), tripotassium phosphate (67 mg), [1,1'-bis (di-tert-butylphosphino)ferrocene]palladium(II) dichloride (10 mg), 1,4-dioxane (1.1 mL), and water (0.26 mL) was heated and stirred under a nitrogen atmosphere at 100 °C for 2 hours. After the reaction was completed, chloroform was added to the reaction mixture, the organic layer was separated with Phase-Separator®, and then the organic layer was concentrated under reduced pressure. The resulting residue was purified by preparative HPLC (10 mM aqueous ammonium carbonate solution-acetonitrile) to obtain the title compound (39 mg) as a light brown powder.

MS(ESI)m/z:446.2 [M+H]+

Example 164: Synthesis of rel-(4R)-6-[4-(difluoromethoxy)-2-methyl-6-(1-methylpyrazol-4-yl)indazol-3-yl]-8-methoxy-4-methyl-3,4-dihydro-2H-isoquinolin-1-one

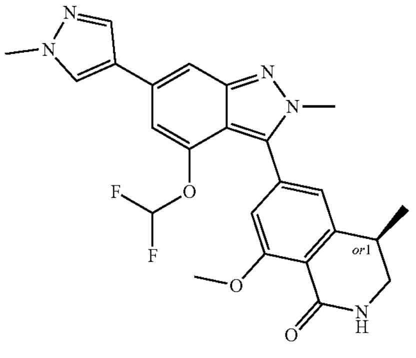

A mixture of rel-(4R)-6-[6-bromo-4-(difluoromethoxy)-2-methyl-indazol-3-yl]-8-methoxy-4-methyl-3,4-dihydro-2H-isoquinolin-1-one (82 mg) described in Reference Example 151, 1-methyl-4-(4,4,5,5-tetramethyl-1,3,2-dioxaborolan-2-yl)pyrazole (44 mg), tripotassium phosphate (75 mg), [1,1'-bis(di-tert-butylphosphino)ferrocene]palladium (II) dichloride (11 mg), 1,4-dioxane (2.0 mL), and water (0.40 mL) was heated and stirred under a nitrogen atmosphere at 100 °C for 2 hours. After the reaction was completed, ethyl acetate and magnesium sulfate were added to the reaction mixture, filtration was performed, and then the filtrate was concentrated under reduced pressure. The resulting residue was sequentially purified by NH silica gel column chromatography (ethyl acetate:methanol=100:0 to 85:15) and preparative HPLC (10 mM aqueous ammonium carbonate solution-acetonitrile) to obtain the title compound (41 mg) as a colorless powder. MS(ESI)m/z:468.3 [M+H]+

Example 165: Synthesis of isomer that elutes earlier under chiral HPLC conditions as described in experimental section in rel-(4R)-8-(difluoromethoxy)-6-[4-methoxy-2-methyl-6-(1-methylpyrazol-4-yl)indazol-3-yl]-4-methyl-3,4-dihydro-2H-isoquinolin-1-one

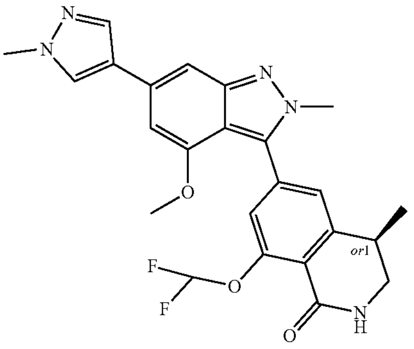

8-(Difluoromethoxy)-6-[4-methoxy-2-methyl-6-(1-methylpyrazol-4-yl)indazol-3-yl]-4-methyl-3,4-dihydro-2H-isoquinolin-1-one (21 mg) described in Example 161 was fractionated using a chiral column [CHIRALPAK® IC (30*250), methanol]. The previous fractions were collected and concentrated to obtain the title compound (9.3 mg) as a white powder. MS(ESI)m/z:468.0 [M+H]+

Example 166: Synthesis of isomer that elutes later under chiral HPLC conditions as described in experimental section in rel-(4R)-8-(difluoromethoxy)-6-[4-methoxy-2-methyl-6-(1-methylpyrazol-4-yl)indazol-3-yl]-4-methyl-3,4-dihydro-2H-isoquinolin-1-one

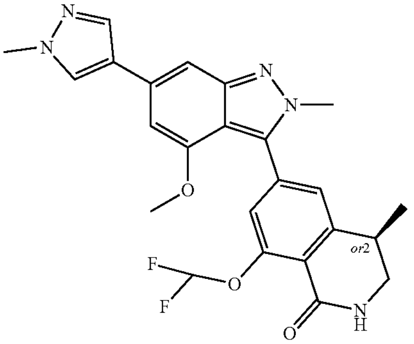

8-(Difluoromethoxy)-6-[4-methoxy-2-methyl-6-(1-methylpyrazol-4-yl)indazol-3-yl]-4-methyl-3,4-dihydro-2H-isoquinolin-1-one (21 mg) described in Example 161 was fractionated using a chiral column [CHIRALPAK® IC (30*250), methanol]. The subsequent fractions were collected and concentrated to obtain the title compound (9.2 mg) as a white powder. MS(ESI)m/z:468.0 [M+H]+

Example 167: Synthesis of 6-(1-isopropylpyrazol-4-yl)-2-methyl-3-[rel-(4R)-8-methoxy-4-methyl-1-oxo-3,4-dihydro-2H-isoquinolin-6-yl]indazole-4-carbonitrile

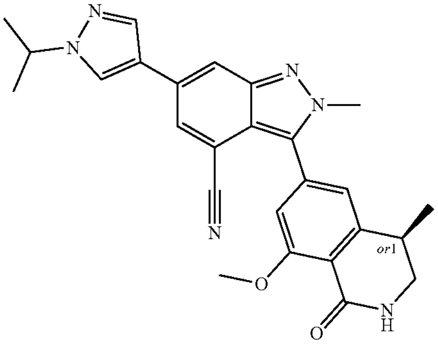 [SMILES: COc1cc(-c2c3c(C#N)cc(-c4cnn(C(C)C)c4)cc3nn2C)cc2c1C(=O)NC[C@@H]2C]

A mixture of an isomer (100 mg) that eluted earlier under chiral HPLC conditions as described in the experimental section of 6-bromo-2-methyl-3-[rel-(4R)-8-methoxy-4-methyl-1-oxo-3,4-dihydro-2H-isoquinolin-6-yl]indazole-4-carbonitrile described in Reference Example 97, 1-isopropyl-4-(4,4,5,5-tetramethyl-1,3,2-dioxaborolan-2-yl)pyrazole (67 mg), tripotassium phosphate (100 mg), [1,1'-bis(di-tert-butylphosphino)ferrocene]palladium(II) dichloride (15 mg), 1,4-dioxane (2.0 mL), and water (0.40 mL) was heated and stirred under a nitrogen atmosphere at 100 °C for 2 hours. After the reaction was completed, ethyl acetate and magnesium sulfate were added to the reaction mixture, filtration was performed, and then the filtrate was concentrated under reduced pressure. The resulting residue was purified by preparative HPLC (10 mM aqueous ammonium carbonate solution-acetonitrile) and then suspended and washed using ethyl acetate and diethyl ether to obtain the title compound (65 mg) as a light yellow powder. MS(ESI)m/z:455.3 [M+H]+

Example 168: Synthesis of 6-(1-butylpyrazol-4-yl)-2-methyl-3-[rel-(4R)-8-methoxy-4-methyl-1-oxo-3,4-dihydro-2H-isoquinolin-6-yl]indazole-4-carbonitrile

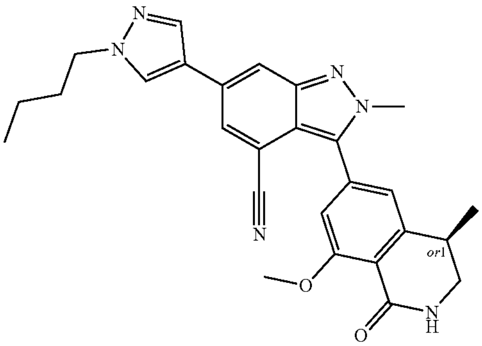 [SMILES: CCCCn1cc(-c2cc(C#N)c3c(-c4cc(OC)c5c(c4)[C@@H](C)CNC5=O)n(C)nc3c2)cn1]

A mixture of an isomer (100 mg) that eluted earlier under chiral HPLC conditions as described in the experimental section of 6-bromo-2-methyl-3-[rel-(4R)-8-methoxy-4-methyl-1-oxo-3,4-dihydro-2H-isoquinolin-6-yl]indazole-4-carbonitrile described in Reference Example 97, 1-butyl-4-(4,4,5,5-tetramethyl-1,3,2-dioxaborolan-2-yl)pyrazole (71 mg), [1,1'-bis(di-tert-butylphosphino)ferrocene]palladium (II) dichloride (15 mg), tripotassium phosphate (100 mg), 1,4-dioxane (2.0 mL), and water (0.40 mL) was heated and stirred under a nitrogen atmosphere at 100 °C for 2 hours.

After the reaction was completed, magnesium sulfate and ethyl acetate were added to the reaction mixture, filtration was performed, and the filtrate was concentrated under reduced pressure. The residue was purified by preparative HPLC (10 mM aqueous ammonium carbonate solution-acetonitrile) and NH silica gel column chromatography (ethyl acetate:methanol=100:0 to 90:10) to obtain the title compound (106 mg) as a light yellow powder. MS(ESI)m/z:469.3 [M+H]+

Example 169: Synthesis of 6-(1-isobutylpyrazol-4-yl)-2-methyl-3-[rel-(4R)-8-methoxy-4-methyl-1-oxo-3,4-dihydro-2H-isoquinolin-6-yl]indazole-4-carbonitrile

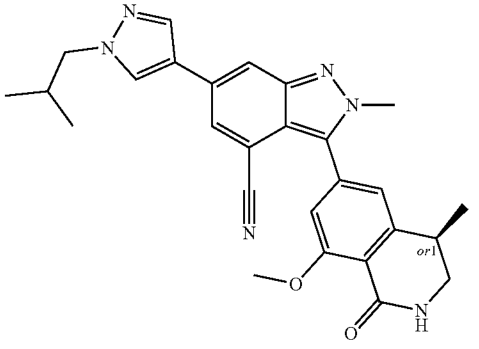 [SMILES: COc1cc(-c2c3c(C#N)cc(-c4cnn(CC(C)C)c4)cc3nn2C)cc2c1C(=O)NC[C@@H]2C]

The same reaction and treatment as in Example 168 were performed using 1-isobutyl-4-(4,4,5,5-tetramethyl-1,3,2-dioxaborolan-2-yl)pyrazole to obtain the title compound. MS(ESI)m/z:469.3 [M+H]+

Example 170: Synthesis of 6-[1-(cyclopropylmethyl)pyrazol-4-yl]-2-methyl-3-[rel-(4R)-8-methoxy-4-methyl-1-oxo-3,4-dihydro-2H-isoquinolin-6-yl]indazole-4-carbonitrile

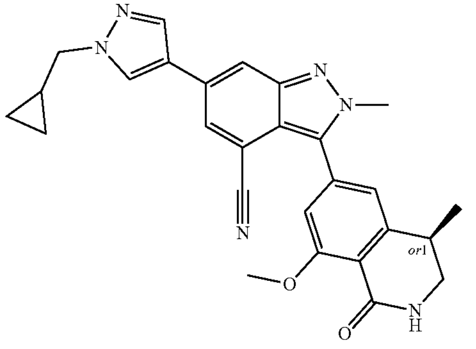 [SMILES: COc1cc(-c2c3c(C#N)cc(-c4cnn(CC5CC5)c4)cc3nn2C)cc2c1C(=O)NC[C@@H]2C]

The same reaction and treatment as in Example 168 were performed using 1-(cyclopropylmethyl)-4-(4,4,5,5-tetramethyl-1,3,2-dioxaborolan-2-yl)pyrazole to obtain the title compound. MS(ESI)m/z:467.3 [M+H]+

Example 171: Synthesis of 6-(1-isopentylpyrazol-4-yl)-2-methyl-3-[rel-(4R)-8-methoxy-4-methyl-1-oxo-3,4-dihydro-2H-isoquinolin-6-yl]indazole-4-carbonitrile

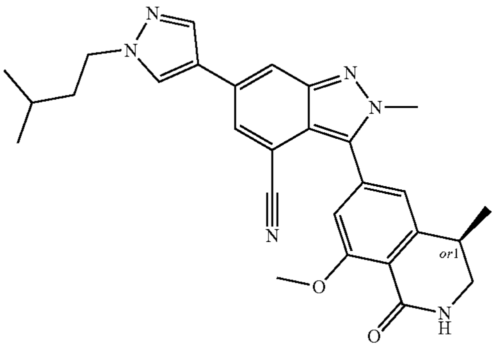 [SMILES: COc1cc(-c2c3c(C#N)cc(-c4cnn(CCC(C)C)c4)cc3nn2C)cc2c1C(=O)NC[C@@H]2C]

A mixture of an isomer (100 mg) that eluted earlier under chiral HPLC conditions as described in the experimental section of 6-bromo-2-methyl-3-[rel-(4R)-8-methoxy-4-methyl-1-oxo-3,4-dihydro-2H-isoquinolin-6-yl]indazole-4-carbonitrile described in Reference Example 97, 1-isopentyl-4-(4,4,5,5-tetramethyl-1,3,2-dioxaborolan-2-yl)pyrazole (75 mg), [1,1'-bis(di-tert-butylphosphino)ferrocene]palladium(II) dichloride (15 mg), tripotassium phosphate (100 mg), 1,4-dioxane (2.0 mL), and water (0.50 mL) was heated and stirred under a nitrogen atmosphere at 100 °C for 2 hours. After the reaction was completed, magnesium sulfate and ethyl acetate were added to the reaction mixture, filtration was performed, and the filtrate was concentrated under reduced pressure. The residue was purified by NH silica gel column chromatography (ethyl acetate:methanol=100:0 to 90:10) and preparative HPLC (10 mM aqueous ammonium carbonate solution-acetonitrile) to obtain the title compound (77 mg) as a colorless powder. MS(ESI)m/z:483.4 [M+H]+

Example 172: Synthesis of isomer that elutes earlier under chiral HPLC conditions as described in experimental section in 6-[1-(2-methoxyethyl)pyrazol-4-yl]-2-methyl-3-[rel-(4R)-8-(difluoromethoxy)-4-methyl-1-oxo-3,4-dihydro-2H-isoquinolin-6-yl]indazole-4-carbonitrile

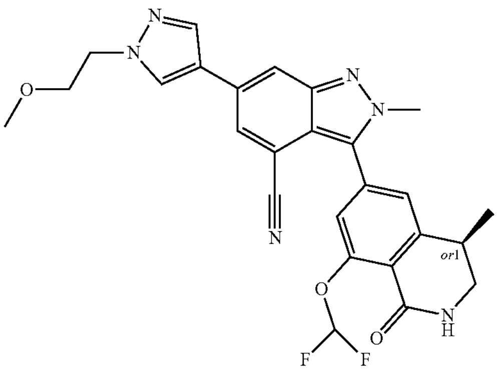

3-[8-(Difluoromethoxy)-4-methyl-1-oxo-3,4-dihydro-2H-isoquinolin-6-yl]-6-[1-(2-methoxyethyl)pyrazol-4-yl]-

2-Methyl-indazole-4-carbonitrile (165 mg) described in Reference Example 155 was fractionated using a chiral column [CHIRALPAK® IE (30*250), ethanol:acetonitrile=88:12]. The previous fractions were collected and concentrated, ethyl acetate was added to the residue, and the mixture was concentrated to obtain the title compound (75 mg) as a white powder. MS(ESI)m/z:507.0 [M+H]+

Example 173: Synthesis of isomer that elutes later under chiral HPLC conditions as described in experimental section in 6-[1-(2-methoxyethyl)pyrazol-4-yl]-2-methyl-3-[rel-(4R)-8-(difluoromethoxy)-4-methyl-1-oxo-3,4-dihydro-2H-isoquinolin-6-yl]indazole-4-carbonitrile

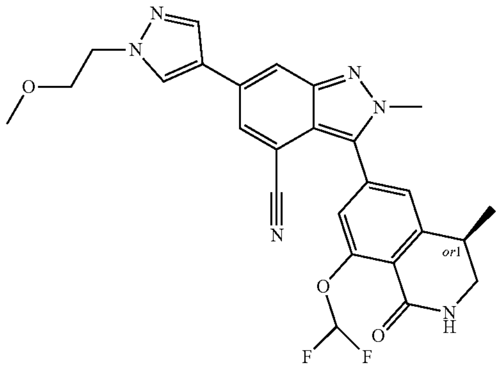

3-[8-(Difluoromethoxy)-4-methyl-1-oxo-3,4-dihydro-2H-isoquinolin-6-yl]-6-[1-(2-methoxyethyl)pyrazol-4-yl]-2-Methyl-indazole-4-carbonitrile (165 mg) described in Reference Example 155 was fractionated using a chiral column [CHIRALPAK® IE (30*250), ethanol:acetonitrile=88:12]. The subsequent fractions were collected and concentrated, ethyl acetate was added to the residue, and the mixture was concentrated to obtain the title compound (71 mg) as a white powder. MS(ESI)m/z:507.0 [M+H]+

Example 174: Synthesis of isomer that elutes later under chiral HPLC conditions as described in experimental section in 6-(1-ethylpyrazol-4-yl)-2-methyl-3-[rel-(4R)-8-(difluoromethoxy)-4-methyl-1-oxo-3,4-dihydro-2H-isoquinolin-6-yl]indazole-4-carbonitrile

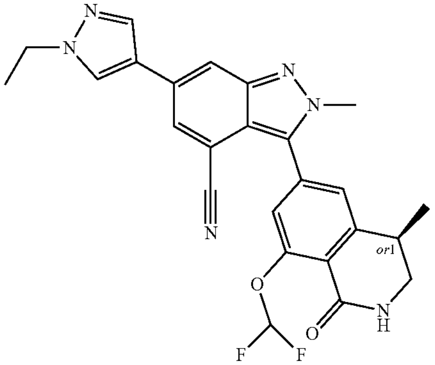 [SMILES: CCn1cc(-c2cc(C#N)c3c(-c4cc(OC(F)F)c5c(c4)[C@@H](C)CNC5=O)n(C)nc3c2)cn1]

3-[8-(Difluoromethoxy)-4-methyl-1-oxo-3,4-dihydro-2H-isoquinolin-6-yl]-6-(1-ethylpyrazol-4-yl)-2-methyl-indazole-4-carbonitrile (45 mg) described in Reference Example 156 was fractionated using a chiral column [CHIRALPAK® IE (20*250), ethanol:acetonitrile=98:2]. The subsequent fractions were collected and concentrated, ethyl acetate was added to the residue, and the mixture was concentrated to obtain the title compound (19 mg) as a light yellow powder.

MS(ESI)m/z:477.0 [M+H]+

Example 175: Synthesis of isomer that elutes earlier under chiral HPLC conditions as described in experimental section in rel-(4R)-8-(difluoromethoxy)-6-[6-[1-[(2S)-2-hydroxypropyl]pyrazol-4-yl]-4-methoxy-2-methyl-indazol-3-yl]-4-methyl-3,4-dihydro-2H-isoquinolin-1-one

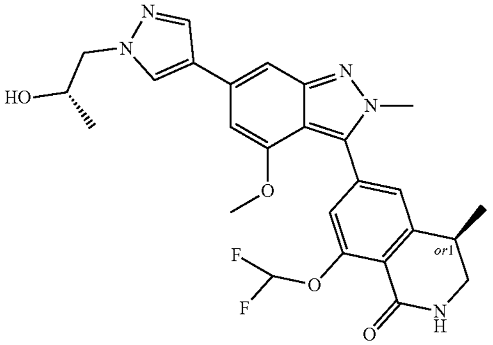 [SMILES: COc1cc(-c2cnn(C[C@H](C)O)c2)cc2nn(C)c(-c3cc(OC(F)F)c4c(c3)[C@@H](C)CNC4=O)c12]

8-(Difluoromethoxy)-6-[6-[1-[(2S)-2-hydroxypropyl]pyrazol-4-yl]-4-methoxy-2-methyl-indazol-3-yl]-4-methyl-3,4-dihydro-2H-isoquinolin-1-one (190 mg) described in Reference Example 157 was fractionated using a chiral column [CHIRALPAK® IK (30*250), hexane:ethanol=30:70]. The previous fractions were collected and concentrated, ethyl acetate was added to the residue, and the mixture was concentrated. Diethyl ether was added to the resulting residue and the mixture was concentrated to obtain the title compound (84 mg) as a light yellow powder.

MS(ESI)m/z:512.1 [M+H]+

Example 176: Synthesis of isomer that elutes later under chiral HPLC conditions as described in experimental section in rel-(4R)-8-(difluoromethoxy)-6-[6-[1-[(2S)-2-hydroxypropyl]pyrazol-4-yl]-4-methoxy-2-methyl-indazol-3-yl]-4-methyl-3,4-dihydro-2H-isoquinolin-1-one

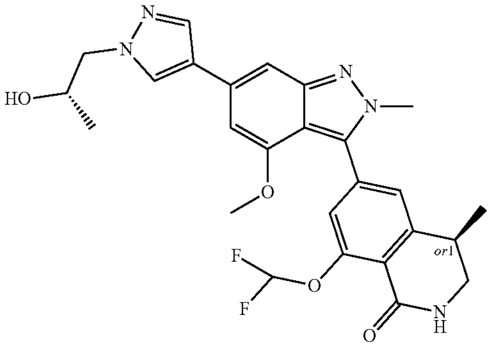 [SMILES: COc1cc(-c2cnn(C[C@H](C)O)c2)cc2nn(C)c(-c3cc(OC(F)F)c4c(c3)[C@@H](C)CNC4=O)c12]

8-(Difluoromethoxy)-6-[6-[1-[(2S)-2-hydroxypropyl]pyrazol-4-yl]-4-methoxy-2-methyl-indazol-3-yl]-4-methyl-3,4-dihydro-2H-isoquinolin-1-one (190 mg) described in Reference Example 157 was fractionated using a chiral column [CHIRALPAK® IK (30*250), hexane:ethanol=30:70]. The subsequent fractions were collected and concentrated, ethyl acetate was added to the residue, and the mixture was concentrated.

Diethyl ether was added to the resulting residue and the mixture was concentrated to obtain the title compound (85 mg) as a light yellow powder.

MS(ESI)m/z:512.1 [M+H]+

Example 177: Synthesis of isomer that elutes earlier under chiral HPLC conditions as described in experimental section in rel-(4R)-8-(difluoromethoxy)-6-[4-methoxy-6-[1-(2-methoxyethyl)pyrazol-4-yl]-2-methyl-indazol-3-yl]-4-methyl-3,4-dihydro-2H-isoquinolin-1-one

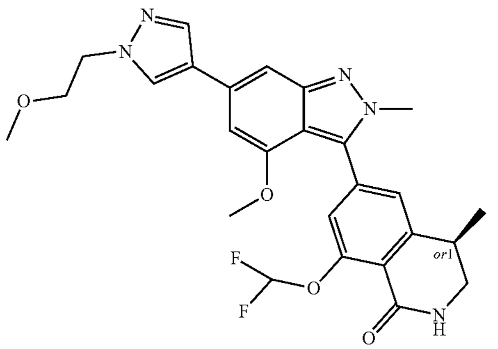

8-(Difluoromethoxy)-6-[4-methoxy-6-[1-(2-methoxy-ethyl)pyrazol-4-yl]-2-methyl-indazol-3-yl]-4-methyl-3,4-dihydro-2H-isoquinolin-1-one (184 mg) described in Reference Example 158 was fractionated using a chiral column [CHIRALPAK® IC (30*250), methanol:acetonitrile=98:2]. The previous fractions were collected and concentrated to obtain the title compound (58 mg) as a colorless powder. MS(ESI)m/z:512.3 [M+H]+

Example 178: Synthesis of isomer that elutes later under chiral HPLC conditions as described in experimental section in rel-(4R)-8-(difluoromethoxy)-6-[4-methoxy-6-[1-(2-methoxyethyl)pyrazol-4-yl]-2-methyl-indazol-3-yl]-4-methyl-3,4-dihydro-2H-isoquinolin-1-one

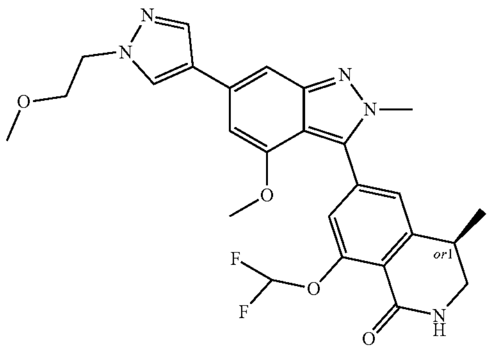

8-(Difluoromethoxy)-6-[4-methoxy-6-[1-(2-methoxy-ethyl)pyrazol-4-yl]-2-methyl-indazol-3-yl]-4-methyl-3,4-dihydro-2H-isoquinolin-1-one (184 mg) described in Reference Example 158 was fractionated using a chiral column [CHIRALPAK® IC (30*250), methanol:acetonitrile=98:2]. The subsequent fractions were collected and concentrated to obtain the title compound (80 mg) as a colorless powder. MS(ESI)m/z:512.3 [M+H]+

Example 179: Synthesis of isomer that elutes earlier under chiral HPLC conditions as described in experimental section in rel-(4R)-8-(difluoromethoxy)-6-[6-(1-ethylpyrazol-4-yl)-4-methoxy-2-methyl-indazol-3-yl]-4-methyl-3,4-dihydro-2H-isoquinolin-1-one

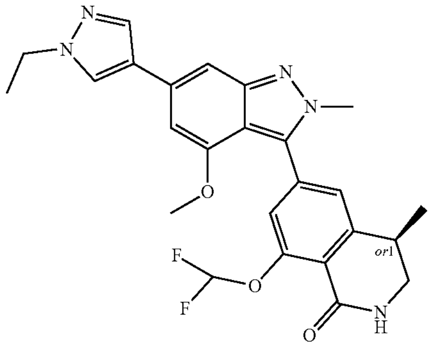 [SMILES: CCn1cc(-c2cc(OC)c3c(-c4cc(OC(F)F)c5c(c4)[C@@H](C)CNC5=O)n(C)nc3c2)cn1]

8-(Difluoromethoxy)-6-[6-(1-ethylpyrazol-4-yl)-4-methoxy-2-methyl-indazol-3-yl]-4-methyl-3,4-dihydro-2H-isoquinolin-1-one (159 mg) described in Reference Example 159 was fractionated using a chiral column [CHIRALPAK® IC (30*250), methanol]. The previous fractions were collected and concentrated to obtain the title compound (67 mg) as a colorless powder. MS(ESI)m/z:482.3 [M+H]+

Example 180: Synthesis of isomer that elutes later under chiral HPLC conditions as described in experimental section in rel-(4R)-8-(difluoromethoxy)-6-[6-(1-ethylpyrazol-4-yl)-4-methoxy-2-methyl-indazol-3-yl]-4-methyl-3,4-dihydro-2H-isoquinolin-1-one

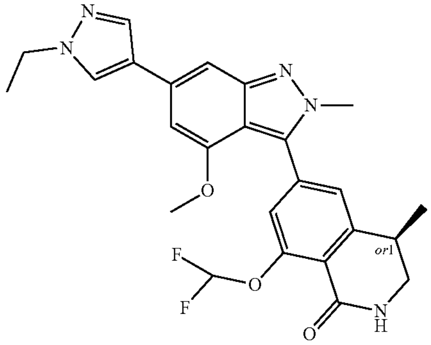 [SMILES: CCn1cc(-c2cc(OC)c3c(-c4cc(OC(F)F)c5c(c4)[C@@H](C)CNC5=O)n(C)nc3c2)cn1]

8-(Difluoromethoxy)-6-[6-(1-ethylpyrazol-4-yl)-4-methoxy-2-methyl-indazol-3-yl]-4-methyl-3,4-dihydro-2H-isoquinolin-1-one (159 mg) described in Reference Example 159 was fractionated using a chiral column [CHIRALPAK® IC (30*250), methanol]. The subsequent fractions were collected and concentrated to obtain the title compound (65 mg) as a colorless powder. MS(ESI)m/z:482.3 [M+H]+

Example 181: Synthesis of isomer that elutes earlier under chiral HPLC conditions as described in experimental section in 2-methyl-6-(1-methylpyrazol-4-yl)-3-[rel-(4R)-8-(difluoromethoxy)-4-methyl-1-oxo-3,4-dihydro-2H-isoquinolin-6-yl]indazole-4-carbonitrile

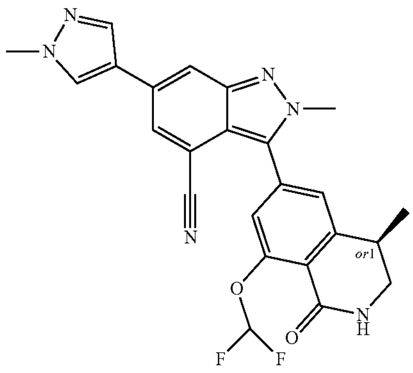

3-[8-(Difluoromethoxy)-4-methyl-1-oxo-3,4-dihydro-2H-isoquinolin-6-yl]-2-methyl-6-(1-methylpyrazol-4-yl)indazol-4-carbonitrile (123 mg) described in Example 160 was fractionated using a chiral column [CHIRALPAK® IE (30*250), methanol:acetonitrile=95:5]. The previous fractions were collected and concentrated, ethyl acetate was added to the residue, and the mixture was concentrated to obtain the title compound (53 mg) as a colorless powder. MS(ESI)m/z:463.3 [M+H]+

Example 182: Synthesis of isomer that elutes later under chiral HPLC conditions as described in experimental section in 2-methyl-6-(1-methylpyrazol-4-yl)-3-[rel-(4R)-8-(difluoromethoxy)-4-methyl-1-oxo-3,4-dihydro-2H-isoquinolin-6-yl]indazole-4-carbonitrile

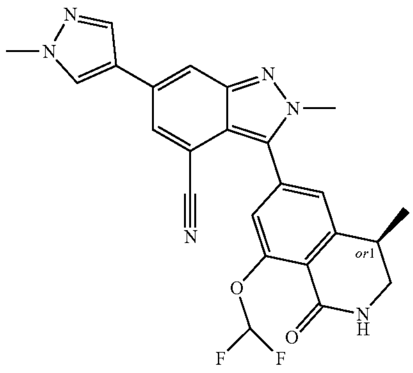

3-[8-(Difluoromethoxy)-4-methyl-1-oxo-3,4-dihydro-2H-isoquinolin-6-yl]-2-methyl-6-(1-methylpyrazol-4-yl)indazol-4-carbonitrile (123 mg) described in Example 160 was fractionated using a chiral column [CHIRALPAK® IE (30*250), methanol:acetonitrile=95:5]. The previous fractions were collected and concentrated, ethyl acetate was added to the residue, and the mixture was concentrated to obtain the title compound (53 mg) as a colorless powder. MS(ESI)m/z:463.3 [M+H]+

Experimental Example 1: SIK1, SIK2, and SIK3 Inhibition Test

Experiment Procedures

Test Compounds

The compounds described in Examples above were used in the SIK1, SIK2, and SIK3 inhibition test. Comparative compounds described below were also used in the test.

Comparative Example 1: Compound No. 53 in Patent Literature 1 (WO 2019/105886) (N-cyclopropyl-2-(difluoromethoxy)-6-methoxy-4-[5-(1-methylpyrazol-4-yl)benzimidazol-1-yl]benzamide)

Comparative Example 2: Compound No. 78 in Patent Literature 1 (WO 2019/105886) (N-(2,2-difluoroethyl)-2,6-dimethoxy-4-[5-(1-methylpyrazol-4-yl)benzimidazol-1-yl]benzamide)

Comparative Example 3: Compound No. 262 in Patent Literature 1 (WO 2019/105886) (2-cyclopropyl-8-methoxy-6-[7-(1-methylpyrazol-4-yl)imidazo[1,2-a]pyridin-3-yl]-3,4-dihydroisoquinolin-1-one)

Comparative Example 4: Compound No. 88 in Patent Literature 2 (WO 2019/238424) (dihydrochloride (8-methoxy-6-[7-(2-morpholinoethoxy)imidazo[1,2-a]pyridin-3-yl]-2-(2,2,2-trifluoroethyl)-3,4-dihydroisoquinolin-1-one dihydrochloride))

Comparative Example 5: Compound No. 219 in Patent Literature 3 (WO 2020/239658) (4-[6 [(1-cyano-1-methyl-ethyl)pyrazolo[1,5-a]pyridin-3-yl]-2-(difluoromethoxy)-N-[(1R,2S)-2-fluorocyclopropyl]-6-methoxy-benzamide])

Comparative Example 6: Compound No. 1 in Patent Literature 4 (WO 2020/239660) (8-methoxy-6-[6-(2-morpholinoethoxy)pyrazolo[1,5-a]pyridin-3-yl]-2-(2,2,2-trifluoroethyl)-3,4-dihydroisoquinolin-1-one)

Comparative Example 7: Compound in Example 1 of Patent Literature 5 (CN 115448881 A) (N-cyclopropyl-2-(difluoromethoxy)-6-methoxy-4-(2-methyl-6-(2-morpholinoethoxy)-2H-indazol-3-yl)benzamide)

Comparative Example 8: Compound in Example 3 of Patent Literature 5 (CN 115448881 A) (8-methoxy-6-(2-methyl-6-(4-methylpiperazin-1-yl)-2H-indazol-3-yl)-2-(2,2,2-trifluoroethyl)-3,4-dihydroisoquinolin-1(2H)-one)

Procedures

The inhibitory activity of the compound for SIK1, SIK2, and SIK3 enzymes was assayed by measuring the amount of ADP, an enzyme reaction product, with ADP-Glo™ Max Assay (Promega). Enzymes, specifically, GST-tagged SIK1 (Carna Biosciences, Inc.), GST-tagged SIK2 (Carna Biosciences, Inc.), and GST-tagged SIK3 (SignalChem) were prepared in a reaction buffer (15 mM tris-hydrochloric acid buffer (pH 7.5), 0.001% Triton X-100, 0.01% BSA) so that the final concentration would be 20 nM, 3 nM, and 100 nM. Enzyme solutions were thus formed. In a reaction buffer, AMARA Peptide (SignalChem) as a substrate with a final concentration of 200 μM (SIK1, SIK2) or 100 μM (SIK3), ATP (Promega) with a final concentration of 1 mM, and magnesium chloride with a final concentration of 5 mM were prepared. Substrate solutions were thus formed. The enzyme solution, the substrate solution, and a DMSO solution of a concentration of the test compound were mixed together and reacted at room temperature for 2 hours. After the reaction, ADP-Glo™ Reagent (Promega) was added, and the reaction was performed at room temperature for 30 minutes. Subsequently, ADP-Glo™ Max Detection Reagent (Promega) was added, and the reaction was performed at room temperature for 30 minutes. The emission by the luciferase reaction was measured with PHERAstar FSX (BMG LABTECH).

The inhibitory ratio (%) was calculated by: % Inhibition={1−(intensity of sample−intensity of blank (no enzyme solution added))/(intensity of control (DMSO alone)−intensity of blank)}×100. The inhibitory concentration $IC_{50}$ was calculated based on 16 data values obtained in the concentration response test. The results are described in Tables 1 and 2 below.

RESULTS OF EXPERIMENTS

TABLE 1

| Example No. | SIK1 $IC_{50}$ (nM) | SIK2 $IC_{50}$ (nM) | SIK3 $IC_{50}$ (nM) |
|---|---|---|---|
| Example 1 | 5.9 | 2.1 | 2.2 |
| Example 2 | 19.8 | 8.3 | 7.8 |
| Example 3 | 7.6 | 4.5 | 2.3 |
| Example 4 | 5.0 | 8.9 | 11.5 |
| Example 5 | 10.8 | 5.0 | 7.6 |
| Example 6 | 2.8 | 7.1 | 8.4 |
| Example 7 | 17.1 | 16.2 | 12.4 |
| Example 8 | 7.2 | 9.7 | 5.8 |
| Example 9 | 16.2 | 12.2 | 10.0 |
| Example 10 | 13.8 | 7.3 | 6.3 |
| Example 11 | 9.8 | 12.3 | 2.4 |
| Example 12 | 12.4 | 7.0 | 7.0 |
| Example 13 | 4.6 | 7.2 | 3.8 |
| Example 14 | 3.6 | 8.8 | 2.4 |
| Example 15 | 9.2 | 10.3 | 1.4 |
| Example 16 | 8.7 | 13.8 | 3.2 |
| Example 17 | 5.4 | 8.5 | 7.1 |
| Example 18 | 1.4 | 3.1 | 7.0 |
| Example 19 | 2.5 | 1.3 | 8.7 |
| Example 20 | 4.4 | 5.8 | 13.7 |
| Example 21 | 16.9 | 5.6 | 4.0 |
| Example 22 | 2.0 | 3.2 | 7.7 |
| Example 23 | 2.1 | 2.5 | 5.0 |
| Example 24 | 6.6 | 6.5 | 11.8 |
| Example 25 | 9.6 | 10.5 | 12.8 |
| Example 26 | 7.1 | 4.3 | 11.2 |
| Example 27 | 13.7 | 12.7 | 16.0 |
| Example 28 | 7.3 | 4.7 | 13.6 |
| Example 29 | 8.6 | 10.3 | 13.2 |
| Example 30 | 5.1 | 6.6 | 3.6 |
| Example 31 | 3.7 | 3.3 | 7.8 |
| Example 32 | 5.0 | 4.5 | 8.9 |
| Example 33 | 4.6 | 2.6 | 8.5 |
| Example 34 | 0.4 | 1.0 | 2.9 |
| Example 35 | 1.9 | 3.0 | 12.9 |
| Example 36 | 12.5 | 15.4 | 10.2 |
| Example 37 | 7.9 | 8.3 | 12.9 |
| Example 38 | 16.8 | 13.8 | 10.1 |
| Example 39 | 16.2 | 18.2 | 9.4 |
| Example 40 | 4.9 | 3.7 | 2.1 |
| Example 41 | 1.3 | 7.6 | 5.3 |
| Example 42 | 2.0 | 12.8 | 10.5 |
| Example 43 | 2.4 | 19.7 | 20.0 |
| Example 44 | 6.7 | 8.4 | 15.5 |
| Example 45 | 18.9 | 8.6 | 9.4 |
| Example 46 | 14.7 | 5.3 | 7.2 |
| Example 47 | 9.0 | 16.2 | 19.2 |
| Example 48 | 3.5 | 10.6 | 11.2 |
| Example 49 | 3.9 | 11.2 | 9.7 |
| Example 50 | 6.8 | 5.0 | 17.1 |
| Example 51 | 8.6 | 8.9 | 14.1 |
| Example 52 | 6.2 | 6.0 | 9.2 |
| Example 53 | 9.1 | 7.3 | 13.6 |
| Example 54 | 10.1 | 3.2 | 5.1 |
| Example 55 | 10.4 | 3.5 | 2.4 |
| Example 56 | 20.0 | 16.1 | 11.8 |

TABLE 1-continued

| Example No. | SIK1 $IC_{50}$ (nM) | SIK2 $IC_{50}$ (nM) | SIK3 $IC_{50}$ (nM) |
|---|---|---|---|
| Example 57 | 16.0 | 10.0 | 9.2 |
| Example 58 | 13.7 | 6.7 | 6.3 |
| Example 59 | 14.1 | 3.8 | 6.6 |
| Example 60 | 6.9 | 4.8 | 4.9 |
| Example 61 | 4.7 | 7.4 | 7.4 |
| Example 62 | 7.9 | 3.9 | 10.4 |
| Example 63 | 7.5 | 4.3 | 9.7 |
| Example 64 | 8.6 | 9.0 | 15.8 |
| Example 65 | 9.6 | 5.6 | 3.0 |
| Example 66 | 11.4 | 14.1 | 5.7 |
| Example 67 | 8.5 | 12.7 | 4.8 |
| Example 68 | 9.4 | 14.2 | 2.5 |
| Example 69 | 8.3 | 10.9 | 2.0 |
| Example 70 | 15.3 | 11.2 | 3.7 |
| Example 71 | 3.0 | 6.1 | 6.8 |
| Example 72 | 3.9 | 5.6 | 5.6 |
| Example 73 | 17.4 | 3.8 | 6.5 |
| Example 74 | 8.4 | 2.6 | 6.1 |
| Example 75 | 14.8 | 2.7 | 13.3 |
| Example 76 | 17.6 | 5.3 | 11.7 |
| Example 77 | 11.8 | 5.2 | 10.1 |
| Example 78 | 12.6 | 5.4 | 6.7 |
| Example 79 | 12.5 | 6.8 | 8.1 |
| Example 80 | 16.5 | 8.7 | 10.1 |
| Example 81 | 13.3 | 7.3 | 10.6 |
| Example 82 | 16.0 | 7.5 | 16.7 |
| Example 83 | 10.5 | 8.1 | 10.2 |
| Example 84 | 13.6 | 11.0 | 12.5 |
| Example 85 | 9.9 | 7.1 | 8.6 |
| Example 86 | 13.7 | 13.1 | 19.4 |
| Example 87 | 18.5 | 14.6 | 4.3 |
| Example 88 | 7.4 | 4.5 | 5.3 |
| Example 89 | 11.0 | 12.0 | 2.3 |
| Example 90 | 17.8 | 10.4 | 7.9 |
| Example 91 | 17.5 | 10.1 | 7.3 |
| Example 92 | 17.0 | 10.9 | 10.2 |
| Example 93 | 19.8 | 13.5 | 5.9 |
| Example 94 | 6.7 | 5.0 | 2.3 |
| Example 95 | 16.0 | 13.3 | 5.7 |
| Example 96 | 14.0 | 3.9 | 5.0 |
| Example 97 | 15.3 | 7.4 | 6.1 |
| Example 98 | 17.9 | 10.5 | 10.3 |
| Example 99 | 19.2 | 5.0 | 4.9 |
| Example 100 | 15.5 | 7.3 | 5.7 |
| Example 101 | 15.0 | 5.8 | 12.0 |
| Example 102 | 19.2 | 5.3 | 5.1 |
| Example 103 | 4.4 | 1.6 | 4.8 |
| Example 104 | 6.4 | 1.8 | 4.8 |
| Example 105 | 10.0 | 3.4 | 8.1 |
| Example 106 | 8.0 | 3.1 | 6.8 |
| Example 107 | 8.3 | 4.0 | 8.0 |
| Example 108 | 16.8 | 6.5 | 2.4 |
| Example 109 | 18.0 | 18.1 | 2.3 |
| Example 110 | 6.5 | 3.2 | 1.7 |
| Example 111 | 6.2 | 1.7 | 1.7 |
| Example 112 | 16.6 | 13.7 | 3.0 |
| Example 113 | 19.7 | 15.6 | 2.7 |
| Example 114 | 12.6 | 4.1 | 0.7 |
| Example 115 | 9.4 | 2.4 | <0.6 |
| Example 116 | 16.1 | 5.8 | 1.1 |
| Example 117 | 12.5 | 9.3 | 1.0 |
| Example 118 | 5.3 | 1.0 | 0.6 |
| Example 119 | 3.9 | 2.6 | 0.7 |
| Example 120 | 7.8 | 3.5 | 0.7 |
| Example 121 | 9.5 | 4.8 | 1.1 |
| Example 122 | 15.8 | 7.9 | 4.4 |
| Example 123 | 4.4 | 1.7 | 0.6 |
| Example 124 | 8.0 | 1.1 | 1.6 |
| Example 125 | 11.5 | 1.8 | 2.9 |
| Example 126 | 7.3 | 1.5 | 5.1 |
| Example 127 | 6.9 | 1.3 | 7.6 |
| Example 128 | 8.2 | 1.0 | 6.6 |
| Example 129 | 5.1 | 0.9 | 6.6 |
| Example 130 | 16.9 | 2.1 | 16.8 |
| Example 131 | 12.2 | 4.5 | 16.3 |
| Example 132 | 16.1 | 4.0 | 5.8 |
| Example 133 | 13.6 | 2.1 | 4.9 |

TABLE 1-continued

| Example No. | SIK1 $IC_{50}$ (nM) | SIK2 $IC_{50}$ (nM) | SIK3 $IC_{50}$ (nM) |
|---|---|---|---|
| Example 134 | 13.6 | 3.3 | 5.7 |
| Example 135 | 17.2 | 6.2 | 5.9 |
| Example 136 | 7.6 | 3.4 | 13.4 |
| Example 137 | 11.6 | 5.8 | 4.7 |
| Example 138 | 16.9 | 7.2 | 6.6 |
| Example 139 | 9.0 | 8.6 | 12.8 |
| Example 140 | 7.8 | 12.3 | 10.3 |
| Example 141 | 17.6 | 2.0 | 2.7 |
| Example 142 | 16.2 | 1.9 | 2.7 |
| Example 143 | 10.5 | 2.2 | 8.6 |
| Example 144 | 10.1 | 3.7 | 7.8 |
| Example 145 | 10.3 | 1.8 | 19.1 |
| Example 146 | 12.6 | 3.6 | 7.8 |
| Example 147 | 6.3 | 3.2 | 13.4 |
| Example 148 | 6.0 | 1.3 | 1.1 |
| Example 149 | 10.4 | 1.3 | 1.6 |
| Example 150 | 10.2 | 2.4 | 1.3 |
| Example 151 | 9.8 | 3.5 | 14.2 |
| Example 152 | 7.2 | 3.4 | 14.4 |
| Example 153 | 8.5 | 1.8 | 2.7 |
| Example 154 | 7.6 | 1.2 | 9.5 |
| Example 155 | 7.4 | 1.5 | 5.5 |
| Example 156 | 4.3 | 0.7 | 2.6 |
| Example 157 | 5.1 | 1.0 | 7.9 |
| Example 158 | 11.7 | 2.2 | 3.6 |
| Example 159 | 13.8 | 2.8 | 4.6 |
| Example 160 | 7.5 | 1.0 | 3.0 |
| Example 161 | 5.6 | 1.3 | 10.0 |
| Example 162 | 8.1 | 2.5 | 3.2 |
| Example 163 | 5.1 | 1.4 | 11.6 |
| Example 164 | 7.1 | 2.0 | 19.7 |
| Example 165 | 5.2 | 1.5 | 6.8 |
| Example 166 | 11.9 | 3.1 | 9.6 |
| Example 167 | 8.5 | 1.7 | 4.1 |
| Example 168 | 6.8 | 1.4 | 2.7 |
| Example 169 | 8.1 | 1.9 | 3.4 |
| Example 170 | 8.5 | 1.7 | 4.3 |
| Example 171 | 9.1 | 2.3 | 4.7 |
| Example 172 | 19.5 | 7.8 | 7.0 |
| Example 173 | 7.5 | 2.1 | 3.5 |
| Example 174 | 8.6 | 2.3 | 2.6 |
| Example 175 | 7.5 | 2.9 | 7.2 |
| Example 176 | 11.0 | 5.9 | 11.9 |
| Example 177 | 5.4 | 3.1 | 10.1 |
| Example 178 | 10.1 | 4.7 | 15.6 |
| Example 179 | 5.7 | 2.0 | 6.1 |
| Example 180 | 13.2 | 5.1 | 12.4 |
| Example 181 | 19.4 | 6.1 | 3.5 |
| Example 182 | 6.4 | 2.5 | 2.0 |

TABLE 2

| Comparative Example No. | SIK1 $IC_{50}$ (nM) | SIK2 $IC_{50}$ (nM) | SIK3 $IC_{50}$ (nM) |
|---|---|---|---|
| Comparative Example 1 | 145.7 | 10.8 | 5.5 |
| Comparative Example 2 | 1003.7 | 86.4 | 39.7 |
| Comparative Example 3 | 398.0 | 22.7 | 6.5 |
| Comparative Example 4 | 7914.1 | 287.3 | 75.0 |
| Comparative Example 5 | >10000.0 | 5482.5 | 52.2 |
| Comparative Example 6 | 5224.3 | 102.5 | 42.0 |
| Comparative Example 7 | 7600.8 | 369.1 | 197.5 |
| Comparative Example 8 | >10000.0 | 683.4 | 886.8 |

Experimental Example 2: TNF-α Production Inhibition Test in LPS-Stimulated Human Monocytes

Experiment Procedures (1) Isolation of Human Peripheral Blood-Derived Mononuclear Cell-Derived Monocytes The compound of Example 106 was used as the test compound.

Cryopreserved mononuclear cells derived from human peripheral blood (LONZA K.K.) were thawed at 37 °C, and human monocytes were isolated using CD14 MicroBeads (Miltenyi Biotec). The isolated human monocytes were mixed with a culture medium (RPMI 1640, 10% FBS, penicillin, streptomycin), and a DMSO solution of a concentration of the test compound was added. The mixture was incubated at 37 °C for 30 minutes. After the incubation, lipopolysaccharide (LPS; Sigma Aldrich) was added so that the final concentration would be 100 ng/ml. The mixture was incubated at 37 °C for 4 hours. After the incubation, the supernatant was recovered and cryopreserved at −80 °C. The cryopreserved supernatant was thawed and the amount of TNF-α production in the supernatant was measured using CBA Human TNF Flex Set (BD Bioscience).

Inhibitory ratio (%) was calculated by: % Inhibition={1−(amount of TNF-α production in sample−amount of TNF-α production without stimulus (DMSO added, not LPS-stimulated))/(amount of TNF-α production in control (DMSO added, LPS-stimulated)−amount of TNF-α production without stimulus (DMSO added, not LPS-stimulated))}×100. The inhibitory concentration $IC_{50}$ was calculated based on 4 data values obtained in the concentration response test. The results are described in Table 3 below.

TABLE 3

| Example | IC50 (μM) |
|---|---|
| 106 | 0.019 |

Experimental Example 3: TNF-α Increase Inhibition Test in LPS-Stimulated Mouse Serums

Experiment Procedures

The compound of Example 106 was used as the test compound. Six-week old male BALB/c mice were orally administered with a suspension (10 mL/kg) of a concentration of the test compound in 0.5% methylcellulose (MC) solution. 30 Minutes later, 20 μg of LPS (Sigma Aldrich) was intraperitoneally administered. 1.5 Hours later, blood was drawn from the inferior vena cava, and serum was obtained. The amount of TNF-α production in the serum was measured using CBA Human TNF Flex Set (BD Bioscience).

The inhibitory ratio (%) was calculated by: % Inhibition={1−(amount of TNF-α production in sample-average amount of TNF-α production without stimulus (MC administered, not LPS-stimulated)/(average amount of TNF-α production in control (MC administered, LPS-stimulated)−average amount of TNF-α production without stimulus (MC administered, not LPS-stimulated))}×100. The results are described in Table 4 below.

Results of Experiments

As a result of the test, the compound of Example at a dose of 1 mg/kg showed an in-serum TNF-α increase inhibition ratio described in Table 4 below.

TABLE 4

| Example | TNF α increase inhibition ratio (1 mg/kg; %) |
|---|---|
| 106 | 47.2** |

**p < 0.01 versus LPS-administered group

Experimental Example 4: Dansyl Glutathione Bonding Test

Assay Procedures

The compounds of Examples were used as the test compounds.

Human liver microsome solution, the test compound, reduced nicotinamide adenine dinucleotide phosphate that was a coenzyme for oxidative metabolic enzymes, and dansyl glutathione (dGSH) that was a fluorescently labeled nucleophilic scavenger glutathione were mixed together. The reaction was performed at 37 °C for a predetermined time. The reaction liquid was pre-purified and was poured into a liquid chromatograph connected to a fluorescent detector to detect unions of the test compound or metabolites thereof with dansyl glutathione.

Assay results

The total amount of the unions of the test compound or metabolites thereof with dansyl glutathione was determined. The results (pmol/h/mg) are described in Table 5. In the table, N.D. indicates not detected.

TABLE 5

| Results of dGSH | | | |
|---|---|---|---|
| Example No. | dGSH | Example No. | dGSH |
| Example 1 | 2138 | Example 7 | N.D. |
| Example 9 | N.D. | Example 10 | 112 |
| Example 11 | N.D. | Example 12 | 161 |
| Example 13 | N.D. | Example 15 | N.D. |
| Example 17 | N.D. | Example 21 | 1052 |
| Example 23 | 85 | Example 25 | N.D. |
| Example 28 | N.D. | Example 34 | N.D. |
| Example 52 | N.D. | Example 54 | N.D. |
| Example 55 | 715 | Example 56 | 46 |
| Example 57 | 82 | Example 58 | 113 |
| Example 59 | 3811 | Example 63 | N.D. |
| Example 64 | N.D. | Example 73 | N.D. |
| Example 75 | 1319 | Example 76 | 52 |
| Example 84 | 59 | Example 85 | 41 |
| Example 87 | N.D. | Example 88 | 80 |
| Example 89 | 24 | Example 91 | N.D. |
| Example 92 | 716 | Example 94 | 227 |
| Example 95 | 156 | Example 96 | N.D. |
| Example 97 | N.D. | Example 102 | N.D. |
| Example 105 | 122 | Example 106 | 38 |
| Example 109 | N.D. | Example 110 | 46 |
| Example 111 | 208 | Example 112 | N.D. |
| Example 113 | N.D. | Example 114 | 181 |
| Example 115 | 90 | Example 116 | N.D. |
| Example 117 | 51 | Example 117 | 51 |
| Example 118 | 127 | Example 120 | N.D. |
| Example 122 | N.D. | Example 123 | 395 |

TABLE 5-continued

| Results of dGSH | | | |
|---|---|---|---|
| Example No. | dGSH | Example No. | dGSH |
| Example 124 | 213 | Example 125 | N.D. |
| Example 126 | 165 | Example 127 | 146 |
| Example 128 | 63 | Example 129 | 19002 |
| Example 130 | N.D. | Example 131 | N.D. |
| Example 132 | N.D. | Example 133 | N.D. |
| Example 134 | N.D. | Example 135 | N.D. |
| Example 136 | N.D. | Example 137 | N.D. |
| Example 138 | N.D. | Example 139 | 17222 |
| Example 140 | 13744 | Example 141 | N.D. |
| Example 142 | N.D. | Example 143 | 16500 |
| Example 145 | 265 | Example 148 | N.D. |
| Example 149 | N.D. | Example 150 | N.D. |
| Example 153 | 536 | Example 154 | N.D. |
| Example 155 | N.D. | Example 156 | 478 |
| Example 157 | 679 | Example 158 | N.D. |
| Example 159 | N.D. | Example 162 | 6099 |
| Example 163 | 231~367 | Example 164 | 1180 |
| Example 165 | N.D. | Example 166 | 132 |
| Example 167 | 110 | Example 169 | 69 |
| Example 170 | 422 | Example 172 | N.D. |
| Example 173 | N.D. | Example 174 | N.D. |
| Example 175 | N.D. | Example 176 | N.D. |
| Example 177 | N.D. | Example 179 | N.D. |
| Example 181 | 65 | Example 182 | N.D. |

Table 5: Results of dGSH

The measurement results of a control compound (troglitazone) known to generate reactive metabolites are described in Table 6.

TABLE 6

| Results of dGSH | |
|---|---|
| Compound name | dGSH (pmol/h/mg) |
| Troglitazone | 2935~3952 |

The contents of Japanese Patent Application No. 2023-085585 (filed May 24, 2023) are incorporated herein by reference in its entirety.

All documents, patent applications, and technical standards referred to herein are incorporated by reference in their entirety to the same extent as if each individual document, patent application, or technical standard was specifically and individually indicated to be incorporated by reference in its entirety.

The invention claimed is:

1. A compound represented by formula (I) below or a pharmacologically acceptable salt thereof:

(I)

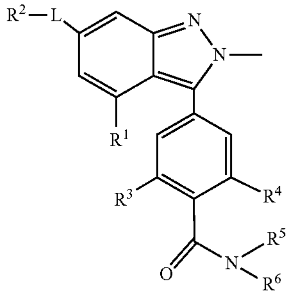

wherein $R^1$ is a cyano group, a $C_{1-4}$ alkyl group optionally substituted with one to three halogen atoms, or a $C_{1-4}$ alkoxy group optionally substituted with one to three substituents independently selected from $R^{1a}$, wherein $R^{1a}$ is a halogen atom; a 5- or 6-membered monocyclic aromatic heterocyclic group optionally substituted with one to three substituents independently selected from the group consisting of cyano groups, halogen atoms, and $C_{1-4}$ alkyl groups; a 4-membered monocyclic aliphatic heterocyclic group; a hydroxyl group; a $C_{3-4}$ cycloalkyl group; and a phenyl group, L is a single bond, a $C_{1-4}$ alkylene group, or a $C_{2-4}$ alkenylene group, $R^2$ is a 5-membered monocyclic aromatic heterocyclic group optionally substituted with $R^{2a}$, wherein $R^{2a}$ is a $C_{1-5}$ alkyl group optionally substituted with one to four substituents independently selected from $R^{2b}$, or a 5-membered monocyclic aliphatic heterocyclic group, wherein $R^{2b}$ is a hydroxyl group; a $C_{3-4}$ cycloalkyl group optionally substituted with a hydroxyl group; a halogen atom; a $C_{1-4}$ alkoxy group; a 4- to 6-membered monocyclic aliphatic heterocyclic group optionally substituted with one to three substituents independently selected from the group consisting of halogen atoms and oxo groups; an oxo group; an amino group optionally substituted with one or two $C_{1-4}$ alkyl groups; a phenyl group; a 5-membered monocyclic aromatic heterocyclic group; and a $C_{1-4}$ alkylsulfonyl group, $R^3$ is a hydrogen atom or a $C_{1-4}$ alkoxy group optionally substituted with one to three halogen atoms, $R^4$ is a $C_{1-4}$ alkoxy group optionally substituted with one to three halogen atoms, $R^5$ is a hydrogen atom, $R^6$ is a hydrogen atom; a $C_{1-4}$ alkyl group substituted with a halocyclopropyl group; or a cyclopropyl group substituted with one or two halogen atoms, or $R^5$ and $R^6$, taken together with the nitrogen atom to which they are bonded, form an azetidine ring wherein the azetidine ring is substituted with one or two substituents independently selected from the group consisting of $C_{1-4}$ alkyl groups optionally substituted with one to three halogen atoms; hydroxyl groups; $C_{1-4}$ alkoxy groups optionally substituted with one or two halogen atoms; cyano groups; and amino groups, or $R^4$ and $R^6$, taken together with the benzene ring to which $R^4$ is bonded, form a tetrahydroisoquinolin-1-one ring wherein the ring is substituted with one or two $C_{1-4}$ alkyl groups.

2. The compound or the pharmacologically acceptable salt thereof according to claim 1, wherein $R^1$ is a cyano group, a $C_{1-4}$ alkyl group optionally substituted with one to three halogen atoms, or a $C_{1-4}$ alkoxy group optionally substituted with one to three halogen atoms, L is a single bond, $R^2$ is a pyrazolyl group optionally substituted with a $C_{1-4}$ alkyl group optionally substituted with a substituent $R^{2b'}$, wherein the substituent $R^{2b'}$ is independently selected from the group consisting of a hydroxyl group, one to three halogen atoms, a $C_{1-4}$ alkoxy group, and a hydroxyl-substituted cyclobutyl group, $R^3$ is a $C_{1-4}$ alkoxy group optionally substituted with one to three halogen atoms, $R^4$ is a $C_{1-4}$ alkoxy group optionally substituted with one to three halogen atoms, $R^5$ is a hydrogen atom, $R^6$ is a hydrogen atom; a $C_{1-4}$ alkyl group substituted with a halocyclopropyl group; or a cyclopropyl group substituted with one or two halogen atoms, or $R^4$ and $R^6$, taken together with the benzene ring to which $R^4$ is bonded, form a tetrahydroisoquinolin-1-one ring wherein the ring is substituted with one or two $C_{1-4}$ alkyl groups at the 4-position of the ring.

3. The compound or the pharmacologically acceptable salt thereof according to claim 2, wherein $R^1$ is a cyano group, a $C_{1-2}$ alkyl group optionally substituted with one to three fluorine atoms, or a $C_{1-2}$ alkoxy group optionally substituted with one to three fluorine atoms, L is a single bond, $R^2$ is a pyrazolyl group optionally substituted with a $C_{1-3}$ alkyl group optionally substituted with a substituent $R^{2b''}$, wherein the substituent $R^{2b''}$ is independently selected from the group consisting of a hydroxyl group, one to three fluorine atoms, a methoxy group, and a hydroxyl-substituted cyclobutyl group, $R^3$ is a methoxy group optionally substituted with one to three fluorine atoms, $R^4$ is a methoxy group optionally substituted with one to three fluorine atoms, $R^5$ is a hydrogen atom, $R^6$ is a hydrogen atom; a fluorocyclopropyl-substituted methyl group; or a cyclopropyl group substituted with one or two fluorine atoms, or $R^4$ and $R^6$, taken together with the benzene ring to which $R^4$ is bonded, form a tetrahydroisoquinolin-1-one ring wherein the ring is substituted with one or two methyl groups at the 4-position of the ring.

4. The compound or the pharmacologically acceptable salt thereof according to claim 3, wherein $R^1$ is a cyano group, $-CHF_2$, $-OCHF_2$, or $-OC_2H_5$.

5. The compound or the pharmacologically acceptable salt thereof according to claim 3, wherein $R^2$-L- is:

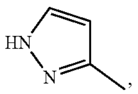,
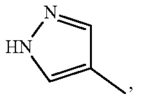, or
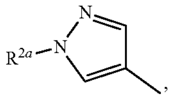, wherein $R^{2a}$ is $-CH_3$, $-CHF_2$, $-CH_2CH_3$, $-CH_2CF_3$, $-CH_2CH_2CH_3$, $-CH_2CH_2OCH_3$, $-CH_2CH(CH_3)OH$, or a 3-hydroxycyclobutylmethyl group.

6. The compound or the pharmacologically acceptable salt thereof according to claim 3, wherein $R^3$ is $-OCH_3$ or $-OCHF_2$.

7. The compound or the pharmacologically acceptable salt thereof according to claim 3, wherein $R^4$ is $-OCH_3$ or $-OCHF_2$, $R^5$ is a hydrogen atom, $R^6$ is a hydrogen atom,

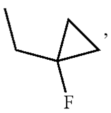, or
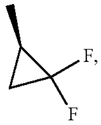, or $R^4$ and $R^6$, taken together with the benzene ring to which $R^4$ is bonded, form a tetrahydroisoquinolin-1-one ring wherein the ring is substituted with one —$CH_3$ at the 4-position of the ring.

8. The compound or the pharmacologically acceptable salt thereof according to claim 3, wherein $R^1$ is a cyano group, —$CHF_2$, —$OCHF_2$, or —$OC_2H_5$, $R^2$-L- is:

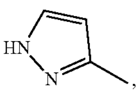,

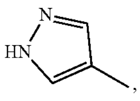, or

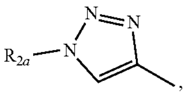, wherein $R^{2a}$ is —$CH_3$, —$CHF_2$, —$CH_2CH_3$, —$CH_2CF_3$, —$CH_2CH_2CH_3$, —$CH_2CH_2OCH_3$, —$CH_2CH(CH_3)OH$, or a 3-hydroxycyclobutylmethyl group, $R^3$ is —$OCH_3$ or —$OCHF_2$, $R^4$ is —$OCH_3$ or —$OCHF_2$, $R^5$ is a hydrogen atom, $R^6$ is a hydrogen atom,

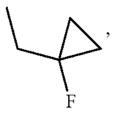, or

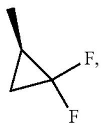

or $R^4$ and $R^6$, taken together with the benzene ring to which $R^4$ is bonded, form a tetrahydroisoquinolin-1-one ring wherein the ring is substituted with one —$CH_3$ at the 4-position of the ring.

9. A compound selected from the group consisting of compounds illustrated below, or a pharmacologically acceptable salt thereof:

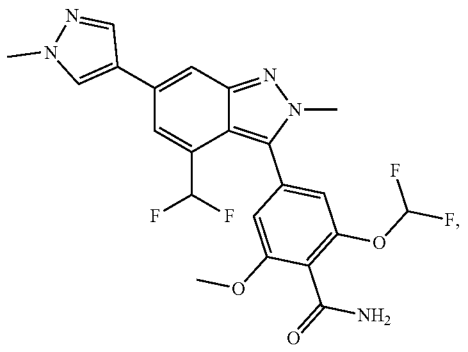

-continued

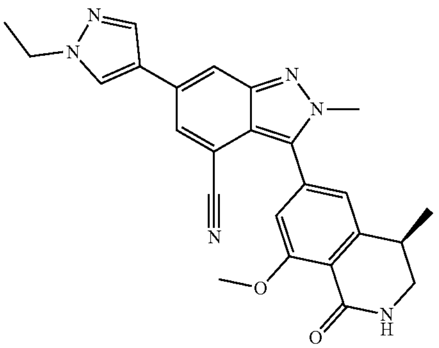

or an enantiomer thereof,

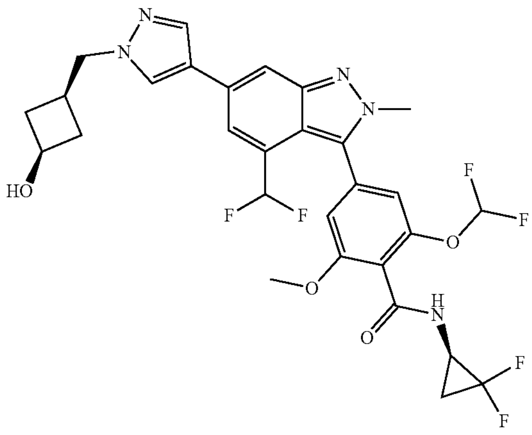 [SMILES: COc1cc(-c2c3c(C(F)F)cc(-c4cnn(C[C@H]5C[C@@H](O)C5)c4)cc3nn2C)cc(OC(F)F)c1C(=O)N[C@@H]1CC1(F)F]

and a mixture of stereoisomers thereof,

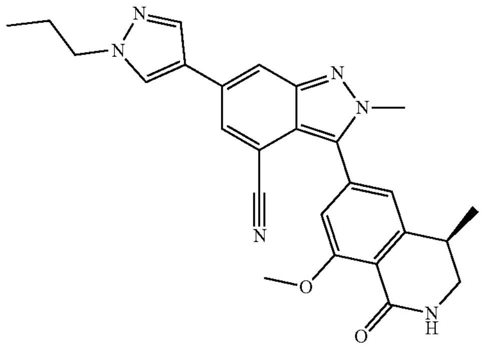 [SMILES: CCCn1cc(-c2cc(C#N)c3c(-c4cc(OC)c5c(c4)[C@@H](C)CNC5=O)n(C)nc3c2)cn1]

or an enantiomer thereof,
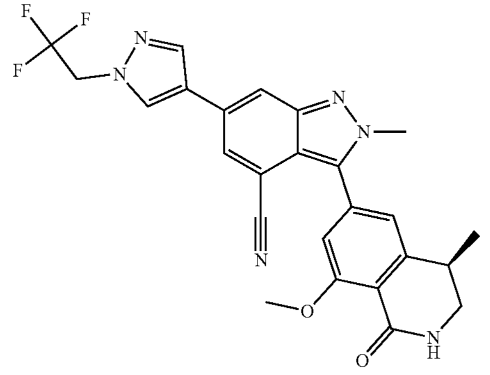 [SMILES: COc1cc(-c2c3c(C#N)cc(-c4cnn(CC(F)(F)F)c4)cc3nn2C)cc2c1C(=O)NC[C@@H]2C]
or an enantiomer thereof,
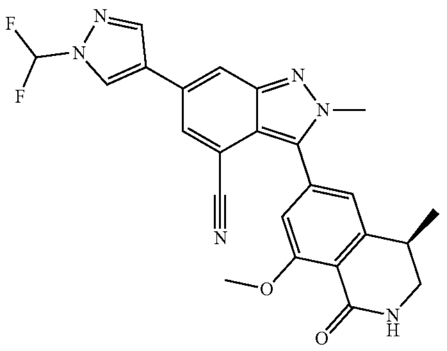 [SMILES: COc1cc(-c2c3c(C#N)cc(-c4cnn(C(F)F)c4)cc3nn2C)cc2c1C(=O)NC[C@@H]2C]
or an enantiomer thereof,
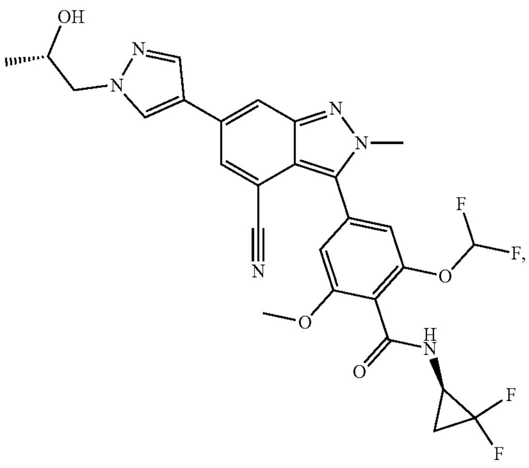
-continued
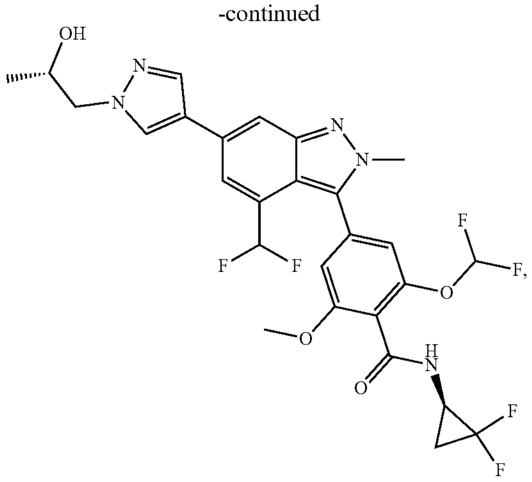
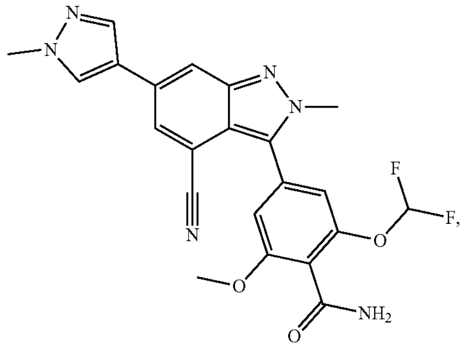
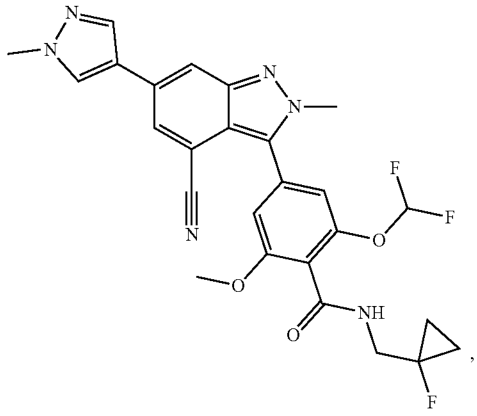
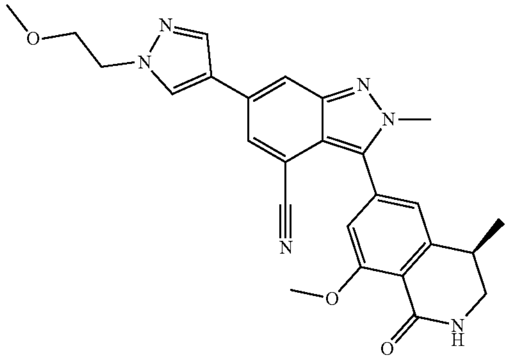

or an enantiomer thereof,
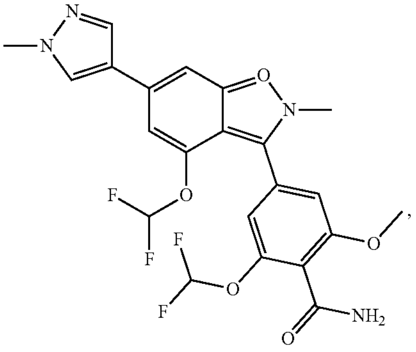
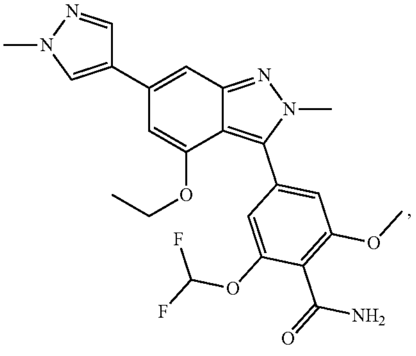
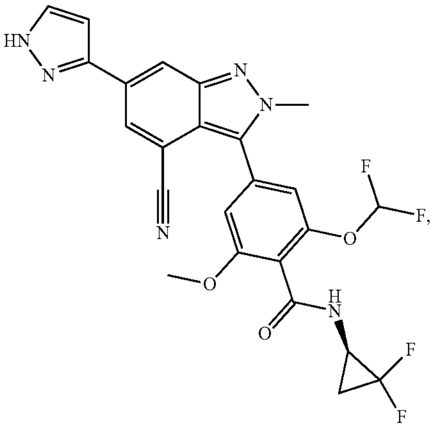
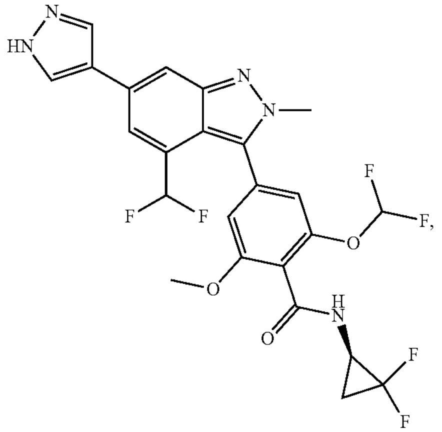
and
-continued
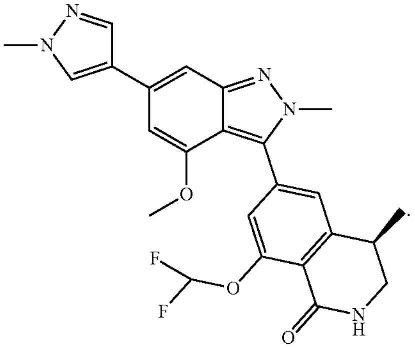
10. A compound selected from the group consisting of compounds illustrated below, or a pharmacologically acceptable salt thereof:
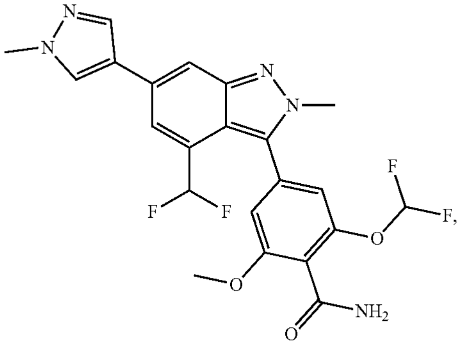
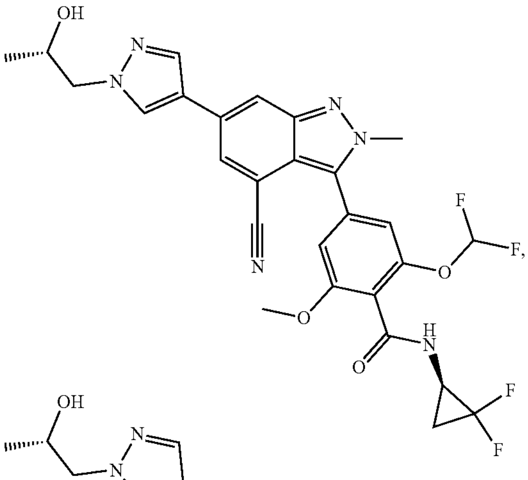
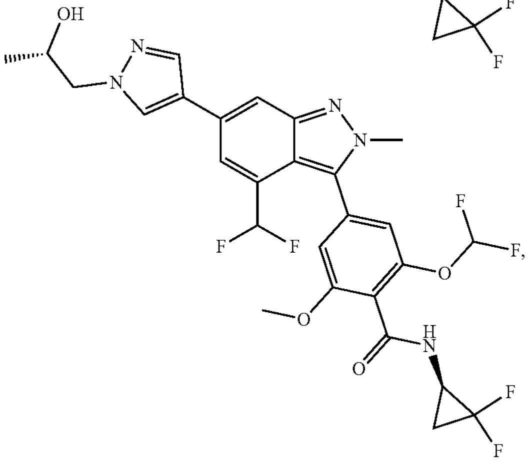

-continued

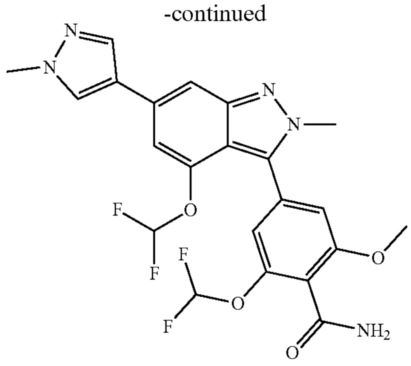

,

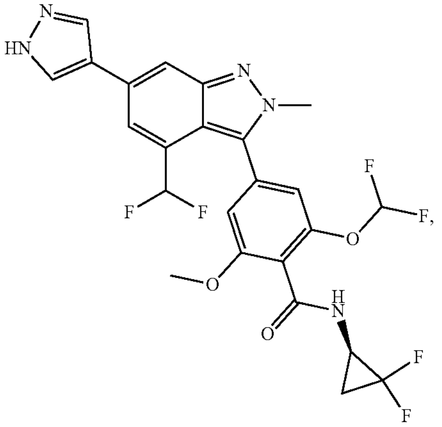

and

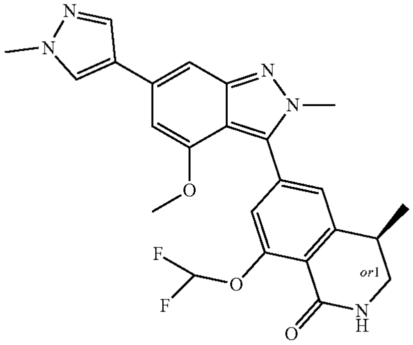

.

11. A pharmaceutical composition comprising the compound or the pharmacologically acceptable salt thereof described in claim 1 as an active ingredient and a pharmaceutically acceptable carrier.

12. A method for treating a disease and/or an accompanying symptom that can be improved by inhibiting salt-inducible kinases (SIK), the method comprising administering a therapeutically effective amount of the compound or the pharmacologically acceptable salt thereof as described in claim 1 to a patient, wherein the disease is selected from inflammatory diseases, autoinflammatory diseases, autoimmune diseases, proliferative diseases, fibrotic diseases, transplant rejections, diseases involving cartilage turnover disorders, congenital cartilage malformations, diseases involving bone turnover disorders, diseases associated with hypersecretion of TNF-α, interferon, IL-6, IL-12, and/or IL-23, respiratory diseases, endocrine and/or metabolic diseases, cardiovascular diseases, skin diseases, and abnormal angiogenesis-related diseases.

13. A method for treating a disease and/or an accompanying symptom that can be improved by inhibiting salt-inducible kinases (SIK), the method comprising administering a therapeutically effective amount of the compound or the pharmacologically acceptable salt thereof as described in claim 1 to a patient, wherein the disease is selected from rheumatoid arthritis, arthritis deformans, psoriatic arthritis, chronic inflammatory demyelinating polyneuropathy, ulcerative colitis, Crohn's disease, autoimmune hepatitis, primary biliary cholangitis, primary sclerosing cholangitis, non-alcoholic fatty liver disease, non-alcoholic steatohepatitis, type 1 diabetes mellitus, type 2 diabetes mellitus, pancreatitis, systemic lupus erythematosus, cutaneous lupus erythematosus, central nervous system lupus, lupus nephritis, antiphospholipid antibody syndrome, chronic kidney disease, acute kidney disease, sarcoidosis, systemic scleroderma, localized scleroderma, Sjogren's syndrome, ANCA-associated vasculitis, immune complex small vessel vasculitis, polyarteritis nodosa, Kawasaki disease, Takayasu arteritis, giant cell arthritis, idiopathic inflammatory muscle disease, polymyositis, dermatomyositis, inclusion body myositis, IgG4-related diseases, juvenile Still's disease, pelvic inflammatory disease, psoriasis, pustular psoriasis, atopic dermatitis, asthma, allergic rhinitis, relapsing polychondritis, mixed connective tissue disease, graft-versus-host disease, idiopathic pulmonary fibrosis, idiopathic interstitial pneumonia, chronic obstructive pulmonary disease, myelofibrosis, multiple sclerosis, cerebral infarction, ischemic stroke, developmental epilepsy, Meniere's disease, narcolepsy, macrophage activation syndrome, sepsis, pulmonary hypertension, hyperlipidemia, Behcet's disease, uveitis, osteoporosis, bone fracture, osteosarcoma, cardiac insufficiency, hypertrophic myocardiopathy, atherosclerosis, female gestosis, ovarian cancer, breast cancer, prostate cancer, malignant lymphoma, leukemia, multiple myeloma, lung cancer, granuloma annulare, esophageal cancer, colorectal cancer, pancreatic cancer, gastric cancer, hepatocellular cancer, melanoma, and secondary hemophagocytic lymphohistiocytosis.

14. The method according to claim 13, wherein the disease is selected from rheumatoid arthritis, arthritis deformans, psoriatic arthritis, ulcerative colitis, primary biliary cholangitis, primary sclerosing cholangitis, pancreatitis, systemic lupus erythematosus, lupus nephritis, systemic scleroderma, Sjogren's syndrome, psoriasis, pustular psoriasis, Behcet's disease, ovarian cancer, and acute myeloid leukemia.

15. The method according to claim 13, wherein the disease is selected from rheumatoid arthritis, arthritis deformans, psoriatic arthritis, ulcerative colitis, pancreatitis, systemic lupus erythematosus, lupus nephritis, systemic scleroderma, Sjogren's syndrome, pustular psoriasis, and Behcet's disease.

16. A pharmaceutical composition comprising the compound or the pharmacologically acceptable salt thereof described in claim 9 as an active ingredient and a pharmaceutically acceptable carrier.

17. A pharmaceutical composition comprising the compound or the pharmacologically acceptable salt thereof described in claim 10 as an active ingredient and a pharmaceutically acceptable carrier.

18. The pharmaceutical composition described in claim 11 that is formulated for oral administration.

19. The pharmaceutical composition described in claim 16 that is formulated for oral administration.

20. The pharmaceutical composition described in claim 17 that is formulated for oral administration.

21. The method according to claim 13, wherein said compound or pharmacologically acceptable salt thereof is administered to said patient orally.

22. The method according to claim 14, wherein said compound or pharmacologically acceptable salt thereof is administered to said patient orally.

23. The method according to claim 15, wherein said compound or pharmacologically acceptable salt thereof is administered to said patient orally.

* * * * *